US012735369B2

(12) United States Patent
Clark et al.

(10) Patent No.: US 12,735,369 B2
(45) Date of Patent: Sep. 15, 2026

(54) SELECTIVE TRANSITION METAL CATALYZED DEUTERIUM INCORPORATION INTO ALKYNE AND ALKENE FUNCTIONALITIES

(71) Applicant: Marquette University, Milwaukee, WI (US)

(72) Inventors: Joseph R. Clark, Milwaukee, WI (US); Zoua Pa Vang, Milwaukee, WI (US); Mitchell Mills, Milwaukee, WI (US); Albert Reyes, Milwaukee, WI (US); Samantha E. Sloane, Milwaukee, WI (US); Emanuel Rivera Torres, Milwaukee, WI (US)

(73) Assignee: Marquette University, Milwaukee, WI (US)

( * ) Notice: Subject to any disclaimer, the term of this patent is extended or adjusted under 35 U.S.C. 154(b) by 560 days.

(21) Appl. No.: 18/034,637

(22) PCT Filed: Nov. 1, 2021

(86) PCT No.: PCT/US2021/057608

§ 371 (c)(1),
(2) Date: Apr. 28, 2023

(87) PCT Pub. No.: WO2022/094420

PCT Pub. Date: May 5, 2022

(65) Prior Publication Data

US 2025/0122133 A1 Apr. 17, 2025

Related U.S. Application Data

(60) Provisional application No. 63/167,439, filed on Mar. 29, 2021, provisional application No. 63/108,145, filed on Oct. 30, 2020.

(51) Int. Cl.

| | |
|---|---|
| *C07B 59/00* | (2006.01) |
| *B01J 31/02* | (2006.01) |
| *B01J 31/24* | (2006.01) |
| *C07C 5/03* | (2006.01) |
| *C07C 41/20* | (2006.01) |

(52) U.S. Cl.

CPC ......... *C07B 59/001* (2013.01); *B01J 31/0202* (2013.01); *B01J 31/0204* (2013.01); *B01J 31/0274* (2013.01); *B01J 31/0275* (2013.01); *B01J 31/2409* (2013.01); *C07B 59/002* (2013.01); *C07C 5/03* (2013.01); *C07C 41/20* (2013.01); *B01J 2531/16* (2013.01); *C07B 2200/05* (2013.01)

(58) Field of Classification Search

None

See application file for complete search history.

(56) References Cited

U.S. PATENT DOCUMENTS

| | | | |
|---|---|---|---|
| 10,479,787 | B2 | 11/2019 | Despande et al. |
| 2011/0015401 | A1 | 1/2011 | Buchwald et al. |

OTHER PUBLICATIONS

Molport ("Tetrahydrofuran-3-acrylic acid methyl ester" Deposit and Available date Mar. 20, 2015) (Year: 2015).*

Esaki et al., Efficient H/D Exchange Reactions of Alkyl-Substituted Benzene Derivatives by Means of the Pd/C—H2—D2O System, Chemistry—A European Journal, 2007, 13(14):4052-4063.

Espinal-Viguri et al., Room Temperature Iron-Catalyzed Transfer Hydrogenation and Regioselective Deuteration of Carbon-Carbon Double Bonds, Journal of the American Chemical Society, 2019, 141(1):572-582.

Evangelisti et al., A chiral tagging strategy for determining absolute configuration and enantiomeric excess by molecule rotational spectroscopy, 72nd International Symposium on Molecular Spectroscopy, 2017, 1 page.

Faler et al., The Kulinkovich reaction in the synthesis of constrained N, N-dialkyl neurotransmitter analogues, Organic Letters, 2007, 9(10):1987-1990.

Falk et al., Design and Scalable Synthesis of N-Alkylhydroxylamine Reagents for the Direct Iron-Catalyzed Installation of Medicinally Relevant Amines, Angewandte Chemie International Edition, 2020, 59(47):21064-21071.

Felpin et al., A Useful, Reliable and Safer Protocol for Hydrogenation and the Hydrogenolysis of O-Benzyl Groups: The In Situ Preparation of an Active Pd0/C Catalyst with Well-Defined Properties, Chemistry—A European Journal, 2010, 16(41):12440-12445.

Fliege et al., Investigation of the Stark Shift of the Benzene-d1 I01-000 Rotational Transition by Microwave Fourier Transform Spectroscopy, Zeitschrift für Naturforschung, 1987, 42a(1):72-78.

Fu et al., Effect of the sample matrix on the determination of indinavir in human urine by HPLC with turbo ion spray tandem mass spectrometric detection, Journal of Pharmaceutical and Biomedical Analysis, 1998, 18(3):347-357.

Fujiwara et al., Successful fluorine-containing herbicide agrochemicals, Journal of Fluorine Chemistry, 2014, 167:16-29.

Furuya et al., Silver-Mediated Fluorination of Functionalized Aryl Stannanes, Journal of the American Chemical Society, 2009, 131(5):1662-1663.

Giagou et al., Kinetic Isotope Effects in Asymmetric Reactions, Chemistry—A European Journal, 2010, 16 (35):10616-10628.

Goering et al., Tris[3-(trifluoromethylhydroxymethylene)-d-camphorato]europium(III), A chiral shift reagent for direct determination of enantiomeric compositions, Journal of the American Chemical Society, 1971, 93(22):5913-5914.

Køgsig et al., Direct Vinylation and Difluorovinylation of Arylboronic Acids Using Vinyl- and 2,2-Difluorovinyl Tosylates via the Suzuki-Miyaura Cross Coupling, The Journal of Organic Chemistry, 2008, 73(9):3404-3410.

(Continued)

*Primary Examiner* — Medhanit W Bahta

(74) *Attorney, Agent, or Firm* — Quarles & Brady LLP

(57) ABSTRACT

Disclosed herein are deuterated compounds and transition metal catalyzed methods for making deuterated compounds. The disclosed methods are regioselective and enantioselective and may be utilized to prepare isomerically and/or enantiomerically pure or enriched deuterated compounds. The disclosed methods also may be modified in order to prepared fluorinated compounds.

10 Claims, 30 Drawing Sheets

(56) References Cited

OTHER PUBLICATIONS

Gómez-Gallego et al., Kinetic Isotope Effects in the Study of Organometallic Reaction Mechanisms, Chemical Reviews, 2011, 111(8):4857-4963 [In Two Parts Due to File Size].
González-Puma et al., Synthesis of Styrene Monomers Hydroxyl Functionalized, Journal of Macromolecular Science, Part A: Pure and Applied Chemistry, 2013, 50(11):1107-1112.
Gordy et al., Microwave Molecular Spectra, Knovel, 1984, Chapter VII, pp. 227-296 [In Three Parts Due to File Size].
Gordy et al., Microwave Molecular Spectra, Knovel, 1984, Chapter XIII, pp. 647-724 [In Three Parts Due to File Size].
Grabow et al., A multioctave coaxially oriented beam-resonator arrangement Fourier-transform microwave spectrometer, Review of Scientific Instruments, 1996, 67(12):4072-4084.
Grant, Using Deuterium in Drug Discovery: Leaving the Label in the Drug, Journal of Medicinal Chemistry, 2014, 57 (9):3595-3611.
Greenhalgh et al., Iron-Catalysed Chemo-, Regio-, and Stereoselective Hydrosilylation of Alkenes and Alkynes using a Bench-Stable Iron (II) Pre-Catalyst, Advanced Synthesis & Catalysis, 2014, 356(2-3):584-590.
Grimme et al., Effects of London dispersion correction in density functional theory on the structures of organic molecules in the gas phase, Physical Chemistry Chemical Physics, 2013, 15(38):16031-16042.
Groendyke et al., Iron-Catalyzed, Fluoroamide-Directed C—H Fluorination, Journal of the American Chemical Society, 2016, 138(39):12771-12774.
Groves et al., Asymmetric hydroxylation by a chiral iron porphyrin, Journal of the American Chemical Society, 1989, 111(22):8537-8538.
Guo et al., Regio- and Enantioselective Cobalt-Catalyzed Sequential Hydrosilylation/Hydrogenation of Terminal Alkynes, Angewandte Chemie International Edition, 2017, 56(2):615-618.
Hagmann, The Many Roles for Fluorine in Medicinal Chemistry, Journal of Medicinal Chemistry, 2008, 51 (15):4359-4369.
Hale et al., Stereoretentive Deuteration of α-Chiral Amines with D2O, Journal of the American Chemical Society, 2016, 138(41):13489-13492.
Harbeson et al., Deuterium Medicinal Chemistry: A New Approach to Drug Discovery and Development, MedChem News, 2014, 24(2):8-22.
Hatakeyama et al., Iron-Catalyzed Suzuki-Miyaura Coupling of Alkyl Halides, Journal of the American Chemical Society, 2010, 132(31):10674-10676.
He et al., Copper-Catalyzed Reagent-Controlled Regioselective Cyanoborylation of Vinylarenes, Organic Letters, 2018, 20(17):5208-5212.
Higashi et al., Methods for differential and quantitativeanalyses of brain neurosteroid levels by LC/MS/MS with ESI-enhancing and isotope-coded derivatization, Journal of Pharmaceutical and Biomedical Analysis, 2016, 117:155-162.
Holcomb et al., Stereochemistry at Carbon of the Cyclometalation of 8-(α-Deuterioethyl)quinoline by Palladium (II) Salts, Organometallics, 1996, 15(20):4228-4234.
Howell et al., Remote Oxidation of Aliphatic C—H Bonds in Nitrogen-Containing Molecules, Journal of the American Chemical Society, 2015, 137(46):14590-14593.
Hsu et al., Synthesis of Erythromycin Derivatives via the Olefin Cross-Metathesis Reaction, The Journal of the Organic Chemistry, 2004, 69(11):3907-3911.
Hu et al., Ligandless nickel-catalyzed transfer hydrogenation of alkenes and alkynes using water as the hydrogen donor, Organic Chemistry Frontiers, 2019, 6(15):2619-2623.
Hua et al., Radical C—H Fluorination Using Unprotected Amino Acids as Radical Precursors, Organic Letters, 2017, 19 (11):2949-2952.
Ichikawa et al., Development of a Unique Heterogeneous Palladium Catalyst for the Suzuki-Miyaura Reaction using (Hetero)aryl Chlorides and Chemoselective Hydrogenation, Advanced Synthesis & Catalysis, 2017, 359(13):2269-2279.
Iglesias et al., Isotopic Labeling of Metabolites in Drug Discovery Applications, Current Drug Metabolism, 2012, 13 (9):1213-1225.
Ikawa et al., Solvent-modulated Pd/C-catalyzed deprotection of silyl ethers and chemoselective hydrogenation, Tetrahedron, 2004, 60(32):6901-6911.
Inoue et al., Contribution of Organofluorine Compounds to Pharmaceuticals, ACS Omega, 2020, 5(19):10633-10640.
Ito et al., New Reactivity of a Reducing Reagent Generated from a Copper(I) Salt and a Hydrosilane: Selective Reduction of Ketones and Olefins Conjugated with an Aromatic Group, Synlett, 2000, 2000(04):479-482.
Jarling et al., Stereochemical Investigations Reveal the Mechanism of the Bacterial Activation of n-Alkanes without Oxygen, Angewandte Chemie International Edition, 2012, 51(6):1334-1338.
Johnstone et al., Heterogeneous Catalytic Transfer Hydrogenation and Its Relation to Other Methods for Reduction of Organic Compounds, Chemical Reviews, 1985, 85(2):129-170.
Jordan et al., Coinage Metal Hydrides: Synthesis, Characterization, and Reactivity, Chemical Reviews, 2016, 116 (15):8318-8372.
Joyce et al., Direct regioisomer analysis of crude reaction mixtures via molecular rotational resonance (MRR) spectroscopy, Chemical Science, 2020, 11(24):6332-6338.
Kaicharla et al., Using Alcohols as Simple H2-Equivalents for Copper-Catalysed Transfer Semihydrogenations of Alkynes, Chemical Communications, 2019, 55(89):13410-13413.
Karlsson et al., Hydrozirconation of (E)-3-methoxy-1-phenyl-1-propene and (E)-3-phenyl-2-propenol, Journal of Organometallic Chemistry, 1991, 403(1-2):133-144.
Kato et al., Transfer Hydrogenation Promoted by N-Heterocyclic Carbene and Water, Chemical Communications, 2015, 51(73):13906-13909.
Kimata et al., Direct Chromatographic Separation of Racemates on the Basis of Isotopic Chirality, Analytical Chemistry, 1997, 69(13):2610-2612.
Klapars et al., Copper-Catalyzed Halogen Exchange in Aryl Halides: An Aromatic Finkelstein Reaction, Journal of the American Chemical Society, 2002, 124(50):14844-14845.
Klinman, A new model for the origin of kinetic hydrogen isotope effects, Journal of Physical Organic Chemistry, 2010, 23(7):606-612.
Klyatskaya et al., Cross-coupling of Aryl lodides with Paramagnetic Terminal Acetylenes Derived from 4,4,5,5-tetramethyl-2-imidazoline-1-oxyl 3-oxide, Russian Chemical Bulletin, International Edition, 2002, 51(1):128-134.
Kondoh et al., Brønsted Base-Catalyzed Transformation of α, β-Epoxyketones Utilizing [1,2]-Phospha-Brook Rearrangement for the Synthesis of Allylic Alcohols Having a Tetrasubstituted Alkene Moiety, Organic Letters, 2020, 22(13):5170-5175.
Korytiaková et al., Copper(i)-Catalysed Transfer Hydrogenations with Ammonia Borane, Chemical Communiactions, 2017, 53(4):732-735.
Kraitchman, Determination of Molecular Structure from Microwave Spectroscopic Data, American Journal of Physics, 1953, 21(1):17-24.
Kratish et al., Convenient Synthesis of Deuterosilanes by Direct H/D Exchange Mediated by Easily Accessible Pt(0) Complexes, ACS Omega, 2017, 2(2):372-376.
Küppers et al., Optically Active 1-Deuterio-1-phenylethane—Preparation and Proof of Enantiopurity, European Journal of Organic Chemistry, 2019, 2019(15):2629-2634.
Landge et al., Iron-Catalyzed Direct Julia-Type Olefination of Alcohols, The Journal of Organic Chemistry, 2020, 85 (15):9876-9886.
Larionov et al., Well-defined transition metal hydrides in catalytic isomerizations, Chemical Communications, 2014, 50(69):9816-9826.
Larock et al., Reduction, In "Comprehensive Organic Transformations: A Guide to Functional Group Preparations," John Wiley & Sons, Inc, 2018, Chapter 1, pp. 5-191.
Lau et al., Amine-Boranes as Transfer Hydrogenation and Hydrogenation Reagents: A Mechanistic Perspective, Angewandte Chemie International Edition, 2021, 60(26):14272-14294.

(56) References Cited

OTHER PUBLICATIONS

Lee et al., Catalytic H/D Exchange of Unactivated Aliphatic C—H Bonds, Organometallics, 2013, 32(21):6599-6604.
Lee et al., Platinum-Catalyzed Terminal-Selective C(sp3)—H Oxidation of Aliphatic Amines, Journal of the American Chemical Society, 2015, 137(40):12796-12799.
Lee et al., Bayesian Analysis of Theoretical Rotational Constants from Low-Cost Electronic Structure Methods, The Journal of Physical Chemistry A, 2020, 124(5):898-910.
Lei et al., Copper-catalyzed enantioselective arylalkynylation of alkenes, Chemical Science, 2020, 11(6):1623-1628.
Leinberger et al., Steric Course of the NIH Shift in the Enzymic Formation of Homogentisic Acid, European Journal of Biochemistry, 1981, 117(2):311-318.
Li et al., Modern Organic Synthesis in the Laboratory: A Collection of Standard Experimental Procedures, Oxford University Press, 2007, pp. 171-172.
Li et al., A selective and cost-effective method for the reductive deuteration of activated alkenes, Tetrahedron Letters, 2017, 58(28):2757-2760.
Li et al., Highly selective electrochemical hydrogenation of alkynes: Rapid construction of mechanochromic materials, Science Advances, 2019, 5(5):eaaw2774, pp. 1-7.
Li et al., Regiodivergent DH or HD Addition to Alkenes: Deuterohydrogenation versus Hydrodeuterogenation, Organic Letters, 2020, 22(4):1628-1632.
Li et al., Indium Tribromide-Catalysed Transfer-Hydrogenation: Expanding the Scope of the Hydrogenation and of the Regiodivergent DH or HD Addition to Alkenes, Chemistry—A European Journal, 2021, 27(43):11221-11225.
Linford-Wood et al., Room temperature iron catalyzed transfer hydrogenation using n-butanol and poly (methylhydrosiloxane), Green Chemistry, 2021, 23(7):2703-2709.
Lipshutz et al., CuH-Catalyzed Asymmetric Conjugate Reductions of Acyclic Enones, Angewandte Chemie International Edition, 2003, 42(39):4789-4792.
Lipshutz et al., Asymmetric 1,4-Hydrosilylations of $\alpha,\beta$-Unsaturated Esters, Journal of the American Chemical Society, 2004, 126(27):8352-8353.
Lipshutz et al., CuH in a Bottle: A Convenient Reagent for Asymmetric Hydrosilylations, Angewandte Chemie International Edition, 2005, 44(39):6345-6348.
Liu et al., Manganese Catalyzed C—H Halogenation, Accounts of Chemical Research, 2015, 48(6):1727-1735.
Liu et al., Probing the C—O Bond-Formation Step in Metalloporphyrin-Catalyzed C—H Oxygenation Reactions, ACS Catalysis, 2017, 7(6):4182-4188.
Liu et al., Controllable deuteration of halogenated compounds by photocatalytic D2O splitting, Nature Communications, 2018, 9(1):80, pp. 1-9.
Liu et al., CuH-Catalyzed Olefin Functionalization: From Hydroamination to Carbonyl Addition, Accounts of Chemical Research, 2020, 53(6):1229-1243.
Loh et al., Photoredox-catalyzed deuteration and tritiation of pharmaceutical compounds, Science, 2017, 358 (6367):1182-1187.
Loi et al., Which Metabolites Circulate?, Drug Metabolism and Disposition, 2013, 41(5):933-951.
Lu et al., Practical carbon-carbon bond formation from olefins through nickel-catalyzed reductive olefin hydrocarbonation, Nature Communications, 2016, 7(1):11129, pp. 1-8.
Lu et al., Ligand-Substrate Dispersion Facilitates the Copper-Catalyzed Hydroamination of Unactivated Olefins, Journal of the American Chemical Society, 2017, 139(46):16548-16555.
Ludwig et al., Catalyst: Sustainable Catalysis, Chem, 2017, 2(3):313-316.
Lüthy et al., Preparation and Detection of Chiral Methyl Groups, Nature, 1969, 221(5187):1213-1215.
Mancheno et al., Copper-Catalyzed Olefin Aminoacetoxylation, Organic Letters, 2010, 12(18):4110-4113.
Mankad et al., Synthesis, Structure, and Alkyne Reactivity of a Dimeric (Carbene)copper(I) Hydride, Organometallics, 2004, 23(14):3369-3371.
Mantsch et al., Deuterium magnetic resonance, applications in chemistry, physics and biology, Progress in Nuclear Magnetic Resonance Spectroscopy, 1977, 11(4):211-272.
Mao et al., Atom-Transfer Radical Addition to Unactivated Alkenes by using Heterogenous Visible-Light Photocatalysis, ChemSusChem Communications, 2017, 10(22):4461-4464.
Mccreary et al., The determination of enantiomeric purity using chiral lanthanide shift reagents, Journal of the American Chemical Society, 1974, 96(4):1038-1054.
Mcgrath et al., A Graphical Journey of Innovative Organic Architectures That Have Improved Our Lives, Journal of Chemical Education, 2010, 87(12):1348-1349.
Meanwell, Synopsis of Some Recent Tactical Application of Bioisosteres in Drug Design, Journal of Medicinal Chemistry, 2011, 54(8):2529-2591.
Meanwell, Fluorine and Fluorinated Motifs in the Design and Application of Bioisosteres for Drug Design, Journal of Medicinal Chemistry, 2018, 61(14):5822-5880.
Meddour et al., Observation of Enantiomers, Chiral by Virtue of Isotopic Substitution, through Deuterium NMR in a Polypeptide Liquid Crystal, Journal of the American Chemical Society, 1994, 116(21):9652-9656.
Meek et al., Deducing Reaction Mechanism: A Guide for Students, Researchers, and Instructors, Journal of Chemical Education, 2016, 93(2):275-286.
Mei et al., Fluorine-Containing Drugs Approved by the FDA in 2018, Chemistry—A European Journal, 2019, 25 (51):11797-11819.
Mei et al., Fluorine-containing drugs approved by the FDA in 2019, Chinese Chemical Letters, 2020, 31(9):2401-2413.
Melnik et al., Identification and Synthesis of Luteolide, a Highly Branched Macrolide Semichemical from the Mantellid Frog *Gephyromantis luteus,* Organic Letters, 2019, 21(8):2851-2854.
Meng et al., Nickel-Catalyzed Removal of Alkene Protecting Group of Phenols, Alcohols via Walking Process, Molecules, 2020, 25(3):602, pp. 1-12.
Michel et al., Nickel-Catalyzed Cyanation of Benzylic and Allylic Pivalate Esters, The Journal of Organic Chemistry, 2018, 83(19):11860-11872.
Miki et al., Copper-Catalyzed Intermolecular Regioselective Hydroamination of Styrenes with Polymethylhydrosiloxane and Hydroxylamines, Angewandte Chemie International Edition, 2013, 41(52):10830-10834.
Sloane et al., Copper-Catalyzed Formal Transfer Hydrogenation/Deuteration of Aryl Alkynes, Organic Letters, 2020, 22(22):9139-9144.
Smith et al., Preparation of cyclohexene isotopologues and stereoisotopomers from benzene, Nature, 2020, 581 (7808):288-293.
Snider et al., Synthesis of the 5-hydroxymethyl-6-aryl-8-oxabicyclo[3.2.1]oct-3-en-2-one natural products descurainin and cartorimine, Tetrahedron, 2006, 62(22):5171-5177.
Soràdová et al., Enantioselective Cu-Catalyzed Functionalizations of Unactivated Alkenes, ChemCatChem, 2016, 8 (16):2581-2588.
Srihari et al., The Stereoselective Total synthesis of (+)-Stagonolide B, Synthesis, 2010, 2010(6):1039-1045.
Stepan et al., Metabolism-guided drug design, MedChemComm, 2013, 4(4):631-652.
Stokvis et al., Stable Isotopically Labeled Internal Standards in Quantitative Bioanalysis Using Liquid Chromatography/Mass Spectrometry: Necessity or not?, Rapid Communications in Mass Spectrometry, 2005, 19 (3):401-407.
Su et al., Cu(I)-Catalyzed 6-endo-dig Cyclization of Terminal Alkynes, 2-Bromoaryl Ketones, and Amides toward 1-Naphthylamines: Applications and Photophysical Properties, Journal of the American Chemical Society, 2019, 141 (6):2535-2544.
Suenram et al., A portable, pulsed-molecular-beam, Fourier-transform microwave spectrometer designed for chemical analysis, Review of Scientific Instruments, 1999, 70(4):2127-2135.

(56) References Cited

OTHER PUBLICATIONS

Talbot et al., Asymmetric Palladium-Catalyzed Directed Intermolecular Fluoroarylation of Styrenes, Journal of the American Chemical Society, 2014, 136(11):4101-4104.
Tayar et al., The lipophilicity of deuterium atoms. A comparison of shake-flask and HPLC methods, International Journal of Pharmaceutics, 1984, 19(3):271-281.
Taylor et al., Rings in Drugs: Miniperspective, Journal of Medicinal Chemistry, 2014, 57(14):5845-5859.
Tew et al., Supramolecular Materials with Electroactive Chemical Functions, Angewandte Chemie International Edition, 2000, 39(3):517-521.
Thomas et al., Mechanistically Guided Design of Ligands That Significantly Improve the Efficiency of CuH-Catalyzed Hydroamination Reactions, Journal of the American Chemical Society, 2018, 140(42):13976-13984.
Timmins, Deuterated drugs; updates and obviousness analysis, Expert Opinion on Therapeutic Patents, 2017, 27 (12):1353-1361.
Turowski et al., Deuterium Isotope Effects on Hydrophobic Interactions: The Importance of Dispersion Interactions in the Hydrophobic Phase, Journal of the American Chemical Society, 2003, 125(45):13836-13849.
Urey et al., A Hydrogen Isotope of Mass 2 and its Concentration, The Physical Review, 1932, 40(1):1-15.
Vang et al., Catalytic Transfer Deuteration and Hydrodeuteration: Emerging Techniques to Selectively Transform Alkenes and Alkynes to Deuterated Alkanes, Chemistry—A European Journal, 2021, 27(39):9988-10000.
Vang et al., Copper-Catalyzed Transfer Hydrodeuteration of Aryl Alkenes with Quantitative Isotopomer Purity Analysis by Molecular Rotational Resonance Spectroscopy, Journal of the American Chemical Society, 2021, 143 (20):7707-7718.
Vedejs et al., Aziridinomitosenes by Anionic Cyclization: Deuterium as a Removable Blocking Group, Journal of the American Chemical Society, 2002, 124(5):748-749.
Vitaku et al., Analysis of the Structural Diversity, Substitution Patterns, and Frequency of Nitrogen Heterocycles among U.S. FDA Approved Pharmaceuticals: Miniperspective, Journal of Medicinal Chemistry, 2014, 57 (24):10257-10274.
Walker et al., Regioselective Transfer Hydrodeuteration of Alkenes with a Hydrogen Deuteride Surrogate Using B (C6F5)3 Catalysis, Organic Letters, 2018, 20(20):6411-6414.
Wang et al., Palladium-Catalyzed Intermolecular Decarboxylative Coupling of 2-Phenylbenzoic Acids with Alkynes via C—H and C—C Bond Activation, Journal of the American Chemical Society, 2010, 132(40):14006-14008.
Wang et al., Copper-catalyzed Z-selective Semihydrogenation of Alkynes with Hydrosilane: a Convenient Approach to Cis-Alkenes, Tetrahedron, 2014, 70(12):2175-2179.
Wang et al., Fluorine in Pharmaceutical Industry: Fluorine-Containing Drugs Introduced to the Market in the Last Decade (2001-2011), Chemical Reviews, 2014, 114(4):2432-2506 [In Two Parts Due to File Size].
Wang et al., The Golden Age of Transfer Hydrogenation, Chemical Reviews, 2015, 115(13):6621-6686.
Wang et al., Transfer Hydrogenation of Alkenes Using Ethanol Catalyzed by a NCP Pincer Iridium Complex: Scope and Mechanism, Journal of the American Chemical Society, 2018, 140(12):4417-4429.
Wang et al., Bi(OTf)3 Catalyzed Synthesis of Acyclic β-sulfanyl Ketones via a Tandem Meyer-Schuster Rearrangement/Conjugate Addition Reaction, Tetrahedron Letters, 2019, 60(30):2030-2034.
Wang et al., Ligand-Promoted Iridium-Catalyzed Transfer Hydrogenation of Terminal Alkynes with Ethanol and Its Application, ACS Omega, 2019, 4(14):16045-16051.
Wang et al., Copper-Catalyzed, Enantioselective Hydrofunctionalization of Alkenes, in "Organic Reactions," John Wiley & Sons, Inc., 2020, Chapter 3, pp. 121-206.
Wang et al., Generalized Chemoselective Transfer Hydrogenation/Hydrodeuteration, Advanced Synthesis & Catalysis, 2020, 362(19):4119-4129.
Wei et al., Decyanative Cross-Coupling of Cyanopyrimidines with O-, S-, and N-Nucleophiles: A Route to Alkoxypyrimidines, Aminopyrimidines and Alkylthiopyrimidines, European Journal of Organic Chemistry, 2019, 2019 (42):7142-7150.
Weingart et al., Applying Le Chatelier's Principle for a Highly Efficient Catalytic Transfer Hydrogenation with Ethanol as the Hydrogen Source, ChemCatChem Communications, 2018, 10(21):4844-4848.
Wenzel et al., New binuclear lanthanide NMR shift reagents effective for aromatic compounds, Journal of the American Chemical Society, 1980, 102(18):5903-5904.
Wenzel et al., Using NMR spectroscopic methods to determine enantiomeric purity and assign absolute stereochemistry, Progress in Nuclear Magnetic Resonance Spectroscopy, 2011, 59(1):1-63.
White et al., Stereochemical dynamics of aliphatic hydroxylation by cytochrome P-450, Journal of the American Chemical Society, 1986, 108(19):6024-6031.
Whitesides et al., The determination of enantiomeric purity using chiral lanthanide shift reagents, Journal of the American Chemical Society, 1971, 93(22):5914-5916.
Whittaker et al., Monophasic Catalytic System for the Selective Semireduction of Alkynes, Organic Letters, 2013, 15(5):1112-1115.
Woof et al., Iron Catalyzed Double Bond Isomerization: Evidence for an FeI/FeIII Catalytic Cycle, Chemistry—A European Journal, 2021, 27(19):5972-5977.
Wrackmeyer, Carbon-13 NMR spectroscopy of boron compounds, Progress in Nuclear Magnetic Resonance Spectroscopy, 1979, 12(4):227-259.
Wu et al., Nickel-Catalyzed Hydrosilylation of Terminal Alkenes with Primary Silanes via Electrophilic Silicon-Hydrogen Bond Activation, Organic Letters, 2021, 23(4):1434-1439.
Xing et al., Case studies of fluorine in drug discovery, in "Fluorine in Life Sciences: Pharmaceuticals, Medicinal Diagnostics, and Agrochemicals," Elsevier, 2019, Chapter 4, pp. 181-211.
Xu et al., Copper-catalyzed regioselective reaction of internal alkynes and diaryliodonium salts, Organic Letters, 2013, 15(9):2096-2099.
Yang et al., Nickel-Catalyzed Asymmetric Transfer Hydrogenation of Olefins for the Synthesis of α- and β-Amino Acids, Angewandte Chemie International Edition, 2014, 53(45):12210-12213.
Yang et al., Copper-mediated 1,2-bis(trifluoromethylation) of arynes, Chemical Science, 2018, 9(47):8871-8875.
Yin et al., Enantioselective Palladium-Catalyzed Hydrofluorination of Alkenylarenes, ACS Catalysis, 2020, 10 (3):1954-1960.
Yoshida et al., A Novel Copper-Containing Hydride Species and its Application to the Reduction of Organic Substances, Journal of the Chemical Society, Chemical Communications, 1974, 18:762-763.
You et al., Copper-Catalyzed Asymmetric Formal Hydroaminomethylation of Alkenes with N,O-Acetals to Access Chiral β-Stereogenic Amines: Dual Functions of the Copper Catalyst, CCS Chemistry, 2019, 1(4):455-463.
Yu et al., Iron-catalysed tritiation of pharmaceuticals, Nature, 2016, 529(7585):195-199.
Zhang et al., Efficient One-pot Synthesis of 4-Ethynylbenzenesulfonamides, Zeitschrift für Naturforschung, 2009, 64 (3):292-296.
Alberti et al., Stereochemistry of the Singlet Oxygenation of Simple Alkenes: A Stereospecific Transformation, Organic Letters, 2008, 10(18):3997-4000.
Al-Etaibi et al., Gas-Phase Pyrolytic Reaction of 4-Aryl-3-buten-2-ols and Allyl Benzyl Ethers: Kinetic and Mechanistic Study, Molecules, 2010, 15(1):407-419.
Alexander et al., Optical Activity in Compounds Containing Deuterium. I. 2,3-Dideutero-trans-Menthane, Journal of the American Chemical Society, 1949, 71(5):1786-1789.
Anslyn et al., Modern physical organic chemistry, University Science Books, 2006, pp. 424-441.
Armstrong et al., A Gas Chromatography-Molecular Rotational Resonance Spectroscopy Based System of Singular Specificity, Angewandte Chemie International Edition, 2020, 59:192-196.

(56) References Cited

OTHER PUBLICATIONS

Atzrodt et al., The Renaissance of H/D Exchange, Angewandte Chemie International Edition, 2007, 46 (41):7744-7765.
Atzrodt et al., Pd- and Pt-catalyzed H/D Exchange Methods and their Application for Internal MS Standard Preparation From a Sanofi-Aventis Perspective, Journal of Labelled Compounds and Radiopharmaceuticals, 2010, 53 (11-12):674-685.
Atzrodt et al., C—H Functionalization for Hydrogen Isotope Exchange, Angewandte Chemie International Edition, 2018, 57(12):3022-3047.
Atzrodt et al., Deuterium- and Tritium-Labelled Compounds: Applications in the Life Sciences, Angewandte Chemie International Edition, 2018, 57(7):1758-1784.
Baldwin et al., Quantitative Analyses of Stereoisomeric 3,4-d 2-Cyclohexenes in the Presence of 3,6-d 2-Cyclohexenes, The Journal of Organic Chemistry, 2009, 74(10):3866-3874.
Balle et al., Fabry-Perot cavity pulsed Fourier transform microwave spectrometer with a pulsed nozzle particle source, Review of Scientific Instruments, 1981, 52(1):33-45.
Bao et al., Diboron-Assisted Copper-Catalyzed Z-Selective Semihydrogenation of Alkynes Using Ethanol as a Hydrogen Donor, The Journal of Organic Chemistry, 2019, 84(6):3579-3589.
Barker et al., Fe(III)/NaBH4-Mediated Free Radical Hydrofluorination of Unactivated Alkenes, Journal of the American Chemical Society, 2012, 134(33):13588-13591.
Battersby et al., Stereochemistry of formation of methyl and ethyl groups in bacteriochlorophyll a, Journal of the Chemical Society, Chemical Communications, 1981, (13):645-647.
Bayeh-Romero et al., Copper Hydride Catalyzed Enantioselective Synthesis of Axially Chiral 1,3-Disubstituted Allenes, Journal of the American Chemical Society, 2019, 141 (35):13788-13794.
Belleau et al., Effect of Deuterium Substitution in Sympathomimetic Amines on Adrenergic Responses, Science, 1961, 133(3446):102-104.
Berger et al., Organic fluorine compounds: a great opportunity for enhanced materials properties, Chemical Society Reviews, 2011, 40(7):3496-3508.
Bew et al., Mild Reaction Conditions for the Terminal Deuteration of Alkynes, Organic Letters, 2012, 14(2):456-459.
Bhawal et al., Overcoming Selectivity Issues in Reversible Catalysis: A Transfer Hydrocyanation Exhibiting High Kinetic Control, ChemRxiv™ Preprint, chemrxiv. 11931633, 2020, 90 pages.
Bigot et al., Enantioselective a-arylation of N-acyloxazolidinones with copper(II)-bisoxazoline catalysts and diaryliodonium salts, Journal of the American Chemical Society, 2011, 133(35):13778-13781.
Bloom et al., A Polycomponent Metal-Catalyzed Aliphatic, Allylic, and Benzylic Fluorination, Angewandte Chemie International Edition, 2012, 51(42):10580-10583.
Bloom et al., Iron(II)-Catalyzed Benzylic Fluorination, Organic Letters, 2013, 15(7):1722-1724.
Brown et al., A broadband Fourier transform microwave spectrometer based on chirped pulse excitation, Review of Scientific Instruments, 2008, 79(5):053103, pp. 1-13.
Bunlaksananusorn et al., t-BuOK-Mediated Hydrophosphination of Funcitonalized Alkenes: A Novel Synthesis of Chiral P,N- and PP-Ligands, The Journal of Organic Chemistry, 2004, 69(14):4595-4601.
Busacca et al., Transition Metal Catalysis in the Pharmaceutical Industry, In "Applications of Transition Metal Catalysis in Drug Discovery and Development: An Industrial Perspective," 2012, John Wiley & Sons, Inc., Chapter 1, pp. 1-24.
Cahard et al., Enantioselective and Regiodivergent Copper-Catalyzed Electrophilic Arylation of Allylic Amides with Diaryliodonium Salts, Journal of the American Chemical Society, 2015, 137(25):7986-7989.
Cantillo et al., A Continuous-Flow Protocol for Light-Induced Benzylic Fluorinations, The Journal of Organic Chemistry, 2014, 79(17):8486-8490.
Cao et al., Copper-Catalyzed Selective Semihydrogenation of Terminal Alkynes with Hypophosphorous Acid, Advanced Synthesis & Catalysis, 2014, 356(4):765-769.
Cargnin et al., A primer of deuterium in drug design, Future Medicinal Chemistry, 2019, 11(16):2039-2042.
Chatterjee et al., Brønsted Acid-Catalyzed Transfer Hydrogenation of Imines and Alkenes Using Cyclohexa-1,4-dienes as Dihydrogen Surrogates, Organic Letters, 2016, 18(10):2463-2466.
Chen et al., High-Throughput Method for Determining the Enantioselectivity of Enzyme-Catalyzed Hydroxylations Based on Mass Spectrometry, Angewandte Chemie International Edition, 2010, 31(49):5278-5283.
Chen et al., Rapid and Efficient Copper-Catalyzed Finkelstein Reaction of (Hetero)Aromatics under Continuous-Flow Conditions, Angewandte Chemie International Edition, 2015, 54(1):263-266.
Chen et al., Palladium-Catalyazed Intermolecular Ditrifluoromethoxylation of Unactivated Alkenes: CF3O-palladation Initiated by Pd(IV), Journal of the American Chemical Society, 2018, 140(4):1207-1210.
Chen et al., Catalyst-Free Annulation of 2-Pyridylacetates and Ynals with Molecular Oxygen: An Access to 3-Acylated Indolizines, The Journal of Organic Chemistry, 2019, 84(3):1630-1639.
Clark et al., Manganese-catalysed benzylic C(sp3)—H amination for late-stage functionalization, Nature Chemistry, 2018, 10(6):583-591.
Clark, Challenges Facing Young Scientists in Academia and Industry in the United States from the Lens of a Millennial Academic, Chemistry—A European Journal, 2020, 26(68):15759-15762.
Crandall et al., Cis Reduction of Acetylenes by Organocopper Reagents, The Journal of Organic Chemistry, 1976, 41(26):4089-4092.
Cummings et al., Tetrahydroxydiboron-Mediated Palladium-Catalyzed Transfer Hydrogenation and Deuteration of Alkenes and Alkynes Using Water as the Stoichiometric H or D Atom Donor, Journal of the American Chemical Society, 2016, 138(19):6107-6110.
Curran et al., 1,2-Asymmetric induction in radical reactions. Deuteration and allylation reactions of β-oxy-α-bromo esters, Tetrahedron, 1993, 49(22):4841-4858.
Czeskis et al., Deuterated active pharmaceutical ingredients: A science-based proposal for synthesis, analysis, and control, Part 1: Framing the problem, Journal of Labelled Compounds and Radiopharmaceuticals, 2019, 62 (11):690-694.
Daeuble et al., Selective Reduction of Alkynes to Cis-Alkenes by Hydrometallation Using [(Ph3P)CuH]6, Tetrahedron Letters, 1990, 31(17):2397-2400.
Das et al., A Survey of the Structures of US FDA Approved Combination Drugs, Journal of Medicinal Chemistry, 2019, 62(9):4265-4311.
Della-Felice et al., Rhodium(III)-Catalyzed Synthesis of Skipped Enynes via C(sp3)—H Alkynylation of Terminal Alkenes, Angewandte Chemie International Edition, 2021, 60(11):5693-5698.
Denmark et al., A Practical Method for Vinylation of Aromatic Halides Using Inexpensive Organosilicon Reagents, Journal of the American Chemical Society, 2008, 130(11):3690-3704.
Deutsch et al., Small but Effective: Copper Hydride Catalyzed Synthesis of a-Hydroxyallenes, Angewandte Chemie International Edition, 2007, 46(10):1650-1653.
Eliel, The Reduction of Optically Active Phenylmethylcarbinyl Chloride with Lithium Aluminum Deuteride, Journal of the American Chemical Society, 1949, 71(12):3970-3972.
Elmore et al., Isotope Chemistry, A Useful Tool in the Drug Discovery Arsenal, Bioorganic & Medicinal Chemistry Letters, 2015, 25(2):167-171.
Elsenbaumer et al., Enantiomerically pure (R)-(+)-2-phenylethanol-2-d and -1, 1,2-d3, and (S)-(+)-1- phenylethane-1-d,-1,2,-d2, -1,2,2-d3, and -1,2,2,2-d4, The Journal of Organic Chemistry, 1979, 44(4):600-604.
Emer et al., cis-Specific Hydrofluorination of Alkenylarenes under Palladium Catalysis through an Ionic Pathway, Angewandte Chemie, 2014, 126(16):4265-4269.

(56) References Cited

OTHER PUBLICATIONS

Eno et al., Nickel-Catalyzed Asymmetric Kumada Cross-Coupling of Symmetric Cyclic Sulfates, Journal of the American Chemical Society, 2016, 138(25):7824-7827.
Zhou, Transition-Metal Catalysis and Organocatalysis: Where Can Progress Be Expected?, Angewandte Chemie International Edition, 2016, 55(18):5352-5353.
Zhu et al., Enantio- and Regioselective CuH-Catalyzed Hydroamination of Alkenes, Journal of the American Chemical Society, 2013, 135(42):15746-15749.
Zhu et al., Modern Approaches for Asymmetric Construction of Carbon-Fluorine Quaternary Stereogenic Centers: Synthetic Challenges and Pharmaceutical Needs, Chemical Reviews, 2018, 118 (7):3887-3964 [In Five Parts Due to File Size].
Zubar et al., Chemoselective Hydrogenation of Alkynes to (Z)-Alkenes Using an Air-Stable Base Metal Catalyst, Organic Letters, 2020, 22(14):5423-5428.
PCT International Search Report and Written Opinion, PCT/US2021/057608, Feb. 25, 2022, 11 pages.
Brunel et al., Scope, limitations and mechanistic aspects in the selective homogeneous palladium-catalyzed reduction of alkenes under transfer hydrogen conditions, Tetrahedron, 2007, 63(18):3899-3906.
Guo et al., Enantioselective Synthesis of [beta]-Amino Acid Derivatives Enabled by Ligand-Controlled Reversal of Hydrocupration Regiochemistry, Angewandte Chemie International Addition, 2020, 59(47):20841-20845.
Teshima et al., Elucidation of stereospecificity of a selenium-containing hydrogenase from methanococcus vannielii—syntheses of (R)- and (S)-[4-2H1] 3,4-dihtdro-7-hydroxy-1-hydroxyethylquinolinone, Tetrahedron Letters, 1985, 26 (3):351-354.
Uccello-Barretta et al., The use of 2H NMR in the elucidation of the catalytic pathway of the hydroformylation reaction, Journal of Organometallic Chemistry, 1991, 417(1-2):111-119.
European Patent Office, European Search Report, Application No. 21887735.5, Sep. 13, 2024, 5 pages.
Miyashita et al., Total Synthesis of Norzoanthamine, Science, 2004, 305(5683):495-499.
Mo et al., Copper-Catalyzed Enantioselective Sonogashira Type Coupling of Alkynes with α-Bromoamides, Angewandte Chemie International Edition, 2020, 59(33):13998-14002.
Mohr et al., Balancing C=C Functionalization and C=O Reduction in Cu—H Catalysis, Angewandte Chemie International Edition, 2016, 55(40):12148-12149.
Morrison et al., Hydrogen vs. deuterium transfer in asymmetric reductions: reduction of phenyl trifluoromethyl ketone by the chiral Grignard reagent from (S)-2-phenyl-1-bromoethane-1,1,2-d3, Journal of the American Chemical Society, 1977, 99(9):3167-3168.
Mosher, Stereochemistry of neopentyl systems, Tetrahedron, 1974, 30(13):1733-1745.
Müller et al., Fluorine in Pharmaceuticals: Looking Beyond Intuition, Science, 2007, 317(5846):1881-1886.
Munslow, Alkyne Reductions, In "Modern Reduction Methods," Wiley-VCH Verlag Gmbh & Co. KGaA, 2008, Chapter 15, pp. 363-385.
Murahashi et al., Hydrogen transfer from 1,3-propanediamine and 2-ethylhexahydropyrimidine to carbon-carbon double bonds, Selective hydrogenation of dienes, Tetrahedron Letters, 1975, 16(48):4235-4238.
National Library of Medicine, Deudextromethorphan, C18H25NO, CID 25052519—PubChem, Retrieved from https://pubchem.ncbi.nlm.nih.gov/compound/Deudextromethorphan, Created on Nov. 24, 2008, 19 pages.
Neill et al., Rotational spectroscopy of iodobenzene and iodobenzene-neon with a direct digital 2-8GHz chirped-pulse Fourier transform microwave spectrometer, Journal of Molecular Spectroscopy, 2011, 269(1):21-29.
Neill et al., Online Stereochemical Process Monitoring by Molecular Rotational Resonance Spectroscopy, Organic Process Research & Development, 2019, 23(5):1046-1051.
Neill et al., Rapid quantification of isomeric and dehalogenated impurities in pharmaceutical raw materials using MRR spectroscopy, Journal of Pharmaceutical and Biomedical Analysis, 2020, 189:113474, pp. 1-8.
Nelson et al., The Use of Deuterium Isotope Effects to Probe the active site properties, Mechanism of Cytochrom P450-Catalyzed Reactions, and Mechanisms of Metabolically Dependent Toxicity, Drug Metabolism and Disposition, 2003, 31(12):1481-1497.
Neubert et al., Ruthenium-Catalyzed Selective α,β-Deuteration of Bioactive Amines, Journal of the American Chemical Society, 2012, 134(29):12239-12244.
Ning et al., Synthesis of α-Deuterated Primary Amines via Reductive Deuteration of Oximes Using D2O as a Deuterium Source, The Journal of Organic Chemistry, 2021, 86(3):2907-2916.
Nishikawa et al., Asymmetric Synthesis of α-Aminoboronic Acid Derivatives by Copper-Catalyzed Enantioselective Hydroamination, Journal of the American Chemical Society, 2015, 137(50):15620-15623.
Nodwell et al., Direct photocatalytic fluorination of benzylic C—H bonds with N-fluorobenzenesulfonimide, Chemical Communications, 2015, 51(59):11783-11786.
Oba, A Convenient Method for Palladium-catalyzed Reductive Deuteration of Organic Substrates using Deuterated Hypophosphite in D2O, Journal of Labelled Compounds and Radiopharmaceuticals, 2015, 58(5):215-219.
Ogston, Interpretation of Experiments on Metabolic processes, using Isotopic Tracer Elements, Nature, 1948, 162 (4129):963.
Oh et al., Copper-Catalyzed 1,2-Bistrifluoromethylation of Terminal Alkenes, Advanced Synthesis & Catalysis, 2019, 361(9):2136-2140.
O'Hagan, Fluorine in health care: Organofluorine containing blockbuster drugs, Journal of Fluorine Chemistry, 2010, 131 (11):1071-1081.
Okuhara et al., Orientation in the addition of HD to butadiene on MoS2, Journal of the Chemical Society, Chemical Communications, 1976, 6:199-200.
Okuhara et al., Oriented adsorption of HD on ZnO and catalytic addition of HD to butadiene It, The Journal of Physical Chemistry, 1977, 81(8):808-809.
Palmer et al., Cobalt-Catalyzed Stereoretentive Hydrogen Isotope Exchange of C(sp3)—H Bonds, ACS Catalysis, 2017, 7(9):5674-5678.
Parker, 1H and 2H nuclear magnetic resonance determination of the enantiomeric purity and absolute configuration of α-deuteriated primary carboxylic acids, alcohols, and amines, Journal of the Chemical Society, Perkin Transactions II, 1983, (1):83-88.
Pate et al., Quantitative chiral analysis by molecular rotational spectroscopy, In "Chiral Analysis (Second Edition): Advances in Spectroscopy, Chromatography, and Emerging Methods," Elsevier, 2018, Chapter 17, pp. 679-729.
Pérez et al., Broadband Fourier transform rotational spectroscopy for structure determination: The water heptamer, Chemical Physics Letters, 2013, 571:1-15.
Peyroux et al., Suzuki Cross-Coupling Reactions between Alkenylboronic Acids and Aryl Bromides Catalysed by a Tetraphosphane-Palladium Catalyst, European Journal of Organic Chemistry, 2004, 2004(5):1075-1082.
Pirali et al., Applications of Deuterium in Medicinal Chemistry, Journal of Medicinal Chemistry, 2019, 62 (11):5276-5297.
Pirnot et al., Copper Hydride Catalyzed Hydroamination of Alkenes and Alkynes, Angewandte Chemie International Edition, 2016, 55(1):48-57.
Puleo et al., Catalytic α-Selective Deuteration of Styrene Derivatives, Journal of the American Chemical Society, 2019, 141(4):1467-1472.
Purser et al., Fluorine in medicinal chemistry, Chemical Society Reviews, 2008, 37(2):320-330.
Qin et al., A Quantitative LC-MS/MS Method for Simultaneous Determination of Deuvortioxetine, Vortioxetine and their Carbox-

(56) References Cited

OTHER PUBLICATIONS ylic Acid Metabolite in Rat Plasma, and its Application to a Toxicokinetic Study, Analytical Methods, 2018, 10 (9):1023-1031.
Quasdorf et al., Total Synthesis of Oxidized Welwitindolinones and (−)-N-Methylwelwitindolinone C Isonitrile, Journal of the American Chemical Society, 2012, 134(3):1396-1399.
Reddy et al., Ethanol as a Hydrogenating Agent: Palladium-Catalyzed Stereoselective Hydrogenation of Ynamides to Give Enamides, Angewandte Chemie International Edition, 2017, 56(24):6984-6988.
Reich et al., Chiral 1-deuterio alcohols. Synthesis and determination of enantiomeric purity by chiral lanthanide nmr shift reagents, Tetrahedron Letters, 1973, 14(17):1505-1508.
Reyes et al., Highly Regioselective Copper-Catalyzed Transfer Hydrodeuteration of Unactivated Terminal Alkenes, Chemistry—A European Journal, 2022, 28(9):e202104340, pp. 1-5.
Ryu et al., Copper(II)-Mediated Stereoselective Reduction of Acetylenic Sulfones by Hydrosilanes, Organometallics, 1989, 8(9):2279-2281.
Satterthwaite et al., Enantiomeric Analysis of Chiral Isotopomers via Microwave Three-Wave Mixing, The Journal of Physical Chemistry A, 2019, 123(14):3194-3198.
Sawama et al., Stainless-Steel Ball-Milling Method for Hydro-/Deutero-genation using H2O/D2O as a Hydrogen/ Deuterium Source, ChemSusChe Communications, 2015, 8(22):3773-3776.
Schmidt, First Deuterated Drug Approved, Nature Biotechnology, 2017, 35(6):493-494.
Schuppe et al., Enantioselective Hydroalkenylation of Olefins with Enol Sulfonates Enabled by Dual Copper Hydride and Palladium Catalysis, Journal of the American Chemical Society, 2021, 143(14):5330-5335.
Schwab, Stereochemistry of an enzymic Baeyer-Villiger reaction. Application of deuterium NMR, Journal of the American Chemical Society, 1981, 103(7):1876-1878.
Semba et al., Copper-Catalyzed Highly Selective Semihydrogenation of Non-Polar Carbon-Carbon Multiple Bonds using a Silane and an Alcohol, Advanced Synthesis & Catalysis, 2012, 354(8):1542-1550.
Shapiro et al., Steric course of hydroxylation at primary carbon atoms, Biosynthesis of 1-octanol from (1R)- and (1S)-[1-3H,2H, 1H; 1-14C]octane by rat liver microsomes, Journal of the American Chemical Society, 1982, 104 (8):2301-2305.
Shen et al., Facile Regio- and Stereoselective Hydrometalation of Alkynes with a Combination of Carboxylic Acids and Group 10 Transition Metal Complexes: Selective Hydrogenation of Alkynes with Formic Acid, Journal of the American Chemical Society, 2011, 133(42):17037-17044.
Shi et al., Copper-catalyzed Selective Hydroamination Reactions of Alkynes, Nature Chemistry, 2015, 7(1):38-44.
Shishkin et al., Influence of Deuteration and Fluorination on the Supramolecular Architecture of Pyridine N-Oxide Crystals, ChemPhysChem, 2013, 14(4):847-856.
Simmons et al., On the Interpretation of Deuterium Kinetic Isotope Effects in C—H Bond Functionalization by Transition-Metal Complexes, Angewandte Chemie International Edition, 2012, 51(13):3066-3072.
Skoda-Foldes et al., Direct and carbonylative vinylation of steroidal triflates in the presence of homogeneous palladium catalysts, Steroids, 1994, 59(12):691-695.
Boyd, et al. Stereochemical and mechanistic aspects of dioxygenase-catalysed benzylic hydroxylation of indene and chromane substrates, Org Biomol Chem, 2003, 1, 1298-1307.
Khaled, et al. An experimental and theoretical study on the kinetic isotope effect of C2H6 and C2D2 reaction with OH, Chemical Physics Letters 641 (2015) 158-162.
Greene, et al. Stereochemistry of Free-Radical Recombination Reactions. The Cage Effect in Decomposition of SS-(−)-Azobis-a-phenylethane, Journal of the American Chemical Society, 1970, 92:4, 867-874.

* cited by examiner

Deutetrabenazine: First and only FDA approved deuterated drug (2017). Used to treat chorea of Huntington's disease.

*Compared to parent drug*:
-Extended active metabolite half-life
-Lower doses are given less frequently
-Reduced daily withdrawal symptoms
-Fewer adverse events b.) *Proposed Mechanism*

| Entry | Ligand | 6 %D inc $C_1$ | $C_2$ | %yield |
|---|---|---|---|---|
| 1 | DTBM-SEGPHOS | 89 | 11 | nd |
| 2 | DTB-DPPBz | 97 | 3 | 73 |

*d.) Ligand Legend*

Ar = 3,5-($^t$Bu)$_2$-$C_6H_3$
DTB-DPPBz

Ar = 3,5-($^t$Bu)$_2$-4-MeO-$C_6H_2$
(*R*)-DTBM-SEGPHOS

7, 78% yield

8, 71% yield

9, 92% yield

10, 73% yield

11, 73% yield

12, 57% yield

13, 78% yield

14, 83% yield

15, 89% yield b.) *Ethylbenzene-$d_1$ Synthesis Through the Decades*

Eliel (1949): no yield reported
-no ee reported

Mosher (1978), Groves (1989, 2017):
34% yield over 7-steps
-no direct, accurate ee measurment

Li (2010): 7% yield over 2-steps
-86% ee by assumption, no data

Christoffers (2019): 72% yield over 2-steps
-92% ee after 4 derivatization steps 1. Regioselectivity Challenges:

2. Enantioselectivity Challenge:

3. ee determination:

d.) Synthesis Results

16

R = $CH_2OSi(CH_3)_2C(CH_3)_3$

R = $CH_2OH$

17, 98% ee
76% yield
(over 2-steps)

18

19, 97.4% ee
53% yield
(1.2 gram scale)

*racemic tag*
*(S, R)* + *(S,S)*

(1)

(2)

*Racemic or*
*Chiral Tag Forms H-bond*
*With Analyte*
*(S,S)* a.) *Regioselective Transfer Hydrodeuteration*

Bioactive molecules that can be hydrodeuterated

Dextromethorphan analog

Erlotinib analog b.) Expanded Transfer Deuteration to Unactivated Alkenes

Evaluation of substituted alkenes and complex bioactive molecules

Complex bioactive molecules

Ethynyl-Estradiol d.) *Enantioselective Transfer Hydrodeuteration*

Styrene scope can be expanded to study additional substituted and unactivated alkenes Metoprolol is metabolized by CYP2D6 and CYP3A4. The enantiomers can be tested to determined which enantiomer inhibits metabolism at the benzylic position.

a)

b.) *Enantioselective Transfer Hydrodeuteration*

1

R = $CH_2OSi(CH_3)_2C(CH_3)_3$

2, R = $CH_2OH$
98% ee
76% yield
(2-steps)

(*R*)-DTBM-SEGPHOS
*Ar* = 3,5-$(^tBu)_2$-4-MeO-$C_6H_2$ b) Additional Substrates a) Asymmetric Hydrofluorination b) Data and Proposed Mechanism

SELECTIVE TRANSITION METAL CATALYZED DEUTERIUM INCORPORATION INTO ALKYNE AND ALKENE FUNCTIONALITIES

CROSS-REFERENCE TO RELATED PATENT APPLICATIONS

The present application is a National stage of International Application No. PCT/US2021/057608 filed Nov. 1, 2021, and published May 5, 2022, as WO 2022/094420 and claims the benefit of priority under 35 U.S.C. 119(e) to U.S. Provisional Application No. 63/167,439, filed on Mar. 29, 2021, and to U.S. Provisional Application No. 63/108,145, filed on Oct. 30, 2020, the contents of all of which are incorporated herein by reference in their entireties.

BACKGROUND

The field of the present invention relates to deuterated compounds and transition metal catalyzed methods for making deuterated compounds. The disclosed methods are regioselective and/or enantioselective and may be utilized to prepare isomerically and/or enantiomerically pure or enriched compounds.

Deuterium, also known as "heavy hydrogen," is an isotope of hydrogen having an extra neutron which doubles its molecular weight. Deuterated compounds have important properties that are utilized in research and therapy. From an organometallic and synthetic organic chemistry context, deuterated compounds often are used to elucidate reaction mechanisms and perform kinetic isotope effect measurements. In physical and analytical chemistry, deuterated compounds serve as valuable tools for spectroscopy or standards for high-resolution mass spectrometry. In medicine, reactions that selectively deuterate small molecules are useful to develop new therapeutics.

In drug discovery, deuterium labeling of metabolically labile sites in drug molecules is performed to alter the drug's absorption, distribution, metabolism, and excretion (ADME) properties. The bond between deuterium and another atom is more difficult to break than a bond between hydrogen and the other atom due to the "primary kinetic isotope effect." For drugs that are metabolized and destroyed through breaking a C—H bond in the liver, replacing the hydrogen atom with a deuterium atom can increase the half-life of the drug in the bloodstream. One or more well-placed deuterium atoms can have a significant effect on how long a drug will circulate in the bloodstream, by slowing down the liver's clearance mechanism.

However, the scarcity of selective reactions for deuterium incorporation remains a bottleneck to using deuterated small molecules as new medicines and stable isotope derivatives for liquid chromatography-mass spectrometry (LC-MS). To address a major unmet need to selectively install deuterium into small molecules, the present inventors are targeting the development of new, highly selective, base metal catalyzed transfer deuteration and transfer hydrodeuteration reactions. A key challenge in developing a selective hydrodeuteration reaction is the ability to distinguish between hydrogen (H) and deuterium (D) atoms for functionalization. While D has a 2-fold higher mass than H and a reduced vibrational stretching frequency exists for a C-D bond versus a C—H bond, it is very difficult to distinguish between H and D given their similar pKa values, molar volumes, lipophilicities and bond lengths when comparing C—H to C-D bonds. For deuteration to be useful in medicinal chemistry, reactivity should occur at the target functional group while leaving the other functionalities in the molecule undisturbed. Other desirable reaction features include using commercial reagents, a first-row transition metal catalyst and commercial ligands. Here, the inventors disclose a method for the selective installation of deuterium into small molecules for the synthesis of previously inaccessible molecules which can be utilized to obtain up to 99% enantiopure molecules.

SUMMARY

Disclosed herein are deuterated compounds and transition metal catalyzed methods for making deuterated compounds. The disclosed methods are regioselective and enantioselective and may be utilized to prepare isomerically and/or enantiomerically pure or enriched compounds. The disclosed methods also may be modified to prepare fluorinated compounds.

DETAILED DESCRIPTION

Figure 1:
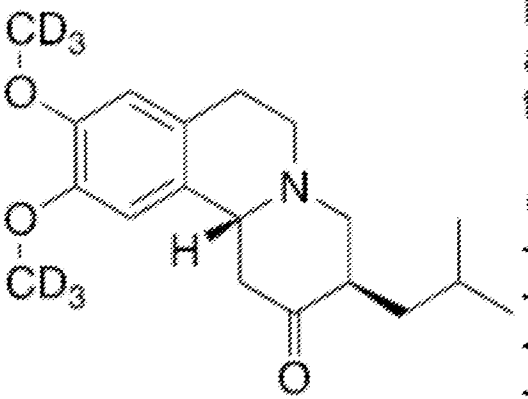
FIG. 1. Molecular structure of Deutetrabenazine, the first and only FDA-approved deuterated drug used to treat chorea of Huntington's disease.

The present invention is described herein using several definitions, as set forth below and throughout the application.

Definitions

The disclosed subject matter may be further described using definitions and terminology as follows. The definitions and terminology used herein are for the purpose of describing particular embodiments only, and the definitions and terminology are not intended to be limiting.

As used in this specification and the claims, the singular forms "a," "an," and "the" include plural forms unless the context clearly dictates otherwise. For example, the term "a substituent" should be interpreted to mean "one or more substituents," unless the context clearly dictates otherwise.

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The phrase "such as" should be interpreted as "for example, including." Moreover, the use of any and all exemplary language, including but not limited to "such as," is intended merely to better illuminate the invention and does not pose a limitation on the scope of the invention unless otherwise claimed.

Furthermore, in those instances where a convention analogous to "at least one of A. B and C, etc." is used, in general such a construction is intended in the sense of one having ordinary skill in the art would understand the convention (e.g., "a system having at least one of A, B and C" would include but not be limited to systems that have A alone, B alone, C alone, A and B together, A and C together, B and C together, and/or A, B, and C together). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of 'A' or 'B or "A and B."

All language such as "up to," "at least," "greater than," "less than," and the like, include the number recited and refer to ranges which can subsequently be broken down into ranges and subranges. A range includes each individual member. Thus, for example, a group having 1-3 members refers to groups having 1, 2, or 3 members. Similarly, a group having 6 members refers to groups having 1, 2, 3, 4, 5 or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use an aspect of a described embodiment or feature contained in the same, or a definitive decision to use a specific skill regarding a described embodiment or feature contained in the same. In this latter context, the modal verb "may" has the same meaning and connotation as the auxiliary verb "can."

Chemical Entities

New chemical entities and uses for chemical entities are disclosed herein. The chemical entities may be described using terminology known in the art and further discussed below.

As used herein, a dash "–" an asterisk "*" or a plus sign "+" may be used to designate the point of attachment for any radical group or substituent group.

The term "alkyl" as contemplated herein includes a straight-chain or branched alkyl radical in all of its isomeric forms, such as a straight or branched group of 1-12, 1-10, or 1-6 carbon atoms, referred to herein as C1-C12 alkyl, C1-C10-alkyl, and C1-C6-alkyl, respectively.

The term "alkylene" refers to a diradical of straight-chain or branched alkyl group (i.e., a diradical of straight-chain or branched $C_1$-C6 alkyl group). Exemplary alkylene groups include, but are not limited to $-CH_2-$, $-CH_2CH_2-$, $—CH_2CH_2CH_2—$, $—CH(CH_3)CH_2—$, $—CH_2CH(CH_3)CH_2—$, $—CH(CH_2CH_3)CH_2—$, and the like.

The term "halo" refers to a halogen substitution. The term "haloalkyl" refers to an alkyl group that is substituted with at least one halogen. For example, $—CH_2F$, $—CHF_2$, $—CF_3$, $—CH_2CF_3$, $—CF_2CF_3$, and the like.

The term "heteroalkyl" as used herein refers to an "alkyl" group in which at least one carbon atom has been replaced with a heteroatom (e.g., an O, N, or S atom). One type of heteroalkyl group is an "alkoxy" group.

The term "alkene" or "alkenyl" as used herein refers to an unsaturated straight or branched hydrocarbon having at least one carbon-carbon double bond, such as a straight or branched group of 2-12, 2-10, or 2-6 carbon atoms, referred to herein as C2-C12-alkenyl, C2-C10-alkenyl, and C2-C6-alkenyl, respectively.

The term "alkyne" or "alkynyl" as used herein refers to an unsaturated straight or branched hydrocarbon having at least one carbon-carbon triple bond, such as a straight or branched group of 2-12, 2-10, or 2-6 carbon atoms, referred to herein as C2-C12-alkynyl, C2-C10-alkynyl, and C2-C6-alkynyl, respectively.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein. e.g., as "C4-8-cycloalkyl," derived from a cycloalkane. Unless specified otherwise, cycloalkyl groups are optionally substituted at one or more ring positions with, for example, alkanoyl, alkoxy, alkyl, haloalkyl, alkenyl, alkynyl, amido or carboxyamido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted. i.e., it is unsubstituted.

The term "cycloheteroalkyl" refers to a monovalent saturated cyclic, bicyclic, or bridged cyclic hydrocarbon group of 3-12, 3-8, 4-8, or 4-6 carbons in which at least one carbon of the cycloalkane is replaced with a heteroatom such as, for example, N, O, and/or S.

The term "cycloalkylene" refers to a cycloalkyl group that is unsaturated at one or more ring bonds.

The term "partially unsaturated carbocyclyl" refers to a monovalent cyclic hydrocarbon that contains at least one double bond between ring atoms where at least one ring of the carbocyclyl is not aromatic. The partially unsaturated carbocyclyl may be characterized according to the number oring carbon atoms. For example, the partially unsaturated carbocyclyl may contain 5-14, 5-12, 5-8, or 5-6 ring carbon atoms, and accordingly be referred to as a 5-14, 5-12, 5-8, or 5-6 membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system. Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido or carboxyamido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted, i.e., it is unsubstituted.

The term "aryl" is art-recognized and refers to a carbocyclic and/or heterocyclic aromatic group. Representative aryl groups include phenyl, naphthyl, anthracenyl, pyridinyl, quinolinyl, furanyl, thionyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido or carboxyamido, carboxylic acid, —C(O)alkyl, $—CO_2$alkyl, carbonyl, carboxyl, alkylthio, sulfonyl, sulfonamido, sulfonamide, ketone, aldehyde, ester, heterocyclyl, aryl or heteroaryl moieties, $—CF_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The terms "heterocyclyl" and "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. The number of ring atoms in the heterocyclyl group can be specified using 5 Cx-Cx nomenclature where x is an integer specifying the number of ring atoms. For example, a C3-C7 heterocyclyl group refers to a saturated or partially unsaturated 3- to 7-membered ring structure containing one to four heteroatoms, such as nitrogen, oxygen, and sulfur. The designation "C3-C7" indicates that the heterocyclic ring contains a total of from 3 to 7 ring atoms, inclusive of any heteroatoms that occupy a ring atom position.

The terms "amine" and "amino" are art-recognized and refer to both unsubstituted and substituted amines (e.g., mono-substituted amines or di-substituted amines), wherein substituents may include, for example, alkyl, cycloalkyl, heterocyclyl, alkenyl, and aryl.

The terms "alkoxy" or "alkoxyl" are art-recognized and refer to an alkyl group, as defined above, having an oxygen radical attached thereto. Representative alkoxy groups include methoxy, ethoxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and the like.

The term "carbonyl" as used herein refers to the radical —C(O)—.

The term "oxo" refers to a divalent oxygen atom —O—.

The term "carboxy" or "carboxyl" as used herein refers to the radical —COOH or its corresponding salts, e.g. —COONa, etc. A carboxy alkyl ester refers to a compound having a moiety —C(O)O—R, where R is alkyl.

The term "amide" or "amido" or "amidyl" as used herein refers to a radical of the form $—R^1C(O)N(R^2)—$, $—R^1C(O)N(R^2)R^3—$, $—C(O)NR^2R^3$, or $—C(O)NH_2$, wherein $R^1$, $R^2$ and $R^3$, for example, are each independently hydrogen, alkyl, alkoxy, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro.

The term "carboxamido" as used herein refers to the radical —C(O)NRR', where R and R' may be the same or different. R and R', for example, may be independently hydrogen, alkyl, aryl, arylalkyl, cycloalkyl, formyl, haloalkyl, heteroaryl, or heterocyclyl.

The term "transition metal" is meant to encompass any element whose atom has a partially filled d sub-shell or which can provide a cation with an incomplete d sub-shell. A "transition metal" may include any element in the d-block of the periodic table, which include scandium (Sc), titanium (Ti), vanadium (V), chromium (Cr), manganese (Mn), iron (Fe), cobalt (Co), nickel (Ni), copper (Cu), zinc (Zn), yttrium (Y), zirconium (Zr), niobium (Nb), molybdenum (Mo), technetium (Tc), ruthenium (Ru), rhodium (Rh), palladium (Pd), silver (Ag), cadmium (Cd), hafnium (Hf), tantalum (Ta), tungsten (W), rhenium (Re), osmium (Os), iridium (Ir), platinum (Pt), gold (Au), mercury (Hg), rutherfordium (Rf), dubnium (Db), seaborgium (Sg), bohrium (Bh), hassium (Hs), meitnerium (Mt), darmstadtium (Ds), roentgenium (Rg), and copernicium (Cn). A "transition metal" includes any element in the first row of the d-block, such as scandium (Sc), titanium (Ti), vanadium (V), chromium (Cr), manganese (Mn), iron (Fe), cobalt (Co), nickel (Ni), copper (Cu), zinc (Zn).

The compounds of the disclosure may be isomeric. In some embodiments, a disclosed compound may be isomerically pure, wherein the compound represents greater than about 99% of all compounds within an isomeric mixture of compounds. Also contemplated herein are compositions comprising, consisting essentially of, or consisting of an isomerically pure compound and/or compositions that are isomerically enriched, which compositions may comprise, consist essential of, or consist of at least about 50%, 60%, 70%, 80%, 90%, 95%, 96%, 97%, 98%, 99%, or 100% of a single isomer of a given compound.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," or "+" or "−" depending on the configuration of substituents around the chiral or stereogenic carbon atom and or the optical rotation observed. The present invention encompasses various stereo isomers of these compounds and mixtures thereof. Stereoisomers include enantiomers and diastereomers. Mixtures of enantiomers or diastereomers may be designated (±)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise. Also contemplated herein are compositions comprising, consisting essentially of, or consisting of an enantiopure compound and/or compositions that are enantiomer enriched, which compositions may comprise, consist essential of, or consist of at least about 50%, 60%, 70%, 80%, 90%, 95%, 96%, 97%, 98%, 99%, or 100% of a single enantiomer of a given compound (e.g., at least about 95% of an R enantiomer of a given compound).

Selective Transition Metal-Catalyzed Deuterium Incorporation into Alkyne and Alkene Functionalities The disclosed subject matter relates to deuterated compounds and transition metal-catalyzed methods for making deuterated compounds. The disclosed methods are regioselective and/or enantioselective and may be utilized to prepare isomerically and/or enantiomerically pure or enriched compounds.

In some embodiments, the disclosed methods for preparing a deuterated compound comprise reacting a reaction mixture where the reaction mixture comprises as components: (i) a substrate compound comprising an alkyne functionality or an alkene functionality (i.e., an unsaturated carbon-carbon bond); (ii) a transition metal catalyst; (iii) a phosphine ligand for the transition metal catalyst; (iv) a substituted silane comprising a donor hydrogen atom and/or a donor deuterium atom (e.g., a substituted silane comprising one of a donor hydrogen atom and a donor deuterium atom); (v) an alcohol comprising a donor hydrogen atom and/or a donor deuterium atom (e.g., an alcohol comprising the other of a donor hydrogen atom and a donor deuterium atom with respect to the substituted silane); and (vi) a solvent; where the reaction mixture is reacted under conditions such that the alkyne functionality or the alkene functionality of the substrate compound is reductively deuterated to provide the deuterated compound.

Suitable substrates for the disclosed methods may include substrates comprising an alkyne functionality and/or an alkene functionality. In the disclosed methods, the substrate having an alkyne functionality and/or an alkene functionality is hydrodeutrated to provide a hydrodeutrated derivative of the substrate where the alkyne functionality and/or the alkene functionality is reduced to an alkane functionality.

Enumerable substrates having an alkyne functionality and/or an alkene functionality are suitable for the disclosed methods. However, in some embodiments, the substrate has a formula selected from the following Formula I and Formula II:

(I)

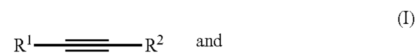

and (II)

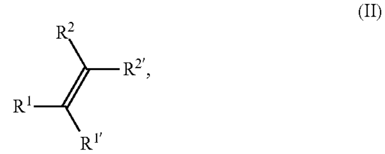

where:

- $R^1$ is $-(CH_2)_m-(O)_n-X$, where m is 0-6, n is 0 or 1, and X is selected from an alkyl moiety, an alkenyl moiety, an aryl moiety (Ar) (which may be a carbocyle aryl moiety or a heterocycle aryl moiety), a cycloalkyl moiety, and a heterocycloalkyl moiety, and $R^1$ optionally is substituted at one or more positions with alkyl (e.g., methyl), hydroxyl which optionally is protected, hydroxyalkyl (e.g., hydroxymethyl which optionally is protected), alkoxy (e.g., methoxy), carboxyl, carboxy alkyl ester, phenyl, phenoxy, benzyl, pyridinyl, piperidinyl, hydroxy(phenyl)methyl which optionally is protected, halogen, haloalkyl, nitro, amino, (alkyl) amino such as dimethylamino, diphenylamino, boronic acid pinocol ester, morpholino (e.g., N-morpholino), sulfonamide, and tosyl (e.g., wherein a nitrogen atom of an aryl ring is protected by a tosyl group);
- $R^{1'}$ is selected from hydrogen, deuterium, and alkyl;

$R^2$ is selected from hydrogen, deuterium, alkyl (butyl), hydroxyalkyl which optionally is protected (e.g., hydroxymethyl, hydroxyethyl, or 2-propanol which optionally are protected), Ar (e.g., phenyl), cycloalkyl, and (alkoxy)alkyl (e.g., 1-methoxyethyl); and $R^{2'}$ is selected from hydrogen, deuterium, and alkyl.

In some embodiments of the disclosed methods, the substrate has a formula selected from:

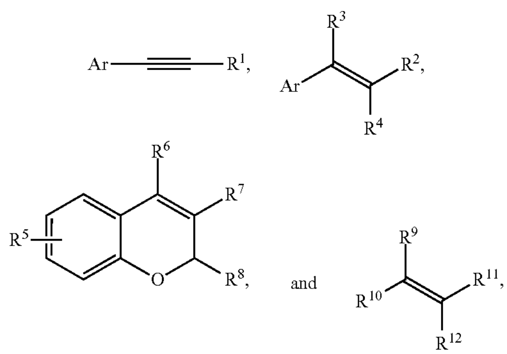

and wherein Ar is aryl (e.g., an aromatic carbocycle and/or an aromatic heterocycle) optionally substituted at one or more positions with a substituent selected from alkyl, carbonyl, carboxy alkyl ester (i.e., —C(O)—O-alkyl), phenyl, phenyoxy, halogen, nitro, sulfonamide, pyridinyl, imidazolyl, morpholino, boronic acid, piperidinyl, pyrazolyl, piperazinyl, and tosyl; $R^1$, $R^2$, $R^3$, $R^4$, $R^5$, $R^6$, $R^7$, and $R^8$ are independently selected from hydrogen, deuterium, alkyl, and Ar optionally substituted with amino, nitro, hydroxyl, alkoxy, carboxyl, carboxy alkyl ester (i.e., —C(O)—O—$R^{13}$ where $R^{13}$ is alkyl), —C(O)—$R^{14}$ wherein $R^{14}$ is alkyl, $C(R^{15})(R^{16})$—$R^{17}$ wherein $R^{15}$ and $R^{16}$ are alkoxy, alkylthiol, sulfonamide, or Ar and $R^{17}$ is alkyl, or —$CH_2C(OR^{18})$—$R^{19}$ wherein $R^{18}$ and $R^{19}$ are hydrogen or alkyl; and $R^9$, $R^{10}$, $R^{11}$, and $R^{12}$ are independently selected from hydrogen, deuterium, alkyl.

Suitable substrates for the disclosed methods may comprise an aryl moiety (Ar). The aryl moiety may comprise one carbocycle or heterocycle or two or more fused carbocycles or heterocycles. In some embodiments, the aryl moiety is selected from phenyl, pyridine, quinoline, 1,2,3,4-tetrahydroquinoline, isoquinoline, naphthalene, biphenyl, indole, furan, benzofuran, imidazole, benzimidazole, pyridine, pyrimidine, carbazole, dibenzofuran, indoline, azaindole, fluorene, 1,3-benzodioxole, thiophene, benzothiophene, and the aryl moiety optionally is substituted with alkyl, alkoxy, carboxyl, carboxy alkyl ester, phenyl, phenoxy, halogen, nitro, sulfonamide, or tosyl. Suitable substrates for the disclosed methods may comprise a heterocycle moiety, which may include, but are not limited to, piperidine, piperazine, oxirane, tetrahydrofuran, pyrrolidine.

In some embodiments, where the disclosed substrates comprise a nitrogen atom, for example as a ring nitrogen atom, the nitrogen atom optionally may be protected. Suitable protecting groups may include, but are not limited to p-toluenesulfonamide (Ts), triphenylamine (Tr), benzylamine (Bz), 9-fluorenylmethyl carbamate (Fmoc), t-butyl carbamate (BOC), benzyl carbamate (Cbz), and acetamide (Ac).

The disclosed substrates may include include hydroxyl groups which optionally may be protected. Suitable hydroxyl protecting groups may include, but are not limited to benzoic acid ester (Bz), pivalic acid ester (Piv), acetic acid ester (Ac), t-butyldiphenylsilyl ether (TBDPS), t-butyldimethylsilyl ether (TBDMS), t-butyldimethylsilyl ether (TBS), trimethylsilyl ether (TMS), benzyl ether (Bn), tetrahydropyranyl ether (THP), and methoxmethylether (MOM).

In some embodiments, the disclosed substrate is a derivative of natural product or a known drug. In some embodiments, the disclosed substrate is a steroid hormone or a derivative of a steroid hormone such as estrogen, for example, estrone or ethynyl-estradiol. In some embodiments, the disclosed substrate is a tocopherol or a derivative of tocopherol such as δ-tocopherol. In some embodiments, the disclosed substrate is dextromethorphan or a derivative thereof. In some embodiments, the discloses substrate is erlotinib or a derivative thereof. In some embodiments, the disclosed substrate is deplancheine or a derivative thereof. In some embodiments, the disclosed substrate is capsaicin or a derivative thereof. In some embodiments, the disclosed substrate is metoprolol. In some embodiments, the disclosed substrate is methyl eugenol.

The disclosed methods typically utilize a phosphine ligand. In some embodiments, the phosphine ligand is a bidentate phosphine ligand. Optionally, the phosphine ligand may be chiral.

In some embodiments, the phosphine ligand of the disclosed methods has a formula selected from:

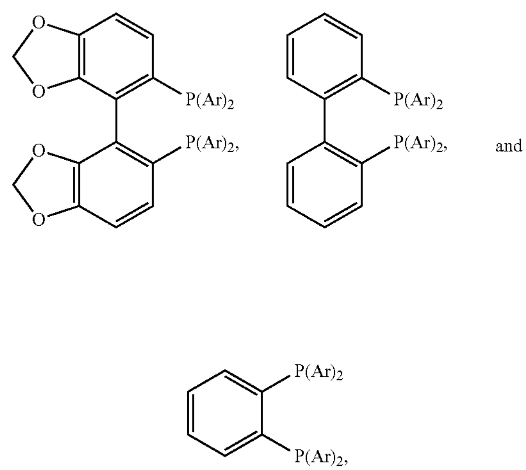

and where Ar is phenyl optionally substituted at one or more positions with alkyl or alkoxy, optionally wherein Ar is phenyl, 3,5-dimethylphenyl, 3,5-di-tert-butylphenyl, or Ar is 3,5-di-tert-butyl-4-methyoxyphenyl. In some embodiments, the phosphine ligand may be selected from (2H,2'H-[4,4'-Bi-1,3-benzodioxole]-5,5'-diyl)bis(diphenylphosphane) (SEGPHOS), [(4R/S)-(4,4'-bi-1,3-benzodioxole)-5,5'-diyl]bis[bis(3,5-dimethylphenyl)phosphine], ((R/S)-DM-SEGPHOS), (R/S)-(−)-5,5'-Bis[di(3,5-di-tert-butyl-4-methoxyphenyl)phosphino]-4,4'-bi-1,3-benzodioxole ((R/S)-DTBM-SEGPHOS), 1,2-bis(bis(3,5-di-tert-butylphenyl)phosphino)benzene (DTB-dppbz), and 1,2-bis(bis(3,5-di-tert-butyl-4-methoxyphenyl)phosphino)benzene (DTBM-dppbz).

The phosphine ligand may be enantiomerically pure. In some embodiments, the phosphine ligand of the disclosed methods has a formula selected from:

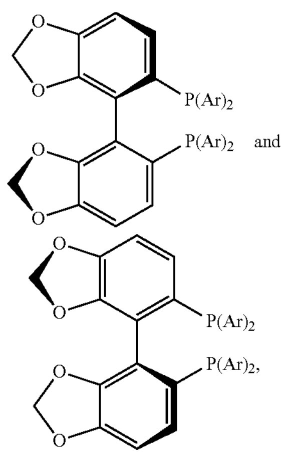

and and Ar optionally is optionally is 3,5-di-tert-butylphenyl or 3,5-di-tert-butyl-4-methyoxyphenyl. In some embodiments, the phosphine ligand is (R)-(−)-5,5'-Bis[di(3,5-di-tert-butyl-4-methoxyphenyl)phosphino]-4,4'-bi-1,3-benzodioxole ((R)-DTBM-SEGPHOS) or (S)-(−)-5,5'-Bis[di(3,5-di-tert-butyl-4-methoxyphenyl)phosphino]-4,4'-bi-1,3-benzodioxole ((S)-DTBM-SEGPHOS).

In some embodiments, the phosphine ligand of the disclosed methods has a formula:

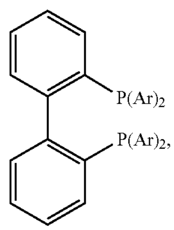

and Ar optionally is optionally is 3,5-di-tert-butylphenyl or 3,5-di-tert-butyl-4-methyoxyphenyl.

In some embodiments, the phosphine ligand of the disclosed methods has a formula selected from:

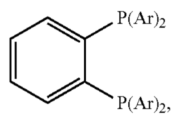

and Ar optionally is optionally is 3,5-di-tert-butylphenyl or 3,5-di-tert-butyl-4-methyoxyphenyl.

The disclosed methods typically utilize a substituted silane as a hydrogen donor and/or as a deuterium donor. In some embodiments, the substituted silane has a formula:

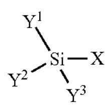

where $Y^1$, $Y^2$, and $Y^3$ are the same or different and are selected from alkyl and alkoxy, and X is the donor hydrogen atom or the donor deuterium atom. In some embodiments, two of $Y^1$, $Y^2$, and $Y^3$ are alkyl (e.g., methyl) and the other of $Y^1$, $Y^2$, and $Y^3$ is alkoxy (e.g., methoxy). In some embodiments, the substituted silane of the disclosed methods has a formula selected from:

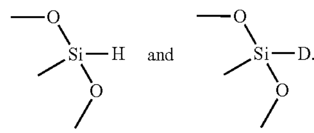

and

The disclosed methods typically utilize an alcohol as a hydrogen donor and/or as a deuterium donor. In some embodiments, the alcohol utilized in the disclosed methods has a formula selected from $C_2H_5O(H/D)$ (i.e., ethanol or deuterated ethanol (EtOD)) and $(CH_3)_2CHO(H/D)$ (i.e., 2-propanol or deuterated 2-propanol (IPA-$d_8$)).

The disclosed methods typically utilize a transition metal catalyst. Suitable transition metal catalysts may include, but are not limited to scandium (Sc), titanium (Ti), vanadium (V), chromium (Cr), manganese (Mn), iron (Fe), cobalt (Co), nickel (Ni), copper (Cu), and zinc (Zn). In some embodiments, the transition metal catalyst is divalent copper Cu(II). For example, the reaction mixture of the disclosed methods may comprise a solubilized divalent copper salt such as a solubilized organic divalent copper salt such as $Cu(OAc)_2$.

The components of the disclosed reaction mixtures may be present in the reaction mixture at selected concentrations.

In some embodiments, the substrate is present in the reaction mixture at a concentration of at least about 0.001, 0.002, 0.005, 0.01, 0.02, 0.05, 0.1, 0.2, 0.5, 1, 2, 5, 10, 20, 50, 100, 200, or 500 mmol, or the substrate is present in the reaction mixture at a concentration of at no more than about 0.001, 0.002, 0.005, 0.01, 0.02, 0.05, 0.1, 0.2, 0.5, 1, 2, 5, 10, 20, 50, 100, 200, or 500 mmol, or the substrate is present in the reaction mixture at a concentration within a range bounded by any of these values (e.g., 0.1-0.5 mmol).

In some embodiments, the transition metal catalyst is present in the reaction mixture at a concentration of at least about 0.01, 0.02, 0.05, 0.1, 0.2, 0.5, 1, 2, 5, 10, 20, or 50 mol %, or the transition metal catalyst is present in the reaction mixture at a concentration of no more than about 0.01, 0.02, 0.05, 0.1, 0.2, 0.5, 1, 2, 5, 10, 20, or 50 mol %, or the transition metal catalyst is present in the reaction mixture at a concentration within a range bounded by any of these values (e.g., 0.5-2 mol %).

In some embodiments, the phosphine ligand is present in the reaction mixture at a concentration of at least about 0.01, 0.02, 0.05, 0.1, 0.2, 0.5, 1, 2, 5, 10, 20, or 50 mol %, or the phosphine ligand is present in the reaction mixture at a concentration of no more than about 0.01, 0.02, 0.05, 0.1, 0.2, 0.5, 1, 2, 5, 10, 20, or 50 mol %, or the phosphine ligand is present in the reaction mixture at a concentration within a range bounded by any of these values (e.g., 0.5-2 mol %).

In some embodiments, the transition metal catalyst (M) and the phosphine ligand (L) are present in the reaction mixture at a selected ratio. In some embodiments, the transition metal catalyst (M) and the phosphine ligand (L) are present in the reaction mixture at a ratio (M:L) selected from 1:0.1, 1:0.2, 1:0.5, 1:1, 1:1.5, 1:2, and 1:5 or the transition metal catalyst (M) and the phosphine ligand (L) are present in the reaction mixture at a ratio within a range bounded by any of these values (e.g., a ratio between 1:0.5 and 1:1.5).

In some embodiments, the substituted silane is present in the reaction mixture at a concentration of at least about 0.5, 1, 1.5, 2, 2.5, 3, 3.5, 4, 4.5, or 5 equivalents relative to the substrate, or the substituted silane is present in the reaction mixture at a concentration of no more than about 0.5, 1, 1.5, 2, 2.5, 3, 3.5, 4, 4.5, or 5 equivalents relative to the substrate, or the substituted silane is present in the reaction mixture at a concentration within a range bounded by any of these values (e.g., 2-5 equivalents).

In some embodiments, the alcohol is present in the reaction mixture at a concentration of at least about 0.5, 1, 1.5, 2, 2.5, 3, 3.5, 4, 4.5, or 5 equivalents relative to the substrate, or the alcohol is present in the reaction mixture at a concentration of no more than about 0.5, 1, 1.5, 2, 2.5, 3, 3.5, 4, 4.5, or 5 equivalents relative to the substrate, or the alcohol is present in the reaction mixture at a concentration within a range bounded by any of these values (e.g., 1-4 equivalents)

The disclosed methods may be performed at a selected temperature. In some embodiments, the disclosed methods are performed at a temperature of at least about 20, 25, 30, 35, 40, 45, 50, 55, 60, 65, 70, 75, or 80° C. or the disclosed methods are performed at a temperature of no more than about 20, 25, 30, 35, 40, 45, 50, 55, 60, 65, 70, 75, or 80° C., or the disclosed methods are performed at a temperature within a range bounded by any of these values (e.g., 30-50° C.).

The disclosed methods may be performed for a selected amount of time. In some embodiments, the disclosed methods are performed for at least about 6, 8, 10, 12, 14, 16, 18, 20, 24, 26, 28, 30, 32, 34, or 36 hours, or the disclosed methods are performed for no more than about 6, 8, 10, 12, 14, 16, 18, 20, 24, 26, 28, 30, 32, 34, or 36 hours, or the disclosed methods are performed for an amount of time within a range bounded by any of these values (e.g., 16-28 hours).

Also disclosed herein are isomerically pure compounds and/or isomerically enriched compounds. In some embodiments, the disclosed compounds are an isomerically pure compound of Formula IIIa or Formula IIIb or a mixture of isomeric compounds comprising the compound of Formula III or Formula IIIb where the compound represents greater than about 80%, 85%, 90%, 95%, 96%, 97%, 98%, or 99% of the isomeric compounds in the mixture:

IIIa

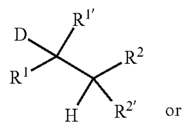

or

IIIb

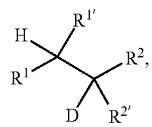

where:

$R^1$ is $-(CH_2)_m-(O)_n-X$, where m is 0-6, n is 0 or 1, and X is selected from an alkyl moiety, an alkenyl moiety, an aryl moiety (Ar) (which may be a carbocycle aryl moiety or a heterocycle aryl moiety), a cycloalkyl moiety, and a heterocycloalkyl moiety, and $R^1$ optionally is substituted at one or more positions with alkyl (e.g., methyl), hydroxyl which optionally is protected, hydroxyalkyl (e.g., hydroxymethyl which optionally is protected), alkoxy (e.g., methoxy), carboxyl, carboxy alkyl ester, phenyl, phenoxy, benzyl, pyridinyl, piperidinyl, hydroxy(phenyl)methyl which optionally is protected, halogen, haloalkyl, nitro, amino, (alkyl) amino such as dimethylamino, diphenylamino, boronic acid pinocol ester, morpholino (e.g., N-morpholino), sulfonamide, and tosyl (e.g., wherein a nitrogen atom of an aryl ring is protected by a tosyl group);

$R^{1'}$ is selected from hydrogen, deuterium, and alkyl;

$R^2$ is selected from hydrogen, deuterium, alkyl (e.g., butyl), hydroxyalkyl which optionally is protected (e.g., hydroxymethyl, hydroxyethyl, or 2-propanol which optionally are protected), Ar (e.g., phenyl), cycloalkyl, and (alkoxy)alkyl (e.g, 1-methoxyethyl); and $R^{2'}$ is selected from hydrogen, deuterium, and alkyl.

In some embodiments, the isomerically pure compounds and/or isomerically enriched compounds have a Formula IIIa(S) or Formula IIIb(S). In some embodiments, the disclosed compounds are an isomerically pure compound of Formula IIIa or Formula IIIb or a mixture of isomeric compounds comprising the compound of Formula IIIa or Formula IIIb where the compound represents greater than about 80%, 85%, 90%, 95%, 96%, 97%, 98%, or 99% of the isomeric compounds in the mixture:

IIIa(DS)

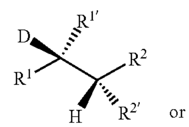

or

IIIb(DS)

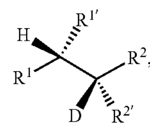

Further disclosed are enantiomerically pure compounds of Formula IIIa'(DS), Formula IIIa'(DR), Formula IIIb'(DS), or Formula IIIb'(DR) or a mixture of enantiomeric compounds comprising the compound of Formula IIIa'(DS), Formula IIIa'(DR), Formula IIIb'(DS), or Formula IIIb'(DR) wherein the compound represents greater than about 80%, 85%, 90%, 95%, 96%, 97%, 98%, or 99% of the enantiomeric compounds in the mixture:

IIIa'(DS)

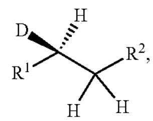

IIIb'(DR)

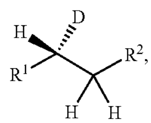

IIIb'(DS)'

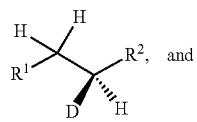

and

-continued

IIIb'(DR)

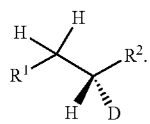

The disclosed methods may be utilized in order to prepare fluorinated compounds. In some embodiments, the disclosed methods comprise reacting a reaction mixture, where the reaction mixture comprises: (i) a substrate compound comprising an alkyne functionality or an alkene functionality as disclosed herein; (ii) a transition metal catalyst as disclosed herein; (iii) a phosphine ligand for the transition metal catalyst as disclosed herein; (iv) a substituted silane comprising a donor hydrogen atom as disclosed herein; (v) a fluorine donor compound; and (vi) a solvent; wherein the reaction mixture is reacted under conditions such that the alkyne functionality or the alkene functionality of the substrate compound is reductively fluorinated to provide the fluorinated compound. Suitable fluorine donor compounds may include, but are not limited to 1-chloromethyl-4-fluoro-1,4-diazoniabicyclo[2.2.2]octane bis(tetrafluoroborate) (Selectfluor), N-fluorobenzenesulfonimide (NFSI), N-fluoropyridinum salts (NFPY), and N-fluoro-N-arylsulfonamides.

ILLUSTRATIVE EMBODIMENTS

The following Embodiments are illustrative and should not be interpreted to limit the scope of the claimed subject matter.

Embodiment 1. A method for preparing a deuterated compound, the method comprising reacting a reaction mixture comprising: (i) a substrate compound comprising an alkyne functionality or an alkene functionality; (ii) a transition metal catalyst; (iii) a phosphine ligand for the transition metal catalyst; (iv) a substituted silane comprising a donor hydrogen atom or a donor deuterium atom; (v) an alcohol comprising a donor hydrogen atom or a donor deuterium atom; and (vi) a solvent; wherein the reaction mixture is reacted under conditions such that the alkyne functionality or the alkene functionality of the substrate compound is reductively deuterated to provide the deuterated compound (e.g., wherein the alkyne functionality or the alkene functionality is reductively deuterated to provide a deteurated alkane functionality). Optionally, the substituted silane comprises one of the donor hydrogen atome and the donor deuterium atom, and the alcohol comprises the other of the donor hydrogen atom and the donor deuterium atom.

Embodiment 2. The method of embodiment 1, wherein the substrate has a formula selected from Formula I and Formula II:

(I)

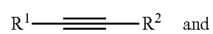

and (II)

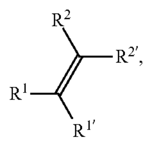

where:

$R^1$ is —$(CH_2)_m$—$(O)_n$—X, where m is 0-6, n is 0 or 1, and X is selected from an alkyl moiety, an alkenyl moiety, an aryl moiety (Ar) (which may be a carbocycle aryl moiety or a heterocycle aryl moiety), a cycloalkyl moiety, and a heterocycloalkyl moiety, and $R^1$ optionally is substituted at one or more positions with alkyl (e.g., methyl), hydroxyl which optionally is protected, hydroxyalkyl (e.g., hydroxymethyl which optionally is protected), alkoxy (e.g., methoxy), carboxyl, carboxy alkyl ester, phenyl, phenoxy, benzyl, pyridinyl, piperidinyl, hydroxy(phenyl)methyl which optionally is protected, halogen, haloalkyl, nitro, amino, (alkyl) amino such as dimethylamino, diphenylamino, boronic acid pinocol ester, morpholino (e.g., N-morpholino), sulfonamide, and tosyl (e.g., wherein a nitrogen atom of an aryl ring is protected by a tosyl group);

$R^{1'}$ is selected from hydrogen, deuterium, and alkyl;

$R^2$ is selected from hydrogen, deuterium, alkyl (butyl), hydroxyalkyl which optionally is protected (e.g., hydroxymethyl, hydroxyethyl, or 2-propanol which optionally are protected), Ar (e.g., phenyl), cycloalkyl, and (alkoxy)alkyl (e.g., 1-methoxyethyl); and $R^{2'}$ is selected from hydrogen, deuterium, and alkyl.

Embodiment 3. The method of embodiment 1 or 2, wherein the substrate comprises an optionally substituted aryl moiety comprising one carbocycle or heterocycle or two or more fused carbocycles or heterocycles, and optionally wherein the aryl moiety is selected from phenyl, pyridine, quinoline, 1,2,3,4-tetrahydroquinoline, isoquinoline, naphthalene, biphenyl, indole, furan, benzofuran, imidazole, benzimidazole, pyridine, pyrimidine, carbazole, dibenzofuran, indoline, azaindole, fluorene, 1,3-benzodioxole, thiophene, benzothiophene, and the aryl moiety optionally is substituted with alkyl, alkoxy, carboxyl, carboxy alkyl ester, phenyl, phenoxy, halogen, nitro, sulfonamide, or tosyl.

Embodiment 4. The method of embodiment 1 or 2, wherein the substrate comprises a an optionally substituted heterocycle moiety, which may include, but are not limited to, piperidine, piperazine, oxirane, tetrahydrofuran, pyrrolidine, and the heterocycle moiety optionally is substituted with alkyl, alkoxy, carboxyl, carboxy alkyl ester, phenyl, phenoxy, halogen, nitro, sulfonamide, or tosyl.

Embodiment 5. The method of any of the foregoing embodiments, wherein the substrate comprise a nitrogen atom, for example as a ring nitrogen atom, and the nitrogen atom optionally is protected, optionally wherein the nitrogen atom is protected with a protecting group selected from p-toluenesulfonamide (Ts), triphenylamine (Tr), benzylamine (Bz), 9-fluorenylmethyl carbamate (Fmoc), t-butyl carbamate (BOC), benzyl carbamate (Cbz), and acetamide (Ac).

Embodiment 6. The method of any of the foregoing embodiments, wherein the substrate comprises a hydroxyl group, and the hydroxyl group optionally is protected with a protecting group selected from benzoic acid ester (Bz), pivalic acid ester (Piv), acetic acid ester (Ac), t-butyldiphenylsilyl ether (TBDPS), t-butyldimethylsilyl ether (TBDMS), t-butyldimethylsilyl ether (TBS), trimethylsilyl ether (TMS), benzyl ether (Bn), tetrahydropyranyl ether (THP), and methoxmethylether (MOM).

Embodiment 7. the method of any of the foregoing embodiments, wherein the substrate comprises a natural product or a known drug, optionally wherein the substrate is selected from a steroid hormone or a derivative of a steroid hormone such as estrogen (e.g., estrone or ethynyl-estradiol), a tocopherol or a derivative of tocopherol such as δ-tocopherol, dextromethorphan or a derivative thereof, erlotinib or a derivative thereof, deplancheine or a derivative thereof, capsaicin or a derivative thereof, and metoprolol, and methyl eugenol or derivative thereof.

Embodiment 8. The method of embodiment 1, wherein the substrate has a formula selected from:

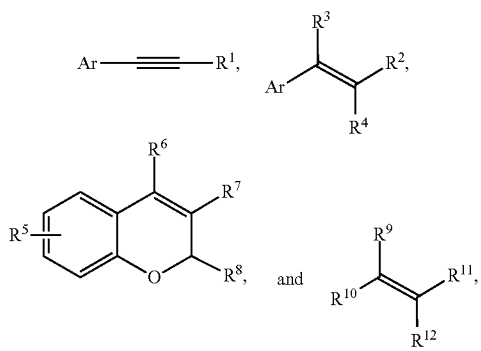

wherein Ar is aryl (e.g., an aromatic carbocycle and/or an aromatic heterocycle) optionally substituted at one or more positions with a substituent selected from alkyl, carbonyl, carboxy alkyl ester (i.e., —C(O)—O-alkyl), phenyl, phenyoxy, halogen, nitro, sulfonamide, pyridinyl, imidazolyl, morpholino, boronic acid, piperidinyl, pyrazolyl, piperazinyl, and tosyl; $R^1$, $R^2$, $R^3$, $R^4$, $R^5$, $R^6$, $R^7$, and $R^8$ are independently selected from hydrogen, deuterium, alkyl, and Ar optionally substituted with amino, nitro, hydroxyl, alkoxy, carboxyl, carboxy alkyl ester (i.e., —C(O)—O—$R^{13}$ where $R^{13}$ is alkyl), —C(O)—$R^{14}$ wherein $R^{14}$ is alkyl, $C(R^{15})(R^{16})$—$R^{17}$ wherein $R^{15}$ and $R^{16}$ are alkoxy, alkylthiol, sulfonamide, or Ar and $R^{17}$ is alkyl, or —$CH_2C(OR^{18})$—$R^{19}$ wherein $R^{18}$ and $R^{19}$ are hydrogen or alkyl; and $R^9$, $R^{10}$, $R^{11}$, and $R^{12}$ are independently selected from hydrogen, deuterium, alkyl.

Embodiment 9. The method of embodiment 2, wherein Ar is selected from optionally substituted phenyl, pyridine, quinoline, isoquinoline, naphthalene, biphenyl, indole, furan, benzofuran, imidazole, benzimidazole, pyrimidine, carbozole, dibenzofuran, indoline, azaindole, and benzothiophene.

Embodiment 10. The method of any of the foregoing embodiments, wherein the phosphine ligand is a bidentate phosphine ligand.

Embodiment 11. The method of any of the foregoing embodiments, wherein the phosphine ligand is chiral.

Embodiment 12. The method of any of the foregoing embodiments, wherein the phosphine ligand is achiral.

Embodiment 13. The method of any of the foregoing embodiments, wherein the phosphine ligand has a formula selected from:

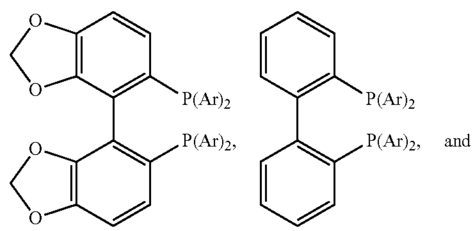

-continued

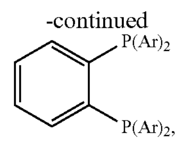

wherein Ar is phenyl optionally substituted at one or more position with alkyl or alkoxy, and optionally wherein Ar is 3,5-di-tert-butylphenyl.

Embodiment 14. The method of any of the foregoing embodiments, wherein the phosphine ligand has a formula selected from:

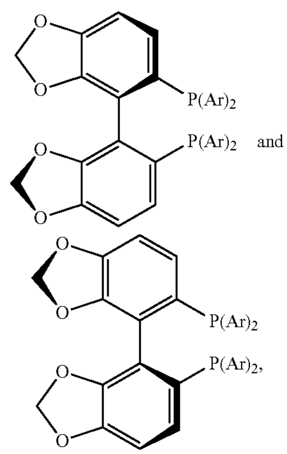

wherein Ar is phenyl optionally substituted at one or more position with alkyl or alkoxy, and optionally wherein Ar is 3,5-di-tert-butylphenyl enyl.

Embodiment 15. The method of any of the foregoing claims, wherein the substituted silane has a formula:

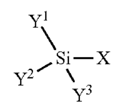

wherein $Y^1$, $Y^2$, and $Y^3$ are the same or different and are selected from alkyl and alkoxy, and X is the donor hydrogen atom or the donor deuterium atom.

Embodiment 16. The method of any of the foregoing claims, wherein the substituted silane has a formula selected from:

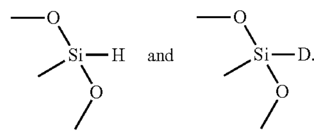

Embodiment 17. The method of any of the foregoing claims, wherein the alcohol has a formula selected from $C_2H_5O(H/D)$, $(CH_3)_2CHO(H/D)$, and $(CD_3)_2COD$.

Embodiment 18. The method of any of the foregoing claims, wherein the transition metal catalyst is selected from scandium (Sc), titanium (Ti), vanadium (V), chromium (Cr), manganese (Mn), iron (Fe), cobalt (Co), nickel (Ni), copper (Cu), zinc (Zn).

Embodiment 19. The method of any of the foregoing claims, wherein the transition metal catalyst is divalent copper Cu(II) or monovalent copper Cu(I).

Embodiment 20. The method of any of the foregoing claims, wherein the reaction mixture comprises a solubilized divalent copper salt or monovalent copper salt.

Embodiment 21. The method of any of the foregoing claims, wherein the reaction mixture comprises a solubilized organic divalent copper salt (e.g., $Cu(OAc)_2$ or CuOAc).

Embodiment 22. A compound prepared by the method of any of the foregoing embodiments.

Embodiment 23. A compound of any of the following formulas, which optionally is an isomerically pure compound or a mixture of isomeric compounds wherein the compound represents greater than about 80%, 85%, 90%, 95%, 96%, 97%, 98%, or 99% of the isomeric compounds in the mixture:

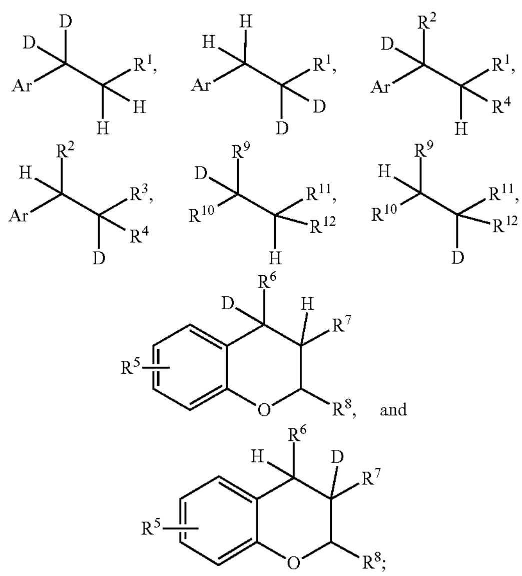

and wherein Ar is aryl (e.g., an aromatic carbocycle and/or an aromatic heterocycle) optionally substituted at one or more positions with a substituent selected from alkyl, carbonyl, carboxy alkyl ester (i.e., —C(O)—O-alkyl), phenyl, phenyoxy, halogen, nitro, sulfonamide, pyridinyl, imidazolyl, morpholino, boronic acid, piperidinyl, pyrazolyl, piperazinyl, and tosyl; $R^1$, $R^2$, $R^3$, $R^4$, $R^5$, $R^6$, $R^7$, and $R^8$ are independently selected from hydrogen, deuterium, alkyl, and Ar optionally substituted with amino, nitro, hydroxyl, alkoxy, carboxyl, carboxy alkyl ester (i.e., —C(O)—O—$R^{13}$ where $R^{13}$ is alkyl), —C(O)—$R^{14}$ wherein $R^{14}$ is alkyl, $C(R^{15})(R^{16})$—$R^{17}$ wherein $R^{15}$ and $R^{16}$ are alkoxy, alkylthiol, sulfonamide, or Ar and $R^{17}$ is alkyl, or —$CH_2C(OR^{18})$—$R^{19}$ wherein $R^{18}$ and $R^{19}$ are hydrogen or alkyl; and $R^9$, $R^{10}$, $R^{11}$, and $R^{12}$ are independently selected from hydrogen, deuterium, alkyl.

Embodiment 24. The compound of embodiment 23, wherein Ar is selected from optionally substituted phenyl, pyridine, quinoline, isoquinoline, naphthalene, biphenyl, indole, furan, benzofuran, imidazole, benzimidazole, pyrimidine, carbozole, dibenzofuran, indoline, azaindole, and benzothiophene Embodiment 25. The compound of embodiment 23 or 24, of a formula selected from:

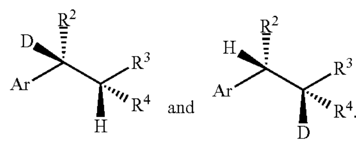

and

Embodiment 26. The compound of embodiment 23 or 24, of a formula selected from:

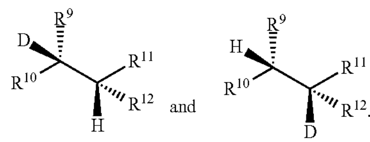

and

Embodiment 27. The compound of embodiment 23 or 24, of a formula selected from:

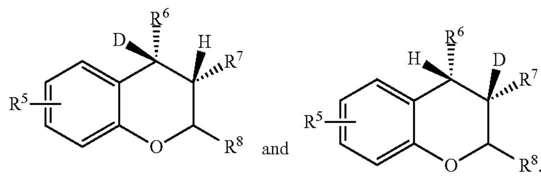

and

Embodiment 28. A method for preparing a fluorinated compound, the method comprising reacting a reaction mixture comprising: (i) a substrate compound comprising an alkyne functionality or an alkene functionality; (ii) a transition metal catalyst; (iii) a phosphine ligand for the transition metal catalyst; (iv) a substituted silane comprising a donor hydrogen atom; (v) a fluorine donor compound; and (vi) a solvent; wherein the reaction mixture is reacted under conditions such that the alkyne functionality or the alkene functionality of the substrate compound is reductively fluorinated to provide the fluorinated compound (e.g., to provide a fluorinated alkane functionality).

Embodiment 29. A compound prepared by the method of embodiment 28.

Embodiment 30. A compound of any of the following formulas, which optionally is an isomerically pure compound or a mixture of isomeric compounds wherein the compound represents greater than about 80%, 85%, 90%, 95%, 96%, 97%, 98%, or 99% of the isomeric compounds in the mixture:

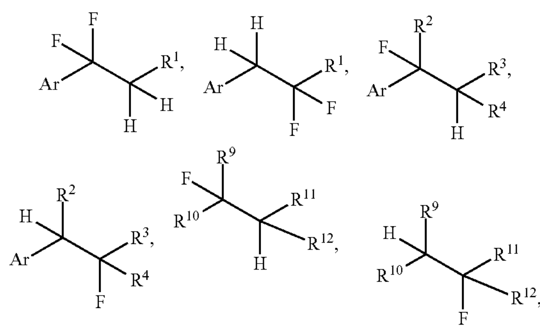

wherein Ar is aryl (e.g., an aromatic carbocycle and/or an aromatic heterocycle) optionally substituted at one or more positions with a substituent selected from alkyl, carbonyl, carboxy alkyl ester (i.e., —C(O)—O-alkyl), phenyl, phenyoxy, halogen, nitro, sulfonamide, pyridinyl, imidazolyl, morpholino, boronic acid, piperidinyl, pyrazolyl, piperazinyl, and tosyl; $R^1$, $R^2$, $R^3$, $R^4$, $R^5$, $R^6$, $R^7$, and $R^8$ are independently selected from hydrogen, deuterium, alkyl, and Ar optionally substituted with amino, nitro, hydroxyl, alkoxy, carboxyl, carboxy alkyl ester (i.e., —C(O)—O—$R^{13}$ where $R^{13}$ is alkyl), —C(O)—$R^{14}$ wherein $R^{14}$ is alkyl, $C(R^{15})(R^{16})$—$R^{17}$ wherein $R^{15}$ and $R^{16}$ are alkoxy, alkylthiol, sulfonamide, or Ar and $R^{17}$ is alkyl, or —$CH_2C(OR^{18})$—$R^{19}$ wherein $R^{18}$ and $R^{19}$ are hydrogen or alkyl; and $R^9$, $R^{10}$, $R^{11}$, and $R^{12}$ are independently selected from hydrogen, deuterium, alkyl.

Embodiment 31. The compound of embodiment 30, wherein Ar is selected from optionally substituted phenyl, pyridine, quinoline, isoquinoline, naphthalene, biphenyl, indole, furan, benzofuran, imidazole, benzimidazole, pyrimidine, carbozole, dibenzofuran, indoline, azaindole, and benzothiophene.

Embodiment 32. The compound of embodiment 30 or 31, of a formula selected from:

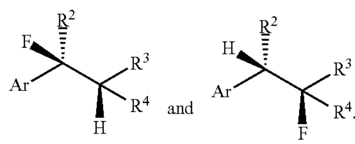

Embodiment 33. The compound of embodiment 30 or 31, orf a formula selected from:

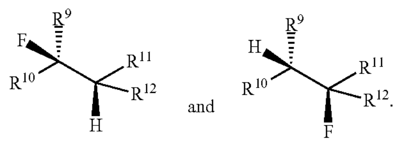

EXAMPLES

The following Examples are illustrative and should not be interpreted to limit the scope of the claimed subject matter.

Example 1—Copper-Catalyzed Transfer Hydrogenation/Deuteration of Aryl Alkanes Reference is made to the manuscript: Sloane et al., "Copper-Catalyzed Transfer Hydrogenation/Deuteration of Aryl Alkanes," Org. Lett. 2020, 22, 22, 9139-9144, published Nov. 10, 2020, the content of which is incorporated herein by reference in its entirety.

Abstract: A copper-catalyzed reduction of alkynes to alkanes and deuterated alkanes is described under transfer hydrogenation and transfer deuteration conditions. Commercially available alcohols and silanes are used interchangeably with their deuterated analogs as the hydrogen or deuterium sources. Transfer deuteration of terminal and internal aryl alkynes occurs with high levels of deuterium incorporation. Alkyne-containing complex natural product analogs undergo transfer hydrogenation and transfer deuteration selectively, in high yield. Mechanistic experiments support the reaction occurring through a cis-alkene intermediate.

The reduction of an alkyne to an alkane is a fundamental reaction in organic chemistry commonly accomplished using a heterogeneous catalyst and hydrogen gas.[1] Transfer hydrogenation represents an alternative approach to reduce an alkyne, obviating the use of flammable hydrogen gas.[2] This not only avoids potential hazards involved with handling $H_2$, but also offers the opportunity for improving reaction selectivity.[1b] Transition metal-catalyzed transfer hydrogenation has been extensively studied for the reduction of polarized π-functionality,[2-3] but remains less frequently explored for the reduction of alkynes to alkanes.[4] Furthermore, adaptation of transfer hydrogenation protocols to perform the selective installation of four deuterium atoms can pose significant challenges.

Recently, there has been a resurgence of interest in new method development focused on the installation of deuterium into small molecules.[5] Deuterated organic molecules are extensively used in chemical research. Small molecules with at least three or four deuterium atoms can serve as valuable standards for high-resolution mass-spectrometry in analytical and bioanalytical chemistry.[5a,6] From an organometallic and synthetic organic chemistry context, deuterium-labeled compounds are used to elucidate reaction mechanisms and perform kinetic isotope effect measurements.[7] In drug discovery, deuterium labeling of metabolically labile sites in drug molecules is performed to alter the drug's absorption, distribution, metabolism and excretion (ADME) properties.[8] The success of this approach came to fruition in 2017 when deutetrabenazine became the first FDA approved deuterated drug.[9]

We are particularly interested in developing new alkyne reduction methods that can be easily manipulated to catalyze the selective installation of at least four deuterium atoms into small molecules under relatively mild conditions. Strategies for the synthesis of highly deuterated small molecules are often limited by low reaction selectivity or lengthy synthetic sequences. Recently, two techniques have been developed to selectively reduce a 1,1-disubstituted aryl alkene functionality to a deuterated alkane, under transfer hydrodeuteration conditions.[10] Due to the relatively mild conditions a transfer hydrogenation approach offers in the reduction of π-bonds, we began to explore a catalytic transfer hydrogenation and transfer deuteration for the reduction and reductive deuteration of alkynes. It is well established that Cu—H is capable of reducing an alkyne to an alkene.[11] Lalic and coworkers elegantly demonstrated a cis-selective transformation that occurs in high yield (Scheme 1a).[11b] Importantly, most Cu—H catalysts are not sufficiently reactive to fully reduce an alkyne to an alkane. To the best of our knowledge, there are no copper-catalyzed transfer deuteration reactions for the reductive deuteration of an alkyne to a deuterated alkane. Recently, a precious metal catalyzed transfer deuteration was demonstrated for the reduction of an alkyne to an alkane.[4a] Although several transfer hydrogenation examples were reported, the Ir-catalyzed transfer deuteration scope was limited to only diphenylacetylene (Scheme 1b).

Scheme 1. Transfer Hydrogenation and Transfer Deuteration of Alkynes (a) Lalic, 2013: Cu-catalyzed transfer hydrogenation

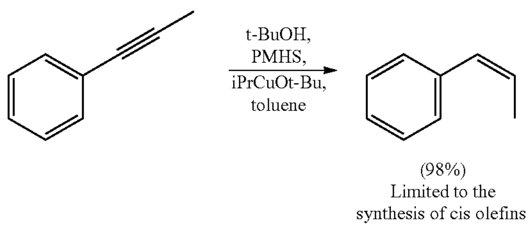

(b) Huang, 2018: Ir-catalyzed transfer deuteration

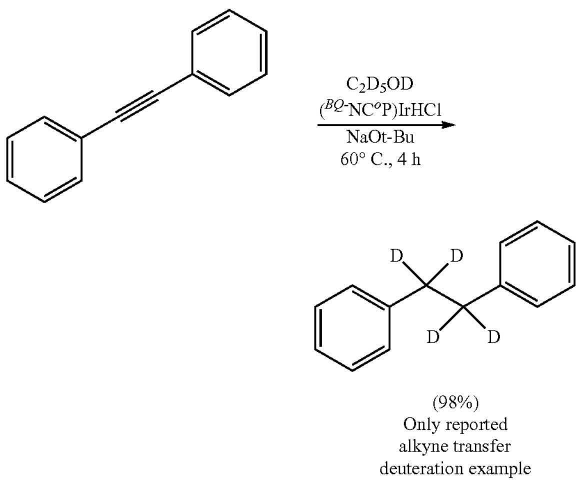

(c) this work

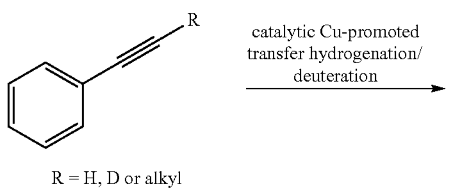

R = H, D or alkyl

-continued

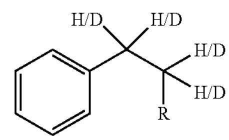

-Mild, chemoselective Cu-cat. reduction
-Products contain up to 5 deuterium atoms
-Deuterated alkanes are valuable standards for MS and ADME studies Based on previous alkene and alkyne hydroamination work, we hypothesized that a highly reactive Cu—H species would promote the reduction of an alkyne to an alkane (Scheme 1c).[12] We considered dimethoxy(methyl)silane (DMMS) and ethanol or isopropanol to be logical choices as hydrogen donors for the desired transfer hydrogenation reactions. We also hypothesized that these reagents could be readily manipulated for use in the corresponding transfer deuteration reaction. Reaction development commenced by screening commercial copper sources and commercial phosphine-based ligands known to promote Cu—H formation when combined in situ with Si—H.[11a]

Commercially available 2-ethynyl-6-methoxynaphthalene 1 was used as the aryl acetylene for reaction optimization. We found that triphenylphosphine and achiral bidentate phosphine ligands were ineffective to provide the desired transfer hydrogenation alkane product (Table 1, entries 1-5). We were hesitant to use chiral bidentate phosphine ligands to perform an achiral process, but given the precedent for these ligand types to support highly reactive Cu—H species, we opted to screen BINAP and SEGPHOS type ligands (entries 6-8). We found that commercially available (R)-DTBM-SEGPHOS was the most effective ligand for the Cu—H catalyzed reduction (entry 8). Reducing the catalyst loading to 1 mol % led to a slight reduction in yield (entry 9). Using 2 mol % catalyst was optimal, and led to a high product yield (91% isolated yield, entry 10). It is noteworthy that (R)-DTBM-SEGPHOS and (S)-DTBM-SEGPHOS can be used interchangeably in this reaction and no alkane product is formed in the absence of $Cu(OAc)_2$ or phosphine ligand (entries 11-12). Gratifyingly, other silane reagents such as poly(methylhydrosiloxane) (PMHS) and diethoxy(methyl)silane (DEMS) were successfully employed in the transfer hydrogenation reaction (entries 13-14). We chose to use DMMS because it is easily removed by evaporation from crude reaction mixtures and can be readily converted to the Si-D for transfer deuteration (vide infra).

TABLE 1

Reaction Optimization[a]

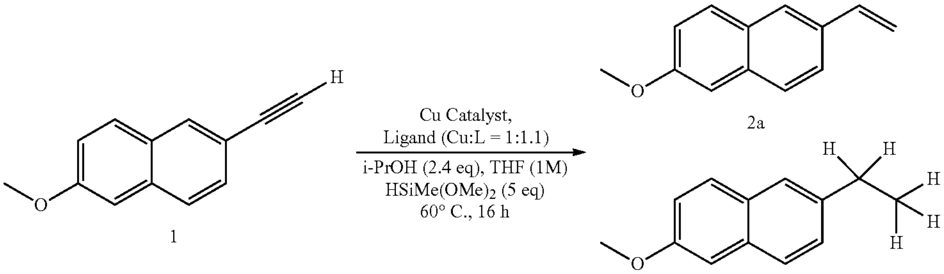

1

2a

2b

TABLE 1-continued
| Entry | Cu Catalyst (mol %)[b] | Ligand | Yield of 2a(%) | Yield of 2b (%) | RSM 1(%) |
|---|---|---|---|---|---|
| 1 | $Cu(OAc)_2$ (5) | L1 | 11 | trace[c] | 48 |
| 2 | Stryker's Reagent (5) | N/A | 53 | trace[c] | 6 |
| 3 | $Cu(OAc)_2$ (5) | L2 | 5 | trace[c] | 82 |
| 4 | $Cu(OAc)_2$ (5) | L3 | 8 | trace[c] | 75 |
| 5 | $Cu(OAc)_2$ (5) | L4 | 11 | trace[c] | 72 |
| 6 | $Cu(OAc)_2$ (5) | L5 | 12 | trace[c] | 49 |
| 7 | $Cu(OAc)_2$ (5) | L6 | 30 | 4[d] | 45 |
| 8 | $Cu(OAc)_2$ (5) | L7 | 0 | 98[d] | 0 |
| 9 | $Cu(OAc)_2$ (1) | L7 | 3.5 | 87[d] | 0 |
| 10 | $Cu(OAc)_2$ (2) | L7 | 0 | 91[d] | 0 |
| 11 | N/A | N/A | 4 | 0[c] | 86 |
| 12 | $Cu(OAc)_2$ (2) | N/A | 3 | 0[c] | 80 |
| 13[e] | $Cu(OAc)_2$ (2) | L7 | 0 | 95[d] | 0 |
| 14[f] | $Cu(OAc)_2$ (2) | L7 | 0 | 93[d] | 0 |
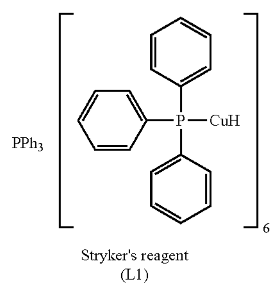
Stryker's reagent
(L1)
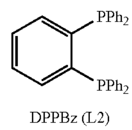
DPPBz (L2)
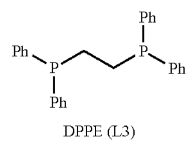
DPPE (L3)
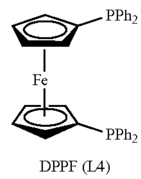
DPPF (L4)
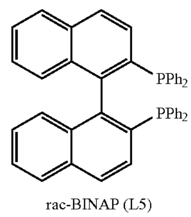
rac-BINAP (L5)
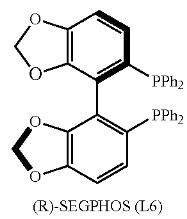
(R)-SEGPHOS (L6)

TABLE 1-continued

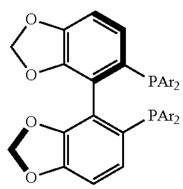

Ar = 3,5-($^t$Bu)$_2$-4-MeO—$C_6H_2$
(R)-DTBM-SEGPHOS (L7)

[a]Reactions were conducted using 0.2 mmol of substrate.
[b]$Cu(OAc)_2$ was used in the reactions as a 0.2M solution in THF.
[c]Yield was determined by $^{1}H$ NMR analysis of the crude reaction mixture, using 1,3,5-trimethylbenzene as an internal standard.
[d]Yield determined after purification by flash column chromatography.
[e]Poly(methylhydrosiloxane) (5 eq) was used instead of dimethoxy(methyl)silane.
[f]Diethoxy(methyl)silane (5 eq) was used instead of dimethoxy(methyl)silane.

We evaluated the substrate scope for this transformation using commercially available $Cu(OAc)_2$, DTBM-SEGPHOS, DMMS and ethanol or isopropanol (Scheme 2). Examples using ethanol for transfer hydrogenation are scarce and we were pleased that this inexpensive feedstock is a viable proton source.[4a,11k,13] During our evaluation of the reaction scope, we noticed that increasing the equivalents of alcohol (up to 5 equivalents) resulted in full conversion of less reactive substrates. Hydrocarbons such as ethyl benzene, 2-ethylnaphthlene, 2-ethyl-9H-fluorene and 4-ethyl-1,1'-biphenyl were prepared from the reduction of their respective alkynes in good yield (4a-4d, 66-79% yield). Substituting aryl acetylenes with electron-donating phenoxy and methoxy groups was beneficial for conversion and led to enhanced yields (4e-4f, 57-84% yield). We attempted a gram-scale reduction on the optimization substrate, 2-ethynyl-6-methoxynaphthalene, and isolated 2b in 95% yield. A chemoselective alkyne reduction occurred in the presence of a benzyl ether under the mild transfer hydrogenation conditions using ethanol instead of 2-propanol (4 g, 65% yield). Importantly, no benzyl deprotection product was observed as previously reported under heterogeneous metal-catalyzed hydrogenation with $H_2$.[14] We also found that a methyl ester para to the alkyne was beneficial for conversion to product (4h, 72% yield). No ester reduction product was seen in the crude $^{1}H$ NMR or after purification.

Scheme 2. Transfer Hydrogenation Substrate Scope

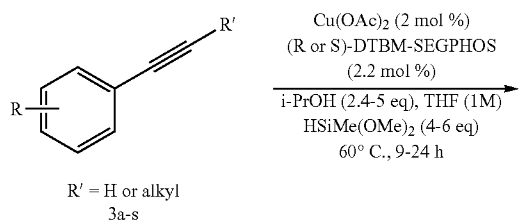

R' = H or alkyl
3a-s

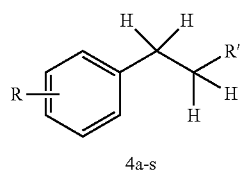

4a-s

-continued

4a

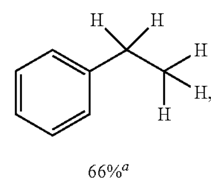

66%[a]

4b

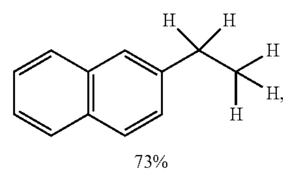

73%

4c

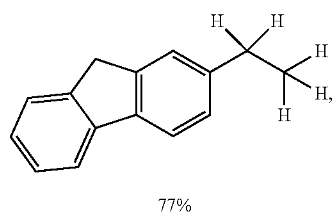

77%

4d

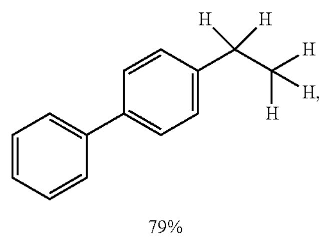

79%

4e

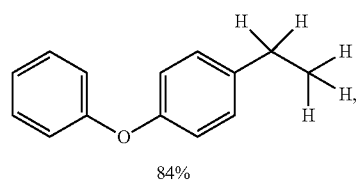

84%

-continued
4f
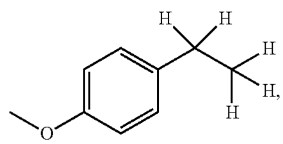
57%
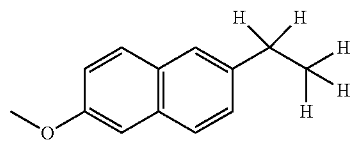
2b, 95% 5.5 mmol scale
4g
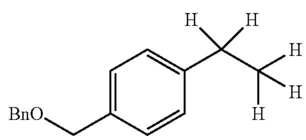
65%[b]
4h
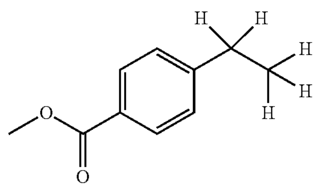
72%[c]
4i
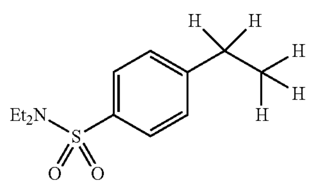
79%[b]
4j
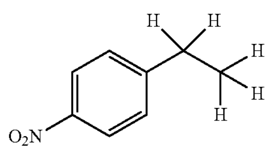
65%[d]
4k
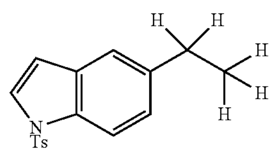
60%[e]
4l
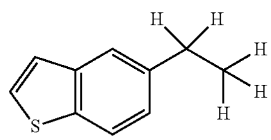
72%
-continued
4m
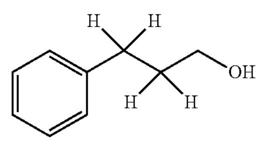
57%
4n
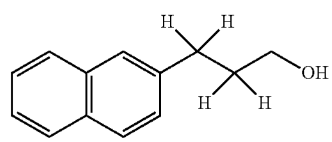
75%
4o
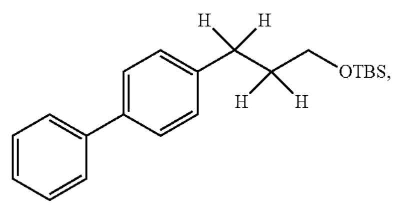
70%
4p
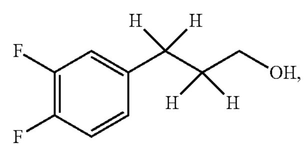
57%
4q
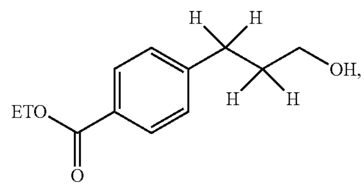
61%
4r
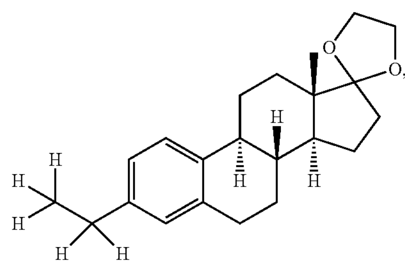
78%
4s
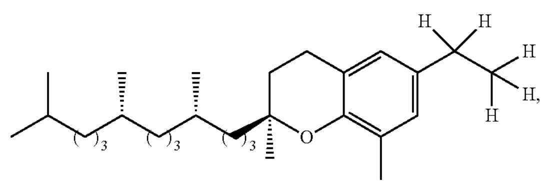
62%[e]

-continued

[a]Yield determined by $^1$H NMR analysis using 1,3,5-trimethylbenzene as an internal standard. [b]2.4-2.6 eq of EtOH used. [c]Reaction performed at 40°C. [d]Reaction performed at 23° C. [e]5 mol % $Cu(OAc)_2$ and 5.5 mol % DTBM-SEGPHOS used.

Due to their prevalence in bioactive molecules, nitrogen containing compounds and heterocycles were examined under the transfer hydrogenation protocol.[15] An electron withdrawing para-benzenesulfonamide was beneficial for reactivity (4i, 79%). Even nitro-groups, which are known to be reduced under heterogeneous reaction conditions, remained intact under the homogeneous transfer hydrogenation conditions (4j, 65% yield).[4c,16] Heterocycle-containing aryl acetylenes such as a tosyl-protected indole and a benzothiophene were efficiently reduced as well (4k-4l, 60-72% yield).

Internal alkynes proved to be more challenging substrates due to the increased steric bulk surrounding the alkyne. Nonetheless, we found that 3-phenyl-2-propyn-1-ol reduced to 3-phenyl-1-propanol in moderate yield (4m, 57% yield) along with naphthyl and biaryl alkynes (4n-4o, 70-75% yield). Further elucidation of the internal alkyne substrate scope revealed that alkynes substituted with electron deficient aryl rings could also be reduced in good yield (4p-4q, 57-61% yield).

We explored the capacity for the Cu—H catalyst to reduce alkyne containing complex natural product analogs to their corresponding alkanes. Estrone analog 4r was isolated in 78% yield after reacting the corresponding alkyne starting material under the standard transfer hydrogenation conditions. Importantly, the alkyne was completely reduced, resulting in full conversion to alkane. A similar result was obtained when δ-tocopherol analog 4s was isolated in 62% yield from the corresponding alkyne analog.

To achieve our goal of selectively installing four deuterium atoms across an alkyne, we hypothesized that using ethanol-OD or 2-propanol-OD and Si-D would permit deuterium installation in a mild manner. Inspired by previously reported work,[17] we were able to develop a scalable and reliable protocol to make the Si-D on a 94 mmol scale (eq 1 below).

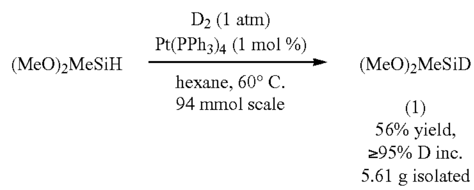

(1)
56% yield,
≥95% D inc.
5.61 g isolated

For deuterated small molecules to be used as internal standards for quantitative bioanalytical liquid chromatography/mass spectrometry assays, it is typical that at least three to four deuterium atoms are contained in the molecule to allow for sufficient separation of peaks in the mass spectrum.[6b,18] For terminal alkynes, we proceeded to exchange the acetylenic hydrogen atom for a deuterium atom prior to transfer deuteration.[19] This permitted the synthesis of substrates with 5 deuterium atoms.

Our investigation into the transfer deuteration of aryl alkynes began with a para-substituted aryl acetylene (6a, 73% yield) (Scheme 3). It is noteworthy that efficient transfer deuteration occurs with electron-withdrawing and electron-donating para-substitution. Polyaromatic compounds such as 2-ethynylnaphthalene and 2-ethynyl-6-methoxynaphthalene along with a biphenyl substituted alkyne were reductively deuterated in high yields (6b-6d, 69-81% yield). A benzyl group was found to be stable under the transfer deuteration conditions (6e, 76% yield) as no alcohol product was detected in the crude reaction mixture. Nitrogen containing substrates such as an aryl sulfonamide or indole substituted alkyne afforded the corresponding $d_5$-alkane in good yields (6f-6g, 78-88% yield). Internal aryl alkynes were also reductively deuterated in high yields, resulting in the synthesis of small molecules containing 4 deuterium atoms (6h-6j, 69-87% yield). Importantly, the copper-catalyzed transfer deuteration was effective for deuterating an alkyne containing natural product. Deuterated estrone analog 6k was isolated in 74% yield from the corresponding alkyne starting material. This represents a mild procedure to make a highly deuterated natural product that is suitable as an analytical standard for mass spectrometry.

Scheme 3. Transfer Deuteration Substrate Scope

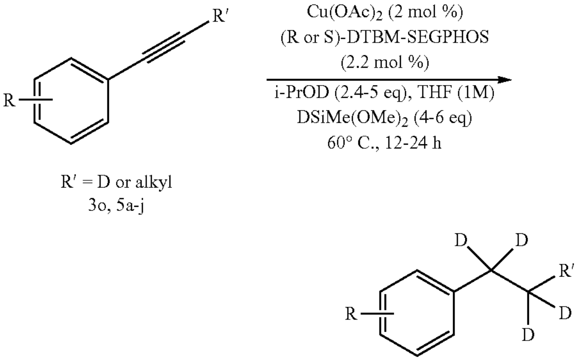

R' = D or alkyl
3o, 5a-j 6a-k[a]

6a

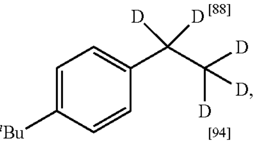

73%[b]

6b

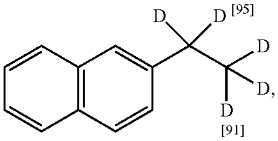

71%

6c

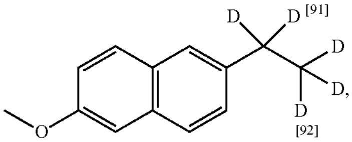

81%[b]

-continued

6d

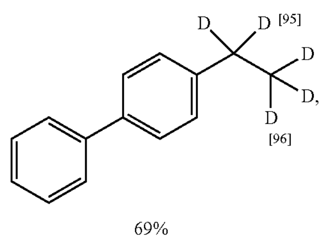

69%

6e

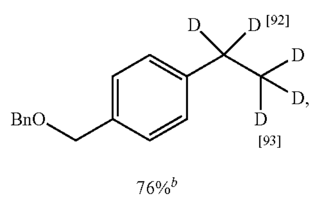

76%[b]

6f

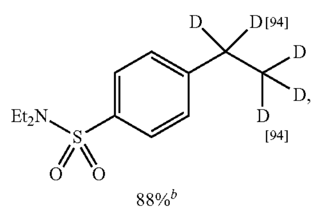

88%[b]

6g

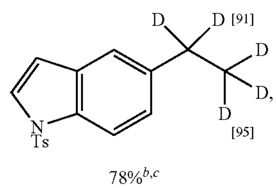

78%[b,c]

6h

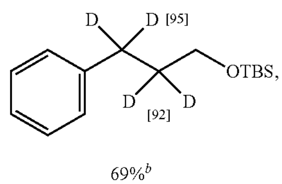

69%[b]

-continued

6i

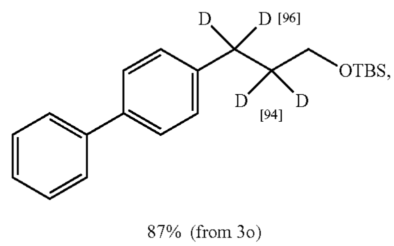

87% (from 3o)

6j

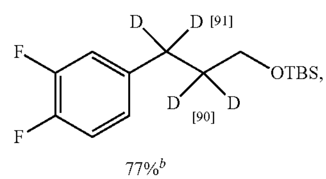

77%[b]

6k

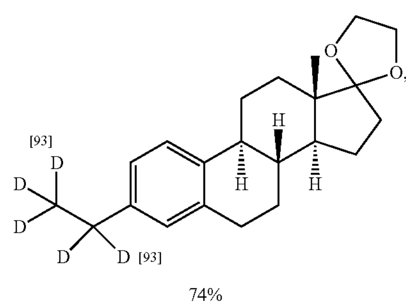

74%

[a]Deuterium incorpration measured by $^{1}H$ NMR and/or $^{2}H$ NMR. [b]i-$PrOD_8$ used and found to be equally effective as i-PrOD. [c]5 mol % $Cu(OAc)_2$ and 5.5 mol % DTBM SEGPHOS used.

Mechanistically, under transfer hydrogenation conditions, we hypothesized that formation of a Cu—H in the presence of dimethoxy(methyl)silane, followed by insertion of Cu—H across an alkyne, would lead to alkenyl Cu species i (Scheme 4). Protodecupration of i with isopropanol would extrude alkene ii. Regeneration of the Cu—H and addition across alkene ii to form alkyl Cu iii, followed by protodecupration of iii, would provide the desired alkane. Simply replacing the Si—H with Si-D and the alcohol with alcohol-OD permits the reaction to operate under transfer deuteration conditions.

Scheme 4. Postulated Reaction Mechanism

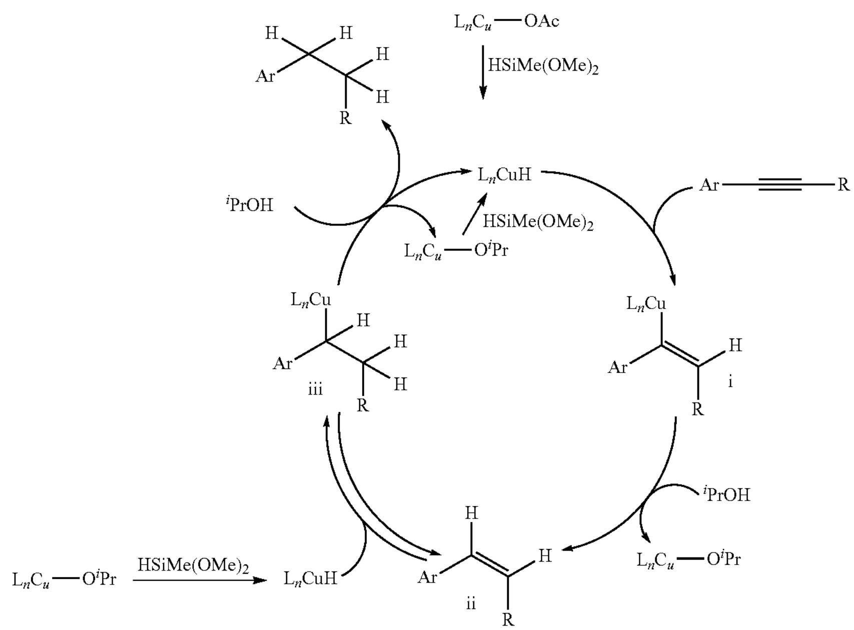

To test our hypothesis of the intermediacy of cis-alkene ii (Scheme 4), we evaluated the reduction of 5h over several time-periods. Consistent with the postulated mechanism, alkene Z-7 appeared in the reaction mixture after 15 minutes (Table 2, entry 1). The appearance of E-7 after 30 minutes (entry 2) suggested that Cu—H insertion into alkene ii to form alkyl copper intermediate iii is reversible. After 180 minutes the reaction was nearly finished (entry 5), and it reached completion after 9 hours (8, 79% yield, entry 6). We also subjected E-7 to the standard transfer hydrogenation conditions and isolated alkane 8 in 83% yield after 23 h.[20] Importantly, trace Z-7 was observed in the crude $^1$H NMR after 1 h. This data further supports that E-7 is a viable and reactive alkene for the second transfer hydrogenation step in the proposed mechanism and Cu—H insertion into alkene ii to form alkyl copper intermediate iii is reversible (Scheme 4).

TABLE 2

Reaction Analysis

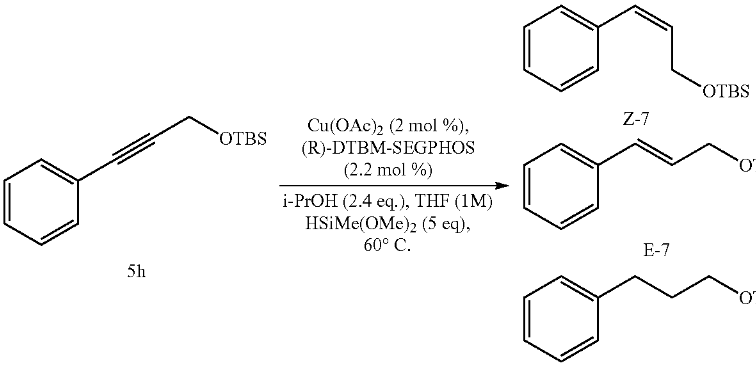

5h

Z-7

E-7

8

| Entry | Reaction Time (min) | Z-7$^a$(%) | E-7$^a$(%) | 8$^a$(%) |
|---|---|---|---|---|
| 1 | 15 | 74 | 0 | 6 |
| 2 | 30 | 48 | 2 | 25 |
| 3 | 45 | 40 | 5 | 36 |
| 4 | 90 | 17 | 7 | 54 |
| 5 | 180 | 7 | 5 | 61 |
| 6 | 9 h | 0 | 0 | 79 |

$^a$Yields of each product were determined by $^1$H NMR of the combined products after purification.

To further probe the mechanism of the transfer hydrogenation, we performed the reaction under transfer hydrodeuteration conditions. We exchanged the alcohol reagent for ethanol-OD and made no changes to the silane. Upon isolating the isotopically labeled alkane 9, we concluded the reaction is mildly regioselective (eq. 2). This supports a mildly regioselective Cu—H addition across the alkyne and/or alkene. Ongoing investigations in our laboratory are focused on enhancing the regioselectivity of this transfer hydrodeuteration reaction.

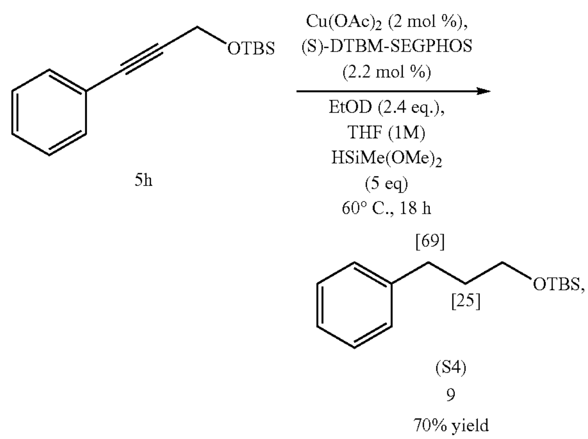

*Percentage deuterium incorperation at each carbon indicated in red brackets

In summary, we have developed a Cu—H catalyzed transfer hydrogenation and transfer deuteration to reduce aryl alkynes to their corresponding alkanes and deuterated alkanes. The relatively mild transfer hydrogenation/deuteration permits the selective reduction of aryl alkynes that contain functionality commonly reduced under heterogeneous metal-catalyzed reductions. The reaction is scalable and due to the modularity of the reaction, a transfer deuteration is possible by simply changing the Si—H and alcohol to Si-D and alcohol-OD. This permitted facile access to aryl alkanes containing up to 5 deuterium atoms. The copper-catalyzed transfer hydrogenation and transfer deuteration protocols were successfully applied to aryl alkyne containing complex natural product analogs. As a result, we anticipate this method could be useful to synthesize highly deuterated analogs of drug molecules for ADME studies.

REFERENCES (1) (a) Munslow, I. J. Alkyne Reductions. In *Modern Reduction Methods*; Andersson, P. G., Munslow, I. J., Eds.; WILEY-VCH Verlag GmbH & Co. KGaA: Weinheim, 2008; 363-385. (b) Johnstone, R. A. W.; Wilby. A. H. Heterogeneous Catalytic Transfer Hydrogenation and Its Relation to Other Methods for Reduction of Organic Compounds. *Chem. Rev.* 1985, 85, 129-170. (c) Larock, R. C.; Zhang, X. Reduction. In *Comprehensive Organic Transformations: A Guide to Functional Group Preparations*, Third Edition; Larock, R. C., Eds; John Wiley & Sons, Inc.: New York, 2018; 1-189.

(2) Wang, D.; Astruc, D. The Golden Age of Transfer Hydrogenation. *Chem. Rev.* 2015, 115, 6621-6686.

(3) (a) Deutsch, C.; Lipshutz, B. H., Krause, N. Small but Effective: Copper Hydride Catalyzed Synthesis of α-Hydroxyallenes. *Angew. Chem. Int. Ed.* 2007, 46, 1650-1653. (b) Kato, T.; Matsuoka, S.; Suzuki, M. Transfer Hydrogenation Promoted by N-Heterocyclic Carbene and Water. *Chem. Commun.* 2015, 51, 13906-13909. (c) Lipshutz, B. H.; Servesko, J. M. CuH-Catalyzed Asymmetric Conjugate Reductions of Acyclic Enones. *Angew. Chem. Int. Ed.* 2003, 42, 4789-4792.

(4) (a) Wang, Y.; Huang, Z.; Leng, X.; Zhu, H.; Liu, G.; Huang, Z. Transfer Hydrogenation of Alkenes Using Ethanol Catalyzed by a NCP Pincer Iridium Complex: Scope and Mechanism. *J. Am. Chem. Soc.* 2018, 140, 4417-4429. (b) Espinal-Viguri, M.; Neale, S. E.; Coles, N. T.; Macgregor, S. A.; Webster, R. L. Room Temperature Iron-Catalyzed Transfer Hydrogenation and Regioselective Deuteration of Carbon-Carbon Double Bonds. *J. Am. Chem. Soc.* 2019, 141, 572-582. (c) Cummings, S. P.; Le, T.; Fernandez, G. E.; Quiambao, L. G.; Stokes, B. J. Tetrahydroxydiboron-Mediated Palladium-Catalyzed Transfer Hydrogenation and Deuteration of Alkenes and Alkynes Using Water as the Stoichiometric H or D Atom Donor. *J Am. Chem. Soc.* 2016, 138, 6107-6110. (d) Shen, R.; Chen, T.; Zhao, Y.; Qiu, R.; Zhou, Y.; Yin, S.; Wang, X.; Goto, M.; Han, L. Facile Regio- and Stereoselective Hydrometalation of Alkynes with a Combination of Carboxylic Acids and Group 10 Transition Metal Complexes: Selective Hydrogenation of Alkynes with Formic Acid. *J. Am. Chem. Soc.* 2011, 133, 17037-17044.

(5) (a) Atzrodt, J.; Derdau, V.; Fey, T.; Zimmermann, J. The Renaissance of H/D Exchange. *Angew. Chem. Int. Ed.* 2007, 46, 7744-7765. (b) Atzrodt, J.; Derdau, V.; Kerr, W. J.; Reid, M. C—H Functionalisation for Hydrogen Isotope Exchange. *Angew. Chem. Int. Ed* 2018, 57, 3022-3047.

(6) (a) Qin, M.; Qiao, H.; Yuan, Y.; Shao, Q. A Quantitative LC-MS/MS Method for Simultaneous Determination of Deuvortioxetine, Vortioxetine and their Carboxylic Acid Metabolite in Rat Plasma, and its Application to a Toxicokinetic Study. *Anal. Methods* 2018, 10, 1023-1031. (b) Atzrodt, J.; Derdau, V. Pd- and Pt-catalyzed H/D Exchange Methods and their Application for Internal MS Standard Preparation From a Sanofi-Aventis Perspective. *J. Labelled Compd. Radiopharm.* 2010, 53, 674-685. (c) Iglesias, J.; Sleno, L.; Volmer, D. A Isotopic Labeling of Metabolites in Drug Discovery Applications *Curr. Drug Metab.* 2012, 13, 1213-1225

(7) (a) Gómez-Gallego, M.; Sierra, M. A. Kinetic Isotope Effects in the Study of Organometallic Reaction Mechanisms. *Chem. Rev.* 2011, 111, 48574963. (b) Meek, S. J.; Pitman, C. L.; Miller, A. J. M. Deducing Reaction Mechanism: A Guide for Students, Researchers, and Instructors. *J. Chem. Educ.* 2016, 93, 275-286. (c) Simmons, E. M.; Hartwig. J. F. On the Interpretation of Deuterium Kinetic Isotope Effects in C—H Bond Functionalization by Transition-Metal Complexes. *Angew. Chem. Int. Ed.* 2012, 51, 3066-3072.

(8) (a) Gant, T. G. Using Deuterium in Drug Discovery: Leaving the Label in the Drug. *J. Med. Chem.* 2014, 57, 3595-3611. (b) Pirali, T.; Serafini, M.; Cargnin, S.; Genazzani, A. A. Applications of Deuterium in Medicinal Chemistry. *J. Med. Chem.* 2019, 62, 5276-5297. (c) Elmore, C. S.; Bragg, R. A. Isotope Chemistry; a Useful Tool in the Drug Discovery Arsenal. *Bioorg. Med. Chem. Lett.* 2015, 25, 167-171. (d) Atzrodt. J.; Derdau, V.; Kerr, W. J.; Reid, M. Deuterium- and Tritium-Labelled Compounds: Applications in the Life Sciences. *Angew. Chem. Int. Ed* 2018, 57, 1758-1784.

(9) Schmidt, C. First Deuterated Drug Approved. *Nat. Biotechnol.* 2017, 35, 493-494.

(10) (a) Li. L.; Hilt, G. Regiodivergent DH or HD Addition to Alkenes: Deuterohydrogenation versus Hydrodeuterogenation. *Org. Lett.* 2020, 22, 1628-1632. (b) Walker, J. C. L.; Oestriech, M. Regioselective Transfer Hydrodeuteration of Alkenes with a Hydrogen Deuteride Surrogate using $B(C_6F_5)_3$ Catalysis. *Org. Lett.* 2018, 20, 6411-6414.

(11) (a) Jordan. A. J.; Lalic, G.; Sadighi, J. P. Coinage Metal Hydrides: Synthesis, Characterization, and Reactivity. *Chem. Rev.* 2016, 116, 8318. (b) Whittaker, A. M.; Lalic, G. Monophasic Catalytic System for the Selective Semireduction of Alkynes. *Org. Lett.* 2013, 15, 1112-1115. (c) Ryu, I.; Kusumoto, N.; Ogawa, A.; Kambe, N.; Sonoda, N. Copper(II)-Mediated Stereoselective Reduction of Acetylenic Sulfones by Hydrosilanes. *Organometallics* 1989, 8, 2279-2281. (d) Ito, H.; Yamanaka, H.; Ishizuka, T.; Tateiwa, J.; Hosomi, A. New Reactivity of a Reducing Reagent Generated from a Copper(I) Salt and a Hydrosilane: Selective Reduction of Ketones and Olefins Conjugated with an Aromatic Group. *Synlett* 2000, 4, 479482. (e) Daeuble, J. F.; McGettigan, C.; Stryker. J. M. Selective Reduction of Alkynes to Cis-Alkenes by Hydrometallation Using $[(Ph_3P)CuH]_6$. *Tetrahedron Lett.* 1990, 31, 2397-2400. (f) Wang, G.; Bin, H.; Sun, M.; Chen, S.; Liu, J.; Zhong, C. Copper-catalyzed Z-selective Semihydrogenation of Alkynes with Hydrosilane: a Convenient Approach to Cis-Alkenes. *Tetrahedron* 2014, 70, 2175-2179. (g) Mankad, N. P.; Laitar, D. S.; Sadighi, J. P. Synthesis, Structure, and Alkyne Reactivity of a Dimeric (Carbene)copper(I) Hydride. *Organometallics* 2004, 23, 3369-3371. (h) Cao, H.; Chen, T.; Zhou. Y.; Han, D.; Yin, S.; Han. L. Copper-Catalyzed Selective Semihydrogenation of Terminal Alkynes with Hypophosphorous *Acid. Adv. Synth. Catal.* 2014, 356, 765-769. (i) Yoshida. T.; Negishi, E. A Novel Copper-Containing Hydride Species and its Application to the Reduction of Organic Substrates. *J. Chem. Soc., Chem. Commun.,* 1974, 762-763. (j) Crandall, J. K.; Collonges, F. Cis Reduction of Acetylenes by Organocopper Reagents. *J. Org. Chem.* 1976, 41, 4089-4092. (k) Bao, H.; Zhou, B.; Jin, H.; Liu, Y. Diboron-Assisted Copper-Catalyzed Z-Selective Semihydrogenation of Alkynes Using Ethanol as a Hydrogen Donor. *J. Org. Chem.* 2019, 84, 3579-3589. (l) Semba, K.; Fujihara. T.; Xu, T.; Terao, J.; Tsuji. Y. Copper-Catalyzed Highly Selective Semihydrogenation of Non-Polar Carbon-Carbon Multiple Bonds using a Silane and an Alcohol. *Adv. Synth. Catal.* 2012, 354, 1542-1550.

(12) Shi, S.; Buchwald, S. L. Copper-catalyzed Selective Hydroamination Reactions of Alkynes. *Nat. Chem.* 2015, 7, 38-44.

(13) (a) Weingart, P.; Thiel. W. R. Applying Le Chatelier's Principle for a Highly Efficient Catalytic Transfer Hydrogenation with Ethanol as the Hydrogen Source. *Chem Cat Chem* 2018, 10, 4858-4862. (b) Wang, C.; Gong, S.; Liang, Z.; Sun, Y.; Cheng, R.; Yang, B.; Liu, Y.; Yang, J.; Sun, F. Ligand-Promoted Iridium-Catalyzed Transfer Hydrogenation of Terminal Alkynes with Ethanol and Its Application. *ACS Omega* 2019, 4, 16045-16051. (c) Reddy, A. S.; Swamy, K. C. K. Ethanol as a Hydrogenating Agent: Palladium-Catalyzed Stereoselective Hydrogenation of Ynamides to Give Enanides. *Angew. Chem. Int. Ed.* 2017, 56, 6984-6988.

(14) (a) Oba, M. A Convenient Method for Palladium-catalyzed Reductive Deuteration of Organic Substrates using Deuterated Hypophosphite in D2O. *J. Labelled Compd. Radiopharm.* 2015, 58, 215-219. (b) Felpin, F.; Fouquet, E. A Useful, Reliable and Safer Protocol for Hydrogenation and the Hydrogenolysis of O-Benzyl Groups: The In Situ Preparation of an Active $Pd^0/C$ Catalyst with Well-Defined Properties. *Chem. Eur. J.* 2010, 16, 12440-12445.

(15) (a) McGrath, N. A.; Brichacek, M.; Njardarson, J. T. A Graphical Journey of Innovative Organic Architectures That Have Improved Our Lives. *J. Chem. Educ.* 2010, 87, 1348-1349. (b) Vitaku, E.; Smith, D. T.; Njardarson, J. T. Analysis of the Structural Diversity, Substitution Patterns, and Frequency of Nitrogen Heterocycles among U.S. FDA Approved Pharmaceuticals. *J. Med. Chem.* 2014, 57, 10257-10274. (c) Taylor, R. D.; MacCoss, M.; Lawson, A. D. G. Rings in Drugs. *J. Med. Chem.* 2014, 57, 5845-5859.

(16) Sawama, Y.; Kawajiri, T.; Niikawa, M.; Goto, R.; Yabe, Y.; Takahashi, T.; Marumoto, T.; Itoh, M.; Kimura, Y.; Monguchi, Y.; Kondo, S.; Sajiki, H. Stainless-Steel Ball-Milling Method for Hydro-/Deutero-genation using $H_2O$/$D_2O$ as a Hydrogen/Deuterium Source. *Chem Sus Chem* 2015, 8, 3773-3776.

(17) Kratish, Y.; Bravo-Zhivotovskii, D.; Apeloig, Y. Convenient Synthesis of Deuterosilanes by Direct H/D Exchange Mediated by Easily Accessible Pt(0) Complexes. *ACS Omega* 2017, 2, 372-376.

(18) Stokvis, E.; Rosing, H.; Beijnen, J. H. Stable Isotopically Labeled Internal Standards in Quantitative Bioanalysis Using Liquid Chromatography/Mass Spectrometry: Necessity or not?*Rapid Commun. Mass Spectrom.* 2005, 19, 401-407.

(19) Bew, S. P.; Hiatt-Gipson, G. D.; Lovell, J. A.; Poullain, C. Mild Reaction Conditions for the Terminal Deuteration of Alkynes. *Org. Lett.* 2012, 14, 456-459.

(20) See the Supporting Information in Example 2 for details.

Example 2—Supplementary Information for Example 1, Copper-Catalyzed Transfer Hydrogenation/Deuteration of Aryl Alkanes

I. General Information

The following chemicals were purchased from commercial vendors and were used as received: $Cu(OAc)_2$ (99.999% from Alfa Aesar); (R)-(−)-4,4'-bis[di(3,5-di-tert-butyl-4-methoxyphenyl)phosphino]-3,3'-bi(1,2-methylenedioxybenzene) ((R)-DTBM-SEGPHOS) and (S)-(+)-4,4'-bis[di(3,5-di-tert-butyl-4-methoxyphenyl)phosphino]-3,3'-bi(1,2-methylenedioxybenzene) ((S)-DTBM-SEGPHOS) (TCI), dimethoxy(methyl)silane (TCI); 2-propanol-OD (Millipore Sigma); 2-propanol-$d_8$ (Acros Organic); ethanol (Oakwood Chemical); tert-butyldimethylsilyl chloride (TBSCl); $D_2O$ (Oakwood Chemical).

Anhydrous tetrahydrofuran (THF) was purified by an MBRAUN solvent purification system (MB-SPS). Prior to use, triethylamine ($Et_3N$) was distilled over $CaH_2$ and stored over 3 Å molecular sieves. Chloroform-d ($CDCl_3$) was stored over 3 Å molecular sieves. Thin-layer chromatography (TLC) was conducted with Silicycle silica gel 60 Å F254 pre-coated plates (0.25 mm) and visualized with UV. Iodine and $KMnO_4$ stains. Flash chromatography was performed using Silia Flash® P60, 40-60 mm (230-400 mesh), purchased from Silicycle. For reactions that required heating (optimization, transfer hydrogenation and deuteration reactions), a PolyBlock for 2-dram vials was used on top of a Heidolph heating/stir plate.

$^1H$ NMR spectra were recorded on a Varian 300 or 400 MHz spectrometer and are reported in ppm using solvent as an internal standard ($CDCl_3$ at 7.26 ppm). Data reported as:

s=singlet, d=doublet, t=triplet, q=quartet, p=pentet, sxt=sextet, hep=heptet, sep=septet, oct=octet, m=multiplet, br=broad; coupling constant(s) in Hz; integration. $^{13}$C NMR spectra were recorded on a Varian 76 MHz or 101 MHz spectrometer and are reported in ppm using solvent as an internal standard ($CDCl_3$ at 77.16 ppm). $^{19}$F NMR spectra were recorded on a Varian 376 MHz spectrometer. $^{2}$H NMR spectra were recorded on a Varian 61 MHz spectrometer. Labeled solvent impurities were calculated out when reporting isolated yields.

High-resolution mass spectra were obtained for all new compounds not previously reported using the resources of the Chemistry Instrument Center (CIC), University at Buffalo, SUNY, Buffalo, NY. Specifically, high resolution accurate mass analysis was conducted using the following instruments: 12T Bruker SolariXR 12 Hybrid FTMS, provided through funding from the National Institutes of Health, NIH S10 RR029517; a Thermo Q-Exactive Focus Orbitrap Liquid Chromatograph Tandem Mass Spectrometer and a Thermo Q-Exactive Orbitrap Gas Chromatograph Tandem Mass Spectrometer, provided through funding from the National Science Foundation, MRI-1919594.

II. Optimization Studies

General procedure A for optimization studies in Table S1. In a $N_2$ filled glovebox, ligand, Cu catalyst (Cu:L=1:1.1), and THF were added to an oven-dried 2-dram vial followed by dropwise addition of dimethoxy(methyl)silane (123 μL, 1 mmol, 5 eq.). A color change from green/blue to orange was observed while stirring for 15 minutes. In a separate oven-dried 1-dram vial was added 2-ethynyl-6-methoxynapthalene (36.4 mg, 0.2 mmol, 1 eq.), THF (0.1 mL), and 2-propanol (37 μL, 0.48 mmol, 2.4 eq.). The solution in the 1-dram vial was added dropwise over 20 seconds to the 2-dram vial. The total volume of THF was calculated based on having a final reaction concentration of 1M based on the alkyne substrate. The 2-dram vial was capped with a red pressure relief cap, taken out of the glovebox, and stirred for 16 h at 60° C. at which point the reaction was filtered through a 1" silica plug with 20 mL of $Et_2O$ or $CH_2Cl_2$ followed by an additional 80 mL of the appropriate solvent to elute the crude product into a 200 mL round bottom flask. The solvent was removed by rotary evaporation, and the product was analyzed by $^{1}$H NMR using 1,3,5-trimethylbenzene as an internal standard. Yields for all entries were obtained by isolating the product after flash column chromatography if greater than 5% NMR yield was observed for 2b in the crude $^{1}$H NMR.

TABLE S1

Reaction Optimization[a]

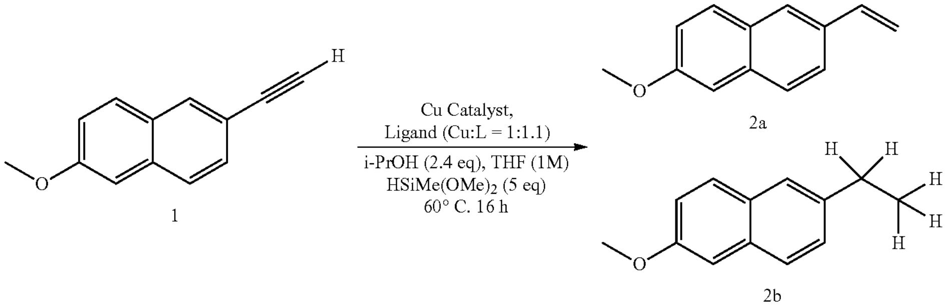

1

2a

2b

| Entry | Cu Catalyst (mol %)[b] | Ligand | Yield of 2a(%) | Yield of 2b (%) | RSM 1 (%) |
|---|---|---|---|---|---|
| 1 | $Cu(OAc)_2$ (5) | L1 | 11 | trace[c] | 48 |
| 2 | Stryker's Reagent (5) | N/A | 53 | trace[c] | 6 |
| 3 | $Cu(OAc)_2$ (5) | L2 | 5 | trace[c] | 62 |
| 4 | $Cu(OAc)_2$ (5) | L3 | 8 | trace[c] | 75 |
| 5 | $Cu(OAc)_2$ (5) | L4 | 11 | trace[c] | 72 |
| 6 | $Cu(OAc)_2$ (5) | L5 | 12 | trace[c] | 49 |
| 7 | $Cu(OAc)_2$ (5) | L6 | 30 | 4[d] | 45 |
| 8 | $Cu(OAc)_2$ (5) | L7 | 0 | 98[d] | 0 |
| 9 | $Cu(OAc)_2$ (1) | L7 | 3.5 | 87[d] | 0 |
| 10 | $Cu(OAc)_2$ (2) | L7 | 0 | 91[d] | 0 |
| 11 | N/A | N/A | 4 | 0[c] | 86 |
| 12 | $Cu(OAc)_2$ (2) | N/A | 3 | 0[c] | 80 |
| 13[e] | $Cu(OAc)_2$ (2) | L7 | 0 | 95[d] | 0 |
| 14[f] | $Cu(OAc)_2$ (2) | L7 | 0 | 93[d] | 0 |

TABLE S1-continued

PPh3

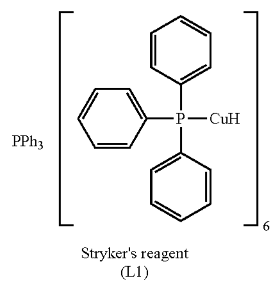

Stryker's reagent
(L1)

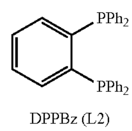

DPPBz (L2)

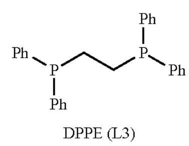 [SMILES: c1ccc(P(CCP(c2ccccc2)c2ccccc2)c2ccccc2)cc1]

DPPE (L3)

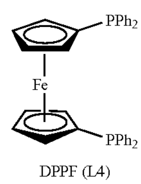

DPPF (L4)

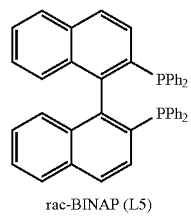

rac-BINAP (L5)

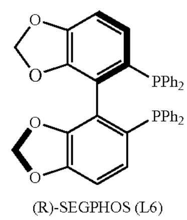

(R)-SEGPHOS (L6)

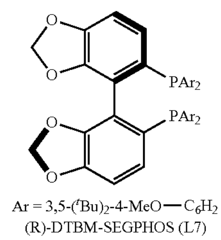

Ar = 3,5-($^t$Bu)$_2$-4-MeO—$C_6H_2$
(R)-DTBM-SEGPHOS (L7)

[a]Reactions were conducted using 0.2 mmol of substrate.

[b]$Cu(OAc)_2$ was used in the reactions as a 0.2M solution in THF.

[c]Yield was determined by $^1$H NMR analysis of the crude reaction mixture using 1,3,5-trimethylbenzene as an internal standard.

[d]Yield determined after purification by flash column chromatography.

[e]Poly(methylhydrosiloxane) (5 eq) was used instead of dimethoxy(methyl)silane.

[f]Diethoxy(methyl)silane (5 eq) was used instead of dimethoxy(methyl)silane

Entry 1. According to the general procedure A for optimization studies, a stirring solution of triphenylphosphine L1 (5.8 mg, 0.022 mmol, 0.11 eq.), $Cu(OAc)_2$ (50 μL of a 0.2 M solution in THF, 0.01 mmol, 0.05 eq.), and dimethoxy(methyl)silane (123 μL, 1.0 mmol, 5 eq.) in THF (0.05 mL) was prepared, and to this was added a solution of 2-ethynyl-6-methoxynaphthalene (36.4 mg, 0.2 mmol, 1 eq.) and 2-propanol (37 μL, 0.48 mmol, 2.4 eq.) in THF (0.1 mL) dropwise. The reaction stirred for 16 h at 60° C., after which it was filtered through a silica plug with $Et_2O$ (20 mL) and eluted with $Et_2O$ (80 mL). The solvent was removed by rotary evaporation, and the crude product was analyzed by $^1H$ NMR with 1,3,5-trimethylbenzene as an internal standard, (11% 2a, trace 2b, 48% RSM 1).

Entry 2. According to the general procedure A for optimization studies, a stirring solution of (triphenylphosphine)copper hydride hexamer (Stryker's Reagent) (3.3 mg, 0.0017 mmol, 0.00083 eq.), and dimethoxy(methyl)silane (123 μL, 1.0 mmol, 5 eq.) in THF (0.1 mL) was prepared, and to this was added a solution of 2-ethynyl-6-methoxynaphthalene (36.4 mg, 0.2 mmol, 1 eq.) and 2-propanol (37 μL, 0.48 mmol, 2.4 eq.) in THF (0.1 mL) dropwise. The reaction stirred for 16 h at 60° C., after which it was filtered through a silica plug with $Et_2O$ (20 mL) and eluted with $Et_2O$ (80 mL). The solvent was removed by rotary evaporation, and the crude product was analyzed by $^1H$ NMR with 1,3,5-trimethylbenzene as an internal standard (53% 2a, 2.5% 2b, 6% RSM 1).

Entry 3. According to the general procedure A for optimization studies, a stirring solution of 1,2-bis(diphenylphosphino)benzene L2 (4.9 mg, 0.011 mmol, 0.055 eq.). $Cu(OAc)_2$ (50 μL of a 0.2 M solution in THF, 0.01 mmol, 0.05 eq.), and dimethoxy(methyl)silane (123 μL, 1.0 mmol, 5 eq.) in THF (0.05 mL) was prepared, and to this was added a solution of 2-ethynyl-6-methoxynaphthalene (36.4 mg, 0.2 mmol, 1 eq.) and 2-propanol (37 μL, 0.48 mmol, 2.4 eq.) in THF (0.1 mL) dropwise. The reaction stirred for 16 h at 60° C., after which it was filtered through a silica plug with $Et_2O$ (20 mL) and eluted with $Et_2O$ (80 mL). The solvent was removed by rotary evaporation, and the crude product was analyzed by $^1H$ NMR with 1,3,5-trimethylbenzene as an internal standard (5% 2a, trace 2b, 82% RSM 1).

Entry 4. According to the general procedure A for optimization studies, a stirring solution of 1,2-bis(diphenylphosphino)ethane L3 (4.4 mg, 0.011 mmol, 0.055 eq.), $Cu(OAc)_2$ (50 μL of a 0.2 M solution in THF, 0.01 mmol, 0.05 eq.), and dimethoxy(methyl)silane (123 μL, 1.0 mmol, 5 eq.) in THF (0.05 mL) was prepared, and to this was added a solution of 2-ethynyl-6-methoxynaphthalene (36.4 mg, 0.2 mmol, 1 eq.) and 2-propanol (37 μL, 0.48 mmol, 2.4 eq.) in THF (0.1 mL) dropwise. The reaction stirred for 16 h at 60° C., after which it was filtered through a silica plug with $Et_2O$ (20 mL) and eluted with $Et_2O$ (80 mL). The solvent was removed by rotary evaporation, and the crude product was analyzed by $^1H$ NMR with 1,3,5-trimethylbenzene as an internal standard (8% 2a, trace 2b, 75% RSM 1).

Entry 5. According to the general procedure A for optimization studies, a stirring solution of 1,1'-bis(diphenylphosphino)-ferrocene L4 (6.1 mg, 0.011 mmol, 0.055 eq.), $Cu(OAc)_2$ (50 μL of a 0.2 M solution in THF, 0.01 mmol, 0.05 eq.), and dimethoxy(methyl)silane (123 μL, 1.0 mmol, 5 eq.) in THF (0.05 mL) was prepared, and to this was added a solution of 2-ethynyl-6-methoxynaphthalene (36.4 mg, 0.2 mmol, 1 eq.) and 2-propanol (37 μL, 0.48 mmol, 2.4 eq.) in THF (0.1 mL) dropwise. The reaction stirred for 16 h at 60° C., after which it was filtered through a silica plug with $Et_2O$ (20 mL) and eluted with $Et_2O$ (80 mL). The solvent was removed by rotary evaporation, and the crude product was analyzed by $^1H$ NMR with 1,3,5-trimethylbenzene as an internal standard (11% 2a, trace 2b, 72% RSM 1).

Entry 6. According to the general procedure A for optimization studies, a stirring solution of (±)-2,2'-bis(diphenylphosphino)-1,1'-binaphthalene L5 (6.8 mg, 0.011 mmol, 0.055 eq.), $Cu(OAc)_2$ (50 μL of a 0.2 M solution in THF, 0.01 mmol, 0.05 eq.), and dimethoxy(methyl)silane (123 μL, 1.0 mmol, 5 eq.) in THF (0.05 mL) was prepared, and to this was added a solution of 2-ethynyl-6-methoxynaphthalene (36.4 mg, 0.2 mmol, 1 eq.) and 2-propanol (37 μL, 0.48 mmol, 2.4 eq.) in THF (0.1 mL) dropwise. The reaction stirred for 16 h at 60° C., after which it was filtered through a silica plug with $Et_2O$ (20 mL) and eluted with $Et_2O$ (80 mL). The solvent was removed by rotary evaporation, and the crude product was analyzed by $^1H$ NMR with 1,3,5-trimethylbenzene as an internal standard (12% 2a, trace 2b, 49% RSM 1).

Entry 7. According to the general procedure A for optimization studies, a stirring solution of (R)-(+)-5,5'-bis(diphenylphosphino)-4,4'-bi-1,3-benzodioxole L6 (6.7 mg, 0.011 mmol, 0.055 eq.), $Cu(OAc)_2$ (50 μL of a 0.2 M solution in THF, 0.01 mmol, 0.05 eq.), and dimethoxy(methyl)silane (123 μL, 1.0 mmol, 5 eq.) in THF (0.05 mL) was prepared, and to this was added a solution of 2-ethynyl-6-methoxynaphthalene (36.4 mg, 0.2 mmol, 1 eq.) and 2-propanol (37 μL, 0.48 mmol, 2.4 eq.) in THF (0.1 mL) dropwise. The reaction stirred for 16 h at 60° C., after which it was filtered through a silica plug with $Et_2O$ (20 mL) and eluted with $Et_2O$ (80 mL). The solvent was removed by rotary evaporation, and the crude product was analyzed by $^1H$ NMR with 1,3,5-trimethylbenzene as an internal standard. The crude product was dry loaded onto silica gel, and was purified by flash column chromatography using gradient elution (50 mL of hexane, 100 mL of 2% ethyl acetate in hexane, and 50 mL of 5% ethyl acetate in hexane) to yield a white solid (28.8 mg, 30% 2a, 4% 2b, 45% RSM 1).

Entry 8. According to the general procedure A for optimization studies, a stirring solution of (R)-(−)-5,5'-bis[di(3,5-di-tert-butyl-4-methoxyphenyl)phosphino]-4,4'-bi-1,3-benzodioxole L7 (13.0 mg, 0.011 mmol, 0.055 eq.), $Cu(OAc)_2$ (50 μL of a 0.2 M solution in THF, 0.01 mmol, 0.05 eq.), and dimethoxy(methyl)silane (123 μL, 1.0 mmol, 5 eq.) in THF (0.05 mL) was prepared, and to this was added a solution of 2-ethynyl-6-methoxynaphthalene (36.4 mg, 0.2 mmol, 1 eq.) and 2-propanol (37 μL, 0.48 mmol, 2.4 eq.) in THF (0.1 mL) dropwise. The reaction stirred for 16 h at 60° C., after which it was filtered through a silica plug with $Et_2O$ (20 mL) and eluted with $Et_2O$ (80 mL). The solvent was removed by rotary evaporation, and the crude product was analyzed by $^1H$ NMR with 1,3,5-trimethylbenzene as an internal standard. The crude product was dry loaded onto silica gel, and was purified by column chromatography using gradient elution (50 mL of hexanes, 100 mL of 2% ethyl acetate in hexane, and 50 mL of 5% ethyl acetate in hexane) to yield a white solid (36.4 mg, 0.195 mmol, 98% yield).

Entry 9. According to the general procedure A for optimization studies, a stirring solution of (R)-(−)-5,5'-bis[di(3,5-di-tert-butyl-4-methoxyphenyl)phosphino]-4,4'-bi-1,3-benzodioxole L7 (2.6 mg, 0.0022 mmol, 0.011 eq.), $Cu(OAc)_2$ (10 μL of a 0.2 M solution in THF, 0.002 mmol, 0.01 eq.), and dimethoxy(methyl)silane (123 μL, 1.0 mmol, 5 eq.) in THF (0.09 mL) was prepared, and to this was added a solution of 2-ethynyl-6-methoxynaphthalene (36.4 mg, 0.2 mmol, 1 eq.) and 2-propanol (37 μL, 0.48 mmol, 2.4 eq.) in THF (0.1 mL) dropwise. The reaction stirred for 16 h at 60° C. after which it was filtered through a silica plug with $Et_2O$ (20 mL) and eluted with $Et_2O$ (80 mL). The solvent was removed by rotary evaporation, and the crude product was analyzed by $^1H$ NMR with 1,3,5-trimethylbenzene as an internal standard. The crude product was dry loaded onto silica gel, and was purified by column chromatography using gradient elution (50 mL of hexane, 100 mL of 2% ethyl acetate in hexane, and 50 mL of 5% ethyl acetate in hexane) to yield a white solid (33.8 mg, 3.5% 2a, 87% 2b).

Entry 10. According to the general procedure A for optimization studies, a stirring solution of (R)-(−)-5,5'-bis[di(3,5-di-tert-butyl-4-methoxyphenyl)phosphino]-4,4'-bi-1,3-benzodioxole L7 (5.2 mg, 0.0044 mmol, 0.022 eq.), $Cu(OAc)_2$ (20 μL of a 0.2 M solution in THF, 0.004 mmol, 0.02 eq.), and dimethoxy(methyl)silane (123 μL, 1.0 mmol, 5 eq.) in THF (0.08 mL) was prepared, and to this was added a solution of 2-ethynyl-6-methoxynaphthalene (36.4 mg, 0.2 mmol, 1 eq.) and 2-propanol (37 μL, 0.48 mmol, 2.4 eq.) in THF (0.1 mL) dropwise. The reaction stirred for 16 h at 60° C., after which it was filtered through a silica plug with $Et_2O$ (20 mL) and eluted with $Et_2O$ (80 mL). The solvent was removed by rotary evaporation, and the crude product was analyzed by $^1H$ NMR with 1,3,5-trimethylbenzene as an internal standard. The crude product was dry loaded onto silica gel, and was purified by column chromatography using gradient elution (50 mL of hexane, 100 mL of 2% ethyl acetate in hexane, and 50 mL of 5% ethyl acetate in hexane) to yield a white solid (33.8 mg, 0.182 mmol, 91% yield).

Entry 11. According to the general procedure A for optimization studies, a stirring solution of dimethoxy(methyl)silane (123 μL, 1.0 mmol, 5 eq.) in THF (0.1 mL) was prepared, and to this was added a solution of 2-ethynyl-6-methoxynaphthalene (36.4 mg, 0.2 mmol, 1 eq.) and 2-propanol (37 μL, 0.48 mmol, 2.4 eq.) in THF (0.1 mL) dropwise. The reaction stirred for 16 h at 60° C., after which it was filtered through a silica plug with $Et_2O$ (20 mL) and eluted with $Et_2O$ (80 mL). The solvent was removed by rotary evaporation, and the crude product was analyzed by $^1H$ NMR with 1,3,5-trimethylbenzene as an internal standard (4% 2a, 86% RSM 1).

Entry 12. According to the general procedure A for optimization studies, a stirring solution of ($Cu(OAc)_2$ (20 μL of a 0.2 M solution in THF, 0.004 mmol, 0.02 eq.) and dimethoxy(methyl)silane (123 μL, 1.0 mmol, 5 eq.) in THF (0.08 mL) was prepared, and to this was added a solution of 2-ethynyl-6-methoxynaphthalene (36.4 mg, 0.2 mmol, 1 eq.) and 2-propanol (37 μL, 0.48 mmol, 2.4 eq.) in THF (0.1 mL) dropwise. The reaction stirred for 16 h at 60° C., after which it was filtered through a silica plug with $Et_2O$ (20 mL) and eluted with $Et_2O$ (80 mL). The solvent was removed by rotary evaporation, and the crude product was analyzed by $^1H$ NMR with 1,3,5-trimethylbenzene as an internal standard (3% 2a, 80% RSM 1).

Entry 13. According to the general procedure A for optimization studies, a stirring solution of (S)-(−)-5,5'-bis[di(3,5-di-tert-butyl-4-methoxyphenyl)phosphino]-4,4'-bi-1,3-benzodioxole L7 (5.2 mg, 0.0044 mmol, 0.022 eq.), $Cu(OAc)_2$ (20 μL of a 0.2 M solution in THF, 0.004 mmol, 0.02 eq.), and poly(methylhydrosiloxane) (67 μL, 1.0 mmol, 5 eq.) in THF (0.08 mL) was prepared, and to this was added a solution of 2-ethynyl-6-methoxynaphthalene (36.4 mg, 0.2 mmol, 1 eq.) and 2-propanol (37 μL, 0.48 mmol, 2.4 eq.) in THF (0.1 mL) dropwise. The reaction stirred for 16 h at 60° C., after which it was filtered through a silica plug with $Et_2O$ (20 mL) and eluted with $Et_2O$ (80 mL). The solvent was removed by rotary evaporation, and the crude product was analyzed by $^1H$ NMR with 1,3,5-trimethylbenzene as an internal standard. The crude product was dry loaded onto silica gel, and was purified by column chromatography using gradient elution (50 mL of hexane, 100 mL of 2% ethyl acetate in hexane, and 50 mL of 5% ethyl acetate in hexane) to yield a white solid (35.4 mg, 0.19 mmol, 95% yield).

Entry 14. According to the general procedure A for optimization studies, a stirring solution of (S)-(−)-5,5'-bis[di(3,5-di-tert-butyl-4-methoxyphenyl)phosphino]-4,4'-bi-1,3-benzodioxole L7 (5.2 mg, 0.0044 mmol, 0.022 eq.), $Cu(OAc)_2$ (20 μL of a 0.2 M solution in THF, 0.004 mmol, 0.02 eq.), and diethoxy(methyl)silane (160 μL, 1.0 mmol, 5 eq.) in THF (0.08 mL) was prepared, and to this was added a solution of 2-ethynyl-6-methoxynaphthalene (36.4 mg, 0.2 mmol, 1 eq.) and 2-propanol (37 μL, 0.48 mmol, 2.4 eq.) in THF (0.1 mL) dropwise. The reaction stirred for 16 h at 60° C., after which it was filtered through a silica plug with $Et_2O$ (20 mL) and eluted with $Et_2O$ (80 mL). The solvent was removed by rotary evaporation, and the crude product was analyzed by $^1H$ NMR with 1,3,5-trimethylbenzene as an internal standard. The crude product was dry loaded onto silica gel, and was purified by column chromatography using gradient elution (50 mL of hexane, 100 mL of 2% ethyl acetate in hexane, and 50 mL of 5% ethyl acetate in hexane) to yield a white solid (34.7 mg, 0.186 mmol, 93% yield).

III. Transfer Hydrogenation Reaction Scope

General procedure for transfer hydrogenation (C). In a $N_2$ filled glovebox, (R or S)-DTBM-SEGPHOS (10.4 mg, 0.0088 mmol, 0.022 eq.), $Cu(OAc)_2$ (40 μL of a 0.2 M solution in THF, 0.008 mmol, 0.02 eq.), and THF (0.16 mL) were added to an oven-dried 2-dram vial followed by dropwise addition of dimethoxy(methyl)silane (247 μL, 2 mmol, 5 eq.). A color change from green/blue to orange was observed while stirring for 15 minutes. In a separate oven-dried 1-dram vial was added the alkyne substrate (0.4 mmol, 1 eq.), THF (0.2 mL), and either ethanol or 2-propanol (2.4-5 eq. based on substrate). The solution in the 1-dram vial was added dropwise over 20 seconds to the 2-dram vial. The total volume of THF was calculated based on having a final reaction concentration of 1M based on the alkyne substrate. The 2-dram vial was capped with a red pressure relief cap, taken out of the glovebox, and stirred for 9-24 h at the appropriate temperature at which point the reaction was filtered through a 1" silica plug with 20 mL of $Et_2O$ followed by 80 mL of $Et_2O$ to elute the remaining product into a 200 mL round bottom flask. After removing the $Et_2O$ by rotary evaporation, the crude product was isolated by flash column chromatography.

General purification for alcohol containing substrates after transfer hydrogenation reaction (D). The crude product was dissolved in THF (1.6 mL) and tetrabutylammonium fluoride (0.8 mL of 1.0 M in THF solution, 2 eq.) was added. The reaction was stirred at room temperature for 1-2 hours until complete by TLC analysis. Upon completion, reaction mixture was diluted with $Et_2O$ (10 mL) and quenched with saturated aqueous $NH_4Cl$ (5 mL). The aqueous layer was extracted with $Et_2O$ (3×10 mL) and the combined organic layers were washed with water (10 mL) and brine (10 mL), then dried over anhydrous $Na_2SO_4$. The mixture was filtered, and the solvent was removed by rotary evaporation. The crude product was purified by flash column chromatography to give the desired product.

Scheme S1. Transfer Hydrogenation Substrate Scope

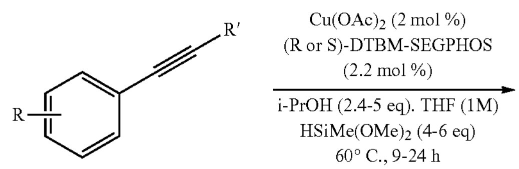

R′ = H or alkyl 3a-s

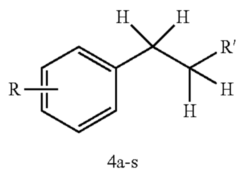

4a-s

4a

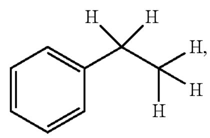

66%[a]

4b

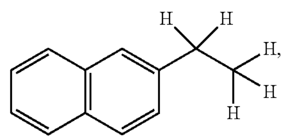

73%

4c

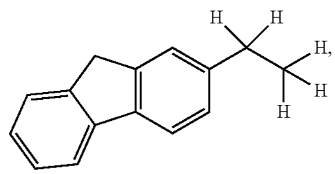

77%

-continued

4d

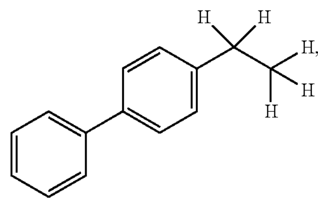

79%

4e

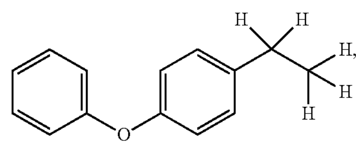

84%

4f

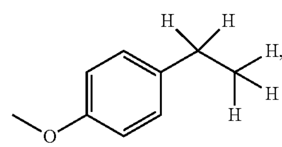

57%

2b

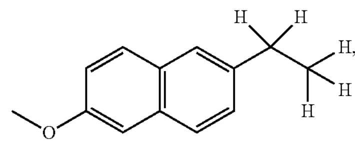

95% 5.5 mmol scale

4g

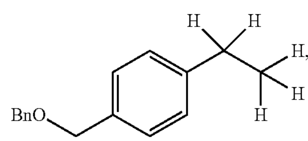

65%[b]

4h

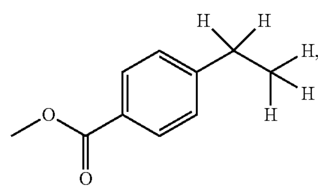

72%[c]

4i

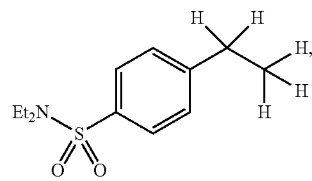

79%[b]

4j

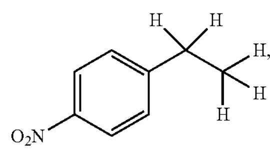

65%[d]

-continued

4k

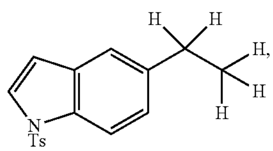

60%[e]

4l

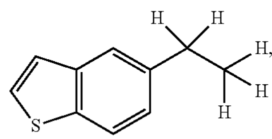

72%

4m

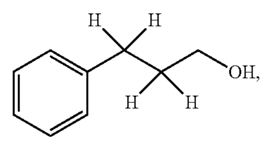

57%

4n

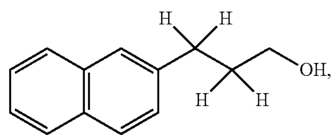

75%

4o

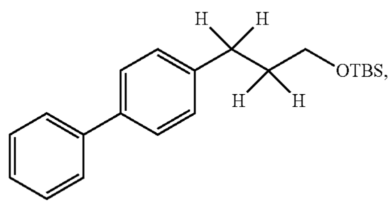

70%

4p

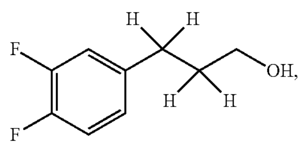

57%

4q

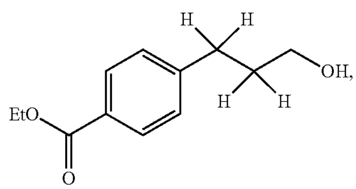

61%

-continued

4r

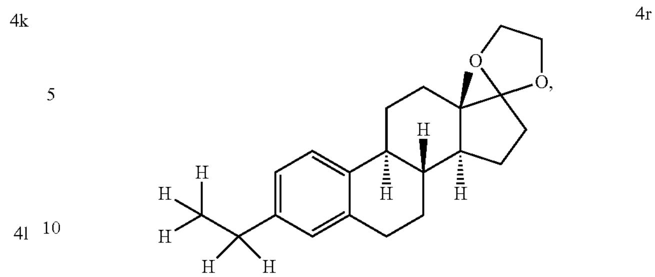

78%

4s

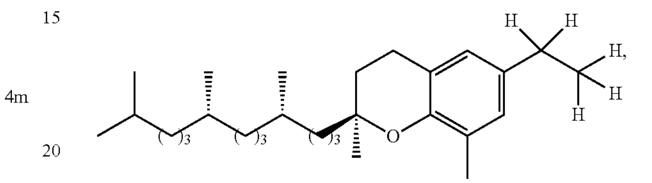

62%[e]

[a]Yield determined by $^1H$ NMR analysis using 1,3,5-trimethylbenzene as an internal standard. [b]2.4-2.6 eq of EtOH used. [c]Reaction performed at 40° C. [d]Reaction performed at 23° C. [e]5 mol % $Cu(OAc)_2$ and 5.5 mol % DTBM-SEGPHOS used.

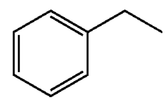

Ethyl Benzene [4a]. According to the general transfer hydrogenation procedure C, (S)-DTBM-SEGPHOS (10.4 mg, 0.0088 mmol, 0.022 eq.), $Cu(OAc)_2$ (40 μL of a 0.2 M solution in THF, 0.008 mmol, 0.02 eq.), THF (0.16 mL), then dimethoxy(methyl)silane (247 μL, 2 mmol, 5 eq.) were combined in a 2-dram vial followed by addition of a solution of ethynylbenzene (40.9 mg, 0.4 mmol, 1 eq.), THF (0.2 mL), and 2-propanol (74 μL, 0.96 mmol, 2.4 eq.). The 2-dram vial was capped with a red pressure relief cap, and the reaction stirred for 10 h at 60° C. After silica plug filtration using diethyl ether (100 mL) as the eluent, the solvent was concentrated, and 18.5 μL of 1,3,5-trimethylbenzene was used as an internal standard to determine the $^1H$ NMR crude yield (66% crude yield by $^1H$ NMR).

$^1H$ NMR: (400 MHz, $CDCl_3$) δ 7.29 (t, J=7.6 Hz, 2H), 7.25-7.16 (m, 3H), 2.66 (q, J=7.6 Hz, 2H), 1.27 (t, J=7.6 Hz, 3H).

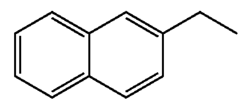

2-Ethylnaphthalene [4b]. According to the general transfer hydrogenation procedure C, (S)-DTBM-SEGPHOS (10.4 mg, 0.0088 mmol, 0.022 eq.), $Cu(OAc)_2$ (40 μL of a 0.2 M solution in THF, 0.008 mmol, 0.02 eq.), THF (0.16 mL), then dimethoxy(methyl)silane (247 μL, 2 mmol, 5 eq.) were combined in a 2-dram vial followed by addition of a solution of 2-ethynyl-napthalene (60.9 mg, 0.4 mmol, 1 eq.), THF (0.2 mL), and 2-propanol (74 μL, 0.96 mmol, 2.4 eq.). The 2-dram vial was capped with a red pressure relief cap, and the reaction stirred for 14 h at 60° C. After silica plug filtration using diethyl ether (100 mL) as the eluent, the solvent was concentrated, and the crude brown oil was dry loaded onto a silica gel column. Flash chromatography using 350 mL of hexanes as eluent gave the pure product as a clear, colorless oil (45.8 mg, 0.29 mmol, 73% yield).

$^1$H NMR: (400 MHz, $CDCl_3$) δ 7.86-7.76 (m, 3H), 7.65 (s, 1H), 7.51-7.39 (m, 2H), 7.38 (d, J=8.4 Hz, 1H), 2.84 (q, J=7.6 Hz, 2H), 1.36 (t, J=7.6 Hz, 3H). $^{13}$C NMR: (101 MHz, $CDCl_3$) δ 141.90, 133.85, 132.09, 127.94, 127.74, 127.56, 127.22, 125.96, 125.68, 125.14, 29.19, 15.66.

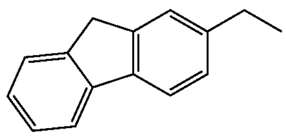

2-Ethyl-9H-fluorene [4c]. According to the general transfer hydrogenation procedure C, (S)-DTBM-SEGPHOS (10.4 mg, 0.0088 mmol, 0.022 eq.), $Cu(OAc)_2$ (40 μL of a 0.2 M solution in THF, 0.008 mmol, 0.02 eq.), THF (0.16 mL), then dimethoxy(methyl)silane (247 μL, 2 mmol, 5 eq.) were combined in a 2-dram vial followed by addition of a solution of 2-ethynyl-9H-Fluorene (76.1 mg, 0.4 mmol, 1 eq.), THF (0.2 mL), and 2-propanol (74 μL, 0.96 mmol, 2.4 eq.). The 2-dram vial was capped with a red pressure relief cap, and the reaction stirred for 9 h at 60° C. After silica plug filtration using diethyl ether (100 mL) as the eluent, the solvent was concentrated. The crude brown oil was dry loaded onto a silica gel column. Flash chromatography using 100 mL of hexanes as eluent gave the pure product as a yellow solid (60.0 mg, 0.309 mmol, 77% yield).

$^1$H NMR: (400 MHz, $CDCl_3$) δ 7.77 (d, J=7.6, 1H), 7.71 (d, J=7.8 Hz, 1H), 7.56-7.52 (m, 1H), 7.42-7.34 (m, 2H), 7.31-7.26 (m, 1H), 7.25-7.21 (m, 1H), 3.89 (s, 2H), 2.75 (q, J=7.6 Hz, 2H), 1.31 (t, J=7.6 Hz, 3H). $^{13}$C NMR: (101 MHz, $CDCl_3$) δ 143.66, 143.27, 143.26, 141.93, 139.49, 126.78, 126.62, 126.34, 125.09, 124.67, 119.80, 119.70, 36.96, 29.21, 16.10.

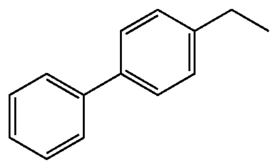

4-Ethyl-1,1'-biphenyl [4d]. According to the general transfer hydrogenation procedure C, (S)-DTBM-SEGPHOS (10.4 mg, 0.0088 mmol, 0.022 eq.), $Cu(OAc)_2$ (40 μL of a 0.2 M solution in THF, 0.008 mmol, 0.02 eq.), THF (0.16 mL), then dimethoxy(methyl)silane (247 μL, 2 mmol, 5 eq.) were combined in a 2-dram vial followed by addition of a solution of 4-ethynyl-1,1'-Biphenyl (71.3 mg, 0.4 mmol, 1 eq.), THF (0.2 mL), and 2-propanol (74 μL, 0.96 mmol, 2.4 eq.). The 2-dram vial was capped with a red pressure relief cap, and the reaction stirred for 9 h at 60° C. After silica plug filtration using diethyl ether (100 mL) as the eluent, the solvent was concentrated, and the crude brown oil was dry loaded onto a silica gel column. Flash chromatography using 100 mL of hexanes as eluent gave the pure product as a clear, yellow oil (57.5 mg, 0.316 mmol, 79% yield).

$^1$H NMR: (400 MHz, $CDCl_3$) δ 7.63-7.60 (m, 2H), 7.58-7.53 (m, 2H), 7.48-7.43 (m, 2H), 7.38-7.33 (m, 1H), 7.31 (d, J=8.1 Hz, 2H), 2.73 (q, J=7.6 Hz, 2H), 1.32 (t, J=7.6 Hz, 3H). $^{13}$C NMR: (101 MHz, $CDCl_3$) δ 143.52, 141.35, 138.77, 128.84, 128.42, 127.22, 127.16, 127.10, 28.66, 15.72.

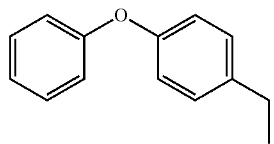

1-Ethyl-4-phenoxybenzene [4e]. According to the general transfer hydrogenation procedure C, (S)-DTBM-SEGPHOS (10.4 mg, 0.0088 mmol, 0.022 eq.), $Cu(OAc)_2$ (40 μL of a 0.2 M solution in THF, 0.008 mmol, 0.02 eq.), THF (0.16 mL), then dimethoxy(methyl)silane (247 μL, 2 mmol, 5 eq.) were combined in a 2-dram vial followed by addition of a solution of 1-ethynyl-4-phenoxy-benzene (77.7 mg, 0.4 mmol, 1 eq.), THF (0.2 mL), and 2-propanol (74 μL, 0.96 mmol, 2.4 eq.). The 2-dram vial was capped with a red pressure relief cap, and the reaction stirred for 9 h at 60° C. After silica plug filtration using diethyl ether (100 mL) as the eluent, the solvent was concentrated, and the crude brown oil was dry loaded onto a silica gel column. Flash chromatography using 100 mL of hexanes as eluent gave the pure product as a clear, yellow oil (66.5 mg, 0.335 mmol, 84% yield).

$^1$H NMR: (400 MHz, $CDCl_3$) δ 7.37-7.30 (m, 2H), 7.18 (d, J=8.5 Hz, 2H), 7.12-7.06 (m, 1H), 7.04-6.99 (m, 2H), 6.98-6.94 (m, 2H), 2.66 (q, J=7.6 Hz, 2H), 1.26 (t, J=7.6 Hz, 3H). $^{13}$C NMR: (101 MHz, $CDCl_3$) δ 157.91, 155.04, 139.44, 129.78, 129.16, 122.95, 119.21, 118.58, 28.31, 15.86.

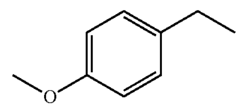

1-Ethyl-4-methoxybenzene [4f]. According to the general transfer hydrogenation procedure C, (S)-DTBM-SEGPHOS (10.4 mg, 0.0088 mmol, 0.022 eq.), $Cu(OAc)_2$ (40 μL of a 0.2 M solution in THF, 0.008 mmol, 0.02 eq.), THF (0.16 mL), then dimethoxy(methyl)silane (247 μL, 2.0 mmol, 5 eq.) were combined in a 2-dram vial followed by addition of a solution of 1-ethynyl-4-methoxybenzene (52.9 mg, 0.4 mmol, 1 eq.), THF (0.2 mL), and 2-propanol (153 μL, 2.0 mmol, 5 eq.). The 2-dram vial was capped with a red pressure relief cap, and the reaction stirred for 12 h at 60° C. After silica plug filtration using diethyl ether (100 mL) as the eluent, the solvent was concentrated, and the crude colorless liquid was dry loaded onto a silica gel column. Flash chromatography using 100 mL of hexanes as eluent gave the pure product as a clear and colorless liquid (30.9 mg, 0.227 mmol, 57% yield).

$^1$H NMR: (300 MHz, $CDCl_3$) δ 7.12 (d, J=8.5 Hz, 2H), 6.84 (d, J=8.5 Hz, 2H), 3.79 (s, 3H), 2.60 (q, J=7.6 Hz, 2H), 1.22 (t, J=7.5 Hz, 3H). $^{13}$C NMR: (75 MHz, $CDCl_3$) δ 157.74, 136.53, 128.85, 113.88, 55.42, 28.10, 16.04.

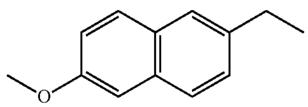

2-Ethyl-6-methoxynaphthlene [2b]. According to the general transfer hydrogenation procedure C, (S)-DTBM-SEGPHOS (142.4 mg, 0.12 mmol, 0.022 eq.), $Cu(OAc)_2$ (0.549 mL of a 0.2 M solution in THF, 0.11 mmol, 0.02 eq.), THF (2.5 mL), then dimethoxy(methyl)silane (3.39 mL, 27.45 mmol, 5 eq.) were combined in a 20-dram vial followed by addition of a solution of 2-ethynyl-6-methoxynapthalene (1.0 g, 5.49 mmol, 1 eq.), THF (2.5 mL), and 2-propanol (1.01 mL, 13.18 mmol, 2.4 eq.). The 20-dram vial was capped with a red pressure relief cap, and the reaction stirred for 15 h at 60° C. After silica plug filtration using diethyl ether (200 mL) as the eluent, the solvent was concentrated under vacuum. Purification by flash chromatography using gradient elution (100 mL of hexanes, 200 mL of 5% of ethyl acetate in hexanes, 500 mL of 8% ethyl acetate in hexanes) gave the pure product as a cream colored solid (0.97 g, 5.21 mmol, 95% yield).

$^1$H NMR: (400 MHz, $CDCl_3$) δ 7.70-7.64 (m, 2H), 7.57-7.54 (m, 1H), 7.32 (dd, J=8.4, 1.8 Hz, 1H), 7.15-7.09 (m, 2H), 3.91 (s, 3H), 2.78 (q, J=7.6 Hz, 2H), 1.31 (t, J=7.6, 0.6 Hz, 3H). $^{13}$C NMR: (101 MHz, $CDCl_3$) δ 157.23, 139.59, 133.04, 129.32, 129.04, 127.69, 126.82, 125.56, 118.72, 105.83, 55.42, 28.97, 15.75.

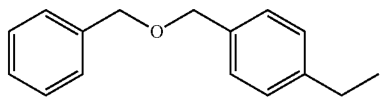 [SMILES: CCc1ccc(COCc2ccccc2)cc1]

1-((Benzyloxy)methyl)-4-ethylbenzene [4g]. According to the general transfer hydrogenation procedure C, (S)-DTBM-SEGPHOS (10.4 mg, 0.0088 mmol, 0.022 eq.). $Cu(OAc)_2$ (40 μL of a 0.2 M solution in THF, 0.008 mmol, 0.02 eq.). THF (0.16 mL), then dimethoxy(methyl)silane (296 μL, 2.4 mmol, 6 eq.) were combined in a 2-dram vial followed by addition of a solution of 1-ethynyl-4-[(phenylmethoxy) methyl]-benzene (88.9 mg, 0.4 mmol, 1 eq.), THF (0.2 mL), and ethanol (61 μL, 1.04 mmol, 2.6 eq.). The 2-dram vial was capped with a red pressure relief cap, and the reaction stirred for 18 h at 60° C. After silica plug filtration using diethyl ether (100 mL) as the eluent, the solvent was concentrated, and the crude brown oil was dry loaded onto a silica gel column. Flash chromatography using gradient elution (75 mL of hexanes, 100 mL of 1% ethyl acetate in hexanes, 100 mL of 2% ethyl acetate in hexanes, 200 mL of 5% ethyl acetate in hexanes) gave the pure product as a clear, yellow oil (58.5 mg, 0.26 mmol, 65% yield).

$^1$H NMR: (400 MHz, $CDCl_3$) δ 7.43-7.35 (m, 4H), 7.34-7.28 (m, 3H), 7.22 (d, J=7.9 Hz, 2H), 4.57 (d, J=7.6 Hz, 4H), 2.68 (q, J=7.6 Hz, 2H), 1.26 (t, J=7.6 Hz, 3H). $^{13}$C NMR: (101 MHz, $CDCl_3$) δ 143.87, 138.56, 135.64, 128.51, 128.09, 128.04, 127.90, 127.70, 72.16, 72.11, 28.75, 15.76. ATR-IR ($cm^{-1}$): 3029, 2964, 2929, 2856, 1718, 1090, 1072.

HRMS. ($ESI^+$) m/z: $[M+Na]^+$ Calcd for $C_{16}H_{18}NaO$ 249.1250; Found 249.1257.

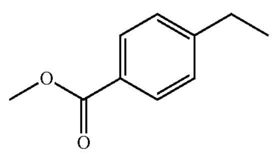

Methyl 4-ethylbenzoate [4h]. According to the general transfer hydrogenation procedure C, (S)-DTBM-SEGPHOS (10.4 mg, 0.0088 mmol, 0.022 eq.), $Cu(OAc)_2$ (40 μL of a 0.2 M solution in THF, 0.008 mmol, 0.02 eq.), THF (0.16 mL), then dimethoxy(methyl)silane (247 μL, 2 mmol, 5 eq.) were combined in a 2-dram vial followed by addition of a solution of methyl 4-ethynylbenzoate (64.1 mg, 0.4 mmol, 1 eq.), THF (0.2 mL), and 2-propanol (74 μL, 0.96 mmol, 2.4 eq.). The 2-dram vial was capped with a red pressure relief cap, and the reaction stirred for 22 h at 40° C. After silica plug filtration using diethyl ether (100 mL) as the eluent, the solvent was concentrated under vacuum. Purification by flash chromatography using gradient elution (100 mL of hexanes, 200 mL of 10% of DCM in hexanes, 200 mL of 20% DCM in hexanes, 200 mL of 30% DCM in hexanes) gave the pure product as a clear colorless liquid (47.0 mg, 0.286 mmol, 72% yield).

$^1$H NMR: (400 MHz, $CDCl_3$) δ 7.95 (d, J=8.2 Hz, 2H), 7.25 (d, J=8.1 Hz, 2H), 3.89 (s, 3H), 2.70 (q, J=7.6 Hz, 2H), 1.25 (t, J=7.6 Hz, 3H). $^{13}$C NMR: (101 MHz, $CDCl_3$) δ 167.31, 149.86, 129.82, 128.00, 127.75, 52.07, 29.07, 15.34.

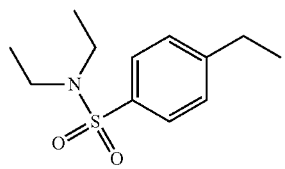 [SMILES: CCc1ccc(S(=O)(=O)N(CC)CC)cc1]

N,N,4-Triethylbenzenesulfonamide [4i]. According to the general transfer hydrogenation procedure C, (S)-DTBM-SEGPHOS (10.4 mg, 0.0088 mmol, 0.022 eq.). $Cu(OAc)_2$ (40 μL of a 0.2 M solution in THF, 0.008 mmol, 0.02 eq.), THF (0.16 mL), then dimethoxy(methyl)silane (247 μL, 2 mmol, 5 eq.) were combined in a 2-dram vial followed by addition of a solution of N,N-diethyl-4-ethynyl-benzene-sulfonamide (95 mg, 0.4 mmol, 1 eq.), THF (0.2 mL), and ethanol (56 μL, 0.96 mmol, 2.4 eq.). The 2-dram vial was capped with a red pressure relief cap, and the reaction stirred for 20 h at 60° C. After silica plug filtration using diethyl ether (100 mL) as the eluent, the solvent was concentrated, and the crude brown oil was dry loaded onto a silica gel column. Flash chromatography using gradient elution (100 mL of hexanes, 100 mL of 5% ethyl acetate in hexanes, 100 mL of 6% ethyl acetate in hexanes, 200 mL of 8% ethyl acetate in hexanes, 200 mL of 10% ethyl acetate in hexanes, 200 mL of 12% ethyl acetate in hexanes) gave the pure product as a clear, yellow oil (76.4 mg, 0.317 mmol, 79% yield).

$^1$H NMR: (400 MHz, $CDCl_3$) δ 7.70 (d, J=8.3 Hz, 2H), 7.29 (d, J=8.1 Hz, 2H), 3.21 (q, J=7.2 Hz, 4H), 2.69 (q, J=7.6 Hz, 2H), 1.24 (t, J=7.6 Hz, 3H), 1.11 (t, J=7.2 Hz, 6H). $^{13}$C NMR: (101 MHz, $CDCl_3$) δ 149.15, 137.72, 128.51, 127.22, 42.15, 28.84, 15.22, 14.29.

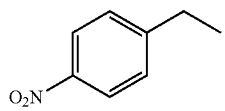

4-Ethylnitrobenzene [4j]. According to the general transfer hydrogenation procedure C, (S)-DTBM-SEGPHOS (10.4 mg, 0.0088 mmol, 0.022 eq.), $Cu(OAc)_2$ (40 μL of a 0.2 M solution in THF, 0.008 mmol, 0.02 eq.), THF (0.16 mL), then dimethoxy(methyl)silane (247 μL, 2 mmol, 5 eq.) were combined in a 2-dram vial followed by addition of a solution of methyl-4-ethynylnitrobenzene (58.9 mg, 0.4 mmol, 1 eq.), THF (0.2 mL), and 2-propanol (74 μL, 0.96 mmol, 2.4 eq.). The 2-dram vial was capped with a red pressure relief cap, and the reaction stirred for 24 h at room temperature. After silica plug filtration using diethyl ether (100 mL) as the eluent, the solvent was concentrated, under vacuum. Purification by flash chromatography using gradient elution (100 mL of hexanes, 200 mL of 5% ethyl acetate in hexanes 200 mL of 10% of ethyl acetate in hexanes, 200 mL of 20% ethyl acetate in hexanes) gave the pure product as a clear brown liquid (39.4 mg, 0.26 mmol, 65% yield).

$^1$H NMR: (400 MHz, $CDCl_3$) δ 8.13 (d, J=8.7 Hz, 2H), 7.33 (d, J=8.5 Hz, 2H), 2.75 (q, J=7.6 Hz, 2H), 1.27 (t, J=7.6 Hz, 3H). $^{13}$C NMR: (101 MHz, $CDCl_3$) δ 152.15, 146.32, 128.74, 123.72, 28.95, 15.15.

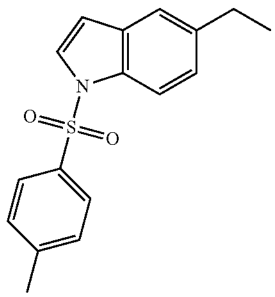 [SMILES: CCc1ccc2c(ccn2S(=O)(=O)c2ccc(C)cc2)c1]

5-Ethyl-1-tosyl-1H-indole [4k]. According to the general transfer hydrogenation procedure C, (S)-DTBM-SEGPHOS (13.0 mg, 0.011 mmol, 0.055 eq.), $Cu(OAc)_2$ (50 μL of a 0.2 M solution in THF, 0.01 mmol, 0.05 eq.), THF (0.05 mL), then dimethoxy(methyl)silane (123 μL, 1.0 mmol, 5 eq.) were combined in a 2-dram vial followed by addition of a solution of 5-ethynyl-1-tosyl-1H-indole (59.1 mg, 0.2 mmol, 1 eq.), THF (0.1 mL), and 2-propanol (77 μL, 1.0 mmol, 5 eq.). The 2-dram vial was capped with a red pressure relief cap, and the reaction stirred for 24 h at 60° C. After silica plug filtration using diethyl ether (100 mL) as the eluent, the solvent was concentrated, and the crude brown liquid was dry loaded onto a silica gel column. Flash chromatography using gradient elution (100 mL of 10% ethyl acetate in hexanes, 100 mL of 20% ethyl acetate in hexanes followed by 200 mL of 30% ethyl acetate in hexanes) gave the pure product as a clear and colorless oil (36.1 mg, 0.12 mmol, 60% yield).

$^1$H NMR: (400 MHz, $CDCl_3$) δ 7.90 (d, J=8.5 Hz, 1H), 7.76 (d, J=8.3 Hz, 2H), 7.53 (d, J=3.6 Hz, 1H), 7.33 (s, 1H), 7.20 (d, J=8.2 Hz, 2H), 7.16 (d, J=8.5 Hz, 1H), 6.59 (d, J=3.6 Hz, 1H), 2.70 (q, J=7.6 Hz, 2H), 2.33 (s, 3H), 1.25 (t, J=7.6 Hz, 3H). $^{13}$C NMR: (101 MHz, $CDCl_3$) δ 144.91, 139.52, 135.50, 133.33, 131.12, 129.96, 126.93, 126.50, 125.10, 120.11, 113.41, 109.08, 28.84, 21.67, 16.12. ATR-IR ($cm^{-1}$): 2962, 2926, 2873, 1596, 1367, 1130. HRMS: ($ESI^+$) m/z: $[M+Na]^+$ Calcd for $C_{17}H_{17}NNaO_2S$ 322.0872; Found 322.0882.

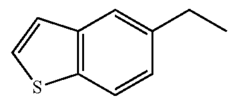

5-Ethylbenzo[b]thiophene [4l]. According to the general transfer hydrogenation procedure C, (S)-DTBM-SEGPHOS (10.4 mg, 0.0088 mmol, 0.022 eq.). $Cu(OAc)_2$ (40 μL of a 0.2 M solution in THF, 0.008 mmol, 0.02 eq.), THF (0.16 mL), then dimethoxy(methyl)silane (247 μL, 2 mmol, 5 eq.) were combined in a 2-dram vial followed by addition of a solution of 5-ethynylbenzo[b]thiophene (63 mg, 0.4 mmol, 1 eq.), THF (0.2 mL), and 2-propanol (74 μL, 0.96 mmol, 2.4 eq.). The 2-dram vial was capped with a red pressure relief cap, and the reaction stirred for 13 h at 60° C. After silica plug filtration using diethyl ether (100 mL) as the eluent, the solvent was concentrated under vacuum. Purification by flash chromatography using gradient elution (100 mL of hexanes, 200 mL of 5% ethyl acetate in hexanes) gave the pure product as a clear red oil (46.9 mg, 0.289 mmol, 72% yield).

$^1$H NMR: (400 MHz, $CDCl_3$) δ 7.82 (d, J=8.1 Hz, 1H), 7.69-7.66 (m, 1H), 7.43 (d, J=5.4 Hz, 1H), 7.31 (dd, J=5.4, 0.8 Hz, 1H), 7.24 (dd, J=8.2, 1.7 Hz, 1H), 2.80 (q, J=7.6 Hz, 2H), 1.33 (t, J=7.6 Hz, 3H). $^{13}$C NMR: (101 MHz, $CDCl_3$) δ 140.56, 140.09, 137.26, 126.51, 125.12, 123.76, 122.43, 122.33, 28.98, 16.17. ATR-IR ($cm^{-1}$): 2962, 2928, 2868, 1738, 808, 691. HRMS: ($EI^+$) m/z: $[M]^+$ Calcd for $C_{10}H_{10}S$ 162.0503; Found 162.0496.

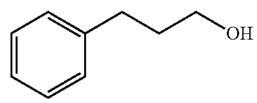

3-Phenyl-1-propanol [4m]. According to the general transfer hydrogenation procedure C, (S)-DTBM-SEGPHOS (10.4 mg, 0.0088 mmol, 0.022 eq.), $Cu(OAc)_2$ (40 μL of a 0.2 M solution in THF, 0.008 mmol, 0.02 eq.), THF (0.16 mL), then dimethoxy(methyl)silane (247 μL, 2.0 mmol, 5 eq.) were combined in a 2-dram vial followed by addition of a solution of 3-phenyl-2-propyn-1-ol (52.9 mg, 0.4 mmol, 1 eq.), THF (0.2 mL), and 2-propanol (74 μL, 0.96 mmol, 2.4 eq.). The 2-dram vial was capped with a red pressure relief cap, and the reaction stirred for 18 h at 60° C. After silica plug filtration using diethyl ether (100 mL) as the eluent, the solvent was concentrated. The clear crude oil was treated with tetrabutylammonium fluoride following the general procedure D. Flash chromatography using gradient elution (100 mL of hexanes, 100 mL of 5% ethyl acetate in hexanes, 100 mL of 10% ethyl acetate in hexanes, 200 mL of 15% ethyl acetate in hexanes) gave the pure product as a clear and colorless oil (31 mg, 0.227 mmol, 57% yield).

$^1$H NMR (400 MHz, $CDCl_3$) δ 7.33-7.27 (m, 2H), 7.24-7.17 (m, 3H), 3.68 (t, J=6.5 Hz, 2H), 2.72 (t, J=7.64 Hz, 2H), 1.95-1.86 (m, 2H), 1.64 (s, 1H). $^{13}$C NMR (101 MHz, $CDCl_3$) δ 141.94, 128.54, 128.51, 125.98, 62.35, 34.33, 32.19.

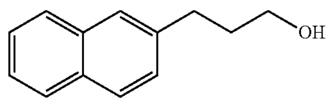 [SMILES: OCCCc1ccc2ccccc2c1]

2-Naphthalenepropanol [4n]. According to the general transfer hydrogenation procedure C, (S)-DTBM-SEGPHOS (10.4 mg, 0.0088 mmol, 0.022 eq.). $Cu(OAc)_2$ (40 μL of a 0.2 M solution in THF, 0.008 mmol, 0.02 eq.), THF (0.16 mL), then dimethoxy(methyl)silane (247 μL, 2.0 mmol, 5 eq.) were combined in a 2-dram vial followed by addition of a solution of 3-(2-Napthhalenyl)-2-propyn-1-ol (72.8 mg, 0.4 mmol, 1 eq.), THF (0.2 mL), and 2-propanol (74 μL, 0.96 mmol, 2.4 eq.). The 2-dram vial was capped with a red pressure relief cap, and the reaction stirred for 18 h at 60° C. After silica plug filtration using diethyl ether (100 mL) as the eluent, the solvent was concentrated. The clear crude oil was treated with tetrabutylammonium fluoride following the general procedure D. Flash chromatography using gradient elution (100 mL of hexanes, 100 mL of 5% ethyl acetate in hexanes, 200 mL of 10% ethyl acetate in hexanes, 200 mL of 15% ethyl acetate in hexanes) gave the pure product as a white solid (56 mg, 0.30 mmol, 75% yield).

$^1H$ NMR (400 MHz, $CDCl_3$) δ 7.85-7.74 (m, 3H), 7.65 (s, 1H), 7.50-7.40 (m, 2H), 7.36 (d, J=8.4 Hz, 1H), 3.72 (t, J=6.4, 5.3 Hz, 2H), 2.89 (t, J=7.6 Hz, 2H), 2.01 (p, 2H), 1.76 (s, 1H). $^{13}C$ NMR (75 MHz, $CDCl_3$) δ 139.43, 133.72, 132.11, 128.05, 127.71, 127.50, 127.37, 126.51, 126.04, 125.27, 62.26, 34.14, 32.28.

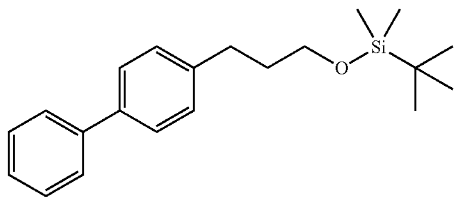 [SMILES: CC(C)(C)[Si](C)(C)OCCCc1ccc(-c2ccccc2)cc1]

(3-([1,1'-Biphenyl]-4-yl)propoxy)(tert-butyl)dimethylsilane [4o]. According to the general transfer hydrogenation procedure C, (S)-DTBM-SEGPHOS (8.0 mg, 0.0068 mmol, 0.022 eq.), $Cu(OAc)_2$ (31 μL of a 0.2 M solution in THF, 0.0628 mmol, 0.02 eq.), THF (0.12 mL), then dimethoxy (methyl)silane (191 μL, 1.55 mmol, 5 eq.) were combined in a 2-dram vial followed by addition of a solution of ((3-([1, 1'-biphenyl]-4-yl)prop-2-yn-1-yl)oxy)(tert-butyl)dimethylsilane (100 mg, 0.31 mmol, 1 eq.), THF (0.15 mL), and 2-propanol (119 μL, 1.55 mmol, 5 eq.). The 2-dram vial was capped with a red pressure relief cap, and the reaction stirred for 10 h at 60° C. After silica plug filtration using diethyl ether (100 mL) as the eluent, the solvent was concentrated. Flash chromatography using gradient elution (100 mL of hexanes, 100 mL of 2% ethyl acetate in hexanes, 100 mL of 5% ethyl acetate in hexanes gave the pure product as a white crystalline solid (71 mg, 0.217 mmol, 70% yield).

$^1H$ NMR: (400 MHz, $CDCl_3$) δ 7.59 (d, J=7.2 Hz, 2H), 7.52 (d, J=8.2 Hz, 2H), 7.44 (t, J=7.6 Hz, 2H), 7.36-7.30 (m, 1H), 7.30-7.26 (m, 2H), 3.68 (t, J=6.3 Hz 2H), 2.76-2.70 (m, 2H), 1.95-1.83 (m, 2H), 0.93 (s, 9H), 0.08 (s, 6H). $^{13}C$ NMR: (75 MHz, $CDCl_3$) δ 141.56, 141.29, 138.79, 129.04, 128.84, 127.17, 127.12, 127.11, 62.51, 34.58, 31.88, 26.12, 18.49, −5.10. FT-IR (thin film, $cm^{-1}$): 2930, 2925, 2854, 1250, 1098, 1077. HRMS: ($ESI^+$) m/z: $[M+Na]^+$ Calcd for $C_{21}H_{30}NaOSi$ 349.1958; Found 349.1968.

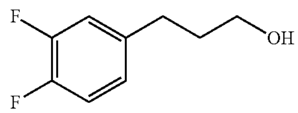 [SMILES: OCCCc1ccc(F)c(F)c1]

3,4-Difluorobenzenepropanol [4p]. According to the general transfer hydrogenation procedure C, (S)-DTBM-SEGPHOS (10.4 mg, 0.0088 mmol, 0.022 eq.). $Cu(OAc)_2$ (40 μL of a 0.2 M solution in THF, 0.008 mmol, 0.02 eq.), THF (0.16 mL), then dimethoxy(methyl)silane (247 μL, 2.0 mmol, 5 eq.) were combined in a 2-dram vial followed by addition of a solution of 3,4-difluorobenzenepropynol (67.3 mg, 0.4 mmol, 1 eq.), THF (0.2 mL), and 2-propanol (74 μL, 0.96 mmol, 2.4 eq.). The 2-dram vial was capped with a red pressure relief cap, and the reaction stirred for 19 h at 60° C. After silica plug filtration using diethyl ether (100 mL) as the eluent, the solvent was concentrated. The clear crude oil was treated with tetrabutylammonium fluoride following the general procedure D. Flash chromatography using gradient elution (100 mL of hexanes, 100 mL of 5% ethyl acetate in hexanes, 100 mL of 10% ethyl acetate in hexanes, 200 mL of 15% ethyl acetate in hexanes) gave the pure product as a clear oil (39.0 mg, 0.227 mmol, 57% yield).

$^1H$ NMR (400 MHz, $CDCl_3$) δ 7.10-6.95 (m, 2H), 6.92-6.86 (m, 1H), 3.66 (q, J=5.9 Hz, 2H), 2.67 (t, J=7.4, 2H), 1.90-1.81 (m, 2H), 1.31 (s, 1H). $^{13}C$ NMR (101 MHz, $CDCl_3$) δ 150.79 (dd, J=144.6, 12.6 Hz), 148.34 (dd, J=142.6, 12.7 Hz), 138.88 (dd, J=5.5, 3.9 Hz), 124.31 (dd, J=6.0, 3.5 Hz), 117.21 (d, J=16.6 Hz), 117.10 (d, J=16.8 Hz), 61.93, 34.06, 31.33. $^{19}F$ NMR (376 MHz, $CDCl_3$) δ −138.53, −142.39. ATR-IR ($cm^{-1}$): 3319, 2934, 2868, 1717, 1510, 1209, 1116, 1048. HRMS: ($ESI^+$) m/z: $[M+H]^+$ Calcd for $C_9H_{11}OF_2$ 173.0778; Found 173.0780.

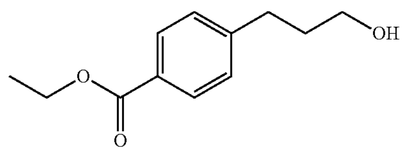

Ethyl-4-(-3-hydroxypropyl)benzoate [4q]. According to the general transfer hydrogenation procedure C, (S)-DTBM-SEGPHOS (10.4 mg, 0.0088 mmol, 0.022 eq.), $Cu(OAc)_2$ (40 μL of a 0.2 M solution in THF, 0.008 mmol, 0.02 eq.), THF (0.16 mL), then dimethoxy(methyl)silane (247 μL, 2.0 mmol, 5 eq.) were combined in a 2-dram vial followed by addition of a solution of ethyl-4-(-3-hydroxypropynyl)benzoate (81.8 mg, 0.4 mmol, 1 eq.), THF (0.2 mL), and 2-propanol (73.9 μL, 0.96 mmol, 2.4 eq.). The 2-dram vial was capped with a red pressure relief cap, and the reaction stirred for 18 h at 60° C. After silica plug filtration using diethyl ether (100 mL) as the eluent, the solvent was concentrated. The clear crude oil was treated with tetrabutylammonium fluoride following the general procedure D. Flash chromatography using gradient elution (100 mL of hexanes, 100 mL of 5% ethyl acetate in hexanes, 100 mL of 10% ethyl acetate in hexanes, 200 mL of 15% ethyl acetate in hexanes) gave the pure product as a clear yellow oil (51 mg, 0.244 mmol, 61% yield).

$^1H$ NMR (400 MHz, $CDCl_3$) δ 7.95 (d, J=8 Hz, 2H), 7.25 (d, J=7.7 Hz, 2H), 4.35 (q, J=7 Hz, 2H), 3.66 (t, J=6.3 Hz, 2H), 2.76 (t, J=8, 2H), 1.90 (p, 2H), 1.65 (s, 1H), 1.37 (t, J=7.1 Hz, 3H). $^{13}C$ NMR (101 MHz, $CDCl_3$) δ 166.82, 147.49, 129.77, 128.50, 128.24, 61.95, 60.91, 33.92, 32.17, 14.40. ATR-IR ($cm^{-1}$): 3412, 2986, 2933, 2873, 1713, 1610, 1272, 1102, 1041, 1020. HRMS: ($ESI^+$) m/z: $[+Na]^+$ Calcd for $C_{12}H_{16}NaO_3$ 231.0992; Found 231.0999.

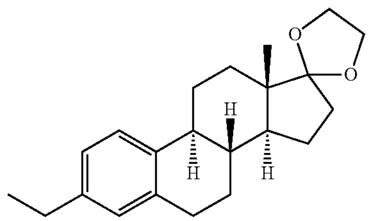

(8R,9S,13S,14S)-3-Ethyl-13-methyl-6,7,8,9,11,12,13,14,15,16-decahydrospiro[cyclopenta[a]phenanthrene-17,2'-[1,3]dioxolane] [4r]. According to the general procedure C, (S)-DTBM-SEGPHOS (5.7 mg, 0.00486 mmol, 0.022 eq.), $Cu(OAc)_2$ (22 μL of a 0.2 M solution in THF, 0.0044 mmol, 0.02 eq.), THF (0.1 mL), then dimethoxy(methyl)silane (136 μL, 1.1 mmol, 5 eq.) were combined in a 2-dram vial followed by addition of a solution of (8R,9S,13S,14S)-3-(ethynyl)-13-methyl-6,7,8,9,11,12,13,14,15,16-decahydrospiro[cyclopenta[a]phenanthrene-17,2'-[1,3]dioxolane] (71.3 mg, 0.22 mmol, 1 eq.), THF (0.1 mL), and 2-propanol (85 μL, 1.1 mmol, 5 eq.). The 2-dram vial was capped with a red pressure relief cap, and the reaction stirred for 19 h at 60° C. After silica plug filtration using dichloromethane as the eluent (100 mL), the solvent was concentrated, and the crude brown oil was dry loaded onto a silica gel column. Flash chromatography using gradient elution (100 mL of hexanes, 100 mL of 3% ethyl acetate in hexanes, 100 mL of 5% ethyl acetate in hexanes, 10 mL of 8% ethyl acetate in hexanes, 200 mL of 9% ethyl acetate in hexanes, 100 mL of 10% ethyl acetate in hexanes) gave the pure product as a clear, yellow oil (56.2 mg, 0.172 mmol, 78% yield).

$^1H$ NMR (400 MHz, $CDCl_3$) δ 7.25 (d, J=7.9 Hz, 1H), 7.00 (d, J=8.0 Hz, 1H), 6.95 (s, 1H), 4.02-3.86 (m, 4H), 2.94-2.80 (m, 2H), 2.60 (q, J=7.6 Hz, 2H), 2.41-2.23 (m, 2H), 2.11-2.00 (m, 1H), 1.96-1.73 (m, 4H), 1.71-1.60 (m, 1H), 1.59-1.30 (m, 5H), 1.24 (t, J=7.6 Hz, 3H), 0.90 (s, 3H). $^{13}C$ NMR (101 MHz, $CDCl_3$) δ 141.55, 137.78, 136.73, 128.59, 125.47, 125.28, 119.57, 65.39, 64.71, 49.59, 46.29, 44.10, 39.07, 34.36, 30.90, 29.70, 28.44, 27.16, 26.10, 22.49, 15.77, 14.46. ATR-IR ($cm^{-1}$): 2965, 2933, 2872, 1735, 1693, 1610, 1103, 1040. HRMS: ($ESI^+$) m/z: $[M+H]^+$ Calcd for $C_{22}H_{31}O_2$ 327.2319; Found 327.2329.

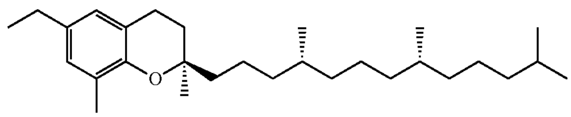 [SMILES: CCc1cc(C)c2c(c1)CC[C@@](C)(CCC[C@H](C)CCC[C@H](C)CCCC(C)C)O2]

(R)-6-Ethyl-2,8-dimethyl-2-((4R,8R)-4,8,12-trimethyltridecyl)chromane [4s]. According to the general procedure C, (S)-DTBM-SEGPHOS (13 mg, 0.011 mmol, 0.055 eq.), $Cu(OAc)_2$ (50 μL of a 0.2 M solution in THF, 0.01 mmol, 0.05 eq.), THF (0.05 mL), then dimethoxy(methyl)silane (99 μL, 0.8 mmol, 4 eq.) were combined in a 2-dram vial followed by addition of a solution of (R)-6-ethynyl-2,8-dimethyl-2-((4R,8R)-4,8,12-trimethyltridecyl)chromane (82.1 mg, 0.2 mmol, 1 eq.), THF (0.1 mL), and 2-propanol (77 μL, 1.0 mmol, 5 eq.). The 2-dram vial was capped with a red pressure relief cap, and the reaction stirred for 16 h at 60° C. After silica plug filtration using diethyl ether (100 mL) as the eluent, the solvent was concentrated, and the crude colorless liquid was dry loaded onto a silica gel column. Flash chromatography using gradient elution (100 mL of hexanes followed by 200 mL of 2% ethyl acetate in hexanes) gave the pure product as a clear and colorless liquid (51.2 mg, 0.124 mmol, 62% yield).

$^1H$ NMR: (400 MHz, $CDCl_3$) δ 6.80 (s, 1H), 6.73 (s, 1H), 2.80-2.66 (m, 2H), 2.53 (q, J=7.6 Hz, 2H), 2.15 (s, 3H), 1.87-1.68 (m, 2H), 1.62-1.47 (m, 3H), 1.46-1.01 (m, 24H), 0.92-0.81 (m, 12H). $^{13}C$ NMR: (101 MHz, $CDCl_3$) δ 150.17, 134.45, 128.00, 126.09, 126.02, 120.25, 75.87, 40.37, 39.53, 37.61, 37.57, 37.44, 32.96, 32.85, 31.45, 28.14, 28.12, 24.97, 24.61, 24.45, 22.89, 22.79, 22.52, 21.15, 19.91, 19.82, 16.21, 16.08. ATR-IR ($cm^{-1}$): 2957, 2924, 2854, 1733, 1598, 1220, 1151. HRMS: ($ESI^+$) m/z: $[M+H]^+$ Calcd for $C_{29}H_{51}O$ 415.3934; Found 415.3946.

IV. Transfer Deuteration Reaction Scope

Procedure for the Synthesis of Dimethoxy(Methyl)Silane-d

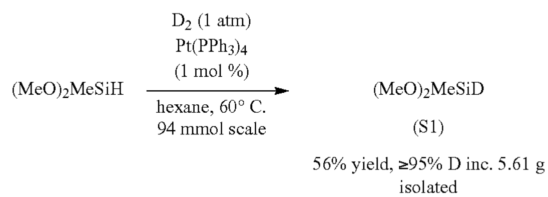

The procedure was adapted from a previously reported method.[1] To an oven-dried 500 mL Schlenk flask equipped with a Teflon stir bar in a $N_2$ filled glovebox was added the $Pt(PPh_3)_4$ (1.17 g, 0.941 mmol, 0.01 eq.), dimethoxy(methyl)silane (11.6 mL, 94.1 mmol, 1 eq.), and 5.0 mL of degassed anhydrous hexanes. The Schlenk flask was sealed with a rubber septum and removed from the glovebox, connected to a manifold line, and cooled to −78° C. A single freeze-pump-thaw cycle was performed, and the Schlenk flask was backfilled with $D_2$ gas from a $D_2$ purged balloon at room temperature. The flask was sealed with parafilm and heated to 60° C. After 2 hours, the reaction was cooled to room temperature and then a single freeze-pump-thaw was performed again, backfilling with $D_2$ gas. The process was repeated 6 times or until the $^1H$ NMR showed ≥95% D incorporation. It is important to maintain a $N_2$ (g) inert atmosphere while obtaining a minimal quantity of sample for $^1H$ NMR analysis.

The solution was purified through a distillation apparatus; the set up consisted of a flame-dried 25 mL round-bottom receiving flask and a cannula. The 25 mL round-bottom receiving flask was flame-dried, and then filled with $N_2$. Once the receiving flask reached room temperature, the cannula was inserted, maintaining positive pressure, and tightly sealed with parafilm to prevent condensation from entering. Upon confirmation of positive $N_2$ flow, the open end of the cannula was inserted into the Schlenk reaction flask. The 25 mL round-bottom receiving flask was cooled to −78° C. and closed to the manifold line, and then the Schlenk flask was heated to 80° C. The heat initiated the distillation of the dimethoxy(methyl)silane-d and the hexane through the cannula which were trapped in the cold 25 mL round-bottom receiving flask. Vacuum was also applied to the 25 mL round-bottom receiving flask to promote this process. Once all of the silane and hexane were trapped in the 25 mL round-bottom receiving flask, the flask was removed from the heat and the manifold was closed to vacuum line while the 25 mL round-bottom receiving flask warmed to room temperature. Under positive nitrogen flow, the cannula was removed from the 25 mL round-bottom receiving flask, while keeping it inserted in the Schlenk reaction flask. The 25 mL round-bottom receiving flask was tightly sealed with parafilm, and stored in the −4° C. freezer. The final product was in a solution of hexane, and the molarity was calculated by $^1H$ NMR using 1,3,5-trimethylbenzene as an internal standard, and used for the transfer deuteration reactions (5.61 g in a 5.29 M hexane solution, 52.9 mmol, 56% yield).

Note: it is important to monitor that the end of the cannula does not get clogged by frozen solvent/silane. If this occurs, remove the Schlenk reaction flask from heat and close manifold to vacuum line. Warm the 25 mL round-bottom receiving flask until the solids on the tip of the cannula melt, and then distillation can be resumed.

General procedure for transfer deuteration. (E). In a $N_2$ filled glovebox. (R or S)-DTBM-SEGPHOS (10.4 mg, 0.0088 mmol, 0.022 eq.), $Cu(OAc)_2$ (40 μL of a 0.2 M solution in THF, 0.008 mmol, 0.02 eq.), and THF (0.16 mL) were added to an oven-dried 2-dram vial followed by dropwise addition of dimethoxy(methyl)silane-d in hexanes (2 mmol, 5 eq.). A color change from green/blue to orange was observed while stirring for 15 minutes. In a separate 1-dram vial was added the alkyne substrate (0.4 mmol, 1 eq.), THF (0.2 mL), and either 2-propanol-OD or 2-propanol-$d_8$ (2.4-5 eq. based on substrate). The solution in the 1-dram vial was added dropwise over 20 seconds to the 2-dram vial. The total volume of THF was calculated based on having a final reaction concentration of 1M based on the alkyne substrate. The 2-dram vial was capped with a red pressure relief cap, taken out of the glovebox, and stirred for 9-24 h at 60° C. at which point the reaction was filtered through a 1" silica plug with 20 mL of $Et_2O$ followed by 80 mL of $Et_2O$ to elute the remaining product into a 200 mL round bottom flask. After removing the $Et_2O$ by rotary evaporation, the crude product was isolated by flash chromatography.

Method for calculating deuterium incorporation at each labeled carbon of each substrate:

In the $^1H$ NMR spectra, if both benzylic and homobenzylic peaks were clearly visible and no overlap with other peaks was observed, then the deuterium incorporation was calculated from the integration of the protonated peak. If overlap of other peaks was observed in the homobenzylic region of the $^1H$ NMR spectra, a $^1H$ NMR spectra was obtained. The ratio of the two peaks that appear in the $^2H$ NMR spectra was correlated to the calculated deuterium incorporation at the benzylic peak in the $^1H$ NMR spectra.

2-propanol-$d_8$ was used due to a 2-propanol-OD back-order from the supplier during COVID-19.

Scheme S2. Transfer Deuteration Substrate Scope

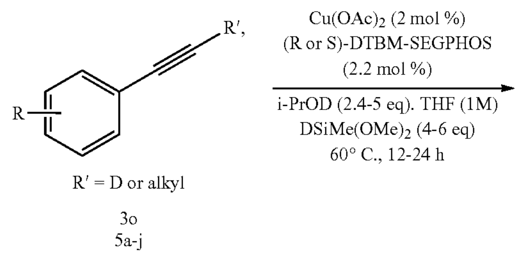

R′ = D or alkyl 3o
5a-j

-continued

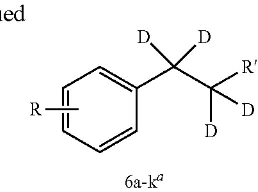

6a-k[a]

6a

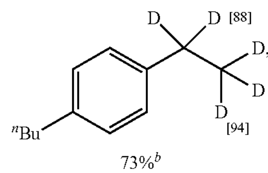

73%[b]

6b

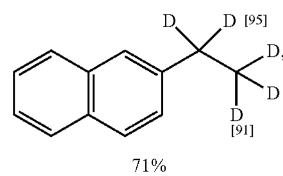

71%

6c

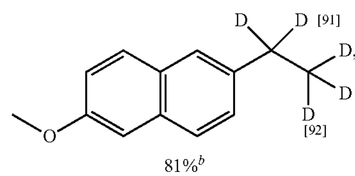

81%[b]

6d

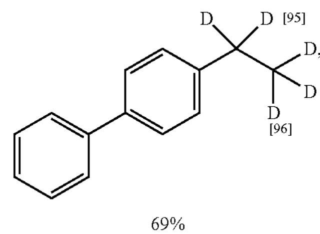

69%

6e

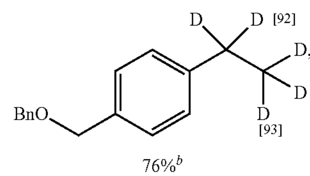

76%[b]

6f

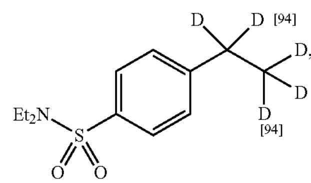

88%[b]

6g

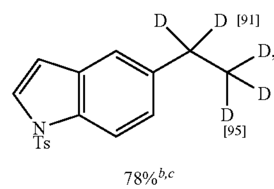

78%[b,c]

-continued

6h

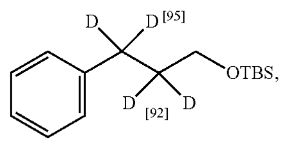

69%[b]

6i

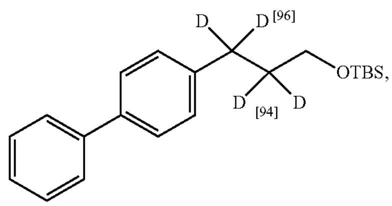

87% (from 3o)

6j

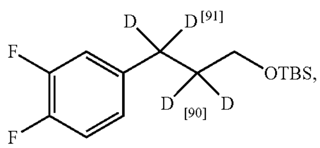

77%[b]

6k

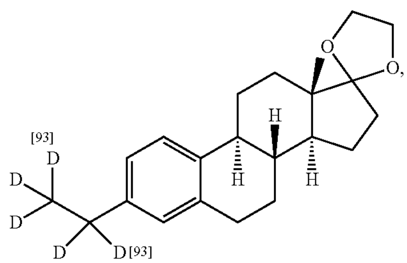

74%

[a]Deuterium incorporation measured by $^1H$ NMR and/or $^2H$ NMR.
[b]i-PrOD$_8$ used and found to be equally effective as i-PrOD. [c]5 mol % Cu(OAc)$_2$ and 5.5 mol % DTBM SEGPHOS used.

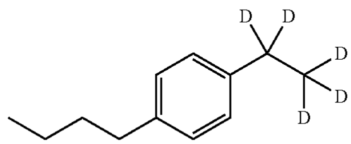 [SMILES: [2H]C([2H])([2H])C([2H])([2H])c1ccc(CCCC)cc1]

1-Butyl-4-(ethyl-d$_5$)benzene [6a]. According to the general procedure E, (S)-DTBM-SEGPHOS (5.2 mg, 0.0044 mmol, 0.022 eq.). Cu(OAc)$_2$ (20 μL of a 0.2 M solution in THF, 0.004 mmol, 0.02 eq.). THF (0.08 mL), then dimethoxy(methyl)silane-d (0.17 mL of a 5.9 M solution in hexanes, 1.0 mmol, 5 eq.) were combined in a 2-dram vial followed by addition of a solution of 1-butyl-4-(ethynyl-d) benzene (31.8 mg, 0.2 mmol, 1 eq.), THF (0.1 mL), and 2-propanol-d$_8$ (77 μL, 1.0 mmol, 5 eq.). The 2-dram vial was capped with a red pressure relief cap, and the reaction stirred for 17 h at 60° C. After silica plug filtration using diethyl ether (100 mL) as the eluent, the solvent was concentrated, and the crude yellow liquid was dry loaded onto a silica gel column. Flash chromatography using 200 mL of hexanes as eluent gave the pure product as a colorless oil (24.4 mg, 0.146 mmol, 73% yield).

$^1H$ NMR: (400 MHz, $CDCl_3$) δ 7.12 (s, 4H), 2.62-2.57 (m, 2.24H due to overlap of two benzylic sites), 1.65-1.55 (m, 2H), 1.43-1.31 (m, 2H), 1.19 (br s, integration not determined due to overlap with grease), 0.94 (t, J=7.3 Hz, 3H). $^2H$ NMR: (61 MHz, $CHCl_3$) δ 2.58 (br s, 1.76D), 1.19 (br s, 2.82D). $^{13}C$ NMR: (101 MHz, $CDCl_3$) δ 141.43, 140.21, 128.46, 127.83, 35.40, 33.95, 28.34-27.21 (m), 22.58, 15.53-14.61 (m), 14.14. ATR-IR ($cm^{-1}$): 2956, 2927, 2857, 2222, 2079, 1514. HRMS: ($EI^+$) m/z: $[M]^+$ Calcd for $C_{12}H_{13}D_5$ 168.1722; Found 167.1716.

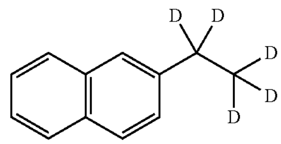 [SMILES: [2H]C([2H])([2H])C([2H])([2H])c1ccc2ccccc2c1]

2-(Ethyl-d$_5$)naphthalene [6b]. According to the general procedure E, (S)-DTBM-SEGPHOS (10.4 mg, 0.0088 mmol, 0.022 eq.), Cu(OAc)$_2$ (40 μL of a 0.2 M solution in THF, 0.008 mmol, 0.02 eq.), THF (0.16 mL), then dimethoxy(methyl)silane-d (0.38 mL of 5.3 M solution in hexanes, 2 mmol, 5 eq.) were combined in a 2-dram vial followed by addition of a solution of 2-(ethynyl-d)naphthalene (61.2 mg, 0.4 mmol, 1 eq.), THF (0.2 mL), and 2-propanol-OD (74 μL, 0.96 mmol, 2.4 eq.). The 2-dram vial was capped with a red pressure relief cap, and the reaction stirred for 21 h at 60° C. After silica plug filtration using diethyl ether (100 mL) as the eluent, the solvent was concentrated, and the crude brown oil was dry loaded onto a silica gel column. Flash chromatography using 350 mL of hexanes as eluent gave the pure product as a clear, yellow oil (46.0 mg, 0.285 mmol, 71% yield).

$^1H$ NMR: (400 MHz, $CDCl_3$) δ 7.85-7.75 (m, 3H), 7.64 (s, 1H), 7.51-7.40 (m, 2H), 7.37 (d, J=8.4, 1H), 2.80 (br s, 0.11H), 1.30 (br s, integration not determined due to overlap with grease). $^1H$ NMR: (61 MHz, $CHCl_3$) δ 2.80 (br s, 1.89D), 1.31 (br s, 2.72D). $^{13}C$ NMR: (101 MHz, $CDCl_3$) δ 141.85, 133.88, 132.11, 127.94, 127.74, 127.56, 127.22, 125.96, 125.69, 125.14, 28.97-27.70 (m), 15.45-13.94 (m). FT-IR (thin film, $cm^{-1}$): 2961, 2922, 2851, 2221, 1508, 1462. HRMS: ($EI^+$) m/z: $[M]^+$ Calcd for $C_{12}H_7D_5$ 161.1253; Found 161.1247.

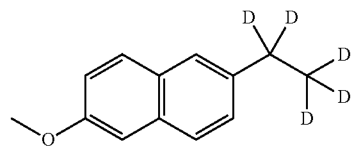 [SMILES: [2H]C([2H])([2H])C([2H])([2H])c1ccc2cc(OC)ccc2c1]

2-(Ethyl-d$_5$)-6-methoxynaphthalene [6c]. According to the general procedure E, (R)-DTBM-SEGPHOS (5.2 mg, 0.0044 mmol, 0.022 eq.), Cu(OAc)$_2$ (20 μL of a 0.2 M solution in THF, 0.004 mmol, 0.02 eq.), THF (0.08 mL), then dimethoxy(methyl)silane-d (0.17 mL of a 5.9 M solution in hexanes, 1.0 mmol, 5 eq.) were combined in a 2-dram vial followed by addition of a solution of 2-(ethynyl-d)-6-methoxynaphthalene (36.6 mg, 0.2 mmol, 1 eq.), THF (0.10 mL), and 2-propanol-d$_8$ (77 μL, 1.0 mmol, 5 eq.). The 2-dram vial was capped with a red pressure relief cap, and the reaction stirred for 17 h at 60° C. After silica plug filtration using diethyl ether (100 mL) as the eluent, the solvent was concentrated and the crude colorless solid was dry loaded onto a silica gel column. Flash chromatography using elution (50 mL of hexanes, 200 mL of 2% ethyl acetate in hexanes) gave the pure product as a white solid (31.0 mg, 0.162 mmol, 81% yield).

$^1$H NMR: (400 MHz, $CDCl_3$) δ 7.72-7.67 (m, 2H), 7.58 (d, J=0.9 Hz, 1H), 7.34 (dd, J=8.4, 1.7 Hz, 1H), 7.17-7.12 (m, 2H), 3.93 (s, 3H), 2.77 (br s, 0.18H), 1.29 (br s, integration not determined due to overlap with grease). $^2$H NMR: (61 MHz, $CHCl_3$) δ 2.77 (br s, 1.82D), 1.30 (br s, 2.77D). $^{13}$C NMR: (101 MHz, $CDCl_3$) δ 157.17, 139.50, 132.99, 129.27, 129.02, 127.68, 126.81, 125.55, 118.72, 105.74, 55.41, 28.60-27.72 (m), 15.23-14.51 (m). ATR-IR ($cm^{-1}$): 2961, 2938, 2838, 2218, 2062, 1161. HRMS: ($ESI^+$) m/z: $[M+H]^+$ Calcd for $C_{13}H_{10}D_5O$ 192.1436; Found 192.1426.

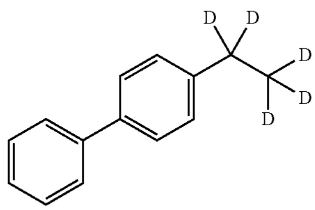 [SMILES: [2H]C([2H])([2H])C([2H])([2H])c1ccc(-c2ccccc2)cc1]

4-(Ethyl-$d_5$)-1,1'-biphenyl [6d]. According to the general procedure E, (S)-DTBM-SEGPHOS (10.4 mg, 0.0088 mmol, 0.022 eq.), $Cu(OAc)_2$ (40 μL of a 0.2 M solution in THF, 0.008 mmol, 0.02 eq.), THF (0.16 mL), then dimethoxy(methyl)silane-d (0.51 mL of 3.9 M solution in hexanes, 2 mmol, 5 eq.) were combined in a 2-dram vial followed by addition of a solution of 4-ethynyl-d-1,1'-biphenyl (71.6 mg, 0.4 mmol, 1 eq.), THF (0.2 mL), and 2-propanol-OD (74 μL, 0.96 mmol, 2.4 eq.). The 2-dram vial was capped with a red pressure relief cap, and the reaction stirred for 13 h at 60° C. After silica plug filtration using diethyl ether (100 mL) as the eluent, the solvent was concentrated, and the crude brown oil was dry loaded onto a silica gel column. Flash chromatography using 350 mL of hexanes as eluent gave the pure product as a clear, yellow oil (51.6 mg, 0.276 mmol, 69% yield).

$^1$H NMR (400 MHz, $CDCl_3$) δ 7.68-7.59 (m, 2H), 7.59-7.52 (m, 2H), 7.50-7.42 (m, 2H), 7.40-7.33 (m, 1H), 7.33-7.29 (m, 2H), 2.70 (br s, 0.10H), 1.27 (br s, integration not determined due to overlap with grease). $^2$H NMR: (61 MHz, $CHCl_3$) δ 2.70 (br s, 1.90D), 1.28 (br s, 2.87D). $^{13}$C NMR (75 MHz, $CDCl_3$) δ 143.45, 141.34, 138.74, 128.84, 128.42, 127.21, 127.15, 127.10, 28.60-27.02 (m), 15.66-14.08 (m). ATR-IR ($cm^{-1}$); 3054, 3028, 2936, 2221, 2067. HRMS: ($EI^+$) m/z: $[M+H]^+$ Calcd for $C_{14}H_9D_5$ 187.1409; Found 187.1404.

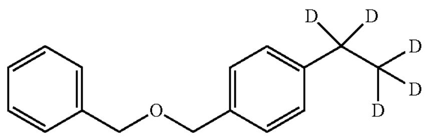 [SMILES: [2H]C([2H])([2H])C([2H])([2H])c1ccc(COCc2ccccc2)cc1]

1-((Benzyloxy)methyl)-4-(ethyl-$d_5$)benzene [6e]. According to the general procedure E. (S)-DTBM-SEGPHOS (5.2 mg, 0.0044 mmol, 0.022 eq.), $Cu(OAc)_2$ (20 μL of a 0.2 M solution in THF, 0.004 mmol, 0.02 eq.), THF (0.08 mL), then dimethoxy(methyl)silane-d (0.20 mL of a 5.9 M solution in hexanes, 1.2 mmol, 6 eq.) were combined in a 2-dram vial followed by addition of a solution of 1-((benzyloxy)methyl)-4-(ethynyl-d)benzene (45 mg, 0.2 mmol, 1 eq.), THF (0.1 mL), and 2-propanol-$d_8$ (77 μL, 1.0 mmol, 5 eq.). The 2-dram vial was capped with a red pressure relief cap, and the reaction stirred for 18 h at 60° C. After silica plug filtration using diethyl ether (100 mL) as the eluent, the solvent was concentrated, and the crude brown oil was dry loaded onto a silica gel column. Flash chromatography using gradient elution (50 mL of hexanes, 100 mL of 3% ethyl acetate in hexanes, 200 mL of 5% ethyl acetate in hexanes) gave the pure product as a colorless oil (35.0 mg, 0.151 mmol, 76% yield).

$^1$H NMR: (400 MHz, $CDCl_3$) δ 7.42-7.35 (m, 4H), 7.34-7.29 (m, 3H), 7.22 (d, J=8.1 Hz, 2H), 4.58 (s, 2H), 4.56 (s, 2H), 2.64 (br s, 0.17H), 1.21 (br s, integration not determined due to overlap with grease). $^2$H NMR: (61 MHz, $CHCl_3$) δ 2.64 (br s, 1.83D), 1.22 (br s, 2.78D). $^{13}$C NMR: (101 MHz, $CDCl_3$) δ 143.80, 138.50, 135.56, 128.51, 128.09, 128.04, 127.91, 127.70, 72.13, 72.07, 28.43-27.29 (m), 15.47-14.26 (m). ATR-IR ($cm^{-1}$): 3029, 2853, 2222, 2081, 1615, 1090, 1071. HRMS: ($ESI^+$/FTICR) m/z: $[M+Na]^+$ Calcd for $C_{16}H_{13}D_5NaO$ 254.1564; Found 254.1570.

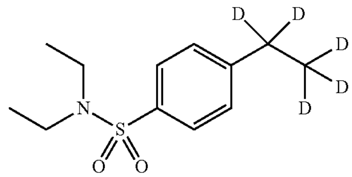 [SMILES: [2H]C([2H])([2H])C([2H])([2H])c1ccc(S(=O)(=O)N(CC)CC)cc1]

N,N-Diethyl-4-(ethyl-$d_5$)benzenesulfonamide [6f]. According to the general procedure E. (S)-DTBM-SEGPHOS (10.4 mg, 0.0088 mmol, 0.022 eq.), $Cu(OAc)_2$ (40 μL of a 0.2 M solution in THF, 0.008 mmol, 0.02 eq.), THF (0.16 mL), then dimethoxy(methyl)silane-d (0.38 mL of 5.3 M solution in hexanes, 2 mmol, 5 eq.) were combined in a 2-dram vial followed by addition of a solution of N,N-diethyl-4-(ethynyl-d)benzenesulfonamide (95 mg, 0.4 mmol, 1 eq.), THF (0.2 mL), and 2-propanol-$d_8$ (153 μL, 2.0 mmol, 5 eq.). The 2-dram vial was capped with a red pressure relief cap, and the reaction stirred for 24 h at 60° C. After silica plug filtration using diethyl ether (100 mL) as the eluent, the solvent was concentrated, and the crude brown oil was dry loaded onto a silica gel column. Flash chromatography using gradient elution (100 mL of hexanes, 100 mL 4% ethyl acetate in hexane, 300 mL of 8% ethyl acetate in hexanes) gave the pure product as a clear, yellow oil (86.1 mg, 0.35 mmol, 88% yield).

$^1$H NMR (400 MHz, $CDCl_3$) δ 7.68 (d, J=8.3 Hz, 2H), 7.27 (d, J=8.2 Hz, 2H), 3.19 (q, J=7.2 Hz, 4H), 2.63 (br s, 0.12H), 1.16 (br s, integration not determined due to overlap with grease), 1.09 (t, J=7.2 Hz, 6H). $^1$H NMR: (61 MHz, $CHCl_3$) δ 2.63 (br s, 1.88D), 1.17 (br s, 2.83D). $^{13}$C NMR (101 MHz, $CDCl_3$) δ 149.02, 137.62, 128.44, 127, 1, 42.10, 32.27-31.63 (m), 28.47-27.35 (m), 14.21. ATR-IR ($cm^{-1}$): 2976, 2936, 2870, 2225, 2079, 1332, 1150. HRMS: ($ESI^+$/FTICR) m/z: $[M+Na]^+$ Calcd for $C_{12}H_{14}D_5NNaO_2S$ 269.1343; Found 269.1351.

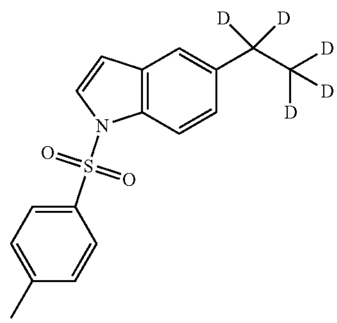 [SMILES: [2H]C([2H])([2H])C([2H])([2H])c1ccc2c(ccn2S(=O)(=O)c2ccc(C)cc2)c1]

5-(Ethyl-$d_5$)-1-tosyl-1H-indole [6g]. According to the general procedure E, (S)-DTBM-SEGPHOS (13.0 mg, 0.011 mmol, 0.055 eq.), $Cu(OAc)_2$ (50 μL of a 0.2 M solution in THF, 0.01 mmol, 0.05 eq.), THF (0.05 mL), then dimethoxy(methyl)silane-d (0.17 mL of a 5.9 M solution in hexanes, 1.0 mmol, 5 eq.) were combined in a 2-dram vial followed by addition of a solution of 5-(ethynyl-d)-1-tosyl-1H-indole (59.3 mg, 0.2 mmol, 1 eq.), THF (0.1 mL), and 2-propanol-$d_8$ (77 μL, 1.0 mmol, 5 eq.). The 2-dram vial was capped with a red pressure relief cap, and the reaction stirred for 24 h at 60° C. After silica plug filtration using diethyl ether (100 mL) as the eluent, the solvent was concentrated, and the crude brown liquid was dry loaded onto a silica gel column. Flash chromatography using gradient elution (100 mL of hexanes, 100 mL of 5% ethyl acetate in hexanes, 200 mL of 10% ethyl acetate in hexanes) gave the pure product as a colorless oil (47.7 mg, 0.156 mmol, 78% yield).

$^1$H NMR: (400 MHz, $CDCl_3$) δ 7.90 (d, J=8.5 Hz, 1H), 7.76 (d, J=8.3 Hz, 2H), 7.53 (d, J=3.6 Hz, 1H), 7.33 (d, J=1.4 Hz, 1H), 7.20 (d, J=8.4 Hz, 2H), 7.16 (dd, J=8.5, 1.4 Hz, 1H), 6.60 (d, J=3.6 Hz, 1H), 2.66 (br s, 0.18H), 2.32 (s, 3H), 1.20 (br s, integration not determined due to overlap with grease). $^2$H NMR: (61 MHz, $CHCl_3$) δ 2.66 (br s, 1.82D), 1.21 (br s, 2.84D). $^{13}$C NMR: (101 MHz, $CDCl_3$) δ 144.90, 139.42, 135.43, 133.28, 131.09, 129.93, 126.89, 126.47, 125.07, 120.09, 113.37, 109.07, 28.50-27.43 (m), 21.65, 15.86-14.60 (m). ATR-IR ($cm^{-1}$): 3038, 2922, 2221, 2081, 1367, 1130. HRMS: ($ESI^+$/FTICR) m/z: $[M+Na]^+$ Calcd for $C_{17}H_{12}D_5NNaO_2S$ 327.1186; Found 327.1195.

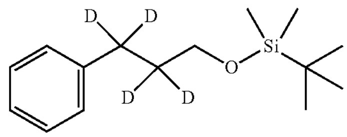 [SMILES: [2H]C([2H])(CO[Si](C)(C)C(C)(C)C)C([2H])([2H])c1ccccc1]

tert-Butyldimethyl(3-phenylpropoxy-2,2,3,3-$d_4$)silane [6h]. According to the general procedure E, (R)-DTBM-SEGPHOS (7.8 mg, 0.0066 mmol, 0.022 eq.), $Cu(OAc)_2$ (30 μL of a 0.2 M solution in THF, 0.006 mmol, 0.02 eq.), THF (0.12 mL), then dimethoxy(methyl)silane-d (0.28 mL, 1.5 mmol, 5.3 M solution in hexanes, 5 eq.) were combined in a 2-dram vial followed by addition of a solution of ((3-(phenyl)prop-2-yn-1-yl)oxy)(tert-butyl)dimethylsilane (73.8 mg, 0.3 mmol, 1 eq.), THF (0.15 mL), and 2-propanol-$d_8$ (115 μL, 1.5 mmol, 5.0 eq.). The 2-dram vial was capped with a red pressure relief cap, and the reaction stirred for 19 h at 60° C. After silica plug filtration using diethyl ether (100 mL) as the eluent, the solvent was concentrated, and the crude brown oil was dry loaded onto a silica gel column. Flash chromatography using gradient elution (100 mL of hexanes) gave the pure product as a clear and colorless oil (53.0 mg, 0.208 mmol, 69% yield).

$^1$H NMR (300 MHz, $CDCl_3$) δ 7.38-7.26 (m, 2H), 7.22-7.19 (m, 3H), 3.65 (s, 2H), 2.67 (br s, 0.11H), 1.83 (br s, 0.16H), 0.94 (s, 9H), 0.08 (s, 6H). $^{13}$C NMR (75 MHz, $CDCl_3$) δ 142.34, 128.61, 128.41, 125.80, 62.37, 34.54-33.06 (m), 32.18-30.70 (m), 26.11, 18.48, −5.13. ATR-IR ($cm^{-1}$): 2928, 2894, 2856, 2211, 2116, 1085. HRMS: ($ESI^+$) m/z: $[M+H]^+$ Calcd for $C_{15}H_{23}D_4OSi$ 255.2082; Found 255.2072.

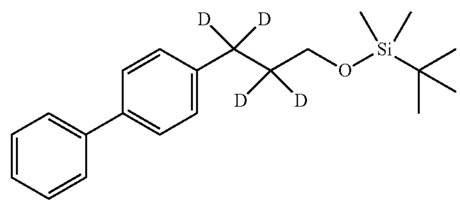 [SMILES: [2H]C([2H])(CO[Si](C)(C)C(C)(C)C)C([2H])([2H])c1ccc(-c2ccccc2)cc1]

(3-([1,1'-Biphenyl]-4-yl)propoxy-2,2,3,3-$d_4$)(tert-butyl)dimethylsilane [6i]. According to the general procedure E, (S)-DTBM-SEGPHOS (8 mg, 0.0068 mmol, 0.022 eq.), $Cu(OAc)_2$ (31 μL of a 0.2 M solution in THF, 0.0062 mmol, 0.02 eq.), THF (0.13 mL), then dimethoxy(methyl)silane-d (0.29 mL, 1.55 mmol, 5.3M solution in hexanes, 5 eq.) were combined in a 2-dram vial followed by addition of a solution of ((3-([1,1'-biphenyl]-4-yl)prop-2-yn-1-yl)oxy)(tert-butyl)dimethylsilane (100 mg, 0.31 mmol, 1 eq.). THF (0.15 mL), and 2-propanol-OD (119 μL, 1.55 mmol, 5 eq.). The 2-dram vial was capped with a red pressure relief cap, and the reaction stirred for 24 h at 60° C. After silica plug filtration using diethyl ether (100 mL) as the eluent, the solvent was concentrated. Flash chromatography using gradient elution (100 mL of hexanes, 100 mL of 2% ethyl acetate in hexanes, 100 mL of 5% ethyl acetate in hexanes gave the pure product as a white crystalline solid (89 mg, 0.27 mmol, 87% yield).

$^1$H NMR: (400 MHz, $CDCl_3$) δ 7.64-7.59 (m, 2H), 7.55 (d, J=8.2 Hz, 2H), 7.46 (t, J=8.4 Hz, 2H), 7.38-7.32 (m, 1H), 7.32-7.27 (m, 2H), 3.69 (s, 2H), 2.73 (br s, 0.08H), 1.88 (t, J=6.6 Hz, 0.13H), 0.96 (d, J=2.6 Hz, 9H), 0.11 (d, J=1.3 Hz, 6H). $^{13}$C NMR: (101 MHz, $CDCl_3$) δ 141.49, 141.28, 138.77, 129.03, 128.84, 127.16, 127.13, 127.11, 62.38, 34.31-33.20 (m), 31.45-30.72 (m), 26.12, 18.49, −5.11. ATR-IR ($cm^{-1}$): 2953, 2926, 2854, 2203, 2115, 1251, 1110, 1065. HRMS: ($ESI^+$/FTICR) m/z: $[M+Na]^+$ Calcd for $C_{21}H_{26}D_4NaOSi$ 353.2209; Found 353.2219.

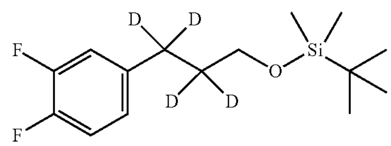 [SMILES: [2H]C([2H])(CO[Si](C)(C)C(C)(C)C)C([2H])([2H])c1ccc(F)c(F)c1]

tert-Butyl(3-(3,4-difluorophenyl)propoxy-2,2,3,3-$d_4$)dimethylsilane [6j]. According to the general procedure E, (S)-DTBM-SEGPHOS (5.2 mg, 0.0044 mmol, 0.022 eq.), $Cu(OAc)_2$ (20 μL of a 0.2 M solution in THF, 0.004 mmol, 0.02 eq.), THF (0.08 mL), then dimethoxy(methyl)silane-d (0.14 mL of a 5.9 M solution in hexanes, 0.8 mmol, 4 eq.) were combined in a 2-dram vial followed by addition of a solution of 1-((benzyloxy)methyl)-4-(ethynyl-d)benzene (56.5 mg, 0.2 mmol, 1 eq.), THF (0.1 mL), and 2-propanol-$d_8$ (77 μL, 1.0 mmol, 5 eq.). The 2-dram vial was capped with a red pressure relief cap, and the reaction stirred for 24 h at 60° C. After silica plug filtration using diethyl ether (100 mL) as the eluent, the solvent was concentrated, and the crude colorless oil was dry loaded onto a silica gel column. Flash chromatography using gradient elution (100 mL of hexanes followed by 200 mL of 1% ethyl acetate in hexanes) gave the pure product as a clear and colorless oil (44.6 mg, 0.154 mmol, 77% yield).

$^1H$ NMR: (400 MHz, $CDCl_3$) δ 7.08-6.95 (m, 2H), 6.90-6.85 (m, 1H), 3.60 (s, 2H), 2.61 (br s, 0.19H), 1.76 (br s, 0.20H), 0.91 (s, 9H), 0.05 (s, 6H). $^{13}C$ NMR: (75 MHz, $CDCl_3$) δ 150.25 (dd, J=247.1, 12.6 Hz), 148.77 (dd, J=245.1, 12.6 Hz), 139.25 (dd, J=4.3 Hz), 124.33 (dd, J=5.7, 3.5 Hz), 117.26 (d, J=16.6 Hz), 116.97 (d, J=16.9 Hz), 61.87, 34.20-32.83 (m), 31.26-30.07 (m), 26.08, 18.46, −5.17. $^{19}F$ NMR: (376 MHz, $CDCl_3$) δ −138.80, −142.71. ATR-IR ($cm^{-1}$): 2955, 2929, 2857, 2211, 2119, 1607, 1518, 1254, 1087. HRMS: ($ESI^+$) m/z: $[M+H]^+$ Calcd for $C_{15}H_{21}D_4F_2OSi$ 291.1894; Found 291.1881.

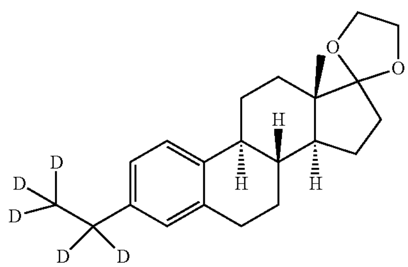

(8R,9S,13S,14S)-3-(Ethyl-$d_5$)-13-methyl-6,7,8,9,11,12,13,14,15,16-decahydrospiro[cyclopenta[a]phenanthrene-17,2'-[1,3]dioxolane] [6k]. According to the general procedure E, (R)-DTBM-SEGPHOS (5.2 mg, 0.0044 mmol, 0.022 eq.), $Cu(OAc)_2$ (20 μL of a 0.2 M solution in THF, 0.004 mmol, 0.02 eq.), THF (0.08 mL), then dimethoxy(methyl)silane-d (0.19 mL of 5.3 M solution in hexanes, 1 mmol, 5 eq.) were combined in a 2-dram vial followed by addition of a solution of (8R,9S,13S,14S)-3-(ethynyl-d)-13-methyl-6,7,8,9,11,12,13,14,15,16-decahydrospiro[cyclopenta[a]phenanthrene-17,2'-[1,3]dioxolane] (64.6 mg, 0.2 mmol, 1 eq.), THF (0.1 mL), and 2-propanol-OD (77 μL, 1.0 mmol, 5 eq.). The 2-dram vial was capped with a red pressure relief cap, and the reaction stirred for 38 h at 60° C. After silica plug filtration using diethyl ether (100 mL) as the eluent, the solvent was concentrated, and the crude brown oil was dry loaded onto a silica gel column. Flash chromatography using gradient elution (100 mL of hexanes, 100 mL of 3% ethyl acetate in hexane, 100 mL of 5% ethyl acetate in hexanes, 100 mL of 8% ethyl acetate in hexanes, 200 mL of 9% ethyl acetate in hexanes, 100 mL of 10% ethyl acetate in hexanes) gave the pure product as a clear, yellow oil (48.7 mg, 0.147 mmol, 74% yield).

$^1H$ NMR (400 MHz, $CDCl_3$) δ 7.25 (d, J=8.0 1H), 7.01 (d, J=8.0, 1H), 6.95 (s, 1H), 4.08-3.83 (m, 4H), 2.92-2.83 (m, 2H), 2.58 (br s, 0.15H), 2.41-2.24 (m, 2H), 2.11-2.00 (m, 1H), 1.96-1.74 (m, 4H), 1.71-1.61 (m, 1H), 1.60-1.30 (m, 5H), 1.20 (br s, 0.20H), 0.90 (s, 3H), $^2H$ NMR: (61 MHz, $CHCl_3$) δ 2.58 (br s, 1.85D), 1.21 (br s, 2.80D). $^{13}C$ NMR (101 MHz, $CDCl_3$) δ 141.46, 137.78, 136.71, 128.57, 125.45, 125.28, 119.58, 65.38, 64.71, 49.62, 46.31, 44.11, 39.10, 34.37, 30.92, 29.70, 28.12-27.41 (m), 27.18, 26.12, 22.51, 15.46-14.21 (m), 14.46. ATR-IR ($cm^{-1}$): 2966, 2936, 2872, 2221, 2075, 1700, 1610, 1103, 1042. HRMS: ($ESI^+$) m/z: $[M+Na]^+$ Calcd for $C_{22}H_{25}D_5NaO_2$ 354.2452; Found 354.2462.

V. Mechanistic Studies

General Procedure for Time Reaction Analysis. In a $N_2$ filled glovebox, (R)-DTBM-SEGPHOS (5.2 mg, 0.0044 mmol, 0.022 eq.), $Cu(OAc)_2$ (20 μL of a 0.2 M solution in THF, 0.004 mmol, 0.02 eq.), and THF (0.08 mL) were added to an oven-dried 2-dram vial followed by dropwise addition of dimethoxy(methyl)silane (123 μL, 1 mmol, 5 eq.). A color change from green/blue to orange was observed while stirring for 15 minutes. In a separate oven-dried 1-dram vial was added the ((3-(phenyl)prop-2-yn-1-yl)oxy)(tert-butyl) dimethylsilane (49 mg, 0.2 mmol, 1 eq.), THF (0.1 mL), and 2-propanol (37 μL, 0.48 mmol, 2.4 eq.). The solution in the 1-dram vial was added dropwise over 20 seconds to the 2-dram vial. The total volume of THF was calculated based on having a final reaction concentration of 1M based on the alkyne substrate. The 2-dram vial was capped with a red pressure relief cap, taken out of the glovebox, and stirred at 60° C. for the designated time. The reaction mixture was then filtered through a 1" silica plug with 20 mL of $Et_2O$ followed by 80 mL of $Et_2O$ to elute the remaining product into a 200 mL round bottom flask. After removing the $Et_2O$ by rotary evaporation, the crude product was isolated by flash column chromatography using gradient elution (100 mL of hexanes followed by 200 mL of 5% ethyl acetate in hexanes) to give tert-butyldimethyl(3-phenylpropoxy)silane as a clear, colorless oil. The spectra matched the previously reported NMR data.[15]

TABLE S2

Reaction Analysis

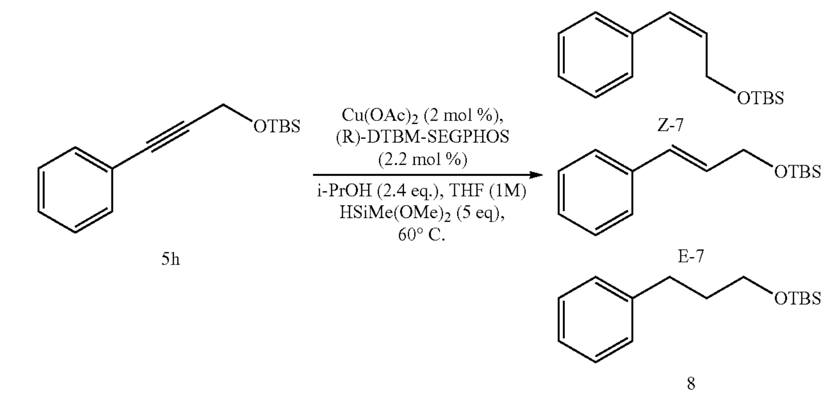

5h

Z-7

E-7

8

| Entry | Reaction Time (min) | Z-7[a](%) | E-7[a](%) | 8[a](%) |
|---|---|---|---|---|
| 1 | 15 | 74 | 0 | 6 |
| 2 | 30 | 48 | 2 | 25 |
| 3 | 45 | 40 | 5 | 36 |
| 4 | 90 | 17 | 7 | 54 |
| 5 | 180 | 7 | 5 | 61 |
| 6 | 9 h | 0 | 0 | 79 |

[a]Yields of each product were determined by $^1H$ NMR of the combined products after purification.

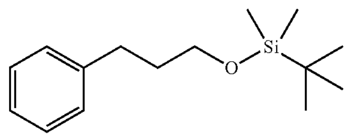 [SMILES: CC(C)(C)[Si](C)(C)OCCCc1ccccc1]

tert-Butyldimethyl(3-phenylpropoxy)silane (8)

$^1H$ NMR (400 MHz, $CDCl_3$) δ 7.33-7.25 (m, 2H), 7.23-7.16 (M, 3H), 3.65 (t, J=6.3 Hz, 2H), 2.69 (t, J=7.9 Hz, 2H), 1.90-1.80 (m, 2H), 0.93 (s, 9H), 0.07 (s, 6H). $^{13}C$ NMR (101 MHz, $CDCl_3$) δ 142.40, 128.62, 128.41, 125.81, 62.51, 34.61, 32.24, 26.11, 18.49, −5.12

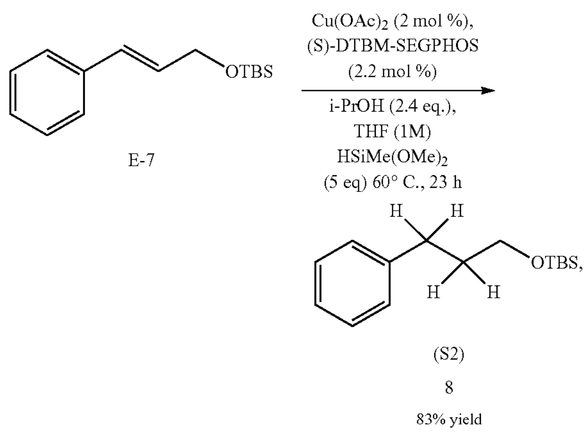

E-7

(S2)

8 tert-Butyldimethyl(3-phenylpropoxy)silane (8). In a $N_2$ filled glovebox, (S)-DTBM-SEGPHOS (7.8 mg, 0.0066 mmol, 0.022 eq.), $Cu(OAc)_2$ (30 μL of a 0.2 M solution in THF, 0.006 mmol, 0.02 eq.), and THF (0.12 mL) were added to an oven-dried 2-dram vial followed by dropwise addition of dimethoxy(methyl)silane (185 μL, 1.5 mmol, 5 eq.). A color change from green/blue to orange was observed while stirring for 15 minutes. In a separate oven-dried 1-dram vial was added the E-7 (74.5 mg, 0.3 mmol, 1 eq.), THF (0.15 mL), and 2-propanol (55 μL, 0.72 mmol, 2.4 eq.). The solution in the 1-dram vial was added dropwise over 20 seconds to the 2-dram vial. The total volume of THF was calculated based on having a final reaction concentration of 1M based on the alkyne substrate. The 2-dram vial was capped with a red pressure relief cap, taken out of the glovebox, and stirred at 60° C. for 23 h. The reaction mixture was then filtered through a 1" silica plug with 20 mL of $Et_2O$ followed by 80 mL of $Et_2O$ to elute the remaining product into a 200 mL round bottom flask. After removing the $Et_2O$ by rotary evaporation, the crude product was isolated by flash column chromatography using gradient elution (100 mL of hexanes followed by 100 mL of 2% ethyl acetate in hexanes) to give tert-butyldimethyl(3-phenylpropoxy)silane as a clear, colorless oil (62 mg, 0.248 mmol, 83% yield). The spectra matched the previously reported NMR data.

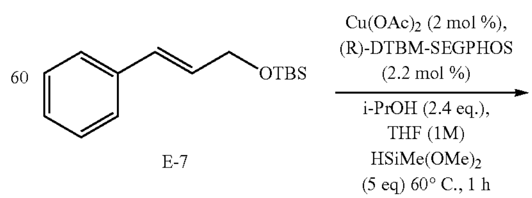

E-7

-continued

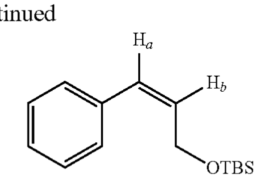

Z-7

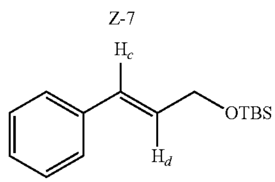

E-7

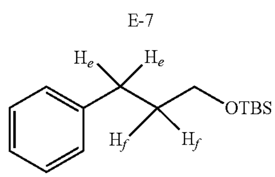

8

(S3)

tert-Butyldimethyl(3-phenylpropoxy)silane (8). In a $N_2$ filled glovebox, (S)-DTBM-SEGPHOS (7.8 mg, 0.0066 mmol, 0.022 eq.). $Cu(OAc)_2$ (30 μL of a 0.2 M solution in THF, 0.006 mmol, 0.02 eq.), and THF (0.12 mL) were added to an oven-dried 2-dram vial followed by dropwise addition of dimethoxy(methyl)silane (185 μL, 1.5 mmol, 5 eq.). A color change from green/blue to orange was observed while stirring for 15 minutes. In a separate oven-dried 1-dram vial was added the E-7 (74.5 mg, 0.3 mmol, 1 eq.), THF (0.15 mL), and 2-propanol (55 μL, 0.72 mmol, 2.4 eq.). The solution in the 1-dram vial was added dropwise over 20 seconds to the 2-dram vial. The total volume of THF was calculated based on having a final reaction concentration of 1M based on the alkyne substrate. The 2-dram vial was capped with a red pressure relief cap, taken out of the glovebox, and stirred at 60° C. for 1 h. The reaction mixture was then filtered through a 1" silica plug with 20 mL of $Et_2O$ followed by 80 mL of $Et_2O$ to elute the remaining product into a 200 mL round bottom flask. After removing the $Et_2O$ by rotary evaporation, the crude product was isolated by flash column chromatography using gradient elution (100 mL of hexanes followed by 100 mL of 2% ethyl acetate in hexanes) to give tert-butyldimethyl(3-phenylpropoxy)silane as a clear, colorless oil (61 mg combination of all products, 42% alkane 8, 39% E-7, trace Z-7). See $^1H$ NMR below.

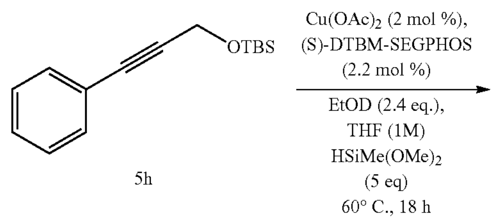

5h

-continued

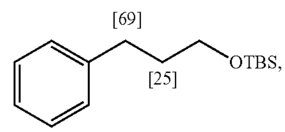

9

70% yield (S4)

*Percentage deuterium incorperation at each carbon indicated in red brackets

Transfer Hydrodeuteration Experiment: In a $N_2$ filled glovebox, (S)-DTBM-SEGPHOS (7.8 mg, 0.0066 mmol, 0.022 eq.), $Cu(OAc)_2$ (30 μL of a 0.2 M solution in THF, 0.006 mmol, 0.02 eq.), and THF (0.12 mL) were added to an oven-dried 2-dram vial followed by dropwise addition of dimethoxy(methyl)silane (185 μL, 1.5 mmol, 5 eq.). A color change from green/blue to orange was observed while stirring for 15 minutes. In a separate oven-dried 1-dram vial was added the ((3-(phenyl)prop-2-yn-1-yl)oxy)(tert-butyl)dimethylsilane (73.8 mg, 0.3 mmol, 1 eq.), THF (0.15 mL), and ethanol-OD (42 μL, 0.72 mmol, 2.4 eq.). The solution in the 1-dram vial was added dropwise over 20 seconds to the 2-dram vial. The 2-dram vial was capped with a red pressure relief cap, taken out of the glovebox, and stirred at 60° C. for 18 h. The reaction mixture was then filtered through a 1" silica plug with 20 mL of $Et_2O$ followed by 80 mL of $Et_2O$ to elute the remaining product into a 200 mL round bottom flask. After removing the $Et_2O$ by rotary evaporation, the crude product was isolated by flash column chromatography using gradient elution (100 mL of hexanes followed by 100 mL of 2% ethyl acetate in hexanes) to give tert-butyldimethyl(3-phenylpropoxy)silane-$d_2$ as a clear, colorless oil (53 mg, 0.21 mmol, 70% yield).

$^1H$ NMR (400 MHz, $CDCl_3$): δ 7.34-7.27 (m, 2H), 7.25-7.17 (m, 3H), 3.70-3.63 (m, 2H), 2.75-2.64 (m, 0.62H), 1.88-1.83 (m, 1.51H), 0.94 (s, 9H), 0.09 (s, 6H). $^{13}C$ NMR (101 MHz, $CDCl_3$):

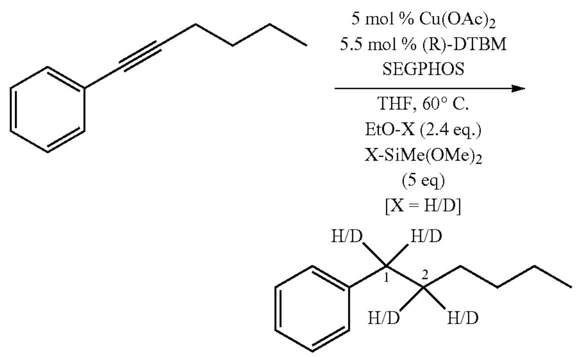

Cond. A: $C_1$ = 80% d inc., $C_2$ = 7% d inc.
Cond. B: $C_1$ = 23% d inc., $C_2$ = 67% d inc.

Cond. A:

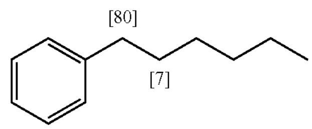

*Percentage deuterium incorperation at each carbon indicated in red brackets

Hexylbenzene-$d_2$ [10]. In a $N_2$ filled glovebox. (R)-DTBM-SEGPHOS (13 mg, 0.0011 mmol, 0.055 eq.), $Cu(OAc)_2$ (50 μL of a 0.2 M solution in THF, 0.01 mmol, 0.05 eq.), and THF (0.05 mL) were added to an oven-dried 2-dram vial followed by dropwise addition of dimethoxy (methyl)silane (123 μL, 1 mmol, 5 eq.). A color change from green/blue to orange was observed while stirring for 15 minutes. In a separate oven-dried 1-dram vial was added the 1-hexyn-1-yl-benzene (31.7 mg, 0.2 mmol, 1 eq.), THF (0.1 mL), and 2-propanol-$d_8$ (77 μL, 1 mmol, 5 eq.). The solution in the 1-dram vial was added dropwise over 20 seconds to the 2-dram vial. The 2-dram vial was capped with a red pressure relief cap, taken out of the glovebox, and stirred at 60° C. for 21 h. The reaction mixture was then filtered through a 1" silica plug with 20 mL of $Et_2O$ followed by 80 mL of $Et_2O$ to elute the remaining product into a 200 mL round bottom flask. After removing the $Et_2O$ by rotary evaporation, the crude product was isolated by flash column chromatography using gradient elution (200 mL of hexanes) to give hexylbenzene-$d_2$ as a clear, colorless oil (28 mg, 0.17 mmol, 85% yield).

$^1$H NMR (400 MHz, $CDCl_3$) δ 7.32-7.24 (m, 2H), 7.22-7.13 (m, 3H), 2.64-2.55 (m, 0.41H), 1.66-1.54 (m, 2H), 1.40-1.21 (m, 6H), 0.89 (t, J=6.7 Hz, 3H). $^2$H NMR: (61 MHz, $CHCl_3$) δ 2.59 (br s, 1.59D), 1.62 (br s, 0.13D). ATR-IR ($cm^{-1}$): 3084, 3061, 3025, 2956, 2923, 2855, 2361, 2191. HRMS: ($EI^+$) m/z: $[M]^+$ Calcd for $C_{12}H_{16}D_2$ 164.1500. Found 164.1528.

Cond. B:

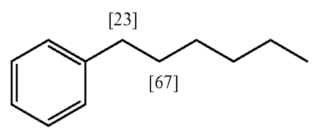

*Percentage deuterium incorperation at each carbon indicated in red brackets

Hexylbenzene-$d_2$ [11]. In a $N_2$ filled glovebox. (R)-DTBM-SEGPHOS (26 mg, 0.022 mmol, 0.055 eq.), $Cu(OAc)_2$ (100 μL of a 0.2 M solution in THF, 0.02 mmol, 0.05 eq.), and THF (0.15 mL) were added to an oven-dried 2-dram vial followed by dropwise addition of dimethoxy (methyl)silane-d (288 μL, 2 mmol, 5 eq.). A color change from green/blue to orange was observed while stirring for 15 minutes. In a separate oven-dried 1-dram vial was added the 1-hexyn-1-yl-benzene (63 mg, 0.4 mmol, 1 eq.), THF (0.15 mL), and 2-propanol (153 μL, 2 mmol, 5 eq.). The solution in the 1-dram vial was added dropwise over 20 seconds to the 2-dram vial. The 2-dram vial was capped with a red pressure relief cap, taken out of the glovebox, and stirred at 60° C. for 21 h. The reaction mixture was then filtered through a 1" silica plug with 20 mL of $Et_2O$ followed by 80 mL of $Et_2O$ to elute the remaining product into a 200 mL round bottom flask. After removing the $Et_2O$ by rotary evaporation, the crude product was isolated by flash column chromatography using gradient elution (200 mL of hexanes) to give hexylbenzene-$d_2$ as a clear, colorless oil (52 mg, 0.317 mmol, 79% yield).

$^1$H NMR (400 MHz, $CDCl_3$) δ 7.33-7.27 (m, 2H), 7.24-7.17 (m, 3H), 2.66-2.58 (m, 1.54H), 1.69-1.56 (m, 0.76H), 1.42-1.24 (m, 6H), 0.92 (t, J=6.8 Hz, 3H). $^1$H NMR: (61 MHz, $CHCl_3$) δ 2.61 (br s, 0.46D), 1.60 (br s, 1.34D). $^{13}$C NMR (101 MHz, $CDCl_3$) δ 143.1, 128.5, 128.4, 125.7, 36.2-35.3 (m), 31.9, 31.7-30.9 (m), 29.1, 22.8, 14.3. ATR-IR ($cm^{-1}$): 3085, 3063, 3026, 2956, 2921, 2871, 2855, 2361, 2150. HRMS: ($EI^+$) m/z: $[M]^+$ Calcd for $C_{12}H_{16}D_2$ 164.1500; Found 164.1528. δ 142.36 (t, J=3.4 Hz), 128.61, 128.41, 125.81, 62.46 (t, J=2.6 Hz), 34.68-33.88 (m), 32.31-31.42 (m), 26.11, 18.48, −5.13.

VIII. References

1. Kratish, Y.; Bravo-Zhivotovskii, D.; Apeloig, Y. Convenient Synthesis of Deuterosilanes by Direct H/D Exchange Mediated by Easily Accessible Pt(0) Complexes. *ACS Omega* 2017, 2, 372-376.
2. Chen, Z.; Liang, P.; Ma, X.; Luo, H.; Xu, G.; Liu, T.; Wen, X.; Zheng, J.; Ye, H. Catalyst-Free Annulation of 2-Pyridylacetates and Ynals with Molecular Oxygen: An Access to 3-Acylated Indolizines. *J. Org. Chem.* 2019, 84, 1630-1639.
3. Klapars, A.; Buchwald, S. L. Copper-Catalyzed Halogen Exchange in Aryl Halides: An Aromatic Finkelstein Reaction. *J. Am. Chem. Soc.* 2002, 124, 14844-14845.
4. Klyatskaya, S. V.; Tretyakov, E. V.; Vasilevsky, S. F. Cross-coupling of Aryl Iodides with Paramagnetic Terminal Acetylenes Derived from 4,4,5,5-tetramethyl-2-imidazoline-1-oxyl 3-oxide. *Russ. Chem. Bull. Int. Ed.* 2002, 51, 128-134.
5. Li, J. J.; Limberakis, C.; Pflum, D. A. *Modern Organic Synthesis in the Laboratory*; Oxford University Press: New York, 2007; 1, 171-172.
6. Guo, J.; Shen, X.; Lu, Z. Regio- and Enantioselective Cobalt-Catalyzed Sequential Hydrosilylation/Hydrogenation of Terminal Alkynes. *Angew. Chem. Int. Ed.* 2017, 56, 615-618.
7. Chen, M.; Ichikawa, S.; Buchwald, S. L. Rapid and Efficient Copper-Catalyzed Finkelstein Reaction of (Hetero)Aromatics under Continuous-Flow Conditions. *Angew. Chem. Int. Ed.* 2015, 54, 263-266.
8. Zhang, W., Kuang, C.; Yang, Q. Efficient One-pot Synthesis of 4-Ethynylbenzenesulfonamides. *Z. Naturforsch* 2009, 64b, 292-296.
9. Shi, S.; Buchwald, S. L. Copper-catalyzed Selective Hydroamination Reactions of Alkynes. *Nat. Chem.* 2015, 7, 38-44.
10. Wang, Y.; Yin, Y.; Zhang, Q.; Pan, W.; Guo, H., Pei, K. $Bi(OTf)_3$ Catalyzed Synthesis of Acyclic β-sulfanyl Ketones via a Tandem Meyer-Schuster Rearrangement/Conjugate Addition Reaction. *Tetrahedron Lett.* 2019, 60, 2030-2034.
11. Furuya, T.; Strom, A. E.; Ritter, T. Silver-Mediated Fluorination of Functionalized Aryl Stannanes. *J. Am. Chem. Soc.* 2009, 131, 1662-1663.
12. Su, L.; Ren, T.; Dong, J.; Liu, L.; Xie, S.; Yuan, L.; Zhou, Y.; Yin, S. Cu(I)-Catalyzed 6-endo-dig Cyclization of Terminal Alkynes, 2-Bromoaryl Ketones, and Amides toward 1-Naphthylamines: Applications and Photophysical Properties. *J. Am. Chem. Soc.* 2019, 141, 2535-2544

13. Wang, C.; Rakshit, S.; Glorius, F. Palladium-Catalyzed Intermolecular Decarboxylative Coupling of 2-Phenylbenzoic Acids with Alkynes via C—H and C—C Bond Activation. *J. Am. Chem. Soc.* 2010, 132, 14006-14008.
14. Bew, S. P.; Hiatt-Gipson, G. D.; Lovell, J. A.; Poullain, C. Mild Reaction Conditions for the Terminal Deuteration of Alkynes. *Org. Lett.* 2012, 14, 456-459.
15. Ichikawa, T.; Netsu, M.; Mizuno, M.; Mizusaki, T.; Takagi, Y.; Sawama, Y.; Monguchi, Y.; Sajiki, H. Development of a Unique Heterogeneous Palladium Catalyst for the Suzuki-Miyaura Reaction using (Hetero)aryl Chlorides and Chemoselective Hydrogenation. *Adv. Synth. Catal.* 2017, 359, 2269-2279.

Example 3—Making Deuterated Small Molecules Selectively with Precision

Overview

The vision of this research program is to modernize the synthesis of deuterated small molecules. Organic chemists have grown accustom to highly selective transition metal-catalyzed reactions to forge C—C, C—O and C—N bonds using non-toxic, inexpensive and commercially available metals, ligands and reagents. Considering these advances in selective functionalization, deuterium installation should also be possible with full stereocontrol and without over- and under-deuteration impurities. However, this level of control exists only in rare cases and spectroscopic techniques to support advances in selective deuteration reactions are lagging. We are developing safe, base metal-catalyzed reactions, utilizing commercial ligands and reagents to selectively deuterate small molecules. In collaboration with leading spectroscopy experts in academia and industry, we are developing high-throughput, accurate and precise analytical chemistry methods to support the timely development of these reactions. Successful outcomes from this research program will cause a paradigm shift in how chemists view functionalizing a molecule with deuterium. Highly regioselective and enantioselective deuterations without significant isotopologue or isotopomer impurities will be possible. These methodological advances will enable chemists to make a deuterated compound that has exactly the number of desired deuterium, installed precisely at the desired location (s). They will be equipped with powerful spectroscopic techniques to make stereochemical assignments and enantiomeric excess determinations of chiral deuterated molecules while being able to measure deuterium impurities. We anticipate this research program will set the standards for future deuteration reactions and sufficiently expand the available deuterated chemical space to handle the ever-increasing demands for novel deuterated small molecules in the pharmaceutical industry.

Background

Deuterated small molecules are extensively used in chemical research and medicine. From an organometallic and synthetic organic chemistry context, they are often used to elucidate reaction mechanisms and perform kinetic isotope effect measurements.[1-4] In physical and analytical chemistry, they serve as valuable tools for spectroscopy or standards for high-resolution mass spectrometry.[5-8] In biochemistry, isotopically labeled compounds are used to elucidate biosynthetic pathways or determine the stereochemical course of microbiological and enzymatic reactions.[8-16] Deuterated small molecules are now commonly deployed to alter absorption, distribution, metabolism and excretion (ADME) properties of drug molecules[6, 8, 17-21] From a public health perspective, reactions that selectively deuterate small molecules are useful to develop new therapeutics. Designing deuterated bioisosteres holds tremendous potential for the development of safer therapeutics, and unlike fluorinated drug analogs,[17, 22-27] deuterated analogs usually retain the original potency and selectivity of the parent drug.[6, 8, 18, 23] Despite these advantages, only one FDA approved deuterated drug, deutetrabenazine, is currently available while another is in phase 3 clinical trials (FIG. 1).[28, 29]

A cross-functional team of scientists with expertise in process chemistry, isotope chemistry, analytical chemistry, and drug metabolism and pharmacokinetics established by the International Consortium for Innovation and Quality in Pharmaceutical Development are developing guidance to address deuterated active pharmaceutical ingredients (APIs) .[30] The team recognizes the current and future positive impact of deuterated APIs in medicine. They explain that synthetic access to deuterated compounds that are free of isotopic impurities, and analytical methods to support the characterization and quality control of the target molecules remain bottlenecks to unleashing the full potential of deuterated APIs in drug discovery. Citing that isotopologues or isotopomers lacking deuteriums at the metabolically active site(s) will result in shorter half-life values, coupled with impractical purification strategies to separate isotopic impurities, the team states: "Therefore, it is critical that manufacturing processes have robust control strategies to ensure that the desired degree of deuteration is produced and that appropriate safety and performance indicating specifications be established for any isotopologue or isotopomer present in the API."[30] To meet this current and future demand for selectively deuterated small molecules, we are pioneering a research program that addresses both the synthetic and analytical chemistry bottlenecks. We will develop highly selective, base metal-catalyzed transfer deuteration and transfer hydrodeuteration reactions. We will also pioneer new analytical chemistry methods that are required to unlock this field of chemistry. Synthetically, a key challenge we will tackle is the ability to distinguish between hydrogen (H) and deuterium (D) atoms for selective functionalization. While D has a 2-fold higher mass than H and a reduced vibrational stretching frequency exists for a C-D bond versus a C—H bond, it is very difficult to distinguish between H and D given their similar $pK_a$ values, molar volumes, lipophilicities and bond lengths when comparing C—H to C-D bonds.[6, 17, 19, 31, 32] Furthermore, for deuteration to be useful in medicinal chemistry, reactivity should occur at the target functional group while leaving other functionalities in the molecule undisturbed. Other desirable reaction features we will target include using commercial reagents, a first-row transition metal catalyst and commercial ligands.

Deuterium was reported by Urey in 1932.[33] Despite this report 88 years ago, it was not until a growing demand for isotopically labeled internal standards for mass spectrometry (MS) sparked significant research efforts towards selective deuterium installation.[7, 34] The state-of-the-art methods for selective deuterium incorporation include metal-catalyzed hydrogen isotope exchange (HIE) and selective reductive deuteration processes. While significant progress has been made in the HIE field, a major drawback to metal-catalyzed HIE reactions is controlling site-selectivity. Oftentimes, over-deuteration of multiple reactive C—H bonds within a molecule and incomplete deuteration of the desired sites are reported.[7, 34-39] While heterogeneous metal-catalyzed HIE is also routinely used, it typically proceeds with even less control over site-selectivity as reaction tuning is limited in the absence of a tunable ligand.[7, 34, 40, 41]

In selective reductive deuteration chemistry, the state-of-the-art regioselective and/or stereoselective methods highlight the tremendous potential for selective deuterium installation but remain very limited in scope and practicality. For example, a method to prepare cyclohexene isotopologues and stereoisotopomers from benzene in the presence of stoichiometric tungsten and $H/D^+$ reagents was recently reported.[42] However, the stoichiometric tungsten complex remains bound to the deuterated cyclohexene product(s) and further high-temperature (200° C.) transformations are required to liberate the product from the metal complex. The recently reported selective transfer hydrodeuterations represent the first highly regioselective transformations to incorporate H and D across an alkene.[43, 44] Aside from these reports, only modest selectivities had been reported for selective hydrodeuteration.[45-48] Yet, the reaction scopes are limited to only very activated alkenes (i.e. 1,1-disubstituted alkenes with electron donating substituents) where at least one substituent is an aryl group.[49] Furthermore, no conversion is observed in the presence of nitrogen containing heterocycles and the transfer hydrodeuteration sources are not commercial and require multistep syntheses.

Recent Progress

Figure 2:
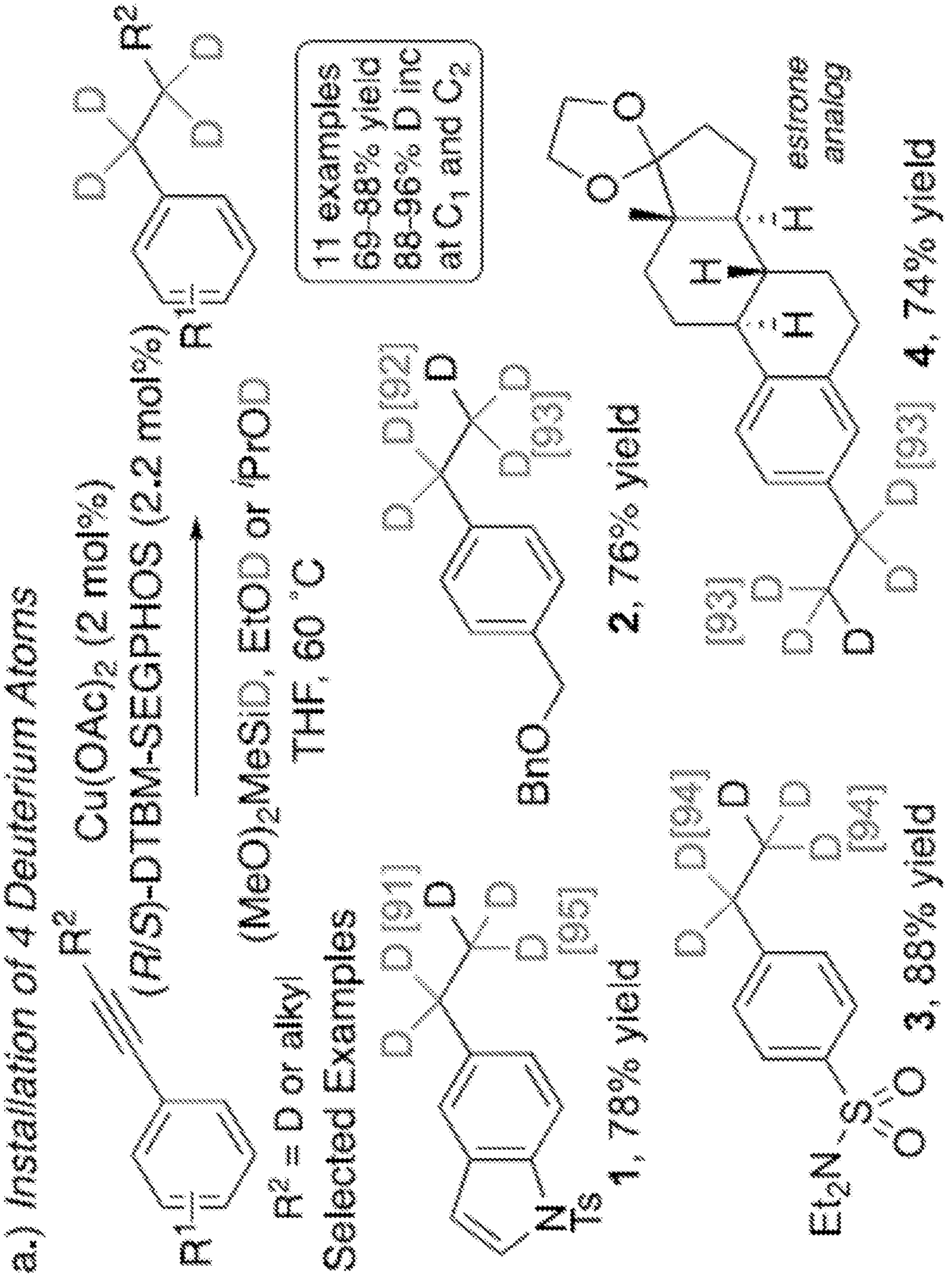
FIG. 2. Selective Cu-catalyzed alkyne transfer deuteration/hydrodeuteration. a) installation of 4 deuterium atoms; b) proposed mechanism; c) catalyst-controlled regioselective transfer hydrodeuteration; and d) ligand legend.
Figure 2:
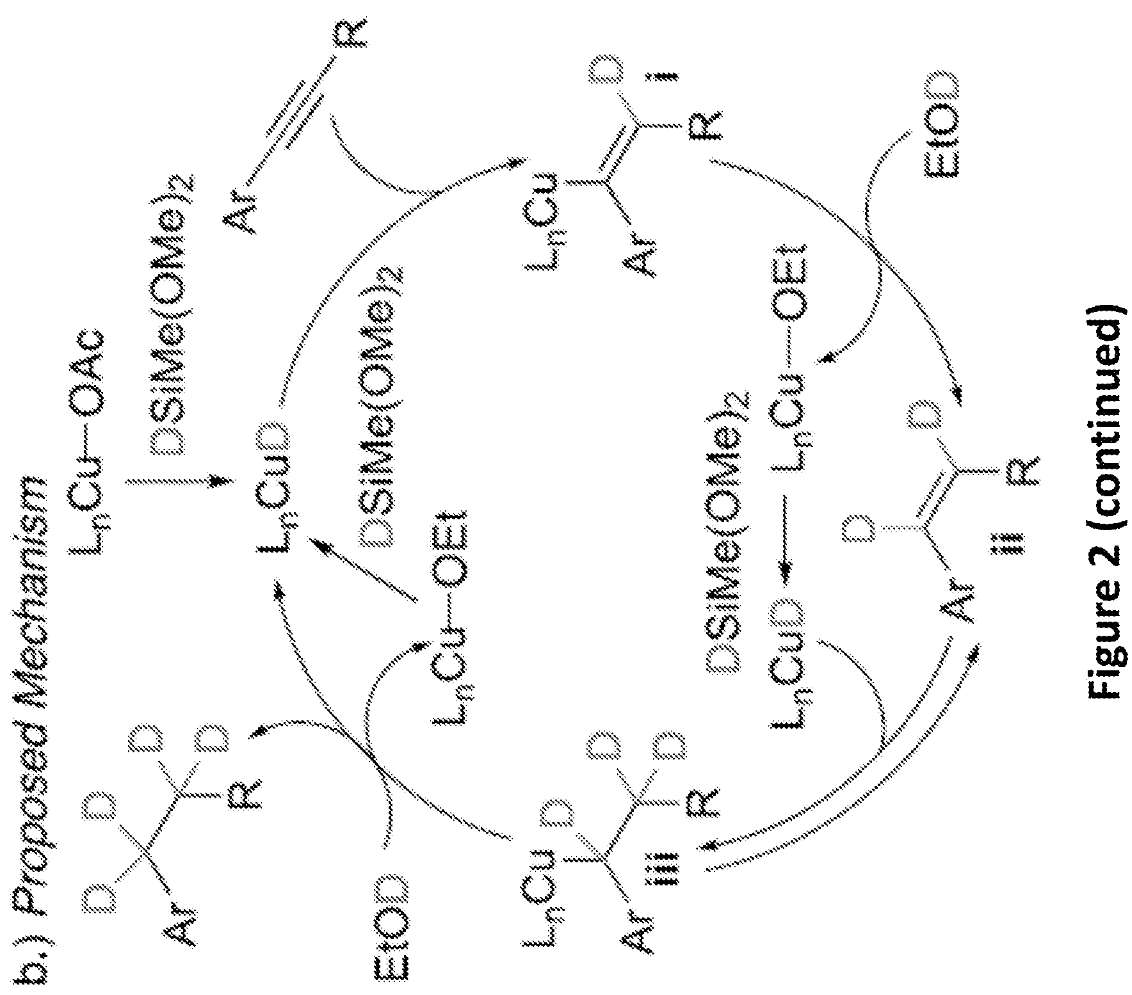
Figure 2:
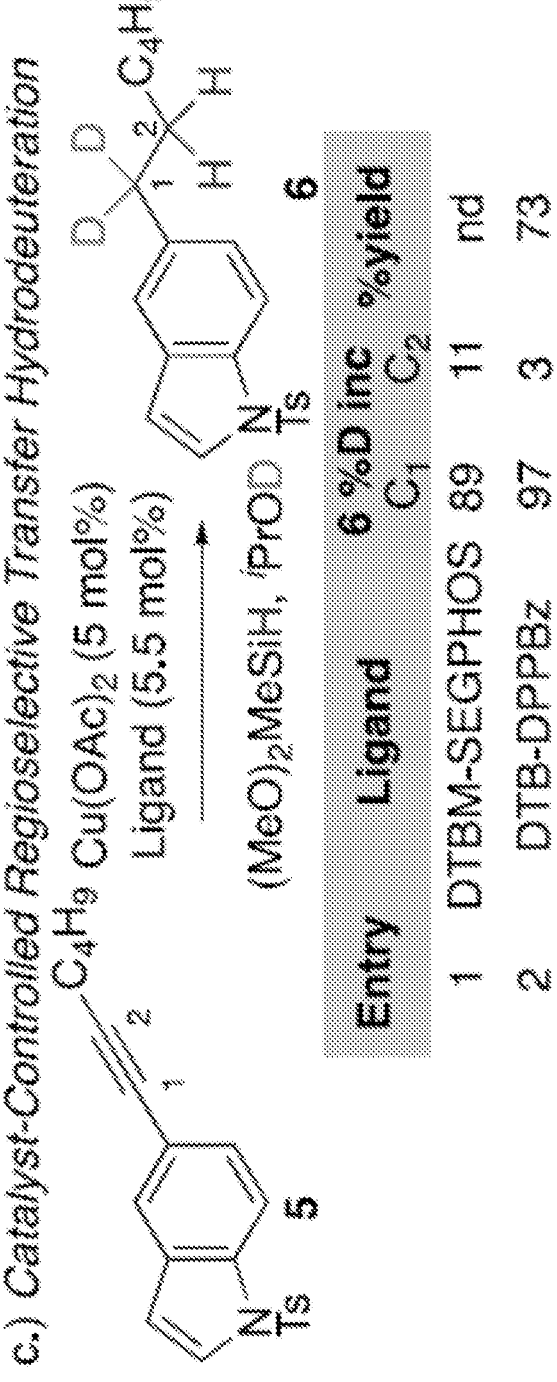
Figure 2:
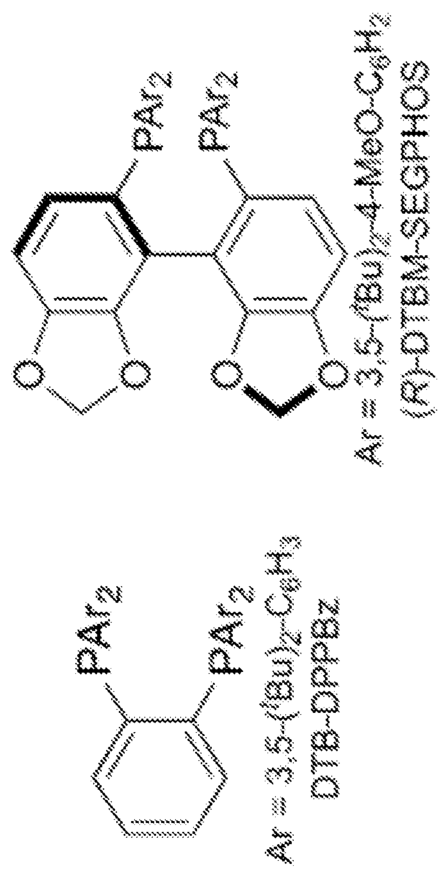

Having considered the aforementioned challenges and desirable reaction features of a selective deuteration, we sought to develop reactions that operate under catalyst control, so that selectivity can be tuned for targeted deuteration. Transfer deuteration and hydrodeuteration processes that use base-metal catalysts in combination with commercially available or readily accessible reagents and ligands are practical for selective deuteration. Transfer hydrogenation/deuteration processes obviate the use of flammable $H_2$ or $D_2$ gas by using alternative H and D sources (i.e. alcohols or silanes).[50] Transfer deuteration also provides an avenue for exploring a selective hydrodeuteration where H and D can be distinguished in a reaction.[43, 44] Inspired by previous highly selective reactions utilizing Cu—H catalysts,[51-55] we began exploring a Cu-catalyzed transfer deuteration of aryl alkynes. We established a mild, chemoselective protocol, orthogonal to precious metal-catalyzed reactions requiring $D_2$ gas. The reaction selectively deuterates alkyne functionality in the presence of other reduceable functionality and heterocycles (FIG. 2*a*). To demonstrate the potential of this method for use in late-stage transfer deuterations, we deuterated an estrone natural product analog at the reactive alkyne site (4, 74% yield, FIG. 2*a*).

Mechanistically, we believe that formation of a Cu-D in the presence of Si-D followed by insertion of Cu-D across an alkyne leads to alkenyl Cu species i (FIG. 2*b*). Deuterodecupration of i with ethanol-OD or 2-propanol-OD then extrudes alkene ii. Regeneration of the Cu-D and addition across alkene ii to form alkyl Cu iii, followed by deuterodecupration of iii, provides the desired alkane. With our mechanistic hypothesis in mind, we recognized that by simply switching the Si-D (a reagent we prepare on a multiple gram scale in one-step from commercial reagents and a commercial catalyst)[56] to the commercially available Si—H, a regioselective transfer hydrodeuteration might be possible. We tested this hypothesis with an alkynyl indole substrate using the DTBM-SEGPHOS ligand and achieved good selectivity (6, 89% D inc. at $C_1$ and 11% D inc. at $C_2$, FIG. 2*c*, entry 1). We monitored the reaction over 2 hours by $^1H$ NMR and noticed that alkyne transfer hydrodeuteration is moderately regioselective while alkene transfer hydrodeuteration is highly regioselective. This is likely due to the enhanced stabilization of a benzyl copper species (intermediate iii, FIG. 2*b*) versus a vinyl copper species (intermediate i, FIG. 2*b*). We hypothesized that compared to DTBM-SEGPHOS, a ligand with less steric hindrance would increase alkyne transfer hydrodeuteration selectivity. Ligand screening resulted in identification of DTB-DPPBz as the optimal ligand (6, 97% D inc. at $C_1$ and 3% D inc. at $C_2$, FIG. 2*c*, entry 2) for this reaction.

Figure 3:
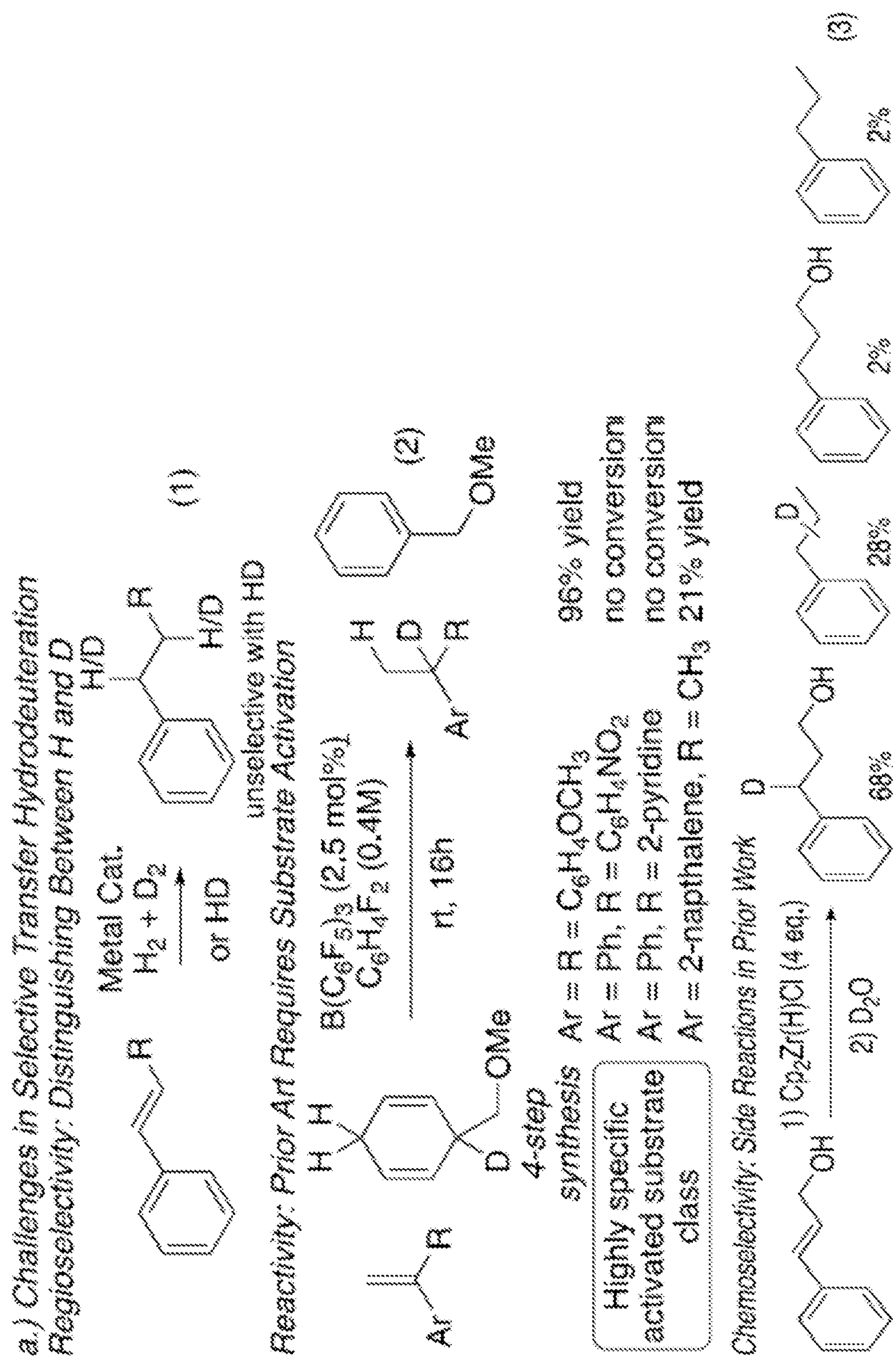
FIG. 3. Tackling challenges in selective transfer hydrodeuteration. a) challenges in selective transfer hydrodeuteration regioselectivity: distinguishing between H and D; b) styrene regioselective transfer hydrodeuteration; and c) aryl alkyne regioselective transfer hydrodeuteration.
Figure 3:
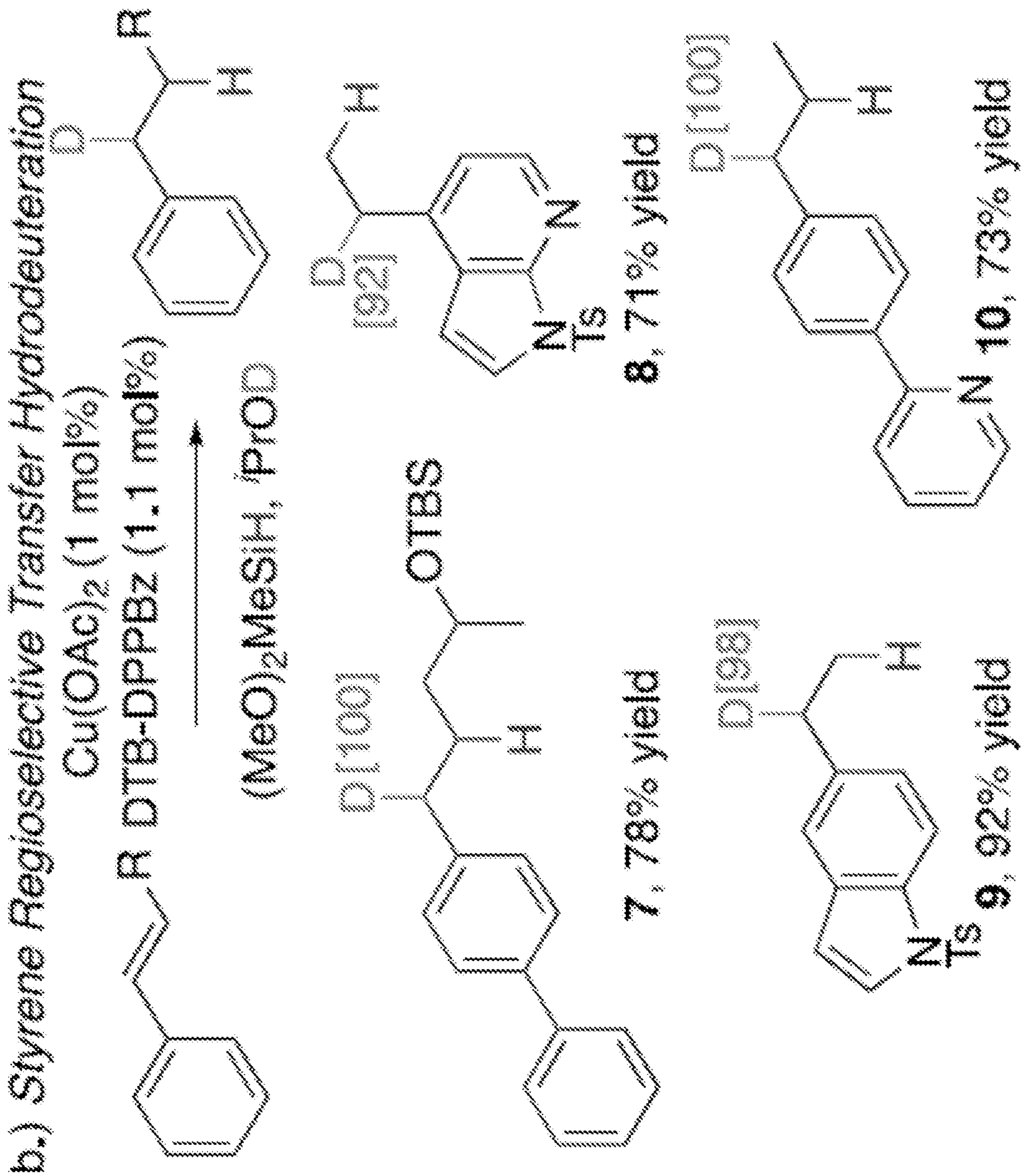
Figure 3:
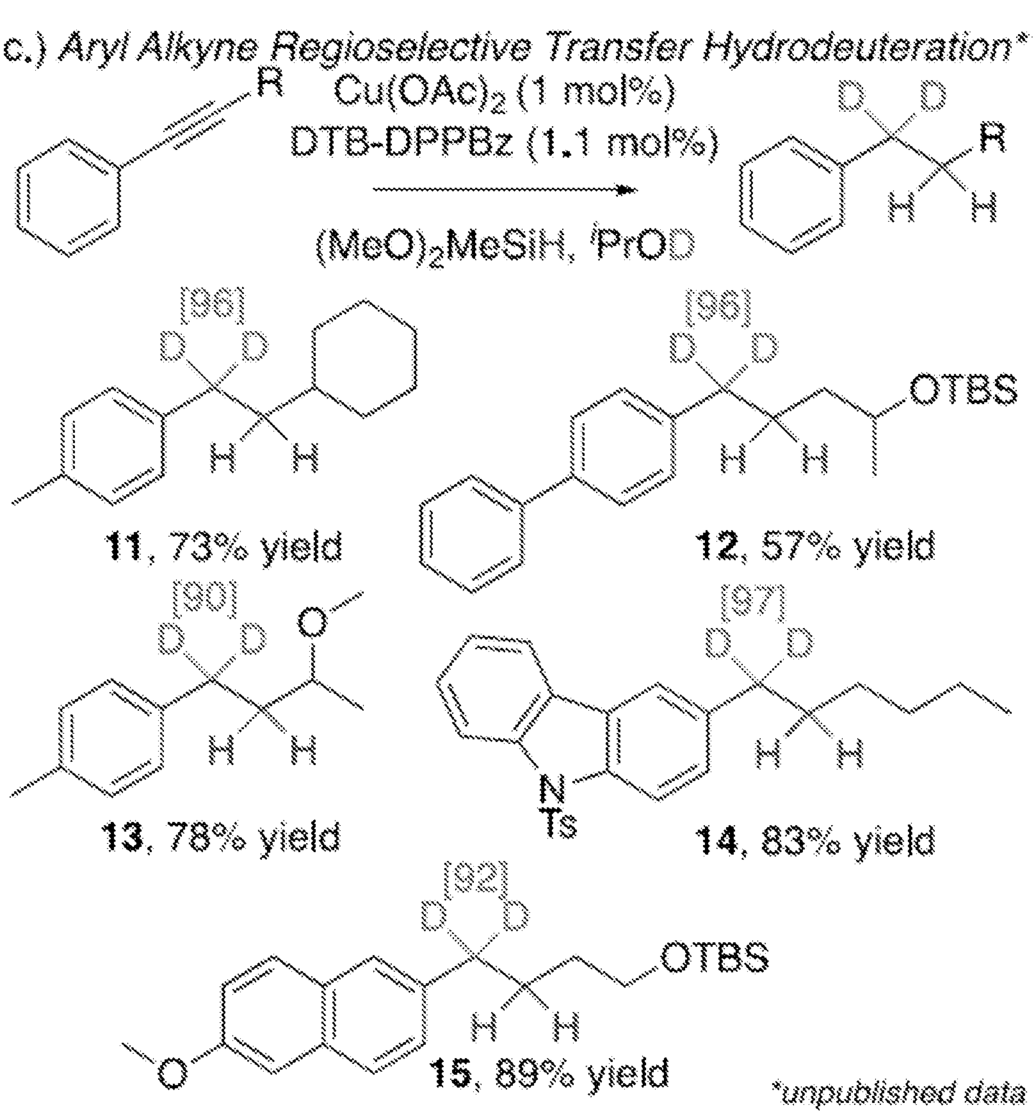

A practical, highly regioselective metal-catalyzed hydrodeuteration of an alkene or alkyne would push the frontier of regioselective chemistry because of the requirement to distinguish between chemically similar atoms (H and D) (FIG. 3*a*, eq 1). Aside from recently reported methods to make a very specific class of deuterated compounds (FIG. 3*a*, eq 2),[43, 44] regioselective deuterium incorporation is only mildly selective or commonly achieved with a stoichiometric Zr—H addition across an alkene followed by a $D_2O$ workup.[48, 57] The Zr—H addition across an alkene is accompanied by undesirable side reactions that eliminate heteroatom functionality (FIG. 3*a*, eq 3). We began to develop an alkenyl arene transfer hydrodeuteration reaction that addresses limitations in selective deuteration chemistry. Currently, we measure the regioselectivity by $^1H$ NMR and it appears that deuterium is installed into aryl alkenes almost exclusively at $C_1$ when commercial DTB-DPPBz is used as a ligand (FIG. 3*b*). We have started to unravel the reaction scope and found that both oxygenated and nitrogen heterocycle containing substrates are efficiently and selectively deuterated. To demonstrate the generality of the reaction, we will expand the reaction scope by exploring other nitrogen containing heterocycles and sulfur or oxygen containing heterocycles. We will also extend this protocol to complex bioactive molecules.

With the discovery of DTB-DPPBz as an enabling ligand for a regioselective aryl alkene transfer hydrodeuteration, we have continued to explore the regioselective Cu-catalyzed transfer hydrodeuteration of alkynes. This type of reaction is unprecedented in the literature. Mechanistically, an additional challenge of a second regioselective Cu—H addition (alkyne hydrocupration then alkene hydrocupration) is required for the reaction to reach synthetically useful levels of regioselectivity. For deuterated small molecules to be used as new drug leads or in ADME studies, labeling should occur at the desired location. Our aim is to achieve >90% deuterium incorporation at the desired site. To date, we have performed highly regioselective transfer hydrodeuterations on 6 substrates (FIGS. 2*c* and 3*c*, 6, 11-15, 57-89% yields). Importantly, regioselectivity is only mildly affected by the steric environment of the substrate and regioselectivity seems to be influenced by the catalyst.

Figure 4:
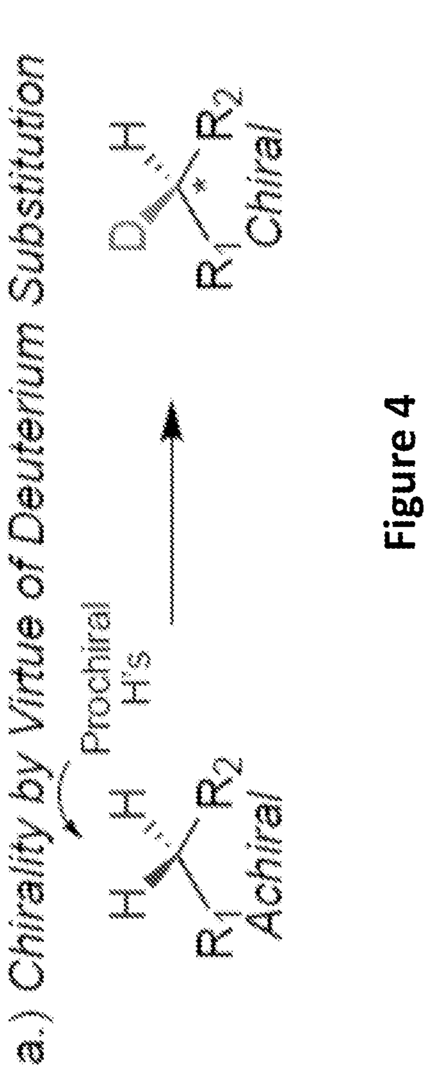
FIG. 4. Cu-catalyzed enantioselective transfer hydrodeuteration and characterization. a) enantio-enriched ethylbenzene-$d_1$; b) ethylbenzene-$d_1$, synthesis through the decades; c) enantioselective transfer hydrodeuteration challenges; d) preliminary results; and e) racemic and chiral tags utilized for molecular rotational resonance (MRR) characterization of analytes.
Figure 4:
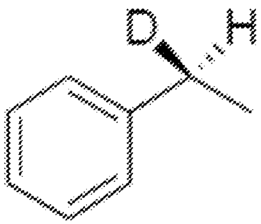
Figure 4:
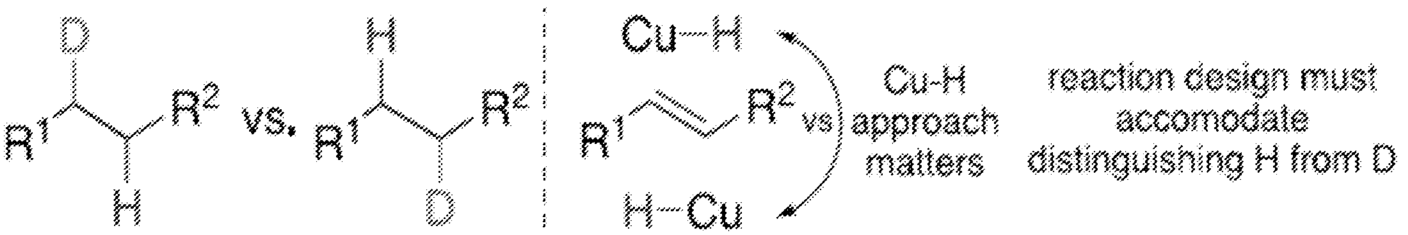
Figure 4:
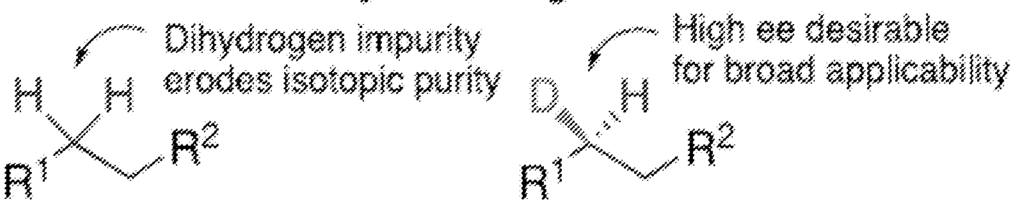
Figure 4:
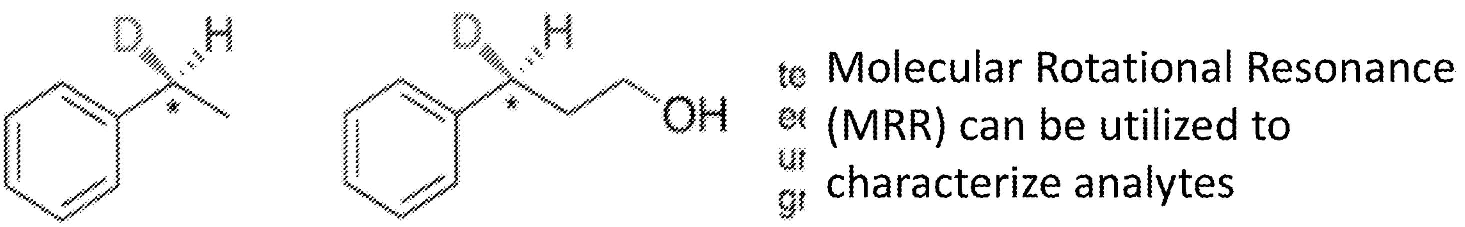
Figure 4:
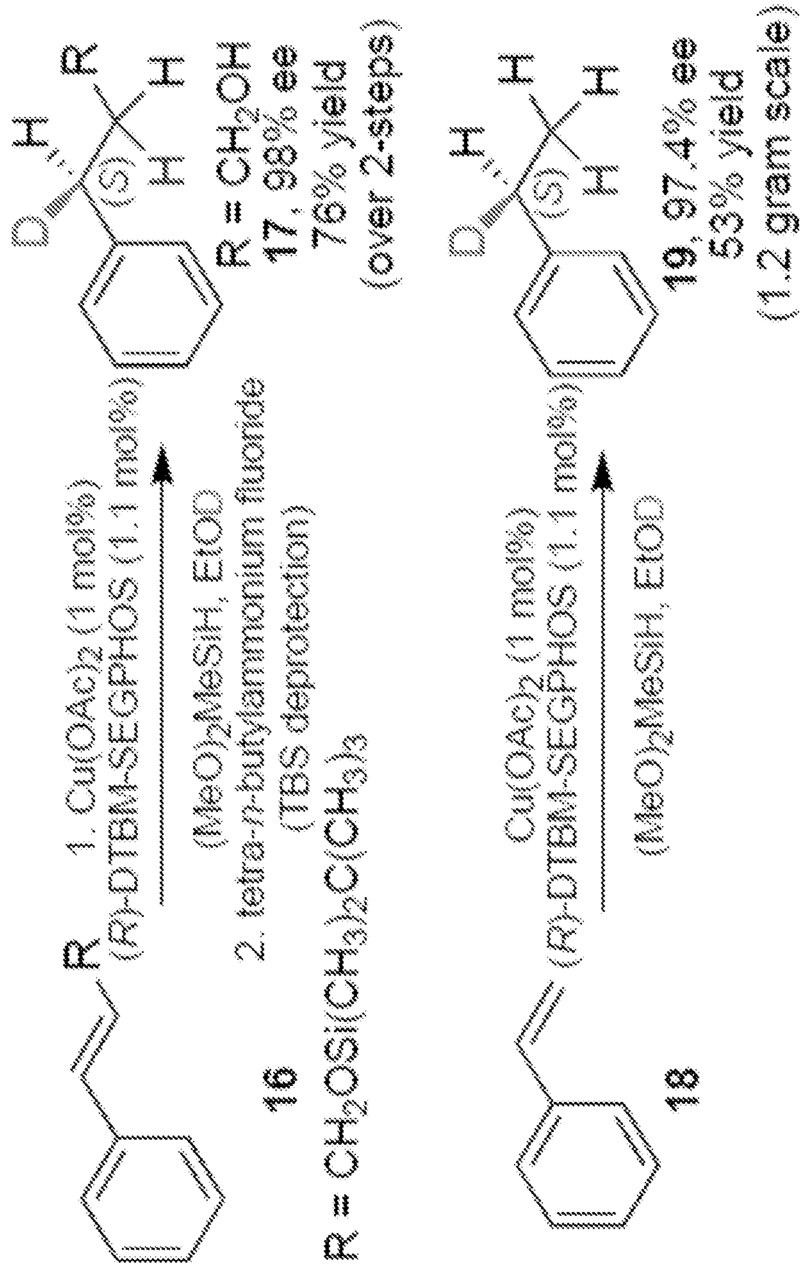
Figure 4:
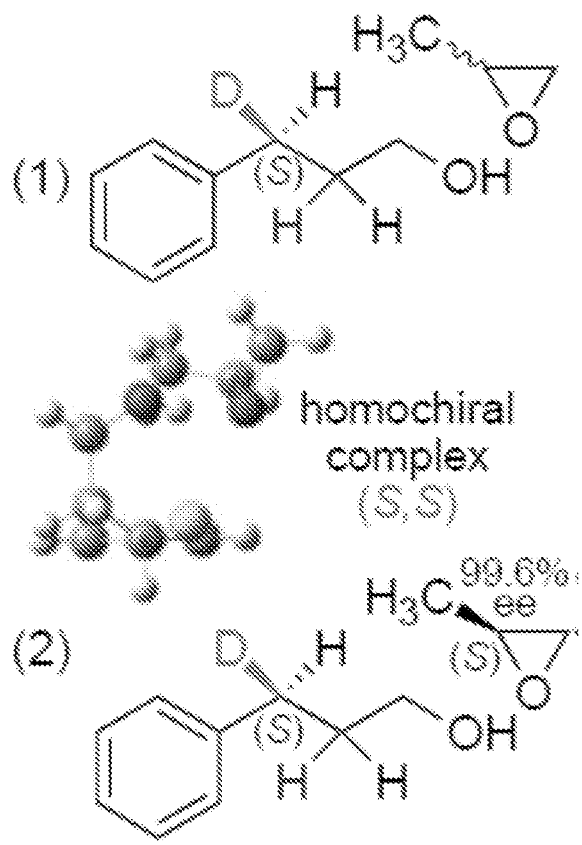

To address a longstanding challenge to selectively prepare compounds that are chiral by virtue of deuterium substitution, we began exploring an enantioselective Cu-catalyzed alkene transfer hydrodeuteration. The unique compounds we are interested in preparing exhibit optical activity due to chirality induced at prochiral hydrogens when a hydrogen is replaced with deuterium (FIG. 4*a*).[58-60] This represents the most conservative of atomistic changes. Consequently, the synthesis of compounds such as (S)-ethylbenzene-d1, in high enantiopurity, has challenged chemists for decades (FIG. 4*b*).[61-64] Synthetically, several barriers exist to develop a general and practical catalytic, enantioselective synthesis of compounds that are chiral by virtue of deuterium substitution (FIG. 4*c*). The reaction must be completely regioselective, otherwise the dihydrogen impurity will erode the overall isotopic purity of the desired compound. This means the catalytic reaction must be designed to distinguish between chemically similar atoms (H and D). For synthetic utility, the reaction must also be highly enantioselective (>90% ee). Finally, a spectroscopic technique to characterize the products will need to be developed. Currently, there are no general analytical methods for both ee and absolute configuration determination of compounds that are chiral by virtue of deuterium substitution.

If all of these challenges can be addressed, we anticipate the products will be useful in high-throughput methods for determining enantioselectivity of catalyzed processes,[62] for mechanistic studies,[65-69] ADME studies and novel building blocks for new drug development.[6] To address the reactivity and regioselectivity challenges, we began by evaluating alkene 16 and the commercially available (R)-DTBM-SEGPHOS ligand for the Cu-catalyzed enantioselective transfer hydrodeuteration (FIG. 4*d*). Gratifyingly, aryl alkane product 17 was isolated in 76% yield (over 2-steps, 90% yield for transfer hydrodeuteration) and the regioselectivity was measured by $^1H$ NMR and found to be >20:1. With this exciting result in hand, our progress was immediately halted as we attempted to determine the stereochemical assignment and measure the ee of 17. Discrimination of isotopically chiral molecules is a long-standing challenge in chiral analysis.[70] Classical separation approaches to ee determination (chiral high-performance liquid chromatography (HPLC), chiral gas chromatography (GC)) are usually unable to separate enantiomers of chiral by virtue of deuterium substitution compounds. Examples are considered "extremes" in separation science and chiral separation of chiral isotopomers has only been reported in rare cases.[71] The chemical similarity of chiral isotopomers has challenged the limits of spectroscopy.[70] The most common approach to determination of enantiopurity is synthetic chiral derivatization followed by analysis of diastereomers by $^1H$ and $^2H$ NMR.[72] In fact, a general, reliable and direct ee determination of compounds such as (R) and (S)-ethylbenzene-d1, that are chiral by virtue of deuterium substitution, has eluded chemists for over 70 years.[59, 61-66, 73-78]

To solve this seemingly insurmountable challenge of direct determination of ee and absolute configuration, we initiated a collaboration with the Pate group at the University of Virginia and BrightSpec Inc. They are studying molecular rotational resonance (MRR), a spectroscopic method useful for rapidly discriminating between all types of isomers and providing quantitative characterization data.[79-82] MRR spectroscopy identifies molecules through their mass distribution as quantified by the principal moments-of-inertia for overall rotation of the gas phase molecule. There are two key features of MRR spectroscopy that make it a powerful technique for isotopomer analysis: 1.) All isotopic variants of the substrate have the same equilibrium geometry so that one geometry is all that is needed to predict the spectral signatures of all isotopomers, 2.) Geometries with sufficient accuracy for isotopomer analysis can be obtained from quantum chemistry. The general advantages of MRR are that the high spectral resolution makes it possible to directly analyze crude mixtures, there is no need for reference samples to identify isotopomers and isotopologues with high confidence, and measurements take only 10-20 minutes each.

MRR has recently been used for isotopologue and isotopomer analysis where the ability to identify 15 different isotopic isomers in a synthetic sample at 100:1 dynamic range was demonstrated.[42] Importantly, chiral analysis is possible by MRR spectroscopy with general applicability using the chiral tag methodology.[80, 82] In May 2020, we worked with the Pate group and BrightSpec Inc. to develop a methodology to analyze isotopically chiral samples and to extend it to high-throughput analysis. Our strategy achieves chiral discrimination by binding a small chiral tag, such as propylene oxide to the substrate in the gas phase during pulsed jet sample injection into the spectrometer. The methodology is illustrated in FIG. 4*d* for the first analysis we performed of 3-phenyl-1-propanol-d1 tagged with propylene oxide: 1.) The structure of the chiral tag complex is analyzed using the normal isotopic version of the substrate, 3-phenyl-1-propanol, which is typically available at low cost. Because all isotopic variants of a molecular complex have the same equilibrium geometry, the structure obtained from this measurement can be used to predict the spectral signature of any isotopic variant, 2.) The tag complex structure is validated by observing both diastereomeric complexes of the deuterated substrate. This can be accomplished using a racemic sample of the chiral tag. Even if the substrate is enantioenriched (S)-3-phenyl-1-propanol as indicated in FIG. 4*d*, this measurement will produce an equimolar mixture of the (S,R) and (S,S) diastereomeric complex resulting in characteristic spectral transitions for both of the two diastereomeric complexes. The accuracy of the quantum chemistry equilibrium geometry is validated in these measurements through its ability to predict the spectrum of the two diastereomeric complexes, 3.) The enantiomeric excess and absolute configuration of the dominant enantiomer of the substrate is determined in a final measurement using high enantiopurity tag sample ((S)-propylene oxide) as shown in FIG. 4*d*, eq 2. The spectrum for the homochiral (S,S) complex can be characterized by an increase in intensity of some of transients present in the spectrum for the (S,R) and (S,S) diastereomeric complex, which are transients are indicative of the homochiral (S,S) complex, and a decrease in intensity of other transients present in the spectrum for the (S,R) and (S,S) diastereomeric complex which are indicative of the heterochiral (S,R) complex. The diastereomeric excess of the tag complexes can be measured quantitatively from these spectra and this correlates directly to the enantiomeric excess of the deuterated substrate.

We have successfully characterized 5 unique products at the time of this submission (≥%% ee for all 5 products). As proof of principal, and to push the frontier of this reaction, we developed the first highly enantioselective, 1-step synthesis of 19, (S)-ethylbenzene-d1 (97.4% ee) on gram scale (FIG. 4*d*), from an achiral, structurally simple, bulk commodity starting material (styrene). The reaction was also found to be highly regioselective with only trace amounts of another isotopologue present. Through verification by MRR, only trace dihydrogen (non-deuterated ethylbenzene) impurity (<0.1%) was present in the product and no isotopomer impurities were observed. In addition to ee determination and trace impurity determination, MRR obviates determination of absolute configuration by X-ray diffraction and provides stereochemical assignments (R or S) of the deuterated chiral centers. This unequivocally demonstrates that no polar functionality or synthetic manipulations are necessary to measure ee or determine absolute stereochemistry of a compound that is chiral by virtue of deuterium substitution. To date, our work with the Pate group has resulted in the first general, direct ee measurement of compounds that are chiral by virtue of deuterium substitution. It also represents the first general, direct determination of absolute configuration for this class of compounds. As part of this project, we will continue to pioneer the use of MRR spectroscopy for chemical analysis of deuterated compounds.

The Pate group will support this project as part of their NSF-sponsored research program that is developing chiral tag methods (NSF CHE-1904686). We will also work with BrightSpec Inc. on high-throughput analysis techniques and our collaboration will guide their commercialization effort. The collaboration will include graduate student visits to the University of Virginia and BrightSpec. This student training experience has already started with an initial weeklong visit in August 2020.

Overview of Future Research Plans

Having access to site specific deuterated small molecules will considerably expand the accessible deuterated chemical space. In medicinal chemistry and pharmacology, knowing the exact location of an atom in a bioactive molecule is important. Strategic labelling of therapeutics can mitigate inhibition risks caused by cytochrome P450 (CYP). This has the potential to revive failed drug candidates or make FDA approved small molecule drugs safer with minimal to no impact on drug potency.[6, 17, 19, 23] Constitutional isomers, stereoisomers and enantiomers of bioactive molecules each have their own unique pharmacokinetic profile. Enzymes can differentiate between heterotopic atoms at prochiral centers,[12, 21, 83] and beyond studying the stereochemical course of enzymes, we believe this level of differentiation could be further leveraged in drug discovery if highly selective deuterium installation is possible. Our recent progress demonstrates that deuterium can be selectively installed into the metabolically important benzylic position of small molecules. Utilizing the new analytical techniques we are pioneering in our collaboration with the Pate group and BrightSpec Inc., we are positioned to expand on this preliminary work. Until now, selective deuteration methods that enable the precise placement of deuterium at specific locations within small molecules were rare. We are developing practical, highly selective deuteration reactions and implementing analytical methods to rapidly characterize and support the timely optimization, development and delivery of these reactions for academic and commercial use.

Figure 5:
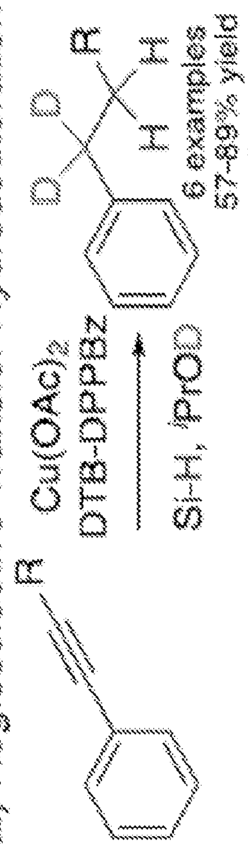
FIG. 5. Additional work related to regioselective and enantioselective deuteration. a) regioselective transfer hydrodeuteration; b) expansion of transfer deuteration to unactivated alkenes; c) selective alkyne transfer hydrodeuteration; d) enantioselective transfer hydrodeuteration; and e) tunable and switchable selectivity.
Figure 5:
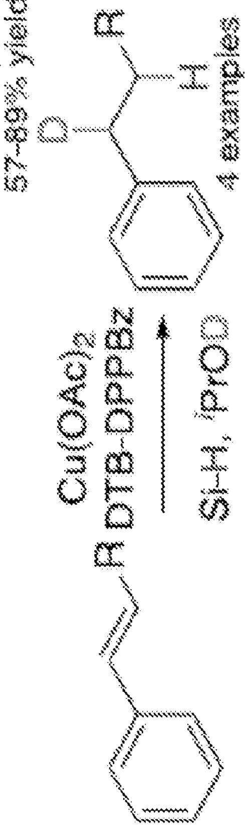
Figure 5:
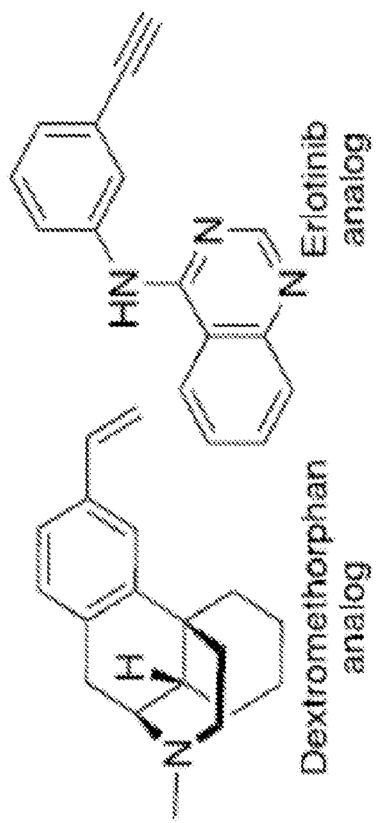
Figure 5:
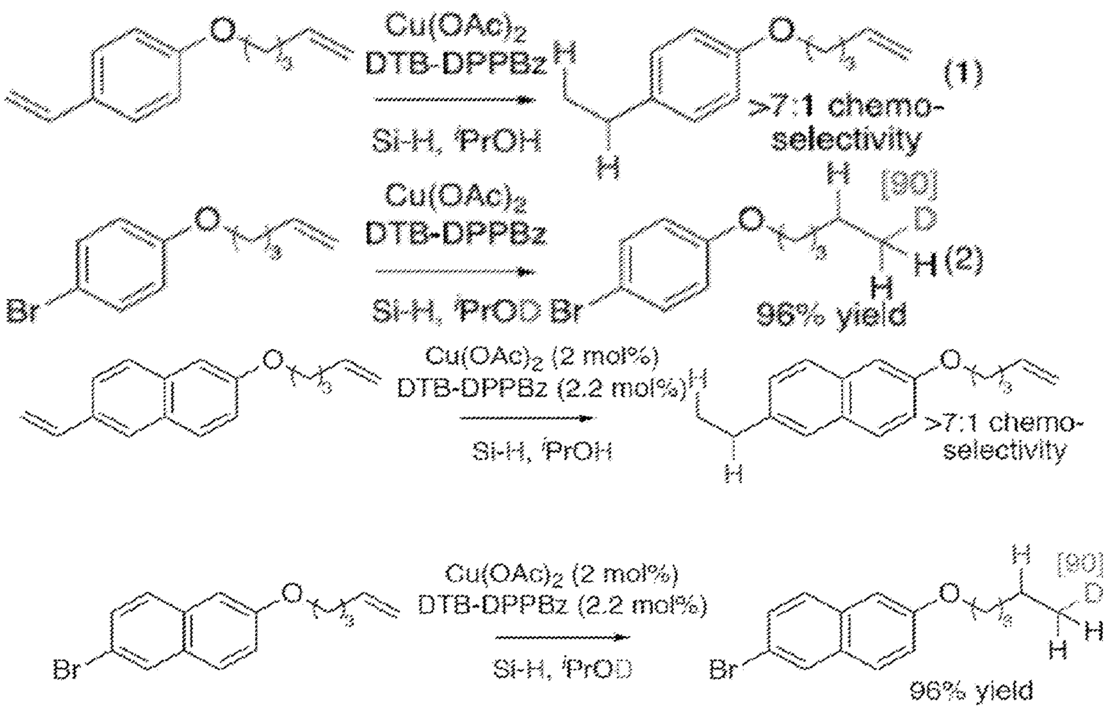
Figure 5:
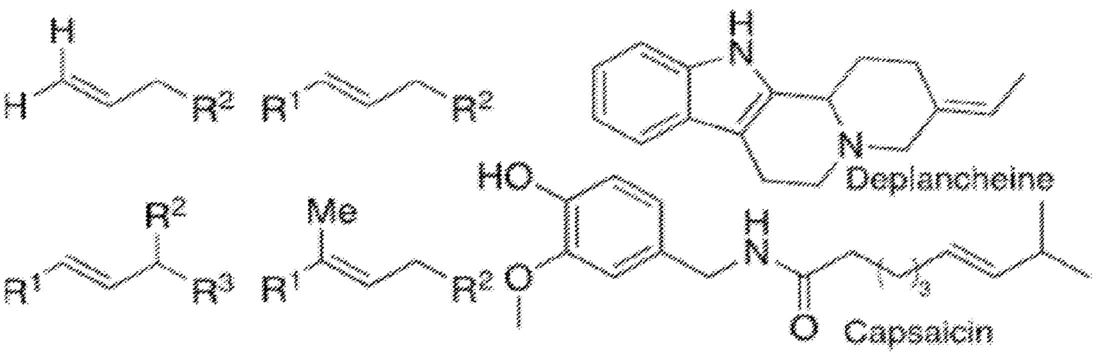
Figure 5:
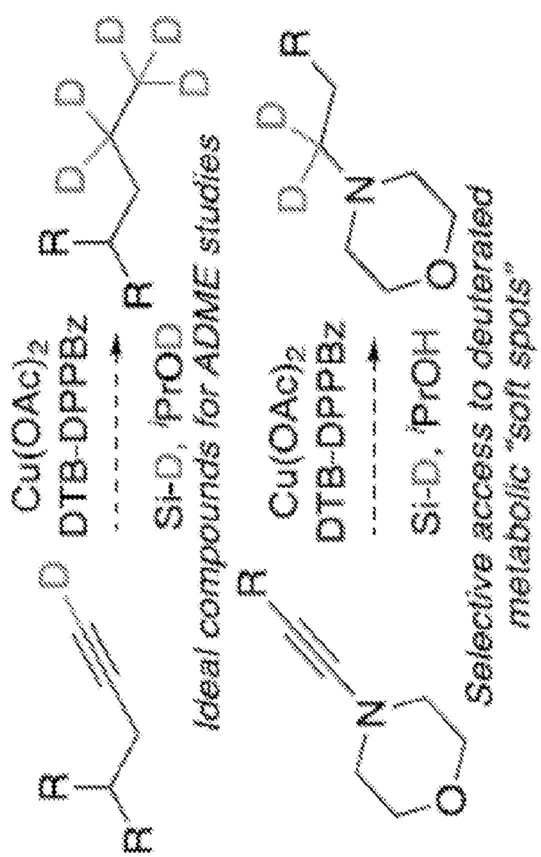
Figure 5:
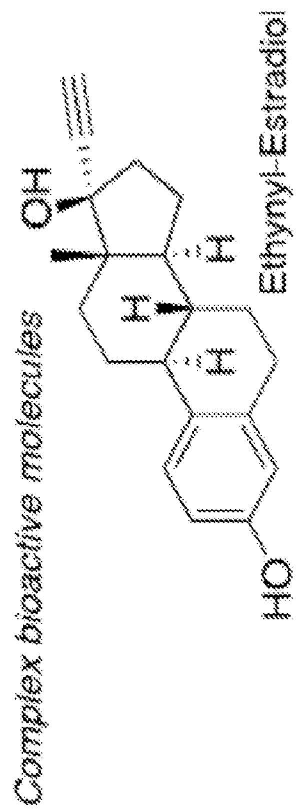
Figure 5:
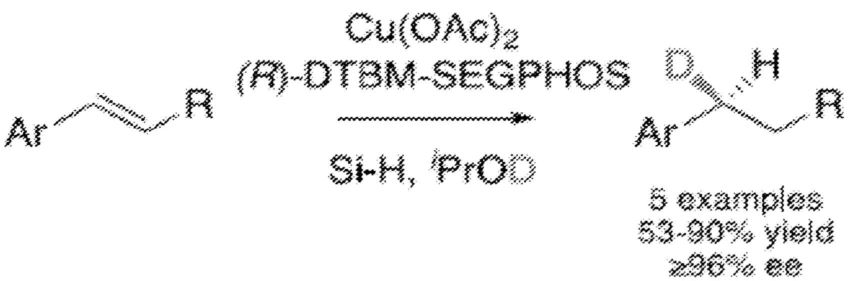
Figure 5:
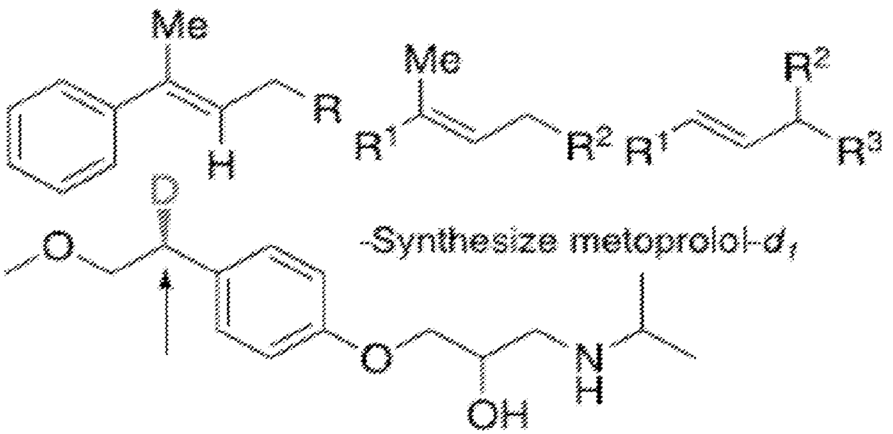
Figure 5:
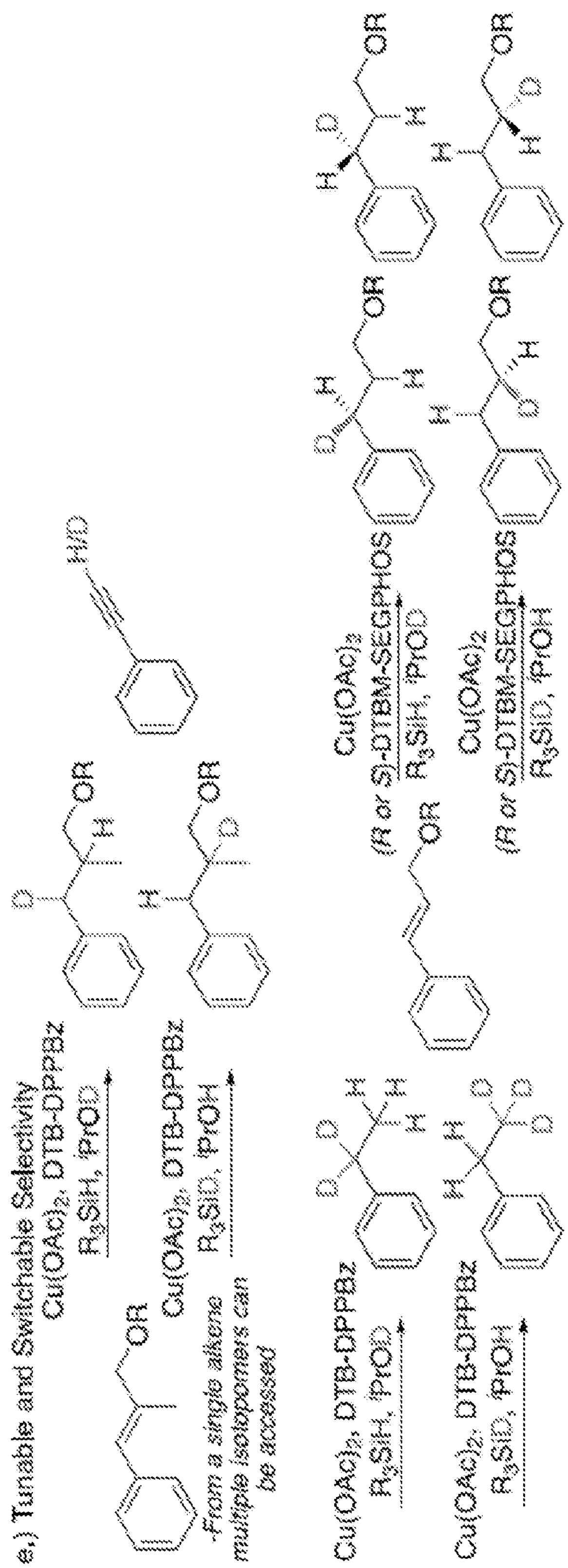

We will focus on expanding the substrate scope of the regioselective transfer hydrodeuteration of aryl alkynes and aryl alkenes and use MRR spectroscopy to measure regioselectivity. Given the prevalence of heterocycles in medicine, we plan to further evaluate alkyne substituted heterocycles for transfer hydrodeuteration reactivity (FIG. 5*a*).[84-86] This will position us to expand the reactions for use in late-stage transfer hydrodeuteration of complex bioactive molecules. Across all of our transfer deuteration/hydrodeuteration results, we have successfully used indole, azaindole, carbazole, benzofuran, dibenzofuran, benzothiophene, pyridine and quinoline containing substrates. Preliminary data also demonstrates high reactivity for unactivated alkenes (FIG. 5*b*). We found that the analogous transfer hydrogenation reaction is selective for an aryl alkene when an unactivated alkene is present in the molecule (FIG. 5*b*, eq 1). This chemoselectivity will be optimized and explored for transfer hydrodeuteration in substrates containing multiple alkenes. Excitingly, in the absence of the conjugated alkene, the unactivated alkene undergoes transfer hydrodeuteration in 96% yield (FIG. 5*b*, eq 2). We will also initiate investigations into more sterically hindered tri-substituted alkenes. We anticipate this will be used for early-stage or late-stage deuteration of small molecules and will explore several late-stage alkene transfer hydrodeuteration reactions in our future work. We will leverage the success of this reaction to expand into unactivated alkynes (FIG. 5*c*). We will initially explore a transfer deuteration of unactivated alkynes to make compounds containing 4 deuterium atoms. This proposed reaction is ideal to access substrates for ADME studies where it is required that at least 3 or more deuterium atoms are contained in the substrate. By simply switching one of the deuterium transfer reagents to the hydrogen transfer reagent, we will regioselectively install two deuterium atoms into metabolic "soft spots" of small molecules. Our ultimate goal is to expand the alkyne transfer deuteration/hydrodeuteration chemistry for use in labeling late-stage molecules such as natural products. In collaboration with the Pate group and BrightSpec Inc., the reaction optimization for all of these transformations will be assisted by knowledge of all isotopic impurities, determined by MRR.

Recognizing the potentially transformative impact of the enantioselective Cu-catalyzed transfer hydrodeuteration reaction and product characterization, we believe many avenues exist for new reaction development. We will initially focus on expanding the aryl alkene substrate scope by exploring heterocycle containing substrates and expanding to complex bioactive molecules (FIG. 5*d*). Currently, we have completed the highly enantioselective synthesis of five chiral deuterated small molecules (≥96% ee). To make the proposed selective deuteration chemistry practical for late-stage reactions, a collaborative aim is to further advance the capability of MRR to perform rapid ee determination of complex small molecules. Another biologically relevant area of expansion will involve unactivated alkenes. Specifically, selective access to deuterated, enantioenriched 3° C. ($sp^3$)-D chiral centers remains elusive. It is well-known that 3° C. ($sp^3$)-H bonds in bioactive small molecules can be metabolically active.[87] Currently, it is challenging to install a deuterium into one of these sites. Chiral 3° carbon centers can play a significant role in a molecule's bioactivity and we anticipate that a highly selective deuteration of unactivated alkenes in combination with a powerful analytic technique for rapid characterization will draw significant interest from both academia and industry.

A unique design feature of the proposed methods that we plan to exploit and fully explore is the tunable and switchable selectivity (FIG. 5*e*). For example, by using Si-D and $^i$PrOD, we are able to install 4 deuterium atoms into an alkyne. If we simply switch the Si-D to Si—H and keep the $^i$PrOD, we are able to perform regioselective transfer hydrodeuteration. We are proposing to leverage this strategy to flip the selectivity in all of the aforementioned transfer hydrodeuteration reactions by also using Si-D and $^i$PrOH. Being able to explore this avenue of research will enable us to access a tremendous amount of chemical space for deuterated molecules. Coupled with using MRR for characterization, we will rapidly optimize all of these proposed reactions and be able to make deuterated small molecules selectively with precision.

In conclusion, a research program involving the selective placement of deuterium into small molecules and the analytical techniques required to support the timely development of new selective deuteration reactions is described. These novel and highly selective catalytic methods for deuterium incorporation will begin to meet the demands for selectively labeled small molecules across all fields of chemistry. These advances will unlock novel and desirable deuterated chemical space to support and expand efforts by scientists utilizing labeled small molecules as sources of new and innovative medicines.

REFERENCES

1. Simmons, E. M.; Hartwig, J. F., On the Interpretation of Deuterium Kinetic Isotope Effects in C—H Bond Functionalizations by Transition-Metal Complexes. Angewandte Chemie International Edition 2012, 51 (13), 3066-3072.

2. Giagou. T.; Meyer, M. P., Kinetic Isotope Effects in Asymmetric Reactions. Chemistry—A European Journal 2010, 16 (35), 10616-10628.
3. Anslyn, E. V.; Dougherty, D. A., Modern physical organic chemistry. University Science Books 2006.
4. Meek, S. J.; Pitman, C. L.; Miller, A. J. M., Deducing Reaction Mechanism: A Guide for Students, Researchers, and Instructors. Journal of Chemical Education 2016, 93 (2), 275-286.
5. Fu, I.; Woolf, E. J.; Matuszewski, B. K., Effect of the sample matrix on the determination of indinavir in human urine by HPLC with turbo ion spray tandem mass spectrometric detection. Journal of Pharmaceutical and Biomedical Analysis 1998, 18 (3), 347-357.
6. Pirali, T.; Serafini, M.; Cargnin, S.; Genazzani, A. A., Applications of Deuterium in Medicinal Chemistry. Journal of Medicinal Chemistry 2019, 62 (11), 5276-5297.
7. Atzrodt, J.; Derdau, V.; Kerr, W. J.; Reid, M., C—H Functionalisation for Hydrogen Isotope Exchange. Angewandte Chemie International Edition 2018, 57 (12), 3022-3047.
8. Atzrodt, J.; Derdau, V.; Kerr, W. J.; Reid, M., Deuterium- and Tritium-Labelled Compounds: Applications in the Life Sciences. Angewandte Chemie International Edition 2018, 57 (7), 1758-1784.
9. Schwab, J. M., Stereochenistry of an enzymic Baeyer-Villiger reaction. Application of deuterium NMR Journal of the American Chemical Society 1981, 103 (7), 1876-1878.
10. Leinberger, R.; Rétey, A.; Hull, W. E.; Simon, H., Steric Course of the NIH Shift in the Enzymic Formation of Homogentisic Acid. European Journal of Biochemistry 1981, 117 (2), 311-318.
11. Battersby, A. R.; Gutman. A. L.; Fookes, C. J. R.; Günther, H.; Simon, H., Stereochemistry of formation of methyl and ethyl groups in bacteriochlorophyll a. Journal of the Chemical Society, Chemical Communications 1981, (13), 645-647.
12. Lüthy, J.; Rétey, J.; Arigoni, D., Asymmetric Methyl Groups: Preparation and Detection of Chiral Methyl Groups. Nature 1969, 221 (5187), 1213-1215.
13. Klinman, J. P., A new model for the origin of kinetic hydrogen isotope effects. Journal of Physical Organic Chemistry 2010, 23 (7), 606-612.
14. White, R. E.; Miller, J. P.; Favreau, L. V.; Bhattacharyya, A., Stereochemical dynamics of aliphatic hydroxylation by cytochrome P-450. Journal of the American Chemical Society 1986, 108 (19), 6024-6031.
15. Shapiro, S.; Piper, J. U.; Caspi, E., Steric course of hydroxylation at primary carbon atoms. Biosynthesis of 1-octanol from (1R)- and (1S)-[1-3H,2H,1H; 1-14C]octane by rat liver microsomes. Journal of the American Chemical Society 1982, 104 (8), 2301-2305.
16. Jarling, R.; Sadeghi, M.; Drozdowska. M.; Lahme, S.; Buckel, W.; Rabus, R; Widdel, F.; Golding, B. T.; Wilkes, H., Stereocheniucal Investigations Reveal the Mechanism of the Bacterial Activation of n-Alkanes without Oxygen. Angewandte Chemie International Edition 2012, 51 (6), 1334-1338.
17. Meanwell, N. A., Synopsis of Some Recent Tactical Application of Bioisosteres in Drug Design. Journal of Medicinal Chemistry 2011, 54 (8), 2529-2591.
18. Harbeson, S. L.; Tung, R. D., Deuterium Medicinal Chemistry: A New Approach to Drug Discovery and Development. Medchem News 2014, 24 (2), 8-22.
19. Gant, T. G., Using Deuterium in Drug Discovery: Leaving the Label in the Drug. Journal of Medicinal Chemistry 2014, 57 (9), 3595-3611.
20. Nelson, S. D.; Trager, W. F., The Use of Deuterium Isotope Effects to Probe the active site properties, Mechanism of Cytochrom P450-Catalyzed Reactions, and Mechanisms of Metabolically Dependent Toxicity. Drug Metabolism and Disposition 2003, 31 (12), 1481-1497.
21. Belleau, B.; Burba. J.; Pindell, M.; Reiffenstein, J., Effect of Deuterium Substitution in Sympathomimetic Amines on Adrenergic Responses. Science 1961, 133 (3446), 102-104.
22. Meanwell, N. A., Fluorine and Fluorinated Motifs in the Design and Application of Bioisosteres for Drug Design. Journal of Medicinal Chemistry 2018, 61 (14), 5822-5880.
23. Stepan, A. F.; Mascitti. V.; Beaumont. K.; Kalgutkar, A. S., Metabolism-guided drug design. MedChemComm 2013, 4 (4), 631-652.
24. Xing, L.; Honda, T.; Fitz, L.; Ojima, I., 4—Case studies of fluorine in drug discovery. In Fluorine in Life Sciences: Pharmaceuticals, Medicinal Diagnostics, and Agrochemicals, Haufe, G.; Leroux, F. R., Eds. Academic Press: 2019; pp 181-211.
25. Müller, K.; Faeh, C.; Diederich, F., Fluorine in Pharmaceuticals: Looking Beyond Intuition. Science 2007, 317 (5846), 1881-1886.
26. Hagmann, W. K., The Many Roles for Fluorine in Medicinal Chemistry. Journal of Medicinal Chemistry 2008, 51 (15), 4359-4369.
27. Purser, S.; Moore, P. R.; Swallow, S.; Gouvemeur, V., Fluorine in medicinal chemistry. Chemical Society Reviews 2008, 37 (2), 320-330.
28. Schmidt, C., First deuterated drug approved. Nature Biotechnology 2017, 35 (6), 493-494.
29. National Center for Biotechnology Information (2020). PubChem Compound Summary for CID 25052519, Deudextromethorphan. Retrieved Sep. 14, 2020 from https://pubchem.ncbi.nlm.nih.gov/compoundLDeudextromethorphan.
30. Czeskis. B.; Elmore, C. S.; Haight. A.; Hesk, D.; Maxwell, B. D.; Miller, S. A.; Raglione, T.; Schildknegt. K.; Traverse, J. F.; Wang, P., Deuterated active pharmaceutical ingredients: A science-based proposal for synthesis, analysis, and control. Part 1: Framing the problem. Journal of Labelled Compounds and Radiopharmaceuticals 2019, 62 (11), 690-694.
31. Tayar, N. E.; van de Waterbeemd, H.; Gryllaki. M.; Testa, B.; Trager, W. F., The lipophilicity of deuterium atoms. A comparison of shake-flask and HPLC methods. International Journal of Pharmaceutics 1984, 19 (3), 271-281.
32. Turowski, M.; Yamakawa, N.; Meller, J.; Kimata, K.; Ikegami, T., Hosoya, K.; Tanaka. N.; Thornton. E. R., Deuterium Isotope Effects on Hydrophobic Interactions: The Importance of Dispersion Interactions in the Hydrophobic Phase. Journal of the American Chemical Society 2003, 125 (45), 13836-13849.
33. Urey. H. C. B., F. G.; Murphy, G. M., A Hydrogen Isotope of Mass 2 and its Concentration. Physical Review 1932, 40 (1), 1-15.
34. Atzrodt, J.; Derdau. V.; Fey, T.; Zimmermann, J., The Renaissance of H/D Exchange. Angewandte Chemie International Edition 2007, 46 (41), 7744-7765.

35. Lee, S. H.; Gorelsky, S. I.; Nikonov, G. I., Catalytic HVD Exchange of Unactivated Aliphatic C—H Bonds. Organometallics 2013, 32 (21), 6599-6604.

36. Neubert, L.; Michalik, D.; BAhn, S.; Imm, S.; Neumann. H.; Atzrodt, J.; Derdau. V.; Holla, W.; Beller, M., Ruthenium-Catalyzed Selective α,β-Deuteration of Bioactive Amines. Journal of the American Chemical Society 2012, 134 (29), 12239-12244.

37. Loh, Y. Y.; Nagao, K.; Hoover, A. J.; Hesk, D.; Rivera, N. R.; Colletti, S. L.; Davies, I. W.; MacMillan, D. W. C., Photoredox-catalyzed deuteration and tritiation of pharmaceutical compounds. Science 2017, 358 (6367), 1182-1187.

38. Hale, L. V. A.; Szymczak, N. K., Stereoretentive Deuteration of α-Chiral Amines with D2O. Journal of the American Chemical Society 2016, 138 (41), 13489-13492.

39. Palmer, W. N.; Chirik, P. J., Cobalt-Catalyzed Stereoretentive Hydrogen Isotope Exchange of C(sp3)-H Bonds. ACS Catalysis 2017, 7 (9), 5674-5678.

40. Esaki, H.; Aoki, F.; Umemura, M.; Kato, M.; Maegawa, T.; Monguchi, Y.; Sajiki, H., Efficient H/D Exchange Reactions of Alkyl-Substituted Benzene Derivatives by Means of the Pd/C—H2-D2O System. Chemistry—A European Journal 2007, 13 (14), 4052-4063.

41. Atzrodt, J.; Derdau, V., Pd- and Pt-catalyzed H/D exchange methods and their application for internal MS standard preparation from a Sanofi-Aventis perspective. Journal of Labelled Compounds and Radiopharmaceuticals 2010, 53 (11-12), 674-685.

42. Smith, J. A.; Wilson, K. B.; Sonstrom, R. E.; Kelleher, P. J.; Welch, K. D.; Pert, E. K.; Westendorff, K. S.; Dickie, D. A.; Wang, X.; Pate, B. H.; Harman, W. D., Preparation of cyclohexene isotopologues and stereoisotopomers from benzene. Nature 2020, 581 (7808), 288-293.

43. Walker, J. C. L.; Oestreich, M., Regioselective Transfer Hydrodeuteration of Alkenes with a Hydrogen Deuteride Surrogate Using B(C6F5)3 Catalysis. Organic Letters 2018, 20 (20), 6411-6414.

44. Li. L.; Hilt, G., Regiodivergent DH or HD Addition to Alkenes: Deuterohydrogenation versus Hydrodeuterogenation. Organic Letters 2020, 22 (4), 1628-1632.

45. Okuhara. T.; Kondo, T.; Tanaka, K., Oriented adsorption of hydrogen deuteride on zinc oxide and addition to butadiene. The Journal of Physical Chemistry 1977, 81 (8), 808-809.

46. Okuhara, T.; Tanaka, K.-I., Orientation in the addition of HD to butadiene on MoS2. Journal of the Chemical Society, Chemical Communications 1976, (6), 199-200.

47. Murahashi, S.-I.; Yano, T.; Hino, K-i., Hydrogen transfer from 1,3-propanediamine and 2-ethylhexahydropyrimidine to carbon-carbon double bonds. Selective hydrogenation of dienes. Tetrahedron Letters 1975, 16 (48), 4235-4238.

48. Espinal-Viguri, M.; Neale, S. E.; Coles, N. T.; Macgregor, S. A.; Webster, R. L., Room Temperature Iron-Catalyzed Transfer Hydrogenation and Regioselective Deuteration of Carbon-Carbon Double Bonds. Journal of the American Chemical Society 2019, 141 (1), 572-582.

49. Liu, R. Y.; Buchwald, S. L., CuH-Catalyzed Olefin Functionalization: From Hydroamination to Carbonyl Addition. Accounts of Chemical Research 2020, 53 (6), 1229-1243.

50. Wang, D.; Astruc, D., The Golden Age of Transfer Hydrogenation. Chemical Reviews 2015, 115 (13), 6621-6686.

51. Lipshutz, B. H.; Servesko, J. M.; Taft, B. R., Asymmetric 1,4-Hydrosilylations of α,β-Unsaturated Esters. Journal of the American Chemical Society 2004, 126 (27), 8352-8353.

52. Miki, Y.; Hirano, K.; Satoh, T.; Miura, M., Copper-Catalyzed Intermolecular Regioselective Hydroamination of Styrenes with Polymethylhydrosiloxane and Hydroxylamines. Angewandte Chemie International Edition 2013, 52 (41), 10830-10834.

53. Zhu, S.; Niljianskul. N.; Buchwald, S. L., Enantio- and Regioselective CuH-Catalyzed Hydroamination of Alkenes. Journal of the American Chemical Society 2013, 135 (42), 15746-15749.

54. Shi, S.-L.; Buchwald, S. L., Copper-catalysed selective hydroamination reactions of alkynes. Nature Chemistry 2015, 7 (1), 38-44.

55. Jordan, A. J.; Lalic, G.; Sadighi, J. P., Coinage Metal Hydrides: Synthesis, Characterization, and Reactivity. Chemical Reviews 2016, 116 (15), 8318-8372.

56. Kratish, Y.; Bravo-Zhivotovskii, D.; Apeloig, Y., Convenient Synthesis of Deuterosilanes by Direct H/D Exchange Mediated by Easily Accessible Pt(0) Complexes. ACS Omega 2017, 2 (2), 372-376.

57. Karlsson, S.; Hallberg, A.; Gronowitz, S., Hydrozirconation of (E)-3-methoxy-1-phenyl-1-propene and (E)-3-phenyl-2-propenol. Journal of Organometallic Chemistry 1991, 403 (1), 133-144.

58. Alexander, E. R.; Pinkus, A. G., Optical Activity in Compounds Containing Deuterium. I, 2,3-Dideutero-trans-Menthane. Journal of the American Chemical Society 1949, 71 (5), 1786-1789.

59. Reich, C. J.; Sullivan, G. R.; Mosher, H. S., Chiral 1-deuterio alcohols. Synthesis and determination of enantiomeric purity by chiral lanthanide nmr shift reagents. Tetrahedron Letters 1973, 14 (17), 1505-1508.

60. Mosher, H. S., Stereochemistry of neopentyl systems. Tetrahedron 1974, 30 (13), 1733-1745.

61. Elsenbaumer, R L.; Mosher, H. S., Enantiomerically pure (R)-(+)-2-phenylethanol-2-d and -1,1,2-d3, and (S)-(+)-1-phenylethane-1-d, -1,2,-$d_2$, -1,2,2-d3, and -1,2,2,2-d4. The Journal of Organic Chemistry 1979, 44 (4), 600-604.

62. Chen, Y.; Tang, W. L.; Mou, J.; Li, Z., High-Throughput Method for Determining the Enantioselectivity of Enzyme-Catalyzed Hydroxylations Based on Mass Spectrometry. Angewandte Chemie International Edition 2010, 49 (31), 5278-5283.

63. Eliel, E. L., The Reduction of Optically Active Phenylmethylcarbinyl Chloride with Lithium Aluminum Deuteride. Journal of the American Chemical Society 1949, 71 (12), 3970-3972.

64. Küppers, J.; Rabus, R.; Wilkes, H.; Christoffers, J., Optically Active 1-Deuterio-1-phenylethane—Preparation and Proof of Enantiopurity. European Journal of Organic Chemistry 2019, 2019 (15), 2629-2634.

65. Groves, J. T.; Viski, P., Asymmetric hydroxylation by a chiral iron porphyrin. Journal of the American Chemical Society 1989, 111 (22), 8537-8538.

66. Liu, W.; Cheng, M.-J.; Nielsen, R. J.; Goddard, W. A.; Groves, J. T., Probing the C—O Bond-Formation Step in Metalloporphyrin-Catalyzed C—H Oxygenation Reactions. ACS Catalysis 2017, 7 (6), 4182-4188.

67. Morrison, J. D.; Tomaszewski, J. E.; Mosher, H. S.; Dale, J.; Miller, D.; Elsenbaumer, R. L., Hydrogen vs. deuterium transfer in asymmetric reductions: reduction of phenyl trifluoromethyl ketone by the chiral Grignard reagent from (S)-2-phenyl-1-bromoethane-1,1,2-d3. Journal of the American Chemical Society 1977, 99 (9), 3167-3168.
68. Curran, D. P.; Ramamoorthy, P. S., 1,2-Asymmetric induction in radical reactions. Deuteration and allylation reactions of β-oxy-α-bromo esters. Tetrahedron 1993, 49 (22), 4841-4858.
69. Alberti, M. N.; Vassilikogiannakis, G.; Orfanopoulos, M., Stereochemistry of the Singlet Oxygenation of Simple Alkenes: A Stereospecific Transformation. Organic Letters 2008, 10 (18), 3997-4000.
70. Satterthwaite, L.; Pérez, C.; Steber, A. L.; Finestone, D.; Broadrup, R. L.; Patterson, D., Enantiomeric Analysis of Chiral Isotopomers via Microwave Three-Wave Mixing. The Journal of Physical Chemistry A 2019, 123 (14), 3194-3198.
71. Kimata, K.; Hosoya, K.; Araki, T.; Tanaka, N., Direct Chromatographic Separation of Racemates on the Basis of Isotopic Chirality. Analytical Chemistry 1997, 69 (13), 2610-2612.
72. Parker. D., 1H and 2H nuclear magnetic resonance determination of the enantiomeric purity and absolute configuration of α-deuteriated primary carboxylic acids, alcohols, and amines. Journal of the Chemical Society. Perkin Transactions 2 1983, (1), 83-88.
73. McCreary, M. D.; Lewis, D. W.; Wernick, D. L.; Whitesides, G. M., Determination of enantiomeric purity using chiral lanthanide shift reagents. Journal of the American Chemical Society 1974, 96 (4), 1038-1054.
74. Whitesides, G. M.; Lewis, D. W., Determination of enantiomeric purity using chiral lanthanide shift reagents. Journal of the American Chemical Society 1971, 93 (22), 5914-5916.
75. Goering, H. L.; Eikenberry, J. N.; Koermer, G. S., Tris[3-(trifluoromethylhydroxymethylene)-d-camphorato]europium(III). Chiral shift reagent for direct determination of enantiomeric compositions. Journal of the American Chemical Society 1971, 93 (22), 5913-5914.
76. Holcomb, H. L.; Nakanishi, S.; Flood, T. C., Stereochemistry at Carbon of the Cyclometalation of 8-(α-Deuterioethyl)quinoline by Palladium(II) Salts. Organometallics 1996, 15 (20), 4228-4234.
77. Wenzel, T. J.; Bettes, T. C.; Sadlowski, J. E.; Sievers, R. E., New binuclear lanthanide NMR shift reagents effective for aromatic compounds. Journal of the American Chemical Society 1980, 102 (18), 5903-5904.
78. Meddour, A.; Canet, I.; Loewenstein, A.; Pechine, J. M.; Courtieu, J., Observation of Enantiomers, Chiral by Virtue of Isotopic Substitution, through Deuterium NMR in a Polypeptide Liquid Crystal. Journal of the American Chemical Society 1994, 116 (21), 9652-9656.
79. Neill, J. L.; Yang, Y.; Muckle, M. T.; Reynolds, R. L.; Evangelisti, L.; Sonstrom, R. E.; Pate, B. H.; Gupton, B. F., Online Stereochemical Process Monitoring by Molecular Rotational Resonance Spectroscopy. Organic Process Research & Development 2019, 23 (5), 1046-1051.
80. Pate, B. H. E., L.; Caminati, W.; Xu. Y.; Thomas, J.; Patterson, D.; Perez, C.; Schnell, M., Quantitative chiral analysis by molecular rotational spectroscopy. In Chiral Analysis: Advances in Spectroscopy, Chromatography, and Emerging Methods, 2 ed.; Polavarapu, P., Ed. Elsevier: 2018.
81. Joyce, L. A.; Schultz. Danielle M.; Sherer, E. C.; Neill, J. L.; Sonstrom, R. E.; Pate, B. H., Direct regioisomer analysis of crude reaction mixtures via molecular rotational resonance (MRR) spectroscopy. Chemical Science 2020, 11 (24), 6332-6338.
82. Neill, J. L.; Mikhonin, A. V.; Chen, T.; Sonstrom, R. E.; Pate, B. H., Rapid quantification of isomeric and dehalogenated impurities in pharmaceutical raw materials using MRR spectroscopy. Journal of Pharmaceutical and Biomedical Analysis 2020, 189, 113474.
83. Ogston, A. G., Interpretation of Experiments on Metabolic processes, using Isotopic Tracer Elements. Nature 1948, 162 (4129), 963-963.
84. Taylor, R. D.; MacCoss, M.; Lawson, A. D. G., Rings in Drugs. Journal of Medicinal Chemistry 2014, 57 (14), 5845-5859.
85. Das, P.; Delost, M. D.; Qureshi, M. H.; Smith, D. T.; Njardarson, J. T., A Survey of the Structures of US FDA Approved Combination Drugs. Journal of Medicinal Chemistry 2019, 62 (9), 4265-4311.
86. Vitaku, E.; Smith, D. T.; Njardarson, J. T., Analysis of the Structural Diversity, Substitution Patterns, and Frequency of Nitrogen Heterocycles among U.S. FDA Approved Pharmaceuticals. Journal of Medicinal Chemistry 2014, 57 (24), 10257-10274.
87. Loi, C.-M., Smith, D. A.; Dalvie, D., Which Metabolites Circulate?Drug Metabolism and Disposition 2013, 41 (5), 933-951.

Example 4—Synthesis and Characterization of Enantioenriched Deuterated and Fluorinated Small Molecules A. Expected Significance. Deuterated small molecules are extensively used in chemical research and medicine. From an organometallic and synthetic organic chemistry context, they are often used to elucidate reaction mechanisms and perform kinetic isotope effect measurements.[1-4] In physical and analytical chemistry, they serve as valuable tools for spectroscopy or standards for high-resolution mass spectrometry.[5-8] In biochemistry, isotopically labeled compounds are used to elucidate biosynthetic pathways or determine the stereochemical course of microbiological and enzymatic reactions.[8-16] Fluorinated small molecules are also extensively used in chemical research, especially in the synthesis and development of agrochemicals and organic materials.[17, 18] Importantly, both deuterated and fluorinated bioisosteres, structurally distinct compounds recognized similarly by biological systems, have profoundly impacted the design and development of new medicines.[6, 8, 19-28] Given the importance of deuterated and fluorinated molecules in chemical research and medicine, efficient and selective methods to install deuterium or fluorine into small molecules is key to advance these areas.

Since its inception in 2018, my research group has been working to selectively install deuterium into small molecules. Organic chemists have grown accustomed to enantioselective transition metal-catalyzed reactions to forge chiral C—C, C—O and C—N bonds using inexpensive and commercially available metals, ligands and reagents. Our goal is to bring enantioselective deuteration and fluorination chemistry to the same level of control that chemists expect for other functional group manipulations. In the context of selective deuteration, we are now able to distinguish between protium (H) and deuterium (D) and precisely insert them into small molecules. However, a major bottleneck to unlocking the field of selective deuteration is the lack of spectroscopic techniques available to characterize deuterated small molecules and isotopologue and isotopomer impurities. In this proposal, the enantioselective synthesis of molecules that are chiral by virtue of deuterium incorporation and the challenges facing the characterization of specific classes of deuterated small molecules are discussed. Using the knowledge gained from enantioselective deuterium incorporation, we propose to extend our synthetic methodology to develop a new Cu-catalyzed method for the enantioselective hydrofluorination of alkenyl arenes. To address the spectroscopic challenges facing the characterization of chiral isotopomers and isotopic impurities, we established a productive collaboration with rotational spectroscopy experts at the University of Virginia and BrightSpec Inc. Our synthetic expertise and new reaction development coupled with powerful rotational spectroscopy techniques has positioned our research program to accomplish the objectives outlined in this proposal for the selective synthesis of chiral deuterated or fluorinated small molecules.

We propose three objectives in this application to support the development of key areas in our research program. Objective #1 is to develop a novel, enantioselective Cu-catalyzed transfer hydrodeuteration of aryl alkenes. While syntheses of compounds such as (S)-ethylbenzene-d1 have been reported over the past 60 years, they all require inefficient multi-step procedures, and no definitive direct measurement has been reported for measuring enantiomeric excess (ee) or assigning absolute configuration. Using molecular rotational resonance (MRR) spectroscopy for ee measurement and determination of absolute configuration, we will be equipped to fully develop the proposed Cu-catalyzed enantioselective transfer hydrodeuteration reaction.

Objective #2 will serve to develop and enhance the visibility of modern analytical techniques for the characterization of chiral compounds in synthetic chemistry while establishing the foundational spectroscopic techniques required for Objective #1 to succeed. In collaboration with the Pate group, pioneers of the chirped-pulse Fourier transform rotational spectroscopy technique, and Brightspec Inc., the first company to market a line of spectrometers based on MRR spectroscopy, MRR will be established as an enabling and high-throughput technique for ee determination and assignment of absolute configuration for compounds that are chiral by virtue of deuterium substitution. To accomplish this objective, classical synthetic routes for the synthesis of chiral by virtue of deuterium substituted compounds will be executed. The final chiral isotopologue products will be used to carry out the first direct ee and absolute stereochemistry determination for this class of compounds.

Recognizing the importance of selective methods for the synthesis of bioisosteres, we will use the fundamental knowledge gleaned from the Cu-catalyzed enantioselective transfer deuteration (Objective #1) as the basis for Objective #3, in which we will develop an enantioselective hydrofluorination of aryl alkenes. Transition metal-catalyzed selective reactions are now a cornerstone in drug discovery. Funding from this grant would support the development of new analytical techniques and new reactions to access valuable, underexplored chemical space. Working at the interface of spectroscopy and novel reaction discovery serves as a unique training platform for multiple graduate and undergraduate students for productive careers in synthetic chemistry and drug discovery.

Objective #1: Enantioselective Cu-Catalyzed Transfer Hydrodeuteration of Aryl Alkenes.

B.1. Introduction. Molecules that are chiral by virtue of deuterium substitution exhibit optical activity due to chirality induced at prochiral hydrogens when a hydrogen is replaced with deuterium (FIG. 4*a*).[29-31] This represents the most conservative of atomistic changes, consequently making this class of compounds challenging to access. The challenges facing synthetic chemists in the preparation and characterization of chiral by virtue of deuterium substitution compounds is highlighted over the decades in the pursuit of making (S)-ethylbenzene-d1 in high enantiopurity (FIG. 4*b*).[32-35] While some reports offer short, 2-step routes, they can be low yielding and lack characterization data regarding enantiopurity and absolute stereochemistry.[32, 34, 35] Other reported routes to provide (S)-ethylbenzene-d1 in an assumed high enantiopurity require significant synthetic overhead with a lengthy 7-step synthesis.[33, 36, 37]

The synthetic challenges aside, the few chiral by virtue of deuterium substitution molecules that have been successfully prepared were deployed as valuable tools to study reactions. For example, these chiral entities have been used as stereochemical and mechanistic probes in transition metal-catalyzed reactions.[3-40] They have also been used as ligands to study the stereochemistry of fundamental mechanistic steps in organometallic chemistry.[41] For decades, scientists have employed them to elucidate biosynthetic pathways or determine the stereochemical course of microbiological and enzymatic reactions.[8-16, 34] In medicinal chemistry and pharmacology, knowing the exact location of an atom in a bioactive molecule is important. Strategic labelling of therapeutics can mitigate inhibition risks caused by cytochrome P450 (CYP). This has the potential to revive failed drug candidates or make FDA approved small molecule drugs safer with minimal to no impact on drug potency.[6, 24, 26, 28] Constitutional isomers, stereoisomers and enantiomers of bioactive molecules each have their own unique pharmacokinetic profile. Enzymes can differentiate between heterotopic atoms at prochiral centers[12, 42, 43] and beyond studying the stereochemical course of enzymes, we believe this level of differentiation could be further leveraged in drug discovery if highly selective deuterium installation is possible. We hypothesize that lengthy synthetic sequences and lack of spectroscopy tools for characterization are bottlenecks to fully unleashing the potential these chiral molecules have.

B.2. Background. Deuterium was reported by Urey in 1932.[44] Despite this report 88 years ago, it was not until a growing demand for isotopically labeled internal standards for mass spectrometry (MS) sparked significant research efforts towards selective deuterium installation.[7, 45] The state-of-the-art methods for selective deuterium incorporation include metal-catalyzed hydrogen isotope exchange (HIE) and selective reductive deuteration processes. While significant progress has been made in the HIE field, a major drawback to metal-catalyzed HIE reactions is controlling site-selectivity. Oftentimes, over-deuteration of multiple reactive C—H bonds within a molecule and incomplete deuteration of the desired sites are reported.[7, 45-50] While heterogeneous metal-catalyzed HIE is also routinely used, it typically proceeds with even less control over site-selectivity as reaction tuning is limited in the absence of a tunable ligand.[7, 45, 51, 52] Since achieving high levels of site-selectivity remains elusive, enantioselective HIE remains unattainable.

We therefore turned our attention to selective reductive deuteration chemistry to guide our reaction development. The state-of-the-art regioselective and/or stereoselective methods highlight the tremendous potential for selective deuterium installation. For example, a method to prepare cyclohexene isotopologues and stereoisotopomers from benzene in the presence of stoichiometric tungsten and $H/D^+$ reagents was recently reported.[53] However, enantioselective deuterium installation is not currently possible under this protocol. Even if an enantioselective transformation was possible, the stoichiometric tungsten complex remains bound to the deuterated cyclohexene product(s) and further high temperature transformations (200° C.) are required to liberate the product from the metal complex. Instead, a regioselective deuterium incorporation is commonly achieved with a stoichiometric Zr—H addition across an alkene, followed by a $D_2O$ workup.[54] This reaction is accompanied by undesirable side reactions that eliminate heteroatom functionality. The recently reported selective transfer hydrodeuterations are the most relevant breakthroughs, representing the first regioselective transformations to selectively incorporate H and D across an alkene in one step.[55, 56] Aside from these reports, only modest selectivities have been reported for selective hydrodeuteration.[57] Despite this significant advance, the reported reaction scopes are not enantioselective and limited to only very activated alkenes (i.e. 1,1 disubstituted alkenes) where at least one substituent is an aryl group. Nitrogen heterocycles are not compatible with these reactions and a platform for this reaction to be enantioselective seems unattainable.

We are not the only scientists that are aware of the major deficiencies in selective deuteration chemistry. In fact, a cross-functional team of scientists with expertise in process chemistry, isotope chemistry, analytical chemistry, and drug metabolism and pharmacokinetics established by the International Consortium for Innovation and Quality in Pharmaceutical Development are developing guidance to address deuterated active pharmaceutical ingredients (APIs).[58] The team recognizes the tremendous impact deuterated APIs will play in medicine and identifies that synthetic access to deuterated compounds free of isotopic impurities and analytical methods to support the characterization and quality control of the target molecules are bottlenecks to unleashing the full potential of deuterated APIs in drug discovery. They explain that isotopologues or isotopomers lacking deuteriums at the metabolically active site(s) will result in shorter half-life values of APIs. When coupled with impractical purification strategies to separate isotopic impurities, unselective deuterations have restricted utility. Recognizing the limitations in selective deuteration chemistry, we sought to address the longstanding challenge of preparing compounds that are chiral by virtue of deuterium substitution, by exploring an enantioselective Cu-catalyzed transfer hydrodeuteration.

Transfer hydrodeuteration reactions offer significant advantages over methods utilizing $H_2$, HD or $D_2$ gas. Transfer hydrogenation/deuteration processes obviate the use of flammable $H_2$, HD or $D_2$ gas by using alternative H and D sources (i.e. alcohols or silanes).[59] Transfer hydrogenation/deuteration processes also provide an avenue for exploring a selective hydrodeuteration where H and D can be distinguished in a reaction. Synthetically, several challenges must be addressed to develop a general and practical catalytic, enantioselective synthesis of compounds that are chiral by virtue of deuterium substitution (FIG. 4*c*). The reaction must be completely regioselective, otherwise the dihydrogen impurity will erode the isotopic purity of the compound. This means the catalytic reaction must be designed to distinguish between chemically similar atoms (H and D). We knew this was achievable under transfer hydrodeuteration conditions based on the literature precedent.[55, 56] However, the reaction must also be highly enantioselective (>90% ee). There is no precedent for achieving any enantioselectivity in this type of reaction. Finally, a spectroscopic technique for determination of ee and absolute configuration of the products would need to be developed. Using the MRR spectroscopy techniques developed in our collaboration (discussed in Objective #2), we began to explore a Cu-catalyzed transfer hydrodeuteration for the synthesis of compounds that are chiral by virtue of deuterium substitution.

Figure 6:
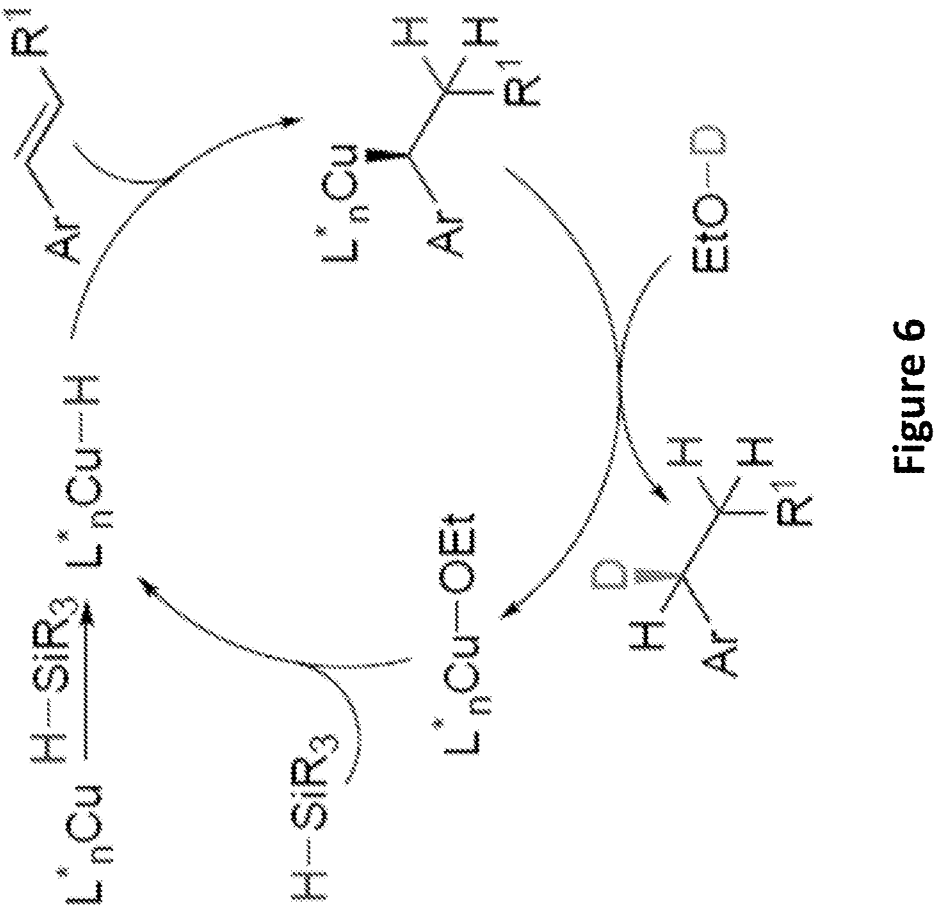
FIG. 6. Overview of enantioselective reaction. a) proposed mechanism; and b) enantioselective transfer hydrodeuteration.
Figure 6:
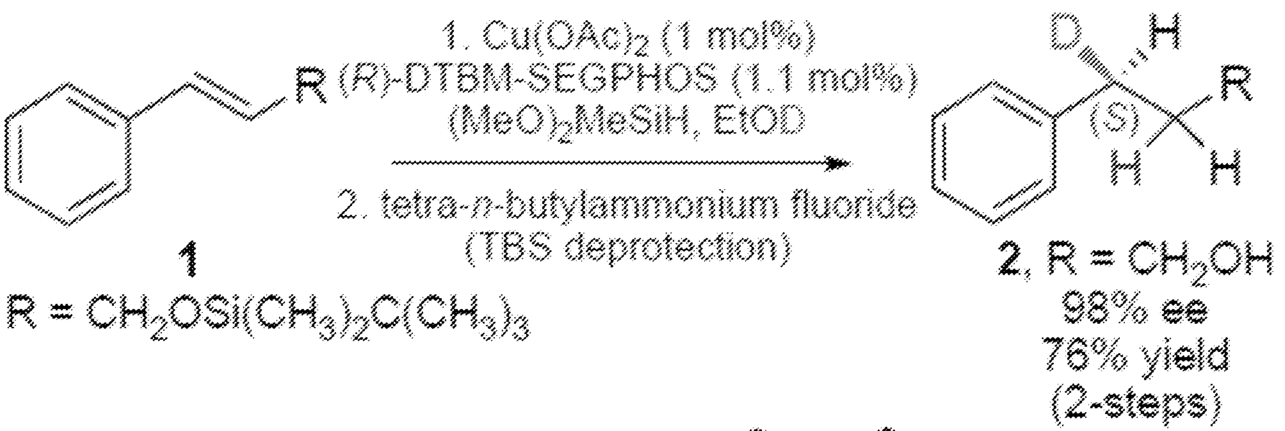
Figure 6:
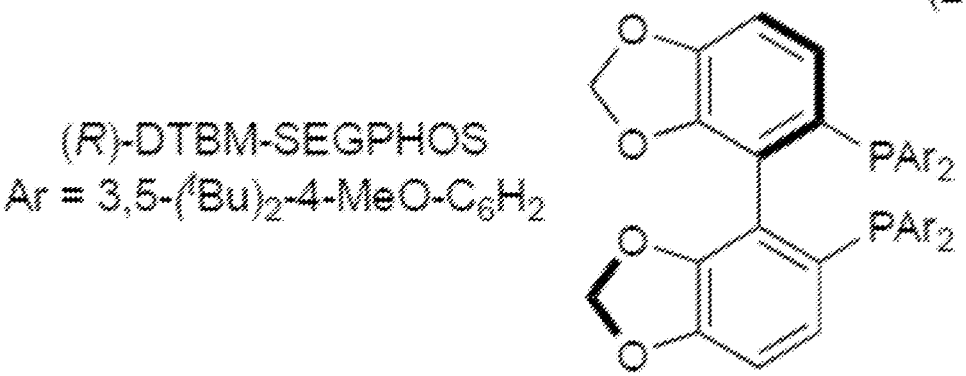

B.3. Reaction Development and Preliminary Results. Inspired by previous highly selective reactions utilizing highly reactive Cu—H catalysts[60-65] and our recently completed alkyne transfer deuteration chemistry which has been submitted for publication, we began exploring an enantioselective transfer hydrodeuteration of aryl alkenes. We envisioned a mechanistic scenario where H and D can be distinguished using ethanol-OD and $R_3Si$—H and hypothesized that combining $Cu(OAc)_2$, DTBM-SEGPHOS and a Si—H will form the active chiral Cu—H catalyst (FIG. 6).[66] Insertion across an aryl alkene should occur both regioselectively and enantioselectively, with the Cu—H adding to form the stabilized benzylic copper intermediate. In the presence of ethanol-OD, we postulate that deuterodecupration should occur to release the chiral by virtue of deuterium substitution product. We began evaluating cinnamyl alcohol derivative 1 for reactivity in the presence of $Cu(OAc)_2$, DTBM-SEGPHOS, Si—H, ethanol-OD and tetrahydrofuran (THF). Gratifyingly, we isolated in the deuterated product 2 in 76% yield (over 2-steps, 90% yield for transfer hydrodeuteration) (FIG. 6*b*).

We evaluated the regioselectivity by $^1H$ and $^{13}C$ NMR and determined that deuterium selectively added to the benzylic position and we could not find any detectable levels of deuterium incorporation into other carbons. MRR confirmed that less than 0.1% of the dihydrogen impurity and regioisomer impurity was formed. The Pate group was able to determine the absolute configuration of the stereogenic center to be (S) and measured a 98% ee of the product by MRR spectroscopy (data not shown). A detailed description of how ee determination and absolute configuration assignment is performed using MRR is given in Objective #2. For compound 2, the ee and absolute configuration of the dominant enantiomer of 2 was determined using high enantiopurity tag sample ((S)-propylene oxide) as shown in FIG. 4*e*, eq 2. For the spectrum in eq. 2, the homochiral (S,S) complex is the principal species in the sample. The diastereomeric excess of the tag complexes can be measured quantitatively from these spectra and this correlates directly to the enantiomeric excess of the deuterated substrate.

We encountered a moderately selective reaction with 4-vinylbiphenyl and proceeded to evaluate alternate reaction conditions to improve ee (Table 3). At 40° C. the reaction reached completion, was highly regioselective, but gave a moderate 77% ee (entry 1). We immediately recognized that to find optimal reaction conditions, a spectroscopic method that could perform high-throughput analysis of our samples is desirable. MRR spectroscopy has this potential since no chemical manipulations are necessary for ee determination and multiple samples can be analyzed daily. By performing the reaction at room temperature, we were able to isolate the product in 80% yield, which contained a synthetically useful 92% ee (entry 2). Importantly, further lowering the reaction temperature to 5° C. resulted in a 98% yield of the product with 96% ee (entry 3). Other parameters were evaluated such as solvents and solvent concentration (entries 4-9). Notably, performing the reaction with 1:1 or 1:4 dioxane: THF solvent mixture was highly selective, even at 40° C. (91-92% ee, entries 7-8). Importantly, reactivity and regioselectivity is high for all of the reaction conditions, as each of the entries in Table 3 reached completion, no starting material was seen in the crude $^1$H NMR and all regioselectivities were >20:1. A modification we will explore in the future is using a milder silane such as poly(methylhydroxysilane) (PMHS) for this reaction.

TABLE 3

Optimization Studies.

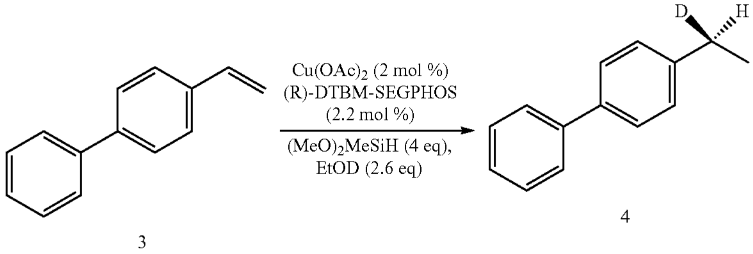

3

4

| Entry | Solvent[a] | Concentration[b] | Temp. | 4% Yield | 4% ee |
|---|---|---|---|---|---|
| 1 | THF | 1M | 40° C. | 85 | 77 |
| 2 | THF | 1M | 23° C. | 80 | 92 |
| 3 | THF | 1M | 5° C. | 98 | 96 |
| 4 | THF | 0.5M | 40° C. | 76 | 67 |
| 5 | 1,4-dioxane | 1M | 40° C. | 90 | 85 |
| 6 | 4:1 (D:T) | 1M | 40° C. | 95 | 85 |
| 7 | 1:1 (D:T) | 1M | 40° C. | 99 | 91 |
| 8 | 1:4 (D:T) | 1M | 40° C. | 96 | 92 |
| 9 | MTBE | 1M | 40° C. | 94 | 88 |

[a] d:t (1,4-dioxane:THF)
[b] Based on 0.3 mmol of substrate

Figure 7:
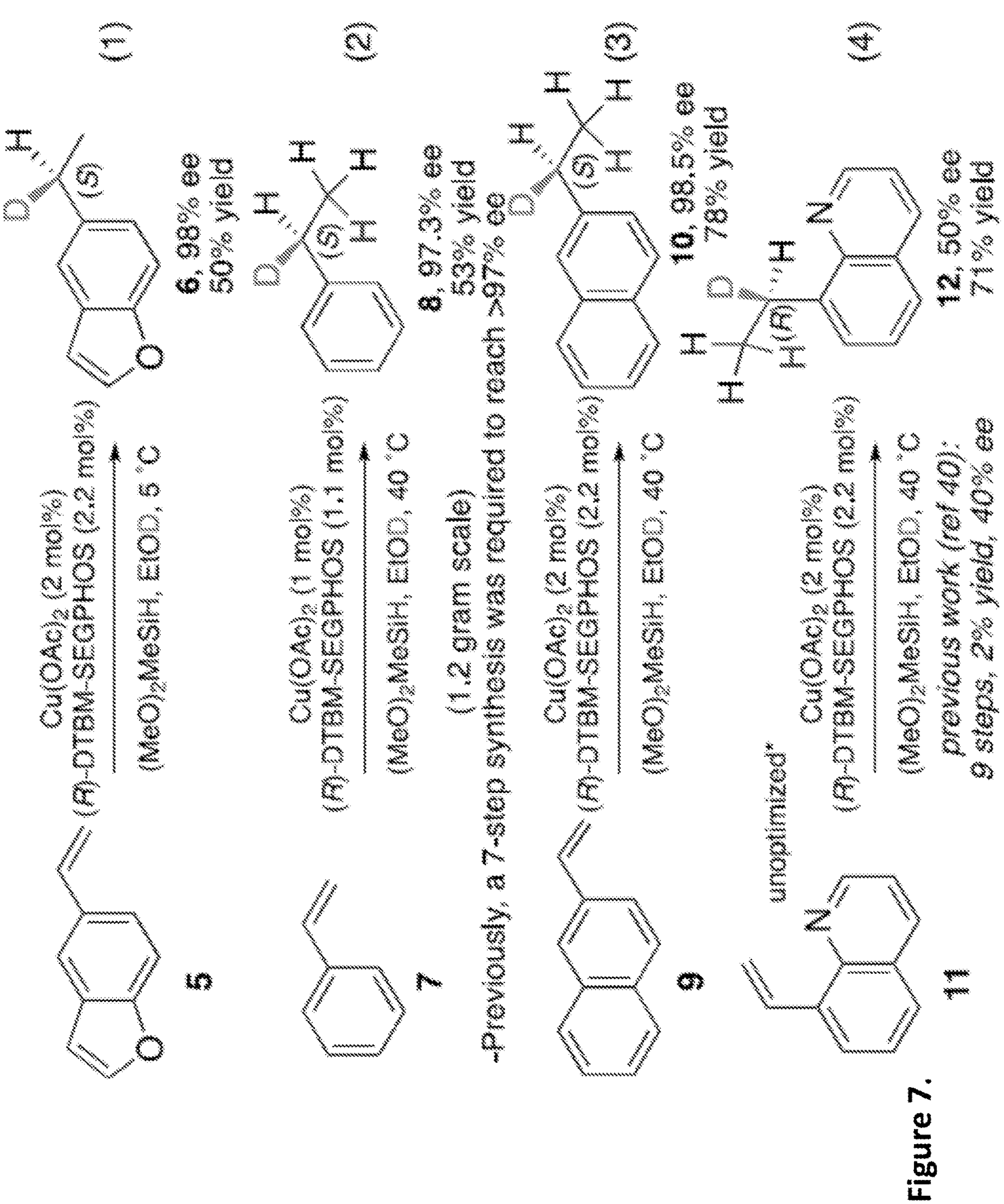
FIG. 7. Substrate scope of enantioselective reaction.

Recognizing that lower temperatures can be beneficial for achieving higher enantioselectivity, we attempted the enantioselective transfer hydrodeuteration with vinyl benzofuran substrate 5. After product isolation, MRR analysis revealed a 98.7% ee for the (S)-5-(α-deuterioethyl)-benzofuran 6 (FIG. 7, eq 1). We also sought to address the longstanding challenge of efficiently and selectively making (S)-ethylbenzene-d1 in one-step. Using our Cu-catalyzed transfer hydrodeuteration protocol we have now developed the first, highly enantioselective, 1-step synthesis of (S)-ethylbenzene-d1 (8, 97.3% ee) on gram scale (FIG. 7, eq 2). Importantly, the reaction uses an achiral, structurally simple, bulk commodity starting material (styrene, 7). Contrary to all previous techniques to make this class of chiral by virtue of deuterium substitution compounds, a chiral starting material is not required. The reaction was also found to be highly regioselective with only trace amounts of another isotopologue present. Through verification by MRR, only trace dihydrogen (non-deuterated ethylbenzene) impurity (<0.1%) was present in the product.

Using 2-vinylnaphthalene 9 for enantioselective transfer hydrodeuteration was also successful (FIG. 7, eq. 3). The ee nearly reached the theoretical limits of enantiopurity achievable through this reaction and was measured to be 98.5% ee for 2-ethylnapthalene-d1 10. Almost no isotopic impurities were detected (<0.1%), indicating a nearly perfect regioselectivity and the product was formed in 78% yield using just 2 mol % of a base metal-catalyst. Inspired by the 1996 Flood report that describes a 9-step procedure to access (R)-(−)-8-(α-deuterioethyl)quinoline in 2% yield with a 40% ee,[41] we were interested in attempting our Cu-catalyzed transfer hydrodeuteration on 8-vinylquinoline 11 to provide access to the product 12 in 1-step (FIG. 7, eq 4). The major regioisomer (>20:1 regioselectivity) was observed in 71% yield, but the ee was moderate at just 50%. While this represents a significant improvement from the previously reported synthesis, optimization will be required to increase enantioselectivity. We will evaluate the reaction at 5° C. and based on our preliminary data, we hypothesize this will be beneficial to enhancing enantioselectivity.

Figure 8:
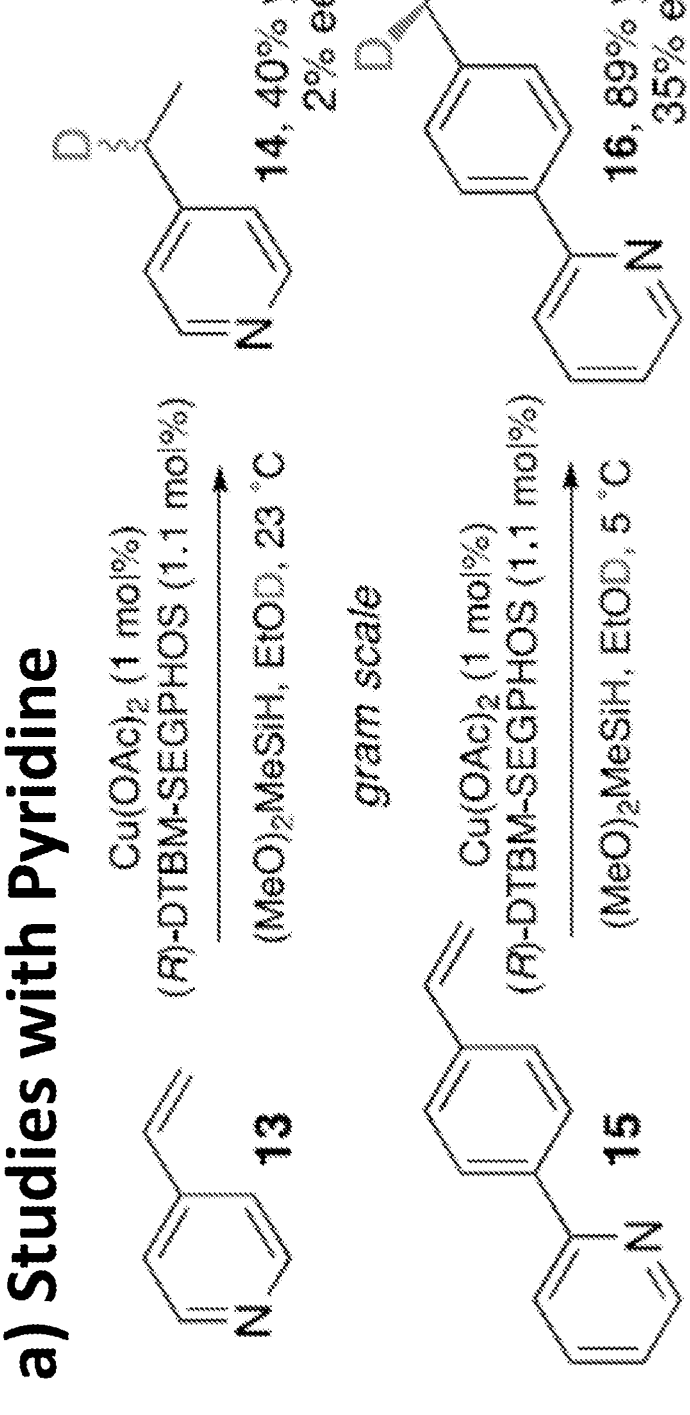
FIG. 8. Proposed complexation strategy. a) current studies with pyridine; and b) potential additional substrates.
Figure 8:
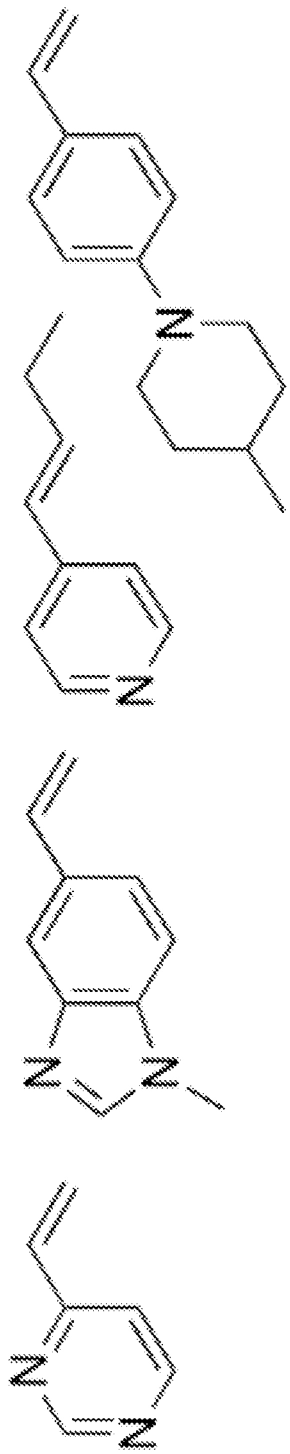
Figure 9:
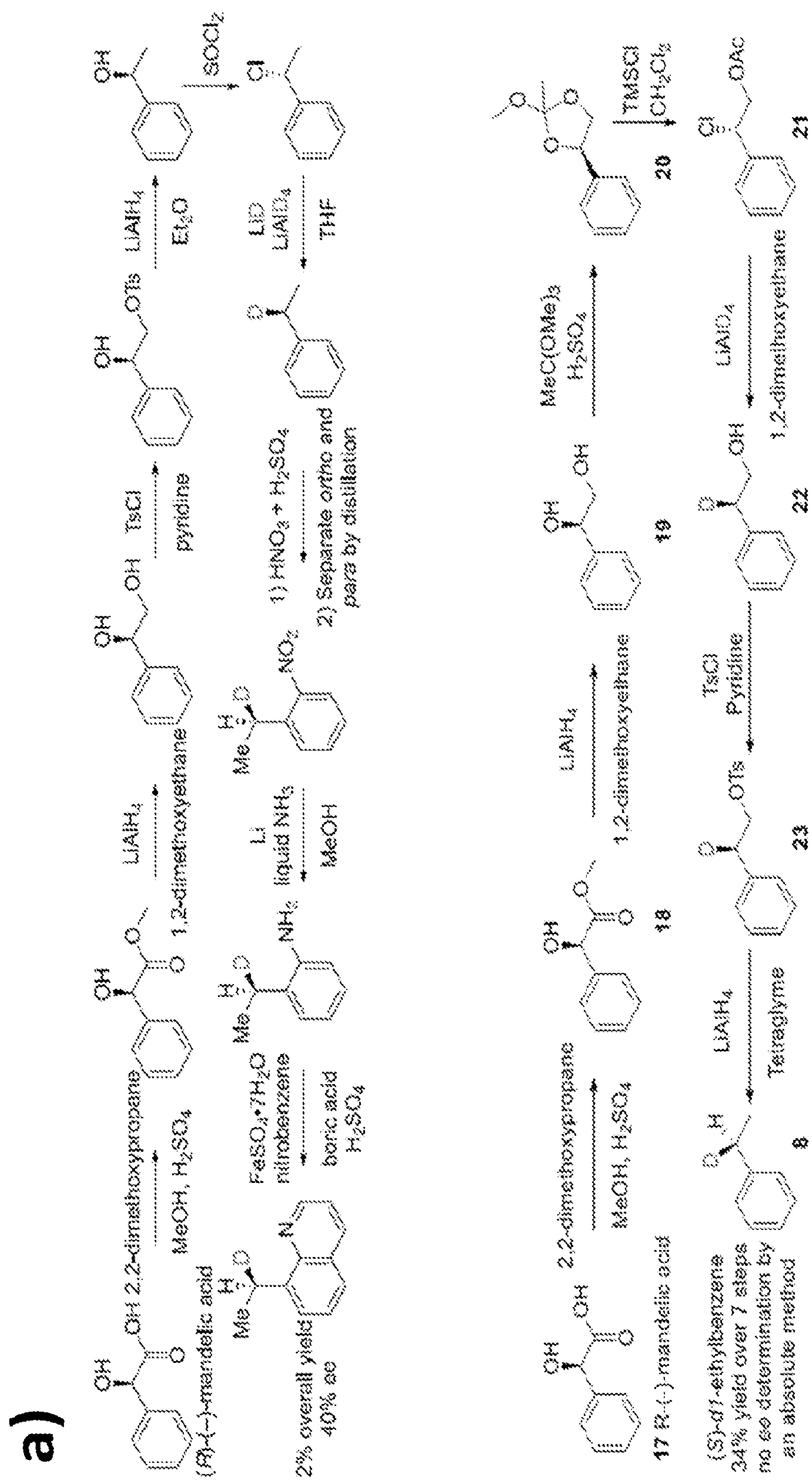
FIG. 9. Scheme for prior synthesis of (R)-8-(α-deuterioethyl)quinolone.

Having successfully performed a chiral hydrodeuteration on an oxygen containing heterocycle, and having achieved moderate success with a vinylquinoline substrate, we looked to expand the reaction to include other nitrogen-containing heterocycles. We are especially interested in exploring nitrogen-containing heterocycles commonly found in small molecule drugs.[67, 68] Since pyridine is one the most prevalent heterocycles in FDA approved drugs.[69] we began with pyridine containing aryl alkenes. Disappointingly, we encountered our first major enantioselectivity setback with 4-vinylpyridine 13 at 40° C., using THF as the solvent (FIG. 8*a*). This resulted in a nearly racemic 4-(α-deuterioethyl) pyridine product 14. Lowering the reaction temperature to 23° C. did not result in an improved ee. Notably, another pyridine-containing substrate, 3-(4-vinylphenyl)-pyridine 15, also underwent regioselective transfer hydrodeuteration. However, enantioselectivity was only low to moderate and not at a synthetically useful level, even at 5° C. (16, 35% ee, FIG. 8*a*). With these results in hand, we began to hypothesize why enantioselectivity is diminished in these substrates. We believe that competitive binding of the basic nitrogen functionality in the pyridine containing substrates to the Cu-catalyst erodes enantioselectivity. To test our hypothesis, we will evaluate a piperidine containing substrate to see if enantioselectivity is also diminished. We will also evaluate if using pyridine as a ligand (in the absence of (R)-DTBM-SEGPHOS) will still promote the Cu-catalyzed transfer hydrodeuteration.

The presence of basic nitrogen functionality in transition metal-catalyzed reactions has been reported to inhibit catalysis or alter desired site-selectivity.[70-72] Our research group is uniquely qualified to tackle challenges such as heterocycle tolerance in selective base metal-catalyzed processes. While performing postdoctoral research under the guidance of Prof. Christina White, the PI of this grant worked on the development of a basic nitrogen quaternization strategy for pyridine containing substrates.[71, 72] While the quaternization strategy was applied in base metal-catalyzed aliphatic C—H oxidation and C—H amination reactions, we believe this strategy will be effective for base metal-catalyzed transfer hydrodeuteration reactions. We will perform the quaternization with $BF_3 \cdot OEt_2$ and evaluate the modified substrate under the transfer hydrodeuteration conditions. A potential challenge may arise with substrate solubility. To overcome solubility problems, we can pivot to more polar solvents such as 1,4-dioxane and we will screen increasing the equivalents of ethanol-OD in the reaction. Success of this strategy will lead to expanding the nitrogen-containing heterocycle substrate scope (FIG. 8*b*).

Objective #2: Implement Molecular Rotational Resonance (MRR) as an Enabling Technique for Enantiomeric Excess (Ee) Determination and Assignment of Absolute Configuration for Compounds that are Chiral by Virtue of Deuterium Substitution.

C.1. Introduction. For selectively labeled small molecules to gain widespread use in the scientific community, two major challenges must be addressed. 1) Robust synthetic methods to selectively and precisely install deuterium into small molecules must be developed and 2) reliable, high-throughput analytical techniques to characterize both achiral and chiral isotopomers and isotopologues must exist. The predicament in addressing these challenges is their codependency. Robust synthetic methods cannot be developed if analytical techniques to support their development do not exist. Alternatively, the analytical methods cannot be developed if the molecules of interest are too challenging to access. For this reason, we are collaborating with rotational spectroscopy experts at the University of Virginia and BrightSpec Inc. to develop MRR as an enabling technique for enantiomeric excess (ee) determination and assignment of absolute configuration for compounds that are chiral by virtue of deuterium substitution. Importantly, the success of Objective #1 is dependent on the success of Objective #2. We believe the preliminary data obtained at the time of this submission substantiates our claims that both Objective #1 and #2 can be achieved.

C.2. Syntheses of (S)-(+)-ethylbenzene-d1. The challenges facing synthetic chemists in the preparation and characterization of chiral by virtue of deuterium substitution compounds is highlighted over the decades in the pursuit of making (S)-ethylbenzene-d1 in high enantiopurity.[32-35] While some reports offer short, 2-step routes, they can be low yielding and lack characterization data regarding enantiopurity and absolute stereochemistry.[32, 34, 35] Other reported routes to provide (S)-ethylbenzene-d1 in an assumed high enantiopurity require significant synthetic overhead with a lengthy 7-step synthesis.[33, 36, 37] Due to the lack of absolute ee measurement or determination of absolute configuration, we embarked on repeating two syntheses of (S)-ethylbenzene-d1 and worked with the Pate group to characterize the products using MRR spectroscopy.

The first synthesis we repeated was developed by the Mosher group in 1979.[33] It has been repeated several times in the literature, most notably by the Groves group in 1989 and 2017.[36, 37] The synthesis begins with (R)-(−)-mandelic acid 17 (100% ee) and after 7 synthetic manipulations, (S)-(+)-ethylbenzene-d1 8 is obtained in an overall 34% yield. While the ee of alcohol 22 could be determined using a chiral shift reagent reported by Whitesides' group,[73] the ee of (S)-ethylbenzene-d1 8 could only be derived from the optical rotation. The final paragraph of the article states "We conclude that one must use extraordinary care with purity when using optical rotation for determining enantiomeric purity for compounds such as these. It is essential wherever possible that enantiomeric purity be determined by an absolute method."[33] Lastly, the authors assign absolute configuration based on the mechanistic course of the reactions employed.

It was not until 40 years later that the ee for (S)-ethylbenzene-d1 8 was determined by an absolute method.[35] The Christoffers group recognized and explained that determination of enantiopurity that relies on the optical rotation measurement is generally associated with relatively large uncertainty. To accomplish the absolute ee determination, they used a modified 2-step procedure to make (S)-ethylbenzene-d1 8 from (S)-phenylethanol 24. The authors then embark on two, two-step derivatizations of (S)-ethylbenzene-d1 8 to make diastereomers that gave distinct signals by $^1$H NMR for ee determination. The authors concluded the enantiopurity of (S)-ethylbenzene-d1 8 to be 92% ee. Interestingly, the optical rotation of 8 prior to derivatization was determined to be zero ($[\alpha]^{20}_D=0$). For comparison, Mosher reported an optical rotation of $[\alpha]^{20}_D=0.710$.[33] After repeating the Mosher and Christoffers syntheses to (S)-ethylbenzene-d1 8, we sought to employ an absolute method for ee determination for our two samples.

C.3. Molecular Rotational Resonance Background. Molecular rotational resonance (MRR) is a spectroscopic method useful for rapidly discriminating between all types of isomers and providing quantitative characterization data.[74-77] MRR spectroscopy identifies molecules through their mass distribution as quantified by the principal moments-of-inertia for overall rotation of the gas phase molecule. There are two key features of MRR spectroscopy that make it a powerful technique for isotopomer analysis: 1.) All isotopic variants of the substrate have the same equilibrium geometry so that one geometry is all that is needed to predict the spectral signatures of all isotopomers. 2.) Geometries with sufficient accuracy for isotopomer analysis can be obtained from quantum chemistry. The general advantages of MRR are that the high spectral resolution makes it possible to directly analyze crude mixtures, there is no need for reference samples to identify isotopomers and isotopologues with high confidence, and measurements take only 10-20 minutes each.

MRR has recently been used for isotopologue and isotopomer analysis where the ability to identify 15 different isotopic isomers in a synthetic sample at 100:1 dynamic range was demonstrated.[53] Importantly, chiral analysis is possible by MRR spectroscopy with general applicability using the chiral tag methodology.[75, 77] In May 2020, we worked with the Pate group and BrightSpec Inc. to develop a methodology to analyze isotopically chiral samples obtained by repeating the Mosher and Christoffers syntheses of (S)-ethylbenzene-d1 8. Our goal is to establish MRR as a practical analytical technique for ee determination of compounds that are chiral by virtue of deuterium substitution. We also want to establish MRR as an analytical tool for absolute configuration assignment. We recognized that optimizing reaction parameters for Objective #1 is possible if a high-throughput strategy for ee determination and absolute stereochemical assignment existed.

C.4. Preliminary Results for EE Measurement and Determination of Absolute Configuration. The MRR analysis of the chiral isotopomer ethylbenzene-d1 8 is summarized to illustrate the procedure. The method is similar to chiral derivatization approaches in NMR spectroscopy[78]—the enantiomers of ethylbenzene-d1, which have identical rotational spectra, are converted to distinguishable diastereomers by adding an additional, known chiral center. In MRR the "discriminating" chiral center is added through non-covalent interactions by forming a 1:1 complex between the analyte and a small chiral tag molecule.[75, 79] Weakly bound complexes are ubiquitous in pulsed jet expansions and, therefore, a single tag molecule can be successfully used for the analysis of a wide range of substrates. For the specific case of molecules that are chiral by virtue of deuteration, chiral tag MRR spectroscopy offers a method for both quantitative ee determination and high-confidence assignment of the absolute configuration. The unique feature of chiral isotopomer analysis is that the spectroscopic analysis can use the normal isotopic variant of the analyte to determine the structure of the chiral tag complex. The nondeuterated sample is often available at low cost. Under the Born-Oppenheimer approximation, the structure of all isotopic variants of the molecule have the same equilibrium geometry so that changes in the rotational constants come simply from the mass change of the substituted deuterium nucleus.[80]

The analysis for ethylbenzene-d1 used trifluoroisopropanol (TFIP) as the chiral tag. The structures of low energy isomers of the complex of ethylbenzene (nondeuterated) and TFIP are predicted by quantum chemistry using dispersion corrected density functional theory (B2PLYPD3 def2TZVP).[81] The dominant spectrum observed in the experiment matches the lowest energy isomer for the tag complex predicted by theory as verified by the experimental carbon atom framework geometry obtained from a Kraitchman analysis of the carbon atom positions using the assigned rotational spectra of singly-substituted $^{13}C$ isotopomers observed in natural abundance.[80, 82] A second isomer is also observed in the experiment with a spectrum consistent with the second lowest energy structure from theory.

With validated theoretical structures, the MRR spectra of the chiral tag complexes formed with ethylbenzene-d1 can be predicted to high accuracy by simply changing the mass of the substituted nucleus in the structure and applying a scale factor obtained from the ratio of the experimental and theoretical rotational constants of the normal isotopic species. The predictions of the homochiral and heterochiral MRR spectra are validated by making a measurement using the ethylbenzene-d1 and a racemic sample of the TFIP tag to ensure that equal number densities of the diastereomeric complexes are produced in the pulsed jet expansion. The analysis of MRR spectra, where there is a single deuterium substitution, is used to obtain the principal axis coordinates of the substituted H/D-atom in the tag complex.

For chiral analysis, the tag sample is switched to a high enantiopurity (ee=99.4) sample of (S)-TFIP. For a high enantiopurity sample of ethylbenzene-d1, the resulting MRR spectrum will be dominated by a single diastereomer. Because the geometries of the complexes associated with each spectrum are known, and the absolute configuration of the (S)-TFIP tag is also known, the absolute configuration of the analyte, (S)-ethylbenzene-d1 8, is determined with high confidence.

The enantiomeric excess of the analyte is determined by the transition intensity ratio of the spectroscopic transitions for the two diastereomers of the complex in a manner analogous to analysis of a chiral chromatographic separation (the analysis also includes the effects of the actual (S)-TFIP enantiopurity). However, unlike in chromatography, there are many peaks that can be used in the ee determination. The MRR analysis uses the transition intensity of many peaks to determine the ee and standard error from the histogram of all possible ee determinations for different transition pairs. The new Cu-catalyzed methodology achieved an ee=97.3 (8, FIG. 7).

The full spectroscopic analysis and ee determination of the ethylbenzene-d1 sample is performed on a broadband chirped-pulse Fourier transform microwave spectrometer using about 50 mg of sample.[83] One key advantage of MRR spectroscopy is that the measurement can also be performed inside a resonator to increase the measurement sensitivity using spectrometers that employ the design principles introduced by Balle and Flygare[84] and offered commercially by BrightSpec. Inc. The cavity-enhanced instruments reduce measurement times and sample consumption by a factor of 100-1000 compared to broadband instruments. However, they can only monitor a single rotational transition at a time due to the width of the cavity resonance. Once the spectroscopic analysis has been performed in the CP-FTMW spectrometer, subsequent ee determinations can be performed in the cavity-enhanced instruments, thus providing a high-throughput chiral analysis technique to screen reaction conditions so that the synthetic methodology can be optimized.

We believe MRR has the potential to be at the forefront of spectroscopic methods for ee determination, isotopologue characterization and isotopic impurity measurement in organic synthesis. We will repeat a known synthesis of (R)-(−)-8-(α-deuterioethyl)quinoline in which enantiopurity is lost during one or more synthetic steps (Scheme 2).[41] Using MRR, we will measure the ee of each product in the synthetic route. We will also determine the isotopic purity and identify any isotopic impurities at each step. This information will permit the determination of the synthetic steps where isotopic impurities are introduced or enantioenrichment is depleted. The authors make this compound to uncover mechanistic details in an organometallic reaction. The synthesis includes intermediates that are chiral by virtue of deuterium substitution and a final product that is chiral by virtue of deuterium substitution. We hypothesize that with MRR spectroscopy, we will be able to determine the ee of all chiral intermediates, determine which step(s) in the synthesis enantiopurity is lost and determine the percent deuteration at the benzylic position of all intermediates. The synthesis by Flood and coworkers begins with making (R)-ethylbenzene-d1 using previously reported methods.[32, 33] Interestingly, the authors report an 80% ee based on optical rotation measurements. This is not in agreement with the value previously reported by Mosher and may be indicative of the degree of error involved in measuring ee from optical rotation values.

The synthesis continues with a nitration of (R)-ethylbenzene-d1. This involves a spinning-band distillation at reduced pressure to isolate the ortho isomer from the ortho/para mixture. The deuterated o-nitroaromatic was then subjected to a Li/$NH_3$ reduction to provide the deuterated o-ethyl-aniline. A modified Skraup synthesis provided the final (R)-(−)-8-(α-deuterioethyl)quinoline product. Due to the proximity of the nitrogen atom to the chiral center, a chiral shift reagent was employed in the $^1H$ NMR sample to separate the chiral α-H signals. The authors report a 40% ee of the final product and mention that separation of the enantiomer peaks was never achieved so ee was determined by peak deconvolution. The isotopic purity of the final product had also dropped to 91%. These lower ee and isotopic purity values indicated that one or more synthetic steps beginning with nitration of (R)-ethylbenzene-d1 was problematic. We will repeat this synthesis and use MRR spectroscopy to measure ee and isotopic purity at each step.

We anticipate the outcomes of this study will be two-fold: A.) Using the chiral tag methodology, a high-throughput MRR spectroscopy technique will be established for rapid determination of enantiopurity of chiral small molecules. This will support the success of Objective #1. B.) MRR spectroscopy will be recognized as an analytical tool for characterizing products of each synthetic step so problematic reactions in a synthetic sequence can be identified for optimization. This will support the objectives of not only this proposal but support successful outcomes for the Pate Group's NSF sponsored chiral tag methodology research (NSF CHE-1904686).

Objective #3: Enantioselective Cu-Catalyzed Hydrofluorination of Aryl Alkenes.

D.1. Introduction. Fluorinated small molecules are prevalent in medicine and agrochemistry. While fluorinated small molecules are the least abundant natural organohalides,[19] fluorinated bioactive molecules can be highly potent and comprise more than 50% of the blockbuster drugs.[21, 85, 86] They comprise about 20% of the commercial pharmaceuticals (340 currently available).[87] In fact, over 40% of the new FDA small molecule drugs in both 2018 and 2019 contain fluorine. This is not surprising considering that fluorine substitution can alter $pK_a$, increase lipophilicity and influence metabolism, potency, conformation and membrane permeability of a bioactive molecule.[23] Incorporating fluorine into specific positions within a bioactive molecule is a key design principle in the synthesis of novel bioisosteres used in developing new drugs.[24, 28] Among the fluorine-containing drugs approved by the FDA in 2019, over 50% of them contain at least one stereogenic center and were approved to be administered in enantiomerically pure form.[85] Despite this, less than 1% of all fluorine-containing medicines on the market feature a C—F stereogenic center.[88] While selective methods that incorporate fluorine into small molecules are in large demand and synthetic efforts are underway to address these demands, there are no general methods for a highly enantioselective hydrofluorination of alkenes. We believe this remains as a bottleneck to developing bioactive molecules with a fluorinated stereogenic center and inspired us to explore a Cu-catalyzed enantioselective hydrofluorination reaction for the synthesis of small molecules with chiral benzylic $C(sp^3)$-F functionality.

Figure 10:
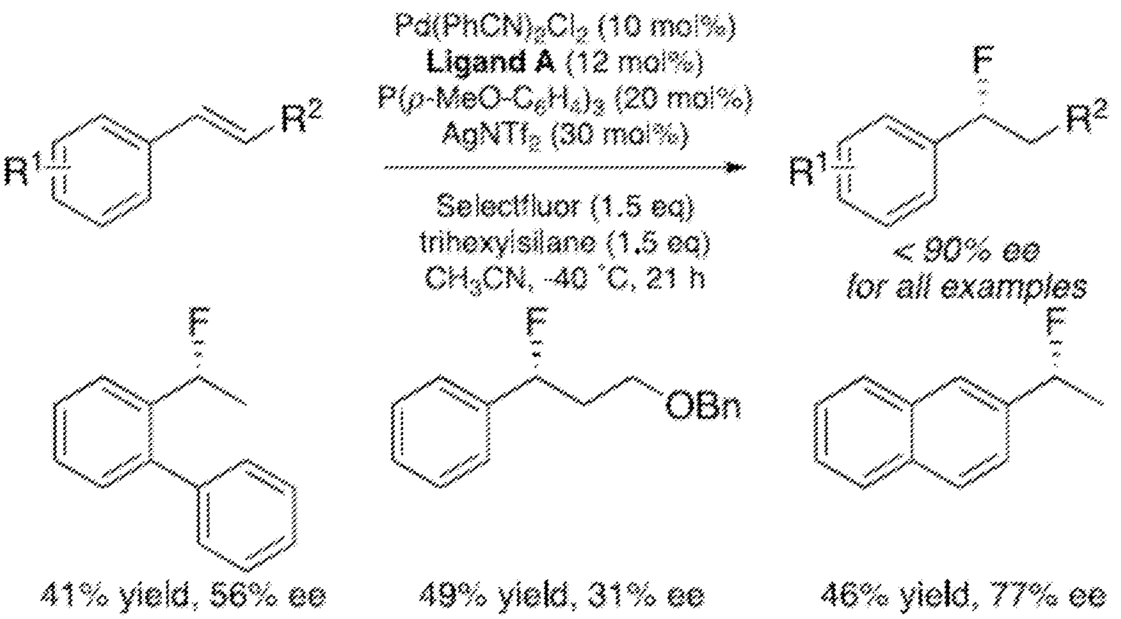
FIG. 10. Asymmetric hydrofluorination of alkenyl arenes. A) state-of-the-art asymmetric hydrofluorination; and b) preliminary data and proposed mechanism.
Figure 10:
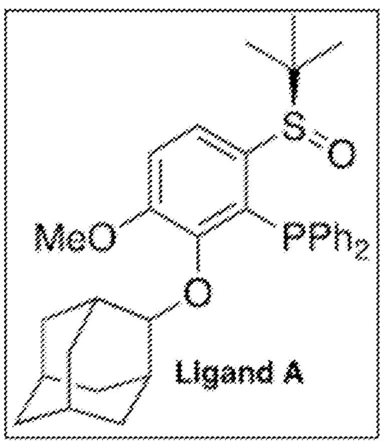
Figure 10:
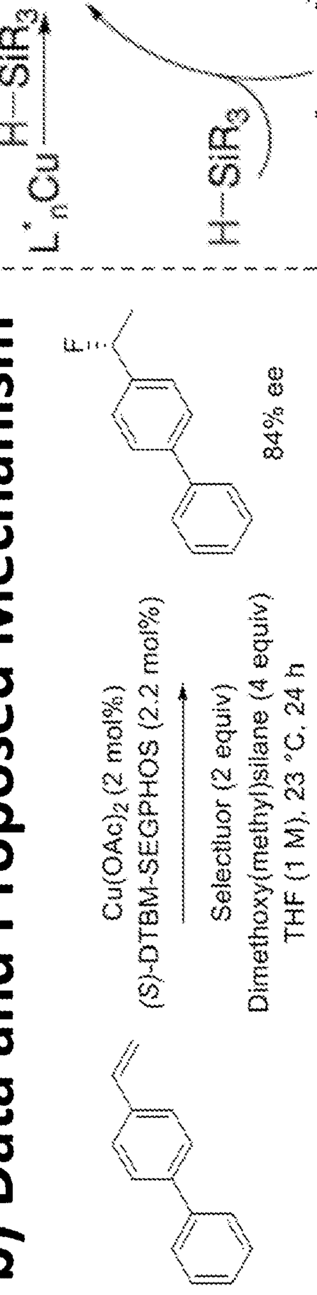
Figure 10:
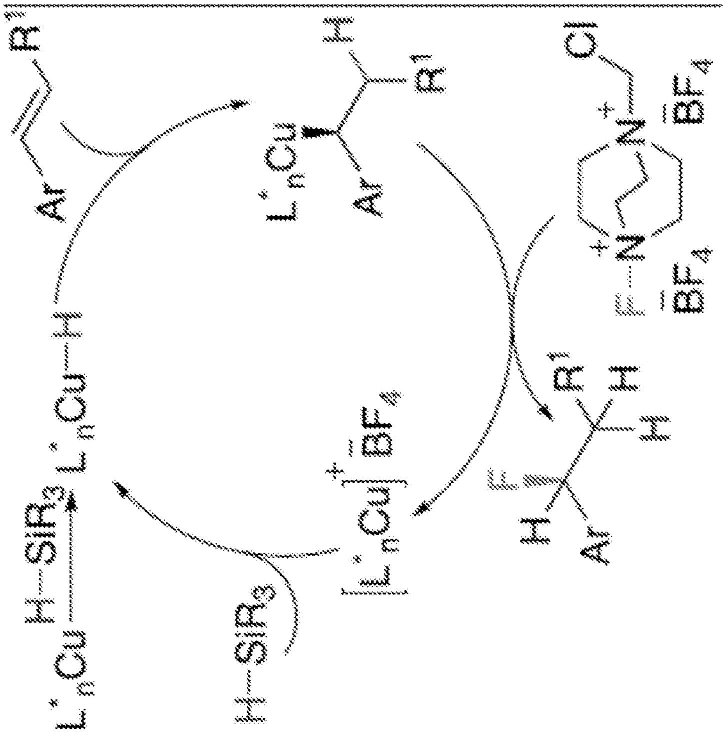

D.2. Background. Several reliable transition metal-catalyzed methods to synthesize small molecules containing a benzylic fluorine have been reported in the past decade. Importantly, direct benzylic C—H fluorination offers opportunity for late-stage fluorination of complex molecules[89-95] and alkene hydrofluorinations can be performed with excellent regioselectivity.[96, 97] Despite all of this progress, a highly enantioselective method to make chiral benzylic fluorine substituted molecules has eluded chemists.[96, 98] In hydrofluorination chemistry, the state-of-the-art, enantioselective alkenyl arene hydrofluorination cannot access chiral fluorine products with 90% or greater ee (FIG. 10*a*). Starting from internal alkenes, the fluorinated products do not exceed 31% ee. Furthermore, the transformation employs high loadings of a precious metal catalyst with high loadings of a chiral ligand that is not commercial and only accessible through a multi-step synthesis.[98] An asymmetric precious metal-catalyzed directed fluoroarylation of styrenes has also been reported. However, this method is an alkene difunctionalization and requires a directing group.[99]

Homogeneous transition metal-catalyzed reactions offer unique advantages to tackling reactivity, selectivity and efficiency challenges in the synthesis of high-value organic compounds. Reactions operating under catalyst control can be modified and tuned in order to optimize reactivity and selectivity. Lower activation barriers in catalytic reactions permit milder conditions compared to uncatalyzed processes.[100] Additional benefits such as lower cost and toxicity are associated with first-row transition metal-catalysis. Several challenging hydrofunctionalizations of alkenes have been accomplished under Cu—H promoted conditions and we believe Cu—H catalysis not only holds promise for enantioselective transfer hydrodeuteration reactions (Objective #1) but also enantioselective hydrofluorination reactions.

D.3. Preliminary Result. Our preliminary data supports our hypothesis that a Cu-catalyzed enantioselective hydrofluorination of alkenyl arenes is possible. We reasoned that exchanging the ethanol-OD in the enantioselective transfer hydrodeuteration protocol (FIG. 6*b*) with an electrophilic fluorine source would enable a hydrofluorination process to occur. Encouragingly, an unoptimized asymmetric hydrofluorination of 4-vinylbiphenyl provides the corresponding benzylic fluorine product 28 in 32% yield, >20:1 regioselectivity and 84% ee (FIG. 10*b*). Given the tremendous success we have encountered in the asymmetric transfer hydrodeuteration of alkenyl arenes and the implementation of MRR spectroscopic techniques for high-throughput characterization of isotopically chiral compounds during this challenging time (Objectives #1-2), we are confident that we can advance this reaction in the upcoming months to give high yields and enantioselectivities (Objective #3). For example, we know that mixed solvent systems such as a 1:4 dioxane:THF mixture can enhance enantioselectivity. Additionally, we know that lowering the reaction temperature is also beneficial for achieving higher enantioselectivities in transfer hydrodeuteration. In addition to changing the aforementioned reaction parameters, we will use Selectfluor but also explore other electrophilic fluorine sources such as N-fluoro-o-benzenedisulfonimide (NFOBS) and N-fluorobenzenesulfonimide (NFSI). Other chiral bidentate phosphine ligands known to support highly enantioselective Cu—H hydrofunctionalization of alkene reactions will also be evaluated.[61, 65, 101, 102] This includes but is not limited to Me-Duphos, Ph-BPE and DTBM-BINAP. Lastly, we will explore using a milder silane such as PMHS for this reaction.

We anticipate that the success of Objective #3 will position us to tackle frontier challenges in organic synthesis. For example, enantioselective hydrofluorination reactions to make quaternary fluorinated stereocenters are challenging. We will extend the reaction scope to include more highly substituted alkenyl arenes for the synthesis of quaternary fluorinated stereocenters. Beyond alkenyl arenes, we will look to extend this reaction to perform an enantioselective hydrofluorination of unactivated alkenes. Enantioselective Cu-catalyzed hydrofunctionalization of unactivated alkenes is well-established,[65] but hydrofluorination of unactivated alkenes remains elusive. We will use the in-depth knowledge gained from the proposed hydrofluorination of alkenyl arenes to extend the reactivity to unactivated olefins.

Broader Impacts

E. The broader impacts that this proposed work will have on society are numerous. Deuterated small molecules are extensively used in chemical research and medicine. Specifically, novel reactions that selectively deuterate small molecules are useful to develop new therapeutics. Deuterated small molecules are often deployed to alter the absorption, distribution, metabolism and excretion (ADME) properties of drug molecules.[6, 24, 26, 28] As a result, deuterated drugs have now come to the forefront of new drug development as the first FDA approved deuterated drug, deutetrabenazine, became available in 2017 and several more are in the pipeline.[103] It is well-known that enantiomers of bioactive molecules each have their own unique pharmacokinetic profile. Therefore, the demand for selectively deuterated small molecules as pharmaceuticals has increased in recent years and exposed a major deficiency in selective transition metal-catalyzed deuterations. Selective deuteration with full stereocontrol and without over- and under-deuteration impurities is not only rare, but spectroscopic techniques to support advances in selective deuteration reactions are lagging. This proposal will develop a highly enantioselective transfer hydrodeuteration (Objective #1) and the spectroscopic techniques (Objective #2) required to unlock this valuable field of selective chemistry.

Fluorinated small molecules are in high demand across many scientific disciplines.[88] In particular, fluorine-containing molecules have significantly impacted drug discovery for decades. Furthermore, the fact that more than 50% of all blockbuster drugs contain at least one fluorine speaks to the tremendous potential fluorinated small molecules hold for developing novel therapeutics. Despite the importance of selective fluorine installation, enantioselective hydrofluorination of aryl alkenes is primitive and only moderate enantioselectivities can be achieved using a precious metal catalyst and a non-commercial ligand. Our proposed enantioselective transfer hydrofluorination reaction (Objective #3) parallels the proposed enantioselective transfer hydrodeuteration in Objective #1 and utilizes a first-row transition metal catalyst with a commercially available chiral ligand. The preliminary data demonstrates the potential for high enantioselectivities after thorough reaction optimization studies, and we anticipate this method has potential for widespread use in the fabrication of novel fluorinated small molecule drug candidates.

REFERENCES

1. Simmons, E. M.; Hartwig, J. F., On the Interpretation of Deuterium Kinetic Isotope Effects in C—H Bond Functionalizations by Transition-Metal Complexes. Angewandte Chemie International Edition 2012, 51 (13), 3066-3072.
2. Giagou. T.; Meyer, M. P., Kinetic Isotope Effects in Asymmetric Reactions. Chemistry—A European Journal 2010, 16 (35), 10616-10628.
3. Anslyn, E. V.; Dougherty, D. A., Modern physical organic chemistry. University Science Books 2006.
4. Meek, S. J.; Pitman, C. L.; Miller, A. J. M., Deducing Reaction Mechanism: A Guide for Students, Researchers, and Instructors. Journal of Chemical Education 2016, 93 (2), 275-286.
5. Fu, I.; Woolf, E. J.; Matuszewski, B. K., Effect of the sample matrix on the determination of indinavir in human urine by HPLC with turbo ion spray tandem mass spectrometric detection. Journal of Pharmaceutical and Biomedical Analysis 1998, 18 (3), 347-357.
6. Pirali, T.; Serafini, M.; Cargnin, S.; Genazzani, A. A., Applications of Deuterium in Medicinal Chemistry. Journal of Medicinal Chemistry 2019, 62 (11), 5276-5297.
7. Atzrodt, J.; Derdau, V.; Kerr, W. J.; Reid, M., C—H Functionalisation for Hydrogen Isotope Exchange. Angewandte Chemie International Edition 2018, 57 (12), 3022-3047.
8. Atzrodt, J.; Derdau, V.; Kerr, W. J.; Reid, M., Deuterium- and Tritium-Labelled Compounds: Applications in the Life Sciences. Angewandte Chemie International Edition 2018, 57 (7), 1758-1784.
9. Schwab, J. M., Stereochemistry of an enzymic Baeyer-Villiger reaction. Application of deuterium NMR. Journal of the American Chemical Society 1981, 103 (7), 1876-1878.
10. Leinberger, R.; Rétey, A.; Hull, W. E.; Simon, H., Steric Course of the NIH Shift in the Enzymic Formation of Homogentisic Acid. European Journal of Biochemistry 1981, 117 (2), 311-318.
11. Battersby, A. R.; Gutman, A. L., Fookes, C. J. R.; Gunther, H.; Simon, H., Stereochemistry of formation of methyl and ethyl groups in bacteriochlorophyll a. Journal of the Chemical Society, Chemical Communications 1981, (13), 645-647.
12. Lathy, J.; Rétey, J.; Arigoni, D., Asymmetric Methyl Groups: Preparation and Detection of Chiral Methyl Groups. Nature 1969, 221 (5187), 1213-1215.
13. Klinman, J. P., A new model for the origin of kinetic hydrogen isotope effects. Journal of Physical Organic Chemistry 2010, 23 (7), 606-612.
14. White, R. E.; Miller, J. P.; Favreau. L. V.; Bhattacharyya, A., Stereochemical dynamics of aliphatic hydroxylation by cytochrome P-450. Journal of the American Chemical Society 1986, 108 (19), 6024-6031.
15. Shapiro, S.; Piper, J. U.; Caspi, E., Steric course of hydroxylation at primary carbon atoms. Biosynthesis of 1-octanol from (1R)- and (1S)-[1-3H,2H,1H; 1-14C]octane by rat liver microsomes. Journal of the American Chemical Society 1982, 104 (8), 2301-2305.
16. Jarling, R.; Sadeghi, M.; Drozdowska, M.; Lahme, S.; Buckel, W.; Rabus, R.; Widdel, F.; Golding, B. T.; Wilkes, H., Stereochemical Investigations Reveal the Mechanism of the Bacterial Activation of n-Alkanes without Oxygen. Angewandte Chemie International Edition 2012, 51 (6), 1334-1338.
17. Fujiwara, T.; O'Hagan, D., Successful fluorine-containing herbicide agrochemicals. Journal of Fluorine Chemistry 2014, 167, 16-29.
18. Berger, R.; Resnati, G., Metrangolo, P.; Weber, E.; Hulliger. J., Organic fluorine compounds: a great opportunity for enhanced materials properties. Chemical Society Reviews 2011, 40 (7), 3496-3508.
19. Müller, K.; Faeh, C.; Diederich, F., Fluorine in Pharmaceuticals: Looking Beyond Intuition. Science 2007, 317 (5846), 1881-1886.
20. O'Hagan, D., Fluorine in health care: Organofluorine containing blockbuster drugs. Journal of Fluorine Chemistry 2010, 131 (11), 1071-1081.
21. Wang, J.; Sánchez-Roselló. M.; Aceña. J. L.; del Pozo. C.; Sorochinskv, A. E.; Fustero, S.; Soloshonok, V. A.; Liu, H., Fluorine in Pharmaceutical Industry: Fluorine-Containing Drugs Introduced to the Market in the Last Decade (2001-2011). Chemical Reviews 2014, 114 (4), 2432-2506.
22. Purser, S.; Moore, P. R.; Swallow, S.; Gouverneur, V., Fluorine in medicinal chemistry. Chemical Society Reviews 2008, 37 (2), 320-330.
23. Meanwell, N. A., Fluorine and Fluorinated Motifs in the Design and Application of Bioisosteres for Drug Design. Journal of Medicinal Chemistry 2018, 61 (14), 5822-5880.
24. Meanwell, N. A., Synopsis of Some Recent Tactical Application of Bioisosteres in Drug Design. Journal of Medicinal Chemistry 2011, 54 (8), 2529-2591.

25. Harbeson, S. L.; Tung, R. D., Deuterium Medicinal Chemistry: A New Approach to Drug Discovery and Development. Medchem News 2014, 24 (2), 8-22.

26. Gant, T. G., Using Deuterium in Drug Discovery: Leaving the Label in the Drug. Journal of Medicinal Chemistry 2014, 57 (9), 3595-3611.

27. Nelson, S. D.; Trager, W. F., The Use of Deuterium Isotope Effects to Probe the active site properties, Mechanism of Cytochrom P450-Catalyzed Reactions, and Mechanisms of Metabolically Dependent Toxicity. Drug Metabolism and Disposition 2003, 31 (12), 1481-1497.

28. Stepan, A. F., Mascitti, V.; Beaumont, K.; Kalgutkar, A. S., Metabolism-guided drug design. Med Chem Comm 2013, 4 (4), 631-652.

29. Alexander, E. R.; Pinkus, A. G., Optical Activity in Compounds Containing Deuterium. I. 2,3-Dideutero-trans-Menthane. Journal of the American Chemical Society 1949, 71 (5), 1786-1789.

30. Reich, C. J.; Sullivan, G. R.; Mosher, H. S., Chiral 1-deuterio alcohols. Synthesis and determination of enantiomeric purity by chiral lanthanide nmr shift reagents. Tetrahedron Letters 1973, 14 (17), 1505-1508.

31. Mosher, H. S., Stereochemistry of neopentyl systems. Tetrahedron 1974, 30 (13), 1733-1745.

32. Eliel, E. L., The Reduction of Optically Active Phenylmethylcarbinyl Chloride with Lithium Aluminum Deuteride. Journal of the American Chemical Society 1949, 71 (12), 3970-3972.

33. Elsenbaumer. R. L.; Mosher, H. S., Enantiomerically pure (R)-(+)-2-phenylethanol-2-d and -1,1,2-d3, and (S)-(+)-1-phenylethane-1-d, -1,2,-d2, -1,2,2-d3, and -1,2,2,2-d4. The Journal of Organic Chemistry 1979, 44 (4), 600-604.

34. Chen. Y.; Tang, W. L.; Mou, J.; Li, Z., High-Throughput Method for Determining the Enantioselectivity of Enzyme-Catalyzed Hydroxylations Based on Mass Spectrometry. Angewandte Chemie International Edition 2010, 49 (31), 5278-5283.

35. Küppers, J.; Rabus, R.; Wilkes, H.; Christoffers, J., Optically Active 1-Deuterio-1-phenylethane—Preparation and Proof of Enantiopurity. European Journal of Organic Chemistry 2019, 2019 (15), 2629-2634.

36. Groves, J. T.; Viski, P., Asymmetric hydroxylation by a chiral iron porphyrin. Journal of the American Chemical Society 1989, 111 (22), 8537-8538.

37. Liu, W.; Cheng, M.-J.; Nielsen, R. J.; Goddard, W. A.; Groves, J. T., Probing the C—O Bond-Formation Step in Metalloporphyrin-Catalyzed C—H Oxygenation Reactions. ACS Catalysis 2017, 7 (6), 4182-4188.

38. Morrison, J. D.; Tomaszewski, J. E.; Mosher. H. S.; Dale. J.; Miller, D.; Elsenbaumer, R. L., Hydrogen vs. deuterium transfer in asymmetric reductions: reduction of phenyl trifluoromethyl ketone by the chiral Grignard reagent from (S)-2-phenyl-1-bromoethane-1,1,2-d3. Journal of the American Chemical Society 1977, 99 (9), 3167-3168.

39. Alberti, M. N.; Vassilikogiannakis, G., Orfanopoulos. M., Stereochemistry of the Singlet Oxygenation of Simple Alkenes: A Stereospecific Transformation. Organic Letters 2008, 10 (18), 3997-4000.

40. Curran, D. P.; Ramamoorthy, P. S., 1,2-Asymmetric induction in radical reactions. Deuteration and allylation reactions of β-oxy-α-bromo esters. Tetrahedron 1993, 49 (22), 4841-4858.

41. Holcomb, H. L.; Nakanishi, S.; Flood, T. C., Stereochemistry at Carbon of the Cyclometalation of 8-(α-Deuterioethyl)quinoline by Palladium(II) Salts. Organometallics 1996, 15 (20), 4228-4234.

42. Ogston, A. G., Interpretation of Experiments on Metabolic processes, using Isotopic Tracer Elements. Nature 1948, 162 (4129), 963-963.

43. Belleau, B.; Burba, J.; Pindell, M.; Reiffenstein, J., Effect of Deuterium Substitution in Sympathomimetic Amines on Adrenergic Responses. Science 1961, 133 (3446), 102-104.

44. Urey, H. C. B., F. G.; Murphy, G. M., A Hydrogen Isotope of Mass 2 and its Concentration. Physical Review 1932, 40 (1), 1-15.

45. Atzrodt, J.; Derdau, V.; Fey, T.; Zimmermann. J., The Renaissance of H/D Exchange. Angewandte Chemie International Edition 2007, 46 (41), 7744-7765.

46. Lee, S. H.; Gorelsky, S. I.; Nikonov, G. I., Catalytic H/D Exchange of Unactivated Aliphatic C—H Bonds. Organometallics 2013, 32 (21), 6599-6604.

47. Neubert, L.; Michalik, D.; Bähn, S.; Imm, S.; Neumann, H.; Atzrodt, J.; Derdau, V.; Holla, W.; Beller, M., Ruthenium-Catalyzed Selective α,β-Deuteration of Bioactive Amines. Journal of the American Chemical Society 2012, 134 (29), 12239-12244.

48. Loh, Y. Y.; Nagao, K.; Hoover. A. J.; Hesk, D.; Rivera. N. R.; Colletti, S. L.; Davies, I. W.; MacMillan, D. W. C., Photoredox-catalyzed deuteration and tritiation of pharmaceutical compounds. Science 2017, 358 (6367), 1182-1187.

49. Hale, L. V. A.; Szymczak, N. K., Stereoretentive Deuteration of α-Chiral Amines with D2O. Journal of the American Chemical Society 2016, 138 (41), 13489-13492.

50. Palmer, W. N.; Chirik, P. J., Cobalt-Catalyzed Stereoretentive Hydrogen Isotope Exchange of C(sp3)-H Bonds. ACS Catalysis 2017, 7 (9), 5674-5678.

51. Esaki, H.; Aoki, F.; Umemura, M.; Kato, M.; Maegawa, T.; Monguchi, Y.; Sajiki, H., Efficient H/D Exchange Reactions of Alkyl-Substituted Benzene Derivatives by Means of the Pd/C—H2-D2O System. Chemistry—A European Journal 2007, 13 (14), 4052-4063.

52. Atzrodt, J.; Derdau, V., Pd- and Pt-catalyzed H/D exchange methods and their application for internal MS standard preparation from a Sanofi-Aventis perspective. Journal of Labelled Compounds and Radiopharmaceuticals 2010, 53 (11-12), 674-685.

53. Smith, J. A.; Wilson, K. B.; Sonstrom, R. E.; Kelleher, P. J.; Welch, K. D.; Pert, E. K.; Westendorff, K. S.; Dickie, D. A., Wang, X.; Pate, B. H.; Harman, W. D., Preparation of cyclohexene isotopologues and stereoisotopomers from benzene. Nature 2020, 581 (7808), 288-293.

54. Karlsson, S.; Hallberg. A.; Gronowitz, S., Hydrozirconation of (E)-3-methoxy-1-phenyl-1-propene and (E)-3-phenyl-2-propenol. Journal of Organometallic Chemistry 1991, 403 (1), 133-144.

55. Walker, J. C. L.; Oestreich, M., Regioselective Transfer Hydrodeuteration of Alkenes with a Hydrogen Deuteride Surrogate Using B(C6F5)3 Catalysis. Organic Letters 2018, 20 (20), 6411-6414.

56. Li, L.; Hilt, G., Regiodivergent DH or HD Addition to Alkenes: Deuterohydrogenation versus Hydrodeuterogenation. Organic Letters 2020, 22 (4), 1628-1632.

57. Espinal-Viguri, M.; Neale, S. E.; Coles, N. T.; Macgregor, S. A.; Webster, R. L., Room Temperature Iron-Catalyzed Transfer Hydrogenation and Regioselective Deuteration of Carbon-Carbon Double Bonds. Journal of the American Chemical Society 2019, 141 (1), 572-582.

58. Czeskis. B.; Elmore, C. S.; Haight, A.; Hesk, D.; Maxwell, B. D.; Miller, S. A.; Raglione, T.; Schildknegt, K.; Traverse, J. F.; Wang, P., Deuterated active pharmaceutical ingredients: A science-based proposal for synthesis, analysis, and control. Part 1: Framing the problem. Journal of Labelled Compounds and Radiopharmaceuticals 2019, 62 (11), 690-694.

59. Wang, D.; Astruc, D., The Golden Age of Transfer Hydrogenation. Chemical Reviews 2015, 115 (13), 6621-6686.

60. Lipshutz, B. H.; Servesko, J. M.; Taft, B. R., Asymmetric 1,4-Hydrosilylations of α,β-Unsaturated Esters. Journal of the American Chemical Society 2004, 126 (27), 8352-8353.

61. Miki, Y.; Hirano, K.; Satoh, T.; Miura, M., Copper-Catalyzed Intermolecular Regioselective Hydroamination of Styrenes with Polymethylhydrosiloxane and Hydroxylamines. Angewandte Chemie International Edition 2013, 52 (41), 10830-10834.

62. Zhu, S.; Niljianskul, N.; Buchwald, S. L., Enantio- and Regioselective CuH-Catalyzed Hydroamination of Alkenes. Journal of the American Chemical Society 2013, 135 (42), 15746-15749.

63. Shi, S.-L.; Buchwald, S. L., Copper-catalysed selective hydroamination reactions of alkynes. Nature Chemistry 2015, 7 (1), 38-44.

64. Jordan, A. J.; Lalic, G.; Sadighi, J. P., Coinage Metal Hydrides: Synthesis, Characterization, and Reactivity. Chemical Reviews 2016, 116 (15), 8318-8372.

65. Liu. R. Y.; Buchwald, S. L., CuH-Catalyzed Olefin Functionalization: From Hydroamination to Carbonyl Addition. Accounts of Chemical Research 2020, 53 (6), 1229-1243.

66. Lipshutz, B. H.; Frieman. B. A., CuH in a Bottle: A Convenient Reagent for Asymmetric Hydrosilylations. Angewandte Chemie International Edition 2005, 44 (39), 6345-6348.

67. Taylor, R. D.; MacCoss, M.; Lawson, A. D. G., Rings in Drugs. Journal of Medicinal Chemistry 2014, 57 (14), 5845-5859.

68. Das, P.; Delost, M. D.; Qureshi, M. H.; Smith, D. T.; Njardarson, J. T., A Survey of the Structures of US FDA Approved Combination Drugs. Journal of Medicinal Chemistry 2019, 62 (9), 4265-4311.

69. Vitaku, E.; Smith, D. T.; Njardarson, J. T., Analysis of the Structural Diversity. Substitution Patterns, and Frequency of Nitrogen Heterocycles among U.S. FDA Approved Pharmaceuticals. Journal of Medicinal Chemistry 2014, 57 (24), 10257-10274.

70. Lee, M.; Sanford, M. S., Platinum-Catalyzed, Terminal-Selective C(sp3)-H Oxidation of Aliphatic Amines. Journal of the American Chemical Society 2015, 137 (40), 12796-12799.

71. Howell, J. M.; Feng, K.; Clark, J. R.; Trzepkowski, L. J.; White, M. C., Remote Oxidation of Aliphatic C—H Bonds in Nitrogen-Containing Molecules. Journal of the American Chemical Society 2015, 137 (46), 14590-14593.

72. Clark, J. R.; Feng, K.; Sookezian, A.; White, M. C., Manganese-catalysed benzylic C(sp3)-H amination for late-stage functionalization. Nature Chemistry 2018, 10 (6), 583-591.

73. McCreary. M. D.; Lewis. D. W.; Wernick, D. L.; Whitesides, G. M., Determination of enantiomeric purity using chiral lanthanide shift reagents. Journal of the American Chemical Society 1974, 96 (4), 1038-1054.

74. Neill, J. L.; Yang, Y.; Muckle, M. T.; Reynolds, R. L.; Evangelisti, L.; Sonstrom, R. E.; Pate, B. H.; Gupton, B. F., Online Stereochemical Process Monitoring by Molecular Rotational Resonance Spectroscopy. Organic Process Research & Development 2019, 23 (5), 1046-1051.

75. Pate, B. H. E., L.; Caminati, W.; Xu, Y.; Thomas, J.; Patterson, D.; Perez, C.; Schnell, M., Quantitative chiral analysis by molecular rotational spectroscopy. In Chiral Analysis: Advances in Spectroscopy, Chromatography, and Emerging Methods, 2 ed.; Polavarapu, P., Ed. Elsevier: 2018.

76. Joyce, L. A.; Schultz, Danielle M.; Sherer, E. C.; Neill, J. L.; Sonstrom, R. E.; Pate, B. H., Direct regioisomer analysis of crude reaction mixtures via molecular rotational resonance (MRR) spectroscopy. Chemical Science 2020, 11 (24), 6332-6338.

77. Neill, J. L.; Mikhonin, A. V.; Chen, T.; Sonstrom, R. E.; Pate, B. H., Rapid quantification of isomeric and dehalogenated impurities in pharmaceutical raw materials using MRR spectroscopy. Journal of Pharmaceutical and Biomedical Analysis 2020, 189, 113474.

78. Wenzel, T. J.; Chisholm, C. D., Using NMR spectroscopic methods to determine enantiomeric purity and assign absolute stereochemistry. Progress in Nuclear Magnetic Resonance Spectroscopy 2011, 59 (1), 1-63.

79. B. H. Pate, C. T. W., Y. Xu, J. Thomas. D. Patterson, W. Caminati, and L. Evangelisti, A chiral tagging strategy for determining absolute configuration and enantiomeric excess by molecule rotational spectroscopy. International Symposium on Molecular Spectroscopy 2017, DOI: https://dx.doi.org/10.15278/isms.2017.RG03.

80. W. Gordy, R. L. C., Microwave Molecular Spectra, 3rd Edition. Knovel 1984.

81. Grimme, S.; Steinmetz, M., Effects of London dispersion correction in density functional theory on the structures of organic molecules in the gas phase. Physical Chemistry Chemical Physics 2013, 15 (38), 16031-16042.

82. Kraitchman, J., Determination of Molecular Structure from Microwave Spectroscopic Data. American Journal of Physics 1953, 21 (1), 17-24.

83. Brown, G. G.; Dian, B. C.; Douglass, K. O.; Geyer, S. M.; Shipman, S. T.; Pate, B. H., A broadband Fourier transform microwave spectrometer based on chirped pulse excitation. Review of Scientific Instruments 2008, 79 (5), 053103.

84. Balle, T. J.; Flygare, W. H., Fabry-Perot cavity pulsed Fourier transform microwave spectrometer with a pulsed nozzle particle source. Review of Scientific Instruments 1981, 52 (1), 33-45.

85. Mei, H.; Remete, A. M.; Zou, Y.; Moriwaki, H.; Fustero, S.; Kiss, L.; Soloshonok, V. A.; Han, J., Fluorine-containing drugs approved by the FDA in 2019. Chinese Chemical Letters 2020, 31 (9), 2401-2413.

86. Mei, H.; Han, J.; Fustero, S.; Medio-Simon, M.; Sedgwick, D. M.; Santi, C.; Ruzziconi, R.; Soloshonok, V. A., Fluorine-Containing Drugs Approved by the FDA in 2018. Chemistry—A European Journal 2019, 25 (51), 11797-11819.

87. Inoue, M.; Sumii, Y.; Shibata, N., Contribution of Organofluorine Compounds to Pharmaceuticals. ACS Omega 2020, 5 (19), 10633-10640.

88. Zhu. Y.; Han, J.; Wang, J.; Shibata, N.; Sodeoka. M.; Soloshonok, V. A.; Coelho, J. A. S.; Toste, F. D., Modern Approaches for Asymmetric Construction of Carbon- Fluorine Quaternary Stereogenic Centers: Synthetic Challenges and Pharmaceutical Needs. Chemical Reviews 2018, 118 (7), 3887-3964.

89. Liu. W.; Groves, J. T., Manganese Catalyzed C—H Halogenation. Accounts of Chemical Research 2015, 48 (6), 1727-1735.

90. Bloom, S.; Pitts, C. R.; Woltomist, R.; Griswold, A.; Holl, M. G.; Lectka. T., Iron(II)-Catalyzed Benzylic Fluorination. Organic Letters 2013, 15 (7), 1722-1724.

91. Cantillo, D.; de Frutos, O.; Rincćn, J. A.; Mateos, C.; Kappe, C. O., A Continuous-Flow Protocol for Light-Induced Benzylic Fluorinations. The Journal of Organic Chemistry 2014, 79 (17), 8486-8490.

92. Bloom, S.; Pitts, C. R; Miller, D. C.; Haselton, N.; Holl, M. G.; Urheim, E.; Lectka. T., A Polycomponent Metal-Catalyzed Aliphatic, Allylic, and Benzylic Fluorination. Angewandte Chemie International Edition 2012, 51 (42), 10580-10583.

93. Groendyke, B. J.; AbuSalim, D. I.; Cook, S. P., Iron-Catalyzed, Fluoroamide-Directed C—H Fluorination. Journal of the American Chemical Society 2016, 138 (39), 12771-12774.

94. Hua, A. M.; Mai, D. N.; Martinez, R.; Baxter, R. D., Radical C—H Fluorination Using Unprotected Amino Acids as Radical Precursors. Organic Letters 2017, 19 (11), 2949-2952.

95. Nodwell, M. B.; Bagai, A.; Halperin, S. D.; Martin, R. E., Knust, H.; Britton, R., Direct photocatalytic fluorination of benzylic C—H bonds with N-fluorobenzenesulfonimide. Chemical Communications 2015, 51 (59), 11783-11786.

96. Emer, E.; Pfeifer, L.; Brown, J. M.; Gouvemeur, V., cis-Specific Hydrofluorination of Alkenylarenes under Palladium Catalysis through an Ionic Pathway. Angewandte Chemie International Edition 2014, 53 (16), 4181-4185.

97. Barker, T. J.; Boger, D. L., Fe(III)/NaBH4-Mediated Free Radical Hydrofluorination of Unactivated Alkenes. Journal of the American Chemical Society 2012, 134 (33), 13588-13591.

98. Yin, X.; Chen, B.; Qiu, F.; Wang, X.; Liao, Y.; Wang, M.; Lei, X.; Liao, J., Enantioselective Palladium-Catalyzed Hydrofluorination of Alkenylarenes. ACS Catalysis 2020, 10 (3), 1954-1960.

99. Talbot, E. P. A.; Fernandes, T. d. A.; McKenna, J. M.; Toste, F. D., Asymmetric Palladium-Catalyzed Directed Intermolecular Fluoroarylation of Styrenes. Journal of the American Chemical Society 2014, 136 (11), 4101-4104.

100. Busacca, C. A.; Fandrick, D. R.; Song, J. J.; Senanayake, C. H., Transition Metal Catalysis in the Pharmaceutical Industry. In Applications of Transition Metal Catalysis in Drug Discovery and Development, 2012; pp 1-24.

101. Lu, G.; Liu, R. Y.; Yang, Y.; Fang, C.; Lambrecht, D. S.; Buchwald, S. L.; Liu, P., Ligand-Substrate Dispersion Facilitates the Copper-Catalyzed Hydroamination of Unactivated Olefins. Journal of the American Chemical Society 2017, 139 (46), 16548-16555.

102. Bayeh-Romero, L.; Buchwald, S. L., Copper Hydride Catalyzed Enantioselective Synthesis of Axially Chiral 1,3-Disubstituted Allenes. Journal of the American Chemical Society 2019, 141 (35), 13788-13794.

103. Schmidt, C., First deuterated drug approved. Nature Biotechnology 2017, 35 (6), 493-494.

104. Clark, J. R., Challenges Facing Young Scientists in Academia and Industry in the United States from the Lens of a Millennial Academic. Chemistry—A European Journal 2020, DOI: 10.1002/chem.202002665.

Example 5—Copper-Catalyzed Transfer Hydrodeuteration of Aryl Alkenes with Quantitative Isotopomer Purity Analysis by Molecular Rotational Resonance Spectroscopy Reference is mad to the manuscript: Vang et al., "Copper-Catalyzed Transfer Hydrodeuteration of Aryl Alkenes with Quantitative Isotopomer Purity Analysis by Molecular Rotational Resonance Spectroscopy," J. Am. Chem. Soc., 2021, 143 7707-7718, published May 17, 2021, the content of which is incorporated herein by reference in its entirety.

Abstract

A copper-catalyzed alkene transfer hydrodeuteration reaction that selectively incorporates one hydrogen and one deuterium atom across an aryl alkene is described. The transfer hydrodeuteration protocol is selective across a variety of internal and terminal alkenes and is also demonstrated on an alkene-containing complex natural product analog. Beyond using $^{1}H$, $^{2}H$ and $^{13}C$ NMR analysis to measure reaction selectivity, six transfer hydrodeuteration products were analyzed by molecular rotational resonance (MRR) spectroscopy. The application of MRR spectroscopy to the analysis of isotopic impurities in deuteration chemistry is further explored through a measurement methodology that is compatible with high-throughput sample analysis. In the first step, the MRR spectroscopy signatures of all isotopic variants accessible in the reaction chemistry are analyzed using a broadband chirped-pulse Fourier transform microwave spectrometer. With the signatures in hand, measurement scripts are created to quantitatively analyze the sample composition using a commercial cavity enhanced MRR spectrometer. The sample consumption is below 10 mg with analysis times on the order of 10 minutes using this instrument—both representing order-of-magnitude reduction compared to broadband MRR spectroscopy. To date, these measurements represent the most precise spectroscopic determination of selectivity in a transfer hydrodeuteration reaction and confirms that product regioselectivity ratios of >140:1 are achievable under this mild protocol.

1. INTRODUCTION

Reactions that incorporate deuterium into molecular scaffolds are of topical relevance to scientists across several disciplines. Among many applications, deuterated small molecules are used as standards for high-resolution mass spectrometry,[1-3] and can serve as probes to study reaction mechanisms,[4-5] perform kinetic isotope effect experiments,[6-7] determine the stereochemical course of microbiological or enzymatic reactions and elucidate biosynthetic pathways.[8-17] Importantly, deuterated small molecules are also deployed to alter absorption, distribution, metabolism and excretion (ADME) properties of drug molecules.[18-19] Consequently, designing deuterated bioisosteres to modify the metabolic "soft spots" of small molecule drugs holds much potential for the development of safer therapeutics.[20-24]

Transition metal catalyzed reactions are commonly used to selectively install oxygen, nitrogen or carbon functionality into small molecules.[25-26] Mild protocols and modular catalytic frameworks are often exploited in these reactions to optimize both reactivity and selectivity. However, highly selective transition metal catalyzed methods for deuterium incorporation remain underdeveloped. For example, transition metal catalyzed hydrogen isotope exchange (HIE) reactions efficiently incorporate deuterium into small molecules, but significant challenges exist to control the quantity and precise placement of deuterium in a given molecule.[27-28] Specific to making small molecules with one deuterium atom installed at a benzylic carbon, a general technique to access small molecules with a benzylic C($sp^2$)-D bond was recently reported.[29] However, to make a small molecule with exactly one benzylic C($sp^3$)-D bond, chemists typically use reactions involving stoichiometric organometallic intermediates.[30]

The similar physical properties of deuterium relative to hydrogen further complicates unselective deuteration reactions. Isotopic mixtures are not only inseparable using common purification techniques, but common spectroscopic techniques used to characterize organic compounds are insufficient at measuring the precise location and quantity of deuterium in isotopic product mixtures. This can have major implications in drug discovery and guidance to address deuterated active pharmaceutical ingredients (APIs) is being developed for these spectroscopic and synthetic challenges.[31] Ultimately, synthetic access to deuterated compounds free of isotopic impurities and analytical methods to identify all isotopic species in a product mixture will be crucial for developing novel deuterated APIs.

Scheme 1. Transfer Hydrodeuteration of Alkenes (a) Webster, 2019: Fe-catalyzed transfer hydrodeuteration

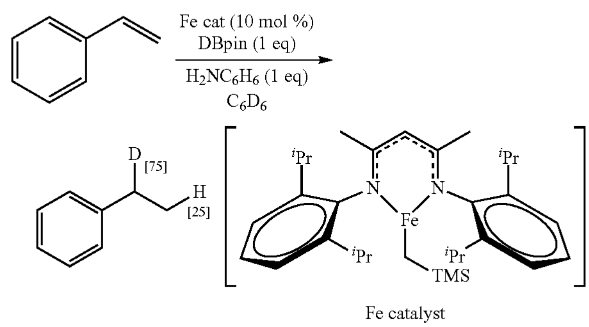

Fe catalyst (b) Oestreich, 2018: Boron-catalyzed transfer hydrodeuteration

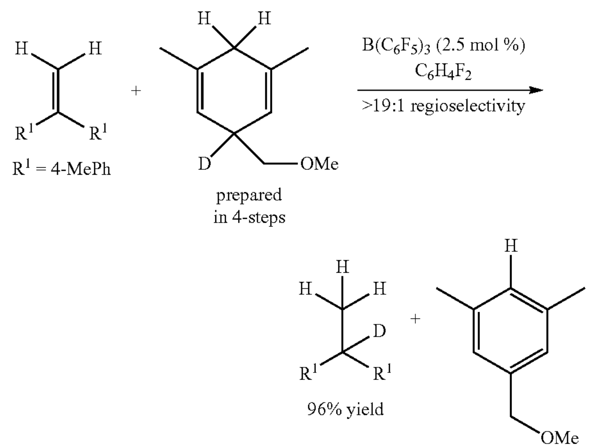

(c) Cu-catalyzed transfer hydrodeuteration (this work)

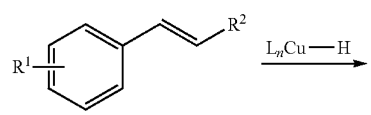

-continued

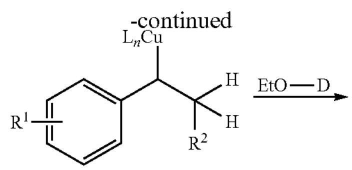

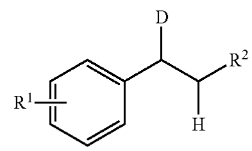

Highest transfer hydrodeuteration regioselectivities reported to date
Mild conditions (no $H_2$, HD or $D_2$ gas required) and excellent FG compatibility
Utilizes commercially available catalyst, ligand, silane and deuterium source
Precise characterization of 6 examples using MRR spectroscopy Catalytic transfer hydrogenations represent powerful and mild methods for the reduction of alkene functionality.[32-35] We believe that mechanistically similar catalytic transfer hydrodeuteration reactions hold much promise for making selectively deuterated small molecules. Until recently, selective catalytic hydrodeuteration reactions were rare and usually employed as mechanistic probes for alkyne semireductions.[36-38] A major challenge in catalytic transfer hydrodeuteration is discriminating between hydrogen (H) and deuterium (D) for selective incorporation into alkene functionality.[39-40] Catalytic alkene transfer hydrodeuteration reactions are now possible on a variety of alkenes.[41-45] Transition metal catalyzed transfer hydrodeuteration typically occurs in a regioselective manner for unactivated terminal alkenes, but selectivity is generally lower for terminal aryl alkene substrates (Scheme 1a).[41-43] Alternatively, using a boron catalyst, highly selective installation of deuterium into activated 1,1-diarylalkenes is possible, but with a limited alkene scope (Scheme 1b).[44-45]

2. REACTION OPTIMIZATION AND SCOPE

Based on insight gleaned from our recently published Cu-catalyzed regioselective aryl alkyne transfer hydrodeuteration studies, we hypothesized that a highly regioselective aryl alkene transfer hydrodeuteration may be possible (Scheme 1c).[46] Cu-catalyzed aryl alkene hydroamination reactions are also regioselective and we envisioned the transfer hydrodeuteration occurring with excellent regioselectivity because of the thermodynamic favorability of the benzylic copper intermediate depicted in Scheme 1c.[47-51] Under transfer hydrodeuteration conditions, we reasoned that the H-donor and D-donor would operate at distinct points during the reaction and therefore allow for precise insertion of each atom at the desired location within the aryl alkene.

TABLE 1

Reaction Optimization[a]

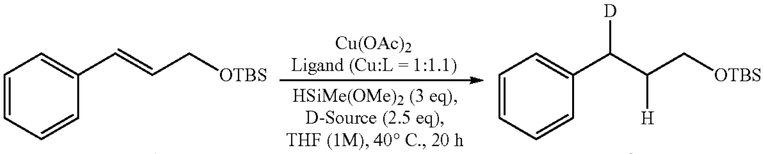

trans-1 2

| entry | $Cu(OAc)_2$ | ligand | D-source | 1 (%) | 2(%) |
|---|---|---|---|---|---|
| 1 | 2 mol % | L1 | EtOD | 69[b] | — |
| 2 | 2 mol % | L2 | EtOD | 70[b] | — |
| 3 | 2 mol % | L3 | EtOD | 89[b] | — |
| 4 | 2 mol % | L4 | EtOD | 47[b] | — |
| 5 | 2 mol % | L5 | EtOD | — | 85[c] |
| 6 | 2 mol % | L5 | MeOD | 8[c] | 69[c] |
| 7 | 2 mol % | L5 | $D_2O$ | 59[c] | 21[c] |
| 8 | 1 mol % | L5 | IPA-$d_8$ | — | 85[c] |
| 9 | 1 mol % | L5 | EtOD | — | 90[c] |

[a]Reactions conducted using 0.2 mmol of substrate. $Cu(OAc)_2$ was used as a 0.2M solution in THF.
[b]Yield was determined by $^1H$ NMR analysis of the crude reaction mixture, using mesitylene as an internal standard.
[c]Denotes isolated product yield.

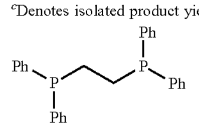

L1: DPPE

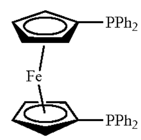

L2: DPPF

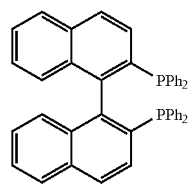

L3: rac-BINAP

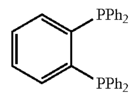

L4: DPPBz

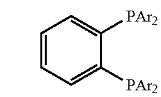

Ar = 3,5-di(tert-butyl)$C_6H_3$
L5: DTB-DPPBz

Accordingly, tert-butyldimethylsilyl-protected (TBS) cinnamyl alcohol 1 was chosen as the aryl alkene for reaction optimization. In the presence of catalytic $Cu(OAc)_2$, dimethoxymethylsilane (DMMS was chosen for the optimization studies because it can be easily removed under vacuum prior to product purification) and EtOD, we found that bidentate phosphine ligands such as DPPE, DPPF, rac-BINAP and DPPBz were not efficient at supporting the desired transformation (Table 1, entries 1-4). Switching to the more sterically crowded DTB-DPPBz ligand dramatically affected reactivity and deuterated aryl alkane 2 was isolated in 85% yield (entry 5). Importantly, evaluation of the product by $^1H$, $^2H$ and $^{13}C$ NMR revealed that one deuterium atom was incorporated exclusively at the benzylic position (>20:1 regioselective ratio). Varying the deuterium source revealed that using CHOD led to a slight decrease in yield (entry 6), while $D_2O$ only led to partial conversion to product 2 (entry 7). Employing 2-propanol-$d_8$ permitted the catalyst loading to be lowered and was similarly efficient as EtOD (entry 8). Ultimately, returning to the reaction conditions from entry 5 and decreasing the catalyst loading to 1 mol % was found to be optimal (entry 9).

With the optimal reaction conditions in hand, we evaluated the substrate scope of the reaction (Scheme 2). Electron-rich monosubstituted alkenyl arenes containing oxygen functionality performed well in the reaction and excellent yields of the desired deuterated products were obtained (Scheme 2a, 4a-4d, 73-97% yield). Alternatively, an alkenyl arene substituted with an electron-withdrawing nitro group also undergoes transfer hydrodeuteration to provide the deuterated aryl alkane, albeit in modest yield (4e, 47% yield). Nitrogen substitution is permitted on the alkenyl arene substrate (4f-4g, 57-97% yield). Importantly, we demonstrated that polymethylhydrosiloxane could be used instead of DMMS in the synthesis of 4g. We also found that (4-vinylphenyl)boronic acid pinacol ester can undergo Cu-catalyzed transfer hydrodeuteration (4h, 67% yield).

Scheme 2. Aryl Alkene Transfer Hydrodeuteration Substrate Scope

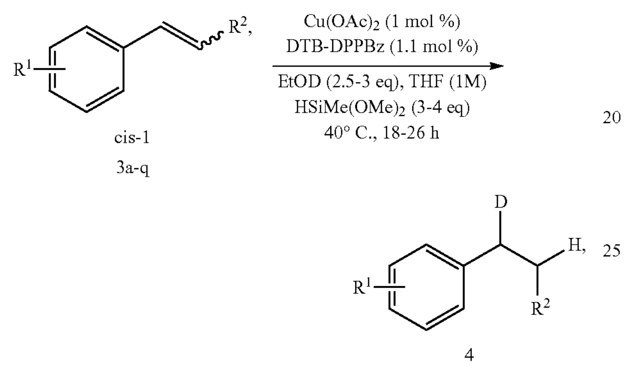

cis-1

3a-q

4

(a) Monosubstituted Alkene Substrate Scope

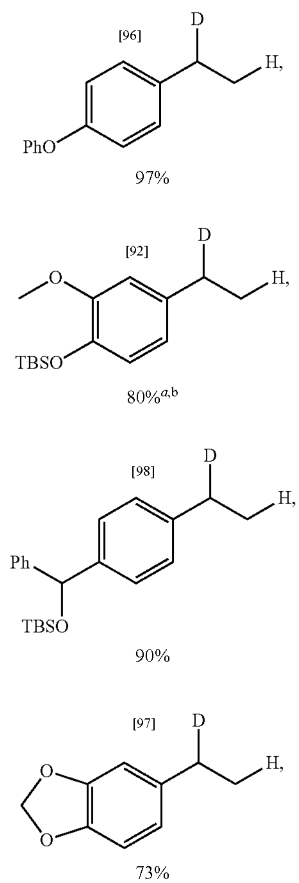

4a

[96]

97%

4b

[92]

80%[a,b]

4c

[98]

90%

4d

[97]

73%

-continued

4e

[95]

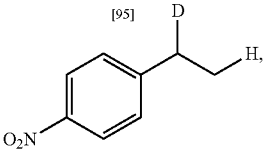

47%[c]

4f

[90]

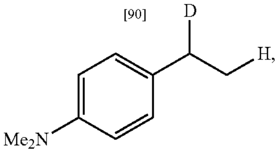

57%[a,b]

4g

[99]

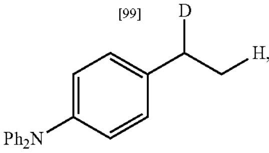

97%[d]

4h

[99]

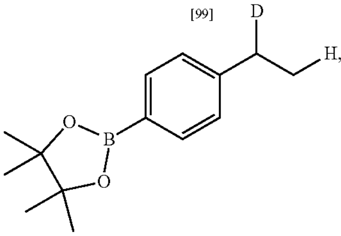

67%

4i

[97]

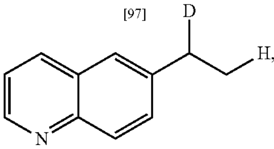

54%

4j

[98]

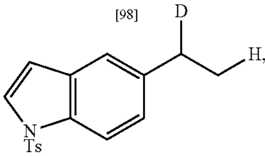

73%

4k

[98]

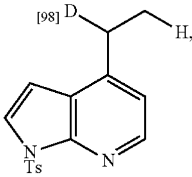

70%

-continued

4l

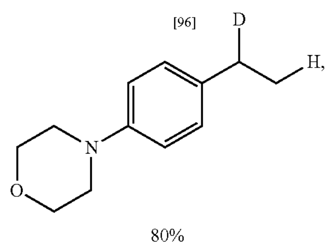

80%

(b) 1,2-Disubstituted Alkene Substrate Scope

2

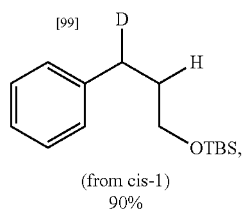

(from cis-1)
90%

4m

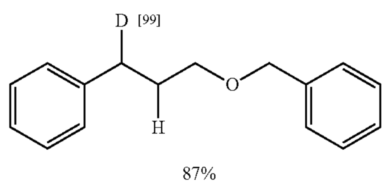

87%

4n

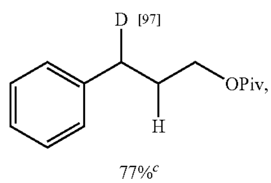

77%[c]

4o

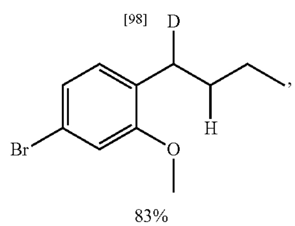

83%

4p

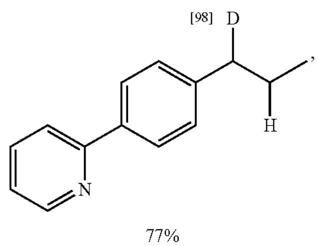

77%

-continued (c) Estrone Analog

4q

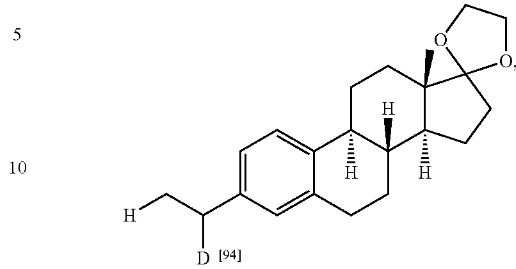

73%[a]

(d) 1,1-Disubstituted Alkene Example

4r

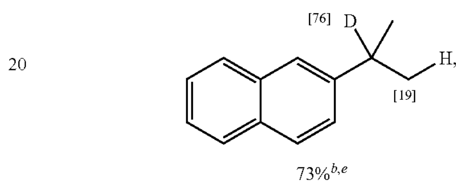

73%[b,e]

4r from:

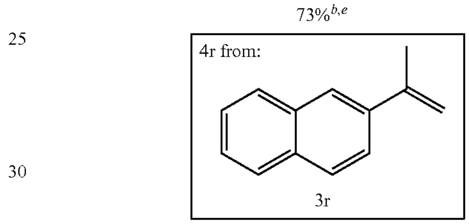

3r

[a]2 mol % $Cu(OAc)_2$ and 2.2 mol % DTB-DPPBZ used. [b]IPA-$d_8$ (3 equiv) used instead of EtOD. [c]Reaction conducted at 5° C. [d]Polymethylhydrosiloxane (3 equiv) used instead of $HSiMe(OMe)_2$.
[e]3 mol % $Cu(OAc)_2$, 3.3 mol % DTB-DPPBz, and $HSiMe(OMe)_2$ (4 equiv) used at 60° C.

Due to their prevalence in bioactive molecules, nitrogen- and oxygen-containing heterocycles were examined under the transfer hydrodeuteration protocol.[52-53] We found that quinoline, indole and azaindole substituted alkenes perform well in the transfer hydrodeuteration reaction (4i-4k, 54-73% yield). Alternatively, an alkenyl arene substituted with a morpholine ring is efficiently converted to the deuterated aryl alkane product (4l, 80% yield). Internal alkene substrates are also viable candidates for transfer hydrodeuteration. Cinnamyl alcohol derivatives were evaluated when the alcohol was protected with a TBS, benzyl (Bn), or pivaloyl (Piv) group (Scheme 2b). All three derivatives were deuterated in high yield (2, 4m-4n, 77-90% yield). Notably, product 2 was synthesized from the cis-alkene starting material, whereas in Table 1 it was synthesized from the trans-alkene starting material. Substitution on the arene is also possible for internal alkene substrates. A bromine substituted alkenyl arene and pyridine substituted alkenyl arene underwent transfer hydrodeuteration in high yield (4o-4p, 77-83% yield). Notably, no dehalogenation product was observed in the synthesis of 4o. We also explored the capacity for the Cu-catalyzed transfer hydrodeuteration to proceed in a complex small molecule setting (Scheme 2c). Accordingly, a vinyl substituted estrone analog was deuterated in good yield (4q, 73% yield). Lastly, we evaluated the transfer hydrodeuteration reaction selectivity for a 1,1-disubstituted aryl alkene (Scheme 2d). The reaction of 3r was only modestly selective with deuterium incorporation favoring the benzylic position (4:1 benzylic:methyl selectivity).

We attribute the modest selectivity to the demanding steric environment of this 1,1-disubstituted alkene inhibiting the Cu-catalyst from approaching the benzylic site.

Scheme 3. Substrate Scope Analyzed by Molecular Rotation Resonance

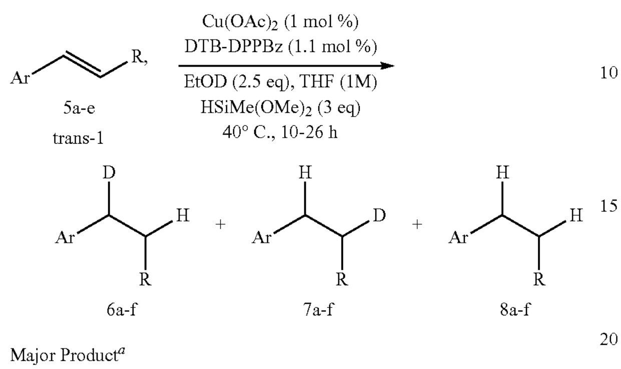

5a-e
trans-1

6a-f + 7a-f + 8a-f

Major Product[a]

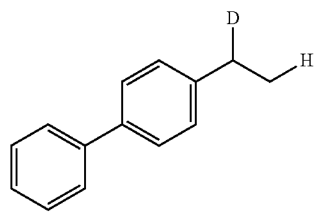

91% yield (6a + 7a + 8a)
98.4:(nd)[b]:1.6

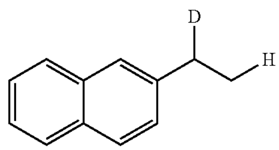

83% yield (6b + 7b + 8b)
94.8:0.8:4.4

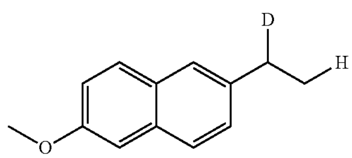

87% yield (6c + 7c + 8c)
96.8:(nd)[b]:3.2

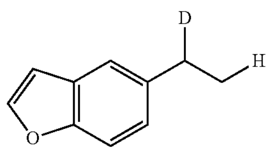

83% yield (6d + 7d + 8d)
95.1:3.2:1.7

-continued

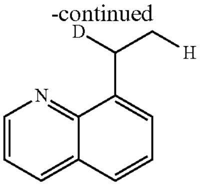

86% yield[c] (6e + 7e + 8e)
98.3:(nd)[b]:1.7

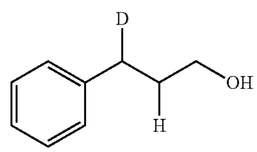

76% over 2 steps[d] (6f + 7f + 8f)
99.0:(nd)[b]:1.0

The alkenyl arene transfer hydrodeuteration scope was extended and the resulting isotopic products were analyzed using molecular rotational resonance (MRR) spectroscopy (Scheme 3, see below for analysis details). In addition to a vinyl biphenyl substrate, polyaromatic compounds such as 2-vinylnaphthalene and 2-methoxy-6-vinylnaphthalene were readily converted to their corresponding deuterated products (6a-c, 83-91% yield). Heterocycle-containing aryl alkenes and an internal alkene were also evaluated under the transfer hydrodeuteration protocol (6d-6f 76-86% yield). In all six examples, the major products (6a-f) were formed in high yield in a highly regioselective manner. In addition to providing higher sensitivity measurements for isotopic product analysis, using MRR to analyze the reaction products depicted in Scheme 3 further validates our claims that this reaction is highly regioselective. It removes any ambiguity when analyzing isotopic product mixtures consisting of isotopologues and isotopomers that share deuterium substitution at the same atom, such that several isotopic species contribute to the same $^1H/^2H$ resonance in an NMR spectrum. It also precisely quantifies each regioisomer, even when the do-species is present in the product mixture.

To demonstrate the versatility of the reaction, we hypothesized that flipping the regioselectivity of the reaction would be possible by simply replacing the Si—H and EtOD with Si-D and EtOH. This was examined with vinyl biphenyl substrate 5a (Scheme 4a) and resulted in an 80% yield of desired product 7a. An increase of the "underdeuterated" transfer hydrogenation side product 8a was observed in this reaction likely because of the reduced deuterium content in the Si-D reagent.

Scheme 4. Reaction Studies (a) Switchable Selectivity Example

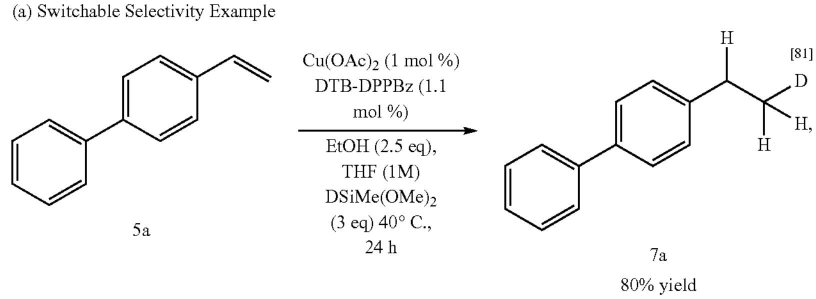

5a 7a
80% yield (b) Chemoselectivity Probes

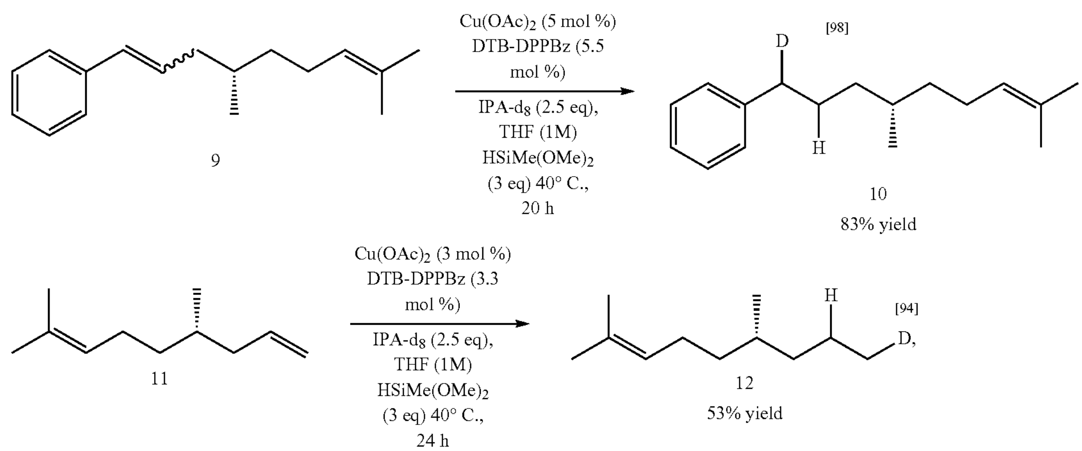

9

10
83% yield

11

12
53% yield (c) Mechanistic Probe

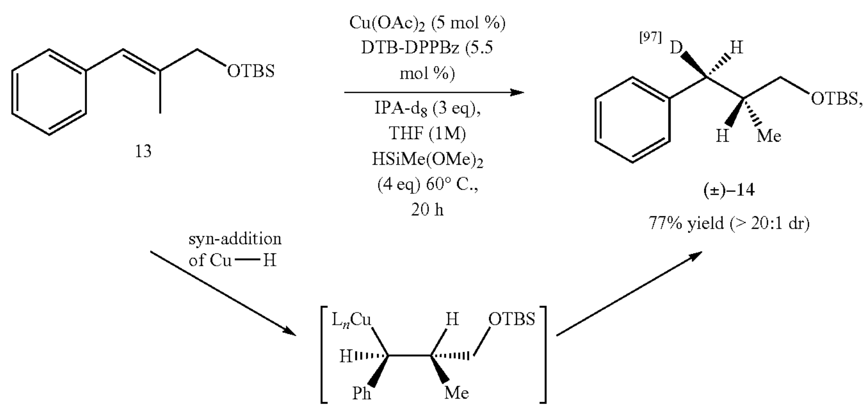

13

(±)-14
77% yield (> 20:1 dr)

To probe the chemoselectivity of the reaction, we performed the transfer hydrodeuteration on a substrate containing both a 1,2-disubstituted styrenyl alkene and 1,1,2-trisubstituted alkene (Scheme 4b, substrate 9). We were pleased to find the reaction was not only highly selective for incorporation of deuterium at the benzylic site of 10, but also chemoselective, as no reduction of the 1,1,2-trisubstituted alkene was observed. Another chemoselectivity probe was carried out using substrate 11. In this case, the chemoselective reaction of an unactivated terminal alkene was evaluated in the presence of a more sterically hindered internal alkene. Furthermore, substrate 11 evaluated the potential for an unactivated alkene to undergo regioselective Cu-catalyzed transfer hydrodeuteration using the DTB-DPPBz ligand. Isolation of deuterated product 12 revealed that the reaction was highly selective for copper inserting into the less sterically hindered terminal position of the terminal alkene as no reduction of the trisubstituted alkene was observed. Ongoing studies in our research group are underway to explore the scope of the Cu-catalyzed alkene transfer hydrodeuteration for unactivated alkenes. Lastly, we probed whether the selectivity of the Cu—H insertion into the alkene occurred with syn or anti-addition using 1,2,2-trisubstituted alkene 13. We isolated product (±)-14 in 77% yield (>20:1 dr) which suggests that syn-addition of the Cu—H across the alkene is operative (Scheme 4c). Furthermore, this example also indicates that trisubstituted alkenes are viable substrates for regioselective transfer hydrodeuteration.

3. SPECTROSCOPIC ANALYSIS OF PRODUCTS

Quantitative Sample Analysis by Molecular Rotational Resonance Spectroscopy—A New Tool for Deuteration Chemistry. The isotopic composition of the reaction products depicted in Scheme 3 was analyzed by molecular rotational resonance (MRR) spectroscopy. The measurements provide high resolution and specificity for the analysis of isotopic species and represent the first quantitative assessment of the MRR spectroscopy technique for deuterated impurity analysis. In MRR spectroscopy, the rotational spectrum arises through electric-dipole transitions between the quantized rotational kinetic energy levels of the molecule.[54] In the rigid rotor approximation, the energy levels can be calculated from the three rotational constants (A, B, C) derived from the moments-of-inertia for rotation about the three principal rotational axes ($I_A$, $I_B$, $I_C$)

$$A = (\hbar/2)I_A^{-1} \quad (1)$$

where the moment-of-inertia is calculated from the nuclear masses and the shortest distance of each nucleus to the rotation axis.

$$I_A = \sum_i m_i r_{A_i}^2 \quad (2)$$

The intensities for the rotational transitions are governed by the electric dipole moment and the molecule must be polar to have a rotational spectrum.

MRR spectroscopy provides measurement solutions for several of the challenges that have been highlighted for the analysis of deuterated molecules.[31] The important feature of rotational spectroscopy in this application is that each isotopic variant has its own unique spectral signature. In particular, isotopomers have distinct MRR spectra and can be separately analyzed within a complex mixture.[55] By comparison, mass spectrometry can only analyze the isotopologue composition. NMR spectroscopy also has limitations and cannot perform the composition analysis when isoptologues and isotopomers in the mixture share deuterium substitution at the same atom such that several isotopic species contribute to the same $^1H/^2H$ resonance. MRR spectroscopy has two additional advantages in this application. First, MRR spectroscopy has exceptionally high spectral resolution so that spectral overlap is not an issue even for complex mixtures. Second, the rotational spectrum for any isotopic variant can be predicted to high accuracy using the equilibrium geometry obtained from quantum chemistry so that high-confidence identification of isotopic species is possible without the need for reference samples.[55-57]

For the products depicted in Scheme 3, the rotational spectrum was measured using a chirped-pulse Fourier transform microwave (CP-FTMW) spectrometer operating in the 2-8 GHz frequency range.[58-60] The broadband spectral coverage makes it possible to capture enough of the rotational spectrum to obtain a highly characteristic spectral pattern for each isotopic variant of the analyte present in the sample. The adiabatic expansion of a dilute mixture of the analyte in neon (0.1% mixture) into the spectrometer vacuum chamber produces a cold gas with a rotational temperature of about 1 K. The cooling of the gas increases the measurement sensitivity through reduction of the partition function. The reduced Doppler broadening of the pulsed jet expansion produces a high-resolution spectrum (line width of about 70 kHz FWHM). This feature is crucial in isotopologue/isotopomer analysis because it is not possible to separate the different species by chromatography to simplify the analysis.[61] CP-FTMW instruments have a large linear dynamic range so that quantitative analysis can be performed using the spectral transition intensities even for trace impurities.[58]

Figure 11:
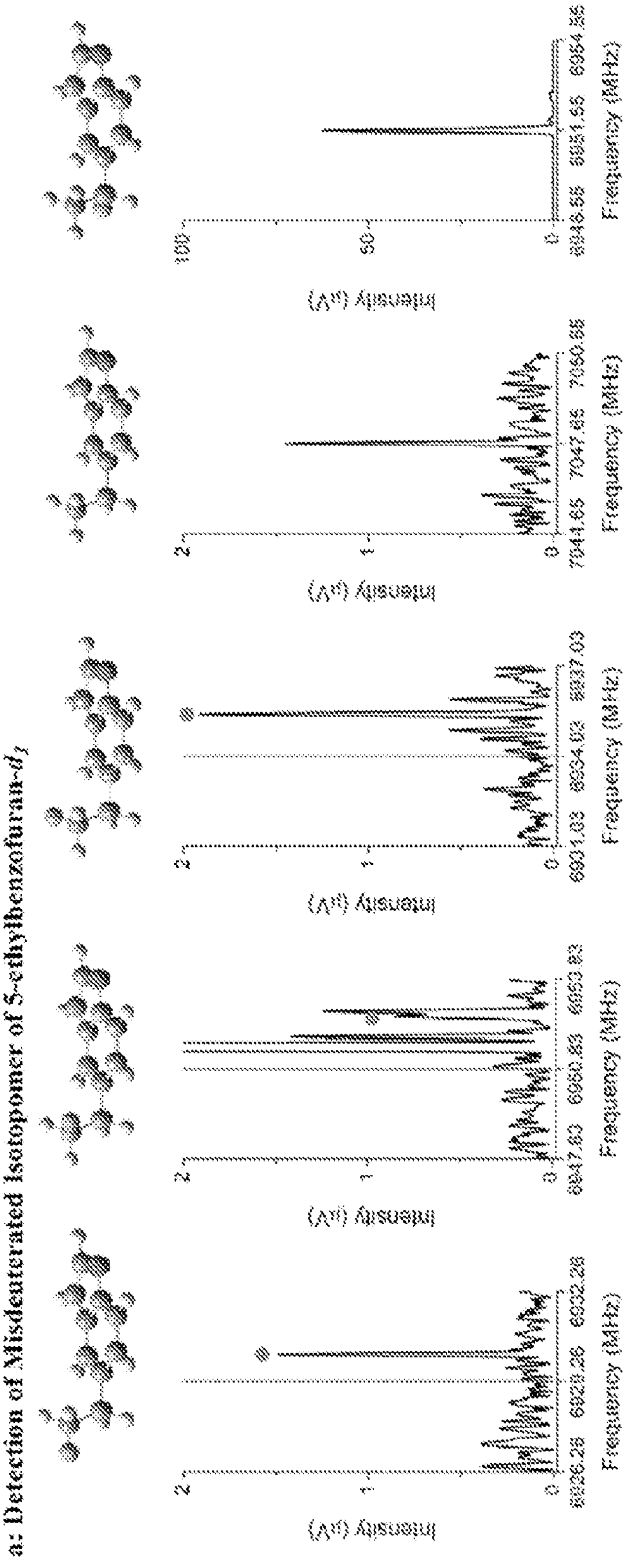
FIG. 11. The isotopologue and isotopomer analysis of two of the reaction products is illustrated. Part (a) shows the analysis of the 5-ethylbenzofuran-$d_1$ sample (6d, 7d, 8d). The first three panels show a 6 MHz window of the rotational spectrum centered on the predicted transition frequency for the strongest transition in the spectrum (also marked by the vertical red line). The conformers of the $d_1$-methyl isotopomer give different spectra and the deuteration position for each transition is denoted by the purple colored atom in the structure above the spectral region. A transition assigned to each isotopomer rotational spectrum is observed and marked by the red dot. The fourth panel is centered on the observed frequency of the underdeuterated isotopologue. The fifth panel shows the rotational transition for one of the two conformers of the desired isotopomer of 5-ethylbenzofuran-$d_1$ (note the change in the intensity axis scale). Part (b) shows the same analysis using the strongest rotational transition of 2-ethylnaphthalene-$d_1$ (7b). In this case, no transitions in the prediction window for the misdeuterated isotopomer can be assigned to rotational spectra. The lack of detection of any rotational transitions is used to derive the upper limit to misdeuterated 2-ethylnaphthalene-$d_1$ reported in the supplemental information provided in Example 6.
Figure 11:
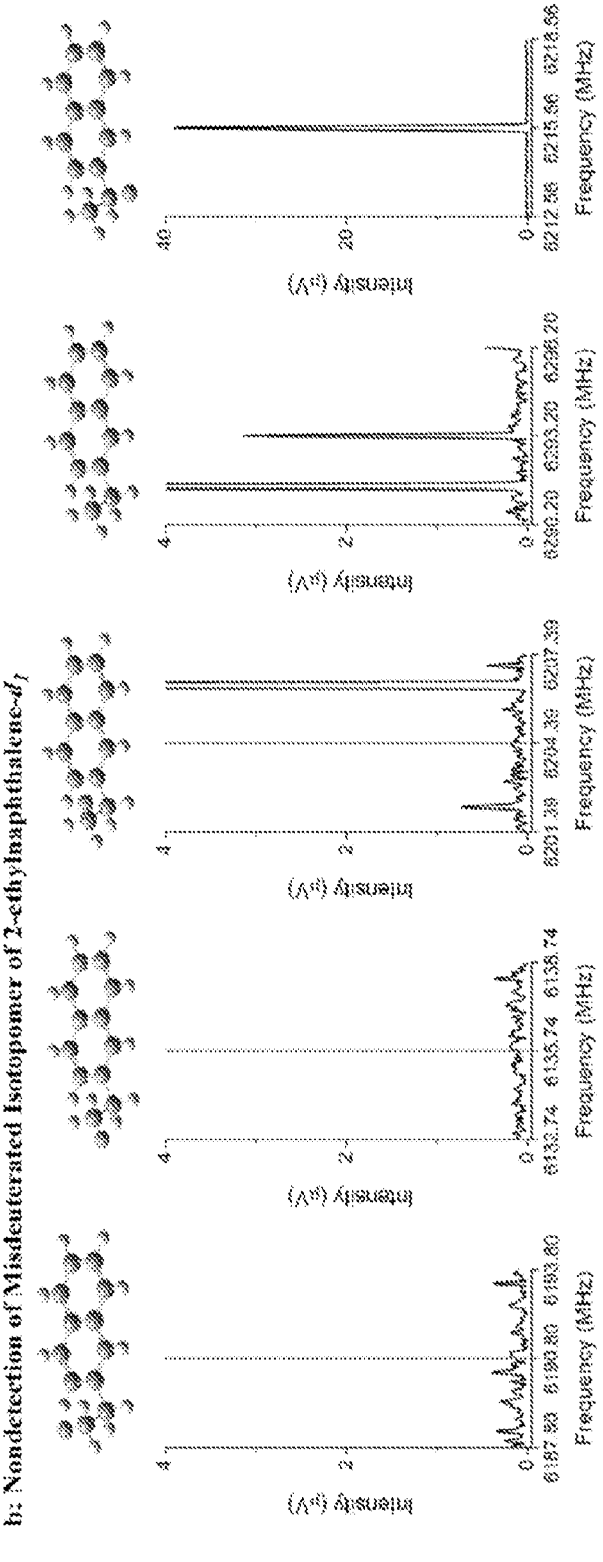

In the Cu-catalyzed transfer hydrodeuteration reaction, a possible impurity is the "misdeuterated" reaction product that results from deuterium inserting at the homobenzylic position and hydrogen at the benzylic position (minor product 7 in Scheme 3). The reaction is also expected to produce "underdeuterated" reaction product where there is no deuterium incorporation (minor product 8 in Scheme 3). This reaction product is expected from the hydrogen impurities in the alcohol-OD or trace $H_2O$ in the alkenyl arene substrate, silane and alcohol-OD. An overview of the MRR analysis for two of the reaction products is shown in FIG. 11. The top panel of figures shows narrow regions of the measured spectrum where the strongest transition in the rotational spectrum of different isotopic variants of 5-ethylbenzofuran (6d, 7d, 8d) are expected. The dominant isotopic species in the sample is the desired reaction product 6d as indicated by the strong observed transition in the rotational spectrum assigned to this isotopomer. The attribution of the observed spectrum to the specific isotopomer is based on the agreement between experimental and theoretical rotational constants. For the transfer hydrodeuteration of 5-vinylbenzofuran, the underdeuterated impurity 8d is also observed.

In the case of the misdeuterated reaction product 7d, three equal intensity rotational spectra are expected from the conformational isomers of this isotopomer. The first three spectral regions shown in FIG. 11*a* are 6 MHz frequency bandwidth windows centered on the predicted transition frequency obtained using the quantum chemistry equilibrium geometry calculated using the B3LYP density functional theory with Grimme's D3 dispersion correction including Becke-Johnson damping and the 6-311++G(d,p) basis set model chemistry in Gaussian16.[62] The transitions marked by the red dot are assigned to the rotational spectra of the three conformers of the $d_1$-methyl isotopomer. The conformational geometry associated with the spectral transition is indicated by the purple atom in the molecular structure shown above the section of the spectrum. The $^2H$ NMR spectrum of the ethylbenzofuran sample is shown in the supporting information and the resonance for the methyl group is barely detectable. The MRR measurement has about an order-of-magnitude higher sensitivity than the $^2H$ NMR measurement. FIG. 11*b* illustrates the analysis of the transfer hydrodeuteration of 2-vinylnaphthalene (6b, 7b, 8b), where no misdeuteration reaction product is identified at the measurement sensitivity using the broadband MRR instrument.

After the initial analyses of the six reaction products depicted in Scheme 3 (these results are tabulated in the SI), a modified MRR analysis approach was developed to address some weaknesses in the application of MRR to the development of synthetic methodologies for selective deuteration chemistry. One issue with the CP-FTMW analysis is the possibility that the spectral signature of an isotopic impurity is missed because the quantum chemistry predictions of the rotational spectrum make it difficult to identify the spectrum when it is near the detection limit. The sample consumption for the analysis is also a potential limitation. The broadband MRR analysis initially performed for the products depicted in Scheme 3 consumed 60-100 mg to reach a detection limit of about 1% on the expected isotopic impurities. Finally, the measurement time is approximately 3 hours. Shorter measurement times are needed to facilitate screening of reaction conditions to optimize the deuteration selectivity.

The new measurement approach combines broadband MRR spectroscopy to obtain the spectral signatures of all possible isotopic species accessible from the transfer hydrodeuteration chemistry, with high-throughput sample analysis performed on an IsoMRR instrument.[63] The IsoMRR instrument uses the tunable cavity-enhanced FTMW design introduced by Balle and Flygare.[64] The instrument employs coaxial injection of the sample through a solenoid valve mounted in the resonator mirror as introduced by Grabow, Stahl, and Dreizler to increase the measurement sensitivity.[65] The compact instrument design is based off the mini-FTMW instrument design from NIST.[66] The IsoMRR spectrometer has approximately an order-of-magnitude greater sensitivity than the broadband spectrometer for equal sample consumption. The instrument is also capable of performing high-throughput sample screening.[67] The tradeoff of using a cavity-enhanced FTMW spectrometer is that the cavity resonator limits the measurement bandwidth to about 1 MHz. Due to the small bandwidth window, efficient use of the instrument relies on the availability of the transition frequencies of each isotopic species to be studied and these are supplied from the broadband analysis.

The sample analyzed by broadband MRR is prepared by performing the reaction with a 1:1 mixture of H and D reagents so that a "cocktail" of all possible reaction products is produced (eq 3). Once this sample is analyzed, the spectral signatures are used to set up a high-speed measurement script using a cavity-enhanced Fourier transform microwave (FTMW) spectrometer. This measurement methodology was tested on the isolated products from the Cu-catalyzed "cocktail" reactions performed with 5a, 5b and 5d shown in (3) below:

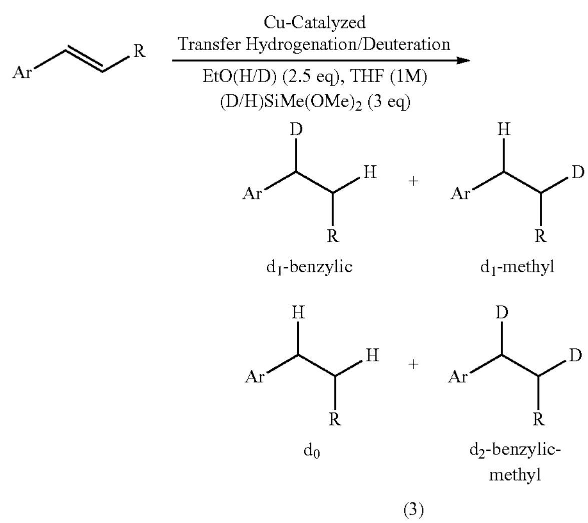

$d_1$-benzylic + $d_1$-methyl $d_0$ + $d_2$-benzylic-methyl (3)

"Cocktail Reaction" will produce all possible isotopic variants

Figure 12:
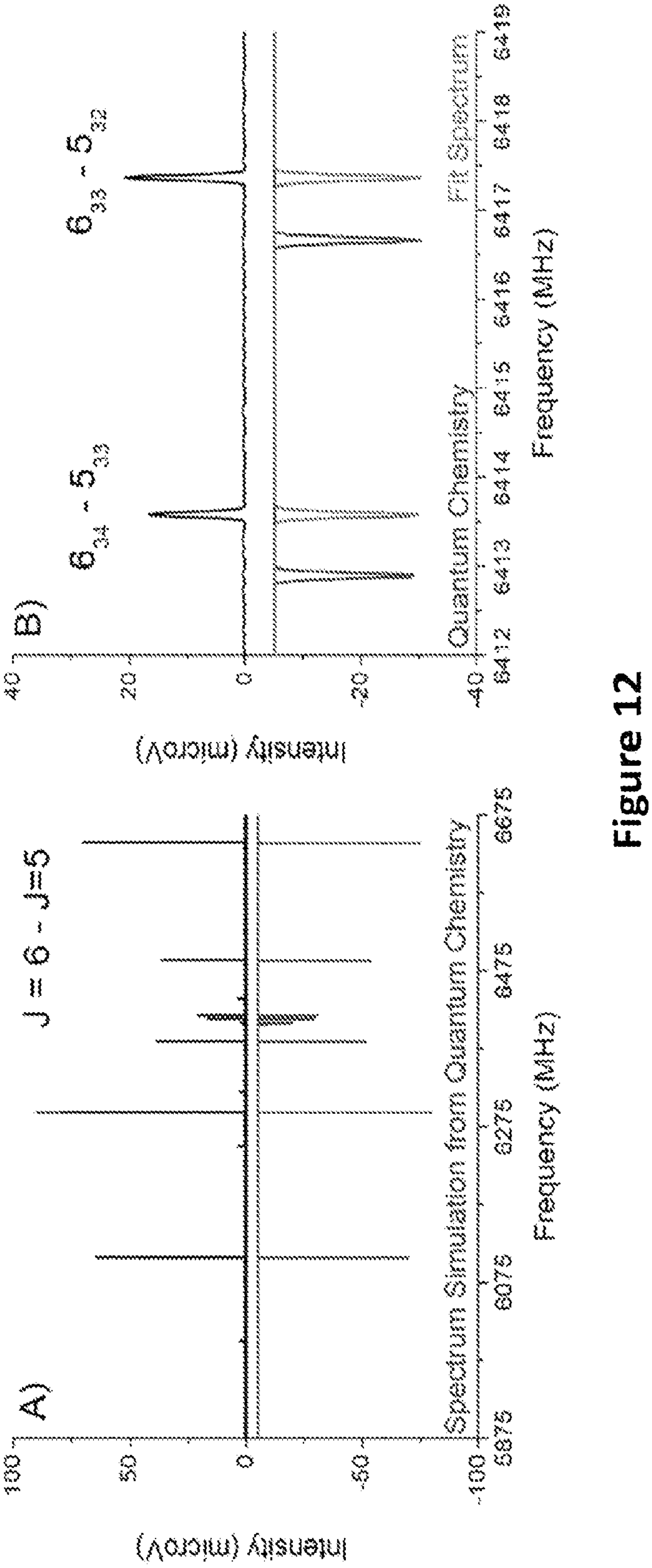
FIG. 12. Predicted and Experimental Analysis of 2-Ethylnaphthalene Product Mixture from the Cocktail Reaction. Illustrated is the method for analyzing the reaction product mixture when a near 1:1 mixture of H and D-reagents is used in the Cu-catalyzed transfer hydrogenation/deuteration reaction. Panels A and B show the basic MRR analysis process for a commercial sample of 2-ethylnaphthalene-do. The simulation of the spectrum from quantum chemistry is used to guide an experimental fit of the rotational constants (Panel B) of the spectrum. The results from this initial fit are used to make scaled predictions for the rotational constants for other isotopic species. The predicted transitions for the six conformers of the $d_2$-benzylic-methyl isotopomer are shown in Panel C. The transition marked with a red asterisk is unassigned. All strong transitions are assigned to four chemical species ($d_0$, $d_1$-benzylic, $d_1$-methyl, $d_2$-benzylic-methyl) and no further species could be identified in the residuals of the reaction product mixture spectrum shown in Panel D (blue, with the intensity multiplied by a factor of 10).
Figure 12:
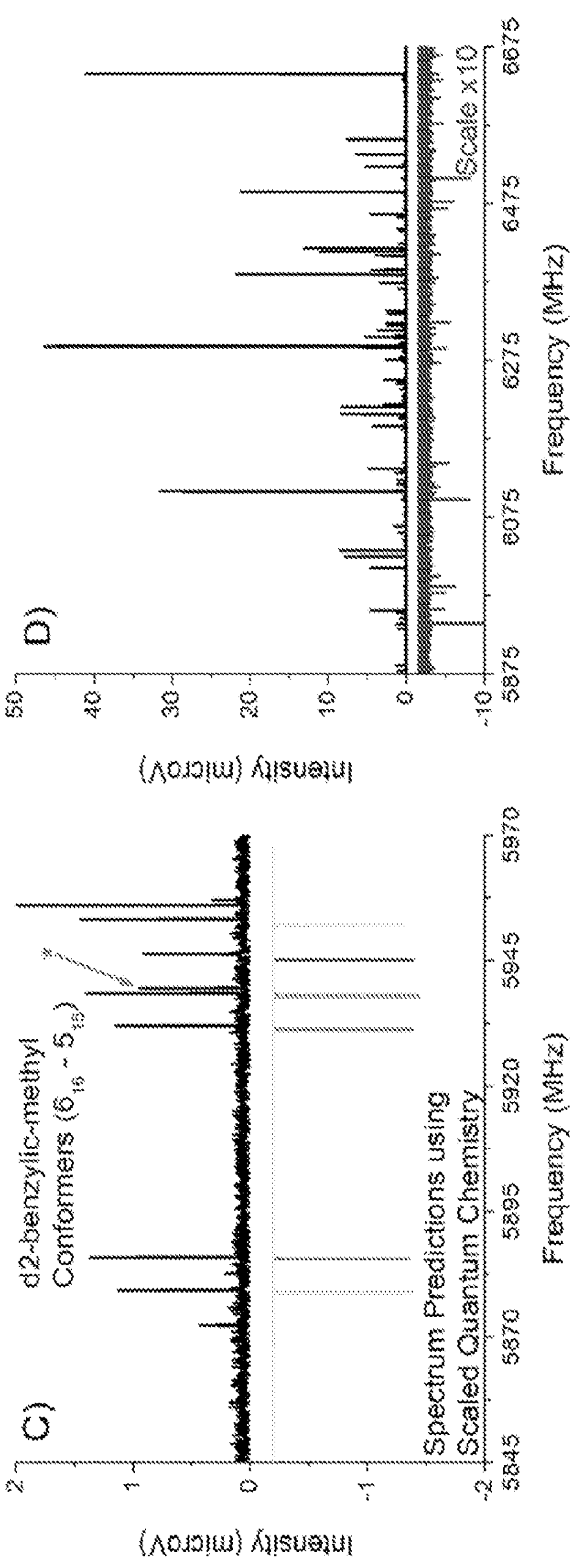

The analysis of the reaction mixture using the broadband CP-FTMW spectrometer is illustrated in FIG. 12 for the Cu-catalyzed "cocktail" reaction of 2-vinylnaphthalene 5b. Panels A and B show the spectrum for a commercial sample of ethylnaphthalene-do for simplicity (this species is also the dominant species in the cocktail reaction mixture). Panel A shows the MRR spectrum in a small frequency range of the full 2-8 GHz measured spectrum. The rotational spectrum prediction from the equilibrium geometry and dipole moments obtained from the quantum chemistry geometry optimization is shown in blue and is a close match to the observed pattern. Panel B shows an expanded frequency region for two of the transitions in ethylnaphthalene-$d_0$. The assignment listed above each transition uses the usual notation in rotational spectroscopy that labels the energy levels $J_{KaKc}$.[54] The blue spectrum simulation is from quantum chemistry. The red simulation uses the experimental fit rotational constants which are given in the supplemental material provided in Example 6.

The spectral signatures of each deuterated 2-ethylnaphthalene species can be predicted to high accuracy using the theoretical equilibrium geometry and scale factors obtained from the theoretical and fit constants of ethylnaphthalene-$d_0$. This process is described in the supplemental material provided in Example 6 and is a common analysis tool in rotational spectroscopy where it is used to identify $^{13}C$ (and other) isotopomers in natural abundance in structure determination.[68] The accuracy of this analysis is illustrated in Panel C where the predicted transitions of the $6_{16}$-$5_{15}$ rotational transitions of the six conformers of the $d_2$-benzylic-methyl isotopomer are compared to the measured spectrum. The supplemental material gives the comparison between the scaled rotational constant predictions and the experimental fit rotational constants for the 11 isotopic species identified in the spectrum. Agreement is on the order of 0.01%. Panel D shows the J=6–J=5 spectral region of the reaction product mixture and the residual spectrum (blue) after all isotopic species (including the rotational spectra for the 12 singly-substituted $^{13}C$ isotopomers of the dominant ethylnaphthalene-$d_0$ species) are cut from the spectrum. The only isotopomers identified in the spectrum are $d_0$, $d_1$-benzylic, $d_1$-methyl, and $d_2$-benzylic-methyl and this is consistent with the proposed reaction products.

The broadband spectrum can be used to perform quantitative analysis of the reaction product mixture. To average fluctuations from the frequency-dependent electric field of the chirped excitation pulse, the total intensity of a set of rotational transitions is used. The analysis needs to include the spectral intensity from all conformers of a given isotopomer. The result using 8 transitions in the 2-ethylnaphthalene spectrum is shown in Table 2. Analysis of the results for the 5-ethylbenzofuran and ethylbiphenyl product mixtures are included in the supplemental material provided in Example 6.

There are two important spectroscopy details in the analysis. First, the analysis assumes that the dipole moment is the same for all isotopic variants so that the total spectral intensity is directly proportional to the isotopic composition. The dipole moment differs for the different species through two effects. Deuterium substitution reorients the principal axis system for molecular rotation and changes the components of the dipole moment vector in this axis system. This effect can be calculated from the equilibrium geometry and is negligible in the samples analyzed in this work. For example, the value of $m_a^2$—the square of the component of the electric dipole moment along the a-principal axis which governs the intensities of the transitions used in the analysis—varies by just 0.1% for the 12 rotationally distinct structures analyzed for ethylnaphthalene. The dipole moment also changes magnitude upon deuteration from changes in the zero-point motion of the C—H bond. These effects have been measured and the bond dipole changes are on the order of 0.01 D which is small compared to the dipole moments of the molecules in this study (>0.4 D).[69] The second spectroscopy issue that can affect the quantitative analysis is the presence of nuclear quadrupole hyperfine splitting in the spectrum from the deuterium nucleus (I=1). The quantitative analysis uses only a-type rotational transitions where the hyperfine structure is small compared to the linewidth and can, therefore, be neglected.

TABLE 2

Isotopic Composition of the 2-Ethylnaphthalene Mixture Giving the Total Intensity for 8 Transitions of Each Conformer for the Four Chemically Distinct Isotopic Variants Observed in the Spectrum

| | $d_0$ | $d_1$- benzylic | | $d_1$- methyl | | $d_1$- benzylic-methyl | |
|---|---|---|---|---|---|---|---|
| | 280 μV | D19[a] | 57.0 μV | D22 | 38.0 μV | D19 D22 | 8.17 μV |
| | | D20 | 55.4 μV | D23 | 36.3 μV | D19 D23 | 8.72 μV |
| | | | | D24 | 41.9 μV | D19 D24 | 7.82 μV |
| | | | | | | D20 D22 | 9.25 μV |
| | | | | | | D20 D23 | 9.38 μV |
| | | | | | | D20 D24 | 10.6 μV |
| Total | 280 μV | | 112.4 μV | | 116.2 μV | | 53.9 μV |
| % | 49.8 | | 20.0 | | 20.7 | | 9.6 |
| $d_1$-methyl conformers: | | | | Mean: 38.7 μV | | σ = 2.84 μV | |
| $d_2$-benzylic-methyl conformers: | | | | Mean: 8.99 μV | | σ = 0.98 μV | |

[a]The isotope labels, like D19, refer to the atom labeling from the quantum chemistry geometry optimization as shown in the Supporting Information.

The accuracy of the sample composition analysis by broadband MRR spectroscopy has been validated by comparison to integration of specific resonances in the $^1H$ and $^2H$ NMR spectra of the reaction mixture. It is important to note that NMR spectroscopy cannot analyze the composition of this reaction mixture. The resonances used in the NMR analysis are assigned to the benzylic and methyl protons. However, the reaction mixture contains three isotopic species ($d_1$-benzylic, $d_1$-methyl, and $d_2$-benzylic-methyl) that contribute to the two resonances making it impossible to analyze the sample composition by NMR. This simple example illustrates the limitations of NMR spectroscopy for reaction product analysis in deuteration chemistry. MRR can perform the analysis because all isotopic variants have a unique spectral signature.

The accuracy of the MRR composition is assessed by calculating the expected NMR integration for the sample using the MRR results reported in Table 2 (2-ethylnaphthalene) and the supplemental information (5-ethylbenzofuran and ethylbiphenyl). For example, the integration of the methyl proton resonance using the fractional composition of the sample is:

$$^1H\ \text{Methyl} = (f_{d0})*3 + (f_{d1-benzylic})*3 + (f_{d1-methyl})*2 + (f_{d2-benzylic-methyl})*2 \quad (4)$$

The quantitative comparison between MRR and NMR resonance integrations is presented in Table 3 for four reaction mixtures that were analyzed in this work (this includes a second ethylbiphenyl mixture where the ratio of H:D reagents was 1:2 to increase the contribution from the deuterated species). The mean absolute percent difference between the results is 1% for the $^1H$ integration.

TABLE 3

Comparison Between Calculated NMR Integration Using MRR Sample Composition and Measure NMR Integration

| | Ethylbenzofuran | | Ethylnaphthalene | | Ethylbiphenyl | | Ethylbiphenyl (D-enhanced) | |
|---|---|---|---|---|---|---|---|---|
| NMR Resonance | MRR[a] | NMR | MRR | NMR | MRR | NMR | MRR | NMR |
| Methyl $^1H$ | 2.72(1) | 2.69 | 2.70(2) | 2.71 | 2.69(2) | 2.73 | 2.46(2) | 2.46 |
| Benzylic $^1H$ | 1.45(2) | 1.43 | 1.70(2) | 1.71 | 1.66(2) | 1.69 | 1.31(2) | 1.29 |
| Methyl $^2H$ | 0.28(1) | 0.31 | 0.30(2) | 0.29 | 0.31(2) | 0.27 | 0.54(2) | 0.52 |
| Benzylic $^2H$ | 0.55(2) | 0.57 | 0.30(2) | 0.28 | 0.34(2) | 0.30 | 0.69(2) | 0.71 |
| Mean Absolute Percent Difference ($^1H$ Only): | | | | | 1.0% | | | |
| Mean Absolute Percent Difference (All): | | | | | 4.0% | | | |

[a]The MRR integrations give the 1σ uncertainty derived from the composition uncertainty.

The reaction product mixtures prepared using a 1:1 ratio of H:D reagents were subsequently analyzed using the IsoMRR instrument. A measurement script was designed to permit detection of the four chemically distinct isotopic species at the 1% level for each of the three analytes. These scripts are described in the supplemental material. The measurement script does not need to make measurements for all conformers of a given isotopomer. As shown in Table 2, equal amounts of the conformers are observed in the spectrum (within a 10% intensity uncertainty) so that the measurement can use just one and then apply the statistical factor to get the total sample composition for the isotopomer. The sample composition from the IsoMRR measurements is compared to the CP-FTMW analysis in Table 4.

The composition analysis from the two MRR instruments are in good agreement with a percentage variation of about 5%. However, the 5% accuracy has little practical importance in applications of high-throughput screening where the measurement precision (better than 1%) is needed to determine which samples have higher purity. The lower accuracy of the IsoMRR measurements results from the instrument design which uses a cavity-resonator with high quality factor (Q) to enhance the measurement sensitivity. There has been no attempt to correct for frequency-dependent variation in the cavity Q in these measurements (although transitions in a narrow frequency range are used to minimize variations in the cavity Q). In practice, the IsoMRR measurements can achieve both high precision and accuracy by calibrating the instrument response using a reference sample that has been analyzed by broadband rotational spectroscopy where the quantitative accuracy is demonstrated in Table 3.

TABLE 4

Comparison of Sample Composition Analysis by Broadband and Cavity-Enhanced MRR Spectroscopy

| | Run 1 | Run 2 | Run 3 | IsoMRR[a] | CP-FTMW[b] | \|Difference\| |
|---|---|---|---|---|---|---|
| Ethylbenzofuran | | | | | | |
| $d_0$ | 29.4% | 30.3% | 30.0% | 29.9(0.45) | 34(2.4) | 4.1% |
| $d_1$-benzylic | 33.7% | 31.9% | 31.8% | 32.6(1.1) | 38(2.1) | 5.4% |
| $d_1$-methyl | 13.4% | 14.3% | 15.1% | 14.3(0.85) | 11.4(0.8) | 2.9% |
| $d_2$-methyl-benzylic | 23.5% | 23.5% | 23.1% | 23.4(0.23) | 16.8(0.9) | 6.6% |
| Ethylnaphthalene | | | | | | |
| $d_0$ | 55.2% | 54.3% | 54.2% | 54.6(0.55) | 50(2.7) | 4.6% |
| $d_1$-benzylic | 14.9% | 15.1% | 14.8% | 14.9(0.15) | 20(1.6) | 5.1% |
| $d_1$-methyl | 21.0% | 21.5% | 21.4% | 21.3(0.26) | 21(1.4) | 0.3% |
| $d_2$-methyl-benzylic | 9.0% | 9.2% | 9.6% | 9.3(0.31) | 9.6(0.6) | 0.3% |
| Ethylbiphenyl | | | | | | |
| $d_0$ | 49.7% | 51.7% | | 30.7(1.4) | 46(2.7) | 4.9% |
| $d_1$-benzylic | 18.7% | 18.0% | | 18.4(0.49) | 23(1.7) | 4.7% |
| $d_1$-methyl | 20.8% | 20.3% | | 20.6(0.35) | 21(1.4) | 0.4% |
| $d_2$-methyl-benzylic | 10.8% | 9.9% | | 10.4(0.64) | 10.6(0.7) | 0.2% |

[a]The IsoMRR results are the mean value of the replicate measurements with a 1σ sample standard deviation reported in parenthesis.
[b]The measurement uncertainty reported for the CP-FTMW broadband measurements is a 1σ standard deviation determined by assuming that there is a 10% relative uncertainty in the intensity measurement (($\sigma_I$/I) = 0.1) for each rotationally distinct species in the sample mixture.

The more important feature of the IsoMRR measurements is the repeatability in back-to-back analysis runs which is about 1%. This measurement precision shows that the technique would be able to reliably detect changes in the sample composition for high-throughput screening of reaction conditions. The IsoMRR measurement for 2-ethylnaphthalene and 5-ethylbenzofuran uses 2.5 mg of sample (for ethylbiphenyl where the spectrum is weaker, the sample consumption is 5 mg). The measurement time is approximately 10 minutes (20 minutes for ethylbiphenyl). Both performance metrics are order-of-magnitude improvements over sample analysis by broadband MRR using the CP-FTMW spectrometer.

The IsoMRR instrument was also used to analyze the reaction products depicted in Scheme 3. These measurements detected the presence of the $d_1$-methyl isotopomer in ethylnaphthalene that was not observable in the broadband analysis (FIG. 11*b*): (94.9% $d_1$-benzylic (6b), 4.4% $d_0$ (8b), 0.8% $d_1$-methyl (7b), <0.6% $d_2$ (nd)). For ethylbenzofuran, the IsoMRR analysis agrees with the broadband analysis within the performance comparison limits of Table 4: (95.1% $d_1$-benzylic (6d), 1.7% $d_0$ (8d), 3.2% $d_1$-methyl (7d), <0.7% $d_2$ (nd)). For ethylbiphenyl, only the underdeuterated isotopic impurity was detected: (98.4% $d_1$-benzylic (6a), 1.6% $d_0$ (8a), <0.7% $d_1$-methyl (7a) (nd), <1.3% $d_2$ (nd)). In addition, three separate preparations of ethylbiphenyl using the optimized chemistry were analyzed. The only two species detected were the desired $d_1$-benzylic and the underdeuterated $d_0$ isotopologue. The amount of $d_0$ (8a) impurity in the three samples was: 1.6%, 2.3%, and 1.8%.

4. CONCLUSIONS

In summary, a highly regioselective alkene transfer hydrodeuteration for the synthesis of deuterated small molecules where deuterium is incorporated at the benzylic position is reported. The Cu-catalyzed reaction is able to incorporate both an H and a D across an alkene with high levels of precision. This mild protocol can be carried out across a broad range of aryl alkene substrates, including those containing heterocycles and reduceable functionality. A detailed characterization of six reaction product mixtures was performed using molecular rotational resonance spectroscopy. MRR provides a general method to perform isotopomer composition analysis of deuteration reactions. The following advantages of MRR spectroscopy for characterization of isotopic products were outlined during the characterization of six isotopic product mixtures from the alkene transfer hydrodeuteration reaction. (1) Isotopomers have distinct MRR spectra that can be predicted to high accuracy from the theoretical equilibrium geometry from quantum chemistry. This feature makes it possible to identify the isotopomers with high confidence without the need for reference samples. (2) Instruments for MRR provide high spectral resolution so that isotopologue and isotopomer mixtures can be quantitatively analyzed without issues arising from signal overlap. (3) High-throughput analysis is possible using cavity-enhanced FTMW spectrometers making it possible to screen a wide range of reaction conditions for isotopic reactions. These capabilities were especially important for analyzing the reaction products from the reported Cu-catalyzed alkene transfer hydrodeuteration reaction. Reaction mixtures may contain three isotopic species ($d_1$-benzylic, $d_1$-methyl, and $d_2$-benzylic-methyl), and these contribute to two NMR resonances. This scenario made it challenging to analyze the sample composition by NMR. In addition to the enhanced sensitivity of MRR, the identification of the $d_1$-methyl isotopomer 7b (the minor regioisomer from the transfer hydrodeuteration of 2-ethylnaphthalene) was possible. This species was not detected by NMR. Ultimately, using MRR spectroscopy to analyze the isotopic products formed from the reported highly regioselective Cu-catalyzed alkene transfer hydrodeuteration reaction led the highest regioselectivities ever reported for this reaction. We anticipate that the advances reported for the selective hydrodeuteration chemistry and MRR spectroscopy will facilitate new reaction discovery in selective deuteration chemistry and expand the utility of deuterium-labelled organic compounds in applications that require the molecule has high deuterium content at precisely the desired site.

REFERENCES (1) Atzrodt, J.; Derdau, V., Pd- and Pt-catalyzed H/D exchange methods and their application for internal MS standard preparation from a Sanofi-Aventis perspective. *J. Labelled Compd. Radiopharm.* 2010, 53, 674-685.

(2) Qin, M.; Qiao, H.-q.; Yuan, Y.-j.; Shao, Q., A quantitative LC-MS/MS method for simultaneous determination of deuvortioxetine, vortioxetine and their carboxylic acid metabolite in rat plasma, and its application to a toxicokinetic study. *Anal. Methods.* 2018, 10, 1023-1031.

(3) Iglesias, J.; Sleno. L.; Volmer, D. A., Isotopic Labeling of Metabolites in Drug Discovery Applications. *Curr. Drug Metab.* 2012, 13, 1213-1225.

(4) Meek, S. J.; Pitman, C. L.; Miller, A. J. M., Deducing Reaction Mechanism: A Guide for Students, Researchers, and Instructors. *J. Chem. Educ.* 2016, 93, 275-286.

(5) Anslyn, E. V.; Dougherty, D. A., Modern physical organic chemistry. *University Science Books.* 2006, p. 424-441.

(6) Simmons, E. M.; Hartwig, J. F., On the Interpretation of Deuterium Kinetic Isotope Effects in C—H Bond Functionalizations by Transition-Metal Complexes. *Angew. Chem. Int. Ed.* 2012, 51, 3066-3072.

(7) Giagou, T.; Meyer, M. P., Kinetic Isotope Effects in Asymmetric Reactions. *Chem. Eur. J* 2010, 16, 10616-10628.

(8) Atzrodt, J.; Derdau, V.; Kerr, W. J., Reid, M., Deuterium- and Tritium-Labelled Compounds: Applications in the Life Sciences. *Angew. Chem. Int. Ed.* 2018, 57, 1758-1784.

(9) Jarling, R.; Sadeghi, M.; Drozdowska, M.; Lahme, S.; Buckel, W.; Rabus, R; Widdel, F.; Golding, B. T.; Wilkes, H., Stereochemical Investigations Reveal the Mechanism of the Bacterial Activation of n-Alkanes without Oxygen. *Angew. Chem. Int. Ed* 2012, 51, 1334-1338.

(10) Klinman, J. P., A new model for the origin of kinetic hydrogen isotope effects. *J. Phys. Org. Chem.* 2010, 23, 606-612.

(11) Schwab, J. M., Stereochemistry of an enzymic Baeyer-Villiger reaction. Application of deuterium NMR. *J. Am. Chem. Soc.* 1981, 103, 1876-1878.

(12) Battersby, A. R.; Gutman, A. L.; Fookes, C. J. R; Günther, H.; Simon, H., Stereochemistry of formation of methyl and ethyl groups in bacteriochlorophyll a. *J Chem. Soc., Chem. Commun.* 1981, 645-647.

(13) Leinberger, R.; Retey, A.; Hull, W. E.; Simon, H., Steric Course of the NIH Shift in the Enzymic Formation of Homogentisic Acid. *Eur. J. Biochem.* 1981, 117, 311-318.

(14) Lüthy, J.; Rétey, J.; Arigoni, D., Asymmetric Methyl Groups: Preparation and Detection of Chiral Methyl Groups. *Nature* 1969, 221, 1213-1215.

(15) White, R. E.; Miller, J. P.; Favreau. L. V.; Bhattacharyya, A., Stereochemical dynamics of aliphatic hydroxylation by cytochrome P450. *J Am. Chem. Soc.* 1986, 108, 6024-6031.

(16) Shapiro, S.; Piper, J. U.; Caspi, E., Steric course of hydroxylation at primary carbon atoms. Biosynthesis of 1-octanol from (1R)- and (1S)-[1-3H,2H,1H; 1-14C]octane by rat liver microsomes. *J. Am. Chem. Soc.* 1982, 104, 2301-2305.

(17) Nelson, S. D.; Trager, W. F., The Use of Deuterium Isotope Effects to Probe the active site properties, Mechanism of Cytochrom P450-Catalyzed Reactions, and Mechanisms of Metabolically Dependent Toxicity. *Drug Metab. Dispos.* 2003, 31, 1481-1497.

(18) Pirali, T.; Serafini, M. Cargnin, S.; Genazzani, A. A., Applications of Deuterium in Medicinal Chemistry. *J. Med. Chem.* 2019, 62, 5276-5297.

(19) Gant, T. G., Using Deuterium in Drug Discovery: Leaving the Label in the Drug. *J. Med. Chem.* 2014, 57, 3595-3611.

(20) Meanwell, N. A., Synopsis of Some Recent Tactical Application of Bioisosteres in Drug Design. *J Med. Chem.* 2011, 54, 2529-2591.

(21) Stepan, A. F.; Mascitti, V.; Beaumont, K.; Kalgutkar, A. S., Metabolism-guided drug design. *Medchemcommun.* 2013, 4, 631-652.

(22) Belleau, B.; Burba, J.; Pindell, M.; Reiffenstein, J., Effect of Deuterium Substitution in Sympathomimetic Amines on Adrenergic Responses. *Science* 1961, 133, 102-104.

(23) Harbeson, S. L.; Tung, R. D., Deuterium Medicinal Chemistry: A New Approach to Drug Discovery and Development. *Medchem News* 2014, 24, 8-22.

(24) Schmidt, C., First deuterated drug approved. *Nat Biotechnol.* 2017, 35, 493-494.

(25) Ludwig. J. R.; Schindler, C. S., Catalyst: Sustainable Catalysis. *Chem.* 2017, 2, 313-316.

(26) Zhou, Q.-L., Transition-Metal Catalysis and Organocatalysis: Where Can Progress Be Expected?*Angew. Chem. Int. Ed.* 2016, 55, 5352-5353.

(27) Atzrodt, J.; Derdau, V.; Fey, T.; Zimmermann, J., The Renaissance of H/D Exchange. *Angew. Chem. Int. Ed* 2007, 46, 7744-7765.

(28) Atzrodt, J.; Derdau. V.; Kerr. W. J.; Reid, M., C—H Functionalisation for Hydrogen Isotope Exchange. *Angew. Chem. Int. Ed* 2018, 57, 3022-3047.

(29) Puleo, T. R.; Strong, A. J.; Bandar, J. S., Catalytic α-Selective Deuteration of Styrene Derivatives. *J. Am. Chem. Soc.* 2019, 141, 1467-1472.

(30) Karlsson, S.; Hallberg, A.; Gronowitz, S., Hydrozirconation of (E)-3-methoxy-1-phenyl-1-propene and (E)-3-phenyl-2-propenol. *J. Organomet. Chem.* 1991, 403, 133-144.

(31) Czeskis, B.; Elmore, C. S.; Haight, A.; Hesk, D.; Maxwell, B. D.; Miller, S. A.; Raglione, T.; Schildknegt, K.; Traverse, J. F.; Wang, P., Deuterated Active Pharmaceutical Ingredients: A Science-Based Proposal for Synthesis, Analysis, and Control. Part 1: Framing the Problem. *J. Labelled Compd. Radiopharm.* 2019, 62, 690-694.

(32) Wang, D.; Astruc, D., The Golden Age of Transfer Hydrogenation. *Chem. Rev.* 2015, 115, 6621-6686.

(33) Korytiaková, E.; Thiel, N. O.; Pape, F.; Teichert, J. F., Copper(i)-Catalysed Transfer Hydrogenations with Ammonia Borane. *Chem. Commun.* 2017, 53, 732-735.

(34) Chatterjee, I.; Oestreich, M., Brønsted Acid-Catalyzed Transfer Hydrogenation of Imines and Alkenes Using Cyclohexa-1,4-dienes as Dihydrogen Surrogates. *Org. Lett.* 2016, 18, 2463-2466.

(35) Lau, S.; Gasperini, D.; Webster, R. L., Amine-Boranes as Transfer Hydrogenation and Hydrogenation Reagents: A Mechanistic Perspective. *Angew. Chem. Int. Ed.* 2021, DOI: 10.1002/anie.202010835.

(36) Semba, K.; Fujihara, T.; Xu, T.; Terao, J.; Tsuji, Y., Copper-Catalyzed Highly Selective Semihydrogenation of Non-Polar Carbon-Carbon Multiple Bonds using a Silane and an Alcohol. *Adv. Synth. Catal.* 2012, 354, 1542-1550.

(37) Whittaker, A. M.; Lalic, G., Monophasic Catalytic System for the Selective Semireduction of Alkynes. *Org. Lett.* 2013, 15, 1112-1115.

(38) Kaicharla, T.; Zimmermann, B. M.; Oestreich, M.; Teichert, J. F., Using Alcohols as Simple $H_2$-Equivalents for Copper-Catalysed Transfer Semihydrogenations of Alkynes. *Chem. Commun.* 2019, 55, 13410-13413.

(39) Okuhara, T.; Tanaka, K.-I., Orientation in the Addition of HD to Butadiene on $MoS_2$. *J. Chem. Soc., Chem. Commun.* 1976, 199-200.

(40) Okuhara, T.; Kondo, T.; Tanaka, K., Oriented Adsorption of Hydrogen Deuteride on Zinc Oxide and Addition to Butadiene. *J. Phys. Chem.* 1977, 81, 808-809.

(41) Espinal-Viguri, M.; Neale, S. E.; Coles, N. T.; Macgregor, S. A.; Webster, R. L., Room Temperature Iron-Catalyzed Transfer Hydrogenation and Regioselective Deuteration of Carbon-Carbon Double Bonds. *J. Am. Chem. Soc,* 2019, 141, 572-582.

(42) Wang, Y.; Cao, X.; Zhao, L.; Pi, C.; Ji, J.; Cui, X; Wu, Y., Generalized Chemoselective Transfer Hydrogenation/Hydrodeuteration. *Adv. Synth. Catal.* 2020, 362, 4119-4129.

(43) Linford-Wood, T. G.; Coles, N. T.; Webster, R. L., Room temperature iron catalyzed transfer hydrogenation using n-butanol and poly(methylhydrosiloxane). *Green Chem.* 2021, 23, 2703-2709.

(44) Walker, J. C. L.; Oestreich, M., Regioselective Transfer Hydrodeuteration of Alkenes with a Hydrogen Deuteride Surrogate Using $B(C_6F_5)_3$ Catalysis. *Org. Lett.* 2018, 20, 6411-6414.

(45) Li, L.; Hilt, G., Regiodivergent DH or HD Addition to Alkenes: Deuterohydrogenation versus Hydrodeuterogenation. *Org. Lett.* 2020, 22, 1628-1632.

(46) Sloane. S. E.; Reyes, A.; Vang, Z. P.; Li, L.; Behlow, K. T.; Clark, J. R., Copper-Catalyzed Formal Transfer Hydrogenation/Deuteration of Aryl Alkynes. *Org. Lett.* 2020, 22, 9139-9144.

(47) Liu, R. Y.; Buchwald, S. L., CuH-Catalyzed Olefin Functionalization: From Hydroamination to Carbonyl Addition. *Acc. Chem. Res.* 2020, 53, 1229-1243.

(48) Zhu. S.; Niljianskul, N.; Buchwald, S. L. Enantio- and Regioselective CuH-Catalyzed Hydroamination of Alkenes. *J. Am. Chem. Soc.* 2013, 135, 15746-15749.

(49) Miki, Y.; Hirano, K.; Satoh, T.; Miura. M., Copper-Catalyzed Intermolecular Regioselective Hydroamination of Styrenes with Polymethylhydrosiloxane and Hydroxylamines. *Angew. Chem. Int. Ed* 2013, 52, 10830-10834.

(50) Sorádová, Z.; Šebesta. R., Enantioselective Cu-Catalyzed Functionalizations of Unactivated Alkenes. *Chem Cat Chem* 2016, 8, 2581-2588.

(51) Mohr, J.; Oestreich, M., Balancing C═C Functionalization and C═O Reduction in Cu—H Catalysis. *Angew. Chem. Int. Ed.* 2016, 55, 12148-12149.

(52) Vitaku. E.; Smith, D. T.; Njardarson, J. T., Analysis of the Structural Diversity, Substitution Patterns, and Frequency of Nitrogen Heterocycles among U.S. FDA Approved Pharmaceuticals. *J. Med. Chem.* 2014, 57, 10257-10274.

(53) Taylor, R. D.; MacCoss, M.; Lawson. A. D. G., Rings in Drugs. *J. Med. Chem.* 2014, 37, 5845-5859.

(54) W. Gordy, R. L. C., Microwave Molecular Spectra, 3rd ed., Chapter VII, 227-296*; Knovel.* 1984.

(55) Smith, J. A.; Wilson, K. B.; Sonstrom, R. E.; Kelleher, P. J.; Welch, K. D.; Pert, E. K.; Westendorff, K. S.; Dickie, D. A.; Wang, X.; Pate. B. H.; Harman, W. D., Preparation of cyclohexene isotopologues and stereoisotopomers from benzene. *Nature* 2020, 581, 288-293.

(56) Grimme, S.; Steinmetz, M., Effects of London dispersion correction in density functional theory on the structures of organic molecules in the gas phase. *Phys. Chem. Chem. Phys.* 2013, 15, 16031-16042.

(57) Lee, K. L. K.; McCarthy, M., Bayesian Analysis of Theoretical Rotational Constants from Low-Cost Electronic Structure Methods. *J. Phys. Chem. A* 2020, 124, 898-910.

(58) Brown, G. G.; Dian, B. C.; Douglass, K. O.; Geyer, S. M.; Shipman, S. T.; Pate, B. H., A broadband Fourier transform microwave spectrometer based on chirped pulse excitation. *Rev. Sci. Instrum.* 2008, 79, 053103.

(59) Neill, J. L.; Shipman, S. T.; Alvarez-Valtierra, L.; Lesarri, A.; Kisiel, Z.; Pate, B. H., Rotational spectroscopy of iodobenzene and iodobenzene-neon with a direct digital 2-8 GHz chirped-pulse Fourier transform microwave spectrometer. *J. Mol. Spectrosc.* 2011, 269, 21-29.

(60) Pérez, C.; Lobsiger, S.; Seifert, N. A.; Zaleski, D. P.; Temelso. B.; Shields, G. C.; Kisiel, Z.; Pate, B. H., Broadband Fourier transform rotational spectroscopy for structure determination: The water heptamer. *Chem. Phys. Lett.* 2013, 571, 1-15.

(61) Armstrong. D. W.; Talebi, M.; Thakur, N.; Wahab, M. F.; Mikhonin, A. V.; Muckle, M. T.; Neill. J. L., A Gas Chromatography-Molecular Rotational Resonance Spectroscopy Based System of Singular Specificity. *Angew. Chem. Int. Ed.* 2020, 59, 192-196.

(62) Frisch, M. J.; Trucks G. W.; Schlegel, H. B.; Scuseria, G. E.; Robb, M. A., Cheeseman. J. R., Scalmani. G.; Barone, V.; Petersson, G. A.; Nakatsuji, H.; Li, X.; Caricato, M.; Marenich, A. V.; Bloino, J.; Janesko, B. G.; Gomperts. R.; Mennucci, B.; Hratchian, H. P.; Ortiz, J. V.; Izmaylov, A. F.; Sonneberg, J. L.; Williams-Young, D.; Ding, F.; Lipparini, F.; Egidi, F.; Goings, J.; Peng, B.; Petrone, A.; Henderson, T.; Ranasinghe, D.; Zakrzewski, V. G.; Gao, J.; Rega, N.; Zheng, G.; Liang, W.; Hada, M.; Ehara. M.; Toyota, K.; Fukuda. R.; Hasegawa, J.; Ishida, M.; Nakajima, T.; Honda. Y.; Kitao, O.; Nakai. H.; Vreven, T.; Throssell, K.; Montgomery, J. A., Jr.; Peralta, J. E.; Ogliaro, F.; Bearpark, M. J.; Heyd, J. J.; Brothers, E. N.; Kudin, K. N.; Staroverov, V. N.; Keith, T. A.;

Kobayashi, R.; Normand, J.; Raghavachari, K.; Rendell, A. P.; Burat, J. C.; Iyengar, S. S.; Tomasi, J.; Cossi, M.; Millam, J. M.; Klene, M.; Adamo, C.; Cammi, R.; Ochterski, J. W.; Martin, R. L.; Morokuma, K.; Farkas, O.; Foresman, J. B.; Fox, D. J. Gaussian 16 *Rev. C*.01. Wallingford, Ct. 2016.

(63) The IsoMRR instrument is available from BrightSpec Inc.

(64) Balle, T. J.; Flygare, W. H., Fabry-Perot cavity pulsed Fourier transform microwave spectrometer with a pulsed nozzle particle source. *Rev. Sci. Instrum.* 1981, 52, 33-45.

(65) Grabow, J.; Stahl, W.; Dreizler, H., A multioctave coaxially oriented beam-resonator arrangement Fourier-transform microwave spectrometer, *Rev. Sci. Instrum.* 1996, 67, 4072-4084.

(66) Suenram, R. D.; Grabow, J. U.; Zuban, A.; Leonov, I., A portable, pulsed-molecular-beam, Fourier-transform microwave spectrometer designed for chemical analysis. *Rev. Sci. Instrum.* 1999, 70, 2127-2135.

(67) Neill, J. L.; Mikhonin, A. V.; Chen, T.; Sonstrom, R. E.; Pate, B. H., Rapid Quantitation of Isomeric and Dehalogenated Impurities in Pharmaceutical Raw Materials Using MRR Spectroscopy. *J. Pharm. Biomed. Anal.* 2020, 189, 113474.

(68) W. Gordy, R. L. C., Microwave Molecular Spectra, 3rd ed., Chapter XIII, 647-724*; Knovel,* 1984.

(69) Fliege, E.; Dreizler, H., Investigation of the Stark Shift of the Benzene-$d_1$ $1_{01}$-$0_{00}$ Rotational Transition by Microwave Fourier Transform Spectroscopy, *Z. Naturforsch.* 1987, 42a, 72-78.

Example 6—Supplementary Information for Example 5, Copper-Catalyzed Transfer Hydrodeuteration of Aryl Alkenes with Quantitative Isotopomer Purity Analysis by Molecular Rotational Resonance Spectroscopy

I. General Information

The following chemicals were purchased from commercial vendors and were used as received: $Cu(OAc)_2$ (99.999% from Alfa Aesar); 1,2-Bis[bis[3,5-di(t-butyl)phenyl]phosphino]benzene (DTB-DPPBz) (Wako Pure Chemical Industries), dimethoxy(methyl)silane (TCI); ethanol-OD (Millipore Sigma); 2-propanol-$d_8$ (Millipore Sigma); poly(methylhydrosiloxane) average $M_n$ 1700-3200 (Millipore Sigma); tert-butyldimethylsilyl chloride (TBSCl) (Oakwood Chemical); methyltriphenylphosphonium bromide (Oakwood Chemical); Sodium hydride (in oil dispersion) 60% dispersion in mineral oil (Oakwood Chemical); sodium bis(trimethylsilyl)amide 2M in THF (Oakwood Chemical) potassium trifluoro(vinyl)borate (Oak-wood Chemical); cesium carbonate (Ambeed Inc.); n-butyl lithium (Millipore Sigma).

Anhydrous tetrahydrofuran (THF) was purified by an MBRAUN solvent purification system (MB-SPS). Chloroform-d ($CDCl_3$) was stored over 3 Å molecular sieves. Thin-layer chromatography (TLC) was conducted with Silicycle silica gel 60 Å F254 pre-coated plates (0.25 mm) and visualized with UV and a $KMnO_4$ stain. Flash chromatography was performed using SiliaFlash® P60, 40-60 mm (230-400 mesh), purchased from Silicycle. For reactions that required heating (optimization, transfer hydrodeuteration), a PolyBlock for 2-dram vials was used on top of a Heidolph heating/stir plate.

$^1$H NMR spectra were recorded on a Varian 300 or 400 MHz spectrometer and are reported in ppm using deuterated solvent as an internal standard ($CDCl_3$ at 7.26 ppm). Data reported as: s=singlet, d=doublet, t=triplet, q=quartet, p=pentet, sxt=sextet, m=multiplet, br=broad; coupling constant(s) in Hz; integration. $^{13}$C NMR spectra were recorded on a Varian 76 MHz or 101 MHz spectrometer and are reported in ppm using deuterated solvent as an internal standard ($CDCl_3$ at 77.16 ppm). $^2$H NMR spectra were recorded on a Varian 61 MHz spectrometer. $^{11}$B NMR spectra were recorded on a Varian 128 MHz spectrometer.

High-resolution mass spectra were obtained for all new compounds not previously reported using the resources of the Chemistry Instrument Center (CIC), University at Buffalo, SUNY, Buffalo, NY. Specifically, high resolution accurate mass analysis was conducted using the following instruments: 12T Bruker SolariXR 12 Hybrid FTMS with Imaging MALDI and Nano-LC, provided through funding from the National Institutes of Health, NIH S10 RR029517: a Thermo Q-Exactive Focus Orbitrap Liquid Chromatograph Tandem Mass Spectrometer and a Thermo Q-Exactive Orbitrap Gas Chromatograph Tandem Mass Spectrometer, provided through funding from the National Science Foundation, MRI-1919594.

II. Optimization Studies

General Procedure a for Optimization Studies in Table S1 and Table S2

In a $N_2$ filled glovebox, ligand. Cu catalyst (Cu:L=1:1.1), and THF were added to an oven-dried 2-dram vial followed by dropwise addition of $R_3Si$—H (0.60 mmol, 3 eq.). A color change from green/blue to yellow was observed while stirring for 15 minutes. In a separate oven-dried 1-dram vial was added (E)-1-tert-butyldimethylsilyloxy-3-phenyl-2-propene (50 mg, 0.20 mmol, 1 eq.), THF (0.100 mL), and D-Source (0.50 mmol, 2.5 eq.). The solution in the 1-dram vial was added dropwise over 20 seconds to the 2-dram vial. The total volume of THF was calculated based on having a final reaction concentration of 1M based on the alkene substrate. The 2-dram vial was capped with a red pressure relief cap, taken out of the glovebox, and stirred for 20 h at 40° C. at which point the reaction was filtered through a 1" silica plug with 100 mL of diethyl ether into a 200 mL round bottom flask. The solvent was removed by rotary evaporation, and the product was analyzed by $^1$H NMR using 1,3,5-trimethylbenzene as an internal standard. Yields for all entries were obtained by isolating the product after flash column chromatography if greater than 5% NMR yield was observed for 2 in the crude $^1$H NMR.

TABLE S1

Reaction Optimization[a]

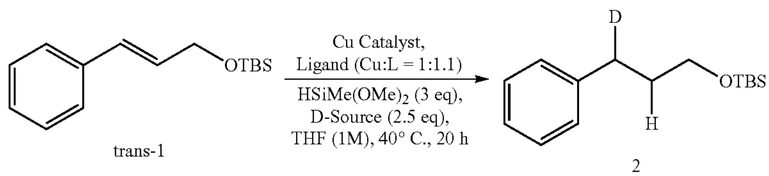 [SMILES: CC(C)(C)[Si](C)(C)OC/C=C/c1ccccc1 ; [2H]C(CCO[Si](C)(C)C(C)(C)C)c1ccccc1]

trans-1 2

| Entry | $Cu(OAc)_2$ | Ligand | D-source | 1 (%) | 2 (%) |
|---|---|---|---|---|---|
| 1 | 2 mol % | L1 | EtOD | 69%[b] | — |
| 2 | 2 mol % | L2 | EtOD | 70%[b] | — |
| 3 | 2 mol % | L3 | EtOD | 89%[b] | — |
| 4 | 2 mol % | L4 | EtOD | 47%[b] | — |
| 5 | 2 mol % | L5 | EtOD | — | 85%[c] |
| 6 | 2 mol % | L5 | MeOD | 8%[c] | 69%[c] |
| 7 | 2 mol % | L5 | $D_2O$ | 59%[c] | 21%[c] |
| 8 | 1 mol % | L5 | IPA-$d_8$ | — | 85%[c] |
| 9 | 1 mol % | L5 | EtOD | — | 90%[c] |

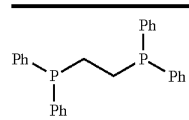

L1: DPPE

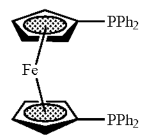

L2: DPPF

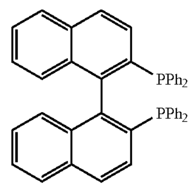

L3: rac-BINAP

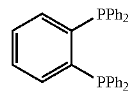

L4: DPPBz

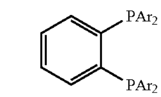

Ar = 3,5-di(tert-butyl)$C_6H_3$

L5: DTB-DPPBz

[a]Reactions conducted using 0.2 mmol of substrate. $Cu(OAc)_2$ was used as a 0.2M solution in THF.

[b]Yield was determined by $^1H$ NMR analysis of the crude reaction mixture, using mesitylene as an internal standard.

[c]Denotes isolated product yield.

Entry 1. According to general procedure A for the optimization studies, a stirring solution of 1,2-Bis(diphenylphosphino)ethane L1 (1.8 mg, 0.0044 mmol, 0.022 eq), $Cu(OAc)_2$ (20 µL of a 0.2 M solution in THF, 0.004 mmol, 0.02 eq.), and dimethoxy(methyl)silane (74 µL, 0.60 mmol, 3 eq.) in THF (0.08 mL) was prepared, and to this was added dropwise a solution of (E)-1-tert-butyldimethylsilyloxy-3-phenyl-2-propene (50 mg, 0.20 mmol, 1 eq.) and ethanol-OD (29 µL, 0.50 mmol, 2.5 eq.) in THF (100 µL). The reaction stirred for 20 h at 40° C., after which it was filtered through a silica plug with diethyl ether (20 mL) and eluted with an additional (80 mL) of diethyl ether. The solvent was removed by rotary evaporation, and the crude product was analyzed by $^1H$ NMR with 1,3,5-trimethylbenzene as an internal standard (1, 69% yield by $^1H$ NMR).

Entry 2. According to general procedure A for optimization studies, a stirring solution of 1,1'-Bis(diphenylphosphino)ferrocene L2 (2.4 mg, 0.0044 mmol, 0.022 eq.), $Cu(OAc)_2$ (20 µL of a 0.2 M solution in THF, 0.004 mmol, 0.02 eq.), and dimethoxy(methyl) silane (74 µL, 0.60 mmol, 3 eq.) in THF (0.080 mL) was prepared, and to this was added dropwise a solution of (E)-1-tert-butyldimethylsilyloxy-3-phenyl-2-propene (50 mg, 0.20 mmol, 1 eq.) and ethanol-OD (29 µL, 0.50 mmol, 2.5 eq.) in THF (0.10 mL). The reaction stirred for 20 h at 40° C., after which it was filtered through a silica plug with diethyl ether (20 mL) and eluted with an additional (80 mL) of diethyl ether. The solvent was removed by rotary evaporation, and the crude product was analyzed by $^1H$ NMR with 1,3,5-trimethylbenzene as an internal standard, (1, 70% yield by $^1H$ NMR).

Entry 3. According to general procedure A for the optimization studies, a stirring solution of (±)-2,2'-Bis(diphenylphosphino)-1,1'-binaphthalene L3 (2.9 mg, 0.0044 mmol, 0.022 eq), $Cu(OAc)_2$ (20 μL of a 0.2 M solution in THF, 0.004 mmol, 0.02 eq.), and dimethoxy(methyl)silane (74 μL, 0.6 mmol, 3 eq.) in THF (0.08 mL) was prepared, and to this was added dropwise a solution of (E)-1-tert-butyldimethylsilyloxy-3-phenyl-2-propene (50 mg, 0.2 mmol, 1 eq.) and ethanol-OD (29 μL, 0.5 mmol, 2.5 eq.) in THF (0.10 mL). The reaction stirred for 20 h at 40° C., after which it was filtered through a silica plug with diethyl ether (20 mL) and eluted with an additional (80 mL) of diethyl ether. The solvent was removed by rotary evaporation, and the crude product was analyzed by $^1H$ NMR with 1,3,5-trimethylbenzene as an internal standard (1, 89% yield by $^1H$ NMR).

Entry 4. According to general procedure A for the optimization studies, a stirring solution of 1,2-Bis(diphenylphosphino)benzene L4 (2.0 mg, 0.0044 mmol, 0.022 eq), $Cu(OAc)_2$ (20 μL of a 0.2 M solution in THF, 0.004 mmol, 0.02 eq.), and dimethoxy(methyl)silane (74 μL, 0.6 mmol, 3 eq.) in THF (0.08 mL) was prepared, and to this was added dropwise a solution of (E)-1-tert-butyldimethylsilyloxy-3-phenyl-2-propene (50 mg, 0.2 mmol, 1 eq.) and ethanol-OD (29 μL, 0.5 mmol, 2.5 eq.) in THF (0.10 mL). The reaction stirred for 20 h at 40° C., after which it was filtered through a silica plug with diethyl ether (20 mL) and eluted with an additional (80 mL) of diethyl ether. The solvent was removed by rotary evaporation, and the crude product was analyzed by $^1H$ NMR with 1,3,5-trimethylbenzene as an internal standard (1, 47% yield by $^1H$ NMR).

Entry 5. According to general procedure A for optimization studies, a stirring solution of 1,2-Bis[bis[3,5-di(t-butyl)phenyl]phosphino]benzene L5 (3.9 mg, 0.0044 mmol, 0.022 eq.), $Cu(OAc)_2$ (20 μL of a 0.2 M solution in THF, 0.004 mmol, 0.02 eq.), and dimethoxy(methyl)silane (74 μL, 0.60 mmol, 3 eq.) in THF (0.08 mL) was prepared, and to this was added dropwise a solution of (E)-1-tert-butyldimethylsilyloxy-3-phenyl-2-propene (50 mg, 0.20 mmol, 1 eq.) and ethanol-OD (29 μL, 0.50 mmol, 2.5 eq.) in THF (0.100 mL). The reaction stirred for 20 h at 40° C., after which it was filtered through a silica plug with diethyl ether (20 mL) and eluted with an additional (80 mL) of diethyl ether. The solvent was removed by rotary evaporation, and the crude product was analyzed by $^1H$ NMR with 1,3,5-trimethylbenzene as an internal standard. The crude product was dry loaded onto silica gel, and purified by flash column chromatography using gradient elution (100 mL of 100%/hexanes, 100 mL of 2% ethyl acetate in hexanes) to yield a clear colorless oil (2, 43 mg, 0.17 mmol, 85% yield).

Entry 6. According to general procedure A for optimization studies, a stirring solution of 1,2-Bis[bis[3,5-di(t-butyl)phenyl]phosphino]benzene L5 (3.9 mg, 0.0044 mmol, 0.022 eq.), $Cu(OAc)_2$ (20 μL of a 0.2 M solution in THF, 0.004 mmol, 0.02 eq.), and dimethoxy(methyl)silane (74 μL, 0.60 mmol, 3 eq.) in THF (0.08 mL) was prepared, and to this was added dropwise a solution of (E)-1-tert-butyldimethylsilyloxy-3-phenyl-2-propene (50 mg, 0.20 mmol, 1 eq.) and methanol-OD (20 μL, 0.50 mmol, 2.5 eq.) in THF (0.10 mL). The reaction stirred for 20 h at 40° C. after which it was filtered through a silica plug with diethyl ether (20 mL) and eluted with an additional (80 mL) of diethyl ether. The solvent was removed by rotary evaporation, and the crude product was analyzed by $^1H$ NMR with 1,3,5-trimethylbenzene as an internal standard. The crude product was dry loaded onto silica gel, and was purified by flash column chromatography using gradient elution (100 mL of 100% hexanes, 100 mL of 2% ethyl acetate in hexanes) to yield a clear colorless oil (1 and 2 isolated as an inseparable mixture, 39 mg (1, 8% yield; 2, 69% yield).

Entry 7. According to general procedure A for optimization studies, a stirring solution of 1,2-Bis[bis[3,5-di(t-butyl)phenyl]phosphino]benzene L5 (3.9 mg, 0.0044 mmol, 0.022 eq.), $Cu(OAc)_2$ (20 μL of a 0.2 M solution in THF, 0.004 mmol, 0.02 eq.), and dimethoxy(methyl)silane (74 μL, 0.60 mmol, 3 eq.) in THF (0.08 mL) was prepared, and to this was added dropwise a solution of (E)-1-tert-butyldimethylsilyloxy-3-phenyl-2-propene (50 mg, 0.20 mmol, 1 eq.) and $D_2O$ (9 μL, 0.50 mmol, 2.5 eq.) in THF (0.10 mL). The reaction stirred for 20 h at 40° C. after which it was filtered through a silica plug with diethyl ether (20 mL) and eluted with an additional (80 mL) of diethyl ether. The solvent was removed by rotary evaporation, and the crude product was analyzed by $^1H$ NMR with 1,3,5-trimethylbenzene as an internal standard. The crude product was dry loaded onto silica gel, and was purified by flash column chromatography using gradient elution (100 mL of 100% hexanes, 100 mL of 2% ethyl acetate in hexanes) to yield a clear colorless oil (1 and 2 isolated as an inseparable mixture, 40 mg (1, 59% yield: 2, 21% yield).

Entry 8. According to general procedure A for optimization studies, a stirring solution of 1,2-Bis[bis[3,5-di(t-butyl)phenyl]phosphino]benzene L5 (3.9 mg, 0.0044 mmol, 0.011 eq.), $Cu(OAc)_2$ (20 μL of a 0.2 M solution in THF, 0.004 mmol, 0.01 eq.), and dimethoxy(methyl)silane (74 μL, 0.60 mmol, 3 eq.) in THF (0.08 mL) was prepared, and to this was added dropwise a solution of (E)-1-tert-butyldimethylsilyloxy-3-phenyl-2-propene (50 mg, 0.20 mmol, 1 eq.) and 2-propanol-$d_8$ (38 μL, 0.50 mmol, 2.5 eq.) in THF (0.10 mL). The reaction stirred for 20 h at 40° C. after which it was filtered through a silica plug with diethyl ether (20 mL) and eluted with an additional (80 mL) of diethyl ether. The solvent was removed by rotary evaporation, and the crude product was analyzed by $^1H$ NMR with 1,3,5-trimethylbenzene as an internal standard. The crude product was dry loaded onto silica gel, and was purified by flash column chromatography using gradient elution (100 mL of 100% hexanes, 100 mL of 2% ethyl acetate in hexanes) to yield a clear colorless oil (2, 42 mg, 0.17 mmol, 85% yield).

Entry 9. According to general procedure A for optimization studies, a stirring solution of 1,2-Bis[bis[3,5-di(t-butyl)phenyl]phosphino]benzene L5 (2.0 mg, 0.0022 mmol, 0.011 eq.), $Cu(OAc)_2$ (10 μL of a 0.2 M solution in THF, 0.002 mmol, 0.01 eq.), and dimethoxy(methyl)silane (74 μL, 0.60 mmol, 3 eq.) in THF (0.09 mL) was prepared, and to this was added dropwise a solution of (E)-1-tert-butyldimethylsilyloxy-3-phenyl-2-propene (50 mg, 0.20 mmol, 1 eq.) and ethanol-OD (29 μL, 0.50 mmol, 2.5 eq.) in THF (0.10 mL). The reaction stirred for 20 h at 40° C., after which it was filtered through a silica plug with diethyl ether (20 mL) and eluted with an additional (80 mL) of diethyl ether. The solvent was removed by rotary evaporation, and the crude product was analyzed by $^1$H NMR with 1,3,5-trimethylbenzene as an internal standard. The crude product was dry loaded onto silica gel, and purified by flash column chromatography using gradient elution (100 mL of 100% hexanes, 100 mL of 2% ethyl acetate in hexanes) to yield a clear colorless oil (2, 46 mg, 0.18 mmol, 90% yield).

TABLE S2

| Reaction Optimization[a] | | | | | |
|---|---|---|---|---|---|
| Entry | $Cu(OAc)_2$ | Ligand | D-source | 1 (%) | 2 (%) |
| 1 | Stryker's Reagent | — | EtOD | >99%[b] | — |
| 2[c] | 2 mol % | L5 | EtOD | 21%[d] | 41%[d] |
| 3 | — | L5 | EtOD | 97%[b] | — |
| 4 | 2 mol % | — | EtOD | 82%[b] | — |
| 5 | 2 mol % | L5 | — | 84%[b] | — |
| 6[e] | 2 mol % | L5 | EtOD | 82%[b] | — |
| 7[f] | 1 mol % | L5 | EtOD | — | 75%[d] |

[a]Reactions conducted using 0.2 mmol of substrate. $Cu(OAc)_2$ was used as a 0.2M solution in THF.

[b]Yield was determined by $^1$H NMR analysis of the crude reaction mixture, using mesitylene as an internal standard.

[c]Poly(methylhydrosiloxane) was used instead of dimethoxy(methyl)silane.

[e]No silane source was used.

[d]Denotes isolated product yield.

[f]Reaction stirred at 23° C.

Entry 1. According to general procedure A for the optimization studies, a stirring solution of (triphenylphosphine)copper hydride hexamer (Stryker's reagent) (7.8 mg, 0.004 mmol, 0.02 eq.), and dimethoxy(methyl) silane (74 μL, 0.60 mmol, 3 eq.) in THF (0.10 mL) was prepared, and to this was added dropwise a solution of (E)-1-tert-butyldimethylsilyloxy-3-phenyl-2-propene (50 mg, 0.20 mmol, 1 eq.) and ethanol-OD (29 μL, 0.50 mmol, 2.5 eq.) in THF (0.10 mL). The reaction stirred for 20 h at 40° C., after which it was filtered through a silica plug with diethyl ether (20 mL) and eluted with an additional (80 mL) of diethyl ether. The solvent was removed by rotary evaporation, and the crude product was analyzed by $^1$H NMR with 1,3,5-trimethylbenzene as an internal standard (1, >99% yield by $^1$H NMR).

Entry 2. According to general procedure A for optimization studies, a stirring solution of 1,2-Bis[bis[3,5-di(t-butyl)phenyl]phosphino]benzene L5 (3.9 mg, 0.0044 mmol, 0.022 eq.), $Cu(OAc)_2$ (20 μL of a 0.2 M solution in THF, 0.004 mmol, 0.02 eq.), and poly(methylhydrosiloxane) (40 μL, 0.60 mmol, 3 eq. based on Si—H)[1] in THF (0.08 mL) was prepared, and to this was added dropwise a solution of (F)-1-tert-butyldimethylsilyloxy-3-phenyl-2-propene (50 mg, 0.20 mmol, 1 eq.) and ethanol-OD (29 μL, 0.50 mmol, 2.5 eq.) in THF (0.10 mL). The reaction stirred for 20 h at 40° C., after which it was filtered through a silica plug with diethyl ether (20 mL) and eluted with an additional (80 mL) of diethyl ether. The solvent was removed by rotary evaporation, and the crude product was analyzed by $^1$H NMR with 1,3,5-trimethylbenzene as an internal standard. The crude product was dry loaded onto silica gel, and was purified by flash column chromatography using gradient elution (100 mL of 100% hexanes, 100 mL of 2% ethyl acetate in hexanes) to yield a clear colorless oil (1 and 2 isolated as an inseparable mixture, 31 mg (1, 21% yield; 2, 41% yield).

Entry 3. According to general procedure A for optimization studies, a stirring solution of 1,2-Bis[bis[3,5-di(t-butyl)phenyl]phosphino]benzene L5 (3.9 mg, 0.0044 mmol, 0.022 eq.) and dimethoxy(methyl)silane (74 μL, 0.60 mmol, 3 eq.) in THF (0.10 mL) was prepared, and to this was added dropwise a solution of (E)-1-tert-butyldimethylsilyloxy-3-phenyl-2-propene (50 mg, 0.20 mmol, 1 eq.) and ethanol-OD (29 μL, 0.50 mmol, 2.5 eq.) in THF (0.10 mL). The reaction stirred for 20 h at 40° C., after which it was filtered through a silica plug with diethyl ether (20 mL) and eluted with an additional (80 mL) of diethyl ether. The solvent was removed by rotary evaporation, and the crude product was analyzed by $^1$H NMR with 1,3,5-trimethylbenzene as an internal standard, (1, 97% yield by $^1$H NMR).

Entry 4. According to general procedure A for the optimization studies, a stirring solution of $Cu(OAc)_2$ (20 μL of a 0.2 M solution in THF, 0.004 mmol, 0.02 eq.), and dimethoxy(methyl)silane (74 μL, 0.60 mmol, 3 eq.) in THF (0.08 mL) was prepared, and to this was added dropwise a solution of (E)-1-tert-butyldimethylsilyloxy-3-phenyl-2-propene (50 mg, 0.20 mmol, 1 eq.) and ethanol-OD (29 μL, 0.50 mmol, 2.5 eq.) in THF (0.10 mL). The reaction stirred for 20 h at 40° C., after which it was filtered through a silica plug with diethyl ether (20 mL) and eluted with an additional (80 mL) of diethyl ether. The solvent was removed by rotary evaporation, and the crude product was analyzed by $^1$H NMR with 1,3,5-trimethylbenzene as an internal standard (1, 82% yield by $^1$H NMR).

Entry 5. According to general procedure A for optimization studies, a stirring solution of 1,2-Bis[bis[3,5-di(t-butyl)phenyl]phosphino]benzene L5 (3.9 mg, 0.0044 mmol, 0.022 eq.), $Cu(OAc)_2$ (20 μL of a 0.2 M solution in THF, 0.004 mmol, 0.02 eq.), and dimethoxy(methyl) silane (74 μL, 0.60 mmol, 3 eq.) in THF (0.08 mL) was prepared, and to this was added dropwise a solution of (E)-1-tert-butyldimethylsilyloxy-3-phenyl-2-propene (50 mg, 0.20 mmol, 1 eq.) in THF (0.10 mL). The reaction stirred for 20 h at 40° C., after which it was filtered through a silica plug with diethyl ether (20 mL) and eluted with an additional (80 mL) of diethyl ether. The solvent was removed by rotary evaporation, and the crude product was analyzed by $^1$H NMR with 1,3,5-trimethylbenzene as an internal standard (1, 84% yield by $^1$H NMR).

Entry 6. According to general procedure A for the optimization studies, a stirring solution of 1,2-Bis[bis[3,5-di(t-butyl)phenyl]phosphino]benzene L5 (3.9 mg, 0.0044 mmol, 0.022 eq) and $Cu(OAc)_2$ (20 μL of a 0.2 M solution in THF, 0.004 mmol, 0.02 eq) in THF (0.08 mL) was prepared, and to this was added dropwise a solution of (E)-1-tert-butyldimethylsilyloxy-3-phenyl-2-propene (50 mg, 0.20 mmol, 1 eq.) and ethanol-OD (29 μL, 0.50 mmol, 2.5 eq.) in THF (0.10 mL). The reaction stirred for 20 hr at 40° C., after which it was filtered through a silica plug with diethyl ether (20 mL) and eluted with an additional (80 mL) of diethyl ether. The solvent was removed by rotary evaporation, and the crude product was analyzed by $^1$H NMR with 1,3,5-trimethylbenzene as an internal standard (1, 82% yield by $^1$H NMR).

Entry 7. According to general procedure A for optimization studies, a stirring solution of 1,2-Bis[bis[3,5-di(t-butyl)phenyl]phosphino]benzene L5 (2.0 mg, 0.0022 mmol, 0.011 eq.), $Cu(OAc)_2$ (10 μL of a 0.2 M solution in THF, 0.002 mmol, 0.01 eq.), and dimethoxy(methyl) silane (74 μL, 0.60 mmol, 3 eq.) in THF (0.09 mL) was prepared, and to this was added dropwise a solution of (L)-1-tert-butyldimethylsilyloxy-3-phenyl-2-propene (50 mg, 0.20 mmol, 1 eq.) and ethanol-OD (29 μL, 0.50 mmol, 2.5 eq.) in THF (0.10 mL). The reaction stirred for 20 h at 23° C., after which it was filtered through a silica plug with diethyl ether (20 mL) and eluted with an additional (80 mL) of diethyl ether. The solvent was removed by rotary evaporation, and the crude product was analyzed by $^1$H NMR with 1,3,5-trimethylbenzene as an internal standard. The crude product was dry loaded onto silica gel, and purified by flash column chromatography using gradient elution (100 mL of 100% hexanes, 100 mL of 2% ethyl acetate in hexanes) to yield a clear colorless oil (2, 37 mg, 0.15 mmol, 75% yield).

III. Transfer Hydrodeuteration Substrate Scope

Scheme 2. Aryl Alkene Transfer Hydrodeuteration Substrate Scope

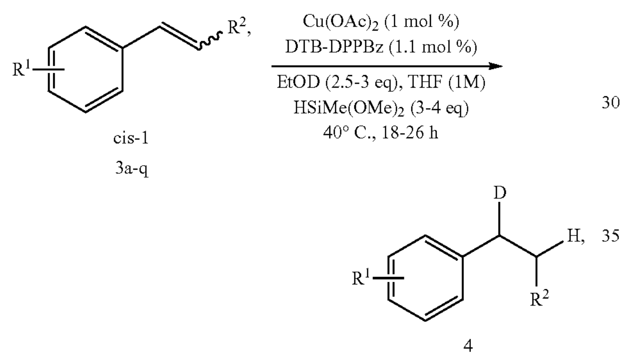

cis-1

3a-q

4

(a) Monosubstituted Alkene Substrate Scope

4a

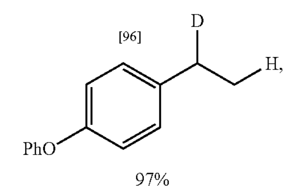

97%

4b

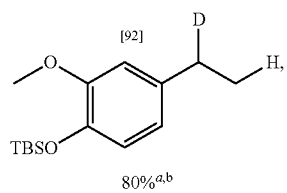

80%[a,b]

4c

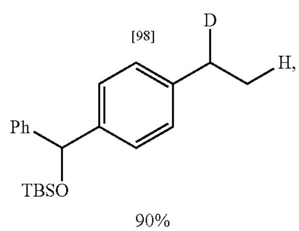

90%

-continued

4d

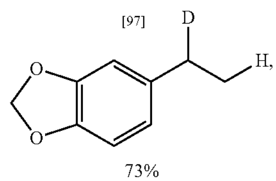

73%

4e

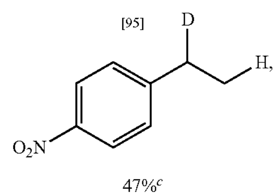

47%[c]

4f

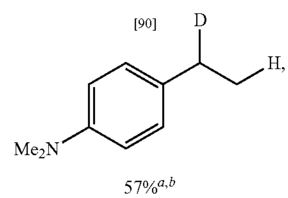

57%[a,b]

4g

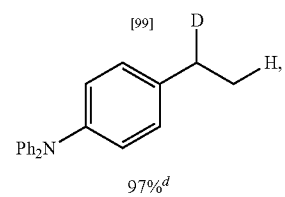

97%[d]

4h

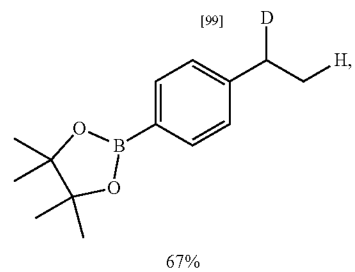

67%

4i

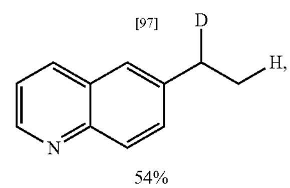

54%

4j

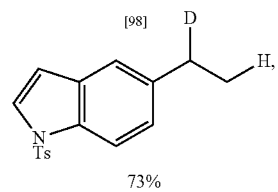

73%

-continued

4k

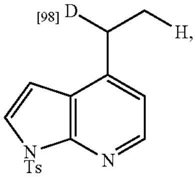

70%

4l

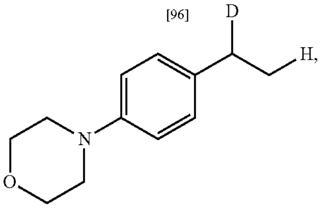

80%

(b) 1,2-Disubstituted Alkene Substrate Scope

2

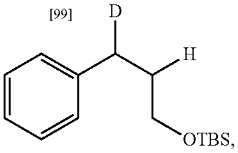

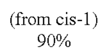
(from cis-1)
90%

4m

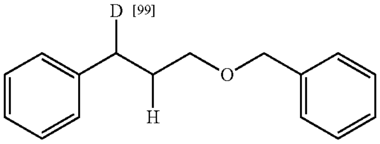

87%

4n

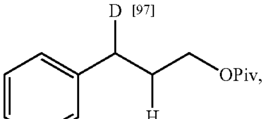

77%[c]

4o

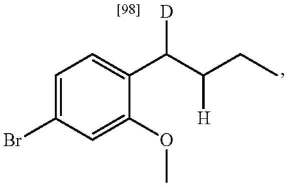

83%

-continued

4p

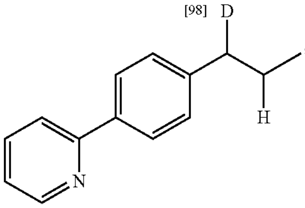

77%

(c) Estrone Analog

4q

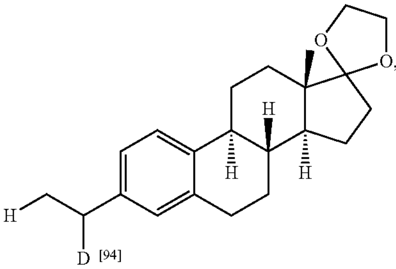

73%[a]

(d) 1,1-Disubstituted Alkene Example

4r

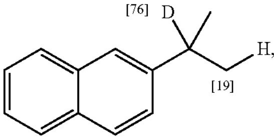

73%[b,e]

4r from:

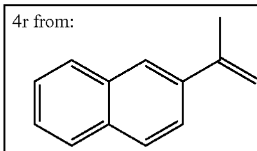

3r

[a]2 mol % $Cu(OAc)_2$ and 2.2 mol % DTB-DPPBZ used. [b]IPA-$d_8$ (3 equiv) used instead of EtOD. [c]Reaction conducted at 5° C. [d]Polymethylhydrosiloxane (3 equiv) used instead of $HSiMe(OMe)_2$.
[e]3 mol % $Cu(OAc)_2$, 3.3 mol % DTB-DPPBz, and $HSiMe(OMe)_2$ (4 equiv) used at 60° C.

General Procedure for Transfer Hydrodeuteration (B)

In a $N_2$ filled glovebox, DTB-DPPBz (3.0 mg, 0.0033 mmol, 0.011 eq.), $Cu(OAc)_2$ (15 μL of a 0.2 M solution in THF, 0.003 mmol, 0.01 eq.), and THF (0.135 mL) were added to an oven-dried 2-dram vial followed by dropwise addition of dimethoxy(methyl)silane (111 μL, 0.90 mmol, 3 eq.) or poly(methylhydrosiloxane) (60 μL, 0.90 mmol, 3 eq based on Si—H)[1]. A color change from green/blue to yellow was observed while stirring for 15 minutes. In a separate oven-dried 1-dram vial was added the alkene substrate (0.30 mmol, 1 eq.), THF (0.150 mL), and ethanol-OD/2-propanol-$d_8$ (2.5 eq based on substrate). The solution in the 1-dram vial was added dropwise over 20 seconds to the 2-dram vial. The total volume of THF was calculated based on having a final reaction concentration of 1M based on the alkene substrate. The 2-dram vial was capped with a red pressure relief cap, taken out of the glovebox, and stirred for 9-24 h at the appropriate temperature at which point the reaction was filtered through a 1" silica plug with 20 mL of diethyl ether followed by 80 mL of diethyl ether to elute the remaining product into a 200 mL round bottom flask. After removing the diethyl ether by rotary evaporation, the crude product was isolated by flash column chromatography.

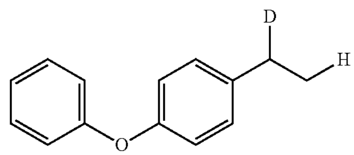 [SMILES: [2H]C(C)c1ccc(Oc2ccccc2)cc1]

1-(ethyl-1-d)-4-phenoxybenzene [4a]. According to the general procedure B, DTB-DPPBz (3.0 mg, 0.0033 mmol, 0.011 eq.), $Cu(OAc)_2$ (15 μL of a 0.2 M solution in THF, 0.003 mmol, 0.01 eq.), and THF (0.135 mL) then dimethoxy (methyl)silane (111 μL, 0.90 mmol, 3 eq.) were combined in a 2-dram vial followed by addition of a solution of 1-Ethenyl-4-phenoxybenzene (59 mg, 0.30 mmol, 1 eq.), THF (0.150 mL), and ethanol-OD (44 μL, 0.75 mmol, 2.5 eq). The 2-dram vial was capped with a red pressure relief cap, and the reaction stirred for 18 h at 40° C. Upon completion, the crude product mixture was dry loaded onto a silica gel column. Flash column chromatography (300 mL of 100% hexanes) to give the pure product as a clear colorless oil (57 mg, 0.29 mmol, 97% yield).

$^1H$ NMR: (400 MHz, $CDCl_3$) δ 7.34 (t, J=8.0 Hz, 2H), 7.18 (d, J=8.4 Hz, 2H), 7.09 (t, J=7.3 Hz, 1H), 7.02 (d, J=8.2 Hz, 2H), 6.96 (d, J=8.4 Hz, 2H), 2.70-2.59 (m, 1.02H), 1.26 (d, J=7.5 Hz, 3H). $^2H$ NMR: (61 MHz, $CHCl_3$): δ 2.64 (s, 0.98D), 1.26 (s, 0.01D). $^{13}C$ NMR: (101 MHz, $CDCl_3$) δ 157.89, 155.02, 139.40, 129.78, 129.16, 122.95, 119.21, 118.56, 27.95 (t, J=19.5 Hz), 15.81. ATR-IR ($cm^{-1}$): 3030, 2962, 2927, 2873, 2136, 1230, 1165. HRMS: ($EI^+$) m % z: $[M]^+$ Calcd for $C_{14}H_{13}DO$ 199.1107. Found 199.1100.

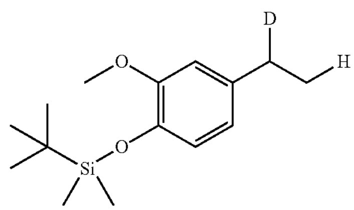 [SMILES: [2H]C(C)c1ccc(O[Si](C)(C)C(C)(C)C)c(OC)c1]

tert-butyl(4-(ethyl-1-d)-2-methoxyphenoxy)dimethylsilane [4b]. According to the general procedure B, DTB-DPPBz (6.0 mg, 0.0066 mmol, 0.022 eq.), $Cu(OAc)_2$ (30 μL of a 0.2 M solution in THF, 0.006 mmol, 0.02 eq.), THF (0.120 mL), then dimethoxy(methyl)silane (148 μL, 1.20 mmol, 4 eq.) were combined in a 2-dram vial followed by addition of a solution of tert-butyl(2-methoxy-4-vinylphenoxy)dimethylsilane (79 mg, 0.30 mmol, 1 eq.), THF (0.150 mL), 2-propanol-$d_8$ (69 μL, 0.90 mmol, 3 eq.). The 2-dram vial was capped with a red pressure relief cap, and the reaction stirred for 25 h at 40° C. After silica plug filtration using diethyl ether (100 mL) as the eluent, the solvent was concentrated, and the crude oil was dry loaded onto a silica gel column. Flash column chromatography using gradient elution (100 mL of 100% HPLC hexanes, 200 mL of 1% ethyl acetate in HPLC hexanes) gave the pure product as a light-yellow oil (65 mg, 0.24 mmol, 80%).

$^1H$ NMR: (400 MHz, $CDCl_3$) δ 6.78 (d, J=7.9 Hz, 1H), 6.70 (s, 1H), 6.65 (d, J=7.9, 1H), 3.81 (s, 3H), 2.64-2.52 (m, 1.08H), 1.22 (d, J=7.6 Hz, 3H), 1.01 (s, 9H), 0.17 (s, 6H). $^2H$ NMR: (61 MHz, $CHCl_3$) δ 2.58 (s, 0.92D), 1.22 (s, 0.08D). $^{13}C$ NMR: (101 MHz, $CDCl_3$) δ 150.77, 142.97, 137.85, 120.74, 119.88, 112.12, 55.59, 28.30 (t, J=19.6 Hz), 25.90, 18.58, 15.78, −4.50. ATR-IR ($cm^{-1}$): 3035, 2957, 2929, 2895, 2856, 2142, 1231, 1162, 1126. HRMS: FT-ICR-MS (+) ion tune m/z: $[M]^+$ Calcd for $C_{15}H_{25}DO_2SiNa$ 290.1665; Found 290.1656.

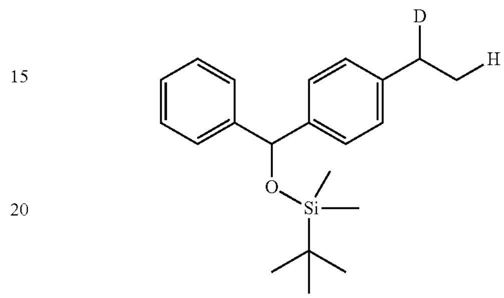

tert-butyl((4-(ethyl-1-d)phenyl) (phenyl)methoxy)dimethylsilane [4c]. According to the general procedure B, DTB-DPPBz (3 mg, 0.0033 mmol, 0.01 eq.), $Cu(OAc)_2$ (15 μL of a 0.2 M solution in THF, 0.003 mmol, 0.01 eq.), THF (0.135 mL), then dimethoxy(methyl)silane (111 μL, 0.90 mmol, 3 eq.) were combined in a 2-dram vial followed by addition of a solution of tert-butyldimethyl(phenyl(4-vinylphenyl)methoxy)silane (97 mg, 0.30 mmol, 1 eq.), THF (0.150 mL), ethanol-OD (44 μL, 0.75 mmol, 2.5 eq.). The 2-dram vial was capped with a red pressure relief cap, and the reaction stirred for 18 h at 40° C. After silica plug filtration using diethyl ether (100 mL) as the eluent, the solvent was concentrated, and the crude oil was dry loaded onto a silica gel column. Flash chromatography using gradient elution (100 mL of 100% HPLC hexanes, 100 mL of 1% ethyl acetate in HPLC hexanes, 100 mL of 2% ethyl acetate in HPLC hexanes, 100 mL of 4% ethyl acetate in HPLC hexanes) gave the pure product as a light-yellow oil (90 mg, 0.27 mmol, 90% yield).

$^1H$ NMR (400 MHz, $CDCl_3$) δ 7.45 (d, J=7.5 Hz, 2H), 7.40-7.33 (m, 4H), 7.29 (d, J=7.3, 1H), 7.20 (d, J=8.1 Hz, 2H), 5.83 (s, 1H), 2.73-2.63 (m, 1.02H), 1.29 (d, J=7.5 Hz, 3H), 1.02 (s, 9H), 0.07 (d, J=3.6 Hz, 6H). $^2H$ NMR (61 MHz, $CHCl_3$) δ 2.67 (s, 0.98D), 1.28 (s, 0.02D). $^{13}C$ NMR (101 MHz, $CDCl_3$ δ 145.60, 142.88, 142.69, 128.27, 127.76, 126.98, 126.42, 126.37, 76.66, 28.27 (t, J=19.4 Hz), 26.03, 18.46, 15.55. −4.66. ATR-IR ($cm^{-1}$): 2956, 2928, 2884, 2856, 2141, 1250, 1084, 1064. HRMS: ($EI^+$) m/z: $[M-C_4H_9]^+$ Calcd for $C_{17}H_{20}DOSi$ 270.1424; Found 270.1418. The major ion peak represents the parent molecule after loss of the t-Bu cation.

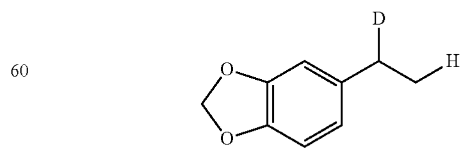

5-(ethyl-1-d)-benzo-1,3-dioxole [4d]. According to the general procedure B, DTB-DPPBz (3.0 mg, 0.0033 mmol, 0.011 eq.), $Cu(OAc)_2$ (15 μL of a 0.2 M solution in THF, 0.003 mmol, 0.01 eq.), THF (0.135 mL), then dimethoxy (methyl)silane (111 μL, 0.90 mmol, 3 eq.) were combined in a 2-dram vial followed by addition of a solution of 5-vinyl-benzo-1,3-dioxole (44 mg, 0.30 mmol, 1 eq.), THF (0.150 mL), ethanol-OD (44 μL, 0.75 mmol, 2.5 eq.). The 2-dram vial was capped with a red pressure relief cap, and the reaction stirred for 18 h at 40° C. Upon completion, the crude product mixture was dry loaded onto a silica gel column. Flash column chromatography (200 mL of 100% HPLC hexanes) gave the pure product as a clear colorless oil (33 mg, 0.22 mmol, 73% yield).

$^1$H NMR: (400 MHz, $CDCl_3$) δ 6.77-6.69 (m, 2H), 6.66 (d, J=7.9 Hz, 1H), 5.92 (s, 2H), 2.62-2.51 (m, 1.03H), 1.21 (d, J=7.6 Hz, 3H), $^2$H NMR: (61 MHz, $CHCl_3$) δ 2.56 (s, 0.97D), 1.21 (s, 0.02D). $^{13}$C NMR: (75 MHz, $CDCl_3$) δ 147.64, 145.53, 138.32, 120.53, 108.55, 108.22, 100.82, 28.44 (t, J=19.2 Hz), 16.03. ATR-IR ($cm^{-1}$): 2963, 2876, 2142, 1233, 1036. HRMS: ($EI^+$) m/z: $[M]^+$ Calcd for $C_9H_9DO_2$ 151.0700; Found 151.0737.

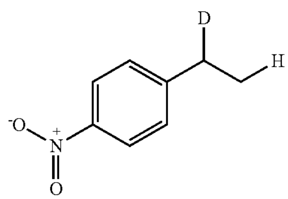

1-(ethyl-1-d)-4-nitrobenzene [4e]. According to the general procedure B, DTB-DPPBz (3.0 mg, 0.0033 mmol, 0.011 eq.), $Cu(OAc)_2$ (15 μL of a 0.2 M solution in THF, 0.003 mmol, 0.01 eq.), THF (0.135 mL), then dimethoxy(methyl) silane (111 μL, 0.90 mmol, 3 eq.) were combined in a 2-dram vial followed by addition of a solution of 1-ethenyl-4-nitrobenzene (45 mg, 0.30 mmol, 1 eq.). THF (0.150 mL), ethanol-OD (44 μL, 0.75 mmol, 2.5 eq.). The 2-dram vial was capped with a red pressure relief cap, and the reaction stirred for 19 h at 5° C. Upon completion, the crude product mixture was dry loaded onto a silica gel column. Flash chromatography using gradient elution (100 mL of 100% HPLC hexanes, 100 mL of 1% ethyl acetate in HPLC Hexanes, 100 mL of 2% ethyl acetate in HPLC hexanes) gave the pure product as a clear yellow oil (22 mg, 0.14 mmol, 47% yield).

$^1$H NMR (400 MHz, $CDCl_3$) δ 8.14 (d, J=8.6 Hz, 2H), 7.34 (d, J=8.4 Hz, 2H), 2.79-2.69 (m, 1.05H), 1.27 (d, J=7.7 Hz, 3H). $^2$H NMR (61 MHz, $CHCl_3$) δ 2.74 (s, 0.95D). $^{13}$C NMR (101 MHz, $CDCl_3$) δ 152.13, 146.36, 128.78, 123.78, 28.66 (t, J=19.7 Hz), 15.13. ATR-IR ($cm^{-1}$): 3078, 2969, 2933, 2876, 1516. HRMS: ($EI^+$) m/z: $[M]^+$ Calcd for $C_8H_8DNO_2$ 152.0696; Found 152.0698.

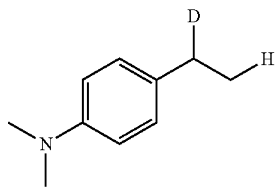

4-(ethyl-1-d)-N,N-dimethylaniline [4f]. According to the general procedure B, DTB-DPPBz (6.0 mg, 0.0066 mmol, 0.022 eq.), $Cu(OAc)_2$ (30 μL of a 0.2 M solution in THF, 0.006 mmol, 0.02 eq.), THF (0.12 mL), then dimethoxy (methyl)silane (148 μL, 1.20 mmol, 4 eq.) were combined in a 2-dram vial followed by addition of a solution of N,N-dimethyl-4-vinylaniline (44 mg, 0.30 mmol, 1 eq.), THF (0.15 mL), 2-propanol-$d_8$ (69 μL, 0.90 mmol, 3 eq.). The 2-dram vial was capped with a red pressure relief cap, and the reaction stirred for 22 h at 40° C. After silica plug filtration using diethyl ether (100 mL) as the eluent, the solvent was concentrated, and the crude oil was dry loaded onto a neutral alumina brock column. Flash column chromatography (300 mL of 100% HPLC hexanes) gave the pure product as a clear colorless oil (26 mg, 0.17 mmol, 57% yield).

$^1$H NMR: (400 MHz, $CDCl_3$) δ 7.11 (d, J=8.1 Hz, 2H), 6.74 (d, J=8.3 Hz, 2H), 2.93 (s, 6H), 2.63-2.51 (m, 1.1H), 1.22 (d, 3H). $^2$H NMR: (61 MHz, $CHCl_3$) δ 2.57 (s, 0.90D), 1.22 (s, 0.08D). $^{13}$C NMR: (101 MHz, $CDCl_3$) δ 149.11, 132.76, 128.53, 113.27, 41.15, 27.58 (t, J=19.0 Hz), 16.00. ATR-IR ($cm^{-1}$): 2959, 2926, 2871, 2796, 2130, 1343. HRMS: ($EI^+$) m/z: $[M]^+$ Calcd for $C_{10}H_{14}DN$ 150.1267; Found 150.1261.

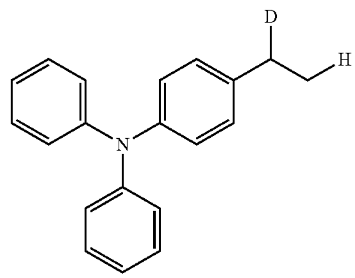 [SMILES: [2H]C(C)c1ccc(N(c2ccccc2)c2ccccc2)cc1]

4-(ethyl-1-d)-N,N-diphenylaniline [4g]. According to the general procedure B, DTB-DPPBz (3.0 mg, 0.0033 mmol, 0.011 eq.), $Cu(OAc)_2$ (15 μL of a 0.2 M solution in THF, 0.003 mmol, 0.01 eq.), THF (0.135 mL), then poly(methylhydrosiloxane) (60 μL, 0.90 mmol, 3 eq. based on Si—H) were combined in a 2-dram vial followed by addition of a solution of N,N-diphenyl-4-vinylaniline (81 mg, 0.30 mmol, 1 eq.), THF (0.150 mL), ethanol-OD (44 μL, 0.75 mmol, 2.5 eq.). The 2-dram vial was capped with a red pressure relief cap, and the reaction stirred for 18 h at 40° C. Upon completion, the crude product mixture was dry loaded onto a silica gel column. Flash column chromatography (200 mL of 100% HPLC hexanes) gave the pure product as a clear colorless oil (79 mg, 0.29 mmol, 97% yield).

$^1$H NMR: (400 MHz, $CDCl_3$) δ 7.27 (t, J=7.6 Hz, 4H), 7.17-7.11 (m, 6H), 7.09 (d, J=8.3 Hz, 2H), 7.02 (t, J=7.3 Hz, 2H), 2.72-2.59 (m, 1.01H), 1.29 (d, J=7.6 Hz, 3H), $^2$H NMR: (61 MHz, $CHCl_3$) δ 2.67 (s, 0.99D), 1.31 (s, 0.01D). $^{13}$C NMR: (101 MHz, $CDCl_3$) δ 148.16, 145.52, 139.13, 129.23, 128.77, 124.94, 123.79, 122.35, 28.01 (t, J=19.3 Hz), 15.63. ATR-IR ($cm^{-1}$): 3059, 3022, 2960, 2927, 2870, 2135, 1269. HRMS: ($ESI^+$) m/z: $[M]^+$ Calcd for $C_{20}H_{18}ND$ 274.1600; Found 274.1575.

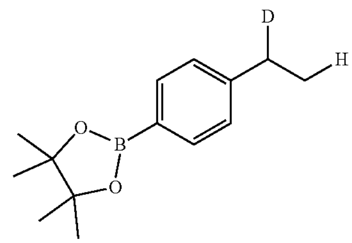 [SMILES: [2H]C(C)c1ccc(B2OC(C)(C)C(C)(C)O2)cc1]

2-[4-(ethyl-1-d)-phenyl]-4,4,5,5-tetramethyl-1,3,2-dioxaborolane [4h]. According to the general procedure B, DTB-DPPBz (3.0 mg, 0.0033 mmol, 0.011 eq.), $Cu(OAc)_2$ (15 μL of a 0.2 M solution in THF, 0.003 mmol, 0.01 eq.), THF (0.135 mL), then dimethoxy(methyl)silane (111 μL, 0.90 mmol, 3.0 eq) were combined in a 2-dram vial followed by addition of a solution of 2-(4-Ethenylphenyl)-4,4,5,5-tetramethyl-1,3,2-dioxaborolane (69 mg, 0.30 mmol, 1 eq.), THF (0.150 mL), ethanol-OD (44 μL, 0.75 mmol, 2.5 eq.). The 2-dram vial was capped with a red pressure relief cap, and the reaction stirred for 18 h at 40° C. Upon completion, the crude product mixture was dry loaded onto a silica gel column. Flash column chromatography using gradient elution (100 mL of 100% HPLC hexanes, 100 mL of 1% ethyl acetate in HPLC hexanes, 100 mL of 2% ethyl acetate in HPLC hexanes) gave the pure product as a clear colorless oil (46 mg, 0.20 mmol, 67% yield).

$^1H$ NMR: (400 MHz, $CDCl_3$) δ 7.75 (d, J=7.8 Hz, 2H), 7.22 (d, J=7.7 Hz, 2H), 2.71-2.61 (m, 1.01H), 1.35 (s, 12H), 1.24 (d, J=7.6, 1.1 Hz, 3H). $^2H$ NMR: (61 MHz, $CHCl_3$) δ 2.67 (0.99 D) $^{13}C$ NMR: (101 MHz, $CDCl_3$) δ 147.83, 135.04, 127.48, 83.74, 28.90 (t, J=19.5 Hz), 24.99, 15.53. *A resonance of a carbon directly attached to boron was not observed due to quadrupolar relaxation.[2] $^{11}B$ NMR: (128 MHz, $CDCl_3$) δ 31.39 *Boron impurity present from boron silicate NMR tube[2] ATR-IR ($cm^{-1}$): 2972, 2929, 2868, 1944, 1140. HRMS; ($EI^+$) m/z: $[M]^+$ Calcd for $C_{14}H_{20}DBO_2$ 233.1697; Found 233.1691.

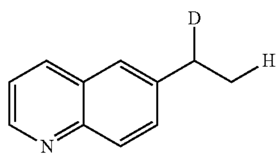 [SMILES: [2H]C(C)c1ccc2ncccc2c1]

6-(ethyl-1-d)-napthalene [4i]. According to the general procedure B, DTB-DPPBz (6.0 mg, 0.0066 mmol, 0.022 eq.), $Cu(OAc)_2$ (30 μL of a 0.2 M solution in THF, 0.0060 mmol, 0.02 eq.), THF (0.120 mL), then dimethoxy(methyl) silane (111 μL, 0.90 mmol, 3 eq) were combined in a 2-dram vial followed by addition of a solution of 6-Vinylnapthalene (47 mg, 0.30 mmol, 1.0 eq.), THF (0.150 mL), ethanol-OD (44 μL, 0.75 mmol, 2.5 eq.). The 2-dram vial was capped with a red pressure relief cap, and the reaction stirred for 18 h at 40° C. Upon completion, the crude product mixture was dry loaded onto a silica gel column. Flash column chromatography using gradient elution (100 mL of 100% HPLC hexanes, 100 mL of 5% ethyl acetate in HPLC hexanes, 100 mL of 7% ethyl acetate in HPLC hexanes) gave the pure product as a clear colorless oil (25 mg, 0.16 mmol, 54% yield).

$^1H$ NMR: (300 MHz, $CDCl_3$) δ 8.87 (br s, 1H), 8.12-7.98 (m, 2H), 7.62-7.56 (m, 2H), 7.41-7.31 (m, 1H), 2.89-2.75 (m, 1.03H), 1.36-1.29 (m, 3H), $^2H$ NMR: (61 MHz, $CHCl_3$) δ 2.85 (s, 0.97D). $^{13}C$ NMR: (101 MHz, $CDCl_3$) δ 149.67, 147.29, 142.72, 135.66, 130.83, 129.42, 125.43, 121.24, 28.64 (t, J=19.7 Hz), 15.44. ATR-IR ($cm^{-1}$): 3012, 2964, 2932, 2906, 2873, 2169, 1363. HRMS: (EST) m/z: $[M+H]^+$ Calcd for $C_{11}H_{10}ND$ 159.1034; Found 159.1025.

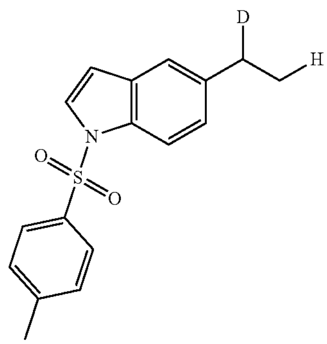 [SMILES: [2H]C(C)c1ccc2c(ccn2S(=O)(=O)c2ccc(C)cc2)c1]

5-(ethyl-1-d)-N-tosylindole [4j]. According to the general procedure B. DTB-DPPBz (3.0 mg, 0.0033 mmol, 0.011 eq.), $Cu(OAc)_2$ (15 μL of a 0.2 M solution in THF, 0.003 mmol, 0.01 eq.), and THF (0.135 mL), then dimethoxy (methyl)silane (111 μL, 0.90 mmol, 3 eq) were combined in a 2-dram vial followed by addition of a solution of 5-vinyl-N-tosylindole (89 mg, 0.3 mmol, 1 eq.), THF (0.150 mL), and ethanol-OD (44 μL, 0.75 mmol, 2.5 eq). The 2-dram vial was capped with a red pressure relief cap, and the reaction stirred for 23 h at 40° C. After silica plug filtration using diethyl ether (100 mL) as the eluent, the solvent was concentrated, and the crude oil was dry loaded onto a silica gel column. Flash column chromatography using gradient elution (100 mL 100% hexanes, 100 mL 3% ethyl acetate in hexanes, and 10×) mL 6% ethyl acetate in hexanes) to give the pure product as a purple oil (66 mg, 0.22 mmol, 73% yield).

$^1H$ NMR: (400 MHz, $CDCl_3$) δ 7.91 (d, J=8.5 Hz, 1H), 7.77 (d, J=8.2 Hz, 2H), 7.53 (d, J=3.7 Hz, 1H), 7.34 (d, J=1.8 Hz, 1H), 7.23-7.14 (m, 3H), 6.60 (d, J=3.6 Hz, 1H), 2.75-2.63 (m, 1.02H), 2.32 (s, 3H), 1.24 (d, J=7.6 Hz, 3H). $^2H$ NMR: (61 MHz, $CHCl_3$) δ 2.70 (s, 0.98D). $^{13}C$ NMR: (101 MHz, $CDCl_3$) δ 144.89, 139.47, 135.47, 133.31, 131.10, 129.93, 126.89, 126.48, 125.07, 120.10, 113.39, 109.06, 28.47 (t, J=19.5 Hz), 21.63, 16.02. ATR-IR ($cm^{-1}$): 3142, 3113, 2963, 2929, 2873, 2360, 1590, 1366, 1170 HRMS: ($EI^+$) m/z: $[M]^+$ Calcd for $C_{17}H_{16}DNO_2S$ 300.1000; Found 300.1035.

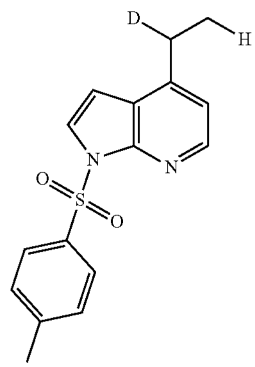 [SMILES: [2H]C(C)c1ccnc2c1ccn2S(=O)(=O)c1ccc(C)cc1]

4-(ethyl-1-d)-1-tosyl-1H-pyrrolo[2,3-b]pyridine [4k]. According to the general procedure B, DTB-DPPBz (3.0 mg, 0.0033 mmol, 0.011 eq.). $Cu(OAc)_2$ (15 μL of a 0.2 M solution in THF, 0.003 mmol, 0.01 eq.), and THF (0.135 mL), then dimethoxy(methyl)silane (111 μL, 0.90 mmol, 3 eq) were combined in a 2-dram vial followed by addition of a solution of 1-tosyl-4-vinyl-1H-pyrrolo[2,3-b]pyridine (90 mg, 0.30 mmol, 1 eq.), THF (0.150 mL), and ethanol-OD (44 μL, 0.75 mmol, 2.5 eq). The 2-dram vial was capped with a red pressure relief cap, and the reaction stirred for 23 h at 40° C. After silica plug filtration using diethyl ether (100 mL) as the eluent, the solvent was concentrated, and the crude oil was dry loaded onto a silica gel column. Flash column chromatography using gradient elution (50 mL 100% hexanes, 100 mL 10% ethyl acetate in hexanes, and 100 mL 15% ethyl acetate in hexanes) to give the pure product as a yellow solid (63 mg, 0.21 mmol, 70% yield).

$^1$H NMR: (400 MHz, $CDCl_3$) δ 8.33 (d, J=5.0 Hz, 1H), 8.06 (d, J=8.5 Hz, 2H), 7.68 (d, J=4.1 Hz, 1H), 7.24 (d, J=8.4 Hz, 2H), 6.99 (d, J=5.1 Hz, 1H), 6.61 (d, J=4.1 Hz, 1H), 2.86-2.74 (m, 1.02H), 2.34 (s, 3H), 1.26 (d, J=7.5 Hz, 3H). $^2$H NMR: (61 MHz, $CHCl_3$) δ 2.82 (s, 0.98D). $^{13}$C NMR: (75 MHz, $CDCl_3$) δ 147.28, 146.73, 145.25, 145.10, 135.63, 129.68, 128.08, 125.60, 122.21, 117.88, 103.66, 25.44 (t, J=19.6 Hz), 21.70, 13.97. ATR-IR ($cm^{-1}$) 3151, 3117, 2964, 2929, 2879, 2323, 1592, 1367, 1145. HRMS: ($ESI^+$) m/z: $[M+H]^+$ Calcd for $C_{16}H_{16}DN_2O_2S$ 302.1080; Found 302.1065.

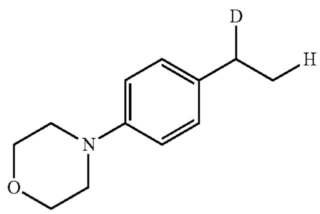 [SMILES: [2H]C(C)c1ccc(N2CCOCC2)cc1]

4-[4-(ethyl-1-d)-phenyl]-morpholine [4l]. According to the general procedure B, DTB-DPPBz (3.0 mg, 0.0033 mmol, 0.011 eq.), $Cu(OAc)_2$ (15 μL of a 0.2 M solution in THF, 0.003 mmol, 0.01 eq.), THF (0.135 mL), then dimethoxy(methyl)silane (111 μL, 0.90 mmol, 3 eq.) were combined in a 2-dram vial followed by addition of a solution of 4-(4-ethenylphenyl)-morpholine (57 mg, 0.30 mmol, 1 eq.), THF (0.150 mL), ethanol-OD (44 μL, 0.75 mmol, 2.5 eq.). The 2-dram vial was capped with a red pressure relief cap, and the reaction stirred for 19 h at 40° C. Upon completion, the crude product mixture was dry loaded onto a silica gel column. Flash chromatography using gradient elution (100 mL 100% HPLC hexanes, 100 mL of 1% ethyl acetate in HPLC hexanes, 100 mL of 2% ethyl acetate in HPLC hexanes, 200 mL of 3% ethyl acetate in HPLC hexanes, 100 mL of 5% ethyl acetate in HPLC hexanes) gave the pure product as a red solid (47 mg, 0.24 mmol, 80% yield).

$^1$H NMR (300 MHz, $CDCl_3$) δ 7.13 (d, J=8.7 Hz, 2H), 6.88 (d, J=8.5 Hz, 2H), 3.87 (t, J=4.6 Hz, 4H), 3.13 (t, J=4.6 Hz, 4H), 2.64-2.52 (m, 1.04H), 1.22 (d, J=7.6 Hz, 3H). $^2$H NMR (61 MHz, $CHCl_3$) δ 2.60 (s, 0.96D), 1.24 (s, 0.04). $^{13}$C NMR (75 MHz, $CDCl_3$) δ 149.46, 136.11, 128.63, 116.10, 67.12, 49.95, 27.68 (t, J=19.4 Hz), 15.80. ATR-IR ($cm^{-1}$): 2959, 2924, 2863, 2833, 2141, 1226, 1118. HRMS: ($ESI^+$) m/z: $[M+H]^+$ Calcd for $C_{12}H_{17}NOD$ 193.1453; Found 193.1445.

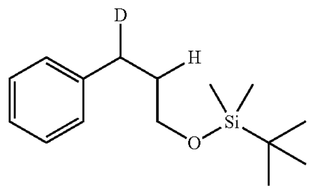 [SMILES: [2H]C(CCO[Si](C)(C)C(C)(C)C)c1ccccc1]

(Z)-1-tert-butyldimethylsilyloxy-3-phenyl-(propane-3-d) [2 from cis-1]: According to the general procedure B. DTB-DPPBz (3.0 mg, 0.0033 mmol, 0.011 eq.), $Cu(OAc)_2$ (15 μL of a 0.2 M solution in THF, 0.003 mmol, 0.01 eq.), THF (0.135 mL), then dimethoxy(methyl)silane (111 mL, 0.90 mmol, 3 eq.) were combined in a 2-dram vial followed by addition of a solution of (Z)-1-tert-butyldimethylsilyloxy-3-phenyl-2-propene (75 mg, 0.30 mmol, 1 eq.), THF (0.150 mL), ethanol-OD (44 μL, 0.75 mmol, 2.5 eq.). The 2-dram vial was capped with a red pressure relief cap, and the reaction stirred for 23 h at 40° C. Upon completion, the crude product mixture was dry loaded onto a silica gel column. Flash chromatography using gradient elution (100 mL of 100% HPLC hexanes, 100 mL of 1% ethyl acetate in HPLC hexanes, 100 mL of 2% ethyl acetate in HPLC hexanes) gave the pure product as a clear colorless oil (67 mg, 0.27 mmol, 90% yield).

$^1$H NMR (400 MHz, $CDCl_3$) δ 7.31 (t, J=7.4 Hz, 2H), 7.25-7.17 (m, 3H), 3.67 (t, J=6.3 Hz, 2H), 2.74-2.65 (m, 1.01H), 1.87 (q, J=6.8 Hz, 2H), 0.95 (s, 9H), 0.09 (s, 6H). $^2$H NMR (61 MHz, $CHCl_3$) δ 2.69 (s, 0.99D) $^{13}$C NMR (101 MHz, $CDCl_3$) δ 142.36, 128.61, 128.41, 125.81, 62.48, 34.55, 31.89 (t, J=19.4 Hz), 26.11, 18.48, −5.13. ATR-IR ($cm^{-1}$): 3026, 2953, 2928, 2893, 2856, 2172, 1252, 1099. HRMS: ($EI^+$) m/z: $[M-C_4H_9]^+$ Calcd for $C_{11}H_{16}DOSi$ 194.1111; Found 194.1105. The major ion peak represents the parent molecule after loss of the t-Bu cation.

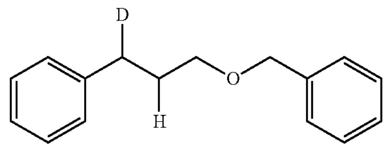 [SMILES: [2H]C(CCOCc1ccccc1)c1ccccc1]

(3-(benzyloxy)propyl-1-d)benzene [4m]. According to the general procedure B, DTB-DPPBz (3.0 mg, 0.0033 mmol, 0.011 eq.), $Cu(OAc)_2$ (15 μL of a 0.2 M solution in THF, 0.003 mmol, 0.01 eq.), THF (0.135 mL), then dimethoxy(methyl)silane (111 μL, 0.90 mmol, 3 eq) were combined in a 2-dram vial followed by addition of a solution of (E)-(3-(benzyloxy)prop-1-en-1-yl)benzene (67 mg, 0.30 mmol, 1 eq.), THF (0.150 mL), ethanol-OD (44 μL, 0.75 mmol, 2.5 eq.). The 2-dram vial was capped with a red pressure relief cap, and the reaction stirred for 18 h at 40° C. Upon completion, the crude product mixture was dry loaded onto a silica gel column. Flash chromatography using gradient elution (100 mL of 100% HPLC hexanes, 100 mL of 1% ethyl acetate in HPLC hexanes) gave the pure product as a clear colorless oil (59 mg, 0.26 mmol, 87% yield).

$^1$H NMR: (400 MHz, $CDCl_3$) δ 7.40 (m, J=4.3 Hz, 4H), 7.37-7.29 (m, 3H), 7.26-7.21 (m, 3H), 4.56 (s, 2H), 3.54 (t, J=6.3 Hz, 2H), 2.80-2.72 (m, 1.01H), 1.99 (q, J=6.7 Hz, 2H)$^2$H NMR: (61 MHz, $CHCl_3$) δ 2.76 (s, 0.99D). $^{13}$C NMR: (101 MHz, $CDCl_3$) δ 142.06, 138.70, 128.59, 128.49, 128.43, 127.78, 127.65, 125.87, 73.03, 69.58, 32.14 (t, J=19.6 Hz), 31.42. ATR-IR ($cm^{-1}$): 3084, 3026, 2933, 2853, 2140, 1603, 1096. HRMS: ($EI^+$) m/z: $[M]^+$ Calcd for $C_{16}H_{17}DO$ 227.1420. Found 227.1412.

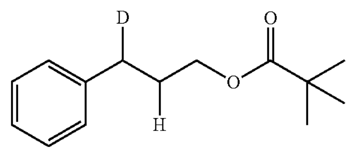 [SMILES: [2H]C(CCOC(=O)C(C)(C)C)c1ccccc1]

3-phenylpropyl-3-d pivalate [4n]: According to the general procedure B, DTB-DPPBz (3.0 mg, 0.0033 mmol, 0.011 eq.), $Cu(OAc)_2$ (15 μL of a 0.2 M solution in THF, 0.003 mmol, 0.01 eq.), THF (0.135 mL), then dimethoxy(methyl) silane (111 μL, 0.90 mmol, 3 eq.) were combined in a 2-dram vial followed by addition of a solution of cinnamyl pivalate (65 mg, 0.30 mmol, 1 eq.), THF (0.150 mL), ethanol-OD (44 μL, 0.75 mmol, 2.5 eq.). The 2-dram vial was capped with a red pressure relief cap, and the reaction stirred for 22 h at 5° C. Upon completion, the crude product mixture was dry loaded onto a silica gel column. Flash chromatography using gradient elution (100 mL of 100% HPLC hexanes, 100 mL of 1% ethyl acetate in HPLC hexanes, 10 mL of 2% ethyl acetate in HPLC hexanes, 100 mL of 3% ethyl acetate in HPLC hexanes) gave the pure product as a clear colorless oil (50 mg, 0.23 mmol, 77% yield).

$^1$H NMR (400 MHz, $CDCl_3$) δ 7.30 (t, J=7.4 Hz, 2H), 7.21 (t, J=7.6 Hz, 3H), 4.09 (t, J=6.4 Hz, 2H), 2.74-2.65 (m, 1.03H), 1.97 (q, J=6.8 Hz, 2H), 1.24 (s, 9H). $^2$H NMR (61 MHz, $CHCl_3$) δ 2.71 (s, 0.97D). $^{13}$C NMR (101 MHz, $CDCl_3$) δ 178.67, 141.34, 128.56, 128.53, 126.11, 63.64, 38.89, 31.92 (t, J=19.3 Hz), 30.35, 27.35. FT-IR (thin film, $cm^{-1}$): 3085, 3062, 3026, 2972, 2934, 2872, 2159, 1728, 1157. HRMS: FT-ICR-MS low mass (+) ion time m/z: $[M+H]^+$ Calcd for $C_{14}H_{20}DO_2$ 222.1606; Found 222.1600.

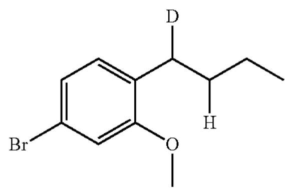

4-bromo-1-butyl-d-2-methoxy-benzene [4o]. According to the general procedure B, DTB-DPPBz (3.0 mg, 0.0033 mmol, 0.011 eq.), $Cu(OAc)_2$ (15 μL of a 0.2 M solution in THF, 0.003 mmol, 0.01 eq.), THF (0.135 mL), then dimethoxy(methyl)silane (111 μL, 0.90 mmol, 3 eq) were combined in a 2-dram vial followed by addition of a solution of (E/Z)-4-bromo-1-(but-1-en-1-yl)-2-methoxy benzene (72 mg, 0.30 mmol, 1 eq.), THF (0.150 mL), ethanol-OD (44 μL, 0.75 mmol, 2.5 eq.). The 2-dram vial was capped with a red pressure relief cap, and the reaction stirred for 17 h at 40° C. Upon completion, the crude product mixture was dry loaded onto a silica gel column. Flash column chromatography (200 mL of 100% HPLC hexanes) gave the pure product as a clear colorless oil (61 mg, 0.25 mmol, 83% yield).

$^1$H NMR: (400 MHz, $CDCl_3$) δ 7.29-7.27 (m, 1H), 7.26-7.24 (m, 1H), 6.72 (d, J=8.4 Hz, 1H), 3.81 (s, 3H), 2.60-2.52 (m, 1.02H), 1.59-1.50 (m, 2H), 1.37 (sxt, J=7.3 Hz, 2H), 0.94 (t, J=7.3 Hz, 3H). $^2$H NMR: (61 MHz, $CHCl_3$) δ 2.57 (s, 0.98 D) $^{13}$C NMR: (101 MHz, $CDCl_3$) δ 156.56, 133.66, 132.34, 129.27, 112.52, 111.82, 55.48, 31.71, 29.43 (t, J=19.6 Hz), 22.53, 13.98. ATR-IR ($cm^{-1}$): 3001, 2955, 2929, 2871, 2860, 2835, 2158, 1240, 1032. HRMS: ($EI^+$) m/z: $[M]^+$ Calcd for $C_{11}H_{14}DOBr$ 243.0369; Found 243.0363.

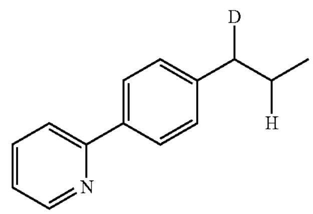 [SMILES: [2H]C(CC)c1ccc(-c2ccccn2)cc1]

2-(4-(propyl-1-d)phenyl)pyridine [4p]. According to the general procedure B, DTB-DPPBz (3.0 mg, 0.0033 mmol, 0.011 eq.), $Cu(OAc)_2$ (15 μL of a 0.2 M solution in THF, 0.003 mmol, 0.01 eq.), and THF (0.135 mL) then dimethoxy (methyl)silane (111 μL, 0.90 mmol, 3 eq.) were combined in a 2-dram vial followed by addition of a solution of (E/Z)-2-(4-(prop-1-en-1-yl)phenyl)pyridine (59 mg, 0.30 mmol, 1 eq.), THF (0.150 mL), and ethanol-OD (44 μL, 0.75 mmol, 2.5 eq). The 2-dram vial was capped with a red pressure relief cap, and the reaction stirred for 22 h at 40° C. After silica plug filtration using diethyl ether (100 mL) as the eluent, the solvent was concentrated, and the crude oil was dry loaded onto a silica gel column. Flash column chromatography using gradient elution (100 mL of 100% HPLC hexanes, 300 mL 3% ethyl acetate in HPLC hexanes, and 100 mL 5% ethyl acetate in HPLC hexanes) to give the pure product as a yellow oil (45 mg, 0.23 mmol, 77% yield).

$^1$H NMR: (400 MHz, $CDCl_3$) δ 8.68 (d, J=4.1 Hz, 1H), 7.92 (d, J=8.0 Hz, 2H), 7.77-7.68 (m, 2H), 7.29 (d, J=7.8 Hz, 2H), 7.24-7.16 (m, 1H), 2.68-2.58 (m, 1.02H), 1.68 (p, J=7.4 Hz, 2H), 0.97 (t, J=7.4 Hz, 3H). $^2$H NMR: (61 MHz, $CHCl_3$) δ 2.63 (s, 0.98D). $^{13}$C NMR: (75 MHz, $CDCl_3$) δ 157.65, 149.72, 143.82, 137.00, 136.75, 129.01, 126.88, 121.88, 120.38, 37.90 (s, peak represents dihydrogen at the benzylic carbon), 37.52 (t, J=19.3 Hz), 24.51, 13.90. ATR-IR ($cm^{-1}$): 3050, 3008, 2958, 2928, 2870, 2359, 1296. HRMS: ($ESI^+$) m/z: $[M+H]^+$ Calcd for $C_{14}H_{15}DN$ 199.1380; Found 199.1338.

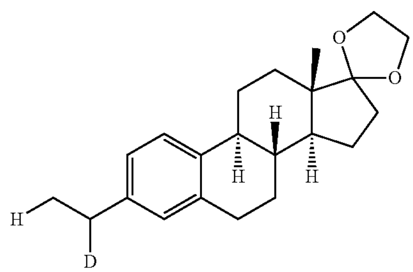

(8R,9S,13S,14S)-3-(ethyl-1-d)-13-methyl-6,7,8,9,11,12,13,14,15,16-decahydrospiro[cyclopenta[a]phenanthrene-17,2'-[1.3]dioxolane][4q]. Following the general procedure B, in a $N_2$ filled glovebox, DTB-DPPBz (6.0 mg, 0.0066 mmol, 0.022 eq.), $Cu(OAc)_2$ (30 μL of a 0.2 M solution in THF, 0.006 mmol, 0.02 eq.), and THF (0.120 mL) then dimethoxy (methyl)silane (111 μL, 0.90 mmol, 3 eq.) were combined in a 2-dram vial followed by addition of a solution of 8R,9S, 13S,14S)-13-methyl-3-vinyl-6,7,8,9,11,12,13,14,15,16-decahydrospiro[cyclopenta[a]phenanthrene-17,2'-[1,3]dioxolane](97 mg, 0.30 mmol, 1 eq.), THF (0.150 mL), and ethanol-OD (44 μL, 0.75 mmol, 2.5 eq). The 2-dram vial was capped with a red pressure relief cap, and the reaction stirred for 26 h at 40° C. After silica plug filtration using diethyl ether (100 mL) as the eluent, the solvent was concentrated, and the crude oil was dry loaded onto a silica gel column. Flash column chromatography using gradient elution (100 mL 100% HPLC hexanes, 100 mL 5% ethyl acetate in HPLC hexanes, and 100 mL 9% ethyl acetate in HPLC hexanes) to give the pure product as a viscous yellow oil (72 mg, 0.22 mmol, 73% yield).

$^1$H NMR: (400 MHz, $CDCl_3$) δ 7.25 (d, J=8.5 Hz, 1H), 7.02 (d, J=8.0 Hz, 1H), 6.95 (s, 1H), 4.04-3.86 (m, 4H), 2.97-2.81 (m, 2H), 2.65-2.54 (m, 1.06H), 2.41-2.24 (m, 2H), 2.11-2.01 (m, 1H), 1.98-1.74 (m, 4H), 1.73-1.61 (m, 1H), 1.61-1.33 (m, 5H), 1.24 (d, J=7.6 Hz, 3H), 0.90 (s, 3H). $^2$H NMR: (61 MHz, $CHCl_3$) δ 2.60 (s, 0.94D), 1.25 (s, 0.02D). $^{13}$C NMR: (101 MHz, $CDCl_3$) δ 141.51, 137.77, 136.72, 128.59, 125.46, 125.28, 119.56, 65.38, 64.71, 49.58, 46.28, 44.09, 39.06, 34.35, 30.89, 29.70, 28.08 (t, J=19.6 Hz), 27.16, 26.09, 22.49, 15.69, 14.45. ATR-IR ($cm^{-1}$): 2933, 2872, 1739, 1614, 1104, 1044. HRMS: ($EI^+$) m/z: $[M]^+$ Calcd for $C_{22}H_{29}DO_2$ 327.2309; Found 327.2303.

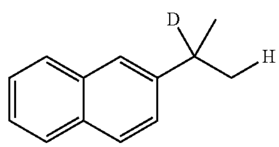

2-(1-methyl-1-d-ethyl)naphthlene [4r]: According to the general procedure B, DTB-DPPBz (8.9 mg, 0.0099 mmol, 0.033 eq.), $Cu(OAc)_2$ (45 µL of a 0.2 M solution in THF, 0.009 mmol, 0.03 eq.), THF (0.105 mL), then dimethoxy (methyl)silane (148 µL, 1.20 mmol, 4 eq.) were combined in a 2-dram vial followed by addition of a solution of 2-(1-methylethenyl)-naphthlene (50 mg, 0.30 mmol, 1 eq.), THF (0.150 mL), 2-propanol-d (69 µL, 0.9 mmol, 3 eq.). The 2-dram vial was capped with a red pressure relief cap, and the reaction stirred for 24 h at 60° C. Upon completion, the crude product mixture was dry loaded onto a silica gel column. Flash chromatography (150 mL of 100% HPLC hexanes) gave the pure product as a clear colorless oil (37 mg, 0.22 mmol, 73% yield).

$^1$H NMR (400 MHz, $CDCl_3$) δ 7.91-7.81 (m, 3H), 7.70 (s, 1H), 7.54-7.42 (m, 3H), 3.13 (m, J=7.1 Hz, 0.24H), 1.39 (s, 5.81H), $^2$H NMR (61 MHz, $CHCl_3$) δ 3.03 (s, 0.76D), 1.33 (s, 0.19D). $^{13}$C NMR (101 MHz, $CDCl_3$) δ 146.42, 133.80, 132.23, 127.97, 127.70, 125.94, 125.86, 125.19, 124.22, 34.29, 33.94 (t, J=19.5 Hz), 24.06, 23.97, 23.77 (t, J=19.2 Hz). FT-IR (thin film, $cm^{-1}$): 3053, 3017, 2959, 2926, 2867, 2145, 1914, 1633, 1600. HRMS: ($EI^+$) m/z: $[M]^+$ Calcd for $C_{13}H_{13}D_1$ 171.1200; Found 171.1151.

IV. Transfer Hydrodeuteration Substrate Scope Analyzed by Molecular Rotational Resonance Scheme S3. Substrate Scope Analyzed by Molecular Rotation Resonance

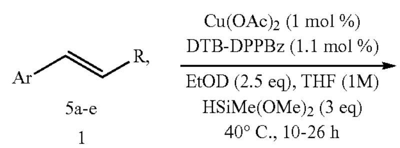

5a-e

1

-continued

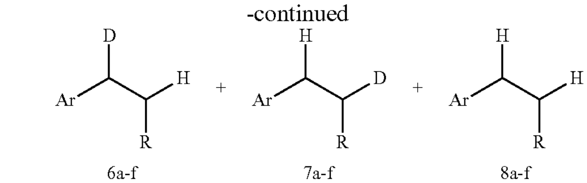

6a-f + 7a-f + 8a-f

Major Product[a]

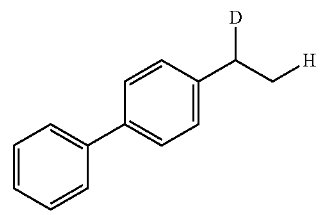

91% yield (6a + 7a + 8a)
98.4:(nd)[b]:1.6

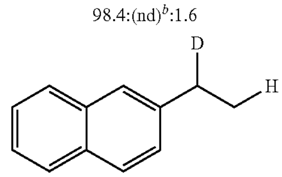

83% yield (6b + 7b + 8b)
94.8:0.8:4.4

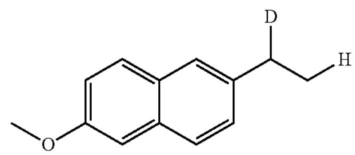

87% yield (6c + 7c + 8c)
96.8:(nd)[b]:3.2

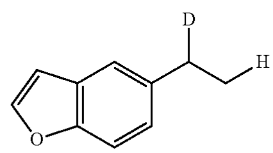

83% yield (6d + 7d + 8d)
95.1:3.2:1.7

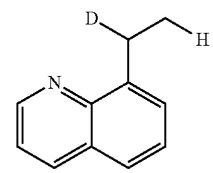

86% yield[c] (6e + 7e + 8e)
98.3:(nd)[b]:1.7

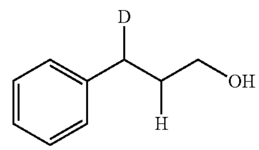

76% over 2 steps[d] (6f + 7f + 8f)
99.0:(nd)[b]:1.0

[a]The major products were 6a-f, the product distribution was determined by MRR and ratio represents the ratio of all products in the product mixture (6a-f:7a-f:8a-f) after purification. [b]Compound not detected (nd) by $^2$H NMR or MRR. See SI for detection limits. [c]2 mol % $Cu(OAc)_2$ and 2.2 mol % DTB-DPPBz were used. [d]Transfer deuteration product was purified then subjected to TBS deprotection.

Scheme S3.1. Substrate Scope Analyzed by MRR - Broadband / IsoMRR Instrument

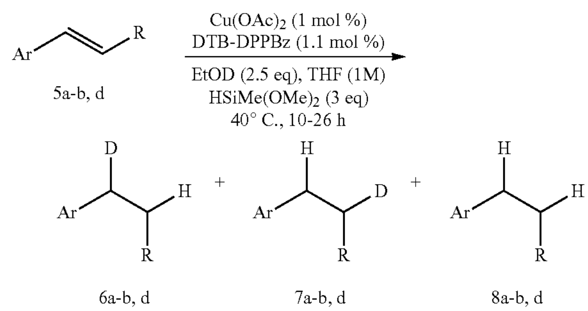

5a-b, d 6a-b, d 7a-b, d 8a-b, d

Major Product analyzed by Broadband[a]

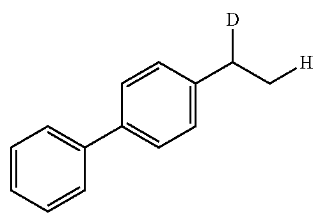 [SMILES: [2H]C(C)c1ccc(-c2ccccc2)cc1]

91% yield[b] (6a + 7a + 8a)
99.3:(nd):0.7

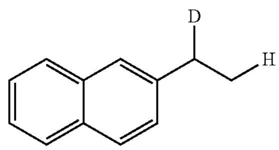

83% yield[b] (6b + 7b + 8b)
96.4:(nd):3.6

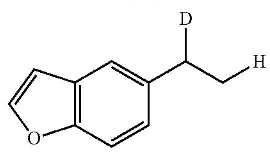

71% yield (6d + 7d + 8d)
96.3:2.8:0.9

Major Product analyzed by IsoMRR[a]

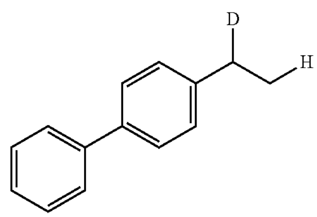

91% yield (6a + 7a + 8a)
98.4:(nd):1.6

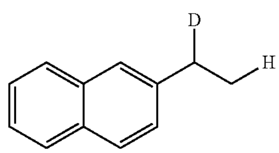

83% yield (6b + 7b + 8b)
94.9:0.8:4.4

-continued

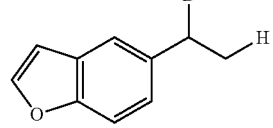

83% yield (6d + 7d + 8d)
95.1:3.2:1.7

[a]The major products were 6a-b, d, and the ratio represents the ratio of all products in the product mixture (6a-b, d: 7a-b, d: 8a-b, d) after purification.

[b]Polymethylhydrosiloxane (3 eq.) used instead of dimethoxy(methyl)silane (3 eq.).

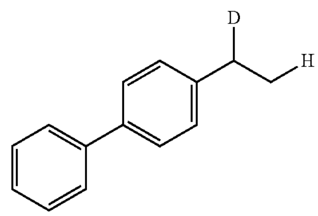

4-(ethyl-1-d)-biphenyl [6a]. According to the general procedure B but on a 2.17× scale, DTB-DPPBz (6.4 mg, 0.00715 mmol, 0.011 eq.), Cu(OAc)$_2$ (33 μL of a 0.2 M solution in THF, 0.0065 mmol, 0.01 eq.), THF (0.297 mL), then poly(methylhydrosiloxane) (130 μL, 1.95 mmol, 3 eq. based on Si—H)[1] were combined in a 2-dram vial followed by addition of a solution of 4-Vinylbiphenyl (117 mg, 0.65 mmol, 1 eq.), THF (0.320 mL), ethanol-OD (95 μL, 1.63 mmol, 2.5 eq.). The 2-dram vial was capped with a red pressure relief cap, and the reaction stirred for 26 h at 40° C. Upon completion, the crude product mixture was dry loaded onto a silica gel column. Flash column chromatography (200 mL of 100% HPLC hexanes) gave the pure product as a white crystalline solid (109 mg, 0.59 mmol, 91% isolated yield of isotopic product mixture). *Product was analyzed by the Broadband instrument.

$^1$H NMR: (300 MHz, $CDCl_3$) δ 7.60 (d, J=7.4 Hz, 2H), 7.54 (d, J=7.9 Hz, 2H), 7.42 (t, J=7.4 Hz, 2H), 7.36-7.30 (m, 1H), 7.27 (d, J=7.9 Hz, 2H), 2.79-2.56 (m, 1H), 1.28 (d, J=7.5 Hz, 3H). $^2$H NMR: (61 MHz, $CHCl_3$) δ 2.68 (s, 1D). $^{13}$C NMR: (75 MHz, $CDCl_3$) δ 143.40, 141.29, 138.72, 128.82, 128.47, 127.18, 127.10, 127.07, 28.29 (t, J=19.5 Hz), 15.64. ATR-R ($cm^{-1}$): 3054, 3028, 2962, 2930, 2873, 2135. HRMS: ($EI^+$) m/z: $[M]^+$ Calcd for $C_{14}H_{13}D$ 183.1200; Found 183.1152. MRR Spectroscopy: See MRR SI for characterization details.

4-(ethyl-1-d)-biphenyl [6a]. According to the general procedure B but on a 2.17× scale, DTB-DPPBz (6.4 mg, 0.00715 mmol, 0.011 eq.), Cu(OAc)$_2$ (33 μL of a 0.2 M solution in THF, 0.0065 mmol, 0.01 eq.), THF (0.297 mL), then dimethoxy(methyl)silane (241 μL, 1.95 mmol, 3 eq.) were combined in a 2-dram vial followed by addition of a solution of 4-Vinylbiphenyl (117 mg, 0.65 mmol, 1 eq.), THF (0.320 mL), ethanol-OD (95 μL, 1.63 mmol, 2.5 eq.). The 2-dram vial was capped with a red pressure relief cap, and the reaction stirred for 19 h at 40° C. Upon completion, the crude product mixture was dry loaded onto a silica gel column. Flash column chromatography (200 mL of 100% HPLC hexanes) gave the pure product as a white crystalline solid (108 mg, 0.59 mmol, 91% isolated yield of isotopic product mixture). *Product was analyzed by the IsoMRR instrument.

$^1$H NMR: (300 MHz, $CDCl_3$) δ 7.59 (d, J=7.2 Hz, 2H), 7.53 (d, J=8.3 Hz, 2H), 7.43 (t, J=7.4 Hz, 2H), 7.37-7.32 (m, 1H), 7.29 (d, J=8.3 Hz, 2H), 2.76-2.62 (m, 1H), 1.27 (d, J=7.7 Hz, 3H). $^2$H NMR: (61 MHz, $CHCl_3$) δ 2.70 (s, 1D). MRR Spectroscopy: See MRR SI for characterization details.

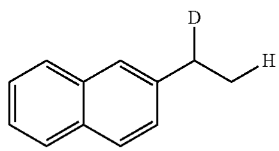 [SMILES: [2H]C(C)c1ccc2ccccc2c1]

2-(ethyl-1-d)-naphthalene [6b]. According to the general procedure B but on a 2.17× scale, DTB-DPPBz (6.4 mg, 0.00715 mmol, 0.011 eq.), $Cu(OAc)_2$ (33 μL of a 0.2 M solution in THF, 0.0065 mmol, 0.01 eq.), THF (0.297 mL), then poly(methylhydrosiloxane) (173 μL, 2.60 mmol, 4 eq. based on Si—H)[1] were combined in a 2-dram vial followed by addition of a solution of 2-Vinylnaphthalene (100 mg, 0.65 mmol, 1 eq.), THF (0.320 mL), ethanol-OD (95 μL, 1.63 mmol, 2.5 eq.). The 2-dram vial was capped with a red pressure relief cap, and the reaction stirred for 9.5 h at 40° C. Upon completion, the crude product mixture was dry loaded onto a silica gel column. Flash column chromatography (200 mL of 100% HPLC hexanes) gave the pure product as a clear colorless oil (85 mg, 0.54 mmol, 83% isolated yield of isotopic product mixture). *Product was analyzed by the Broadband instrument.

$^1$H NMR: (400 MHz, $CDCl_3$) δ 7.88-7.76 (m, 3H), 7.65 (s, 1H), 7.50-7.40 (m, 2H), 7.37 (d, J=8.5 Hz, 1H), 2.88-2.77 (m, 1.01H), 1.34 (d, J=7.6 Hz, 3H). $^2$H NMR: (61 MHz, $CHCl_3$) δ 2.82 (s, 0.99D). $^{13}$C NMR: (101 MHz, $CDCl_3$) δ 141.88, 133.82, 132.06, 127.93, 127.73, 127.55, 127.22, 125.96, 125.68, 125.14, 28.84 (t, J=19.3 Hz), 15.61. ATR-IR ($cm^{-1}$): 3049, 2962, 2930, 2872, 2166, 1506, 1454. HRMS: ($EI^+$) m/z: $[M]^+$ Calcd for $C_{12}H_{11}D$ 157.1000; Found 157.0995. MRR Spectroscopy: See MRR SI for characterization details.

2-(ethyl-1-d)-naphthalene [6b]. According to the general procedure B but on a 2.17× scale, DTB-DPPBz (6.4 mg, 0.00715 mmol, 0.011 eq.), $Cu(OAc)_2$ (33 μL of a 0.2 M solution in THF, 0.0065 mmol, 0.01 eq.), THF (0.297 mL), then dimethoxy(methyl)silane (241 μL, 1.95 mmol, 3 eq.) were combined in a 2-dram vial followed by addition of a solution of 2-Vinylnaphthalene (100 mg, 0.65 mmol, 1 eq.), THF (0.320 mL), ethanol-OD (95 μL, 1.63 mmol, 2.5 eq.). The 2-dram vial was capped with a red pressure relief cap, and the reaction stirred for 20 h at 40° C. Upon completion, the crude product mixture was dry loaded onto a silica gel column. Flash column chromatography (200 mL of 100% HPLC hexanes) gave the pure product as a clear colorless oil (85 mg, 0.54 mmol, 83% isolated yield of isotopic product mixture). *Product was analyzed by the IsoMRR instrument.

$^1$H NMR: (300 MHz, $CDCl_3$) δ 7.87-7.75 (m, 3H), 7.65 (s, 1H), 7.51-7.40 (m, 2H), 7.37 (d, J=8.4 Hz, 1H), 2.90-2.75 (m, 1H), 1.35 (d, J=7.6 Hz, 3H). $^2$H NMR: (61 MHz, $CHCl_3$) δ 2.83, (s, 0.94D). MRR Spectroscopy: See MRR SI for characterization details.

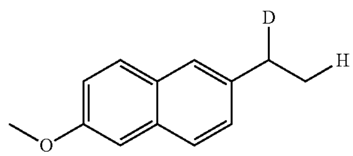

2-(ethyl-1-d)-6-methoxynaphthalene [6c]. According to the general procedure B, DTB-DPPBz (3.0 mg, 0.0033 mmol, 0.011 eq.), $Cu(OAc)_2$ (15 μL of a 0.2 M solution in THF, 0.003 mmol, 0.01 eq.), THF (0.135 mL), then dimethoxy(methyl)silane (111 μL, 0.90 mmol, 3 eq) were combined in a 2-dram vial followed by addition of a solution of 2-Ethenyl-6-methoxynaphthalene (55 mg, 0.30 mmol, 1 eq.), THF (0.150 mL), ethanol-OD (44 μL, 0.75 mmol, 2.5 eq.). The 2-dram vial was capped with a red pressure relief cap, and the reaction stirred for 17 h at 40° C. Upon completion, the crude product mixture was dry loaded onto a silica gel column. Flash column chromatography using gradient elution (100 mL of 100/% HPLC hexanes, 100 mL of 1% ethyl acetate in HPLC hexanes) gave the pure product as a white solid (48 mg, 0.26 mmol, 87% isolated yield of isotopic product mixture).

$^1$H NMR: (300 MHz, $CDCl_3$) δ 7.70 (dd, J=8.0, 2.2 Hz, 2H), 7.58 (s, 1H), 7.34 (dd, J=8.4, 1.8 Hz, 1H), 7.18-7.10 (m, 2H), 3.93 (s, 3H), 2.85-2.72 (m, 1.04H), 1.33 (d, J=7.9 Hz, 3H), $^2$H NMR: (61 MHz, $CHCl_3$) δ 2.78 (s, 0.96 D) $^{13}$C NMR: (75 MHz, $CDCl_3$) δ 157.21, 139.55, 133.02, 129.30, 129.03, 127.68, 126.82, 125.56, 118.72, 105.79, 55.41, 28.62 (t, J=19.2 Hz), 15.69. ATR-IR ($cm^{-1}$): 2980, 2958, 2926, 2908, 2889, 2868, 2280, 1160. HRMS: ($EI^+$) m/z: $[M]^+$ Calcd for $C_{13}H_{13}DO$ 187.1107; Found 187.1101. MRR Spectroscopy: See MRR SI for characterization details.

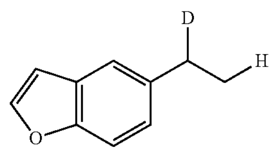 [SMILES: [2H]C(C)c1ccc2occc2c1]

5-(ethyl-1-d)-benzofuran [6d]. According to the general procedure B but on a 2.33× scale, DTB-DPPBz (7.0 mg, 0.0077 mmol, 0.011 eq.), $Cu(OAc)_2$ (35 μL of a 0.2 M solution in THF, 0.007 mmol, 0.01 eq.), THF (0.315 mL), then dimethoxy(methyl)silane (259 μL, 2.10 mmol, 3 eq.) were combined in a 2-dram vial followed by addition of a solution of 5-Vinylbenzofuran (101 mg, 0.70 mmol, 1 eq.), THF (0.350 mL), ethanol-OD (102 μL, 1.75 mmol, 2.5 eq.). The 2-dram vial was capped with a red pressure relief cap, and the reaction stirred for 25.5 h at 40° C. Upon completion, the crude product mixture was dry loaded onto a silica gel column. Flash column chromatography (150 mL of 100% HPLC hexanes) gave the pure product as a clear colorless oil (73 mg, 0.50 mmol, 71% isolated yield of isotopic product mixture). * Product was analyzed by the Broadband instrument.

$^1$H NMR: (400 MHz, $CDCl_3$) δ 7.63-7.59 (m, 1H), 7.48-7.41 (m, 2H), 7.16 (d, J=8.6 Hz, 1H), 6.75-6.72 (m, 1H), 2.80-2.68 (m, 1.05H), 1.30 (d, J=7.6, 3H), $^2$H NMR: (61 MHz, $CHCl_3$) δ 2.75 (s, 0.95D), 1.30 (s, 0.03D) $^{13}$C NMR: (75 MHz, $CDCl_3$) δ 153.62, 145.16, 138.89, 127.61, 124.61, 119.89, 111.11, 106.53, 28.61 (t, J=19.5 Hz), 16.40. ATR-IR ($cm^{-1}$): 3022, 2959, 2923, 2853, 2170, 1258.

HRMS: ($EI^+$) m/z: $[M]^+$ Calcd for $C_{10}H_9DO$ 147.0800; Found 147.0789. MRR Spectroscopy: See MRR SI for characterization details.

5-(ethyl-1-d)-benzofuran [6d]. According to the general procedure B but on a 2.17× scale, DTB-DPPBz (6.4 mg, 0.00715 mmol, 0.011 eq.), $Cu(OAc)_2$ (33 μL of a 0.2 M solution in THF, 0.0065 mmol, 0.01 eq.), THF (0.297 mL), then dimethoxy(methyl)silane (241 μL, 1.95 mmol, 3 eq.) were combined in a 2-dram vial followed by addition of a solution of 5-Vinylbenzofuran (93.7 mg, 0.65 mmol, 1 eq.), THF (0.320 mL), ethanol-OD (95 μL, 1.63 mmol, 2.5 eq.). The 2-dram vial was capped with a red pressure relief cap, and the reaction stirred for 25 h at 40° C. Upon completion, the crude product mixture was dry loaded onto a silica gel column. Flash column chromatography (200 mL of 100% HPLC hexanes) gave the pure product as a clear colorless oil (80 mg, 0.54 mmol, 83% isolated yield of isotopic product mixture). *Product was analyzed by the IsoMRR instrument.

$^1H$ NMR: (400 MHz, $CDCl_3$) δ 7.62-7.58 (m, 1H), 7.46-7.40 (m, 2H), 7.15 (d, J=8.0 Hz, 1H), 6.75-6.70 (m, 1H), 2.79-2.68 (m, 1H), 1.29 (d, J=7.5 Hz, 3H). $^2H$ NMR: (61 MHz, $CHCl_3$) δ 2.75 (s, 0.96D), 1.29 (s, 0.02D). MRR Spectroscopy: See MRR SI for characterization details.

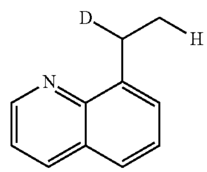 [SMILES: [2H]C(C)c1cccc2cccnc12]

8-(ethyl-1-d)-quinoline [6e]. According to the general procedure B but on a 2.17× scale, DTB-DPPBz (12.8 mg, 0.0143 mmol, 0.022 eq.), $Cu(OAc)_2$ (65 μL of a 0.2 M solution in THF, 0.013 mmol, 0.02 eq.), THF (0.260 mL), then dimethoxy(methyl)silane (241 μL, 1.95 mmol, 3 eq.) were combined in a 2-dram vial followed by addition of a solution of 8-Vinylquinoline (101 mg, 0.65 mmol, 1 eq.), THF (0.325 mL), ethanol-OD (95 μL, 1.63 mmol, 2.5 eq.). The 2-dram vial was capped with a red pressure relief cap, and the reaction stirred for 25 h at 40° C. Upon completion, the crude product mixture was dry loaded onto a neutral alumina brock column. Flash column chromatography using gradient elution (300 mL of 100% HPLC hexanes, 100 mL of 2% ethyl acetate in HPLC hexanes) gave the pure product as a yellow oil (89 mg, 0.56 mmol, 86% isolated yield of isotopic product mixture).

$^1H$ NMR: (400 MHz, $CDCl_3$) δ 8.95 (d, J=4.0 Hz, 1H), 8.17-8.10 (m, 1H), 7.66 (d, J=8.1 Hz, 1H), 7.58 (d, J=7.0 Hz, 1H), 7.48 (t, J=7.5 Hz, 1H), 7.42-7.36 (m, 1H), 3.36-3.25 (m, 1.02H), 1.39 (d, J=7.5 Hz, 3H). $^2H$ NMR: (61 MHz, $CHCl_3$) δ 3.33 (s, 0.98D). $^{13}C$ NMR: (101 MHz, $CDCl_3$) δ 149.37, 146.87, 143.01, 136.50, 128.50, 128.05, 126.55, 125.94, 120.92, 24.40 (t, J=19.4 Hz), 15.10. ATR-IR ($cm^{-1}$): 3039, 3002, 2962, 2930, 2870, 2185, 1364. HRMS: ($ESI^+$) m/z: $[M+H]^+$ Calcd for $C_{11}H_{11}DN$ 159.1080; Found 159.1026. MRR Spectroscopy: See MRR SI for characterization details.

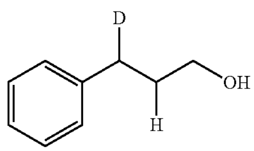 [SMILES: [2H]C(CCO)c1ccccc1]

3-phenyl-(propan-3-d)-1-ol [6f]. According to the general procedure B but on a 4.07× scale, DTB-DPPBz (12.0 mg, 0.0134 mmol, 0.011 eq.), $Cu(OAc)_2$ (61 μL of a 0.2 M solution in THF, 0.0122 mmol, 0.01 eq.), THF (0.549 mL), then dimethoxy(methyl)silane (451 μL, 3.66 mmol, 3 eq.) were combined in a 2-dram vial followed by addition of a solution of 1-tert-butyldimethylsilyloxy-3-phenyl-2-propene (303 mg, 1.22 mmol, 1 eq.). THF (0.610 mL), ethanol-OD (178 μL, 3.05 mmol, 2.5 eq.). The 2-dram vial was capped with a red pressure relief cap, and the reaction stirred for 23 h at 40° C. After silica plug filtration using diethyl ether (200 mL) as the eluent, the solvent was concentrated, and the crude oil was treated with tetrabutylammonium fluoride (2.44 mL, 2 eq.) and THF (5 mL) for 23 h. Upon completion, reaction mixture was quenched with saturated aqueous $NH_4Cl$ (5 mL) and water (10 mL). The aqueous layer was extracted with diethyl ether (3×10 mL) and the combined organic layers were washed with water (10 mL) and brine (10 mL), then dried over anhydrous $Na_2SO_4$. The mixture was filtered, and the solvent was removed by rotary evaporation. Flash column chromatography using gradient elution (100 mL of 100% HPLC hexanes, 100 mL of 5% ethyl acetate in HPLC hexanes, 100 mL of 10% ethyl acetate in HPLC hexanes, 300 mL of 15% ethyl acetate in HPLC hexanes) gave the pure product as a clear colorless oil (127 mg, 0.93 mmol, 76% isolated yield over 2 steps of isotopic product mixture).

$^1H$ NMR: (400 MHz, $CDCl_3$) δ 7.33-7.27 (m, 2H), 7.24-7.17 (m, 3H), 3.68 (td, J=6.5, 1.1 Hz, 2H), 2.75-2.65 (m, 1H), 1.90 (q, J=6.7 Hz, 2H), 1.56 (br s, 1H). $^2H$ NMR: (61 MHz, $CHCl_1$) δ 2.70 (s, 1D). $^{13}C$ NMR: (75 MHz, $CDCl_3$) δ 141.90, 128.55, 128.52, 125.99, 62.37, 34.26, 31.84 (t, J=19.5 Hz). ATR-IR ($cm^1$): 3325, 3060, 3025, 2934, 2873, 2153, 1054. HRMS: ($EI^+$) m/z: $[M]^+$ Calcd for $C_9H_{11}DO$ 137.1000; Found 137.0945. MRR Spectroscopy: See MRR SI for characterization details.

V. Synthesis of dimethoxy(methyl)silane-d

Procedure for the Synthesis of Dimethoxy(Methyl)Silane-d

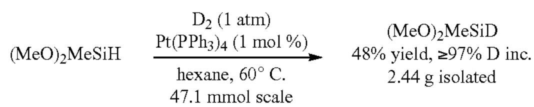

The procedure was adapted from a previously reported method.[3] To an oven-dried 500 mL Schlenk flask equipped with a Teflon stir bar in a $N_2$ filled glovebox was added the $Pt(PPh_3)_4$ (586 mg, 0.471 mmol, 0.01 eq.), dimethoxy(methyl)silane (5.81 mL, 47.1 mmol, 1 eq.), and 2.5 mL of degassed anhydrous hexanes. The Schlenk flask was sealed with a rubber-septa and removed from the glovebox, connected to a manifold line, and cooled to −78° C. A single freeze-pump-thaw cycle was performed, and the Schlenk flask was backfilled with $D_2$ gas from a $D_2$ purged balloon at room temperature. The flask was sealed with parafilm and heated to 60° C. After 2 hours, the reaction was cooled to room temperature and then a single freeze-pump-thaw was performed again, backfilling with $D_2$ gas. This process was repeated 6 times or until the $^1H$ NMR showed 295% D incorporation. It is important to maintain a $N_2$ (g) inert atmosphere while obtaining a minimal quantity of sample for $^1H$ NMR analysis.

After reaction completion, the solution was purified through a distillation apparatus. The set up consist of a flame-dried 25 mL round-bottom receiving flask sealed with a rubber-septum and a cannula inserted along with a line for a positive $N_2$ flow. While the receiving flask cools to room temperature, a positive $N_2$ flow is maintained through the receiving flask and cannula. Upon cooling, the open end of the cannula was inserted into the Schlenk reaction flask. The rubber-septum on the receiving flask was tightly sealed with Parafilm. The 25 mL round-bottom receiving flask was cooled to −78° C. and the $N_2$ flow from the manifold was closed and then the Schlenk flask was heated to 80° C. The heat initiated the distillation of the dimethoxy(methyl)silane-d and the hexane through the cannula, which were trapped as a mixture in the cold 25 mL round-bottom receiving flask. Vacuum was also applied to the 25 mL round-bottom receiving flask to promote this process. Once all of the silane and hexane were trapped in the 25 mL round-bottom receiving flask, the Schlenk flask was removed from the heat and the manifold was closed to the vacuum line and the entire apparatus was put under a positive $N_2$ atmosphere while the 25 mL round-bottom receiving flask warmed to room temperature. Under positive nitrogen flow, the cannula was removed from the 25 mL round-bottom receiving flask, while keeping it inserted in the Schlenk reaction flask. The 25 mL round-bottom receiving flask was tightly sealed with parafilm, and stored in a −4° C. freezer. The final product was in a solution of hexane, and the molarity was calculated by $^1H$ NMR using 1,3,5-trimethylbenzene as an internal standard, and used for the transfer hydrodeuteration reaction as needed (2.44 g in a 5.29 M hexane solution, 22.7 mmol, 48% yield).

Note: During the distillation process, it is important to monitor that the end of the cannula does not get clogged by frozen solvent/silane. If this occurs, remove the Schlenk reaction flask from heat and close the manifold to vacuum line. Warm the 25 mL round-bottom receiving flask until the solids on the tip of the cannula melt, and then distillation can be resumed.

VI. Preparation of Isotopic Mixtures (Cocktail Reactions)

General Procedure for the Synthesis of Isotopic Mixtures (C)

In a $N_2$ filled glovebox, (R)-DTBM-SEGPHOS (57.1 mg, 0.0484 mmol, 0.022 eq.), $Cu(OAc)_2$ (220 µL of a 0.2 M solution in THF, 0.0440 mmol, 0.02 eq.), and THF (0.780 mL) were added to a flame-dried 100 mL round bottom flask followed by dropwise addition of dimethoxy(methyl)silane (407 µL, 3.30 mmol, 1.5 eq.) and dimethoxy(methyl)silane-d (624 µL of a 5.29 M solution in hexanes, 3.30 mmol, 1.5 eq.). A color change from green/blue to brown was observed while stirring for 15 minutes. In a separate oven-dried 2-dram vial was added the alkene substrate (2.2 mmol, 1 eq.), THF (1.20 mL), ethanol (161 µL, 2.75 mmol, 1.25 eq), and ethanol-OD (161 µL, 2.75 mmol, 1.25 eq). The solution in the 2-dram vial was added dropwise over 20 seconds to the 100 mL round bottom flask. The total volume of THF was calculated based on having a final reaction concentration of 1M based on the alkene substrate. The 100 mL round bottom flask was capped with a septum, taken out of the glovebox, and a balloon filled with $N_2$ was inserted through the septum as the reaction stirred for 19-43 h at the appropriate temperature. Upon completion, the crude product mixture was dry loaded onto a silica gel column and purified by flash column chromatography. Since the product contains a mixture of $d_0$, $d_1$ and $d_2$ isotopologues and isotopomers, isolated yields were calculated based on an average deuterium incorporation of one deuterium.

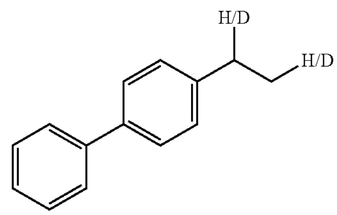

4-ethylbiphenyl isotopic mixture. According to the general procedure C, (R)-DTBM-SEGPHOS (57.6 mg, 0.0488 mmol, 0.022 eq.), $Cu(OAc)_2$ (222 µL of a 0.2 M solution in THF, 0.0444 mmol, 0.02 eq.), and THF (0.778 mL) then dimethoxy(methyl)silane (411 µL, 3.33 mmol, 1.5 eq.) and dimethoxy(methyl)silane-d (629 µL of a 5.29 M solution in hexanes, 3.33 mmol, 1.5 eq.) were combined in a 100 mL round bottom flask followed by addition of a solution of 4-Vinylbiphenyl (400 mg, 2.22 mmol, 1 eq.), THF (1.22 mL), ethanol (162 µL, 2.78 mmol, 1.25 eq.), and ethanol-OD (162 µL, 2.78 mmol, 1.25 eq). The 100 mL round bottom flask was capped with a septum, and the reaction stirred for 23 h at 40° C. Upon completion, the crude product mixture was dry loaded onto a silica gel column. Flash column chromatography (500 mL of 100% HPLC hexanes) to give the pure product as a white crystalline solid (369 mg, 2.01 mmol, 91% isolated yield of the isotopic product mixture).

$^1H$ NMR: (400 MHz, $CDCl_3$) δ 7.59 (d, J=8.1 Hz, 2H), 7.52 (d, J=8.1 Hz, 2H), 7.43 (t, J=7.5 Hz, 2H), 7.36-7.31 (m, 1H), 7.28 (d, J=7.9 Hz, 2H), 2.75-2.64 (m, 1.69H), 1.32-1.23 (m, 2.73H). $^2H$ NMR: (61 MHz, $CHCl_3$) δ 2.71 (s, 0.31D), 1.30 (s, 0.27D). $^{13}C$ NMR: (75 MHz, $CDCl_3$) δ 143.53, 141.34, 138.75, 128.84, 128.43, 127.22, 127.16, 127.10, 28.76-28.51 (m), 15.83-15.58 (m).

4-ethylbiphenyl isotopic mixture. The reaction was performed according to the general procedure C but with an increased ratio of the deuterium sources relative to hydrogen sources. Accordingly, (R)-DTBM-SEGPHOS (16.9 mg, 0.0143 mmol, 0.022 eq.), $Cu(OAc)_2$ (65 µL of a 0.2 M solution in THF, 0.0013 mmol, 0.02 eq.), and THF (0.260 mL) then dimethoxy(methyl)silane (60 µL, 0.49 mmol, 0.75 eq.) and dimethoxy(methyl)silane-d (276 µL of a 5.29 M solution in hexanes, 1.46 mmol, 2.25 eq.) were combined in a 2-dram vial followed by addition of a solution of 4-Vinylbiphenyl (117 mg, 0.65 mmol, 1 eq.), THF (0.325 mL), ethanol (24 µL, 0.41 mmol, 0.63 eq.), and ethanol-OD (71 µL, 1.22 mmol, 1.88 eq). The 2-dram vial was capped with a red pressure relief cap and the reaction stirred for 19 h at 40° C. Upon completion, the crude product mixture was dry loaded onto a silica gel column. Flash column chromatography (200 mL of 100% HPLC hexanes) to give the pure product as a white crystalline solid (114 mg, 0.62 mmol, 95% isolated yield of the isotopic product mixture).

$^1H$ NMR: (400 MHz, $CDCl_3$) δ 7.59 (d, J=8.2 Hz, 2H), 7.53 (d, J=8.0 Hz, 2H), 7.44 (t, J=7.8 Hz, 2H), 7.37-7.32 (m, 1H), 7.30 (d, J=8.0 Hz, 2H), 2.76-2.64 (m, 1.29H), 1.31-1.26 (m, 2.46H). $^2H$ NMR: (61 MHz, $CHCl_3$) δ 2.68 (s, 0.71D), 1.27 (s, 0.52D). $^{13}C$ NMR: (75 MHz, $CDCl_3$) δ 143.51, 141.34, 138.75, 128.84, 128.43, 127.22, 127.15, 127.10, 28.78-27.91 (m), 15.86-15.03 (m).

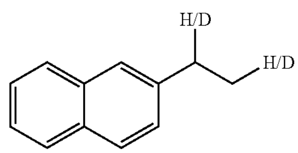

2-ethylnaphthalene isotopic mixture. According to the general procedure C, (R)-DTBM-SEGPHOS (67.2 mg, 0.0570 mmol, 0.022 eq.), $Cu(OAc)_2$ (259 μL of a 0.2 M solution in THF, 0.0518 mmol, 0.02 eq.), and THF (1.03 mL) then dimethoxy(methyl)silane (480 μL, 3.89 mmol, 1.5 eq.) and dimethoxy(methyl)silane-d (735 μL of a 5.29 M solution in hexanes, 3.89 mmol, 1.5 eq.) were combined in a 100 mL round bottom flask followed by addition of a solution of 2-Vinylnaphthalene (400 mg, 2.59 mmol, 1 eq.), THF (1.30 mL), ethanol (189 μL, 3.24 mmol, 1.25 eq.), and ethanol-OD (189 μL, 3.24 mmol, 1.25 eq). The 100 mL round bottom flask was capped with a septum, and the reaction stirred for 23 h at 40° C. Upon completion, the crude product mixture was dry loaded onto a silica gel column. Flash column chromatography (300 mL of 100% HPLC hexanes) to give the pure product as a clear colorless oil (358 mg, 2.28 mmol, 88% isolated yield of the isotopic product mixture).

$^1$H NMR: (400 MHz, $CDCl_3$) δ 7.89-7.75 (m, 3H), 7.66 (s, 1H), 7.53-7.42 (m, 2H), 7.39 (d, J=8.5 Hz, 1H), 2.92-2.78 (m, 1.71H), 1.42-1.30 (m, 2.71H). $^2$H NMR: (61 MHz, $CHCl_3$) δ 2.83 (s, 0.29D), 1.35 (s, 0.29D). $^{13}$C NMR: (101 MHz, $CDCl_3$) δ 141.89, 133.82, 132.05, 127.93, 127.73, 127.55, 127.22, 125.96, 125.67, 125.14, 29.31-28.52 (m), 15.74-15.07 (m).

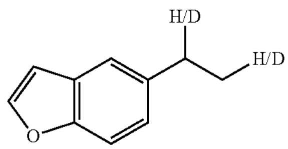

5-ethylbenzofuran isotopic mixture. According to the general procedure C, (R)-DTBM-SEGPHOS (71.8 mg, 0.0609 mmol, 0.022 eq.). $Cu(OAc)_2$ (277 μL of a 0.2 M solution in THF, 0.0554 mmol, 0.02 eq.), and THF (1.11 mL) then dimethoxy(methyl)silane (683 μL, 5.54 mmol, 2 eq.) and dimethoxy(methyl)silane-d (1.05 mL of a 5.29 M solution in hexanes, 5.54 mmol, 2 eq.) were combined in a 100 mL round bottom flask followed by addition of a solution of 5-Vinylbenzofuran (400 mg, 2.77 mmol, 1 eq.), THF (1.38 mL), ethanol (202 μL, 3.46 mmol, 1.25 eq.), and ethanol-OD (202 μL, 3.46 mmol, 1.25 eq). The 100 mL round bottom flask was capped with a septum, and the reaction stirred for 43 h at 23° C. Upon completion, the crude product mixture was dry loaded onto a silica gel column Flash column chromatography (500 mL of 100% HPLC hexanes) to give the pure product as a clear colorless oil (267 mg, 1.81 mmol, 65% isolated yield of the isotopic product mixture).

$^1$H NMR: (400 MHz, $CDCl_3$) δ 7.62-7.59 (m, 1H), 7.45-7.39 (m, 2H), 7.15 (d, J=8.5 Hz, 1H), 6.75-6.71 (m, 1H), 2.80-2.69 (m, 1.43H), 1.32-1.24 (m, 2.69H). $^2$H NMR: (61 MHz, $CHCl_3$) δ 2.75 (s, 0.57D), 1.30 (s, 0.31D). $^{13}$C NMR: (75 MHz, $CDCl_3$) δ 153.62, 145.16, 138.92, 127.61, 124.62, 119.89, 111.11, 106.53, 29.03-28.21 (m), 16.61-15.89 (m).

VII. Reaction Studies (a) Switchable Selectivity

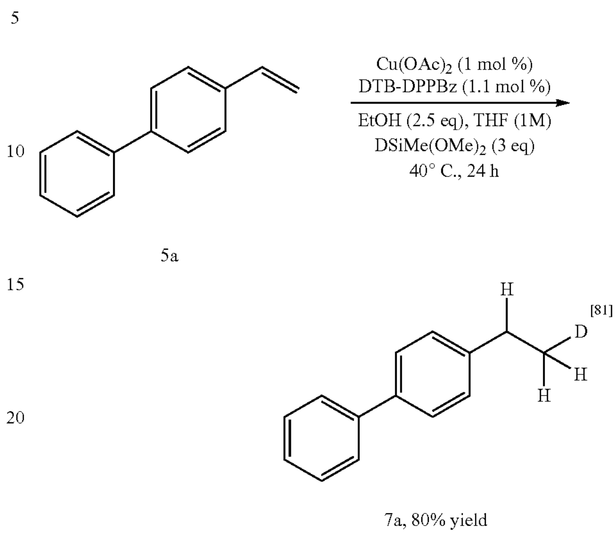

5a 7a, 80% yield 4-(ethyl-2-d)-biphenyl [7a]. According to the general procedure B, DTB-DPPBz (2.0 mg, 0.0022 mmol, 0.011 eq.), $Cu(OAc)_2$ (10 μL of a 0.2 M solution in THF, 0.002 mmol, 0.01 eq.), THF (0.09 mL), then dimethoxy(methyl)silane-d (113 μL of a 5.29 M solution in hexanes, 0.60 mmol, 3 eq.) were combined in a 2-dram vial followed by addition of a solution of 4-Vinylbiphenyl (36 mg, 0.20 mmol, 1 eq.), THF (0.10 mL), ethanol (29 μL, 0.50 mmol, 2.5 eq.). The 2-dram vial was capped with a red pressure relief cap, and the reaction stirred for 24 h at 40° C. After silica plug filtration using diethyl ether (100 mL) as the eluent, the solvent was concentrated, and the crude oil was dry loaded onto a silica gel column. Flash column chromatography (150 mL of 100% HPLC hexanes) gave the pure product as a white crystalline solid (30 mg, 0.16 mmol, 80% yield).

$^1$H NMR: (400 MHz, $CDCl_3$) δ 7.62 (d, J=7.6 Hz, 2H), 7.55 (d, J=7.8 Hz, 2H), 7.46 (t, J=7.6 Hz, 2H), 7.36 (t, J=7.2 Hz, 1H), 7.31 (d, J=7.8 Hz, 2H), 2.72 (t, J=7.6 Hz, 2H), 1.34-1.25 (m, 2.19H). $^2$H NMR: (61 MHz, $CHCl_3$) δ 1.29 (s, 0.81 D)$^{13}$C NMR: (101 MHz, $CDCl_3$) δ 143.52, 141.32, 138.73, 128.84, 128.42, 127.21, 127.15, 127.10, 28.57, 15.45 (t, J=19.5 Hz). ATR-IR ($cm^{-1}$): 3054, 3029, 2930, 2850, 2176. HRMS: ($EI^+$) m/z: $[M]^+$ Calcd for $C_{14}H_{13}D$ 183.1158; Found 183.1151.

(b) Chemoselectivity Probe

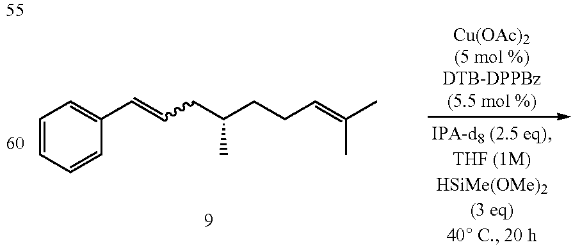

9

-continued

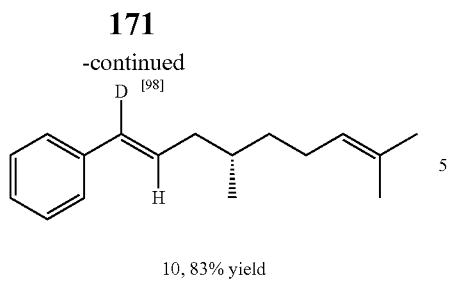

10, 83% yield (S)-(4,8-dimethylnon-7-en-1-yl-1-d)benzene [10]. According to the general procedure B, DTB-DPPBz (14.8 mg, 0.0165 mmol, 0.055 eq.), $Cu(OAc)_2$ (75 μL of a 0.2 M solution in THF, 0.015 mmol, 0.05 eq.), THF (0.075 mL), then dimethoxy(methyl)silane (11 μL, 0.90 mmol, 3 eq) were combined in a 2-dram vial followed by addition of a solution of (E/Z)—(S)-(4,8-dimethylnona-1,7-dien-1-yl) benzene (68 mg, 0.30 mmol, 1 eq.), THF (0.150 mL), 2-propanol-$d_8$ (57 μL, 0.75 mmol, 2.5 eq.). The 2-dram vial was capped with a red pressure relief cap, and the reaction stirred for 20 h at 40° C. Upon completion, the crude product mixture was dry loaded onto a silica gel column. Flash column chromatography (100 mL of 100% HPLC hexanes) gave the pure product as a clear colorless oil (57 mg, 0.25 mmol, 83% yield).

$^1$H NMR: (400 MHz, $CDCl_3$) δ 7.34-7.28 (m, 2H), 7.24-7.18 (m, 3H), 5.14 (t, J=7.1 Hz, 1H), 2.66-2.55 (m, 1H), 2.10-1.91 (m, 2H), 1.73 (s, 3H), 1.64 (s, 3H), 1.70-1.57 (m, 2H) 1.54-1.43 (m, 1H), 1.43-1.32 (m, 2H), 1.27-1.14 (m,

-continued

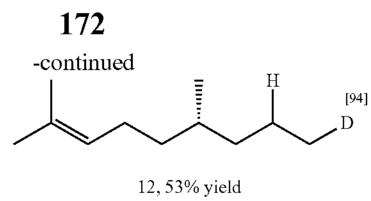

12, 53% yield (−)-2,6-Dimethyl-2-nonene [12]. According to the general procedure B, DTB-DPPBz (11.6 mg, 0.013 mmol, 0.033 eq.), $Cu(OAc)_2$ (60 μL of a 0.2 M solution in THF, 0.012 mmol, 0.03 eq.), THF (0.140 mL), then dimethoxy(methyl) silane (148 μL, 1.2 mmol, 3 eq) were combined in a 2-dram vial followed by addition of a solution of (S)-4,8-Dimethylnona-1,7-diene (61 mg, 0.40 mmol, 1 eq.), THF (0.200 mL), 2-propanol-$d_8$ (57 μL, 1.0 mmol, 2.5 eq.). The 2-dram vial was capped with a red pressure relief cap, and the reaction stirred for 24 h at 40° C. Upon completion, the crude product mixture was dry loaded onto a silica gel column. Flash column chromatography (200 mL of 100% HPLC hexanes) gave the pure product as a clear colorless oil (32 mg, 0.21 mmol, 53% yield).

$^1$H NMR (400 MHz, $CDCl_3$) δ 5.10 (t, J=7.3 Hz, 1H), 2.08-1.85 (m, 2H), 1.69 (s, 3H), 1.61 (s, 3H), 1.47-1.24 (m, 5H), 1.18-1.04 (m, 2H), 0.89-0.83 (m, 5.06H). $^2$H NMR (61 MHz, $CHCl_3$) δ 0.87 (s, 0.94D). $^{13}$C NMR (101 MHz, $CDCl_3$) δ 131.10, 125.25, 39.43, 37.31, 32.31, 25.89, 25.73, 20.18, 19.70, 17.77, 14.26 (t, J=19.2 Hz). ATR-IR ($cm^{-1}$): 2957, 2923, 2851, 2363, 1462, 1376. HRMS: $EI^+$) m/z: $[M]^+$ Calcd for $C_{11}H_{21}D$, 155.1784; Found 155.1778.

(c) Mechanistic Probe

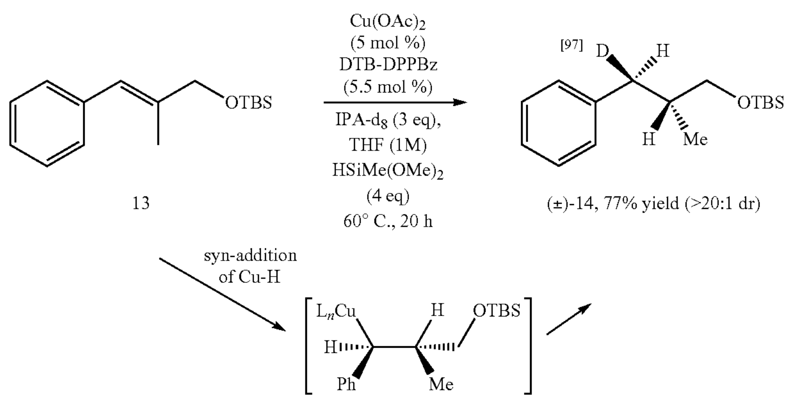

13

(±)-14, 77% yield (>20:1 dr)

2H), 0.91 (d, J=6.6 Hz, 3H), $^2$H NMR (61 MHz, $CDCl_3$) δ 2.60 (s, 0.99D). $^{13}$C NMR: (101 MHz, $CDCl_3$) δ 143.04, 131.15, 128.52, 128.37, 125.71, 125.15, 37.20, 36.77, 36.09 (t, J=19.6 Hz), 32.45, 29.09, 25.87, 25.70, 19.70, 17.77. ATR-IR ($cm^{-1}$): 3084, 2962, 2923, 2855, 2151, 1800, 1604, 740. HRMS: ($EI^+$) m/z. $[M]^+$ Calcd for $C_{17}H_{25}D$, 231.2100; Found 231.2091.

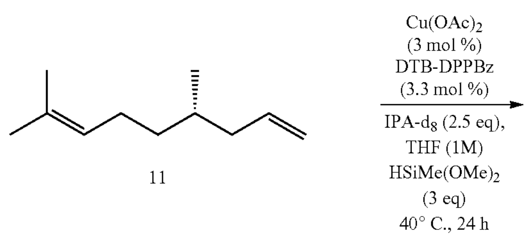

11 tert-butyldimethyl(2-methyl-3-phenylpropoxy-3-d)silane [anti-14]: According to the general procedure B, DTB-DPPBz (14.8 mg, 0.0165 mmol, 0.055 eq.). $Cu(OAc)_2$ (75 μL of a 0.2 M solution in THF, 0.015 mmol, 0.05 eq.). THF (0.075 mL), then dimethoxy(methyl)silane (148 μL, 1.20 mmol, 4 eq.) were combined in a 2-dram vial followed by addition of a solution of (E)-tert-butyldimethyl((2-methyl-3-phenylallyl)oxy)silane (79 mg, 0.30 mmol, 1 eq.), THF (0.150 mL), 2-propanol-$d_8$ (69 μL, 0.9 mmol, 3 eq.). The 2-dram vial was capped with a red pressure relief cap, and the reaction stirred for 24 h at 60° C. Upon completion, the crude product mixture was dry loaded onto a silica gel column. Flash chromatography using gradient elution (200 mL of 100% HPLC hexanes, 100 mL 1% ethyl acetate in HPLC hexanes) gave the pure product as a clear colorless oil (62 mg, 0.23 mmol, 77% yield).[4,5]

$^1$H NMR (400 MHz, CDCl3) δ 7.29 (t, J=7.4 Hz, 2H), 7.24-7.15 (m, 3H), 3.46 (d, J=5.9 Hz, 2H), 2.87-2.78 (m, 0.03H), 2.32 (d, J=8.4 Hz, 1H), 1.90 (hept, J=6.1 Hz, 1H), 0.94 (s, 9H), 0.88 (d, J=6.7 Hz, 2H), 0.07 (s, 6H). *We attribute the signal at 2.87-2.78 ppm that integrates to 0.03 to the do impurity, which is consistent with the measurements in scheme 3. $^{2}H$ NMR (61 MHz, CHCl3) δ 2.83 (s, 0.97H). $^{13}C$ NMR (101 MHz, $CDCl_3$) δ 141.29, 129.36, 128.24, 125.79, 67.62, 39.35 (t, J=19.5 Hz), 38.00, 26.11, 18.49, 16.56, −5.20 (d, J=3.1 Hz). ATR-IR ($cm^{-1}$): 3026, 2954, 2928, 2157, 1802, 1605, 1087. HRMS: ($EI^+$) m/z: $[M]^+$ Calcd for $C_{12}H_{18}DOSi$ 208.1300; Found 208.1260. The major ion peak represents the parent molecule after loss of the t-Bu cation.

VIII. References Cited

1. Nishikawa, D.; Hirano, K.; Miura, M., Asymmetric Synthesis of α-Aminoboronic Acid Derivatives by Copper-Catalyzed Enantioselective Hydroamination. J. Am. Chem. Soc. 2015, 137, 15620-15623.
2. Wrackmeyer, B., Carbon-13 NMR spectroscopy of boron compounds. Progress in Nuclear Magnetic Resonance Spectroscopy 1979, 12, 227-259.
3. Sloane, S. E.; Reyes, A.; Vang, Z. P.; Li, L.; Behlow, K. T.; Clark, J. R., Copper-Catalyzed Formal Transfer Hydrogenation/Deuteration of Aryl Alkynes. Org. Lett. 2020, 22, 9139-9144.
4. Bunlaksananusorn, T.; Knochel, P. t-BuOK-Mediated Hydrophosphination of Funcitonalized Alkenes: A Novel Synthesis of Chiral P,N- and PP-Ligands. J. Org. Chem. 2004, 69, 4595-4601.
5. Eno, M. S.; Lu, A.; Morken, J. P., Nickel-Catalyzed Asymmetric Kumada Cross-Coupling of Symmetric Cyclic Sulfates. J. Am. Chem. Soc. 2016, 138, 7824-7827.
6. Hsu, M. C.; Junia, A. J.; Haight, A. R.; Zhang, W., Synthesis of Erythromycin Derivatives via the Olefin Cross-Metathesis Reaction. J. Org. Chem. 2004, 69, 3907-3911.
7. He, S.-J.; Wang, B.; Lu, X.; Gong, T.-J.; Yang, Y.-N.; Wang, X.-X.; Wang, Y.; Xiao, B.; Fu, Y., Copper-Catalyzed Reagent-Controlled Regioselective Cyanoborylation of Vinylarenes. Org. Lett. 2018, 20, 5208-5212.
8. Ikawa, T.; Hattori, K.; Sajiki, H.; Hirota, K., Solvent-modulated Pd/C-catalyzed deprotection of silyl ethers and chemoselective hydrogenation. Tetrahedron 2004, 60, 6901-6911.
9. Faler, C. A.; Joullié, M. M., The Kulinkovich Reaction in the Synthesis of Constrained N,N-Dialkyl Neurotransmitter Analogues. Org. Lett. 2007, 9, 1987-1990.
10. Snider, B. B.; Grabowski, J. F., Synthesis of the 5-hydroxymethyl-6-aryl-8-oxabicyclo[3.2.1]oct-3-en-2-one natural products descurainin and cartorimine. Tetrahedron 2006, 62, 5171-5177.
11. González-Pluma. M.; Elizalde, L.; Saldivar-Guerra, E.; Telles-Padilla, G.; Raquel, L.; Flores-Guerrero, M., Synthesis of Styrene Monomers Hydroxyl Functionalized. Journal of Macromolecular Science: Pure & Applied Chemistry 2013, 50, 1107-1112.
12. Gøgsig, T. M.; Søbjerg, L. S.; Lindhardt, A. T., Jensen. K. L.; Skrydstrup, T., Direct Vinylation and Difluorovinylation of Arylboronic Acids Using Vinyl- and 2,2-Difluorovinyl Tosylates via the Suzuki-Miyaura Cross Coupling. J. Org. Chem. 2008, 73, 3404-3410.
13. Peyroux, E.; Berthiol, F.; Doucet, H.; Santelli, M., Suzuki Cross-Coupling Reactions between Alkenylboronic Acids and Aryl Bromides Catalysed by a Tetraphosphane-Palladium Catalyst. European Journal of Organic Chemistry 2004, 2004, 1075-1082.
14. Tew, G. N.; Pralle, M. U.; Stupp, S. I., Supramolecular Materials with Electroactive Chemical Functions. Angew. Chem. Int. Ed. 2000, 39, 517-521.
15. Greenhalgh, M. D.; Frank, D. J.; Thomas, S. P., Iron-Catalysed Chemo-, Regio-, and Stereoselective Hydrosilylation of Alkenes and Alkynes using a Bench-Stable Iron(II) Pre-Catalyst. Advanced Synthesis & Catalysis 2014, 356, 584-590.
16. Zubar, V.; Sklyaruk, J.; Brzozowska, A.; Rueping, M., Chemoselective Hydrogenation of Alkynes to (Z)-Alkenes Using an Air-Stable Base Metal Catalyst. Org. Lett. 2020, 22, 5423-5428.
17. Al-Etaibi, A. M. I., M. R., Ibrahim, Y. A.; Al-Awadi, N. A., Gas-Phase Pyrolytic Reaction of 4-Aryl-3-buten-2-ols and Allyl Benzyl Ethers: Kinetic and Mechanistic Study. Molecules 2010, 15, 407-419.
18. Michel, N. W. M.; Jeanneret, A. D. M.; Kim, H.; Rousseaux, S. A. L., Nickel-Catalyzed Cyanation of Benzylic and Allylic Pivalate Esters. J. Org. Chem. 2018, 83 (19), 11860-11872.
19. Furuya, T.; Strom, A. E.; Ritter, T., Silver-Mediated Fluorination of Functionalized Aryl Stannanes. J. Am. Chem. Soc. 2009, 131, 1662-1663.
20. Skoda-Földes, R.; Kollár. L.; Marinelli, F.; Arcadi, A., Direct and carbonylative vinylation of steroidal triflates in the presence of homogeneous palladium catalysts. Steroids 1994, 59, 691-695.
21. Landge, V. G.; Babu, R.; Yadav, V.; Subaramanian, M.; Gupta, V.; Balaraman, E., Iron-Catalyzed Direct Julia-Type Olefination of Alcohols. J. Org. Chem. 2020, 85, 9876-9886.
22. Denmark. S. E.; Butler, C. R., Vinylation of Aromatic Halides Using Inexpensive Organosilicon Reagents. Illustration of Design of Experiment Protocols. J. Am. Chem. Soc. 2008, 130, 3690-3704.
23. Bhawal, B. N.; Reisenbauer, J. C.; Ehinger, C.; Morandi, B., Overcoming Selectivity Issues in Reversible Catalysis: A Transfer Hydrocyanation Exhibiting High Kinetic Control. J. Am. Chem. Soc. 2020, 142, 10914-10920.
24. Melnik. K.; Menke, M., Rakotoarison, M. V.; Schulz, S. Identification and Synthesis of Luteolide, a Highly Branched Macrolide Semichemical from the Mantellid Frog Gephyromantis luteus. Org. Lett. 2019, 21, 2851-2854.
25. Kondoh, A.; Tasato, N.; Aoki, T.; Terada, M., Brønsted Base-Catalyzed Transformation of α,β-Epoxyketones Utilizing [1,2]-Phospha-Brook Rearrangement for the Synthesis of Allylic Alcohols Having a Tetrasubstituted Alkene Moiety. Org. Lett. 2020, 13, 5170-5175.

Example 7—Highly Regioselective Copper-Catalyzed Transfer Hydrodeuteration of Unactivated Terminal Alkenes Reference is made to the manuscript: Reyes et al., "Highly Regioselective Copper-Catalyzed Transfer Hydrodeuteration of Unactivated Terminal Alkenes," to be submitted for publication to Angewandte Chemie International Edition.

Abstract: Catalytic transfer hydrodeuteration of unactivated alkenes is challenging because of the requirement that chemically similar hydrogen and deuterium undergo selective insertion across a π-bond. We now report a highly regioselective catalytic transfer hydrodeuteration of unactivated terminal alkenes across a variety of heteroatom or heterocycle containing substrates. The base-metal catalyzed reaction is also demonstrated on two complex natural products. Reaction studies indicate modular conditions that can also be extended to perform either an alkene transfer hydrogenation or transfer deuteration.

Selectively deuterated small molecules are extensively used in chemical research and in pharmaceuticals. In chemical research, they can serve as probes for mechanistic studies or for the determination of a kinetic isotope effect.[1-4] They are useful tools for determining the stereochemical outcome of reactions,[5-8] and selectively labeled molecules have even been used in total synthesis to control reaction selectivity in key transformations.[9-11] In pharmaceuticals, deuterium is selectively incorporated at sites prone to metabolic oxidation as a strategy to alter the pharmacokinetics of a small molecule drug.[12-17] This has the potential to improve the safety profile of therapeutics without altering the potency and efficacy of the parent drug.[18, 19] These applications have driven demand for the development of precision deuteration reactions, in which deuterium is precisely installed at the target site within a small organic molecule.[12, 15, 20]

Catalytic transfer hydrodeuteration is an emerging area in organic synthesis for the selective deuteration of alkenes (Scheme 1).[20] A unique attribute of transfer hydrodeuteration is that hydrogen (H) can be distinguished from deuterium (D) for regioselective installation across a π-bond. Catalytic transfer hydrodeuteration reactions also obviate the use of $H_2$. HD or $D_2$ gas but can still be reactive with less activated alkene types, especially those found to be unreactive under other reductive deuteration protocols.[21, 22] Despite these benefits, selectivity and reactivity issues persist. Catalytic transfer hydrodeuteration reactions that are highly regioselective are typically limited to activated 1,1-disubstituted and trisubstituted alkenes (Scheme 1a),[21-25] or activated alkenes in conjugation with a carbonyl (e.g. α,β-unsaturated ketone substrates).[20, 26] Alternatively, a Pd-catalyzed transfer hydrodeuteration has been reported for terminal styrenes but is only moderately regioselective and not demonstrated on internal aryl alkenes or unactivated terminal alkene substrate types (Scheme 1b).[27]

We recently reported a mild and general Cu-catalyzed transfer hydrodeuteration reaction that regioselectively incorporates one H and one D across both terminal and internal aryl alkene substrates to make $d_1$-alkanes selectively deuterated at the benzylic position (Scheme 1c).[28] Encouragingly, this report included one example of an unactivated terminal alkene undergoing regioselective transfer hydrodeuteration, however it required that we change the deuterium source to isopropanol-$d_8$ and increase the catalyst loading to 3 mol %. While this single example was successful, we were intrigued that reactions of unactivated terminal alkenes generally did not reach full conversion and trace alkene isomerization byproduct was forming under the standard conditions for promoting alkenyl arene transfer hydrodeuteration (Table 1, entry 1). This was problematic for two reasons. Firstly, unreacted starting material is oftentimes inseparable from the desired product using standard flash chromatography purification techniques. Secondly, an alkene isomerization byproduct is not only inseparable from the desired product but could undergo transfer hydrodeuteration, and thus form inseparable and complex isotopomer product mixtures.

Scheme 1. Catalytic Alkene Hydrodeuteration (THD) Overview a) Hilt (2021)

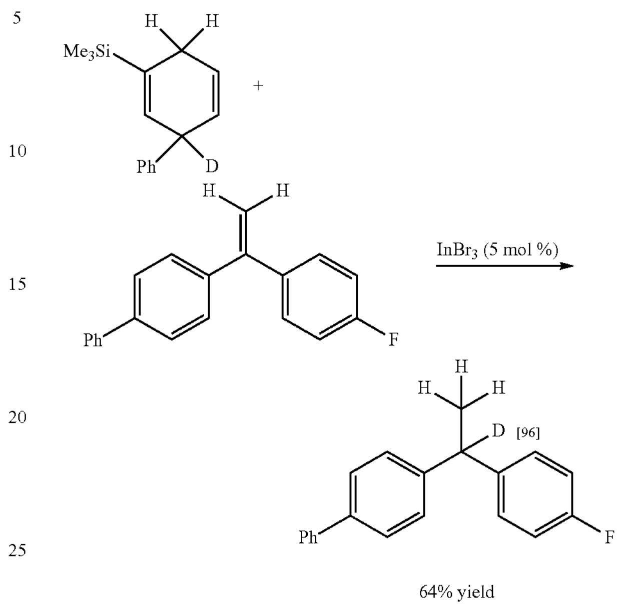

limited to 1,1-disubstituted and trisubstituted aryl alkenes b) Wu & Cui (2020)

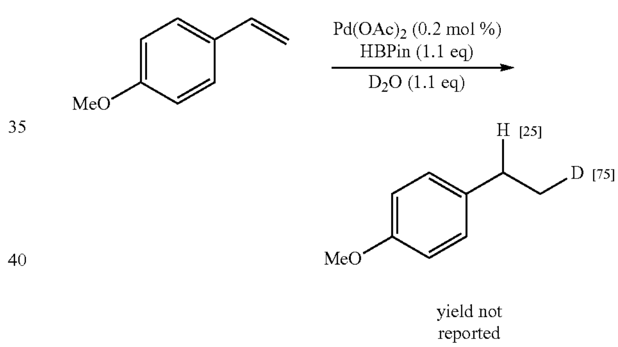

moderately regioselective
no unactivated terminal alkene examples c) Clark (2021)

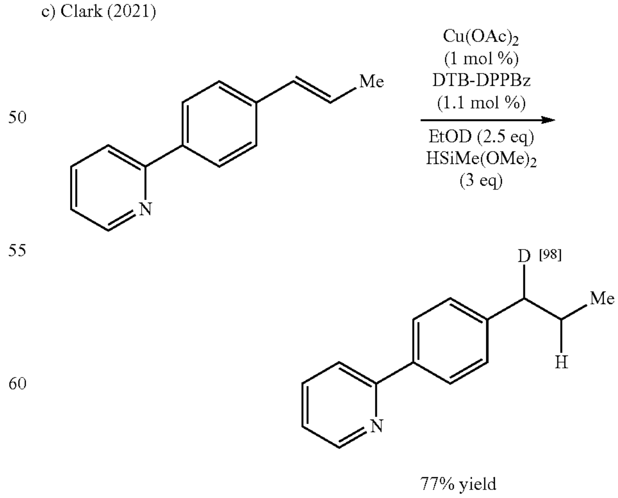

highly regioselective across a broad scope of aryl alkenes
only one example of a terminal unactivated alkene -continued d) Webster (2019)

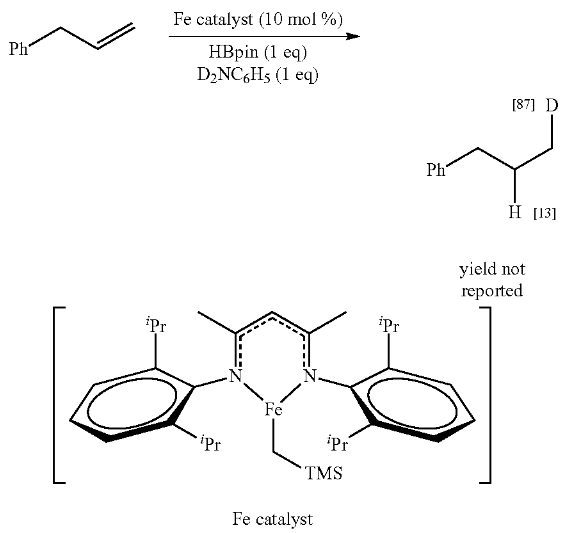

limited scope of unactivated terminal alkenes
isomerization products possible e) This Work

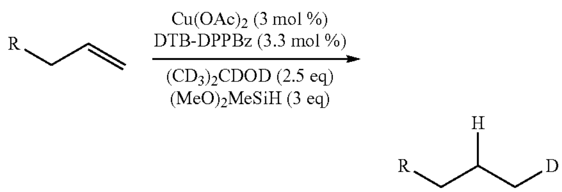

Highly Regio/Chemoselective
High FG Compatibility
Commercial H/D Sources
No Alkene Isomerization
Late-Stage Applications To the best of our knowledge, there exists only two other reports in which metal-catalyzed unactivated terminal alkene transfer hydrodeuteration is performed.[29, 30] Although very few examples of unactivated terminal alkene substrates are reported (Scheme 1d), these fundamental works by Webster and coworkers underscore the reactivity and selectivity challenges hindering the development of a general protocol for selectively installing H and D across an unactivated alkene type (Scheme 1d). While protocols that employ $H_2$, HD or $D_2$ gas are sometimes reactive with unactivated alkenes, they are insufficient at discriminating between H and D for regioselective hydrodeuteration.[31, 32] Under catalytic transfer hydrodeuteration conditions, a different challenge arises where catalysts that react with unactivated terminal alkenes can also promote competing alkene isomerization pathways which can lead to mixtures of inseparable isotopomers.[29, 30, 33]

Given the mild and general protocol we established for the transfer hydrodeuteration of alkenyl arene substrates, we were interested in exploring alternate reactions conditions to extend reactivity to unactivated terminal alkenes while retaining the high reaction selectivities found in our initial report.[28] The regioselectivity of the Cu—H addition across a terminal unactivated alkene is likely influenced by the steric environment of the substrate, where Cu adds to the least sterically hindered alkene position. This has been elegantly demonstrated in several Cu—H catalyzed terminal alkene hydrofunctionalization reactions.[34-37] Therefore, to unlock a highly selective and general terminal unactivated alkene transfer hydrodeuteration, we sought to uncover reaction conditions that quell alkene isomerization pathways and promote full conversion of the alkene to the desired deuterated product. We now report a Cu-catalyzed transfer hydrodeuteration that is both highly reactive for unactivated terminal alkenes and highly regioselective for the precise installation of H and D across the alkene (Scheme 1e).

TABLE 1

Reaction Optimization[a]

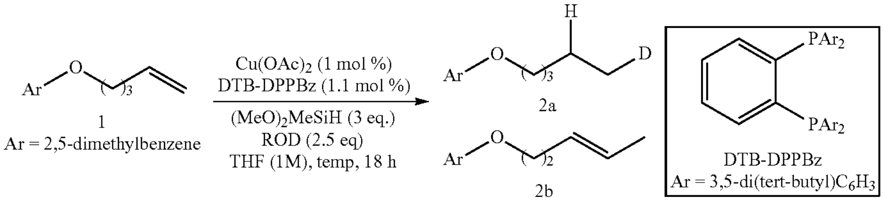

| Entry | Temp. | D-source | 1 (%)[b] | 2a (%)[b] | 2b (%)[b] |
|---|---|---|---|---|---|
| 1 | 40° C. | EtOD | 23 | 60 | 3 |
| 2 | 60° C. | EtOD | — | 85 | 7 |
| 3 | 23° C. | EtOD | 55 | 22 | 5 |
| 4[c] | 40° C. | EtOD | 32 | 34 | 3 |
| 5[d] | 40° C. | EtOD | 42 | 39 | — |
| 6[e] | 40° C. | EtOD | 80 | — | — |
| 7 | 40° C. | IPA-$d_8$ | 6 | 70 | — |
| 8[f] | 40° C. | IPA-$d_8$ | — | 90 | — |
| 9[f] | 40° C. | tBuOD | — | 55 | — |

TABLE 1-continued

| | | | | | |
|---|---|---|---|---|---|
| 10[f] | 40° C. | MeOD | 85 | 3 | — |
| 11[f,g] | 40° C. | IPA-$d_8$ | 7 | 80 | — |

[a]All reactions preformed on a 0.2 mmol scale.
[b]Yields were determined after purification by flash chromatography.
[c]Reaction performed at 2M concentration.
[d]Reaction performed with $PhCH_3$ instead of THF.
[e]Reaction performed with $CH_2Cl_2$ instead of THF.
[f]Reaction performed with 3 mol % $Cu(OAc)_2$ and 3.3 mol % DTB-DPPBz.
[g]Reaction performed with polymethylhydrosiloxane instead of dimethoxymethylsilane.

Returning to the conditions previously reported by our research group for Cu-catalyzed aryl alkene transfer hydrodeuteration, we recognized the necessity to optimize the reaction for complete conversion of alkene 1 to precisely deuterated alkane 2a without promoting the formation of byproduct 2b (Table 1).[28] Unactivated terminal alkene 1 was chosen as the optimization substrate because the terminal alkene is distal from functionality. Compared to our previously reported conditions (entry 1), efforts to increase the yield of desired product 2a were successful by increasing the reaction temperature to 60° C., however this also led to a slightly higher yield of alkene isomerization byproduct 2b that no isomerization product was seen in the crude $^1$H NMR or after purification. In a previous study by our group, we performed a Cu-catalyzed alkyne transfer hydrogenation reaction using isopropanol as one of the H-sources.[41] This study revealed that hydrometalation of the alkene likely occurs in a reversible manner, similar to what is depicted in step i of the proposed alkene transfer hydrodeuteration mechanism (Scheme 2). In the present study, we hypothesize that a Markovnikov addition of the Cu—H across the alkene can lead to formation of the alkene isomerization byproduct. If step i is reversible, this could account for the isomerization product no longer being formed.

Scheme 2. Mechanistic Hypothesis

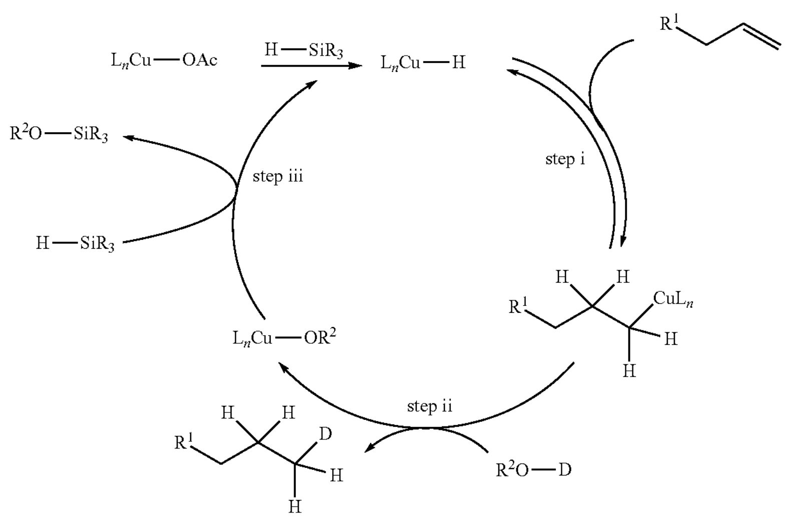

(entry 2). Performing the reaction at room temperature resulted in lower conversion to product 2a and alkene isomerization byproduct was still formed (entry 3). Doubling the reaction concentration also led to a low yield of 2a and trace 2b (entry 4). Changing the reaction solvent to $PhCH_3$ led to a suboptimal yield of 2a while changing to $CH_2Cl_2$ completely inhibited the reaction (entries 5-6). In both cases, no alkene isomerization was detected.

The role of the alcohol and/or silane in Cu-catalyzed alkene and alkyne hydrofunctionalization processes has been previously studied.[28, 38-43] Given that changing temperature, concentration and solvent did not lead to an optimal reaction, we decided to explore other alcohol-OD sources. The alcohol-OD reagent is important in the reaction because it is involved in both the deuterodecupration step (Scheme 2, step ii) and transmetalation step (step iii). We examined using isopropanol-$d_8$ instead of ethanol-OD and isolated the desired product 2a in a higher yield relative to entry 1 (Table 1, entry 7). Furthermore, we were surprised We discovered that full conversion of alkene 1 can be achieved by increasing the catalyst loading to 3 mol % (entry 8, 90% yield of 2a, >20:1 r.r.). Consistent with entry 7, no alkene isomerization byproduct was detected when using isopropanol-$d_8$. We also observed that no alkene isomerization byproduct was detected using the sterically hindered tBuO-D reagent (entry 9). However, only a moderate 55% yield of the desired product was isolated. Switching to the less sterically encumbered $CH_3OD$ led to minimal conversion of alkene 1 to product 2a (entry 10). Lastly, changing the silane reagent to polymethylhydrosiloxane (PMHS) led to a slight decrease in yield because full conversion of alkene 1 to product 2a was not achieved (entry 11).

The substrate scope of unactivated alkenes was investigated on organic molecules containing a 1-pentene substituent (Scheme 3). The reaction was highly chemoselective for alkene transfer hydrodeuteration in the presence of Br, Cl, F or $CF_3$ substituted arenes (4a-4e, 58-93% yield). Importantly, no reductive deuterodehalogenation side products were observed in these reactions. The reaction was also chemoselective for alkene hydrodeuteration in the presence of a tosyl or benzyl protected alcohol (4f-4g, 63-90% yield). Phenol derivatives where the arene is substituted with either a phenyl, tert-butyl, methoxy or phenoxy group efficiently undergo transfer hydrodeuteration at the pendant unactivated terminal alkene (4h-4k, 68-90% yield). The hydrodeuteration protocol was also examined in substrates containing heterocycles commonly found in small molecule drugs and drug candidates.[44-46] This included substrates with N-containing heterocycles such as indole, tetrahydroquinoline, pyridine, pyrimidine, carbazole and piperazine (4l-4q, 83-91%). Even a terminal alkene substrate containing a remote thiophene heterocycle underwent regioselective transfer hydrodeuteration in good yield (4r, 83% yield). Lastly, an aniline containing substrate performed well in the reaction (4s, 65% yield).

Scheme 3. Unactivated dTerminal Alkene Substrate Scope

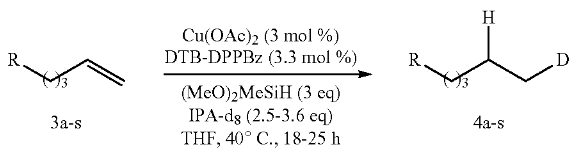

3a-s 4a-s

4a

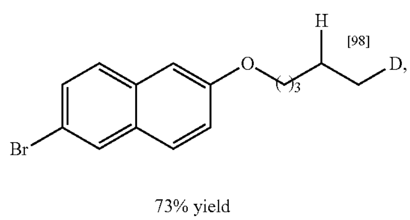

73% yield

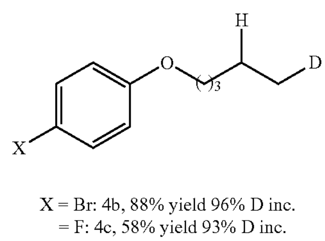

X = Br: 4b, 88% yield 96% D inc.
= F: 4c, 58% yield 93% D inc.

4d

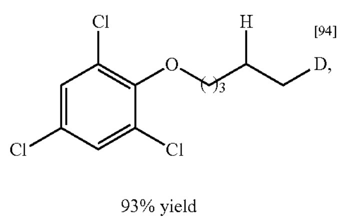

93% yield

4e

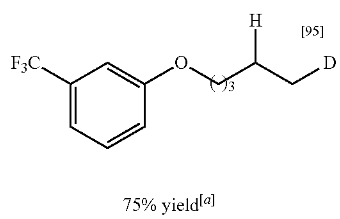

75% yield[a]

-continued

4f

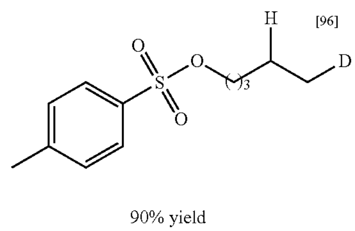

90% yield

4g

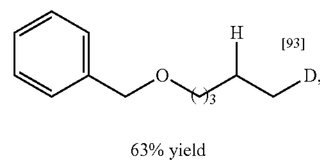

63% yield

4h

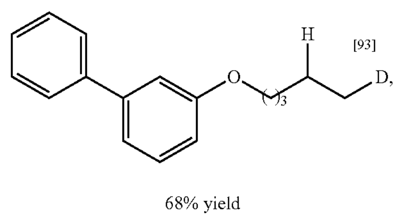

68% yield

4i

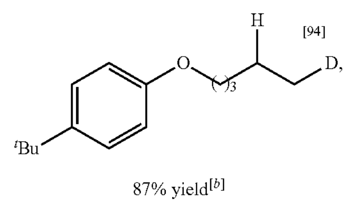

87% yield[b]

4j

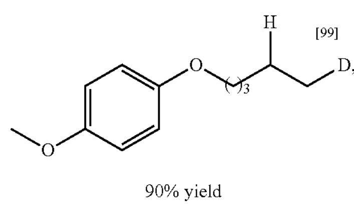

90% yield

4k

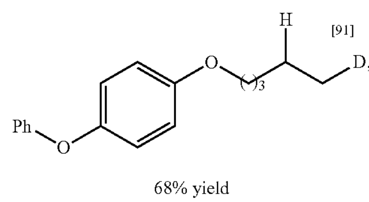

68% yield

4l

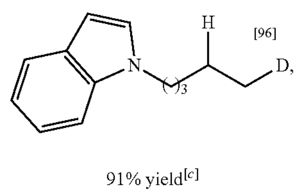

91% yield[c]

-continued

4m

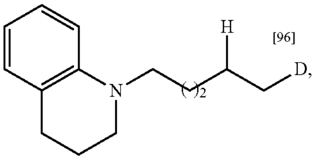

83% yield[b]

4n

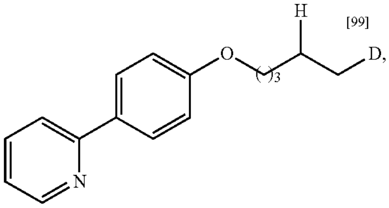

83% yield

4o

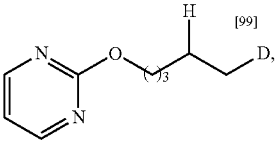

87% yield

4p

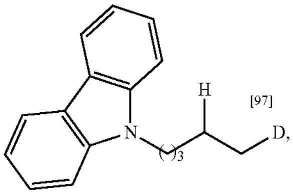

90% yield

4q

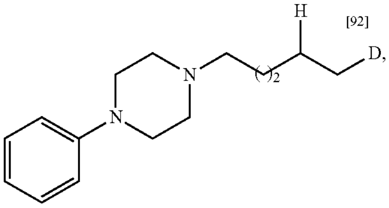

90% yield

4r

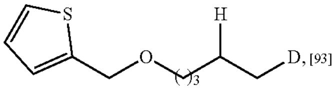

83% yield

4s

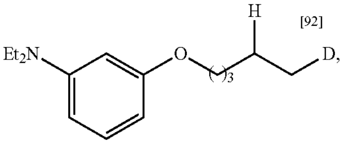

65% yield

[a]4 eq of silane used. [b]4-4.4 mol % $Cu(OAc)_2$, 4.4-4.8 mol % DTB-DPPBz, 4-4.6 eq DMMS used. [c]6 mol % DTB-DPPBz, 4.8 eq. DMMS used.

The reaction was also evaluated in substrates not containing a 1-pentene chain (Scheme 4). Allyl benzene, a substrate type known to undergo a thermodynamically driven metal hydride catalyzed alkene isomerization,[30, 47] underwent hydrodeuteration with high precision at the terminal alkene (6a, 61% yield by $^1H$ NMR). In a similar fashion, methyl eugenol was precisely deuterated at the terminal position when subjected to the Cu-catalyzed transfer hydrodeuteration protocol (6b, 93% yield). Importantly, no deuterium was detected at any other position when 6b was isolated and evaluated by $^1H$, $^2H$ and $^{13}C$ NMR Evaluation of an epoxide-containing substrate revealed hydrodeuteration of the terminal alkene as the major product (6c, 83% yield). No epoxide opening products were observed in this case. We also found that a butene appended to 3-phenylphenol also undergoes regioselective hydrodeuteration in high yield (6d, 90%, yield).

Catalytic alkene transfer hydrodeuteration has been scarcely reported in complex natural product settings.[28] and to the best of our knowledge, there are no reports of unactivated alkenes undergoing alkene transfer hydrodeuteration in complex small molecule settings.[20] Estrone and δ-tocopherol natural product derivatives, each containing a pendant terminal alkene, were evaluated under the Cu-catalyzed transfer hydrodeuteration conditions. In both cases, high yields and regioselectivities were observed after isolation of the deuterated products (6e-6f, 83-85% yield).

Scheme 4. Scope of Various Alkene Chain Lengths and Natural Product Analogs

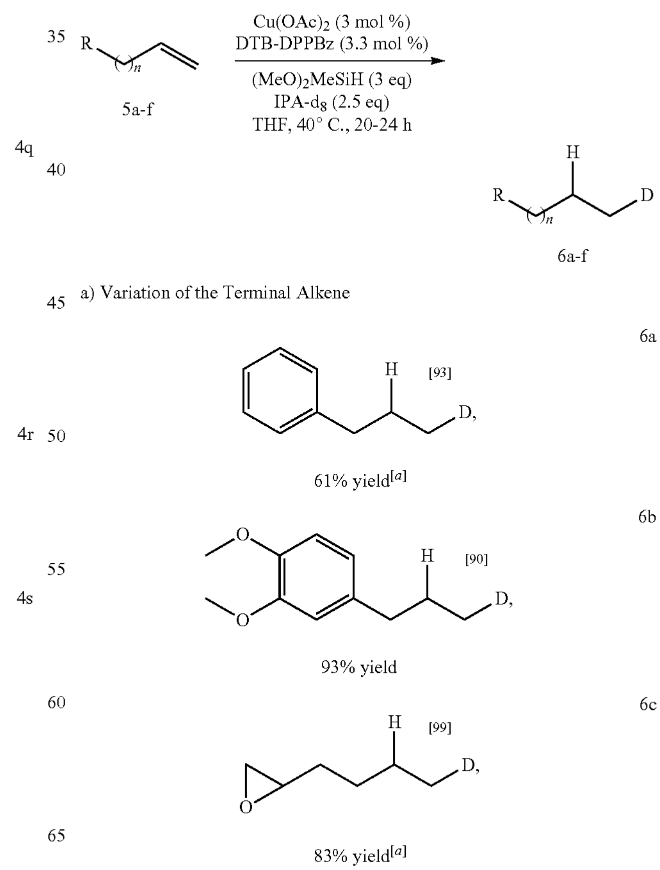

-continued

6d

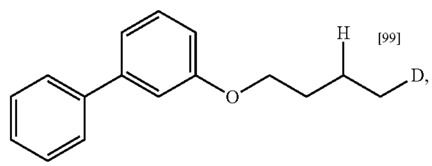

90% yield b) Natural Product Analogs

6e

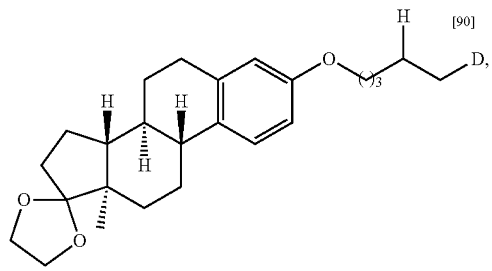

85% yield

6f

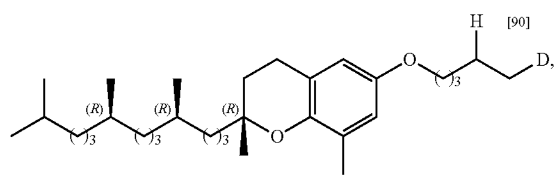

83% yield[b]

[a]Yield determined by $^1$H NMR analysis using 1,3,5-trimethylbenzene as an internal standard. [b]Reaction performed at 60° C.

Due to the modularity of the Cu-catalyzed transfer hydrodeuteration protocol, the corresponding transfer hydrogenation and transfer deuteration protocols can be readily carried out. Returning to substrate 3d, transfer hydrogenation occurs in high yield by simply replacing isopropanol-$d_8$ with isopropanol (Scheme 5a, 7, 90% yield). Changing to the readily accessible Si-D derivative of dimethoxymethylsilane and isopropanol-$d_8$, the corresponding alkene transfer deuteration can also be performed. This led to a 93% yield of the di-deuterated product 8 (Scheme 5b). The reaction was also performed on an oleic acid derivative to evaluate the reaction chemoselectivity when two alkenes are present in a molecule. Importantly, this natural product derivative contains both a cis-internal alkene and a terminal alkene. Under the optimal reaction conditions, only hydrodeuteration of the terminal alkene was observed and product 10 was obtained in excellent yield (Scheme 5c, 90% yield).

Scheme 5. Reaction Modularity and Chemoselectivity Studies a) Alkene Transfer Hydrogenation

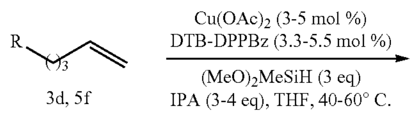

3d, 5f

-continued

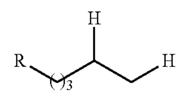

7-8

7

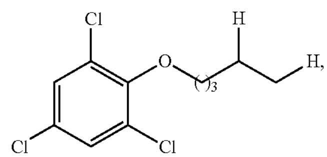

90% yield

8

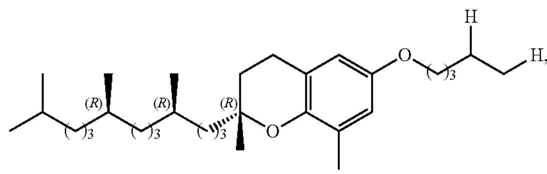

75% yield b) Alkene Transfer Deuteration

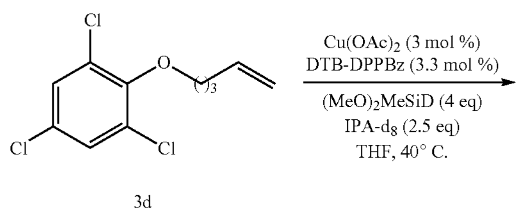

3d

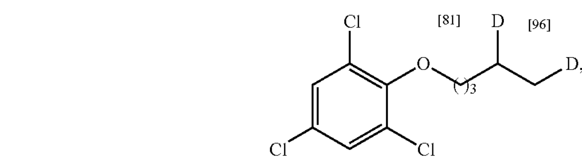

93% yield c) Chemoselective Study

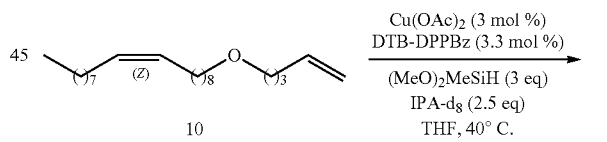

10

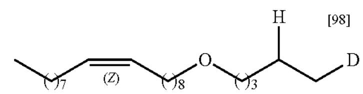

11, 90% yield

In conclusion, a highly regioselective Cu-catalyzed transfer hydrodeuteration of unactivated alkenes is reported. This transformation fills a major void in catalytic transfer hydrodeuteration of alkenes because targeted deuteration can be performed on unactivated terminal alkene substrates in order to make small molecules precisely deuterated at the terminal carbon position. We found that more sterically encumbered alcohol-OD reagents obviate alkene isomerization byproducts and lead to exclusive formation of the desired precisely deuterated alkane product with excellent levels of regioselectivity. A diverse array of functionality is compatible in the reported transformation. In addition to several heterocycle-containing alkene substrates undergoing selective hydrodeuteration, two complex natural product analogs also proved successful in the reaction. The modularity of the reaction permits that both the corresponding alkene transfer hydrogenation and deuteration reactions can be readily carried out. We envision these protocols will find important applications in the development of precisely deuterated pharmaceuticals and isotopically pure deuterated small molecule reaction probes. Ongoing studies in our research group are focused on examining the role that sterically encumbered alcohol reagents play in obviating alkene isomerization pathways.

REFERENCES

[1] Simmons, E. M.; Hartwig, J. F., On the Interpretation of Deuterium Kinetic Isotope Effects in C—H Bond Functionalizations by Transition-Metal Complexes. *Angew. Chem. Int. Ed.* 2012, 51, 3066-3072.

[2] Giagou, T.; Meyer, M. P., Kinetic Isotope Effects in Asymmetric Reactions. *Chem.—Eur. J* 2010, 16, 10616-10628.

[3] Meek, S. J.; Pitman, C. L.; Miller, A. J. M., Deducing Reaction Mechanism: A Guide for Students, Researchers, and Instructors. *J Chem. Educ.* 2016, 93, 275-286.

[4] Gómez-Gallego, M.; Sierra. M. A., Kinetic Isotope Effects in the Study of Organometallic Reaction Mechanisms. *Chem. Rev.* 2011, 111, 4857-4963.

[5] Chen, Y.; Tang, W. L.; Mou, J.; Li, Z., High-Throughput Method for Determining the Enantioselectivity of Enzyme-Catalyzed Hydroxylations Based on Mass Spectrometry. *Angew. Chem. Int. Ed.* 2010, 49, 5278-5283.

[6] White, R. E., Miller, J. P.; Favreau. L. V.; Bhattacharyya, A., Stereochemical dynamics of aliphatic hydroxylation by cytochrome P450. *J. Am. Chem. Soc.* 1986, 108, 6024-6031.

[7] Alberti, M. N.; Vassilikogiannakis, G.; Orfanopoulos, M., Stereochemistry of the Singlet Oxygenation of Simple Alkenes: A Stereospecific Transformation. *Org. Lett.* 2008, 10, 3997-4000.

[8] Schwab, J. M., Stereochemistry of an enzymic Baeyer-Villiger reaction. Application of deuterium NMR. *J. Am. Chem. Soc.* 1981, 103, 1876-1878.

[9] Quasdorf. K. W.; Huters, A. D.; Lodewvk, M. W.; Tantillo, D. J.; Garg, N. K., Total Synthesis of Oxidized Welwitindolinones and (−)-N-Methylwelwitindolinone C Isonitrile. *J. Am. Chem. Soc.* 2012, 134, 1396-1399.

[10] Miyashita, M.; Sasaki, M.; Hattori, I.; Sakai, M.; Tanino, K., Total Synthesis of Norzoanthamine. *Science* 2004, 305, 495-499.

[11] Vedejs. E.; Little, J., Aziridinomitosenes by Anionic Cyclization: Deuterium as a Removable Blocking Group. *J. Am. Chem. Soc.* 2002, 124, 748-749.

[12] Pirali, T.; Serafini, M.; Cargnin, S.; Genazzani, A. A., Applications of Deuterium in Medicinal Chemistry. *J Med. Chem.* 2019, 62, 5276-5297.

[13] Atzrodt, J.; Derdau. V.; Kerr, W. J.; Reid, M., Deuterium- and Tritium-Labelled Compounds: Applications in the Life Sciences. *Angew. Chem. Int. Ed.* 2018, 57, 1758-1784.

[14] Stepan, A. F.; Mascitti, V.; Beaumont. K.; Kalgutkar, A. S., Metabolism-guided drug design. *Med Chem. Commun.* 2013, 4, 631-652.

[15] Cargnin, S.; Serafini, M.; Pirali, T., A primer of deuterium in drug design. *Future Med. Chem.* 2019, 11, 2039-2042.

[16] Gant, T. G., Using Deuterium in Drug Discovery: Leaving the Label in the Drug. *J. Med. Chem.* 2014, 57, 3595-3611.

[17] Meanwell, N. A., Synopsis of Some Recent Tactical Application of Bioisosteres in Drug Design. *J Med. Chem.* 2011, 54, 2529-2591.

[18] Schmidt, C., First deuterated drug approved. *Nat. Biotechnol.* 2017, 35, 493-494.

[19] Nelson, S. D.; Trager, W. F., The Use of Deuterium Isotope Effects to Probe the active site properties, Mechanism of Cytochrome P450-Catalyzed Reactions, and Mechanisms of Metabolically Dependent Toxicity. *Drug Metab. Dispos.* 2003, 31, 1481-1498.

[20] Vang, Z. P.; Hintzsche, S. J.; Clark, J. R., Catalytic Transfer Deuteration and Hydrodeuteration. Emerging Techniques to Selectively Transform Alkenes and Alkynes to Deuterated Alkanes. *Chem. —Eur. J.* 2021, 27, 9988-1000.

[21] Ning, L.; Li, H.; Lai, Z.; Szostak, M.; Chen, X.; Dong, Y.; Jin, S.; An, J., Synthesis of α-Deuterated Primary Amines via Reductive Deuteration of Oximes Using D2O as a Deuterium Source. *J. Org. Chem.* 2021, 86, 2907-2916.

[22] Li, H.; Zhang, B., Dong, Y.; Liu, T.; Zhang, Y.; Nie, H.; Yang, R.; Ma, X.; Ling, Y.; An, J., A selective and cost-effective method for the reductive deuteration of activated alkenes. *Tetrahedron Lett.* 2017, 58, 2757-2760.

[23] Walker, J. C. L.; Oestreich, M., Regioselective Transfer Hydrodeuteration of Alkenes with a Hydrogen Deuteride Surrogate Using B(C6F5)3 Catalysis. *Org. Lett.* 2018, 20, 64114414.

[24] Li, L.; Hilt, G., Regiodivergent DH or HD Addition to Alkenes: Deuterohydrogenation versus Hydrodeuterogenation. *Org. Lett.* 2020, 22, 1628-1632.

[25] Li, L.; Hilt, G., Indium Tribromide-Catalysed Transfer-Hydrogenation: Expanding the Scope of the Hydrogenation and of the Regiodivergent DH or HD Addition to Alkenes. *Chem. —Eur. J.* 2021, 27, 11221-11225.

[26] Yang, P.; Xu, H.; Zhou, J., Nickel-Catalyzed Asymmetric Transfer Hydrogenation of Olefins for the Synthesis of α- and β-Amino Acids. *Angew. Chem. Int. Ed.* 2014, 53, 12210-12213.

[27] Wang, Y.; Cao, X.; Zhao, L.; Pi, C.; Ji. J.; Cui, X.; Wu. Y., Generalized Chemoselective Transfer Hydrogenation/Hydrodeuteration. *Adv. Synth. Catal.* 2020, 362, 4119-4129.

[28] Vang, Z. P.; Reyes, A.; Sonstrom, R. E.; Holdren, M. S.; Sloane, S. E.; Alansari, I. Y.; Neill, J. L.; Pate, B. H.; Clark, J. R., Copper-Catalyzed Transfer Hydrodeuteration of Aryl Alkenes with Quantitative Isotopomer Purity Analysis by Molecular Rotational Resonance Spectroscopy. *J. Am. Chem. Soc.* 2021, 143, 7707-7718.

[29] Espinal-Viguri, M.; Neale, S. E.; Coles, N. T.; Macgregor, S. A.; Webster, R. L., Room Temperature Iron-Catalyzed Transfer Hydrogenation and Regioselective Deuteration of Carbon-Carbon Double Bonds. *J. Am. Chem. Soc.* 2019, 141, 572-582.

[30] Linford-Wood, T. G.; Coles, N. T.; Webster, R. L., Room temperature iron catalyzed transfer hydrogenation using n-butanol and poly(methylhydrosiloxane). *Green Chem.* 2021, 23, 2703-2709.

[31] Okuhara. T.; Tanaka. K.-I., Orientation in the addition of HD to butadiene on MoS2. *J. Chem. Soc., Chem. Commun.* 1976, 199-200.

[32] Okuhara. T.; Kondo, T.; Tanaka, K., Oriented adsorption of hydrogen deuteride on zinc oxide and addition to butadiene. *J. Phys. Chem.* 1977, 81, 808-809.

[33] Woof, C. R.; Durand. D. J.; Fey, N.; Richards, E.; Webster, R. L., Iron Catalyzed Double Bond Isomerization: Evidence for an FeI/FeIII Catalytic Cycle. *Chem.—Eur. J.* 2021, 27, 5972-5977.

[34] Liu, R. Y.; Buchwald, S. L., CuH-Catalyzed Olefin Functionalization: From Hydroamination to Carbonyl Addition. *Acc. Chem. Res.* 2020, 53, 1229-1243.

[35] Wang, H.; Buchwald, S. L., Copper-Catalyzed, Enantioselective Hydrofunctionalization of Alkenes. In *Org. React.,* 2020; pp 121-206.

[36] Zhu, S.; Niljianskul, N.; Buchwald, S. L., Enantio- and Regioselective CuH-Catalyzed Hydroamination of Alkenes. *J. Am. Chem. Soc.* 2013, 135, 15746-15749.

[37] Schuppe, A. W.; Knippel, J. L.; Borrajo-Calleja. G. M., Buchwald, S. L., Enantioselective Hydroalkenylation of Olefins with Enol Sulfonates Enabled by Dual Copper Hydride and Palladium Catalysis. *J. Am. Chem. Soc.* 2021, 143, 5330-5335.

[38] Mankad, N. P.; Laitar, D. S.; Sadighi, J. P., Synthesis, Structure, and Alkyne Reactivity of a Dimeric (Carbene) copper(I) Hydride. *Organometallics* 2004, 23, 3369-3371.

[39] Semba, K.; Fujihara, T.; Xu, T.; Terao, J.; Tsuji, Y., Copper-Catalyzed Highly Selective Semihydrogenation of Non-Polar Carbon-Carbon Multiple Bonds using a Silane and an Alcohol. *Adv. Synth. Catal.* 2012, 354, 1542-1550.

[40] Whittaker, A. M.; Lalic, G., Monophasic Catalytic System for the Selective Semireduction of Alkynes. *Org. Lett.* 2013, 15, 1112-1115.

[41] Sloane, S. E.; Reyes, A.; Vang, Z. P.; Li, L.; Behlow, K. T.; Clark, J. R., Copper-Catalyzed Formal Transfer Hydrogenation/Deuteration of Aryl Alkynes. *Org. Lett.* 2020, 22, 9139-9144.

[42] Jordan, A. J.; Lalic, G.; Sadighi, J. P., Coinage Metal Hydrides: Synthesis, Characterization, and Reactivity. *Chem. Rev.* 2016, 116, 8318-8372.

[43] Shi, S.-L.; Buchwald. S. L., Copper-catalysed selective hydroamination reactions of alkynes. *Nat. Chem.* 2015, 7, 38-44

[44] Taylor, R. D.; MacCoss, M.; Lawson, A. D. G., Rings in Drugs. *J. Med. Chem.* 2014, 57, 5845-5859.

[45] Vitaku, E.; Smith, D. T.; Njardarson, J. T., Analysis of the Structural Diversity, Substitution Patterns, and Frequency of Nitrogen Heterocycles among U.S. FDA Approved Pharmaceuticals. *J. Med Chem.* 2014, 57, 10257-10274.

[46] Das, P.; Delost, M. D.; Qureshi, M. H.; Smith, D. T.; Njardarson, J. T., A Survey of the Structures of US FDA Approved Combination Drugs. *J. Med. Chem.* 2019, 62, 4265-4311.

[47] Larionov, E.; Li, H.; Mazet, C., Well-defined transition metal hydrides in catalytic isomerizations. *Chem. Commun.* 2014, 50, 9816-9826.

Example 8—Supplementary Information for Example 7, Highly Regioselective Copper-Catalyzed Transfer Hydrodeuteration of Unactivated Terminal Alkenes

General Information

The following chemicals were purchased from commercial vendors and were used as received: $Cu(OAc)_2$ (99.999% from Alfa Aesar); 1,2-Bis[bis[3,5-di(t-butyl)phenyl]phosphino]benzene (Wako Pure Chemical Industries) (note this ligand was synthesized according to previously reported procedure[1] part way through the project due to back order from Wako Pure Chemical Industries), dimethoxy(methyl) silane (TCI); ethanol-OD (Millipore Sigma); 2-propanol-$d_8$ (Fischer Scientific), 2-propanol (Alfa Aesar); 5-bromo-1-pentene (Ambeed), 4-penten-1-ol (Ambeed); potassium carbonate (Ambeed); acetonitrile (Millipore Sigma); dimethylformamide (Oakwood Chemicals); methylene chloride ($CH_2Cl_2$) (Fischer Scientific); sodium Hydride 60% in oil dispersion (Oak-wood Chemicals); triethylamine (Oakwood Chemicals).

Anhydrous Tetrahydrofuran (THF) was purified by an MBRAUN solvent purification system (MB-SPS). Chloroform-d ($CDCl_3$) was stored over 3 Å molecular sieves. Triethylamine was dried by distillation at 89° C. and stored under 3 Å molecular sieves. Thin-layer chromatography (TLC) was conducted with Silicycle silica gel 60 Å F254 pre-coated plates (0.25 mm) and visualized with UV and $KMnO_4$ stains. Flash chromatography was performed using Silia Flash® P60, 40-60 mm (230-400 mesh), purchased from Silicycle. For reactions that required heating (optimization, transfer hydrodeuteration, transfer hydrogenation and deuteration reactions), a PolyBlock for 2-dram vials was used on top of a Heidolph heating/stir plate.

$^1H$ NMR spectra were recorded on a Varian 300 or 400 MHz spectrometer and are reported in ppm using solvent as an internal standard ($CHCl_3$ at 7.26 ppm). Data reported as: s=singlet, d=doublet, t=triplet, q=quartet, p=pentet, hep=heptet, m=multiplet, br=broad; coupling constant(s) in Hz; integration. $^{13}C$ NMR spectra were recorded on a Varian 76 MHz or 101 MHz spectrometer and are reported in ppm using solvent as an internal standard ($CDCl_3$ at 77.16 ppm). $^{19}F$ NMR spectra were recorded on a Varian 376 MHz spectrometer. $^2H$ NMR spectra were recorded on a Varian 61 MHz spectrometer using $CHCl_3$. Labeled solvent impurities were calculated out when reporting isolated yields.

High-resolution mass spectra were obtained for all new compounds not previously reported using the resources of the Chemistry Instrument Center (CIC), University at Buffalo, SUNY, Buffalo, NY. Specifically, high resolution accurate mass analysis was conducted using the following instruments: 12T Bruker SolariXR 12 Hybrid FTMS, provided through funding from the National Institutes of Health, NIH S10 RR029517; a Thermo Q-Exactive Focus Orbitrap Liquid Chromatograph Tandem Mass Spectrometer and a Thermo Q-Exactive Orbitrap Gas Chromatograph Tandem Mass Spectrometer, provided through funding from the National Science Foundation, MRI-1919594.

Optimization Studies

In a $N_2$ filled glovebox, ligand, $Cu(OAc)_2$ (Cu:L=1:1), and THF (80 μL) were added to an oven-dried 2-dram vial with an oven-dried stir bar followed by dropwise addition of $R_3Si$—H (3 eq.). A color change from a green/blue to yellow was observed while stirring for 10 mins. In a separate oven-dried 1-dram vial was added the alkene (0.2 mmol, 1 eq.), THF (100 μL), and D-source (2.5 eq.) The overall THF quantity was calculated as 1 M based on the alkene substrate. The solution in the 1-dram vial was added dropwise to the 2-dram vial. The 2-dram vial was capped with a pressure relief cap, removed from the glovebox, and left to stir for 18 h at 40° C. After this time, the reaction was filtered through a 1" silica plug with 100 mL of $CH_2Cl_2$ into a 200 mL round bottom flask. The solvent was removed by rotary evaporation, and the crude product was analyzed by $^1H$ NMR using 1,3,5-trimethylbenzene as an internal standard.

Entry 1. According to general procedure A for the optimization studies, in a $N_2$ filled glovebox, 1,2-Bis[bis[3,5-di(t-butyl)phenyl]phosphino]benzene (DTB- DPPBz) (2.0 mg, 0.0022 mmol, 0.011 eq.), $Cu(OAc)_2$ (10 μL of a 0.2 M solution in THF, 0.002 mmol, 0.01 eq.), and THF (90 μL) followed by dimethoxy(methyl) silane (74 μL, 0.60 mmol, 3 eq.) were added to an oven-dried 2-dram vial with an oven-dried stir bar. In a second oven-dried 1-dram vial, a solution of 1,4-dimethyl-2-(4-penten-1-yloxy)benzene (38 mg, 0.20 mmol, 1 eq.) and ethanol-OD (29 μL, 0.50 mmol, 2.5 eq.) in THF (100 μL) was made and added dropwise to the first vial. The reaction stirred for 18 h at 40° C., after which it was purified by flash column chromatography (250 mL of hexanes) to yield the product mixture as a clear oil (1, 8.5 mg, 0.045 mmol, 23% yield: 2a, 24 mg, 0.12 mmol, 60% yield: 2b, 1.3 mg, 0.0068 mmol, 3% yield).

Entry 2. According to general procedure A for the optimization studies, in a $N_2$ filled glovebox, 1,2-Bis[bis[3,5-di(t-butyl)phenyl]phosphino]benzene (DTB-DPPBz) (2.0 mg, 0.0022 mmol, 0.011 eq.), $Cu(OAc)_2$ (10 μL of a 0.2 M solution in THF, 0.002 mmol, 0.01 eq.), and THF (90 μL) followed by dimethoxy(methyl) silane (74 μL, 0.60 mmol, 3 eq.) were added to an oven-dried 2-dram vial with an oven-dried stir bar. In a second oven-dried 1-dram vial, a solution of 1,4-dimethyl-2-(4-penten-1-yloxy)benzene (38 mg, 0.20 mmol, 1 eq.) and ethanol-OD (29 μL, 0.50 mmol, 2.5 eq.) in THF (100 μL) was made and added dropwise to the first vial. The reaction stirred for 18 h at 60° C., after which it was purified by flash column chromatography (250 mL of hexanes) to yield the product mixture as a clear oil (2a, 32 mg, 0.17 mmol, 85% yield; 2b, 2.5 mg, 0.013 mmol, 7% yield).

Entry 3. According to general procedure A for the optimization studies, in a $N_2$ filled glovebox, 1,2-Bis[bis[3,5-di(t-butyl)phenyl]phosphino]benzene (DTB-DPPBz) (2.0 mg, 0.0022 mmol, 0.011 eq.), $Cu(OAc)_2$ (10 μL of a 0.2 M solution in THF, 0.002 mmol, 0.01 eq.), and THF (90 μL) followed by dimethoxy(methyl) silane (74 μL, 0.60 mmol, 3 eq.) were added to an oven-dried 2-dram vial with an oven-dried stir bar. In a second oven-dried 1-dram vial, a solution of 1,4-dimethyl-2-(4-penten-1-yloxy)benzene (38 mg, 0.20 mmol, 1 eq.) and ethanol-OD (29 μL, 0.50 mmol, 2.5 eq.) in THF (100 μL) was made and added dropwise to the first vial. The reaction stirred for 18 h at 23° C., after which it was purified by flash column chromatography (250 mL of hexanes) to yield the product mixture as a clear oil (1, 20 mg, 0.11 mmol, 55% yield; 2a, 8.6 mg, 0.044 mmol, 22% yield; 2b, 1.8 mg, 0.0095 mmol, 5% yield).

Entry 4. According to general procedure A for the optimization studies, in a $N_2$ filled glovebox, 1,2-Bis[bis[3,5-di(t-butyl)phenyl]phosphino]benzene (DTB-DPPBz) (2.0 mg, 0.0022 mmol, 0.011 eq.), $Cu(OAc)_2$ (10 μL of a 0.2 M solution in THF, 0.002 mmol, 0.01 eq.), and THF (90 μL) followed by dimethoxy(methyl) silane (74 μL, 0.60 mmol, 3 eq.) were added to an oven-dried 2-dram vial with an oven-dried stir bar. In a second oven-dried 1-dram vial, a solution of 1,4-dimethyl-2-(4-penten-1-yloxy)benzene (38 mg, 0.20 mmol, 1 eq.) and ethanol-OD (29 μL, 0.50 mmol, 2.5 eq.) was made and added dropwise to the first vial. The reaction stirred for 18 h at 40° C., after which it was purified by flash column chromatography (250 mL of hexanes) to yield the product mixture as a clear oil (1, 12 mg, 0.063 mmol, 32% yield: 2a, 13 mg, 0.067 mmol, 34% yield; 2b, 1.0 mg, 0.0053 mmol, 3% yield).

Entry 5. According to general procedure A for the optimization studies, in a $N_2$ filled glovebox, a solution of 0.04 M $Cu(OAc)_2$ with 1,2-Bis[bis[3,5-di(r-butyl)phenyl]phosphino]benzene (DTB-DPPBz) in $PhCH_3$ (50 μL, 0.0022 mmol, 0.011 eq.) was added to an oven-dried 2-dram vial with an oven-dried stir bar. An additional 50 μL of $PhCH_3$ was added to the 2-dram vial followed by dimethoxy(methyl)silane (74 μL, 0.60 mmol, 3 eq.). In a second oven-dried 1-dram vial, a solution of 1,4-dimethyl-2-(4-penten-1-yloxy)benzene (38 mg, 0.20 mmol, 1 eq.) and ethanol-OD (29 μL, 0.50 mmol, 2.5 eq.) in $PhCH_3$ (100 μL) was made and added dropwise to the first vial. The reaction stirred for 18 h at 40° C., after which it was purified by flash column chromatography (250 mL of hexanes) to yield the product mixture as a clear oil (1, 16 mg, 0.084 mmol, 42% yield, 2a, 15 mg, 0.078 mmol, 39% yield).

Entry 6. According to general procedure A for the optimization studies, in a $N_2$ filled glovebox, a solution of 0.04 M $Cu(OAc)_2$ with 1,2-Bis[bis[3,5-di(t-butyl)phenyl]phosphino]benzene (DTB-DPPBz) in $CH_2Cl_2$ (50 μL, 0.0022 mmol, 0.011 eq.) was added to an over-dried 2-dram vial with an oven-dried stir bar. An additional 50 μL of $CH_2Cl_2$ was added to the 2-dram vial followed by dimethoxy(methyl)silane (74 μL, 0.60 mmol, 3 eq.). In a second oven-dried 1-dram vial, a solution of 1,4-dimethyl-2-(4-penten-1-yloxy)benzene (38 mg, 0.20 mmol, 1 eq.) and ethanol-OD (29 μL, 0.50 mmol, 2.5 eq.) in $CH_2Cl_2$ (100 μL) was made and added dropwise to the first vial. The reaction stirred for 18 h at 40° C. after which it was purified by flash column chromatography (250 mL of hexanes) to yield the pure product as clear oil (1, 31 mg, 0.16 mmol, 80% yield).

Entry 7. According to general procedure A for the optimization studies, in a $N_2$ filled glovebox, 1,2-Bis[bis[3,5-di(t-butyl)phenyl]phosphino]benzene (DTB-DPPBz) (2.0 mg, 0.0022 mmol, 0.011 eq.), $Cu(OAc)_2$ (10 μL of a 0.2 M solution in THF, 0.002 mmol, 0.01 eq.), and THF (90 μL) followed by dimethoxy(methyl) silane (74 μL, 0.60 mmol, 3 eq.) were added to an oven-dried 2-dram vial with an oven-dried stir bar. In a second oven-dried 1-dram vial, a solution of 1,4-dimethyl-2-(4-penten-1-yloxy)benzene (38 mg, 0.20 mmol, 1 eq.) and IPA-$d_8$ (38 μL, 0.50 mmol, 2.5 eq.) in THF (100 μL) was made and added dropwise to the first vial. The reaction stirred for 18 h at 40° C., after which it was purified by flash column chromatography (250 mL of hexanes) to yield the product mixture as a clear oil (1, 2.3 mg, 0.012 mmol, 6% yield; 2a, 27 mg, 0.14 mmol, 70% yield).

Entry 8. According to general procedure A for the optimization studies, in a $N_2$ filled glovebox, 1,2-Bis[bis[3,5-di(t-butyl)phenyl]phosphino]benzene (DTB-DPPBz) (5.9 mg, 0.0066 mmol, 0.033 eq.), $Cu(OAc)_2$ (30 μL of a 0.2 M solution in THF, 0.006 mmol, 0.03 eq.), and THF (70 μL) followed by dimethoxy(methyl) silane (74 μL, 0.60 mmol, 3 eq.) were added to an oven-dried 2-dram vial with an oven-dried stir bar. In a second oven-dried 1-dram vial, a solution of 1,4-dimethyl-2-(4-penten-1-yloxy)benzene (38 mg, 0.20 mmol, 1 eq.) and IPA-$d_8$ (38 μL, 0.50 mmol, 2.5 eq.) in THF (100 μL) was made and added dropwise to the first vial. The reaction stirred for 18 h at 40° C. after which it was purified by flash column chromatography (250 mL of hexanes) to yield the pure product as clear oil (2a, 34 mg, 0.18 mmol, 90% yield).

Entry 9. According to general procedure A for the optimization studies, in a $N_2$ filled glovebox, 1,2-Bis[bis[3,5-di(t-butyl)phenyl]phosphino]benzene (DTB-DPPBz) (5.9 mg, 0.0066 mmol, 0.033 eq.), $Cu(OAc)_2$ (30 μL of a 0.2 M solution in THF, 0.006 mmol, 0.03 eq.), and THF (70 μL) followed by dimethoxy(methyl)silane (74 μL, 0.60 mmol, 3 eq.) were added to an oven-dried 2-dram vial with an oven-dried stir bar. In a second oven-dried 1-dram vial, a solution of 1,4-dimethyl-2-(4-penten-1-yloxy)benzene (38 mg, 0.20 mmol, 1 eq.) and tert-butanol-OD (48 μL, 0.50 mmol, 2.5 eq.) in THF (100 μL) was made and added dropwise to the first vial. The reaction stirred for 18 h at 40° C., after which it was purified by flash column chromatography (250 mL of hexanes) to yield the pure product as clear oil (2a, 21 mg, 0.11 mmol, 55% yield).

Entry 10. According to general procedure A for the optimization studies, in a $N_2$ filled glovebox, 1,2-Bis[bis[3,5-di(t-butyl)phenyl]phosphino]benzene (DTB-DPPBz) (5.9 mg, 0.0066 mmol, 0.033 eq.), $Cu(OAc)_2$ (30 μL of a 0.2 M solution in THF, 0.006 mmol, 0.03 eq.), and THF (70 μL) followed by dimethoxy(methyl)silane (74 μL, 0.60 mmol, 3 eq.) were added to an oven-dried 2-dram vial with an oven-dried stir bar. In a second oven-dried 1-dram vial, a solution of 1,4-dimethyl-2-(4-penten-1-yloxy)benzene (38 mg, 0.20 mmol, 1 eq.) and MeOD (20 μL, 0.50 mmol, 2.5 eq.) in THF (100 μL) was made and added dropwise to the first vial. The reaction stirred for 18 h at 40° C., after which it was purified by flash column chromatography (250 mL of hexanes) to yield the product mixture as a clear oil (1, 32 mg, 0.17 mmol, 85% yield; 2a, 1.1 mg, 0.0057 mmol, 3% yield).

Entry 11. According to general procedure A for the optimization studies, in a $N_2$ filled glovebox, 1,2-Bis[bis[3,5-di(t-butyl)phenyl]phosphino]benzene (DTB-DPPBz) (5.9 mg, 0.066 mmol, 0.033 eq.), $Cu(OAc)_2$ (30 μL of a 0.2 M solution in THF, 0.006 mmol, 0.03 eq.), and THF (70 μL) followed by polymethylhydrosiloxane (40 μL, 0.60 mmol, 3 eq. based on Si—H)[2] were added to an oven-dried 2-dram vial with an oven-dried stir bar. In a second oven-dried 1-dram vial, a solution of 1,4-dimethyl-2-(4-penten-1-yloxy)benzene (38 mg, 0.20 mmol, 1 eq.) and IPA-$d_8$ (38 μL, 0.50 mmol, 2.5 eq.) in THF (100 μL) was made and added dropwise to the first vial. The reaction stirred for 18 h at 40° C., after which it was purified by flash column chromatography (250 mL of hexanes) to yield the product mixture as a clear oil (1, 2.6 mg, 0.014 mmol, 7% yield, 2a, 30 mg, 0.16 mmol, 80% yield).

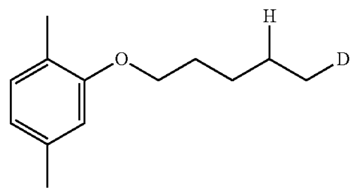

1,4-dimethyl-2-((pentyl-5-d)oxy)-benzene [2a] According to general procedure B, in a $N_2$ filled glovebox, DTB-DPPBz (46.6 mg, 0.052 mmol, 0.033 eq.), $Cu(OAc)_2$ (235 μL of a 0.2 M solution in THF, 0.047 mmol, 0.03 eq.), and THF (500 μL) followed by dimethoxy(methyl)silane (0.58 mL, 4.74 mmol, 3 eq.) were added to an oven-dried 2-dram vial with an oven-dried stir bar. In a separate oven-dried 1-dram vial was added 1,4-dimethyl-2-(4-penten-1-yloxy)benzene (300 mg, 1.58 mmol, 1 eq.), THF (845 μL), and 2-propanol-$d_8$ (302 μL, 3.95 mmol, 2.5 eq.). The solution in the 1-dram vial was added dropwise to the 2-dram vial. The 2-dram vial was capped with a pressure relief cap, removed from the glovebox, and left to stir for 23 h at 40° C. Upon completion, the product was isolated by flash column chromatography using gradient elution (100 mL of 100% distilled hexanes, 300 mL of 1% ethyl acetate in distilled hexanes) to give the pure product as a clear and colorless oil (261 mg, 1.35 mmol, 85% yield).

$^1H$ NMR: (300 MHz, $CDCl_3$) δ 7.04 (d, J=7.4 Hz, 1H), 6.69 (d, J=7.7 Hz, 1H), 6.67 (s, 1H), 3.97 (t, J=6.4 Hz, 2H), 2.34 (s, 3H), 2.22 (s, 3H), 1.83 (p, J=6.7 Hz, 2H), 1.54-1.33 (m, 4H), 1.01-0.91 (m, 2.01H). $^2H$ NMR: (61 MHz, $CHCl_3$) δ 0.95 (s, 0.99D). $^{13}C$ NMR: (75 MHz, $CDCl_3$) δ 157.26, 136.56, 130.38, 123.76, 120.65, 112.08, 67.96, 29.26, 28.46, 22.53, 21.56, 15.95, 13.92 (t, J=19.1 Hz). ATR-IR ($cm^{-1}$): 2928, 2860, 2173, 1508, 1434, 1263, 1129. HRMS: ($ESI^+$) m/z: $[M+H]^+$ Calcd for $C_{13}H_{19}DO$ 194.1655; Found 194.1651.

Transfer Hydrodeuteration Reaction Scope

Scheme S3. Unactivated Terminal Alkene Substrate Scope

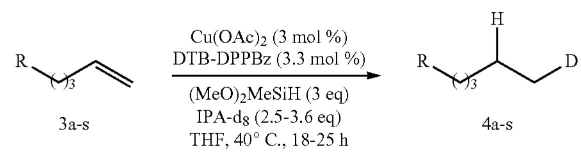

4a

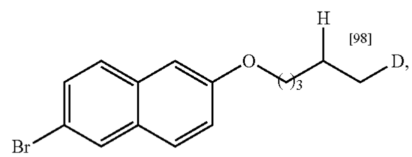

73% yield

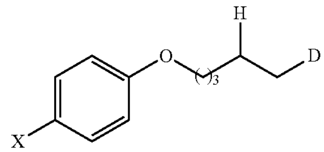

X = Br: 4b, 88% yield 96% D inc.
X = F: 4c, 58% yield 93% D inc.

4d

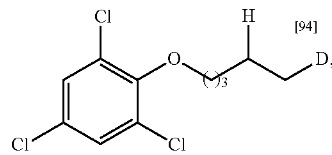

93% yield

4e

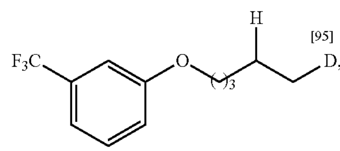

75% yield[a]

-continued
4f
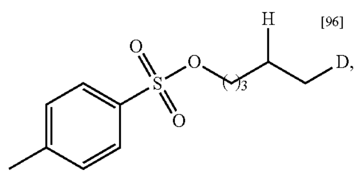
90% yield
4g
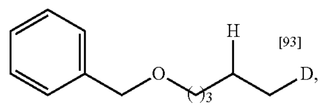
63% yield
4h
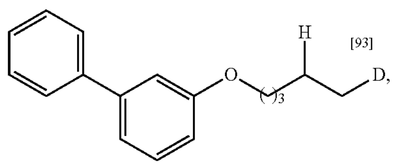
68% yield
4i
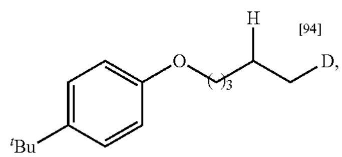
87% yield[b]
4j
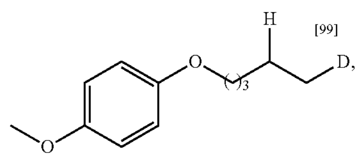
90% yield
4k
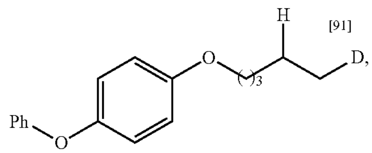
68% yield
4l
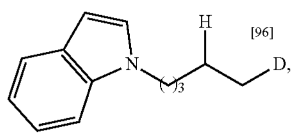
91% yield[c]
-continued
4m
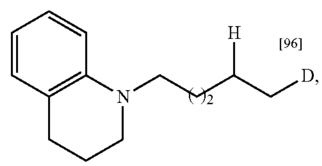
83% yield[b]
4n
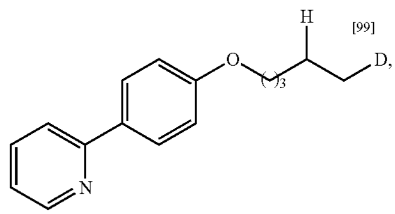
83% yield
4o
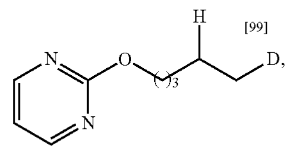
87% yield
4p
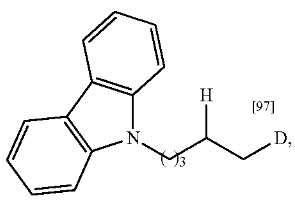
90% yield
4q
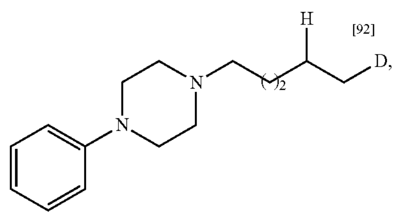
90% yield
4r
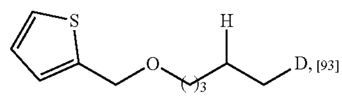
83% yield
4s
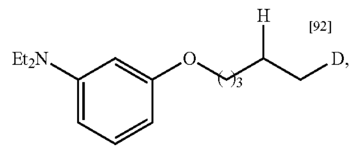
65% yield -continued

[a]4 eq of silane used [b]4-4.4 mol % $Cu(OAc)_2$, 4.4-4.8 mol % DTB-DPPBz, 4-4.6 eq DMMS used [c]6 mol % $Cu(OAc)_2$, 6.6 mol % DTB-DPPBz, 4.8 eq. DMMS used General Procedure for Transfer Hydrodeuteration (B)

In a $N_2$ filled glovebox, DTB-DPPBz (0.033 eq.), $Cu(OAc)_2$ (0.03 eq) and THF followed by dimethoxy(methyl)silane (3 eq.) were added to an oven-dried 2-dram vial with an oven-dried stir bar (*note a color change from a green/blue to yellow was observed while stirring for 10 mins). In a separate oven-dried 1-dram vial was added the alkene (1 eq.), THF, and 2-propanol-$d_8$ (2.5-3.6 eq.). The solution in the 1-dram vial was added dropwise to the 2-dram vial. The total volume of THF was calculated as 1 M based on the alkene substrate. The 2-dram vial was capped with a pressure relief cap, removed from the glovebox, and left to stir for 18-25 h at 40° C. Upon reaction completion, all contents of the reaction were dry loaded onto a silica gel column and purified by column chromatography.

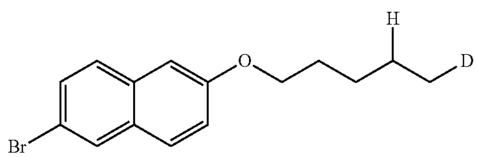 [SMILES: [2H]CCCCCOc1ccc2cc(Br)ccc2c1]

2-Bromo-6-((pentyl-5-d)oxy)naphthalene [4a] According to general procedure B, in a $N_2$ filled glovebox, DTB-DPPBz (11.6 mg, 0.013 mmol, 0.033 eq.), $Cu(OAc)_2$ (60 μL of a 0.2 M solution in THF, 0.012 mmol, 0.03 eq.), and THF (140 μL) followed by dimethoxy(methyl)silane (148 μL, 1.20 mmol, 3 eq.) were added to an oven-dried 2-dram vial with an oven-dried stir bar. In a separate oven-dried 1-dram vial was added 2-bromo-6-(4-penten-1-yloxy)naphthalene (116 mg, 0.40 mmol, 1 eq.), THF (200 μL), and 2-propanol-$d_8$ (77 μL, 1.0 mmol, 2.5 eq.). The solution in the 1-dram vial was added dropwise to the 2-dram vial. The 2-dram vial was capped with a pressure relief cap, removed from the glovebox, and left to stir for 24 h at 40° C. Upon completion, the product was isolated by flash column chromatography using gradient elution (100 mL of 100% hexanes, 100 mL of 1% ethyl acetate in hexanes, 100 mL of 2% ethyl acetate in hexanes) to give the pure product as a beige solid (84 mg, 0.29 mmol, 73% yield).

$^1$H NMR: (400 MHz, $CDCl_3$) δ 7.90 (s, 1H), 7.64 (d, J=9.0 Hz, 1H), 7.58 (d, J=8.8 Hz, 1H), 7.52-7.45 (m, 1H), 7.20-7.12 (m, 1H), 7.08 (s, 1H), 4.05 (t, J=6.6 Hz, 2H), 1.85 (p, J=6.7 Hz, 2H), 1.53-1.36 (m, 4H), 1.00-0.89 (m, 2.02H). $^2$H NMR: (61 MHz, $CHCl_3$) δ 0.94 (s, 0.98D). $^{13}$C NMR: (101 MHz, $CDCl_3$) δ 157.51, 133.21, 130.01, 129.73, 129.62, 128.52, 128.45, 120.19, 116.97, 106.54, 68.17, 29.03, 28.35, 22.53, 13.89 (t, J=19.2 Hz). ATR-IR ($cm^{-1}$): 2929, 2858, 2182, 1585, 1261, 1014. HRMS: ($ESI^+$) m/z: $[M+H]^+$ Calcd for $C_{15}H_{17}DOBr$ 294.0604; Found 294.0595.

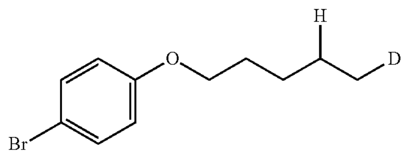 [SMILES: [2H]CCCCCOc1ccc(Br)cc1]

1-Bromo-4-((pentyl-5-d)oxy)benzene [4b] According to general procedure B, in a $N_2$ filled glovebox, DTB-DPPBz (11.6 mg, 0.013 mmol, 0.033 eq.), $Cu(OAc)_2$ (60 μL of a 0.2 M solution in THF, 0.012 mmol, 0.03 eq.), and THF (140 μL) followed by dimethoxy(methyl)silane (148 μL, 1.20 mmol, 3 eq.) were added to an oven-dried 2-dram vial with an oven-dried stir bar. In a separate oven-dried 1-dram vial was added 1-bromo-4-(pent-4-en-1-yloxy)benzene (96 mg, 0.40 mmol, 1 eq.). THF (200 μL), and 2-propanol-$d_8$ (77 μL, 1.0 mmol, 2.5 eq.). The solution in the 1-dram vial was added dropwise to the 2-dram vial. The 2-dram vial was capped with a pressure relief cap, removed from the glovebox, and left to stir for 24 h at 40° C. Upon completion, the product was isolated by flash column chromatography using gradient elution (100 mL of 100% hexanes, 100 mL of 1% ethyl acetate in hexanes, 100 mL of 2% ethyl acetate in hexanes) to give the pure product as a light-yellow oil (86 mg, 0.35 mmol, 88% yield).

$^1$H NMR: (400 MHz, $CDCl_3$) δ 7.40-7.31 (m 2H), 6.81-6.72 (m, 2H), 3.91 (t, J=6.6 Hz, 2H), 1.77 (p, J=6.6 Hz, 2H), 1.51-1.31 (m, 4H), 0.98-0.87 (m, 2.04H). $^2$H NMR: (61 MHz, $CHCl_3$) δ 0.91 (s, 0.96D). $^{13}$C NMR: (101 MHz, $CDCl_3$) δ 158.35, 132.30, 116.39, 112.65, 68.34, 29.00, 28.25, 22.50, 13.87 (t, J=19.0 Hz). ATR-IR ($cm^{-1}$): 2930, 2860, 2170, 1488, 1240, 1001. HRMS: ($EI^+$) m/z: $[M]^+$ Calcd for $C_{11}H_{14}DOBr$ 243.0369; Found 243.0364.

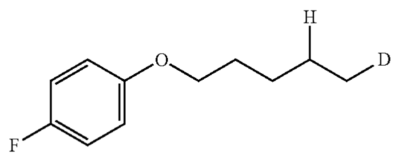 [SMILES: [2H]CCCCCOc1ccc(F)cc1]

1-Fluoro-4-(5-d-pentan-1-yloxy)benzene [4c] According to general procedure B, in a $N_2$ filled glovebox, DTB-DPPBz (11.6 mg, 0.013 mmol, 0.033 eq.). $Cu(OAc)_2$ (60 μL of a 0.2 M solution in THF, 0.012 mmol, 0.03 eq.), and THF (140 μL) followed by dimethoxy(methyl)silane (148 μL, 1.20 mmol, 3 eq.) were added to an oven-dried 2-dram vial with an oven-dried stir bar. In a separate oven-dried 1-dram vial was added 1-fluoro-4-(pent-4-en-1-yloxy)benzene (72 mg, 0.40 mmol, 1 eq.), THF (200 μL), and 2-propanol-$d_8$ (77 μL, 1.0 mmol, 2.5 eq.). The solution in the 1-dram vial was added dropwise to the 2-dram vial. The 2-dram vial was capped with a pressure relief cap, removed from the glovebox, and left to stir for 18 h at 40° C. Upon completion, the product was isolated by flash column chromatography using gradient elution (150 mL of 100% hexanes, 100 mL of 1% ethyl acetate in hexanes, 100 mL of 5% ethyl acetate in hexanes) to give the pure product as a clear and colorless oil (43 mg, 0.23 mmol, 58% yield).

$^1$H NMR: (400 MHz, $CDCl_3$) δ 7.02-6.91 (m, 2H), 6.88-6.78 (m, 2H), 3.91 (t, J=6.6 Hz, 2H), 1.77 (p, J=6.6 Hz, 2H), 1.49-1.34 (m, 4H), 0.98-0.87 (m, 2.07H). $^2$H NMR: (61 MHz. $CHCl_3$) δ 0.92 (s, 0.93D). $^{13}$C NMR: (101 MHz, $CDCl_3$) δ 157.22 (d, J=237.7 Hz), 155.38 (d, J=2.1 Hz), 115.74 (d, J=41.1 Hz), 115.46 (d, J=26.1 Hz), 68.75, 29.13, 28.30, 22.52, 13.87 (t, J=19.4 Hz). $^{19}$F NMR: (61 MHz, $CDCl_3$) δ −124.49-−124.58 (m, 1F). ATR-IR ($cm^{-1}$): 2931, 2864, 2166, 1504, 1247, 1207. HRMS: ($EI^+$) m/z: $[M]^+$ Calcd for $C_{11}H_{14}ODF$ 183.1170; Found 183.1164.

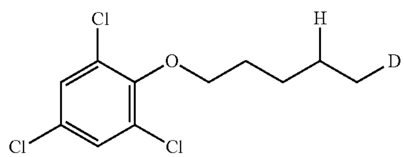 [SMILES: [2H]CCCCCOc1c(Cl)cc(Cl)cc1Cl]

1,3,5-trichloro-2-((pentyl-5-d)oxy)benzene [4d] According to general procedure B, in a $N_2$ filled glovebox, DTB-DPPBz (11.6 mg, 0.013 mmol, 0.033 eq.), $Cu(OAc)_2$ (60 µL of a 0.2 M solution in THF, 0.012 mmol, 0.03 eq.), and THF (140 µL) followed by dimethoxy(methyl)silane (148 µL, 1.20 mmol, 3 eq.) were added to an oven-dried 2-dram vial with an oven-dried stir bar. In a separate oven-dried 1-dram vial was added 1,3,5-trichloro-2-(pent-4-en-1-yloxy)benzene (106 mg, 0.40 mmol, 1 eq.), THF (200 µL), and 2-propanol-$d_8$ (77 µL, 1.0 mmol, 2.5 eq.). The solution in the 1-dram vial was added dropwise to the 2-dram vial. The 2-dram vial was capped with a pressure relief cap, removed from the glovebox, and left to stir for 24 h at 40° C. Upon completion, the product was isolated by flash column chromatography using gradient elution (200 mL of 100% hexanes, 100 mL of 1% ethyl acetate in hexanes) to give the pure product as a colorless oil (99 mg, 0.37 mmol, 93% yield).

$^1$H NMR: (400 MHz, $CDCl_3$) δ 7.29 (s, 2H), 3.98 (t, J=6.7 Hz, 2H), 1.90-1.80 (m, 2H), 1.54-1.45 (m, 2H), 1.44-1.34 (m, 2H), 0.97-0.88 (m, 2.06H). $^2$H NMR: (61 MHz, $CHCl_3$) δ 0.92 (s, 0.94D). $^{13}$C NMR: (101 MHz, $CDCl_3$) δ 150.88, 130.27, 129.31, 128.84, 74.11, 29.84, 28.03, 22.52, 13.87 (t, J=19.2 Hz). ATR-IR ($cm^{-1}$); 2930, 2860, 2174, 1448, 1255, 1138. HRMS: ($EI^+$) m/z: $[M]^+$ Calcd for $C_{11}H_{12}DOCl_3$ 267.0095; Found 267.0087.

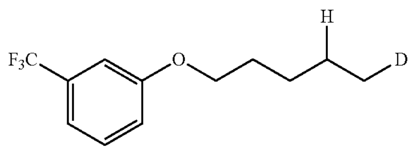 [SMILES: [2H]CCCCCOc1cccc(C(F)(F)F)c1]

1-((pentyl-5-d)oxy)-3-(trifluoromethyl)benzene [4e] According to general procedure B, in a $N_2$ filled glovebox, DTB-DPPBz (11.6 mg, 0.013 mmol, 0.033 eq.), $Cu(OAc)_2$ (60 µL of a 0.2 M solution in THF, 0.012 mmol, 0.03 eq.), and THF (140 µL) followed by dimethoxy(methyl)silane (197 µL, 1.60 mmol, 4 eq.) were added to an oven-dried 2-dram vial with an oven-dried stir bar. In a separate oven-dried 1-dram vial was added 1-(4-penten-1-yloxy)-3-(trifluoromethyl)-benzene (92 mg, 0.40 mmol, 1 eq.), THF (200 µL), and 2-propanol-$d_8$ (107 µL, 1.40 mmol, 3.5 eq.). The solution in the 1-dram vial was added dropwise to the 2-dram vial. The 2-dram vial was capped with a pressure relief cap, removed from the glovebox, and left to stir for 18 h at 40° C. Upon completion, the product was isolated by flash column chromatography using gradient elution (150 mL of 100% hexanes, 100 mL of 1% ethyl acetate in hexanes) to give the pure product as a clear and colorless oil (71 mg, 0.30 mmol, 75% yield).

$^1$H NMR: (400 MHz, $CDCl_3$) δ 7.37 (t, J=8.0 Hz, 1H), 7.19 (d, J=7.6 Hz, 1H), 7.12 (s, 1H), 7.06 (d, J=8.3 Hz, 1H), 3.98 (t, J=6.5 Hz, 2H), 1.81 (p, J=6.7 Hz, 2H), 1.52-1.31 (m, 4H), 0.97-0.88 (m, 2.05H). $^2$H NMR: (61 MHz, $CHCl_3$) δ 0.93 (s, 0.95D). $^{13}$C NMR: (101 MHz, $CDCl_3$) δ 159.41, 131.90 (d, J=32.2 Hz), 130.02, 124.18 (d, J=272.3 Hz), 118.12 (d, J=1.4 Hz), 117.25 (q, J=3.8 Hz), 111.33 (q, J=3.9 Hz), 68.41, 28.98, 28.27, 22.50, 13.85 (t, J=19.1 Hz). $^{19}$F NMR: (61 MHz, $CDCl_3$) δ −62.73 (s, 3F). ATR-IR ($cm^{-1}$): 2934, 2863, 2172, 1449, 1327, 1121. HRMS: ($EI^+$) m/z: $[M]^+$ Calcd for $Cl_2H_{14}DOF_3$ 233.1138; Found 233.1132.

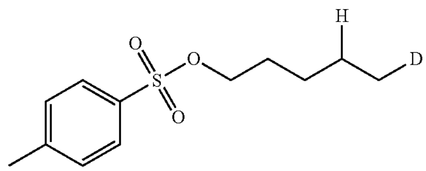 [SMILES: [2H]CCCCCOS(=O)(=O)c1ccc(C)cc1]

Pentyl-5-d 4-methylbenzenesulfonate [4f] According to general procedure B, in a $N_2$ filled glovebox, DTB-DPPBz (11.6 mg, 0.013 mmol, 0.033 eq.), $Cu(OAc)_2$ (60 µL of a 0.2 M solution in THF, 0.012 mmol, 0.03 eq.), and THF (140 µL) followed by dimethoxy(methyl)silane (148 µL, 1.20 mmol, 3 eq.) were added to an oven-dried 2-dram vial with an oven-dried stir bar. In a separate oven-dried 1-dram vial was added 4-penten-1-yl 4-methylbenzenesulfonate (96 mg, 0.40 mmol, 1 eq.), THF (200 µL), and 2-propanol-$d_8$ (77 µL, 1.0 mmol, 2.5 eq.). The solution in the 1-dram vial was added dropwise to the 2-dram vial. The 2-dram vial was capped with a pressure relief cap, removed from the glovebox, and left to stir for 22 h at 40° C. Upon completion, the product was isolated by flash column chromatography using gradient elution (100 mL of 100% hexanes, 100 mL of 1% ethyl acetate in hexanes) to give the pure product as a clear yellow oil (87 mg, 0.36 mmol, 90% yield).

$^1$H NMR: (400 MHz, $CDCl_3$) δ 7.78 (d, J=8.3 Hz, 2H), 7.34 (d, J=8.0 Hz, 2H), 4.01 (t, J=6.5 Hz, 2H), 2.44 (s, 3H), 1.63 (p, J=6.7 Hz, 2H), 1.32-1.16 (m, 4H), 0.88-0.78 (m, 2.04H), $^2$H NMR: (61 MHz, $CHCl_3$) δ 0.82 (s, 0.96D). $^{13}$C NMR: (101 MHz, $CDCl_3$) δ 144.73, 133.30, 129.88, 127.93, 70.79, 28.58, 27.48, 22.00, 21.69, 13.58 (t, J=19.3 Hz). ATR-IR ($cm^{-1}$): 2936, 2864, 2174, 1356, 1188, 1173, 1097. HRMS: ($ESI^+$) m/z: $[M+Na]^+$ Calcd for $C_{12}H_{17}DO_3NaS$ 266.0937; Found 266.0931.

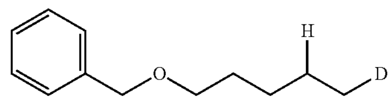 [SMILES: [2H]CCCCCOCc1ccccc1]

(((Pentyl-5-d)oxy)methyl)benzene [4g] According to general procedure B, in a $N_2$ filled glovebox, DTB-DPPBz (11.6 mg, 0.013 mmol, 0.033 eq.), $Cu(OAc)_2$ (60 µL of a 0.2 M solution in THF, 0.012 mmol, 0.03 eq.), and THF (140 µL) followed by dimethoxy(methyl)silane (148 µL, 1.20 mmol, 3 eq.) were added to an oven-dried 2-dram vial with an oven-dried stir bar. In a separate oven-dried 1-dram vial was added the ((4-Penten-1-yloxy)methyl)benzene (71 mg, 0.40 mmol, 1 eq.), THF (200 µL), and 2-propanol-$d_9$ (77 µL, 1.0 mmol, 2.5 eq.). The solution in the 1-dram vial was added dropwise to the 2-dram vial. The 2-dram vial was capped with a pressure relief cap, removed from the glovebox, and left to stir for 25 h at 40° C. Upon completion, the product was isolated by flash column chromatography using gradient elution (100 mL of 100% hexanes, 100 mL of 1% ethyl acetate in hexanes) to give the pure product as a clear yellow oil (45 mg, 0.25 mmol, 63% yield).

$^1$H NMR: (400 MHz, $CDCl_3$) δ 7.40-7.34 (m, 4H), 7.34-7.27 (m, 1H), 4.53 (s, 2H), 3.49 (t, J=6.7 Hz, 2H), 1.65

(p, J=6.8 Hz, 2H), 1.44-1.31 (m, 4H), 0.96-0.88 (m, 2.07H). $^2$H NMR: (61 MHz, $CHCl_3$) δ 0.91 (s, 0.93D). $^{13}$C NMR: (101 MHz, $CDCl_3$) δ 138.83, 128.44, 127.72, 127.56, 72.97, 70.63, 29.60, 28.47, 22.59, 13.87 (t, J=19.1 Hz). ATR-IR ($cm^{-1}$): 2929, 2855, 2173, 1453, 1097, 1008. HRMS: ($EI^+$) m/z: $[M]^+$ Calcd for $C_{12}H_{17}DO$ 179.1420; Found 179.1414.

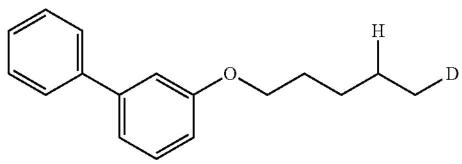 [SMILES: [2H]CCCCCOc1cccc(-c2ccccc2)c1]

3-((pentyl-5-d)oxy)-1,1'-biphenyl [4h] According to general procedure B, in a $N_2$ filled glovebox, DTB-DPPBz (11.6 mg, 0.013 mmol, 0.033 eq.), $Cu(OAc)_2$ (60 μL of a 0.2 M solution in THF, 0.012 mmol, 0.03 eq.), and THF (140 μL) followed by dimethoxy(methyl)silane (148 μL, 1.20 mmol, 3 eq.) were added to an oven-dried 2-dram vial with an oven-dried stir bar. In a separate oven-dried 1-dram vial was added 3-(4-penten-1-yloxy)-1,1'-biphenyl (95 mg, 0.40 mmol, 1 eq.), THF (200 μL), and 2-propanol-$d_8$ (77 μL, 1.0 mmol, 2.5 eq.). The solution in the 1-dram vial was added dropwise to the 2-dram vial. The 2-dram vial was capped with a pressure relief cap, removed from the glovebox, and left to stir for 24 h at 40° C. Upon completion, the product was isolated by flash column chromatography using gradient elution (100 mL of 100% hexanes, 100 mL of 1% ethyl acetate in hexanes, 100 mL of 2% ethyl acetate in hexanes) to give the pure product as a yellow oil (65 mg, 0.27 mmol, 68% yield).

$^1$H NMR: (400 MHz, $CDCl_3$) δ 7.60 (d, J=7.6 Hz, 2H), 7.44 (t, J=7.5 Hz, 2H), 7.35 (t, J=7.7 Hz, 2H), 7.18 (d, J=7.7 Hz, 1H), 7.14 (s, 1H), 6.94-6.86 (m, 1H), 4.03 (t, J=6.6 Hz, 2H), 1.89-1.77 (m, 2H), 1.52-1.37 (m, 4H), 0.98-0.90 (m, 2.07H). $^2$H NMR: (61 MHz, $CHCl_3$) δ 0.94 (s, 0.93D). $^{13}$C NMR: (101 MHz, $CDCl_3$) δ 159.62, 142.81, 141.28, 129.83, 128.83, 127.48, 127.32, 119.58, 113.62, 113.34, 68.14, 29.17, 28.35, 22.54, 13.90 (t, J=19.2 Hz). ATR-IR ($cm^{-1}$): 2928, 2859, 2172, 1295, 1203, 1502, 1017. HRMS: ($ESI^+$) m/z: $[M+H]^+$ Calcd for $C_{17}H_{19}DO$ 242.1655; Found 242.1650.

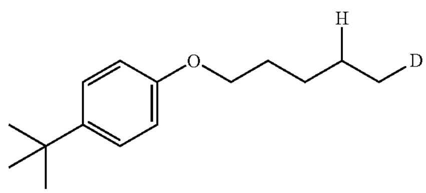 [SMILES: [2H]CCCCCOc1ccc(C(C)(C)C)cc1]

1-(tert-butyl)-4-((pentyl-5-d)oxy)benzene [4i] According to general procedure B, in a $N_2$ filled glovebox, DTB-DPPBz (53.7 mg, 0.060 mmol, 0.048 eq.), $Cu(OAc)_2$ (10 mg, 0.055 mmol, 0.044 eq.), and THF (630 μL) followed by dimethoxy(methyl)silane (722 μL, 5.85 mmol, 4.6 eq.) were added to an oven-dried 100-mL round bottom flask with an oven-dried stir bar. In a separate oven-dried 1-dram vial was added 1-(tert-butyl)-4-(4-penten-1-yloxy)benzene (275 mg, 1.26 mmol, 1 eq.), THF (630 μL), and 2-propanol-$d_8$ (347 μL, 4.53 mmol, 3.6 eq.). The solution in the 1-dram vial was added dropwise to the 100-mL round bottom flask. The round bottom was sealed with a rubber septum, removed from the glovebox, and left to stir for 24 h at 40° C. under $N_2$ gas. Upon completion, the product was isolated by flash column chromatography using gradient elution (300 mL of 100% hexanes, 100 mL of 1% ethyl acetate in hexanes) to give the pure product as a colorless oil (238 mg, 1.09 mmol, 87% yield).

$^1$H NMR: (400 MHz, $CDCl_3$) δ 7.32 (dd, J=8.9, 1.4 Hz, 2H), 6.86 (dd, J=8.7, 1.8 Hz, 2H), 3.96 (t, J=6.6 Hz, 2H), 1.86-1.74 (m, 2H), 1.50-1.35 (m, 4H), 1.32 (s, 9H), 0.99-0.89 (m, 2.06H). $^2$H NMR: (61 MHz, $CHCl_3$) δ 0.93 (s, 0.94D). $^{13}$C NMR: (101 MHz, $CDCl_3$) δ 156.99, 143.19, 126.30, 114.01, 68.02, 34.17, 31.67, 29.20, 28.35, 22.54, 13.89 (t, J=18.9 Hz). ATR-IR ($cm^{-1}$): 2951, 2864, 2172, 1513, 1475, 1244, 1024. HRMS: ($EI^+$) m/z: $[M]^+$ Calcd for $C_{15}H_{23}DO$ 221.1890; Found 221.1883.

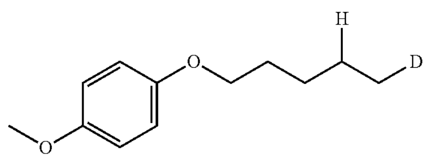

1-methoxy-4-((pentyl-5-d)oxy)benzene [4j] According to general procedure B, in a $N_2$ filled glovebox, DTB-DPPBz (11.6 mg, 0.013 mmol, 0.033 eq.), $Cu(OAc)_2$ (60 μL of a 0.2 M solution in THF, 0.012 mmol, 0.03 eq.), and THF (140 μL) followed by dimethoxy(methyl)silane (148 μL, 1.20 mmol, 3 eq.) were added to an oven-dried 2-dram vial with an oven-dried stir bar. In a separate oven-dried 1-dram vial was added 1-methoxy-4-(4-penten-1-yloxy)-benzene (77 mg, 0.40 mmol, 1 eq.), THF (200 μL), and 2-propanol-$d_8$ (77 μL, 1.0 mmol, 2.5 eq.). The solution in the 1-dram vial was added dropwise to the 2-dram vial. The 2-dram vial was capped with a pressure relief cap, removed from the glovebox, and left to stir for 23 h at 40° C. Upon completion, the product was isolated by flash column chromatography using gradient elution (100 mL of 100% hexanes, 200 mL of 1% ethyl acetate in hexanes) to give the pure product as a clear yellow oil (70 mg, 0.36 mmol, 90% yield).

$^1$H NMR: (400 MHz, $CDCl_3$) δ 6.84 (s, 4H), 3.91 (t, J=6.6 Hz, 2H), 3.77 (s, 3H), 1.77 (p, J=6.7 Hz, 2H), 1.48-1.33 (m, 4H), 0.95-0.87 (m, 2.01H). $^2$H NMR: (61 MHz, $CHCl_3$) δ 0.92 (s, 0.99D). $^{13}$C NMR: (101 MHz, $CDCl_3$) δ 153.76, 153.42, 115.52, 114.71, 68.75, 55.84, 29.23, 28.33, 22.54, 13.87 (t, J=19.2 Hz). ATR-IR ($cm^{-1}$): 2934, 2866, 2180, 1510, 1229, 1035. HRMS: ($EI^+$) m/z: $[M]^+$ Calcd for $C_{12}H_{17}DO_2$ 195.1370; Found 195.1363.

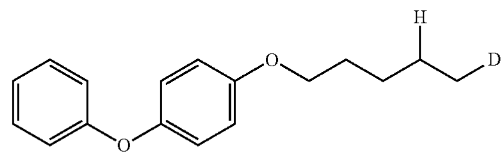 [SMILES: [2H]CCCCCOc1ccc(Oc2ccccc2)cc1]

1-((pentyl-5-d)oxy)-4-phenoxybenzene [4k] According to general procedure B, in a $N_2$ filled glovebox, DTB-DPPBz (11.6 mg, 0.013 mmol, 0.033 eq.). $Cu(OAc)_2$ (60 μL of a 0.2 M solution in THF, 0.012 mmol, 0.03 eq.), and THF (140 μL) followed by dimethoxy(methyl)silane (148 μL, 1.20 mmol, 3 eq.) were added to an oven-dried 2-dram vial with an oven-dried stir bar. In a separate oven-dried 1-dram vial was added 1-(4-penten-1-yloxy)-4-phenoxybenzene (102 mg, 0.40 mmol, 1 eq.), THF (200 μL), and 2-propanol-$d_8$ (77

μL, 1.0 mmol, 2.5 eq.). The solution in the 1-dram vial was added dropwise to the 2-dram vial. The 2-dram vial was capped with a pressure relief cap, removed from the glovebox, and left to stir for 22 h at 40° C. Upon completion, the product was isolated by flash column chromatography (300 mL of 100% hexanes) to give the pure product as a yellow solid (69 mg, 0.27 mmol, 68% yield).

$^1$H NMR: (400 MHz, $CDCl_3$) δ 7.30 (t, J=8.0 Hz, 2H), 7.04 (t, J=7.5 Hz, 1H), 6.96 (t, J=9.6 Hz, 4H), 6.88 (d, J=8.8 Hz, 2H), 3.94 (t, J=6.6 Hz, 2H), 1.79 (p, J=6.8 Hz, 2H), 1.52-1.33 (m, 4H), 0.97-0.89 (m, 2.09H). $^2$H NMR: (61 MHz, $CHCl_3$) δ 0.93 (s, 0.91D). $^{13}$C NMR: (101 MHz, $CDCl_3$) δ 158.70, 155.61, 150.01, 129.71, 122.47, 120.95, 117.65, 115.57, 68.57, 29.17, 28.32, 22.53, 13.88 (t, J=19.1 Hz). ATR-IR ($cm^{-1}$): 2930, 2861, 2173, 1488, 1215, 1023. HRMS: ($EI^+$) m/z: $[M]^+$ Calcd for $C_{17}H_{19}DO_2$ 257.1526; Found 257.1520.

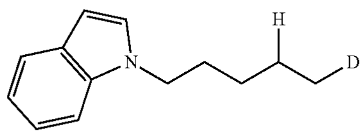 [SMILES: [2H]CCCCCn1ccc2ccccc21]

1-(pentyl-5-d)-1H-indole [4l] According to general procedure B, in a $N_2$ filled glovebox, DTB-DPPBz (79.7 mg, 0.089 mmol, 0.066 eq.), $Cu(OAc)_2$ (405 μL of a 0.2 M solution in THF, 0.081 mmol, 0.06 eq.), and THF (420 μL) followed by dimethoxy(methyl)silane (800 μL, 6.48 mmol, 4.8 eq.) were added to an oven-dried 2-dram vial with an oven-dried stir bar. In a separate oven-dried 1-dram vial was added 1-(4-penten-1-yl)-1H-indole (250 mg, 1.35 mmol, 1 eq.), THF (525 μL), and 2-propanol-$d_8$ (372 μL, 4.86 mmol, 3.6 eq.). The solution in the 1-dram vial was added dropwise to the 2-dram vial, 2-dram vial was capped with a pressure relief cap, removed from the glovebox, and left to stir for 24 h at 40° C. Upon completion, the product was isolated by flash column chromatography (300 mL of distilled hexanes) to give the pure product as a clear and colorless oil (231 mg, 1.23 mmol, 91% yield).

$^1$H NMR: (400 MHz, $CDCl_3$) δ 7.66 (d, J=7.6 Hz, 1H), 7.37 (d, J=8.1 Hz, 1H), 7.29-7.17 (m, 1H), 7.17-7.06 (m, 2H), 6.51 (d, J=3.1 Hz, 1H), 4.13 (t, J=7.2 Hz, 2H), 1.86 (p, J=7.2 Hz, 2H), 1.45-1.23 (m, 4H), 0.96-0.83 (m, 2.04H). $^2$H NMR: (61 MHz, $CHCl_3$) δ 0.89 (s, 0.96D). $^{13}$C NMR: (101 MHz, $CDCl_3$) δ 136.08, 128.69, 127.92, 121.40, 121.05, 119.26, 109.51, 100.93, 46.53, 30.10, 29.26, 22.39, 13.80 (t, J=19.3 Hz). ATR-IR ($cm^{-1}$): 2928, 2858, 2173, 1463, 1314, 1085. HRMS: ($ESI^+$) m/z: $[M+H]^+$ Calcd for $C_{13}H_{17}DN$ 189.1502; Found 189.1497.

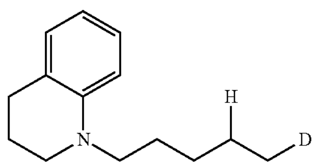 [SMILES: [2H]CCCCCN1CCCc2ccccc21]

1-(pentyl-5-d)-1,2,3,4-tetrahydroquinoline [4m]. According to general procedure B, in a $N_2$ filled glovebox, DTB-DPPBz (11.6 mg, 0.013 mmol, 0.044 eq.). $Cu(OAc)_2$ (60 μL of a 0.2 M solution in THF, 0.012 mmol, 0.04 eq.), and THF (90 μL) followed by dimethoxy(methyl)silane (148 μL, 1.20 mmol, 4 eq.) were added to an oven-dried 2-dram vial with an oven-dried stir bar. In a separate oven-dried 1-dram vial was added 1-(pent-4-en-1-yl)-1,2,3,4-tetrahydroquinoline (60 mg, 0.30 mmol, 1 eq.), THF (150 μL), and 2-propanol-$d_8$ (69 μL, 0.9) mmol, 3 eq.). The solution in the 1-dram vial was added dropwise to the 2-dram vial. The 2-dram vial was capped with a pressure relief cap, removed from the glovebox, and left to stir for 24 h at 40° C. Upon completion, the product was isolated by flash column chromatography using gradient elution (100 mL of 100% hexanes, 100 mL of 2% ethyl acetate in hexanes) to give the pure product as a red oil (51 mg, 0.25 mmol, 83% yield).

$^1$H NMR: (400 MHz, $CDCl_3$) δ 7.09 (t, J=7.8 Hz, 1H), 6.98 (d, J=7.3 Hz, 1H), 6.64-6.55 (m, 2H), 3.32 (t, J=5.7 Hz, 2H), 3.28 (t, J=7.7 Hz, 2H), 2.80 (t, J=6.4 Hz, 2H), 1.99 (p, J=6.1 Hz, 2H), 1.64 (p, J=7.5 Hz, 2H), 1.46-1.29 (m, 4H), 1.04-0.89 (m, 2.04H). $^2$H NMR: (61 MHz, $CHCl_3$) δ 0.96 (s, 0.96D) $^{13}$C NMR: (101 MHz, $CDCl_3$) δ 145.47, 129.21, 127.15, 122.22, 115.27, 110.54, 51.61, 49.54, 29.56, 28.34, 26.02, 22.68, 22.38, 13.94 (t, J=19.2 Hz). ATR-IR ($cm^{-1}$): 2927, 2858, 2173, 1601, 1502, 1456, 1201. HRMS: ($ESI^+$) m/z: $[M+H]^+$ Calcd for $C_{14}H_{21}DN$ 205.1815; Found 205.1830.

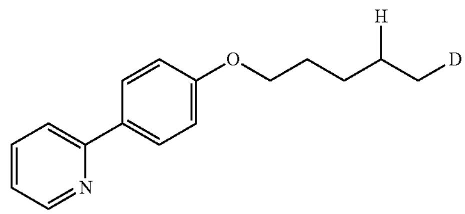 [SMILES: [2H]CCCCCOc1ccc(-c2ccccn2)cc1]

2-(4-((Pentyl-5-d)oxy)-phenyl)pyridine [4n] According to general procedure B, in a $N_2$ filled glovebox, DTB-DPPBz (11.6 mg, 0.013 mmol, 0.033 eq.), $Cu(OAc)_2$ (60 μL of a 0.2 M solution in THF, 0.012 mmol, 0.03 eq.), and THF (140 μL) followed by dimethoxy(methyl)silane (148 μL, 1.20 mmol, 3 eq.) were added to an oven-dried 2-dram vial with an oven-dried stir bar. In a separate oven-dried 1-dram vial was added 2-(4-(4-penten-1-yloxy)phenyl)pyridine (96 mg, 0.40 mmol, 1 eq.), THF (200 μL), and 2-propanol-$d_8$ (77 μL, 1.0 mmol, 2.5 eq.). The solution in the 1-dram vial was added dropwise to the 2-dram vial. The 2-dram vial was capped with a pressure relief cap, removed from the glovebox, and left to stir for 24 h at 40° C. Upon completion, the product was isolated by flash column chromatography using gradient elution (100 mL of 100% hexanes, 100 mL of 2% ethyl acetate in hexanes, 200 mL of 5% ethyl acetate in hexanes) to give the pure product as a clear and colorless oil (81 mg, 0.33 mmol, 83% yield).

$^1$H NMR: (400 MHz, $CDCl_3$) δ 8.69-8.60 (m, 1H), 7.94 (d, J=8.8 Hz, 2H), 7.80-7.60 (m, 2H), 7.21-7.10 (m, 1H), 6.99 (d, J=8.8 Hz, 2H), 4.01 (t, J=6.6 Hz, 2H), 1.89-1.74 (m, 2H), 1.54-1.31 (m, 4H), 1.00-0.86 (m, 2.01H), $^2$H NMR: (61 MHz, $CHCl_3$) δ 0.92 (s, 0.99D). $^{13}$C NMR: (101 MHz, $CDCl_3$) δ 160.16, 157.28, 149.64, 136.73, 131.88, 128.21, 121.44, 119.85, 114.76, 68.17, 29.08, 28.29, 22.51, 13.86 (t, J=19.0 Hz) ATR-IR ($cm^{-1}$); 2938, 2956, 2174, 1463, 1253, 1016. HRMS: ($ESI^+$) m/z: $[M+H]^+$ Calcd for $C_{16}H_{19}DNO$ 243.1607; Found 243.1646.

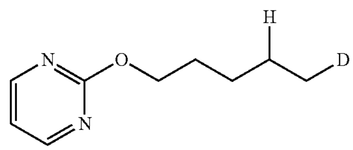 [SMILES: [2H]CCCCCOc1ncccn1]

2-((Pentyl-5-d)oxy)pyrimidine [4o]. According to general procedure B, in a $N_2$ filled glovebox, DTB-DPPBz (8.9 mg, 0.0099 mmol, 0.033 eq.), $Cu(OAc)_2$ (45 μL of a 0.2 M solution in THF, 0.009 mmol, 0.03 eq.), and THF (105 μL) followed by dimethoxy(methyl)silane (111 μL, 0.90 mmol, 3 eq.) were added to an oven-dried 2-dram vial with an oven-dried stir bar. In a separate oven-dried 1-dram vial was added 2-(4-penten-1-yloxy)pyrimidine (49 mg, 0.30 mmol, 1 eq.), THF (150 μL), and 2-propanol-$d_8$ (57 μL, 0.75 mmol, 2.5 eq.). The solution in the 1-dram vial was added dropwise to the 2-dram vial. The 2-dram vial was capped with a pressure relief cap, removed from the glovebox, and left to stir for 22 h at 40° C. Upon completion, the product was isolated by flash column chromatography using gradient elution (100 mL of 100% hexanes, 100 mL of 7% ethyl acetate in hexanes, 100 mL of 14% ethyl acetate in hexanes) to give the pure product as a yellow oil (44 mg, 0.26 mmol, 87% yield).

$^1H$ NMR: (400 MHz, $CDCl_3$) δ 8.51 (br s, 2H), 6.90 (s, 1H), 4.30 (t, J=6.6 Hz, 2H), 1.77 (p, J=6.8 Hz, 2H), 1.48-1.23 (m, 4H), 0.90-0.81 (m, 2.01H). $^2H$ NMR: (61 MHz, $CHCl_3$) δ 0.85 (s, 0.99D). $^{13}C$ NMR: (75 MHz, $CDCl_3$) δ 165.40, 159.10, 115.15, 67.70, 28.53, 28.06, 22.34, 13.71 (t, J=19.1 Hz). ATR-IR ($cm^{-1}$): 2930, 2860, 2182, 1561, 1422, 1320, 1045, 1017. HRMS: ($ESI^+$) m/z: $[M+H]^+$ Calcd for $C_9H_{14}DN_2O$ 168.1247; Found 168.1221.

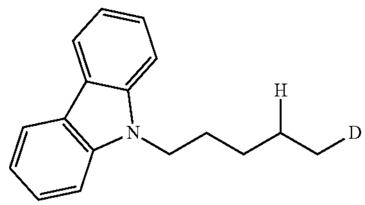 [SMILES: [2H]CCCCCn1c2ccccc2c2ccccc21]

9-(Pentyl-5-d)-9H-carbazole [4p] According to general procedure B, in a $N_2$ filled glovebox, DTB-DPPBz (11.6 mg, 0.013 mmol, 0.033 eq.), $Cu(OAc)_2$ (60 μL of a 0.2 M solution in THF, 0.012 mmol, 0.03 eq.), and THF (140 μL) followed by dimethoxy(methyl)silane (148 μL, 1.20 mmol, 3 eq.) were added to an oven-dried 2-dram vial with an oven-dried stir bar. In a separate oven-dried 1-dram vial was added 9-(4-penten-1-yl)-9H-carbabzole (94 mg, 0.40 mmol, 1 eq.), THF (200 μL), and 2-propanol-$d_8$ (77 μL, 1.0 mmol, 2.5 eq.). The solution in the 1-dram vial was added dropwise to the 2-dram vial. The 2-dram vial was capped with a pressure relief cap, removed from the glovebox, and left to stir for 23 h at 40° C. Upon completion, the product was isolated by flash column chromatography using gradient elution (100 mL of 100% hexanes, 100 mL of 1% ethyl acetate in hexanes) to give the pure product as a yellow oil (85 mg, 0.36 mmol, 90% yield).

$^1H$ NMR: (400 MHz, $CDCl_3$) δ 8.17 (d, J=7.9 Hz, 2H), 7.57-7.48 (m, 2H), 7.46 (d, J=8.0 Hz, 2H), 7.33-7.26 (m, 2H), 4.33 (t, J=7.3 Hz, 2H), 1.98-1.86 (m, 2H), 1.49-1.37 (m, 4H), 0.98-0.88 (m, 2.03H). $^2H$ NMR: (61 MHz, $CHCl_3$) δ 0.92 (s, 0.97D). $^{13}C$ NMR: (75 MHz, $CDCl_3$) δ 140.54, 125.68, 122.92, 120.46, 118.80, 108.7, 43.15, 29.52, 28.81, 22.54, 13.80 (t, J=19.1 Hz). ATR-IR ($cm^{-1}$): 3052, 2925, 2855, 2175, 1924, 1883, 1850, 1768, 1324. HRMS: ($ESI^+$) m/z: $[M+H]^+$ Calcd for $C_{17}H_{19}DN$ 239.1658; Found 239.1653.

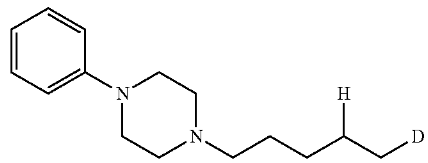 [SMILES: [2H]CCCCCN1CCN(c2ccccc2)CC1]

1-(Pentyl-5-d)-4-phenylpiperazine [4q] According to general procedure B, in a $N_2$ filled glovebox, DTB-DPPBz (11.6 mg, 0.013 mmol, 0.033 eq.), $Cu(OAc)_2$ (60 μL of a 0.2 M solution in THF, 0.012 mmol, 0.03 eq.), and THF (140 μL) followed by dimethoxy(methyl)silane (148 μL, 1.20 mmol, 3 eq.) were added to an oven-dried 2-dram vial with an oven-dried stir bar. In a separate oven-dried 1-dram vial was added 1-(4-penten-1-yl)-4-phenylpiperazine (92 mg, 0.40 mmol, 1 eq.), THF (200 μL), and 2-propanol-$d_h$ (77 μL, 1.0 mmol, 2.5 eq.). The solution in the 1-dram vial was added dropwise to the 2-dram vial. The 2-dram vial was capped with a pressure relief cap, removed from the glovebox, and left to stir for 24 h at 40° C. Upon completion, the product was isolated by flash column chromatography using gradient elution (100 mL of 100% $CH_2Cl_2$, 200 mL 2% MeOH in $CH_2Cl_2$) to give the pure product as an orange oil (84 mg, 0.36 mmol, 90% yield).

$^1H$ NMR: (400 MHz, $CDCl_3$) δ 7.26 (t, J=7.9 Hz, 2H), 6.93 (d, J=8.1 Hz, 2H), 6.85 (t, J=7.5 Hz, 1H), 3.26-3.17 (m, 4H), 2.66-2.58 (m, 4H), 2.40 (t, J=7.9 Hz, 2H), 1.59-1.49 (m, 2H), 1.38-1.27 (m, 4H), 0.92-0.86 (m, 2.08H). $^2H$ NMR: (61 MHz, $CHCl_3$) δ 0.89 (s, 0.92D)$^{13}C$ NMR: (101 MHz, $CDCl_3$) δ 151.43, 129.20, 119.77, 116.15, 53.39, 49.18, 31.51, 29.88, 26.63, 22.66, 13.88 (t, J=19.1 Hz). ATR-IR ($cm^{-1}$): 2928, 2814, 2177, 1600, 1502, 1232. HRMS: ($ESI^+$) m/z: $[M+H]^+$ Calcd for $C_{15}H_{24}N_2$ 234.2080; Found 234.2063.

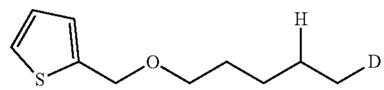 [SMILES: [2H]CCCCCOCc1cccs1]

2-(((Pentyl-5-d)oxy)methyl)thiophene [4r] According to general procedure B, in a $N_2$ filled glovebox, DTB-DPPBz (11.6 mg, 0.013 mmol, 0.033 eq.). $Cu(OAc)_2$ (60 μL of a 0.2 M solution in THF, 0.012 mmol, 0.03 eq.), and THF (140 μL) followed by dimethoxy(methyl)silane (148 μL, 1.20 mmol, 3 eq.) were added to an oven-dried 2-dram vial with an oven-dried stir bar. In a separate oven-dried 1-dram vial was added 2-((4-penten-1-yloxy)methyl)thiophene (73 mg, 0.40 mmol, 1 eq.), THF (200 μL), and 2-propanol-d (77 μL, 1.0 mmol, 2.5 eq.). The solution in the 1-dram vial was added dropwise to the 2-dram vial. The 2-dram vial was capped with a pressure relief cap, removed from the glovebox, and left to stir for 24 h at 40° C. Upon completion, the product was isolated by flash column chromatography using gradient elution (200 mL of 2% ethyl acetate in hexanes, 200 mL of 5% ethyl acetate in hexanes) to give the pure product as a light-yellow oil (62 mg, 0.33 mmol, 83% yield).

$^1H$ NMR: (400 MHz, $CDCl_3$) δ 7.28 (d, J=5.0 Hz, 1H), 7.02-6.95 (m, 2H), 4.67 (s, 2H), 3.48 (t, J=6.7 Hz, 2H), 1.61

(p, J=6.8 Hz, 2H), 1.38-1.29 (m, 4H), 0.93-0.85 (m, 2.07H). $^2$H NMR: (61 MHz, $CHCl_3$) δ 0.89 (s, 0.93D). $^{13}$C NMR: (101 MHz, $CDCl_3$) δ 141.62, 126.66, 126.20, 125.69, 70.29, 67.40, 29.47, 28.37, 22.54, 13.85 (t, J=18.9 Hz). ATR-IR ($cm^{-1}$): 2930, 2853, 2169, 1168, 1088. HRMS: ($EI^+$) m/z: $[M]^+$ Calcd for $C_{10}H_{15}DOS$ 185.0985, Found 185.0978.

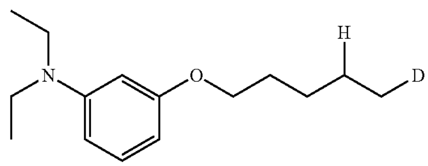 [SMILES: [2H]CCCCCOc1cccc(N(CC)CC)c1]

N,N-diethyl-3-((pentyl-5-d)oxy)aniline [4s] According to general procedure B, in a $N_2$ filled glovebox, DTB-DPPBz (11.6 mg, 0.013 mmol, 0.033 eq.), $Cu(OAc)_2$ (60 μL of a 0.2 M solution in THF, 0.012 mmol, 0.03 eq.), and THF (140 μL) followed by dimethoxy(methyl)silane (148 μL, 1.20 mmol, 3 eq.) were added to an oven-dried 2-dram vial with an oven-dried stir bar. In a separate oven-dried 1-dram vial was added N,N-diethyl-3-(4-penten-1-yloxy)aniline (93 mg, 0.40 mmol, 1 eq.), THF (200 μL), and 2-propanol-$d_8$ (77 μL, 1.0 mmol, 2.5 eq.). The solution in the 1-dram vial was added dropwise to the 2-dram vial. The 2-dram vial was capped with a pressure relief cap, removed from the glovebox, and left to stir for 24 h at 40° C. Upon completion, the product was isolated by flash column chromatography using gradient elution (100 mL of 100% hexanes, 100 mL of 1% ethyl acetate in hexanes, 100 mL of 2% ethyl acetate in hexanes) to give the pure product as a dark green oil (61 mg, 0.26 mmol, 65% yield).

$^1$H NMR: (400 MHz, $CDCl_3$) δ 7.11 (t, J=8.1 Hz, 1H), 6.30 (d, J=8.1 Hz, 1H), 6.25-6.18 (m, 2H), 3.95 (t, J=6.6 Hz, 2H), 3.34 (q, J=6.9 Hz, 4H), 1.84-1.74 (m, 2H), 1.50-1.32 (m, 4H), 1.16 (t, J=7.0 Hz, 6H), 0.95-0.87 (m, 2.08H), $^2$H NMR: (61 MHz, $CHCl_3$) δ 0.92. (s, 0.92D). $^{13}$C NMR: (101 MHz, $CDCl_3$) δ 160.56, 149.18, 129.91, 105.02, 100.76, 99.02, 67.79, 44.49, 29.24, 28.33, 22.52, 13.85 (t, J=19.0 Hz), 12.71. ATR-IR ($cm^{-1}$): 2928, 2868, 2171, 1284, 1214, 1142, 1053. HRMS: ($ESI^+$) m/z: $[M+H]^+$ Calcd for $C_{15}H_{25}DNO$ 237.2077; Found 237.2099.\

Varying Chain Length and Natural Product Analogs

Scheme S4. Scope of Various Alkene Lengths and Natural Product Analogs

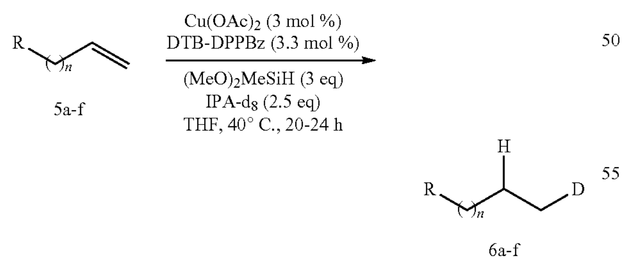

5a-f 6a-f a) Variation of the Terminal Alkene

6a

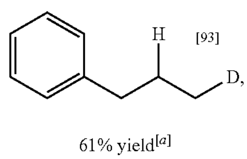

61% yield[a]

-continued

6b

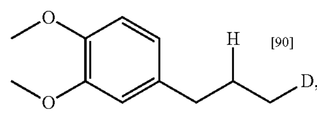

93% yield

6c

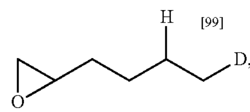

83% yield[a]

6d

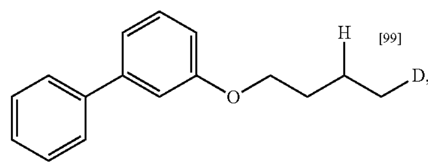

90% yield b) Natural Product Analogs

6e

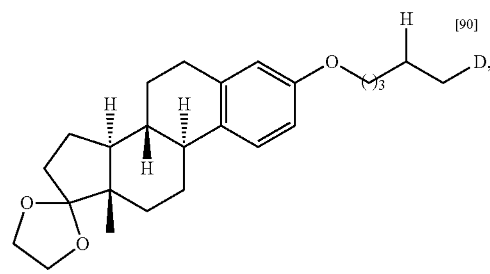

85% yield

6f

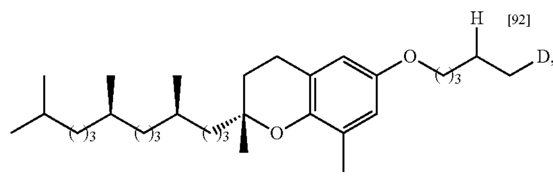

83% yield[b]

[a]Yield determined by $^1$H NMR analysis using 1,3,5-trimethylbenzene as an internal standard. [b]Reaction performed at 60° C.

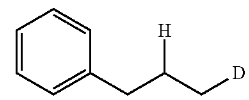

(Propyl-3-d)-benzene [6a]. According to general procedure B, in a $N_2$ filled glovebox, DTB-DPPBz (8.9 mg, 0.009) mmol, 0.033 eq.), $Cu(OAc)_2$ (45 μL of a 0.2 M solution in THF, 0.009 mmol, 0.03 eq.), and THF (105 μL) followed by dimethoxy(methyl)silane (111 μL, 0.90 mmol, 3 eq.) were added to an oven-dried 2-dram vial with an oven-dried stir bar. In a separate oven-dried 1-dram vial was added allyl benzene (35 mg, 0.30 mmol, 1 eq.), THF (150 μL), and 2-propanol-$d_8$ (57 μL, 0.75 mmol, 2.5 eq.). The solution in the 1-dram vial was added dropwise to the 2-dram vial. The 2-dram vial was capped with a pressure relief cap, removed from the glovebox, and left to stir for 23 h at 40° C. Upon completion, ether (24 mL) was added to the crude mixture and filtered through a 1-inch silica plug. Then the mixture was concentrated and 1,3,5-trimethylbenzene (0.33 eq.) was used as an internal standard to determine $^1$H NMR crude yield (61% crude yield by $^1$H NMR).

$^1$H NMR: (400 MHz, $CDCl_3$) of the crude product δ 7.20-7.15 (m, 2H), 7.07 (d, J=7.1 Hz, 3H), 2.50 (t, J=7.5 Hz, 2H), 1.56 (p, J=7.5 Hz, 2H), 0.88-0.82 (m, 2.07H). $^2$H NMR: (61 MHz, $CHCl_3$) of the crude product δ 0.85 (s, 0.93D).

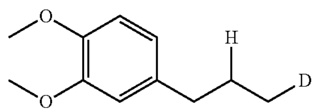

1,2-dimethoxy-4-(propyl-5-d)benzene [6b]. According to general procedure B, in a $N_2$ filled glovebox, DTB-DPPBz (8.9 mg, 0.0099 mmol, 0.033 eq.), $Cu(OAc)_2$ (45 μL of a 0.2 M solution in THF, 0.009 mmol, 0.03 eq.), and THF (105 μL) followed by dimethoxy(methyl)silane (111 μL, 0.90 mmol, 3 eq.) were added to an oven-dried 2-dram vial with an oven-dried stir bar. In a separate oven-dried 1-dram vial was added 3-(3,4-dimethoxyphenyl)-1-propene (53 mg, 0.30 mmol, 1 eq.), THF (150 μL), and 2-propanol-$d_8$ (57 μL, 0.75 mmol, 2.5 eq.). The solution in the 1-dram vial was added dropwise to the 2-dram vial. The 2-dram vial was capped with a pressure relief cap, removed from the glovebox, and left to stir for 23 h at 40° C. Upon completion, the product was isolated by flash column chromatography using gradient elution (100 mL of 100% hexanes, 100 mL of 2% ethyl acetate in hexanes, 100 mL of 4% ethyl acetate in hexanes) to give the pure product as a clear yellow oil (50 mg, 0.28 mmol, 93% yield).

$^1$H NMR: (400 MHz, $CDCl_3$) δ 6.80-6.76 (m, 1H), 6.73-6.70 (m, 2H), 3.87 (s, 3H), 3.85 (s, 3H), 2.53 (t, J=7.5 Hz, 2H), 1.66-1.56 (m, 2H), 0.95-0.88 (m, 2.10H). $^2$H NMR: (61 MHz, $CHCl_3$) δ 0.92 (s, 0.90D). $^{13}$C NMR: (101 MHz, $CDCl_3$) δ 148.71, 147.01, 135.41, 120.22, 111.76, 111.08, 55.92, 55.79, 37.69, 24.76, 13.59 (t, J=19.0 Hz). ATR-IR ($cm^{-1}$): 2952, 2932, 2176, 1513, 1232, 1154, 1028. HRMS: ($ESI^+$) m/z: $[M+H]^+$ Calcd for $C_{11}H_{16}DO_2$182.1291; Found 182.1287.

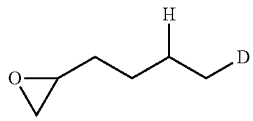

2-(butyl-4-d)oxirane [6c]. According to general procedure B, in a $N_2$ filled glovebox, DTB-DPPBz (11.6 mg, 0.013 mmol, 0.033 eq.), $Cu(OAc)_2$ (60 μL of a 0.2 M solution in THF, 0.012 mmol, 0.03 eq.), and THF (140 μL) followed by dimethoxy(methyl)silane (148 μL, 1.20 mmol, 3 eq.) were added to an oven-dried 2-dram vial with an oven-dried stir bar. In a separate oven-dried 1-dram vial was added 2-butyloxirane (39 mg, 0.40 mmol, 1 eq.), THF (200 μL), and 2-propanol-$d_8$ (77 μL, 1.0 mmol, 2.5 eq.). The solution in the 1-dram vial was added dropwise to the 2-dram vial. The 2-dram vial was capped with a pressure relief cap, removed from the glovebox, and left to stir for 23 h at 40° C. Upon completion, the reaction mixture was filtered with ether (3 mL) through a pasteur pipette loaded with 1 cm of cotton and 3.5 cm of silica gel. Afterwards, 1,3,5-trimethylbenzene (0.33 eq.) was added as internal standard to determine the crude $^1$H NMR yield (83% crude yield by $^1$H NMR).

$^1$H NMR: (400 MHz, $CDCl_3$) of the crude product δ 2.91-2.80 (m, 1H), 2.72-2.65 (m, 1H), 2.43-2.37 (m, 1H), 1.53-1.23 (m, 6H), 0.90-0.80 (m, 2.01H). $^2$H NMR: (61 MHz, $CHCl_3$) of the crude product δ 0.84 (s, 0.99D)

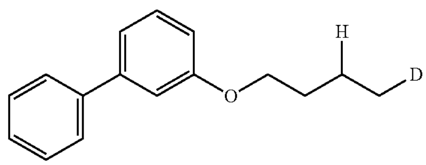 [SMILES: [2H]CCCCOc1cccc(-c2ccccc2)c1]

3-((butyl-4-d)oxy)-1,1'-biphenyl [6d]. According to general procedure B, in a $N_2$ filled glovebox, DTB-DPPBz (8.9 mg, 0.0099 mmol, 0.033 eq.), $Cu(OAc)_2$ (45 μL of a 0.2 M solution in THF, 0.009 mmol, 0.03 eq.), and THF (105 μL) followed by dimethoxy(methyl)silane (111 μL, 0.90 mmol, 3 eq.) were added to an oven-dried 2-dram vial with an oven-dried stir bar. In a separate oven-dried 1-dram vial was added 3-(3-buten-lyloxy)-1,1'-biphenyl (67 mg, 0.30 mmol, 1 eq.), THF (150 μL), and 2-propanol-$d_8$ (57 μL, 0.75 mmol, 2.5 eq.). The solution in the 1-dram vial was added dropwise to the 2-dram vial. The 2-dram vial was capped with a pressure relief cap, removed from the glovebox, and left to stir for 20 h at 40° C. Upon completion, the product was isolated by flash column chromatography using gradient elution (100 mL of 100% hexanes, 100 mL of 2% ethyl acetate in hexanes) to give the pure product as a yellow oil (62 mg, 0.27 mmol, 90% yield).

$^1$H NMR: (300 MHz, $CDCl_3$) δ 7.66 (d, J=7.3 Hz, 2H), 7.48 (t, J=7.4 Hz, 2H), 7.39 (t, J=7.4 Hz, 2H), 7.25-7.18 (m, 2H), 6.95 (d, J=8.3 Hz, 1H), 4.07 (t, J=6.4 Hz, 2H), 1.92-1.78 (m, 2H), 1.65-1.49 (m, 2H), 1.09-0.97 (m, 2.01H). $^2$H NMR: (61 MHz, $CHCl_3$) δ 1.03 (s, 0.99D). $^{13}$C NMR: (75 MHz, $CDCl_3$) δ 159.63, 142.81, 141.28, 129.82, 128.82, 127.47, 127.30, 119.57, 113.62, 113.34, 67.82, 31.48, 19.33, 13.72 (t, J=19.2 Hz). ATR-IR ($cm^{-1}$): 2935, 2868, 2175, 1295, 1202, 1052, 1036. HRMS: ($ESI^+$) m/z: $[M+H]^+$ Calcd for $C_{16}H_{18}DO$ 228.1498; Found 228.1494.

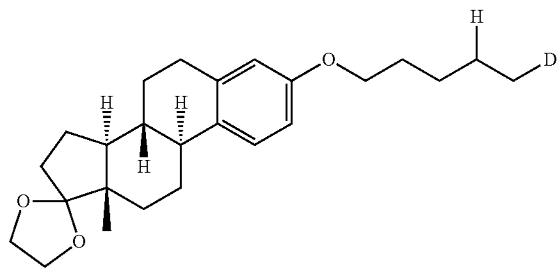

(8R,9S,13S,14S)-13-methyl-3-((pentyl-5-d)oxy)-6,7,8,9,11,12,13,14,15,16-decahydrospiro[cyclopenta[a]phenanthrene-17,2'-[1,3]dioxolane] [6e] According to general procedure B, in a $N_2$ filled glovebox, DTB-DPPBz (11.6 mg, 0.013 mmol, 0.033 eq.), $Cu(OAc)_2$ (60 μL of a 0.2 M solution in THF, 0.012 mmol, 0.03 eq.), and THF (140 μL) followed by dimethoxy(methyl)silane (148 μL, 1.20 mmol, 3 eq.) were added to an oven-dried 2-dram vial with an oven-dried stir bar. In a separate oven-dried 1-dram vial was added the (8R,9S,13S,14S)-13-methyl-3-(4-penten-1-yloxy)-6,7,8,9,11,12,13,14,15,16-decahydrospiro[cyclopenta[a]phenanthrene-17,2'-[1,3]dioxolane (153 mg, 0.40 mmol, 1 eq.), THF (200 μL), and 2-propanol-$d_8$ (77 μL, 1.0 mmol, 2.5 eq.). The solution in the 1-dram vial was added dropwise to the 2-dram vial. The 2-dram vial was capped with a pressure relief cap, removed from the glovebox, and left to stir for 24 h at 40° C. Upon completion, the product was isolated by flash column chromatography using gradient elution (100 mL of 100% hexanes, 100 mL of 2% ethyl acetate in hexanes, 100 mL of 5% ethyl acetate in hexanes) to give the pure product as a pale yellow/green viscous oil (130 mg, 0.34 mmol, 85% yield).

$^1$H NMR: (300 MHz, $CDCl_3$) δ 7.20 (d, J=8.4 Hz, 1H), 6.71 (dd, J=8.6, 2.7 Hz, 1H), 6.63 (d, J=2.7 Hz, 1H), 4.02-3.86 (m, 6H), 2.94-2.77 (m, 2H), 2.38-2.18 (m, 2H), 2.10-1.99 (m, 1H), 1.95-1.73 (m, 6H), 1.72-1.60 (m, 1H), 1.59-1.51 (m, 1H), 1.50-1.29 (m, 8H), 0.96-0.86 (m, 5.10H). $^2$H NMR: (61 MHz, $CHCl_3$) δ 0.92 (s, 0.90D). $^{13}$C NMR: (75 MHz, $CDCl_3$) δ 157.10, 138.05, 132.61, 126.38, 119.56, 114.55, 112.11, 67.99, 65.37, (4.70, 49.48, 46.29, 43.75, 39.20, 34.36, 31.44, 30.86, 29.18, 28.32, 27.14, 26.27, 22.50, 22.49, 14.46, 13.87 (t, J=19.1 Hz). ATR-IR ($cm^{-1}$): 2933, 2867, 2174, 1606, 1497, 1309, 1103, 1045. HRMS: ($ESI^+$) m/z: $[M+H]^+$ Calcd for $C_{25}H_{36}DO_3$ 386.2805; Found 386.2802.

$^1$H NMR: (400 MHz, $CDCl_3$) extra proton observed due to signal overlapping with H grease δ 6.56 (d, J=3.0 Hz, 1H), 6.44 (d, J=3.0 Hz, 1H), 3.86 (t, J=6.6 Hz, 2H), 2.71 (t, J=7.1 Hz, 2H), 2.14 (s, 3H), 1.82-1.70 (m, 4H), 1.60-1.47 (m, 4H), 1.46-1.34 (m, 8H), 1.31-1.21 (m, 10H), 1.18-1.02 (m, 7H), 0.93-0.82 (m, 14H), $^2$H NMR: (61 MHz, $CHCl_3$) δ 0.91 (s) $^{13}$C NMR: (101 MHz, $CDCl_3$) δ 151.78, 146.12, 127.19, 120.97, 115.53, 111.89, 75.59, 68.48, 40.09, 39.53, 37.60, 37.44, 32.95, 32.83, 31.56, 29.88, 29.37, 28.41, 28.13, 24.97, 24.60, 24.28, 22.88, 22.84, 22.79, 22.57, 21.13, 19.90, 19.81, 16.36, 13.91 (t=19.3 Hz). ATR-IR ($cm^{-1}$): 2925, 2859, 2175, 1468, 1250, 1154, 1056. HRMS: ($ESI^+$) m/z: $[M+H]^+$ Calcd for $C_{32}H_{56}DO_2$ 474.4418; Found 474.4415.

Synthesis of Dimethoxy(methyl)silane-d

The procedure was adopted from a previously reported procedure.[2]

To an oven-dried 500 mL Schlenk flask equipped with a Teflon stir bar in a $N_2$ filled glovebox was added the $Pt(PPh_3)_4$ (585.8 mg, 0.471 mmol, 0.01 eq.), dimethoxy (methyl)silane (5.81 mL, 47.1 mmol, 1 eq.), and 2.5 mL of degassed anhydrous hexanes. The Schlenk flask was sealed with a rubber septum, removed from the glovebox, connected to a manifold line, and cooled to −78° C. A single freeze-pump-thaw cycle was performed, and the Schlenk

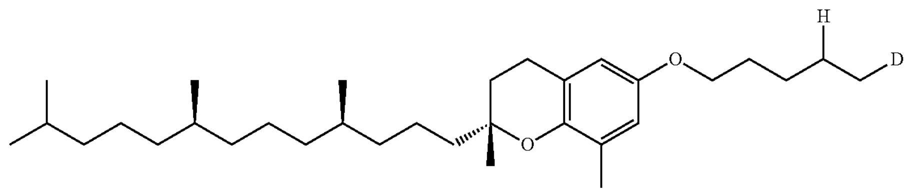 [SMILES: [2H]CCCCCOc1cc(C)c2c(c1)CC[C@@](C)(CCC[C@H](C)CCC[C@H](C)CCCC(C)C)O2]

(R)-2,8-dimethyl-6-((pentyl-5-d)oxy)-2-((4R,8R)-4,8,12-trimethyltridecyl)chromane [6f] According to general procedure B, in a $N_2$ filled glovebox, DTB-DPPBz (8.9 mg, 0.0099 mmol, 0.033 eq.), $Cu(OAc)_2$ (45 μL of a 0.2 M solution in THF, 0.009 mmol, 0.03 eq.), and THF (105 μL) followed by dimethoxy(methyl)silane (111 μL, 0.90 mmol, 3 eq.) were added to an oven-dried 2-dram vial with an oven-dried stir bar. In a separate oven-dried 1-dram vial was added (R)-2,8-dimethyl-6-(4-penten-1-yloxy)-2-((4R,8R)-4,8,12-trimethyltridecyl)chromane (141 mg, 0.30 mmol, 1 eq.), THF (150 μL), and 2-propanol-$d_8$ (57 μL, 0.75 mmol, 2.5 eq.). The solution in the 1-dram vial was added dropwise to the 2-dram vial. The 2-dram vial was capped with a pressure relief cap, removed from the glovebox, and left to stir for 24 h at 60° C. Upon completion, the product was isolated by flash column chromatography using gradient elution (100 mL of 100% hexanes, 200 mL of 0.5%) to give the pure product as a clear oil (118 mg, 0.25 mmol, 83% yield).

To determine deuterium incorporation, a quantitative $^{13}$C NMR was performed. The quantitative $^{13}$C NMR is included along with a zoomed in spectrum of the region containing the triplet corresponding to the terminal carbon with the incorporated deuterium. It was verified by examining the transfer hydrogenation product (8) that the terminal $CH_3$ overlaps with the most downfield peak of the $CH_2D$ triplet. Therefore, each peak of the triplet was separately integrated, and it was determined that the deuterium incorporation was at least 92%.

flask was backfilled with $D_2$ gas from a $D_2$ purged balloon at room temperature. The flask was sealed with parafilm and heated to 60° C. After 2 hours, the reaction was cooled to room temperature and then a single freeze-pump-thaw was performed again, backfilling with $D_2$ gas. The process was repeated 6 times or until the $^1$HNMR showed ≥95% Deuterium incorporation. It is important to maintain a $N_2$ (g) inert atmosphere while obtaining a minimal quantity of sample for $^1$HNMR analysis.

The solution was purified through a distillation apparatus: the set up consisted of a flame-dried 25 mL round-bottom receiving flask and a cannula. The 25 mL round-bottom receiving flask was flame-dried, and then filled with $N_2$. Once the receiving flask reached room temperature, the cannula was inserted, maintaining positive pressure, and tightly sealed with parafilm to prevent condensation from entering. Upon confirmation of positive $N_2$ flow, the open end of the cannula was inserted into the Schlenk reaction flask. The 25 mL round-bottom receiving flask was cooled to −78° C. and closed to the manifold line and then the Schlenk flask was heated to 80° C. The heat initiated the distillation of the dimethoxy(methyl)silane-d and the hexane through the cannula which were trapped in the cold 25 mL round-bottom receiving flask. Vacuum was also applied to the 25 mL round-bottom receiving flask to promote this process. Once all the silane and hexane were trapped in the 25 mL round-bottom receiving flask, the flask was removed from the heat and the manifold was closed to vacuum line while the 25 mL round-bottom receiving flask warmed to room temperature. Under positive nitrogen flow, the cannula was removed from the 25 mL round-bottom receiving flask, while keeping it inserted in the Schlenk reaction flask. The 25 mL round-bottom receiving flask was tightly sealed with Parafilm and stored in the −4° C. freezer. The final product was in a solution of hexane, and the molarity was calculated by $^1$HNMR using 1,3,5-trimethylbenzene as an internal standard, and used for the transfer deuteration reaction (2.66 g in a 6.05 M hexane solution, 24.8 mmol, 53% yield).

Note: it is important to monitor that the end of the cannula does not get clogged by frozen solvent/silane. If this occurs, remove the Schlenk reaction flask from heat and close manifold to vacuum line. Warm the 25 mL round-bottom receiving flask until the solids on the tip of the cannula melt, and then distillation can be resumed.

Keya Reaction Studies

Scheme 5. Reaction Modularity and Chemoselectivity Studies a) Alkene Transfer Hydrogenation

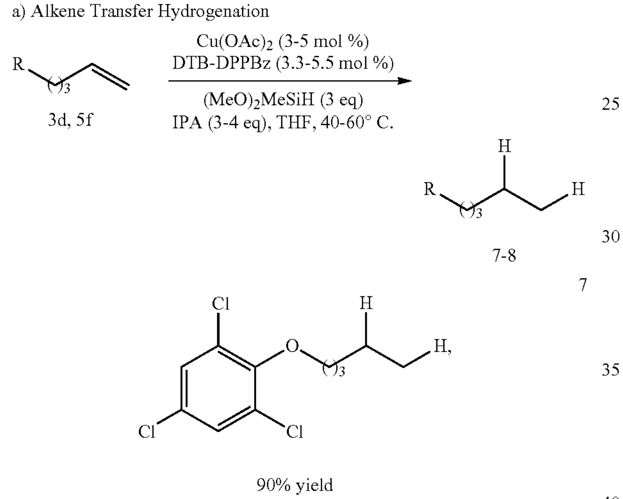

7

8

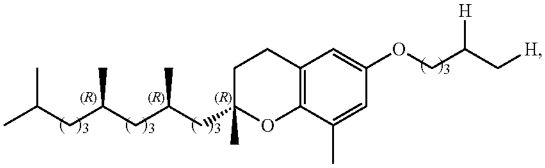

75% yield b) Alkene Transfer Deuteration

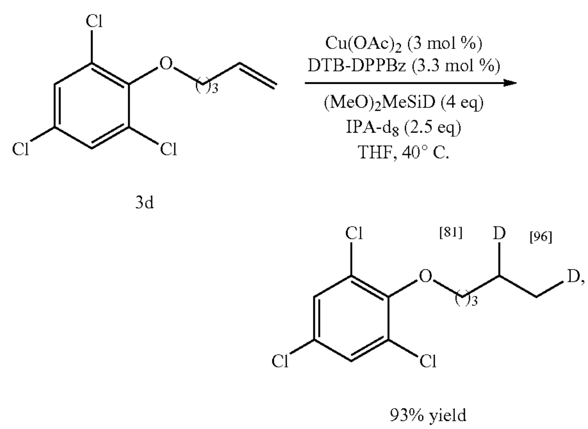

-continued

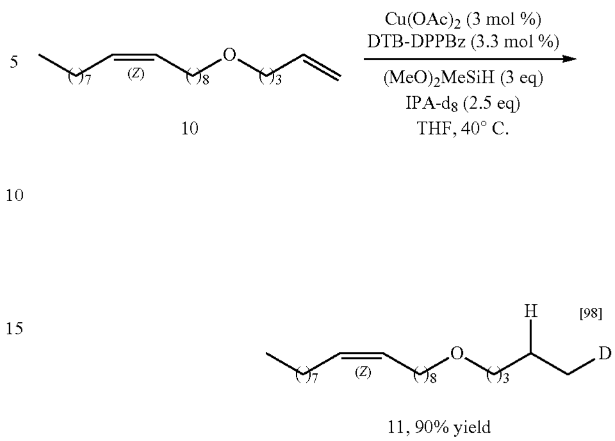

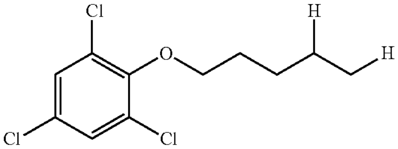 [SMILES: CCCCCOc1c(Cl)cc(Cl)cc1Cl]

1,3,5-Trichloro-2-(pentyloxy)-benzene 171 According to general procedure B, in a $N_2$ filled glovebox, DTB-DPPBz (14.8 mg, 0.0165 mmol, 0.055 eq.), $Cu(OAc)_2$ (75 μL of a 0.2 M solution in THF, 0.015 mmol, 0.05 eq.), and THF (125 μL) followed by dimethoxy(methyl)silane (185 μL, 1.50 mmol, 5 eq.) were added to an oven-dried 2-dram vial with an oven-dried stir bar. In a separate oven-dried 1-dram vial was added 2,4,6-trichloro-4-(5-pentan-1-yloxy)-benzene (80 mg, 0.30 mmol, 1 eq.), THF (100 μL), and 2-propanol (92 μL, 1.2, mmol, 4 eq.). The solution in the 1-dram vial was added dropwise to the 2-dram vial. The 2-dram vial was capped with a pressure relief cap, removed from the glove-box, and left to stir for 24 h at 40° C. Upon completion, the product was isolated by flash column chromatography using gradient elution (200 mL of 100% hexanes, 100 mL of 1% ethyl acetate in hexanes) to give the pure product as a colorless oil (72 mg, 0.27 mmol, 90% yield).

$^1$H NMR: (400 MHz, $CDCl_3$) δ 7.29 (s, 2H), 3.98 (t, J=6.7 Hz, 2H), 1.89-1.78 (m, 2H), 1.54-1.33 (m, 4H), 0.94 (t, J=7.2 Hz, 3H). $^{13}$C NMR: (101 MHz, $CDCl_3$) δ 150.91, 130.28, 129.31, 128.84, 74.11, 29.84, 28.07, 22.61, 14.16. ATR-IR ($cm^{-1}$): 3081.97, 2955.97, 1551.16, 1448.49, 1255.61, 1044.22 HRMS: ($EI^+$) m/z: $[M]^+$ Calcd for $C_{11}H_{13}OCl_3$ 266.0032; Found 266.0037.

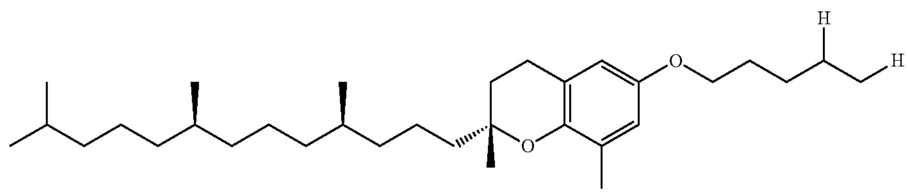

(R)-2,8-dimethyl-6-((pentyl)oxy)-2-((4R,8R)-4,8,12-trimethyltridecyl)chromane [8] According to general procedure B, in a $N_2$ filled glovebox, DTB-DPPBz (5.9 mg, 0.0066 mmol, 0.033 eq.), $Cu(OAc)_2$ (30 μL of a 0.2 M solution in THF, 0.006 mmol, 0.03 eq.), and THF (70 μL) followed by dimethoxy(methyl)silane (74 μL, 0.60 mmol, 3 eq.) were added to an oven-dried 2-dram vial with an oven-dried stir bar. In a separate oven-dried 1-dram vial was added (R)-2,8-dimethyl-6-(4-penten-1-yloxy)-2-((4R,8R)-4,8,12-trimethyltridecyl)chromane (94 mg, 0.20 mmol, 1 eq.), THF (100 μL), and 2-propanol (38 μL, 0.50 mmol, 2.5 eq.). The solution in the 1-dram vial was added dropwise to the 2-dram vial. The 2-dram vial was capped with a pressure relief cap, removed from the glovebox, and left to stir for 24 h at 60° C. Upon completion, the product was isolated by flash column chromatography using gradient elution (100 mL of 100% hexanes, 200 mL of 0.5% ethyl acetate in hexanes) to give the pure product as a clear oil (69 mg, 0.15 mmol, 75% yield). $^1$H NMR: (400 MHz, $CDCl_3$) extra proton observed due to signal overlapping with H grease δ 6.56 (d, J=3.0 Hz, 1H), 6.44 (d, J=3.0 Hz, 1H), 3.86 (t, J=6.6 Hz, 2H), 2.71 (t, J=6.6 Hz, 2H), 2.14 (s, 3H), 1.84-1.68 (m, 4H), 1.61-1.49 (m, 4H), 1.45-1.32 (m, 8H), 1.30-1.19 (m, 11H), 1.17-1.00 (m, 7H), 0.96-0.81 (m, 15H). $^{13}$C NMR: (101 MHz, $CDCl_3$) δ 151.77, 146.14, 127.22, 121.03, 115.53, 111.92, 75.64, 68.54, 40.11, 39.52, 37.60, 37.57, 37.43, 32.95, 32.84, 31.55, 29.35, 28.43, 28.13, 24.96, 24.60, 24.29, 22.88, 22.84, 22.78, 22.65, 21.13, 19.90, 19.81, 16.36, 14.20. ATR-IR ($cm^{-1}$): 2925, 2867, 1606, 1468, 1216, 1057. HRMS: ($ESI^+$) m/z: $[M+H]^+$ Calcd for $C_{32}H_{57}DO_2$ 473.4258; Found 473.4353.

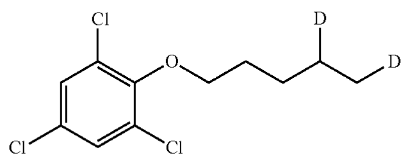

2,4,6-Trichloro-4-(5-(4,5-$d_2$)-pentan-1-yloxy)-benzene [9] According to general procedure B, in a $N_2$ filled glovebox, DTB-DPPBz (8.9 mg, 0.0099 mmol, 0.033 eq.), $Cu(OAc)_2$ (45 μL of a 0.2 M solution in THF, 0.009 mmol, 0.03 eq.), and THF (105 μL) followed by dimethoxy(methyl) silane-d (198 μL of a 6.05 M solution in hexane, 1.20 mmol, 4 eq.) were added to an oven-dried 2-dram vial with an oven-dried stir bar. In a separate oven-dried 1-dram vial was added 2,4,6-trichloro-4-(5-pentan-1-yloxy)-benzene (80 mg, 0.30 mmol, 1 eq.), THF (150 μL), and 2-propanol-$d_8$ (57 μL, 0.75 mmol, 2.5 eq.). The solution in the 1-dram vial was added drop % wise to the 2-dram vial. The 2-dram vial was capped with a pressure relief cap, removed from the glovebox, and left to stir for 24 h at 40° C. Upon completion, the product was isolated by flash column chromatography using gradient elution (200 mL of 100% hexanes, 100 mL of 1% ethyl acetate in hexanes) to give the pure product as a colorless oil (75 mg, 0.28 mmol, 93% yield).

$^1$H NMR: (400 MHz, $CDCl_3$) δ 7.29 (s, 2H), 3.98 (t, J=6.6 Hz, 2H), 1.89-1.78 (m, 2H), 1.48 (q, J=7.6 Hz, 2H), 1.43-1.32 (m, 1.19H), 0.96-0.88 (m, 2.04H). $^2$H NMR: (61 MHz. $CHCl_3$) δ 1.36 (s, 0.81D), 0.91 (s, 0.96D). $^{13}$C NMR: (101 MHz, $CDCl_3$) δ 150.89, 130.27, 129.31, 128.83, 74.11, 29.82, 27.93, 22.13 (t, J=19.2 Hz), 13.75 (t, J=19.1 Hz). ATR-R ($cm^{-1}$): 2928, 2857, 2169, 1448, 1256, 1138. HRMS: ($EI^+$) m/z: $[M]^+$ Calcd for $C_{11}H_{11}D_2OCl_3$ 268.0158; Found 268.0149.

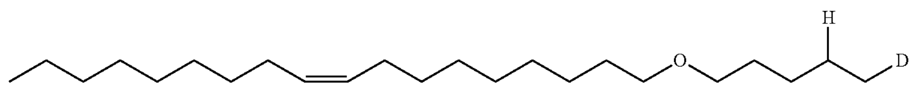 [SMILES: [2H]CCCCCOCCCCCCCC/C=C\CCCCCCCC]

(Z)-(5-d-pentan-1-yloxy)-9-octadecene [11] According to general procedure B, in a $N_2$ filled glovebox, DTB-DPPBz (5.9 mg, 0.0066 mmol, 0.033 eq.), $Cu(OAc)_2$ (30 μL of a 0.2 M solution in THF, 0.006 mmol, 0.03 eq.), and THF (70 μL) followed by dimethoxy(methyl)silane (74 μL, 0.60 mmol, 3 eq.) were added to an oven-dried 2-dram vial with an oven-dried stir bar. In a separate oven-dried 1-dram vial was added (Z)-(5-d-pentan-1-yloxy)-9-octadecene (67 mg, 0.20 mmol, 1 eq.), THF (100 μL), and 2-propanol-$d_8$ (38 μL, 0.50 mmol, 2.5 eq.). The solution in the 1-dram vial was added dropwise to the 2-dram vial. The 2-dram vial was capped with a pressure relief cap, removed from the glovebox, and left to stir for 24 h at 40° C. Upon completion, the product was isolated by flash column chromatography using gradient elution (100 mL of 100% hexanes, 100 mL of 1% ethyl acetate in hexanes, 100 mL of 2% ethyl acetate in hexanes) to give the pure product as a colorless oil (61 mg, 0.18 mmol, 90% yield).

$^1$H NMR: (400 MHz, $CDCl_3$) δ 5.40-5.29 (m, 2H), 3.39 (t, J=6.8 Hz, 4H), 2.09-1.96 (m, 4H), 1.61-1.52 (m, 4H), 1.39-1.23 (m, 26H), 0.92-0.84 (m, 5.02H). $^2$H NMR: (61 MHz, $CHCl_3$) δ 0.88. (s, 0.98D). $^{13}$C NMR: (101 MHz, $CDCl_3$) δ 130.04, 129.97, 71.10, 71.10, 32.06, 29.92, 29.90, 29.68, 29.68, 29.65, 29.65, 29.63, 29.47, 29.47, 29.40, 28.49, 27.34, 27.33, 26.34, 22.83, 22.62, 14.26, 13.90 (t=19.1 Hz). ATR-IR ($cm^{-1}$): 2924, 2856, 2173, 1465, 1117. HRMS: ($ESI^+$) m/z: $[M+H]^+$ Calcd for $C_{23}H_{46}DO$ 340.3689; Found 340.3686.

REFERENCES

1. Hatakeyama, T.; Hashimoto, T.; Kondo, Y.; Fujiwara, Y.; Seike. H.; Takaya, H.; Tamada, Y.; Ono, T.; Nakamura, M.

Iron-Catalyzed Suzuki-Miyaura Coupling of Alkyl Halides. J. Am. Chem. Soc. 2010, 132, 10674-10676.
2. Vang. Z. P.; Reyes. A.; Sonstrom, R. E.; Holdren, M. S.; Sloane, S. E.; Alansari, I. Y.; Neill, J. L.; Pate, B. H.; Clark, J. R. Copper-Catalyzed Transfer Hydrodeuteration of Aryl Alkenes with Quantitative Isotopomer Purity Analysis by Molecular Rotational Resonance Spectroscopy. J. Am. Chem. Soc. 2021, 143, 7707-7718.
3. Lu, X., Xiao. B.; Zhang, Z.; Gong, T.; Su. W.; Yi, J.; Fu, Y.; Liu, L. Practical carbon-carbon bond formation from olefins through nickel-catalyzed reductive olefin hydrocarbonation. Nat. Commun. 2016, 7, 11129.
4. Della-Felice, F.; Zanini, M.; Jie, X.; Tan, E.; Echavarren, A. M. Phodium(II)-Catalyzed Synthesis of Skipped Enynes via C(sp3)-H Alkynylation of Terminal Alkenes. Angew. Chem. Int. Ed. 2021, 60, 5693.
5. M. L.-L. and Cong, H. Atom-Transfer Radical Addition to Unactivated Alkenes by using Heterogenous Visible-Light Photocatalysis. Chemsuschem, 2017, 10, 4461-4464.
6. Meng, C.; Niu, H.; Nig, J; Wu, W.; Yi, J. Nickel-Catalyzed Removal of Alkene Protecting Group of Phenols. Alcohols via Walking Process. Molecules 2020, 25, 602.
7. Thomas, A. A.; Speck, K.; Kevlishvili, I.; Lu, Z.; Liu, P.; Buchwald, S. L. Mechanistically Guided Design of Ligands That Significantly Improve the Efficiency of CuH-Catalyzed Hydroamination Reactions. J. Am. Chem. Soc. 2018, 140, 13976-13984.
8. Mancheno, D. E.; Thornton, A. R.; Stoll, A. R.; Kong, A.; Blakey, S. B. Copper-Catalyzed Olefin Aminoacetoxylation. Org. Lett. 2010, 12, 4110-4113.
9. Srihari, P.; Kumaraswamy, B.; Somaiah, R.; Yadav, J. S. The Stereoselective Total synthesis of (+)-Stagonolide B. Synthesis, 2010, 6, 1039-1045.
10. Chen, C.; Luo, Y.; Fu, L.; Chen, P.; Lan, Y; Liu, G. Palladium-Catalayzed Intermolecular Ditrifluoromethoxylation of Unactivated Alkenes: CF3O-palladation Initiated by Pd(IV). J. Am. Chem. Soc. 2018, 140, 1207-1210.
11. Wei, X.; Zhang, C.; Wang, Y.; Zhan, Q.; Qiu, G.; Fan, L.; Yin, G. Decyanative Cross-Coupling of Cyanopyrimidines with O-, S-, and N-Nucleophiles: A Route to Alkoxypyrimidines, Aminopyrimidines and Alkylthiopyrimidines. Eur. J. Org, 2019, 7142-7150.
12. Oh, H.; Park, A.; Jeong, K.-S.; Han, S. B.; Lee, H. Copper-Catalyzed 1,2-Bistrifluoromethylation of Terminal Alkenes. Adv. Synth. Catal, 2019, 361, 2136-2140.
13. Wu, X.; Ding. G.; Lu. W.; Yang, L.; Wang, J.; Zhang, Y.; Xie, X.; Zhang, Z. Nickel-Catalyzed Hydrosilylation of Terminal Alkenes with Primary Silanes via Electrophilic Silicon-Hydrogen Bond Activation. Org. Lett. 2021, 23, 1434-1439.
14. Falk, E.; Makai, S.; Delcailau, T.; Gurtler, L.; Morandi, B. Design and Scalable Synthesis of N-Alkylhydroxylamine Reagents for the Direct Iron-Catalyzed Installation of Medicinally Relevant Amines. Angew. Chem. Int. Ed. 2020, 59, 21064-21071.
15. Yang, X. and Tsui, G. C. Copper-mediated 1,2-bis (trifluoromethylation) of arynes. Chem. Sci. 2018, 9, 8871-8875.

We claim:

1. A method for preparing a deuterated compound, the method comprising reacting a reaction mixture comprising:

(i) a substrate compound comprising an alkyne functionality or an alkene functionality;

(ii) a transition metal catalyst;

(iii) a phosphine ligand for the transition metal catalyst, wherein the phosphine ligand is (R)-(−)-5,5'-Bis[di(3,5-di-tert-butyl-4-methoxyphenyl)phosphino]-4,4'-bi-1,3-benzodioxole, (S)-(−)-5,5'-Bis[di(3,5-di-tert-butyl-4-methoxyphenyl)phosphino]-4,4'-bi-1,3-benzodioxole, or 1,2-bis(bis(3,5-di-tert-butylphenyl)phosphino)benzene;

(iv) a substituted silane comprising a donor hydrogen atom or a donor deuterium atom;

(v) $D_2O$ or an alcohol comprising a donor hydrogen atom or a donor deuterium atom; and (vi) a solvent;

wherein the reaction mixture is reacted under conditions such that the alkyne functionality or the alkene functionality of the substrate compound is reductively deuterated to a deuterated alkane functionality to provide the deuterated compound.

2. The method of claim 1, wherein the substituted silane comprises one of the donor hydrogen and the donor deuterium atom, and the alcohol comprises the other of the donor hydrogen and the donor deuterium atom.

3. The method of claim 1, wherein the substrate has a formula selected from Formula I and Formula II:

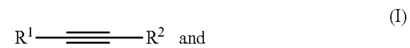 and (I)

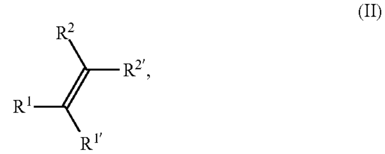 (II)

where:

$R^1$ is $-(CH_2)_m-(O)_n-X$, where m is 0-6, n is 0 or 1, and X is selected from an alkyl moiety, an alkenyl moiety, an aryl moiety (Ar), wherein the aryl moiety is a carbocycle aryl moiety or a heterocycle aryl moiety, a cycloalkyl moiety, and a heterocycloalkyl moiety, and $R^1$ optionally is substituted at one or more positions with alkyl, hydroxyl which optionally is protected, hydroxyalkyl which optionally is protected, alkoxy, carboxyl, carboxy alkyl ester, phenyl, phenoxy, benzyl, pyridinyl, piperidinyl, hydroxy (phenyl)methyl which optionally is protected, halogen, haloalkyl, nitro, amino, (alkyl)amino, diphenylamino, boronic acid pinocol ester, morpholino, sulfonamide, and tosyl;

$R^{1'}$ is selected from hydrogen, deuterium, and alkyl;

$R^2$ is selected from hydrogen, deuterium, alkyl, hydroxyalkyl which optionally is protected, Ar, cycloalkyl, and (alkoxy)alkyl; and $R^{2'}$ is selected from hydrogen, deuterium, and alkyl.

4. The method of claim 1, wherein the substrate comprises an optionally substituted aryl moiety selected from phenyl, pyridine, quinoline, 1,2,3,4-tetrahydroquinoline, isoquinoline, naphthalene, biphenyl, indole, furan, benzofuran, imidazole, benzimidazole, pyridine, pyrimidine, carbazole, dibenzofuran, indoline, azaindole, fluorene, 1,3-benzodioxole, thiophene, benzothiophene, and the aryl moiety optionally is substituted with alkyl, alkoxy, carboxyl, carboxy alkyl ester, phenyl, phenoxy, halogen, nitro, sulfonamide, or tosyl.

5. The method of claim 1, wherein the substrate comprises an optionally substituted heterocycle moiety selected from piperidine, piperazine, oxirane, tetrahydrofuran, pyrrolidine, and the heterocycle moiety optionally is substituted with alkyl, alkoxy, carboxyl, carboxy alkyl ester, phenyl, phenoxy, halogen, nitro, sulfonamide, or tosyl.

6. The method of claim 1, wherein the substrate has a formula selected from:

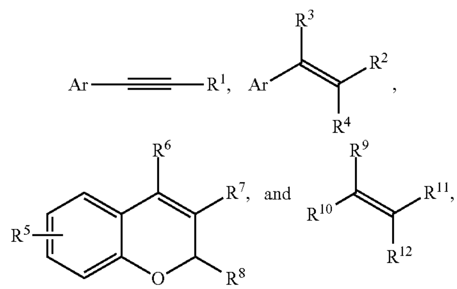

and wherein Ar is an aromatic carbocycle and/or an aromatic heterocycle optionally substituted at one or more positions with a substituent selected from alkyl, carbonyl, carboxy alkyl ester, phenyl, phenyoxy, halogen, nitro, sulfonamide, pyridinyl, imidazolyl, morpholino, boronic acid, piperidinyl, pyrazolyl, piperazinyl, and tosyl; $R^1$, $R^2$, $R^3$, $R^4$, $R^5$, $R^6$, $R^7$, and $R^8$ are independently selected from hydrogen, deuterium, alkyl, and Ar optionally substituted with amino, nitro, hydroxyl, alkoxy, carboxyl, —C(O)—O—$R^{13}$ where $R^{13}$ is alkyl, —C(O)—$R^{14}$ wherein $R^{14}$ is alkyl, C($R^{15}$)($R^{16}$)—$R^{17}$ wherein $R^{15}$ and $R^{16}$ are alkoxy, alkylthiol, sulfonamide, or Ar, and $R^{17}$ is alkyl, or —$CH_2C(OR^{18})$—$R^{19}$ wherein $R^{18}$ and $R^{19}$ are hydrogen or alkyl; and $R^9$, $R^{10}$, $R^{11}$, and $R^{12}$ are independently selected from hydrogen, deuterium, alkyl.

7. The method of claim 6, wherein Ar is selected from optionally substituted phenyl, pyridine, quinoline, isoquinoline, naphthalene, biphenyl, indole, furan, benzofuran, imidazole, benzimidazole, pyrimidine, carbozole, dibenzofuran, indoline, azaindole, and benzothiophene.

8. The method of claim 1, wherein the substituted silane has a formula:

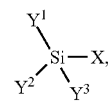

wherein $Y^1$, $Y^2$, and $Y^3$ are the same or different and are selected from alkyl and alkoxy, and X is the donor hydrogen atom or the donor deuterium atom.

9. The method of claim 1, wherein the alcohol has a formula selected from $C_2H_5O(H/D)$, $(CH_3)_2CHO(H/D)$, $(CD_3)_2CDOD$, $CH_3OD$, and $(CH_3)_3COD$.

10. The method of claim 1, wherein the transition metal catalyst is selected from scandium (Sc), titanium (Ti), vanadium (V), chromium (Cr), manganese (Mn), iron (Fe), cobalt (Co), nickel (Ni), copper (Cu), zinc (Zn).

* * * * *